US011440913B2

(12) United States Patent
Mertzman et al.

(10) Patent No.: US 11,440,913 B2
(45) Date of Patent: Sep. 13, 2022

(54) AMINOIMIDAZOPYRIDAZINES AS KINASE INHIBITORS

(71) Applicant: BRISTOL-MYERS SQUIBB COMPANY, Princeton, NJ (US)

(72) Inventors: Michael E. Mertzman, New Hope, PA (US); Carolyn Diane Dzierba, Medford, MA (US); Jason M. Guernon, Pipersville, PA (US); Amy C. Hart, Ewing, NJ (US); Guanglin Luo, Newtown, PA (US); John E. Macor, Washington Crossing, PA (US); William J. Pitts, Newtown, PA (US); Jianliang Shi, Furlong, PA (US); Steven H. Spergel, Warrington, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 107 days.

(21) Appl. No.: 16/758,892

(22) PCT Filed: Oct. 29, 2018

(86) PCT No.: PCT/US2018/057968
§ 371 (c)(1),
(2) Date: Apr. 24, 2020

(87) PCT Pub. No.: WO2019/089442
PCT Pub. Date: May 9, 2019

(65) Prior Publication Data

US 2020/0277296 A1 Sep. 3, 2020

Related U.S. Application Data

(60) Provisional application No. 62/626,853, filed on Feb. 6, 2018, provisional application No. 62/578,607, filed on Oct. 30, 2017.

(51) Int. Cl.
*A61K 31/5025* (2006.01)
*C07D 487/04* (2006.01)

(52) U.S. Cl.
CPC .................................. *C07D 487/04* (2013.01)

(58) Field of Classification Search
CPC .......................... A61K 31/5025; C07D 487/04
USPC .......................................... 514/248; 544/236
See application file for complete search history.

(56) References Cited

U.S. PATENT DOCUMENTS

| | | | | |
|---|---|---|---|---|
| 2009/0163489 A1 | 6/2009 | Booker et al. | | |
| 2010/0075965 A1* | 3/2010 | Ni | A61P 9/10 | 514/235.8 |
| 2015/0191474 A1 | 7/2015 | Takahashi et al. | | |
| 2019/0389859 A1 | 12/2019 | Guo et al. | | |

FOREIGN PATENT DOCUMENTS

| | | |
|---|---|---|
| WO | WO2007095588 A1 | 8/2007 |
| WO | WO2013191112 A1 | 12/2013 |
| WO | WO2014081756 A1 | 5/2014 |
| WO | WO2014144455 A1 | 9/2014 |
| WO | WO2014198594 A1 | 12/2014 |
| WO | WO 2016/027253 | 2/2016 |
| WO | WO2017192930 A1 | 11/2017 |
| WO | WO2018017435 A1 | 1/2018 |
| WO | WO2018148626 A1 | 8/2018 |
| WO | WO2019147782 A1 | 8/2019 |
| WO | WO2020/056072 A1 | 3/2020 |
| WO | WO2020056074 A1 | 3/2020 |

OTHER PUBLICATIONS

Jordan, V. C. Nature Reviews: Drug Discovery, 2, 2003, 205.*
Hackam, et al. JAMA, 296(14), 2006, 1731-1732.*
Harris et al., "Discovery of Small Molecule RIPI Kinase Inhibitors for the Treatment of Pathologies Associated with Necroptosis", Medicinal Chemistry Letters, vol. 4, pp. 1238-1243 (2013).
Harris, et al . . . Discovery of a First-in-Class Receptor Interacting Protein 1 (RIP1) Kinase Specific Clinical Candidate (GSK2982772) for the Treatment of Inflammatory Diseases, journal of Medicinal Chemistry, vol. 60(4), pp. 1247-1261 (2017).

* cited by examiner

*Primary Examiner* — Douglas M Willis
(74) *Attorney, Agent, or Firm* — Mary K. VanAtten

(57) ABSTRACT

Compounds having formula (I), and enantiomers, and diastereomers, stereoisomers, pharmaceutically-acceptable salts thereof, (I) are useful as kinase modulators, including RIPK1 modulation. All the variables are as defined herein.

(I)

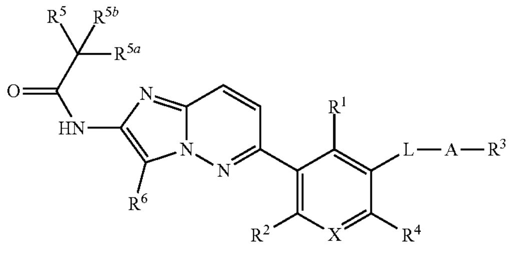

14 Claims, No Drawings

AMINOIMIDAZOPYRIDAZINES AS KINASE INHIBITORS

CROSS REFERENCE TO RELATED APPLICATIONS

This application is a 371 of International Application No. PCT/US2018/057968, filed on Oct. 29, 2018, which is entitled to priority pursuant to 35 U.S.C. § 119(e) to U.S. provisional patent application No. 62/578,607, filed Oct. 30, 2017, and U.S. provisional patent application No. 62/626,853, filed Feb. 6, 2018 which are incorporated herein in their entirety.

FIELD OF THE INVENTION

The present invention relates to novel compounds that inhibit receptor interacting protein kinases and methods of making and using the same. Specifically, the present invention relates to aminoimidazopyridazines as receptor interacting protein kinase 1 (RIPK1) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) Cell Death Differ 16:3-11). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein P & Kroemer G (2007) Trends Biochem. Sci. 32:37-43; Festjens et al. (2006) Biochim. Biophys. Acta 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al. (2000) Nat. Immunol. 1:489-495; Degterev et al. (2008) Nat. Chem. Biol. 4:313-321). This novel mechanism of cell death is termed “programmed necrosis” or “necroptosis” (Degterev et al., (2005) Nat Chem Biol 1:112-119).

Necroptosis can be triggered by a number of mechanisms including of TNF receptor activation, Toll-like receptor engagement, genotoxic stress and viral infection. Downstream of the various stimuli, the signaling pathway that results in necroptosis is dependent on RIPK1 and RIPK3 kinase activity. (He et al., (2009) Cell 137:1100-1111; Cho et. al., (2009) Cell 137:1112-1123; Zhang et al., (2009) Science 325:332-336).

Dysregulation of the necroptosis signaling pathway has been linked to inflammatory diseases such as macrophage necrosis in atheroscelerosis development, virus-induced inflammation, systemic inflammatory response syndrome and ethanol-induced liver injury, neurodegeneration such as detachment of the retina, ischemia, amyotrophic lateral sclerosis (ALS), and Gaucher’s disease (Trichonas et al., (2010) Proc. Natl. Acad. Sci. 107, 21695-21700; Lin et al., (2013) Cell Rep. 3, 200-210; Cho et al., (2009) Cell, 137, 1112-1123; Duprez et al., (2011) Immunity 35, 908-918; Roychowdhury et al., Hepatology 57, 1773-1783; Vandenabeele et al., (2010) Nature 10, 700-714; Vandenabeele et al., (2010) Sci. Signalling 3, 1-8; Zhang et al., (2010) Cellular & Mol. Immunology 7, 243-249; Moriwaki et al., (2013) Genes Dev. 27, 1640-1649; Ito et al., (2016) Science 353, 603-608; Vitner et al., (2014) Nature Med. 20, 204-208).

A potent, selective, small molecule inhibitor of RIPK1 activity would block RIPK1-dependent pro-inflammatory signaling and thereby provide a therapeutic benefit in inflammatory diseases characterized by increased and/or dysregulated RIPK1 kinase activity.

SUMMARY OF THE INVENTION

The present invention provides novel aminoimidazopyridazines including stereoisomers, tautomers, isotopes, prodrugs, pharmaceutically acceptable salts, salts, or solvates thereof, which are useful as inhibitors of RIPK1.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, isotopes, prodrugs, pharmaceutically acceptable salts, salts, or solvates thereof.

The compounds of the invention may be used in the treatment and/or prophylaxis of conditions associated with aberrant RIPK1 activity.

The compounds of the present invention may be used in therapy.

The compounds of the present invention may be used for the manufacture of a medicament for the treatment and/or prophylaxis of a condition associated with aberrant RIPK1 activity.

In another aspect, the present invention is directed to a method of treating diseases mediated at least partially by RIPK1 including inflammatory diseases, ischemia, neurodegeneration, and Gaucher’s disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I) or stereoisomers, tautomers, isotopes, salts, pharmaceutically acceptable salts, solvates, or prodrugs thereof, wherein (I)

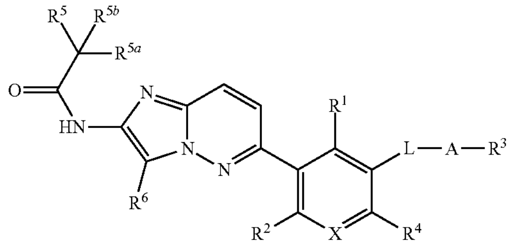

$R^1$ is H, halo, $C_{1-3}$ alkyl, $C_{1-3}$ haloalkyl, $C_{1-3}$ deuteroalkyl, $C_{1-3}$ alkoxy, $C_{1-3}$ haloalkoxy, $C_{1-3}$ alkoxy, $C_{1-3}$ haloalkoxy, or $C_{1-3}$ deuteroalkoxy;

$R^2$ is H, $C_{1-3}$ alkyl, $C_{1-3}$ alkoxy, $C_{1-3}$ haloalkyl, $C_{1-3}$ haloalkoxy, $C_{1-3}$ deuteroalkyl, $C_{1-3}$ deuteroalkoxy, halo, $NH_2$, or CN;

L is $C(O)NR^a$ or —

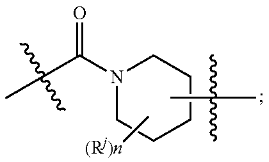

;

alternatively, -L-A- is $—CH_2—NR^aC(O)—$;

$R^a$ is independently H, $C_{1-4}$ alkyl, or $C_{1-4}$ deuteroalkyl;

alternatively, $R^a$ is ((phosphonooxy)alkylcarbonyoxy)alkyl, ((amino)alkylcarbonyloxy)alkyl, ((amino)cycloalkylcarbonyloxy)alkyl, ((((phophonooxy)alkyl)carbonyloxy)alkyl)oxy carbonyl, ((((phophonooxy)cycloalkyl)carbonyloxy)alkyl)oxy carbonyl, ((((amino)alkyl)carbonyloxy) alkyl)oxy carbonyl, ((((amino)cycloalkyl)carbonyloxy) alkyl)oxycarbonyl, or ((((phosphonooxy)(alkoxy) benzoyl)alkyl)oxy carbonyl;

A is $C_{1-4}$ alkyl substituted with 0-1 OH, $C_{1-4}$ alkoxy substituted with 0-1 OH, $C_{1-4}$ deuteroalkyl substituted with 0-1 OH, $C_{3-6}$ cycloalkyl-$C_{1-3}$-alkyl-, $C_{1-3}$-alkyl-$C_{3-6}$ cycloalkyl-, heterocyclyl-$C_{0-3}$ alkyl wherein the alkyl is substitute with 0-1 OH and the heterocycle is a 3-6 membered ring containing 1-2 heteroatoms selected from O, N, or S and is substituted with 0-2 of OH, halo, or $C_{1-3}$ alkyl;

$R^3$ is phenyl, or a 5 to 6 membered heterocycle having 1-4 heteroatoms selected from N and O, wherein any of the phenyl or heteroaryl groups are substituted with 0-3 $R^{3a}$;

$R^{3a}$ is halo, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-6}$ cycloalkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{1-4}$ alkyl-$SO_2$—, $C_{3-6}$ cycloalkyl-$SO_2$—, aryl, $C_{6-10}$ aryl-O—, $C_{6-10}$ aryl-S—, $NR^cR^dCO$—, $(OH)_2P(O)$—O—, heterocycle-, heterocycle-O—, heterocycle-$CH_2$—, heterocycle-C(O)—, wherein each heterocycle is independently a 4-6 membered ring having 1-2 heteroatoms selected from N and O, and wherein each alkyl, cycloalkyl, aryl, or heterocycle is substituted with 0-2 $R^b$;

alternatively, 2 $R^{3a}$ on adjacent atoms may join to form $—O—CH_2—O—$, $—O—CH_2—CH_2—$, $—O—(CH_2)_3—$ or $—O—(CH_2)_2—O—$;

$R^b$, at each occurrence, is independently OH, $C_{1-3}$ alkyl, hydroxy $C_{1-3}$ alkyl, $C_{1-3}$ alkoxy, halo, C═O, or $C_{1-3}$ haloalkyl, or $C_{3-6}$ cycloalkyl;

$R^c$ and $R^d$ are independently selected from H, $C_{1-3}$ alkyl, $C_{1-3}$ deuteroalkyl, $C_{3-6}$ cycloalkyl, or taken together with N to which they are attached to form a 4-6 member heterocyclic ring, having 0-1 additional heteroatoms selected from N, O and S, and being substituted with 0-4 substituents chosen from deuterium or halo;

$R^4$ is H, Cl, F, Br, $C_{1-4}$ alkyl, $C_{1-4}$ alkoxy, $C_{1-4}$ haloalkyl, $C_{1-4}$ deuteroalkyl, $C_{1-4}$ deuteroalkoxy, cyclopropyl, or $NR^eR^f$;

$R^e$ and $R^f$ are independently selected from H, $C_{1-3}$ alkyl, $C_{1-3}$ deuteroalkyl, $C_{3-6}$ cycloalkyl, or taken together with N to which they are attached to form a 4-6 member ring substituted with 0-4 substituents chosen from deuterium or halo;

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl;

$R^{5a}$ and $R^{5b}$ are independently selected from H, $C_{1-3}$ alkyl, or $R^{5a}$ and $R^{5b}$ are taken together to form a 3-6 member carbocyclic or heterocyclic ring which is substituted with 0-2 of F, $C_{1-3}$ alkyl, or $C_{1-3}$ haloalkyl, the heterocyclic ring having 0-2 heteroatoms selected from N, O, and S;

or $R^5$ is absent and $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

$R^g$ and $R^h$ are independently selected from H, $C_{1-3}$ alkyl, $C_{1-3}$ deuteroalkyl, or $C_{3-6}$ cycloalkyl;

alternatively, $R^g$ and $R^h$, along with the nitrogen to which they are attached, join to form piperidinyl, morpholinyl, piperazinyl, pyrrolidinyl, or azetidinyl, any which are substituted with 0-3 $R^i$;

$R^i$ is $C_{1-3}$ alkyl, halo, or $C_{1-3}$ haloalkyl;

$R^j$ is halo or OH;

$R^6$ is H, or $C_{1-3}$ alkyl;

X is N or C—$R^7$; where $R^7$ is H, halo, CN, $C_{1-3}$ alkyl, $C_{1-3}$ alkoxy, $C_{1-3}$ haloalkyl, or $C_{1-3}$ haloalkoxy; and n is 0, 1, or 2.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

(I)

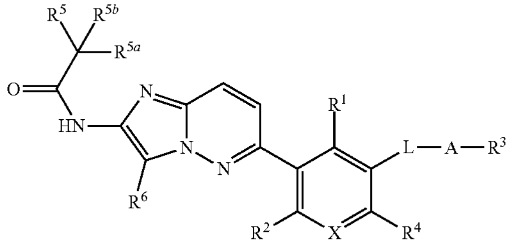

$R^1$ is H, halo, $C_{1-3}$ alkyl, $C_{1-3}$ haloalkyl, $C_{1-3}$ deuteroalkyl, $C_{1-3}$ alkoxy, $C_{1-3}$ haloalkoxy, $C_{1-3}$ alkoxy, $C_{1-3}$ haloalkoxy, or $C_{1-3}$ deuteroalkoxy;

$R^2$ is H, $C_{1-3}$ alkyl, $C_{1-3}$ alkoxy, $C_{1-3}$ haloalkyl, $C_{1-3}$ haloalkoxy, $C_{1-3}$ deuteroalkyl, $C_{1-3}$ deuteroalkoxy, halo, $NH_2$, or CN;

L is $C(O)NR^a$ or $—NR^aC(O)—$;

alternatively, -L-A- is $—CH_2—NR^aC(O)—$;

$R^a$ is independently H, $C_{1-4}$ alkyl, or $C_{1-4}$ deuteroalkyl;

A is $C_{1-4}$ alkyl substituted with 0-1 OH, $C_{1-4}$ deuteroalkyl substituted with 0-1 OH, $C_{3-6}$ cycloalkyl-$C_{1-3}$-alkyl-, $C_{1-3}$-alkyl-$C_{3-6}$ cycloalkyl-;

$R^3$ is phenyl, or a 5 to 6 membered heterocycle having 1-4 heteroatoms selected from N and O, wherein any of the phenyl or heteroaryl groups are substituted with 0-3 $R^{3a}$;

$R^{3a}$ is halo, $C_{1-6}$ alkyl, $C_{1-6}$ alkoxy, hydroxy-$C_{16}$ alkoxy, $C_{1-6}$ deuteroalkyl, $C_{1-6}$ deuteroalkoxy, $C_{1-6}$ haloalkyl, $C_{1-6}$ haloalkoxy, $C_{3-6}$ cycloalkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{13}$ haloalkoxy-, $C_{1-6}$ alkoxy-$C_{1-3}$ alkyl-, $C_{3-6}$ cycloalkoxy-$C_{1-3}$ alkyl-, $C_{1-4}$ alkyl-$SO_2$—, $C_{3-6}$ cycloalkyl-$SO_2$—, $C_{6-10}$ aryl-S—, $NR^cR^dCO$—, heterocycle-, heterocycle-O—, heterocycle-$CH_2$—, wherein each heterocycle is independently a 4-6 membered ring having 1-2 heteroatoms selected from N and O, and wherein each alkyl, cycloalkyl, or heterocycle is substituted with 0-2 $R^b$;

$R^b$, at each occurrence, is independently $C_{1-3}$ alkyl, halo, C═O, or $C_{1-3}$ haloalkyl;

$R^c$ and $R^d$ are independently selected from H, $C_{1-3}$ alkyl, $C_{1-3}$ deuteroalkyl, $C_{3-6}$ cycloalkyl, or taken together with N to which they are attached to form a 4-6 member heterocyclic ring, having 0-1 additional heteroatoms selected from N, O and S, and being substituted with 0-4 substituents chosen from deuterium or halo;

$R^4$ is H, Cl, F, Br, $C_{1-4}$ alkyl, $C_{1-4}$ alkoxy, $C_{1-4}$ haloalkyl, $C_{1-4}$ deuteroalkyl, $C_{1-4}$ deuteroalkoxy, cyclopropyl, or $NR^eR^f$:

$R^e$ and $R^f$ are independently selected from H, $C_{1-3}$ alkyl, $C_{1-3}$ deuteroalkyl, $C_{3-6}$ cycloalkyl, or taken together with N to which they are attached to form a 4-6 member ring substituted with 0-4 substituents chosen from deuterium or halo;

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl;

$R^{5a}$ and $R^{5b}$ are independently selected from H, $C_{1-3}$ alkyl, or $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

or $R^5$ is absent and $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

$R^E$ and $R^h$ are independently selected from H, $C_{1-3}$ alkyl, $C_{1-3}$ deuteroalkyl, or $C_{3-6}$ cycloalkyl;

$R^6$ is H, or $C_{1-3}$ alkyl;

X is N or C—$R^7$; where $R^7$ is H, halo, CN, $C_{1-3}$ alkyl, $C_{1-3}$ alkoxy, $C_{1-3}$ haloalkyl, or $C_{1-3}$ haloalkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

(I)

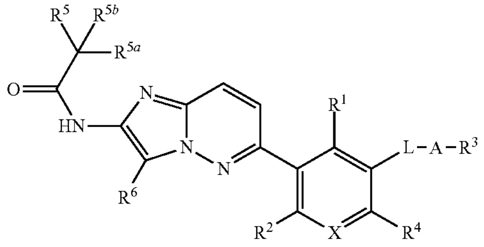

$R^1$ is H, halo, $C_{1-3}$ alkyl, $C_{1-3}$ haloalkyl, $C_{1-3}$ deuteroalkyl, $C_{1-3}$ alkoxy, $C_{1-3}$ haloalkoxy, $C_{1-3}$ alkoxy, $C_{1-3}$ haloalkoxy, or $C_{1-3}$ deuteroalkoxy;

$R^2$ is H, $C_{1-3}$ alkyl, $C_{1-3}$ alkoxy, $C_{1-3}$ haloalkyl, $C_{1-3}$ haloalkoxy, $C_{1-3}$ deuteroalkyl, $C_{1-3}$ deuteroalkoxy, halo, $NH_2$, or CN;

L is $C(O)NR^a$;

alternatively, -L-A- is $—CH_2—NR^aC(O)—$;

$R^a$ is independently H, $C_{1-4}$ alkyl, or $C_{1-4}$ deuteroalkyl;

alternatively, $R^a$ is

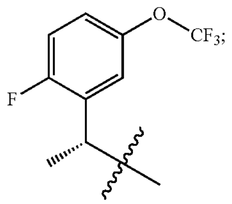 [SMILES: *[C@H](C)c1cc(OC(F)(F)F)ccc1F]

A is $C_{1-4}$ alkyl substituted with 0-1 OH, $C_{1-4}$ deuteroalkyl substituted with 0-1 OH, $C_{3-6}$ cycloalkyl-$C_{1-3}$-alkyl-, $C_{1-3}$-alkyl-$C_{3-6}$ cycloalkyl-;

$R^3$ is phenyl, or a 5 to 6 membered heterocycle having 1-4 heteroatoms selected from N and O, wherein any of the phenyl or heteroaryl groups are substituted with 0-3 $R^{3a}$;

$R^{3a}$ is halo, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-6}$ cycloalkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{1-4}$ alkyl-$SO_2$—, $C_{3-6}$ cycloalkyl-$SO_2$—, $C_{6-10}$ aryl-S—, $NR^cR^dCO$—, $(OH)_2P(O)$—O—, heterocycle-, heterocycle-O—, heterocycle-$CH_2$—, wherein each heterocycle is independently a 4-6 membered ring having 1-2 heteroatoms selected from N and O, and wherein each alkyl, cycloalkyl, or heterocycle is substituted with 0-2 $R^b$;

$R^b$, at each occurrence, is independently $C_{1-3}$ alkyl, halo, C═O, or $C_{1-3}$ haloalkyl;

$R^c$ and $R^d$ are independently selected from H, $C_{1-3}$ alkyl, $C_{1-3}$ deuteroalkyl, $C_{3-6}$ cycloalkyl, or taken together with N to which they are attached to form a 4-6 member heterocyclic ring, having 0-1 additional heteroatoms selected from N, O and S, and being substituted with 0-4 substituents chosen from deuterium or halo;

$R^4$ is H, Cl, F, Br, $C_{1-4}$ alkyl, $C_{1-4}$ alkoxy, $C_{1-4}$ haloalkyl, $C_{1-4}$ deuteroalkyl, $C_{1-4}$ deuteroalkoxy, cyclopropyl, or $NR^eR^f$:

$R^e$ and $R^f$ are independently selected from H, $C_{1-3}$ alkyl, $C_{1-3}$ deuteroalkyl, $C_{3-6}$ cycloalkyl, or taken together with N to which they are attached to form a 4-6 member ring substituted with 0-4 substituents chosen from deuterium or halo;

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl;

$R^{5a}$ and $R^{5b}$ are independently selected from H, $C_{1-3}$ alkyl, or $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

or $R^5$ is absent and $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

$R^g$ and $R^h$ are independently selected from H, $C_{1-3}$ alkyl, $C_{1-3}$ deuteroalkyl, or $C_{3-6}$ cycloalkyl;

$R^6$ is H, or $C_{1-3}$ alkyl;

X is N or C—$R^7$; where $R^7$ is H, halo, CN, $C_{1-3}$ alkyl, $C_{1-3}$ alkoxy, $C_{1-3}$ haloalkyl, or $C_{1-3}$ haloalkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

(I)

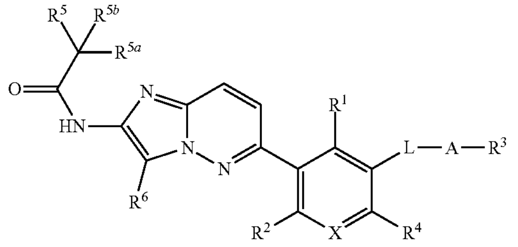

$R^1$ is H, halo, $C_{1-3}$ alkyl, $C_{1-3}$ haloalkyl, $C_{1-3}$ deuteroalkyl, $C_{1-3}$ alkoxy, $C_{1-3}$ haloalkoxy, $C_{1-3}$ alkoxy, $C_{1-3}$ haloalkoxy, or $C_{1-3}$ deuteroalkoxy;

$R^2$ is H, $C_{1-3}$ alkyl, $C_{1-3}$ alkoxy, $C_{1-3}$ haloalkyl, $C_{1-3}$ haloalkoxy, $C_{1-3}$ deuteroalkyl, $C_{1-3}$ deuteroalkoxy, halo, $NH_2$, or CN;

L is $C(O)NR^a$ or —

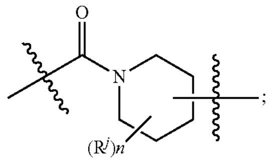
;

alternatively, -L-A- is —$CH_2$—$NR^aC(O)$—;

$R^a$ is independently H, $C_{1-4}$ alkyl, or $C_{1-4}$ deuteroalkyl;

A is $C_{1-4}$ alkyl substituted with 0-1 OH, $C_{1-4}$ alkoxy substituted with 0-1 OH, $C_{1-4}$ deuteroalkyl substituted with 0-1 OH, $C_{3-6}$ cycloalkyl-$C_{1-3}$-alkyl-, $C_{1-3}$-alkyl-$C_{3-6}$ cycloalkyl-, heterocyclyl-$C_{0-3}$ alkyl wherein the alkyl is substitute with 0-1 OH and the heterocycle is a 3-6 membered ring containing 1-2 heteroatoms selected from O, N, or S and is substituted with 0-2 of OH, halo, or $C_{1-3}$ alkyl;

$R^3$ is phenyl, or a 5 to 6 membered heterocycle having 1-4 heteroatoms selected from N and O, wherein any of the phenyl or heteroaryl groups are substituted with 0-3 $R^{3a}$;

$R^{3a}$ is halo, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-6}$ cycloalkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{1-4}$ alkyl-$SO_2$—, $C_{3-6}$ cycloalkyl-$SO_2$—, aryl, $C_{6-10}$ aryl-O—, $C_{6-10}$ aryl-S—, $NR^cR^dCO$—, heterocycle-, heterocycle-O—, heterocycle-$CH_2$—, heterocycle-C(O)—, wherein each heterocycle is independently a 4-6 membered ring having 1-2 heteroatoms selected from N and O, and wherein each alkyl, cycloalkyl, aryl, or heterocycle is substituted with 0-2 $R^b$;

alternatively, 2 $R^{3a}$ on adjacent atoms may join to form —O—$CH_2$—O—, —O—$CH_2$—$CH_2$—, —O—$(CH_2)_3$— or —O—$(CH_2)_2$—O—;

$R^b$, at each occurrence, is independently OH, $C_{1-3}$ alkyl, hydroxy $C_{1-3}$ alkyl, $C_{1-3}$ alkoxy, halo, C═O, or $C_{1-3}$ haloalkyl, or $C_{3-6}$ cycloalkyl;

$R^c$ and $R^d$ are independently selected from H, $C_{1-3}$ alkyl, $C_{1-3}$ deuteroalkyl, $C_{3-6}$ cycloalkyl, or taken together with N to which they are attached to form a 4-6 member heterocyclic ring, having 0-1 additional heteroatoms selected from N, O and S, and being substituted with 0-4 substituents chosen from deuterium or halo;

$R^4$ is H, Cl, F, Br, $C_{1-4}$ alkyl, $C_{1-4}$ alkoxy, $C_{1-4}$ haloalkyl, $C_{1-4}$ deuteroalkyl, $C_{1-4}$ deuteroalkoxy, cyclopropyl, or $NR^eR^f$:

$R^e$ and $R^f$ are independently selected from H, $C_{1-3}$ alkyl, $C_{1-3}$ deuteroalkyl, $C_{3-6}$ cycloalkyl, or taken together with N to which they are attached to form a 4-6 member ring substituted with 0-4 substituents chosen from deuterium or halo;

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl;

$R^{5a}$ and $R^{5b}$ are independently selected from H, $C_{1-3}$ alkyl, or $R^{5a}$ and $R^{5b}$ are taken together to form a 3-6 member carbocyclic or heterocyclic ring which is substituted with 0-2 of F, $C_{1-3}$ alkyl, or $C_{1-3}$ haloalkyl, the heterocyclic ring having 0-2 heteroatoms selected from N, O, and S;

or $R^5$ is absent and $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S;

$R^g$ and $R^h$ are independently selected from H, $C_{1-3}$ alkyl, $C_{1-3}$ deuteroalkyl, or $C_{3-6}$ cycloalkyl;

alternatively, $R^g$ and $R^h$, along with the nitrogen to which they are attached, join to form piperidinyl, morpholinyl, piperazinyl, pyrrolidinyl, or azetidinyl, any which are substituted with 0-3 $R^i$;

$R^i$ is $C_{1-3}$ alkyl, halo, or $C_{1-3}$ haloalkyl;

$R^j$ is halo or OH;

$R^6$ is H, or $C_{1-3}$ alkyl;

X is N or C—$R^7$; where $R^7$ is H, halo, CN, $C_{1-3}$ alkyl, $C_{1-3}$ alkoxy, $C_{1-3}$ haloalkyl, or $C_{1-3}$ haloalkoxy; and n is 0, 1, or 2.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^a$ is independently H, $C_{1-4}$ alkyl, or $C_{1-4}$ deuteroalkyl;

alternatively, $R^a$ is

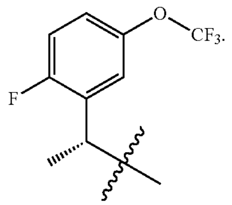 [SMILES: *[C@H](C)c1cc(OC(F)(F)F)ccc1F]

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^3$ is phenyl, or pyridinyl, or pyrrolyl, any of which are substituted with 0-3 $R^{3a}$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^3$ is phenyl, or a 5 to 6 membered heterocycle having 1-4 heteroatoms selected from N and O, wherein any of the phenyl or heteroaryl groups are substituted with 0-3 $R^{3a}$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

A is $C_{1-4}$ alkyl substituted with 0-1 OH, $C_{1-4}$ deuteroalkyl substituted with 0-1 OH.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^3$ is phenyl, substituted with 0-3 $R^{3a}$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^{3a}$ is halo, $C_{1-6}$ alkyl, $C_{1-6}$ alkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^{3a}$ is halo, $C_{1-6}$ alkyl, $C_{1-6}$ alkoxy, or $NR^cR^dCO$—.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

wherein $R^1$ is H, or $C_{1-4}$ alkyl;

$R^2$ is H, $C_{1-3}$ alkyl, or $C_{1-3}$ alkoxy;

$R^4$ is H, Cl, F, or $C_{1-4}$ alkyl, $C_{1-4}$ alkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^1$ is H;

$R^2$ is H, $C_{1-3}$ alkyl, or $C_{1-3}$ alkoxy;

$R^4$ is H, Cl, F, or $C_{1-4}$ alkyl, $C_{1-4}$ alkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

A is $—CH_2—$, $CD_2$-, $—CH_2CH_2—$, $—CH(CH_3)—$, $—CH(CD_3)—$, $—CH_2CH_2CH(CH_3)—$, $—CH_2CH_2CH(OH)—$, or $—CH_2$-cyclopropyl-.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

L is C(O)NH;

$R^6$ is H;

X is N or $CR^7$; and $R^7$ is H or halo.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

X is N.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

X is $CR^7$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

A is $—CH_2—$, or $—CH(CH_3)—$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

wherein $R^3$ is

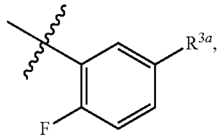
,
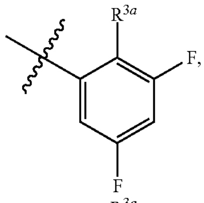
,
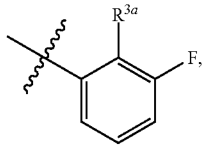
, or
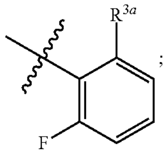
;

and wherein $R^{3a}$ is $C_{1-6}$ alkoxy, $C_{1-6}$ haloalkoxy, or $C_{3-6}$ cycloalkoxy.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

L is $C(O)NR^a$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

L is

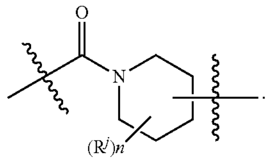

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

A is $C_{1-4}$ alkoxy substituted with 0-1 OH, heterocyclyl-$C_{0-3}$ alkyl wherein the alkyl is substitute with 0-1 OH and the heterocycle is a 3-6 membered ring containing 1-2 heteroatoms selected from O, N, or S and is substituted with 0-2 of OH, halo, or $C_{1-3}$ alkyl.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^a$ is independently H, $C_{1-4}$ alkyl, or $C_{1-4}$ deuteroalkyl.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^{3a}$ is halo, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-6}$ cycloalkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{1-4}$ alkyl-$SO_2$—, $C_{3-6}$ cycloalkyl-$SO_2$—, $C_{6-10}$ aryl-S—, $NR^cR^dCO$—, heterocycle-, heterocycle-O—, heterocycle-$CH_2$—, wherein each heterocycle is independently a 4-6 membered ring having 1-2 heteroatoms selected from N and O, and wherein each alkyl, cycloalkyl, or heterocycle is substituted with 0-2 $R^b$.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^b$, at each occurrence, is independently OH, $C_{1-3}$ alkyl, hydroxy $C_{1-3}$ alkyl, $C_{1-3}$ alkoxy, halo, C═O, or $C_{1-3}$ haloalkyl, or $C_{3-6}$ cycloalkyl.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl;

$R^{5a}$ and $R^{5b}$ are independently selected from H, $C_{1-3}$ alkyl, or $R^{5a}$ and $R^{5b}$ are taken together to form a 3-6 member carbocyclic or heterocyclic ring which is substituted with 0-2 of F, $C_{1-3}$ alkyl, or $C_{1-3}$ haloalkyl, the heterocyclic ring having 0-2 heteroatoms selected from N, O, and S;

or $R^5$ is absent and $R^{5a}$ and $R^{5b}$ are taken together to form a 3-6 member carbocyclic or heterocyclic ring which is substituted with 0-1 of F, or $C_{1-3}$ alkyl, the heterocyclic ring having 0-2 heteroatoms selected from N, O, and S.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^5$ is H, HO—, $C_{1-3}$ alkyl-C(O)O—, CN, $C_{1-3}$ alkoxy, $NR^gR^h$—, $(OH)_2P(O)O$—, or $NH_2CHR^8CO$— where $R^8$ is H, $C_{1-3}$ alkyl, or $C_{1-3}$ alkoxy-$C_{1-3}$ alkyl; and $R^{5a}$ and $R^{5b}$ are independently selected from H, $C_{1-3}$ alkyl.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^{3a}$ is halo, $C_{1-6}$ alkyl, $C_{1-6}$ haloalkyl, $C_{1-6}$ haloalkoxy, $C_{1-6}$ alkoxy or $NR^cR^dCO$—. Another embodiment provides a compound of Formula (I), or stereoisomers, tautomers, isotopes, salts, pharmaceutically acceptable salts, solvates, or prodrugs thereof, wherein the compound is selected from the examples.

The present invention is also directed to pharmaceutical compositions useful in treating diseases associated with kinase modulation, including the modulation of receptor interacting protein kinases such as RIPK1, comprising compounds of formula (I), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK1, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I), wherein the disease is inflammatory bowel disease, Crohn's disease or ulcerative colitis, poriasis, systemic lupus erythematosus (SLE), rheumatoid arthritis, multiple sclerosis (MS), transplant rejection, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from systemic lupus erythematosus (SLE), multiple sclerosis (MS), transplant rejection, acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris and asthma, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from macrophage necrosis in atheroscelerosis development, virus-induced inflammation, systemic inflammatory response syndrome and ethanol-induced liver injury, neurodegeneration such as detachment of the retina, retinal degeneration, wet and dry age-related macular degeneration (AMD), ischemia, amyotrophic lateral sclerosis (ALS), and Gaucher's disease.

The present invention also provides a method of treating a condition comprising administering to a patient in need of such treatment a therapeutically-effective amount of a compound of formula (I), wherein the condition is selected from Inflammatory bowel disease, ulcerative colitis, Crohn's disease, psoriasis, rheumatoid arthritis (RA), heart failure, and nonalcoholic steatohepatitis (NASH).

The present invention also provides a method of treating a condition comprising administering to a patient in need of such treatment a therapeutically-effective amount of a compound of formula (I), wherein the condition is selected from inflammatory bowel disease, Crohn's disease, ulcerative collitis, and psoriasis.

The present invention also provides a method of treating a condition comprising administering to a patient in need of such treatment a therapeutically-effective amount of a compound of formula (I), wherein the condition is selected from nonalcoholic steatohepatitis (NASH), and ischemia reperfusion.

The present invention also provides a method for treating rheumatoid arthritis, comprising administering to a patient in need of such treatment a therapeutically-effective amount of a compound of formula (I), The present invention also provides a method of treating diseases, comprising administering to a patient in need of such treatment a therapeutically-effective amount of a compound of formula (I), or pharmaceutically acceptable salt thereof, in combination with other therapeutic agents.

The present invention also provides the compounds of the present invention or stereoisomers, tautomers, isotopes, salts, pharmaceutically acceptable salts, solvates, or prodrugs thereof, for use in therapy.

In another embodiment, compounds of formula (I), are selected from exemplified examples or combinations of exemplified examples or other embodiments herein.

In another embodiment, the $IC_{50}$ value of compounds of formula (I), in the RIPK1 assays described below is >200 nM.

In another embodiment, the $IC_{50}$ value of compounds of formula (I), in the RIPK1 assays described below is <200 nM.

In another embodiment, the $IC_{50}$ value of compounds of formula (I), in the RIPK1 assays described below is <20 nM.

The present invention also provides the use of the compounds of the present invention or stereoisomers, tautomers, isotopes, salts, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula (I), (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or S(O)H group.

The term "carbocyclyl" or "carbocyclic" refers to a saturated or unsaturated, or partially unsaturated, monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Carbocycles, can include cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, and aromatic heteroary groups as described below, in which at least one of the rings has at least one heteroatom (0, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "$CO_2$" is used herein, this is intended to refer to the group

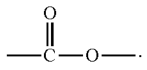

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. In one embodiment, salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. As an example, an alkyl substituent is intended to cover alkyl groups have either hydrogen, deuterium, and/or some combination thereof. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C═N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

UTILITY

The compounds of the invention modulate kinase activity, including the modulation of RIPK1. Accordingly, compounds of formula (I) have utility in treating conditions associated with the modulation of kinase activity, and particularly the selective inhibition of RIPK1 activity. In another embodiment, compounds of formula (I) have advantageous selectivity for RIPK1 activity preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of RIPK1, compounds of Formula (I) are useful in treating RIPK1-associated conditions including, but not limited to, inflammatory diseases such as Crohn's disease and ulcerative colitis, inflammatory bowel disease, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, cerebral ischemias or neurodegenerative disease caused by traumatic injury, oncologic and viral diseases such as metastatic melanoma, Kaposi's sarcoma, multiple myeloma, and HIV infection and CMV retinitis, AIDS; fibrotic conditions such as, nonalcoholic steatohepatitis (NASH); and cardiac conditions such as, ischemia reperfusion; respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, ALS, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from inflammatory bowel disease, Crohn's disease and ulcerative colitis, allograft rejection, rheumatoid arthritis, psoriasis, ankylosing spondylitis, psoriatic arthritis, and pemphigus vulgaris, and nonalcoholic steatohepatitis (NASH), and ischemia reperfusion. Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK1-associated condition" or "RIPK1-associated disease or disorder" are used herein, each is intended to encompass all of the conditions identified above as if repeated at length, as well as any other condition that is affected by RIPK1 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit RIPK1.

The methods of treating RIPK1 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit RIPK1 and/or treat diseases associated with RIPK1.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; anti-inflammatory anti-bodies such as vedolizumab and ustekinumab, anti-infammatory kinase inhibitors such as TYK2 inhibitors, antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, rapamycin (sirolimus or Rapamune) or derivatives thereof, and agonists of FGF21.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK1 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK1 enzyme levels.

MLKL Phosphorylation High-Content Assay

HT29-L23 human colorectal adenocarcinoma cells were maintained in RPMI 1640 medium containing 10% heat-inactivated FBS, 1% Pennicilin-Streptomycin and 10 mM HEPES. Cells were seeded at 2,000 cells/well in 384 w tissue culture-treated microplates (Greiner #781090-3B) and incubated at 37° C. (5% $CO_2$/95% $O_2$) for two days. On the day of assay, the cells were treated with test compounds at final concentrations of 6.25 to 0.106 μM for 30 min at 37° C. (5% $CO_2$/95% $O_2$). Necroptopsis was induced using a mixture of human TNFα (35 ng/mL) (Peprotech #300-01A), SMAC mimetic (from US 2015/0322111 A1) (700 nM) and Z-VAD (140 nM) (BD pharmingen #51-6936). Following six hours incubation at 37° C. (5% $CO_2$/95% $O_2$), the cells were fixed with 4% formaldedye (ACROS 11969-0010) for 15 min at room temperature and then permeabilized with phoshpate buffered saline (PBS) containing 0.2% Triton-X-100 for 10 min. MLKL phosporylation was detected using anti-MLKL (phospho S358) antibody (Abcam # ab187091) (1:1000 dilution in Blocking Buffer [PBS supplemented with 0.1% BSA]) with overnight incubation at 4° C. After washing three times in PBS, goat anti-rabbit Alexa-488 (1:1000 dilution) (Life Technologies, A11008) and Hoechst 33342 (Life Technologies, H3570) (1:2000 dilution) in Blocking Buffer were added for 1 h at room temperature. Following another three cycles of washes in PBS, the microplates were sealed, and cellular images were acquired in the Cellomics ArrayScan VTI high-content imager equipped with an X1 camera. Fluorescent images were taken using a 10× objective and the 386-23 BGRFRN_BGRFRN and 485-20 BGRFRN_BGRFRN filter sets, for nuclei and MLKL phosphorylation, respectively. The image sets were analyzed using the Compartmental Analysis Bioapplication software (Cellomics). The level of MLKL phosphorylation was quantified as MEAN_CircRingAvgIntenRatio. The maximal inhibitory response was defined by the activity induced by Necls (CAS #: 852391-15-2, 6.25 μM). The IC50 value was defined as the concentration of compound that produces 50% of the maximal inhibition. The data were fitted using the 4-parameter logistic equation to calculate the IC50 and Ymax values.

RIPK1 HTRF Binding Assay

A solution was prepared containing 0.2 nM Anti GST-Tb (Cisbio, 61GSTTLB), 90.6 nM probe and 1 nM His-GST-TVMV-hRIPK1(1-324) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 mL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Cloning and Baculovirus Expression of RIPK1 Construct

The coding region of human RIPK1(1-324) flanked by NdeI site at 5' end and stop codon TGA and XhoI site at 3' end was codon optimized and gene synthesized at GenScript USA Inc. (Piscataway, N.J.) and subcloned into a modified pFastBacl vector (Invitrogen, Carlsbad, Calif.) with N-terminal His-GST-TVMV tag, to generate His-GST-TVMV-hRIPK1(1-324)-pFB. The fidelity of the synthetic fragment was confirmed by sequencing.

Baculovirus was generated for the construct using the Bac-to-Bac baculovirus expression system (Invitrogen) according to the manufacturer's protocol. Briefly, recombinant bacmid was isolated from transformed DH10Bac *E. coli* competent cells (Invitrogen) and used to transfect *Spodoptera frugiperda* (Sf9) insect cells (Invitrogen). Baculovirus was harvested 72 hours post transfection and a virus stock was prepared by infecting fresh Sf9 cells at a 1/1000 (v/v) ratio for 66 hours.

For large scale protein production, Sf9 cells (Expression System, Davis, Calif.) grown in ESF921 insect medium (Expression System) at 2×106 cells/ml were infected with virus stock at a 1/100 (v/v) ratio for 66 hours. The production was carried out either at a 10 L scale in a 22 L cellbag (GE Healthcare Bioscience, Pittsburgh, Pa.) or at a 20 L scale in a 50 L cellbag using WAVE-Bioreactor System 20/50 (GE Healthcare Bioscience). The infected cells were harvested by centrifugation at 2000 rpm for 20 min at 4° C. in a SORVALL® RC12BP centrifuge. The cell pellets was stored at −70° C. before protein was purified.

Purification of His-GST-TVMV-hRIPK1(1-324)

RIPK1 containing cell paste was resuspended in 50 mM Tris pH 7.5, 150 mM NaCl, 10 mM imidazole, 5% glycerol, 5 mM $MgSO_4$, 1 mM TCEP, 25 U/ml Benzonase, and Complete Protease Inhibitor tablets (1/50 ml, Roche Diagnostics, Indianapolis, Ind.). The cells were lysed by nitrogen cavitation using an unstirred pressure vessel @ 525 PSI (Parr Instrument Company, Moline, Ill.). The suspension was clarified by centrifugation at 136,000×g for 40 min, at 4° C. The lysate was decanted from the pellet and passed through a 5 ml NiNTA Superflow cartridge (Qiagen, Valencia, Calif.) using an AKTA Pure (GE Healthcare). Column was eluted with 10 CV linear gradient into 50 mM Tris 7.5, 150 mM NaCl, 500 mM imidazole, 5% glycerol, 1 mM TCEP. Peak fractions were pooled and loaded directly onto 5 ml GSTrap 4B column (GE Healthcare). Column was washed with 50 mM Tris 7.0, 150 mM NaCl, 5% glycerol, 1 mM DTT and eluted in 10 CV linear gradient into 50 mM Tris 8.0, 150 mM NaCl, 20 mM reduced glutathione, 5% glycerol, 1 mM DTT. Fractions identified by SDS-PAGE as containing RIPK1 were pooled and concentrated using 30 kDa MWCO spin concentrators (Amicon Ultra-15, Millipore, Billerica, Mass.) and loaded onto a HiLoad 26/600 Superdex 200 column (GE Healthcare) equilibrated in 25 mM Tris 7.5, 150 mM NaCl, 2 mM TCEP, 5% glycerol. The RIPK1 protein eluted as a dimer off the SEC column.

The yield was ~8 mg/L with a purity >95% as determined by Coomassie staind SDS-PAGE gel analysis. LCMS analysis of the protein showed that the protein had lost the N-terminal methionine, had one phosphorylated site, and was partially acetylated. Protein was aliquotted and stored at −80° C.

Using these assays, the $IC_{50}$ values of the following compounds were determined. See Table A.

TABLE A

| Ex | RIPK1 (IC50, nM) | pMLKL (IC50, nM) |
|---|---|---|
| 1 | 101 | 240 |
| 2 | 2 | 4 |
| 3 | 30 | 295 |
| 4 | 2 | 10 |
| 5 | 7 | 11 |
| 6 | 25 | 10 |
| 7 | 14 | 38 |
| 8 | 39 | 41 |
| 9-1 | 25 | 25 |
| 9-2 | 31 | 28 |
| 10 | 11 | 33 |
| 11 | 20 | 89 |
| 12 | 5 | 27 |
| 13-1 | 986 | >6250 |
| 13-2 | 6 | 1 |
| 14 | 33 | 69 |
| 15 | 83 | 198 |
| 16 | 4 | 5 |
| 17 | 27 | 129 |
| 18 | 145 | 177 |
| 19 | 12 | 34 |
| 20 | 46 | 63 |
| 21 | 10 | 29 |
| 22 | 4 | 26 |
| 23 | 124 | 127 |
| 24 | 5 | 10 |
| 25 | 2 | 9 |
| 26 | 25 | 192 |
| 27 | 109 | 108 |
| 28 | 285 | 248 |
| 29 | 257 | 450 |
| 30 | 199 | 341 |
| 31 | 82 | 339 |
| 32 | 78 | 177 |
| 33 | 186 | 183 |
| 34 | 96 | 215 |
| 35 | 25 | 130 |
| 36 | 48 | 92 |
| 37 | 67 | 208 |
| 38 | 13 | 34 |
| 39 | 55 | 119 |
| 40 | 125 | 265 |
| 41 | 63 | 78 |
| 42 | 11 | 13 |
| 43 | 10 | 28 |
| 44 | 17 | 71 |
| 45 | 13 | 25 |
| 46 | 2 | 1 |
| 47 | 161 | 85 |
| 48 | 10 | 87 |
| 49 | 3 | 5 |
| 50 | 2 | 2 |
| 51 | 63 | 200 |
| 52 | 65 | 185 |
| 53 | 62 | 81 |
| 54 | 5 | 24 |
| 55 | 1 | 3 |
| 56 | 13 | 67 |

TABLE A-continued

| Ex | RIPK1 (IC50, nM) | pMLKL (IC50, nM) |
|---|---|---|
| 57 | 10 | 25 |
| 58 | 14 | 21 |
| 59 | 12 | 17 |
| 60 | 6 | 26 |
| 61 | 33 | 258 |
| 62 | 11 | 29 |
| 63 | 149 | 340 |
| 64 | 49 | 45 |
| 65 | 44 | 374 |
| 66 | 9 | 8 |
| 67 | 14 | 14 |
| 68 | 5 | 45 |
| 69 | 15 | 23 |
| 70 | 9 | 9 |
| 71 | 5 | 13 |
| 72 | 17 | 30 |
| 73 | 57 | 82 |
| 74 | 63 | 353 |
| 75 | 11 | 32 |
| 76 | 3 | 8 |
| 77 | 17 | 265 |
| 78 | 16 | 21 |
| 79 | 38 | 46 |
| 80 | 14 | 15 |
| 81 | 5 | 2 |
| 82 | 21 | 18 |
| 83 | 5 | 7 |
| 84 | 19 | 26 |
| 85 | 4 | 12 |
| 86 | | 27 |
| 87 | 3 | 3 |
| 88 | 25 | 42 |
| 89 | 38 | 88 |
| 90 | 5 | 3 |
| 91 | 61 | 442 |
| 92 | 48 | 127 |
| 93 | 50 | 129 |
| 94 | 77 | 87 |
| 95 | 30 | 68 |
| 96 | 10 | 25 |
| 97 | 2 | 2 |
| 98 | 2 | 39 |
| 99 | 6 | 24 |
| 100 | 56 | 203 |
| 101 | | 248 |
| 102 | 7 | 10 |
| 103 | 51 | 188 |
| 104 | 36 | 73 |
| 105 | 5 | 17 |
| 106 | 84 | 95 |
| 107 | 193 | 306 |
| 108 | 4 | 28 |
| 109 | 32 | 85 |
| 110 | 27 | 113 |
| 111 | 19 | 36 |
| 112 | 17 | 73 |
| 113 | 38 | 298 |
| 114 | 8 | 33 |
| 115 | 12 | 65 |
| 116 | 10 | 3 |
| 117 | 6 | 19 |
| 118 | 2 | 28 |
| 119 | 116 | 94 |
| 120 | 170 | 383 |
| 121 | 3 | 9 |
| 122 | 5 | 15 |
| 123 | 37 | 218 |
| 124 | 6 | 14 |
| 125 | 34 | 153 |
| 126 | 73 | 78 |
| 127 | 4 | 33 |
| 128 | 9 | 64 |
| 129 | 1 | 2 |
| 130 | 4 | 3 |
| 131 | 79 | 481 |
| 132 | 10 | 64 |
| 133 | 23 | 8 |
| 134 | 18 | 28 |

TABLE A-continued

| Ex | RIPK1 (IC50, nM) | pMLKL (IC50, nM) |
|---|---|---|
| 135 | 3 | 7 |
| 136 | 17 | 100 |
| 137 | 7 | 14 |
| 138 | 13 | 72 |
| 139 | 15 | 25 |
| 140 | 17 | 77 |
| 141 | 97 | 256 |
| 142 | 29 | 181 |
| 143 | 8 | 4 |
| 144 | 6 | 6 |
| 145 | 5 | 27 |
| 146 | 17 | 48 |
| 147 | 95 | 37 |
| 148 | 4 | 2 |
| 149 | 16 | 74 |
| 150 | 18 | 24 |
| 151 | 8 | 6 |
| 152 | 49 | 69 |
| 153 | 1 | 1 |
| 154 | 13 | 15 |
| 155 | 2 | 6 |
| 156 | 2 | 3 |
| 157 | 17 | 93 |
| 158 | 31 | 336 |
| 159 | 3 | 6 |
| 160 | 489 | 331 |
| 161 | 145 | 311 |
| 162 | 64 | 140 |
| 163 | 12 | 17 |
| 164 | 10 | 32 |
| 165 | 4 | 11 |
| 166 | 4 | 1 |
| 167 | 18 | 13 |
| 168 | 21 | 67 |
| 169 | 3 | 10 |
| 170 | 4 | 3 |
| 171 | 3 | 3 |
| 172 | 15 | 16 |
| 173 | 3 | 2 |
| 174 | 3 | 1 |
| 175 | 4 | 16 |
| 176 | 10 | 12 |
| 177 | 2 | 3 |
| 178 | 4 | 20 |
| 179 | 3 | 13 |
| 180 | 4 | 18 |
| 181 | 103 | 171 |
| 182 | 272 | 455 |
| 183 | 166 | 392 |
| 184 | 9 | 177 |
| 185 | 30 | 81 |
| 186 | 15 | 96 |
| 187 | 18 | 148 |
| 188 | 22 | 217 |
| 189 | 91 | 208 |
| 190 | 23 | 35 |
| 191 | 938 | 86 |
| 192 | 3 | 5 |
| 193 | 56 | 61 |
| 194 | 100 | 141 |
| 195 | 43 | 188 |
| 196 | 45 | 5 |
| 197 | 72 | 23 |
| 198 | 16 | 14 |
| 199 | 13 | 17 |
| 200 | 17 | 34 |
| 201 | 6 | 10 |
| 202 | 32 | 34 |
| 203 | >5,000 | >6250 |
| 204 | 122 | 83 |
| 205 | 27 | 74 |
| 206 | 12 | 37 |
| 207 | 29 | 92 |
| 208 | 5 | 5 |
| 209 | 133 | 202 |
| 210 | 3 | 5 |
| 211 | 62 | 137 |
| 212 | 8 | 4 |

TABLE A-continued

| Ex | RIPK1 (IC50, nM) | pMLKL (IC50, nM) |
|---|---|---|
| 213 | 7 | 6 |
| 214 | 1 | 16 |
| 215 | 8 | 22 |
| 216 | 66 | 397 |
| 217 | 54 | 205 |
| 218 | 6 | 15 |
| 219 | 3 | 1 |
| 220 | 202 | 406 |
| 221 | 49 | 52 |
| 222 | 3 | 2 |
| 223 | 4 | 3 |
| 224 | 157 | 334 |
| 225 | 5 | 3 |
| 226 | 6 | 3 |
| 227 | 8 | 21 |
| 228 | 16 | 193 |
| 229 | 134 | 436 |
| 230 | 19 | 90 |
| 231 | 6 | 60 |
| 232 | 4 | 4 |
| 233 | 38 | 276 |
| 234 | 46 | 71 |
| 235 | 345 | 355 |
| 236 | 95 | 180 |
| 237 | 45 | 77 |
| 238 | 41 | 356 |
| 239 | 13 | 158 |
| 240 | 5 | 8 |
| 241 | 35 | 277 |
| 242 | 4 | 11 |
| 243 | 2 | 3 |
| 244 | 257 | 4 |
| 245 | 486 | 132 |
| 246 | 92 | 105 |
| 247 | 2 | 2 |
| 248 | 13 | 55 |
| 249 | 29 | 132 |
| 250 | 18 | 61 |
| 251 | 53 | 305 |
| 252 | 27 | 133 |
| 253 | 14 | 53 |
| 254 | 101 | 66 |
| 255 | 87 | 263 |
| 256 | 9 | 27 |
| 257 | 61 | 69 |
| 258 | 72 | 57 |
| 259 | 3 | 13 |
| 260 | 18 | 80 |
| 261 | 7 | 8 |
| 262 | 39 | 74 |
| 263 | 107 | 38 |
| 264 | 55 | 240 |
| 265 | 3 | 7 |
| 266 | 3 | 18 |
| 267 | 81 | 383 |
| 268 | 46 | 73 |
| 269 | 55 | 209 |
| 270 | 23 | 204 |
| 271 | 49 | 129 |
| 272 | 26 | 122 |
| 273 | 4 | 43 |
| 274 | 11 | 31 |
| 275 | 32 | 52 |
| 276 | 28 | 39 |
| 277 | 107 | 263 |
| 278 | 6 | 64 |
| 279 | 47 | 51 |
| 280 | 5 | 36 |
| 281 | 6 | 4 |
| 282 | 10 | 8 |
| 283 | 16 | 67 |
| 284 | 5 | 5 |
| 285 | 17 | 23 |
| 286 | 9 | 19 |
| 287 | 4 | 2 |
| 288 | 6 | 1 |
| 289 | 16 | 16 |
| 290 | 7 | 3 |

TABLE A-continued

| Ex | RIPK1 (IC50, nM) | pMLKL (IC50, nM) |
|---|---|---|
| 291 | >5,000 | >6250 |
| 292 | 24 | 37 |
| 293 | 33 | 135 |
| 294 | 10 | 3 |
| 295 | 10 | 23 |
| 296 | 10 | 20 |
| 297 | 11 | 36 |
| 298 | 43 | 79 |
| 299 | 4 | 1 |
| 300 | 4 | 76 |
| 301 | 25 | 22 |
| 302 | 25 | 16 |
| 303 | 22 | 43 |
| 304 | 206 | 67 |
| 305 | 41 | 77 |
| 306 | 5 | 6 |
| 307 | 11 | 5 |
| 308 | 8 | 11 |
| 309 | 19 | 46 |
| 310 | 21 | 125 |
| 311 | 6 | 4 |
| 312 | 7 | 38 |
| 313 | 9 | 22 |
| 314 | 5 | 3 |
| 315 | 5 | 9 |
| 316 | 4 | 8 |
| 317 | 3 | 19 |
| 318 | 3 | 2 |
| 319 | 15 | 29 |
| 321 | 44 | 386 |
| 322 | 8 | 51 |
| 323 | | 9 |
| 324 | | 3 |
| 325 | 9 | 17 |
| 326 | 6 | 10 |
| 327 | 5 | 25 |
| 328 | 36 | 198 |
| 329 | 53 | 88 |
| 330 | 46 | 106 |
| 331 | 42 | 68 |
| 332 | 308 | 25 |
| 333 | 91 | 218 |
| 334 | 15 | 10 |
| 335 | 28 | 9 |
| 336 | 19 | 8 |
| 337 | | 11 |
| 338 | 21 | 50 |
| 339 | 48 | 170 |
| 340 | 67 | 258 |
| 341 | 91 | 492 |
| 342 | 13 | 142 |
| 343 | 9 | 24 |
| 344 | 266 | 37 |
| 345 | | 44 |
| 346 | | 82 |
| 347 | 44 | 89 |
| 348 | 2 | 27 |
| 349 | 51 | 424 |
| 350 | 27 | 169 |
| 351 | 28 | 49 |
| 352 | 125 | 394 |
| 354 | 212 | 223 |
| 355 | 223 | 553 |
| 356 | 150 | 485 |
| 357 | 335 | 219 |
| 358 | 15 | 49 |
| 359 | 78 | 5 |
| 360 | 6 | 9 |
| 361 | 42 | 135 |
| 362 | 6 | 5 |
| 363 | 65 | 47 |
| 364 | 7 | 7 |
| 365 | 37 | 116 |
| 366 | 13 | 123 |
| 367 | 56 | 194 |
| 368 | 25 | 31 |
| 369 | 97 | 61 |
| 370 | 34 | 210 |

TABLE A-continued

| Ex | RIPK1 (IC50, nM) | pMLKL (IC50, nM) |
|---|---|---|
| 371 | 5 | 15 |
| 372 | 13 | 122 |
| 373 | 11 | 51 |
| 374 | | 19 |
| 375 | 12 | 3 |
| 376 | 9 | 9 |
| 377 | 67 | 135 |
| 378 | 6 | 1 |
| 379 | 1 | 5 |
| 380 | 3 | 9 |
| 381 | 8 | 74 |
| 382 | 4 | 2 |
| 383 | 3 | 3 |
| 384 | 48 | 99 |
| 385 | 57 | 189 |
| 386 | 5 | 13 |
| 387 | 8 | 5 |
| 388 | 7 | 2 |
| 389 | 4 | 8 |
| 390 | 5 | 3 |
| 391 | 105 | 274 |
| 392 | 36 | 72 |
| 393 | 4 | 8 |
| 394 | 3 | 3 |
| 395 | 7 | 25 |
| 396 | 1 | 7 |
| 397 | 3 | 3 |
| 398 | 5 | 2 |
| 399 | | 5 |
| 400 | 11 | 11 |
| 401 | 105 | 77 |
| 402 | 56 | 94 |
| 403 | 67 | 262 |
| 404 | 52 | 259 |
| 405 | 14 | 99 |
| 406 | 163 | 454 |
| 407 | 37 | 388 |
| 408 | 8 | 8 |
| 409 | 2 | 13 |
| 410 | 39 | 77 |
| 411 | 9 | 25 |
| 412 | 4 | 1 |
| 413 | 3 | 1 |
| 414 | 91 | 384 |
| 415 | | 4 |
| 416 | 13 | 72 |
| 417 | 4 | 9 |
| 418 | | 26 |
| 419 | 4 | 28 |
| 420 | 90 | 77 |
| 421 | 2 | 10 |
| 422 | 6 | 75 |
| 423 | | 109 |
| 424 | 2 | 3 |
| 425 | >5,000 | 327 |
| 426 | 1 | 7 |
| 427 | 7 | 3 |
| 428 | 12 | 9 |
| 429 | 9 | 20 |
| 430 | 3 | 9 |
| 431 | 7 | 91 |
| 432 | 36 | 149 |
| 433 | | 34 |

Methods of Preparation

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "ON" for overnight, "RT" for retention time, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" or "LC/MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$Ac_2O$ acetic anhydride
Boc (tert-butoxy)carbonyl
BOP benzotriazol-1-yloxytris(dimethylamino)phosphonium hexafluorophosphate
CBz carbobenzyloxy
$CH_2Cl_2$ dichloromethane
$CH_3CN$ or ACN acetonitrile
$CDCl_3$ deutero-chloroform
$CHCl_3$ chloroform
$Cs_2CO_3$ cesium carbonate
DCE 1,2 dichloroethane
DCM dichloromethane
DIEA/DIPEA/Hünig's Base diisopropylethylamine
DMAP 4-dimethylaminopyridine
DME 1,2-dimethoxyethane
DMF dimethyl formamide
DMSO dimethyl sulfoxide
EDC N-(3-dimthylaminopropyl)-N'-ethylcarbodiimide
EDCI N-(3-dimthylaminopropyl)-N'-ethylcarbodiimide hydrochloride
$Et_3N$ or TEA triethylamine
EtOAc ethyl acetate
$Et_2O$ diethyl ether
EtOH ethanol
HCl hydrochloric acid
HATU O-(7-azabenzotriazol-1-yl)-N,N,N',N'-tetramethyluronium hexafluorophosphate
Hex hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
MeI iodomethane
$MgSO_4$ magnesium sulfate
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4C_1$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$PdCl_2(dppf)$ [1,1'-bis(diphenylphosphino)-ferrocene] dichloropalladium(II)
PG protecting group
$POCl_3$ phosphorus oxychloride
i-PrOH or IPA isopropanol
$SiO_2$ silica oxide
TBAI tetra-n-butylammonium iodide
TFA trifluoroacetic acid
THF tetrahydrofuran.

The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates an approach to the synthesis of compounds exemplified by 5. Functionalization of starting material 1 can be achieved through amidation (Tetrahedron, 61:10827-10852, 2005) to yield bromide 2. Acylation of 3 can be accomplished via the anhydride or acid chloride in conjunction with base. Alternatively 3 can be converted to 4 using a carboxylic acid and standard amidation protocols known to those in the art. A Suzuki coupling reaction (Miyaura, N. and Suzuki, A. Chemical Reviews, 95:2457-2483, 1995) can provide compounds of the type exemplified by 5.

Scheme 1

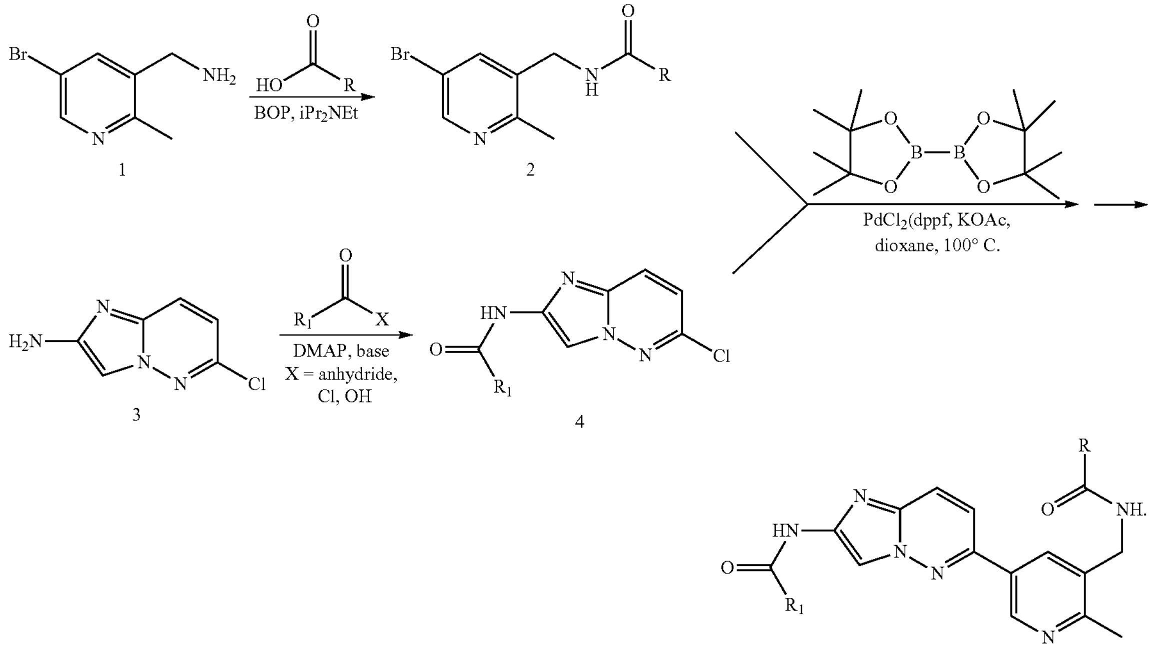

1 2 3 4 5

Compounds exemplified by 10 can be made in multiple ways as shown in Schemes 2 and 3. In Scheme 2, bromide 6 can be converted to its isolable boronate ester 7 under Suzuki coupling conditions. Access to the boronic acid, potassium trifluoroborate salt, or MIDA-boronate intermediates would also be accessible under similar conditions known to those in the art. Subsequent Suzuki coupling to imidazopyridazine 4 would yield intermediates depicted by 8. Hydrolysis of the ester can lead to the penultimate coupling partner 9 which can be converted to 10 under the standard amidation procedure highlighted in Scheme 2. Alternative amidation conditions known to those in the art may also be used in this step.

Scheme 2.

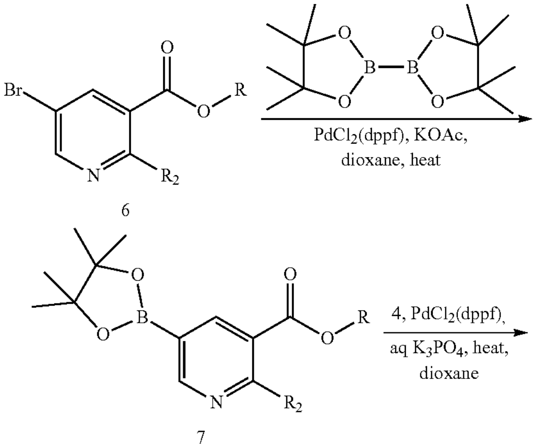

6 7

-continued

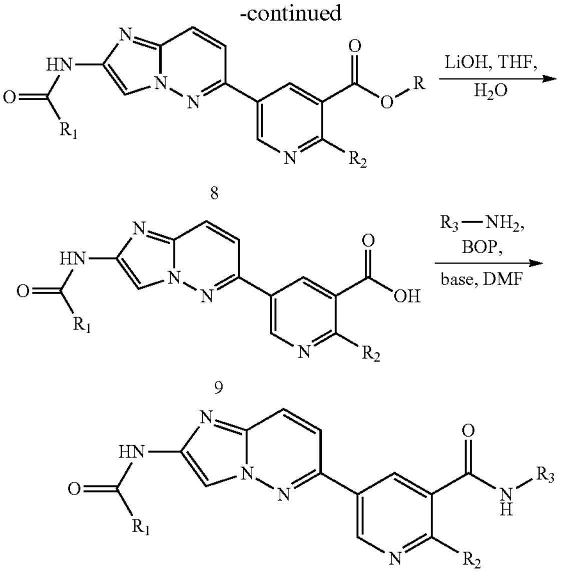

8 9 10

As an alternative to Scheme 2, Scheme 3 allows for late stage functionalization of the imidazopyridazine. Boronate 7 and imidazopyridazine 3 can be coupled utilizing a Suzuki reaction to yield intermediates characterized by 11. Hydrolysis and amide coupling can yield the penultimate compounds exemplified by 13. As described for Scheme 2, a variety of amidation conditions known to those in the art may be employed. Acylation of 13 can be accomplished through base mediated coupling with the acyl anhydride or acid chloride. Alternatively, amidation conditions may be used to access compounds exemplified by 10.

Scheme 3.

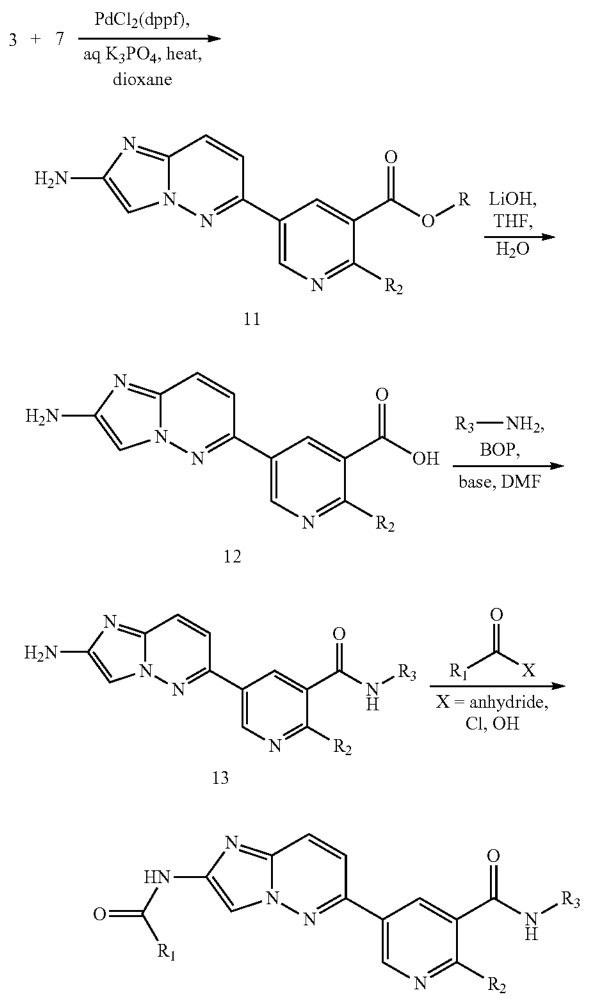

11

12

13

10

In addition to employing the discreet boronates for coupling the imidazopyridazine with the pyridine, 8 can be directly accessed through a one-pot protocol highlighted in Scheme 4. Treatment of imidazopyridazine 4 with bis(pinacolato)diboron, or an alternative diboron reagent known to those in the art, at elevated temperatures and in the presence of anhydrous base can generate the boronate ester or boronic acid in situ. Addition of intermediate 6 and aqueous base can yield 8. This route would be amenable to treating 6 with the bis(pinacolato)diboron first, followed by addition of 4 to access intermediates such as 8.

Scheme 4.

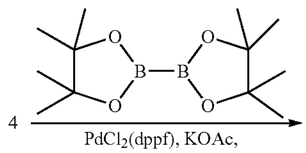

-continued

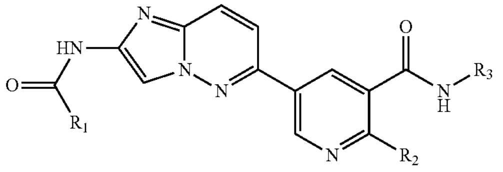

8

Scheme 5 highlights a synthetic route to enable access to 2-alkoxypyridine containing analogs, exemplified by 17. Treatment of 2-hydroxypyridine 14 with an alkyl iodide in the presence of silver carbonate can provide 15. This alkylation can be done by other methods known to those in the art, however the choice of base may affect the ratio of N vs O alkylation. Intermediates such as 15 can be converted to the boronate in situ and treated with 4 and aqueous base to access intermediates characterized by 16. Hydrolysis of the ester, followed by amidation can yield compounds exemplified by 17.

Scheme 5.

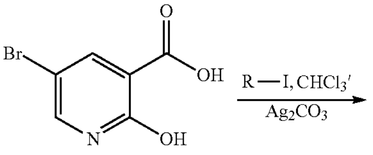

14

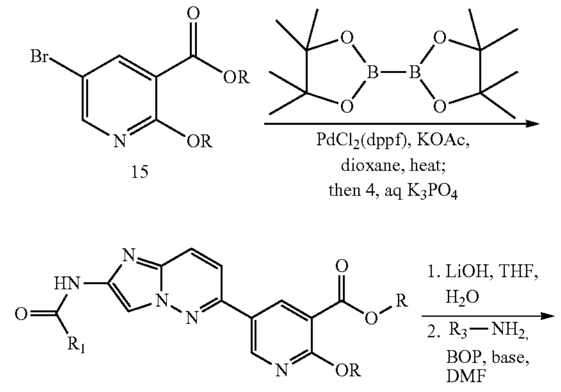

15

16

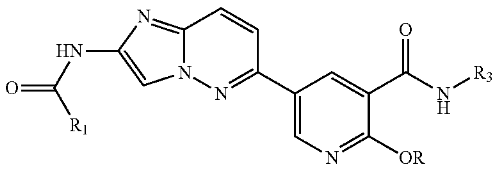

17

In some examples, the boronic acid of the imidazopyridazine, such as 18, may be available. This can undergo Suzuki coupling with an appropriate halide. As shown in Schme 6, bromide 15 can be used to access intermediates such as 16 which can be further elabortaed as described in Scheme 5.

Scheme 6.

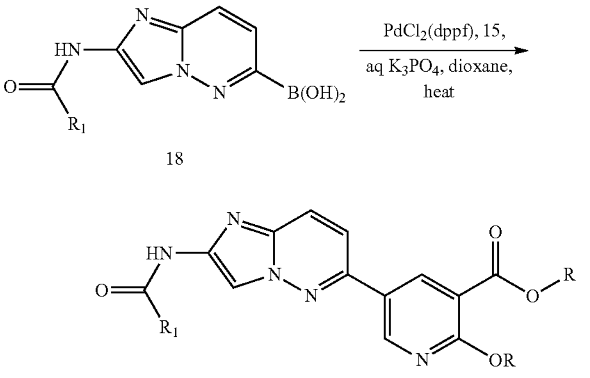

18

16

The amine coupling partners described here are commercially available, previously described in U.S. Patent Application No. 62/458,144 or can be accessed synthetically via the method descibed in Scheme 7. A phenol such as 17 can undergo a Williamson ether synthesis (Williamson, A. Justus Liebigs Ann. Chem, 77:37-49, 1851) to access intermediates such as 18. Alternative methods, including a Mitsunobu reaction (Swamy, K. C. K. et al. Chem. Rev. 109:2551-2651, 2009), could also be used and would be known to those in the art. Reduction of the benzonitrile to access the amines characterized by 19 could be accomplished with sodium borohydride and iodide at elevated temperatures. Access to the deuterated analogs would also be possible with use of sodium borodeuteride under similar conditions. Additional methods for benzonitrile reduction, such as lithium aluminum hydride, would be known to those in the art.

Scheme 7.

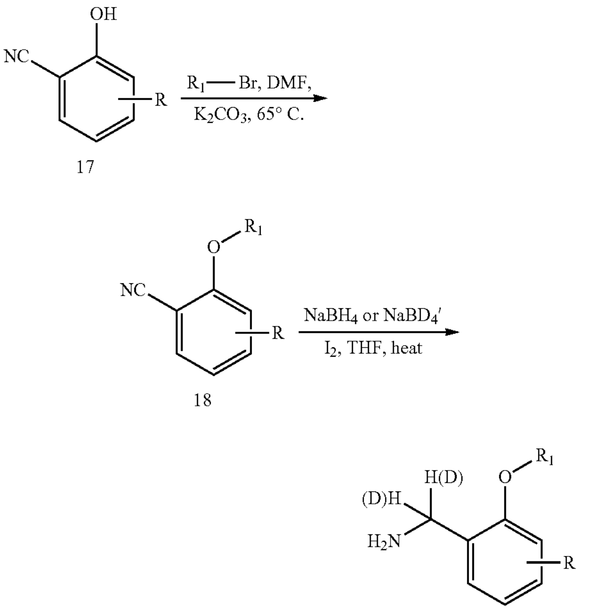

17

18

19

Purification of intermediates and final products was carried out via either normal or reverse phase chromatography. Normal phase chromatography on an ISCO system was carried out using prepacked SiO2 cartridges eluting with either gradients of hexanes and ethyl acetate or dichloromethane and methanol unless otherwise indicated. Reverse phase preparative HPLC or LCMS was carried out using C18 columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analytical LCMS injections were used to determine final purity.

Method A: Column: Waters Acquity UPLC BEH C18, 2.1×50 mm, 1.7 μM particles; Mobile phase A: 5:95 acetonitrile:water with 10 mM ammonium acetate; Mobile phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile phase A: 5:95 acetonitrile:water with 0.1% TFA; Mobile phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm. In a minority of examples analytical HPLC injections were used to determine final purity.

Method A: Column: Sunfire C18, 3.0×150 mm, 3.5 μM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method B: Column: Xbridge Phenyl, 3.0×150 mm, 3.5 μM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method C: Column: XBridge C18, 3.0×150 mm, 3.5 μM particles; Mobile phase A: 5:95 methanol:water with 10 mM ammonium bicarbonate; Mobile phase B: 95:5 methanol: water with 10 mM ammonium bicarbonate; Gradient: 0-100% B over 15 minutes; Flow: 1 mL/min; Detection: UV at 220 and 254 nm.

Method D: Column: XBridge Phenyl, 3.0×150 mm, 3.5 μM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS (ESI) m/z: $[M+H]^+$ BEH C18, 2.11×50 mm, 1.7 m; Mobile phase A: 2:98 water:acetonitrile with 0.1% TFA; Mobile phase B: 98:2 acetonitrile:water with 0.1% TFA; Gradient: 0-100% B over 2 minutes; Flow: 0.8 mL/min; Detection: UV at 220 nm.

NMR spectra were run with water suppression, unless otherwise noted. When water suppression affected characterization of the compounds by NMR, it is noted in the text.

Example 1: N-[(5-{2-acetamidoimidazo[1,2-b]pyridazin-6-yl}-2-methylpyridin-3-yl)methyl]-2-fluoro-5-(trifluoromethoxy)benzamide

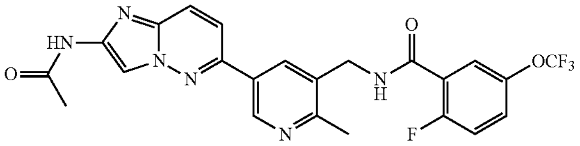 [SMILES: CC(=O)Nc1cn2nc(-c3cnc(C)c(CNC(=O)c4cc(OC(F)(F)F)ccc4F)c3)ccc2n1]

1A: N-((5-Bromo-2-methylpyridin-3-yl)methyl)-2-fluoro-5-(trifluoromethoxy)benzamide: A mixture of (5-bromo-2-methylpyridin-3-yl)methanamine (100 mg, 0.497 mmol), BOP (330 mg, 0.746 mmol) 2-fluoro-5-(trifluoromethoxy)benzoic acid (123 mg, 0.547 mmol) and Hünig's Base (0.434 mL, 2.487 mmol) in DMF (3 mL) was stirred at rt ON. The reaction mixture was diluted to 75 mL with ethyl acetate, then washed 10% aqueous LiCl and brine. The organics were dried over anhydrous sodium sulfate, filtered and concentrated. The crude residue was purified by column chromatography on the Isco system (24 g, 0-100% EtOAc/Hex) to afford N-((5-bromo-2-methylpyridin-3-yl)methyl)-2-fluoro-5-(trifluoromethoxy)benzamide (184 mg, 0.429 mmol, 86% yield).

MS ESI m/z 407.0 (M+H)

1B: N-(6-Chloroimidazo[1,2-b]pyridazin-2-yl)acetamide: To a solution of 6-chloroimidazo[1,2-b]pyridazin-2-amine (840 mg, 4.98 mmol) in DCM (15 mL) was added triethylamine (0.764 mL, 5.48 mmol), DMAP (60.9 mg, 0.498 mmol) and acetic anhydride (0.517 mL, 5.48 mmol) sequentially at rt. The reaction mixture was stirred ON. Hexane (10 mL) was added and the suspension was filtered. Drying of the filter cake afforded N-(6-chloroimidazo[1,2-b]pyridazin-2-yl)acetamide (912 mg, 4.24 mmol, 85% yield) as a light yellow solid. Used as is in subsequent chemistry.

MS ESI m/z 210.9 (M+H)

1: A mixture of N-(6-chloroimidazo[1,2-b]pyridazin-2-yl)acetamide (40 mg, 0.190 mmol), 4,4,4',4',5,5,5',5'-octamethyl-2,2'-bi(1,3,2-dioxaborolane) (77 mg, 0.304 mmol), $PdCl_2(dppf)-CH_2Cl_2$ adduct (15.51 mg, 0.019 mmol) and potassium acetate (55.9 mg, 0.570 mmol) in dioxane (2 mL) was heated to 100° C. for 1 h. After cooling to rt, N-((5-bromo-2-methylpyridin-3-yl)methyl)-2-fluoro-5-(trifluoromethoxy)benzamide (50 mg, 0.123 mmol) and 1,1'-bis(di-tert-butylphosphino)ferrocene palladium dichloride (4.00 mg, 6.14 μmol) in 1,4-dioxane (2 mL) were added and the reaction mixture was degassed by bubbling nitrogen though for 5 min. 2M $K_3PO_4$ (0.184 mL, 0.368 mmol) was added and the mixture stirred 15 min at 100° C. The reaction mixture was concentrated directly onto Celite and purified by column chromatography on the Isco system (12 g, 0-10% MeOH/DCM) to afford N-((5-(2-acetamidoimidazo[1,2-b]pyridazin-6-yl)-2-methylpyridin-3-yl)methyl)-2-fluoro-5-(trifluoromethoxy)benzamide (8.8 mg, 0.017 mmol, 14.05% yield) as a yellow solid. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 min, then a 4-minute hold at 100% B; Flow: 20 mL/min. Fractions containing the desired product were combined and dried via centrifugal evaporation. N-[(5-{2-acetamidoimidazo[1,2-b]pyridazin-6-yl}-2-methylpyridin-3-yl)methyl]-2-fluoro-5-(trifluoromethoxy)benzamide (8.8 mg, 17.5 μmol, 14.2%) was isolated.

MS ESI m/z 502.9 (M+H)

1H NMR (500 MHz, DMSO-d6) δ 10.79 (br s, 1H), 9.02 (br s, 2H), 8.36 (s, 1H), 8.30 (s, 1H), 8.07 (br d, J=8.2 Hz, 1H), 7.77 (d, J=9.4 Hz, 1H), 7.66-7.53 (m, 2H), 7.53-7.42 (m, 1H), 4.61 (br d, J=5.6 Hz, 2H), 2.65 (s, 3H), 2.13 (s, 3H).

Example 2: N-{[3,5-difluoro-2-(oxan-4-yloxy)phenyl] ($D_2$)methyl}-5-[2-(2-hydroxyacetamido)imidazo[1,2-b]pyridazin-6-yl]-2-methoxypyridine-3-carboxamide

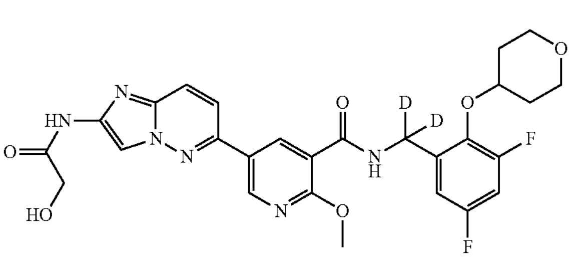 [SMILES: [2H]C([2H])(NC(=O)c1cc(-c2ccc3nc(NC(=O)CO)cn3n2)cnc1OC)c1cc(F)cc(F)c1OC1CCOCC1]

2A: 3,5-Difluoro-2-((tetrahydro-2H-pyran-4-yl)oxy)benzonitrile: To a solution of 3,5-difluoro-2-hydroxybenzonitrile (250 mg, 1.612 mmol) in DMF (5 mL) was added potassium carbonate (1114 mg, 8.06 mmol). After 10 min, 4-bromotetrahydro-2H-pyran (878 mg, 5.32 mmol) was added. The resulting solution was stirred at 65° C. ON. The reaction mixture was diluted with EtOAc (100 mL). Water (15 mL) was added. The aqueous layer was extracted with EtOAc (2×20 mL). The combined organics were washed with 10% lithium chloride solution (2×) and brine (1×). The organics were dried over sodium sulfate, filtered and concentrated to afford 3,5-difluoro-2-((tetrahydro-2H-pyran-4-yl)oxy)benzonitrile (281 mg, 1.116 mmol, 69.2% yield) as a white solid. $^1H$ NMR (400 MHz, DMSO-$d_6$) δ 7.86 (ddd, J=11.9, 8.8, 3.0 Hz, 1H), 7.75 (ddd, J=8.0, 3.0, 1.8 Hz, 1H), 5.42-5.35 (m, 1H), 4.85 (t, J=7.1 Hz, 2H), 4.72-4.66 (m, 2H).

2B: (3,5-Difluoro-2-((tetrahydro-2H-pyran-4-yl)oxy)phenyl)methan-$D_2$-amine: To a mixture of 3,5-difluoro-2-((tetrahydro-2H-pyran-4-yl)oxy)benzonitrile (281 mg, 1.175 mmol) and sodium borodeuteride (113 mg, 2.70 mmol) in THF (10 mL) at 0° C. was added over 45 min, iodine (298 mg, 1.175 mmol) as a solution in 2 mL of THF (2 mL). The reaction mixture was heated at reflux for 2 h. At this time, it was re-cooled to 0° C. and 6N HCl (3 mL) was carefully added. This mixture was heated at reflux for 30 min. After cooling to rt, the mixture was partitioned between EtOAc (100 mL) and 1N NaOH (50 mL). The organic layer was washed with water (20 mL) and brine (20 mL). After drying ($Na_2SO_4$) and filtration, the organic layer was concentrated to afford (3,5-difluoro-2-((tetrahydro-2H-pyran-4-yl)oxy)phenyl)methan-$D_2$-amine (245 mg, 0.899 mmol, 77% yield) as a colorless oil. The crude amine was dissolved in 1N HCl (10 mL) and washed with diethyl ether (2×20 mL). The aqueous layer was basified with 1N NaOH (12 mL) and extracted with EtOAc (2×50 mL). The combined organics were washed with brine and dried over sodium sulfate. Filtration and concentration in vacuo afforded (3,5-difluoro-2-((tetrahydro-2H-pyran-4-yl)oxy)phenyl)methan-d2-amine (245 mg, 0.899 mmol, 77% yield) as a colorless oil.

MS ESI m/z 246.2 (M+H)

2C: Methyl 2-methoxy-5-(4,4,5,5-tetramethyl-1,3,2-dioxaborolan-2-yl)nicotinate: A degassed solution of methyl 5-bromo-2-methoxynicotinate (1.25 g, 5.08 mmol), 4,4,4',4',5,5,5',5'-octamethyl-2,2'-bi(1,3,2-dioxaborolane) (1.806 g, 7.11 mmol), potassium acetate (0.773 g, 7.87 mmol) and $PdCl_2$(dppf)-$CH_2Cl_2$ adduct (0.332 g, 0.406 mmol) in dioxane (15 mL) was heated to 65° C. with vigorous mixing ON. The reaction mixture was concentrated onto Celite and purified by flash chromatography utilizing a 40 g ISCO column, eluting with 0-90% EtOAc in hexanes. Concentration of the pure fractions afforded methyl 2-methoxy-5-(4,4,5,5-tetramethyl-1,3,2-dioxaborolan-2-yl)nicotinate (1.111 g, 3.60 mmol, 70.9% yield).

MS ESI m/z 294.1 (M+H)

2D: 2-(Benzyloxy)-N-(6-chloroimidazo[1,2-b]pyridazin-2-yl)acetamide: A solution of 6-chloroimidazo[1,2-b]pyridazin-2-amine (250 mg, 1,483 mmol), 2-(benzyloxy)acetic acid (259 mg, 1.557 mmol), Hünig's (1.295 mL, 7.41 mmol) and HATU (846 mg, 2.224 mmol) in DMF (6.5 mL) was stirred at rt ON. The reaction mixture was partitioned between EtOAc (125 mL) and water (20 mL). The aqueous layer was extracted with EtOAc. The organics were washed with 10% lithium chloride solution (2×) and brine (1×), dried over sodium sulfate, filtered and concentrated. The crude residue was loaded onto a 24 g ISCO column and purified by flash chromatography, eluting with 0-100% EtOAc in hexanes and then 0-10% MeOH in DCM. Afforded 2-(benzyloxy)-N-(6-chloroimidazo[1,2-b]pyridazin-2-yl)acetamide (428 mg, 1.284 mmol, 87% yield) as a pale yellow solid.

MS ESI m/z 318.3 (M+H)

2E: methyl 5-(2-(2-(benzyloxy)acetamido)imidazo[1,2-b]pyridazin-6-yl)-2-methoxynicotinate: A mixture of 2-(benzyloxy)-N-(6-chloroimidazo[1,2-b]pyridazin-2-yl)acetamide (210 mg, 0.663 mmol), methyl 2-methoxy-5-(4,4,5,5-tetramethyl-1,3,2-dioxaborolan-2-yl)nicotinate (214 mg, 0.729 mmol) and 1,1'-bis(di-tert-butylphosphino)ferrocene palladium dichloride (21.61 mg, 0.033 mmol) in 1,4-dioxane (5 mL) was degassed by bubbling nitrogen though for 5 min. Then 2M $K_3PO_4$ (0.994 mL, 1.989 mmol) was added and the mixture stirred 15 min at 100° C. After 15 min, the reaction is complete and was partitioned between EtOAc (100 mL) water (10 mL). The organics were washed with brine, dried over anhydrous sodium sulfate, filtered and concentrated in vacuo. The crude residue was loaded onto a 12 g ISCO column and purified by column chromatography, eluting with 0-10% MeOH in DCM. Afforded methyl 5-(2-(2-(benzyloxy)acetamido)imidazo[1,2-b]pyridazin-6-yl)-2-methoxynicotinate (159 mg, 0.355 mmol, 53.6% yield) as a yellow solid.

MS ESI m/z 448.1 (M+H)

2F: 5-(2-(2-(benzyloxy)acetamido)imidazo[1,2-b]pyridazin-6-yl)-2-methoxynicotinic acid, lithium salt: To a mixture of methyl 5-(2-(2-(benzyloxy)acetamido)imidazo[1,2-b]pyridazin-6-yl)-2-methoxynicotinate (159 mg, 0.355 mmol) in tetrahydrofuran (5 mL) was added a solution of lithium hydroxide monohydrate (17.89 mg, 0.426 mmol) in water (1.5 mL). The mixture was stirred at rt 3 d. The reaction mixture was concentrated to a solid to afford 5-(2-(2-(benzyloxy)acetamido)imidazo[1,2-b]pyridazin-6-yl)-2-methoxynicotinic acid, lithium salt (150 mg, 0.311 mmol, 88% yield) as a beige solid. Material was used as is in subsequent chemistry MS ESI m/z 434.1 (M+H)

2G: 5-(2-(2-(benzyloxy)acetamido)imidazo[1,2-b]pyridazin-6-yl)-N-((3,5-difluoro-2-((tetrahydro-2H-pyran-4-yl)oxy)phenyl)methyl-d2)-2-methoxynicotinamide: A mixture of 5-(2-(2-(benzyloxy)acetamido)imidazo[1,2-b]pyridazin-6-yl)-2-methoxynicotinic acid, lithium salt (22 mg, 0.051 mmol), BOP (33.7 mg, 0.076 mmol), (3,5-difluoro-2-((tetrahydro-2H-pyran-4-yl)oxy)phenyl)methan-$D_2$-amine, HCl (14.30 mg, 0.051 mmol) and Hünig's Base (0.044 mL, 0.254 mmol) in DMF (2.5 mL) was stirred at rt 3 d. The reaction mixture was diluted to 75 mL with EtOAc and washed with 10% LiCl solution (2×) and brine. The organics were dried over sodium sulfate, filtered and concentrated to afford crude 5-(2-(2-(benzyloxy)acetamido)imidazo[1,2-b]pyridazin-6-yl)-N-((3,5-difluoro-2-((tetrahydro-2H-pyran-4-yl)oxy)phenyl)methyl-$D_2$)-2-methoxynicotinamide (30 mg, 0.041 mmol, 81% yield).

MS ESI m/z 661.5 (M+H)

2: A mixture of crude 5-(2-(2-(benzyloxy)acetamido)imidazo[1,2-b]pyridazin-6-yl)-N-((3,5-difluoro-2-((tetrahydro-2H-pyran-4-yl)oxy)phenyl)methyl-$D_2$)-2-methoxynicotinamide (30 mg, 0.045 mmol) and 10% Pd/C (2.416 mg, 2.270 μmol) in acetic acid (2 mL) was degassed by vacuum, flooded with hydrogen gas and stirred at rt. After stirring ON, the reaction mixture was filtered and concentrated to an oil. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 21-61% B over 20 min, then a 4-minute hold at 100% B; Flow: 20 mL/min. Fractions containing the desired product were combined and dried via centrifugal evaporation. N-{[3,5-difluoro-2-(oxan-4-yloxy)phenyl]($D_2$)methyl}-5-[2-(2-hydroxyacetamido)imidazo[1,2-b]pyridazin-6-yl]-2-methoxypyridine-3-carboxamide (6.8 mg, 11.9 μmol, 26.5%) was isolated.

MS ESI m/z 571.2 (M+H)

$^1H$ NMR (500 MHz, DMSO-d6) δ 10.47-10.27 (m, 1H), 9.02 (d, J=2.4 Hz, 1H), 8.95 (s, 1H), 8.74 (d, J=2.4 Hz, 1H), 8.38 (s, 1H), 8.12 (d, J=9.5 Hz, 1H), 7.89 (d, J=9.5 Hz, 1H), 7.42-7.20 (m, 1H), 7.03 (br d, J=9.3 Hz, 1H), 4.31 (dt, J=9.1, 4.7 Hz, 1H), 4.16-4.10 (m, 2H), 4.09 (s, 3H), 4.00-3.83 (m, 2H), 2.65-2.54 (m, 1H), 1.98 (br d, J=11.3 Hz, 2H), 1.86-1.67 (m, 4H).

Example 3: 2-methoxy-5-[2-(2-methoxyacetamido)imidazo[1,2-b]pyridazin-6-yl]-N-{[2-(trifluoromethoxy)phenyl]methyl}pyridine-3-carboxamide

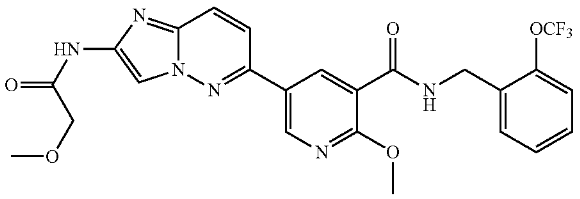 [SMILES: COCC(=O)Nc1cn2nc(-c3cnc(OC)c(C(=O)NCc4ccccc4OC(F)(F)F)c3)ccc2n1]

3A: N-(6-Chloroimidazo[1,2-b]pyridazin-2-yl)-2-methoxyacetamide: A solution of 6-chloroimidazo[1,2-b]pyridazin-2-amine (257 mg, 1.524 mmol), 2-methoxyacetic acid (206 mg, 2.287 mmol), and HATU (869 mg, 2.287 mmol) in DMF (8 mL) and Hünig's base (1.331 mL, 7.62 mmol) was stirred at rt 2 d. The reaction mixture was partitioned between EtOAc (100 mL) 10% LiCl solution (30 mL). The organic layer was washed with 10% LiCl solution and brine. The organics were dried over anhydrous sodium sulfate, filtered and concentrated. The crude residue was loaded onto a 24 g ISCO column and purified by flash chromatography, eluting with 0-100% EtOAc in hexanes followed by 0-10% MeOH in DCM to afford N-(6-chloro-imidazo[1,2-b]pyridazin-2-yl)-2-methoxyacetamide (388 mg, 1.451 mmol, 95% yield) as a yellow solid.

MS ESI m/z 240.9 (M+H)

3B: Methyl 2-methoxy-5-(2-(2-methoxyacetamido)imidazo[1,2-b]pyridazin-6-yl)nicotinate: A mixture of N-(6-chloroimidazo[1,2-b]pyridazin-2-yl)-2-methoxyacetamide (180 mg, 0.748 mmol), methyl 2-methoxy-5-(4,4,5,5-tetramethyl-1,3,2-dioxaborolan-2-yl)nicotinate (252 mg, 0.860 mmol), and 1,1'-bis-di-tert-butylphosphino)ferrocene palladium dichloride (24.37 mg, 0.037 mmol) in 1,4-dioxane (4 mL) was degassed by bubbling nitrogen though for 5 min. 2M $K_3PO_4$ (1.122 mL, 2.244 mmol) was added and the mixture stirred 15 min at 100° C. The reaction mixture was partitioned between EtOAc (100 mL) and water (10 mL). The organic layer was washed with brine and dried over sodium sulfate. After filtering and concentrating in vacuo, the crude residue was loaded onto a 12 g ISCO column, eluting with 0-10% MeOH in DCM to afford methyl 2-methoxy-5-(2-(2-methoxyacetamido)imidazo[1,2-b]pyridazin-6-yl)nicotinate (185 mg, 0.488 mmol, 65.3% yield) as a yellow solid.

MS ESI m/z 372.1 (M+H)

3C: 2-Methoxy-5-(2-(2-methoxyacetamido)imidazo[1,2-b]pyridazin-6-yl)nicotinic acid, lithium salt: To a mixture of methyl 2-methoxy-5-(2-(2-methoxyacetamido)imidazo[1,2-b]pyridazin-6-yl)nicotinate (176 mg, 0.474 mmol) in tetrahydrofuran (4 mL) was added a solution of lithium hydroxide monohydrate (23.87 mg, 0.569 mmol) in water (1 mL). The reaction mixture was stirred at rt 2 h. The reaction mixture was concentrated to a solid and used as is in the next step. 2-Methoxy-5-(2-(2-methoxyacetamido)imidazo[1,2-b]pyridazin-6-yl)nicotinic acid, lithium salt (170 mg, 0.428 mmol, 90% yield) was isolated as a yellow solid.

MS ESI m/z 358.1 (M+H)

3: A mixture of 2-methoxy-5-(2-(2-methoxyacetamido)imidazo[1,2-b]pyridazin-6-yl)nicotinic acid, lithium salt (20 mg, 0.056 mmol), BOP (37.1 mg, 0.084 mmol) (2-(trifluoromethoxy)phenyl)methanamine (10.70 mg, 0.056 mmol) and Hünig's base (0.049 mL, 0.280 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-100% B over 19 min, then a 5-minute hold at 100% B; Flow: 20 mL/min. Fractions containing the desired product were combined and dried via centrifugal evaporation. 2-methoxy-5-[2-(2-methoxyacetamido)imidazo[1,2-b]pyridazin-6-yl]-N-{[2-(trifluoromethoxy)phenyl]methyl}pyridine-3-carboxamide (15.1 mg, 28.5 μmol, 50.8%) was isolated.

MS ESI m/z 531.3 (M+H)

1H NMR (500 MHz, DMSO-d6) δ 10.72 (s, 1H), 9.07-8.91 (m, 2H), 8.76 (d, J=2.4 Hz, 1H), 8.37 (s, 1H), 8.12 (d, J=9.4 Hz, 1H), 7.88 (d, J=9.4 Hz, 1H), 7.59-7.48 (m, 1H), 7.47-7.36 (m, 3H), 4.62 (d, J=6.0 Hz, 2H), 4.15-4.10 (m, 2H), 4.06 (s, 3H). Methoxy $CH_3$ protons from the methoxyacetamide lost in water suppression.

Example 4: N-{[2-(cyclopropylmethoxy)-3,5-difluorophenyl]methyl}-2-methoxy-5-{2-propanamidoimidazo[1,2-b]pyridazin-6-yl}pyridine-3-carboxamide

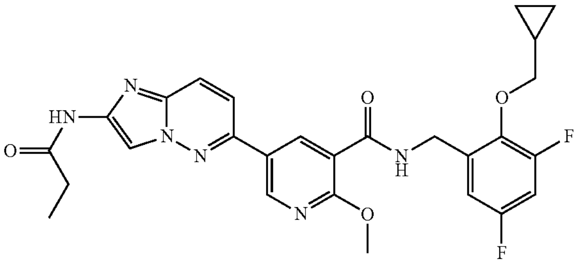 [SMILES: CCC(=O)Nc1cn2nc(-c3cnc(OC)c(C(=O)NCc4cc(F)cc(F)c4OCC4CC4)c3)ccc2n1]

4A: N-(6-chloroimidazo[1,2-b]pyridazin-2-yl)propionamide: A solution of 6-chloroimidazo[1,2-b]pyridazin-2-amine (250 mg, 1.483 mmol), propionic acid (121 mg, 1.631 mmol), HATU (846 mg, 2.224 mmol) and Hünig's base (1.295 mL, 7.41 mmol) in DMF (8 mL) was stirred at rt ON.

After stirring ON, the reaction mixture was partitioned between EtOAc (125 mL) and water (20 mL). The organic layer was washed with 10% lithium chloride solution (2×) and brine. The organics were dried over sodium sulfate, filtered and concentrated. The crude residue was loaded onto a 24 g ISCO column and purified by flash chromatography, eluting with 0-100% EtOAc in hexanes followed by 0-10% MeOH in DCM. N-(6-Chloroimidazo[1,2-b]pyridazin-2-yl)propionamide (310 mg, 1.242 mmol, 84% yield) was isolated as a pale yellow solid.

MS ESI m/z 224.9 (M+H)

4B: Methyl 2-methoxy-5-(2-propionamidoimidazo[1,2-b]pyridazin-6-yl)nicotinate: A mixture of N-(6-chloroimidazo[1,2-b]pyridazin-2-yl)propionamide (155 mg, 0.690 mmol), methyl 2-methoxy-5-(4,4,5,5-tetramethyl-1,3,2-dioxaborolan-2-yl)nicotinate (233 mg, 0.793 mmol) and 1,1'-bis(di-tert-butylphosphino)ferrocene palladium dichloride (22.48 mg, 0.034 mmol) in 1,4-dioxane (4 mL) was degassed by bubbling nitrogen though for 5 min. 2M $K_3PO_4$ (1.035 mL, 2.070 mmol) was added and the mixture stirred 30 min at 100° C. The reaction mixture was partitioned between EtOAc (100 mL) and water (10 mL). The organic layer was washed with brine and dried over sodium sulfate. The mixture was filtered and concentrated. The crude residue was loaded onto a 12 g ISCO column, eluting with 0-10% MeOH in DCM to afford methyl 2-methoxy-5-(2-propionamidoimidazo[1,2-b]pyridazin-6-yl)nicotinate (225 mg, 0.570 mmol, 83% yield) as a yellow solid.

MS ESI m/z 356.1 (M+H)

4C: 2-Methoxy-5-(2-propionamidoimidazo[1,2-b]pyridazin-6-yl)nicotinic acid, lithium salt: To a mixture of methyl 2-methoxy-5-(2-propionamidoimidazo[1,2-b]pyridazin-6-yl)nicotinate (225 mg, 0.633 mmol) in tetrahydrofuran (5 mL) was added a solution of lithium hydroxide monohydrate (31.9 mg, 0.760 mmol) in water (1 mL). The reaction mixture was stirred 2 h at rt. The reaction mixture was concentrated to a solid and used as is in the next step. 2-Methoxy-5-(2-propionamidoimidazo[1,2-b]pyridazin-6-yl)nicotinic acid, lithium salt (199 mg, 0.554 mmol, 87% yield) was isolated as a yellow solid.

MS ESI m/z 342.1 (M+H)

4: A mixture of 2-methoxy-5-(2-propionamidoimidazo[1,2-b]pyridazin-6-yl)nicotinic acid, lithium salt (15 mg, 0.044 mmol), BOP (29.2 mg, 0.066 mmol), (2-(cyclopropylmethoxy)-3,5-difluorophenyl)methanamine (9.37 mg, 0.044 mmol) and Hünig's base (0.038 mL, 0.220 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-74% B over 25 min, then a 5-minute hold at 100% B; Flow: 20 mL/min. Fractions containing the desired product were combined and dried via centrifugal evaporation. N-{[2-(Cyclopropylmethoxy)-3,5-difluorophenyl]methyl}-2-methoxy-5-{2-propanamidoimidazo[1,2-b]pyridazin-6-yl}pyridine-3-carboxamide (14.8 mg, 27.6 μmol, 62.7%) was isolated.

MS ESI m/z 537 (M+H)

1H NMR (500 MHz, DMSO-d6) δ 10.84 (s, 1H), 9.02-8.88 (m, 2H), 8.71 (d, J=2.1 Hz, 1H), 8.31 (s, 1H), 8.05 (d, J=9.5 Hz, 1H), 7.82 (d, J=9.5 Hz, 1H), 7.19 (br t, J=8.9 Hz, 1H), 6.99 (br d, J=8.2 Hz, 1H), 4.61 (br d, J=5.8 Hz, 2H), 4.07 (s, 3H), 3.88 (d, J=7.0 Hz, 2H), 2.47-2.35 (m, 2H), 1.25 (br s, 1H), 1.09 (t, J=7.5 Hz, 3H), 0.57 (br d, J=6.7 Hz, 2H), 0.30 (br d, J=4.3 Hz, 2H).

Example 5: N-{[2-(cyclopropylmethoxy)-3,5-difluorophenyl]methyl}-2-methoxy-5-[2-(2-methylpropanamido)imidazo[1,2-b]pyridazin-6-yl]pyridine-3-carboxamide

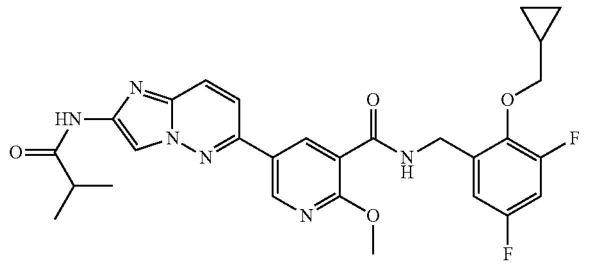 [SMILES: COc1ncc(-c2ccc3nc(NC(=O)C(C)C)cn3n2)cc1C(=O)NCc1cc(F)cc(F)c1OCC1CC1]

5A: N-(6-Chloroimidazo[1,2-b]pyridazin-2-yl)isobutyramide: A solution of 6-chloroimidazo[1,2-b]pyridazin-2-amine (250 mg, 1.483 mmol), isobutyric acid (144 mg, 1.631 mmol), HATU (846 mg, 2.224 mmol) and Hünig's base (1.295 mL, 7.41 mmol) in DMF (8 mL) was stirred at rt ON. After stirring ON, the mixture was partitioned between EtOAc (125 mL) and water (20 mL). The organics were washed with 10% lithium chloride solution (2×) and brine. The organics were dried over sodium sulfate, filtered and concentrated. The crude residue was loaded onto a 24 g ISCO column and purified by flash chromatography, eluting with 0-100% EtOAc in hexanes followed by 0-10% MeOH in DCM. N-(6-Chloroimidazo[1,2-b]pyridazin-2-yl)isobutyramide (312 mg, 1.242 mmol, 84% yield) was isolated as a pale yellow solid.

MS ESI m/z 239.1 (M+H)

5B: Methyl 5-(2-isobutyramidoimidazo[1,2-b]pyridazin-6-yl)-2-methoxynicotinate: A mixture of N-(6-chloroimidazo[1,2-b]pyridazin-2-yl)isobutyramide (160 mg, 0.670 mmol), methyl 2-methoxy-5-(4,4,5,5-tetramethyl-1,3,2-dioxaborolan-2-yl)nicotinate (226 mg, 0.771 mmol) and 1,1'-bis(di-tert-butylphosphino)ferrocene palladium dichloride (21.85 mg, 0.034 mmol) in 1,4-dioxane (4 mL) was degassed by bubbling nitrogen through for 5 min. 2M $K_3PO_4$ (1.006 mL, 2.011 mmol) was added and the mixture stirred 30 min at 100° C. The reaction mixture was partitioned between EtOAc (100 mL) and water (10 mL). The organics were washed with brine, dried over sodium sulfate, filtered and concentrated in vacuo. The crude residue was loaded onto a 12 g ISCO column, eluting with 0-100% EtOAc and then 0-10% MeOH in DCM to afford methyl 5-(2-isobutyramidoimidazo[1,2-b]pyridazin-6-yl)-2-methoxynicotinate (94 mg, 0.252 mmol, 37.6% yield).

MS ESI m/z 370.1 (M+H)

5C: 5-(2-Isobutyramidoimidazo[1,2-b]pyridazin-6-yl)-2-methoxynicotinic acid, lithium salt: To a mixture of methyl 5-(2-isobutyramidoimidazo[1,2-b]pyridazin-6-yl)-2-methoxynicotinate (94 mg, 0.254 mmol) in tetrahydrofuran (2 mL) was added a solution of lithium hydroxide monohydrate (12.81 mg, 0.305 mmol) in water (1 mL). The reaction mixture was stirred 4 h at rt and concentrated to a solid which was used as is in the next step. Afforded 5-(2-isobutyramidoimidazo[1,2-b]pyridazin-6-yl)-2-methoxynicotinic acid, lithium salt (90 mg, 0.228 mmol, 90% yield) as a yellow solid.

MS ESI m/z 356.1 (M+H)

5: A mixture of 5-(2-isobutyramidoimidazo[1,2-b]pyridazin-6-yl)-2-methoxynicotinic acid, lithium salt (15 mg, 0.042 mmol), BOP (28.0 mg, 0.063 mmol), (2-(cyclopropylmethoxy)-3,5-difluorophenyl)methanamine (9.00 mg, 0.042 mmol) and Hünig's base (0.037 mL, 0.211 mmol) in DMF (1.0 mL) was stirred at rt 3 d. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-74% B over 25 min, then a 2-minute hold at 100% B; Flow: 20 mL/min. Fractions containing the desired product were combined and dried via centrifugal evaporation. N-{[2-(cyclopropylmethoxy)-3,5-difluorophenyl]methyl}-2-methoxy-5-[2-(2-methylpropanamido)imidazo[1,2-b]pyridazin-6-yl]pyridine-3-carboxamide (14.2 mg, 25.8 μmol, 61.4%) was isolated.

MS ESI m/z 551 (M+H)

1H NMR (500 MHz, DMSO-d6) δ 10.84 (s, 1H), 9.01-8.90 (m, 2H), 8.71 (d, J=2.1 Hz, 1H), 8.32 (s, 1H), 8.06 (d, J=9.2 Hz, 1H), 7.83 (d, J=9.5 Hz, 1H), 7.19 (t, J=8.9 Hz, 1H), 7.00 (br d, J=8.9 Hz, 1H), 4.61 (br d, J=5.8 Hz, 2H), 4.07 (s, 3H), 3.88 (d, J=7.0 Hz, 2H), 2.84-2.63 (m, 1H), 1.30-1.23 (m, 1H), 1.11 (d, J=6.7 Hz, 6H), 0.57 (br d, J=6.7 Hz, 2H), 0.30 (br d, J=4.6 Hz, 2H).

Example 6: 5-{2-acetamido-3-methylimidazo[1,2-b]pyridazin-6-yl}-N-{[2-fluoro-5-(trifluoromethoxy)phenyl]methyl}-2-methoxypyridine-3-carboxamide

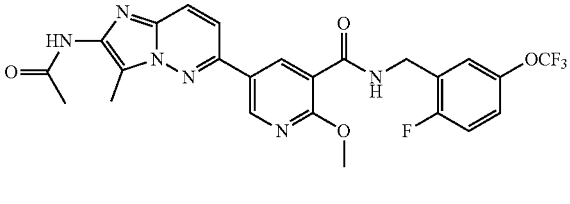 [SMILES: COc1ncc(-c2ccc3nc(NC(C)=O)c(C)n3n2)cc1C(=O)NCc1cc(OC(F)(F)F)ccc1F]

6A: N-(6-Chloropyridazin-3-yl)-4-methylbenzenesulfonamide: A mixture of 6-chloropyridazin-3-amine (2 g, 15.44 mmol) and toluenesulfonyl chloride (4.27 g, 22.39 mmol) in pyridine (30 mL) was stirred at rt for 3 h. The reaction mixture was partitioned between EtOAc (200 mL) and water (200 mL). The organic layer was washed with 1N HCl (3×150 mL) and brine (150 mL). The organic layer was dried over anhydrous sodium sulfate. Filtration and concentration afforded a yellow solid that was chromatographed on a 120 g ISCO silica gel cartridge, eluting with a 0-70% EtOAc/Hex gradient. The pure fractions were concentrated to afford N-(6-chloropyridazin-3-yl)-4-methylbenzenesulfonamide (2.71 g, 9.55 mmol, 61.9% yield) as a light yellow solid.

MS ESI m/z 284.1/286.1 (M+H)

$^1$H NMR (400 MHz, CHLOROFORM-d) δ 7.80 (d, J=8.4 Hz, 2H), 7.45 (br d, J=9.7 Hz, 1H), 7.38-7.32 (m, 1H), 7.29 (d, J=8.1 Hz, 2H), 2.41 (s, 3H).

6B: (E)-2-(3-Chloro-6-(tosylimino)pyridazin-1 (6H)-yl) propanamide: A mixture of N-(6-chloropyridazin-3-yl)-4-methylbenzenesulfonamide (2.65 g, 9.34 mmol), 2-bromopropanamide (1.561 g, 10.27 mmol), and Hünig's base (1.957 mL, 11.21 mmol) in DMF (7 mL) was heated to 60° C. for 14 h. After cooling to rt, water (100 mL) was added and the suspension formed was stirred at rt for 30 min. The suspension was filtered and rinsed with ether. Drying afforded (E)-2-(3-chloro-6-(tosylimino)pyridazin-1(6H)-yl) propanamide (2.9 g, 8.17 mmol, 88% yield) as a tan solid.

MS ESI m/z 355.1/357.1 (M+H).

6C: N-(6-Chloro-3-methylimidazo[1,2-b]pyridazin-2-yl)-2,2,2-trifluoroacetamide: To a suspension of (E)-2-(3-chloro-6-(tosylimino)pyridazin-1(6H)-yl)propanamide (2.88 g, 8.12 mmol) in DCM at rt was added trifluoroacetic anhydride (5.73 mL, 40.6 mmol). The resulting solution was stirred for 2 h at rt. The reaction volume was concentrated by ~⅔ and the remainder was partitioned between EtOAc (125 mL) and 1.5 M dibasic potassium phosphate solution (125 mL). The organic layer was washed with brine (100 mL), dried over anhydrous sodium sulfate and concentrated to afford a solid that was chromatographed on a 80 gm ISCO silica gel cartridge, eluting with a 0-10% MeOH/$CH_{2C}$12 gradient. The pure fractions were concentrated to afford N-(6-chloro-3-methylimidazo[1,2-b]pyridazin-2-yl)-2,2,2-trifluoroacetamide (2.23 g, 8.00 mmol, 99% yield) as a light yellow solid.

MS ESI m/z 279.0/281.0 (M+H)

$^1$H NMR (400 MHz, DMSO-$d_6$) δ 11.84 (s, 1H), 8.18 (d, J=9.4 Hz, 1H), 7.40 (d, J=9.4 Hz, 1H), 2.39 (s, 3H).

6D: 5-(2-Amino-3-methylimidazo[1,2-b]pyridazin-6-yl)-2-methoxynicotinic acid, 1.25 lithium salt: To the stirred crude mixture N-(6-chloro-3-methylimidazo[1,2-b]pyridazin-2-yl)-2,2,2-trifluoroacetamide (400 mg, 1.436 mmol) was added methyl 2-methoxy-5-(4,4,5,5-tetramethyl-1,3,2-dioxaborolan-2-yl)nicotinate (505 mg, 1.723 mmol) and $PdCl_2$(dppf)-$CH_2Cl_2$ adduct (58.6 mg, 0.072 mmol) and the mixture was degassed by bubbling nitrogen though the mixture for 5 min. Tribasic potassium phosphate solution (2 M, 2.153 mL, 4.31 mmol) was quickly added and the reaction mixture heated at 100° C. for 8 h. Additional $PdCl_2$(dppf)-$CH_2Cl_2$ adduct (58.6 mg, 0.072 mmol) and tribasic potassium phosphate solution (2.153 mL, 4.31 mmol) were added and heating was continued for 4 h. The reaction mixture was diluted with water and the dioxane was removed in vacuo. The pH was adjusted to ~4 with 1N HCl. The resulting suspension was filtered and the solid was dried to afford a mixture of ester and acid (400 mg) as a green solid. To a mixture of methyl 5-(2-amino-3-methylimidazo[1,2-b]pyridazin-6-yl)-2-methoxynicotinate and 5-(2-amino-3-methylimidazo[1,2-b]pyridazin-6-yl)-2-methoxynicotinic acid (400 mg) in THF (12 mL) at rt was added lithium hydroxide monohydrate (67.0 mg, 1.596 mmol) as a solution in water (3 mL). The reaction mixture was allowed to stir at rt ON. Concentration and drying afforded 5-(2-amino-3-methylimidazo[1,2-b]pyridazin-6-yl)-2-methoxynicotinic acid, 1.25 lithium salt (393 mg, 1.276 mmol, 100% yield) as a yellow solid. Used as is in subsequent chemistry.

MS ESI m/z 300.2 (M+H)

6E: 5-(2-Amino-3-methylimidazo[1,2-b]pyridazin-6-yl)-N-(2-fluoro-5-(trifluoromethoxy)benzyl)-2-methoxynicotinamide: A mixture of 5-(2-amino-3-methylimidazo[1,2-b]pyridazin-6-yl)-2-methoxynicotinic acid, 1.3 lithium salt (45 mg, 0.146 mmol), (2-fluoro-5-(trifluoromethoxy)phenyl)methanamine (45.8 mg, 0.219 mmol), BOP (71.0 mg, 0.161 mmol) and $Et_3N$ (61.0 μl, 0.438 mmol) in DMF was agitated at rt for 3 d. The reaction mixture was partitioned between EtOAc (30 mL) and water (30 mL). The organic layer was washed with 10% LiCl solution (2×30 mL) and brine (30 mL). After drying ($Na_2SO_4$) and filtration the organic layer was concentrated to afford a yellow residue that was chromatographed on a 4 g ISCO silica gel cartridge, eluting with a 0-10% MeOH/$CH_2Cl_2$ gradient. The pure fractions were concentrated to afford 5-(2-amino-3-methylimidazo[1,2-b]pyridazin-6-yl)-N-(2-fluoro-5-(trifluoromethoxy)benzyl)-2-methoxynicotinamide (31 mg, 0.063 mmol, 43.3% yield) as a yellow solid.

MS ESI m/z 491.2 (M+H).

6: A solution of $Ac_2O$ (0.017 mL, 0.184 mmol) and 5-(2-amino-3-methylimidazo[1,2-b]pyridazin-6-yl)-N-(2-fluoro-5-(trifluoromethoxy)benzyl)-2-methoxynicotinamide (18 mg, 0.037 mmol) in pyridine (0.5 mL) was stirred at rt ON. The reaction mixture was concentrated and the residue was dissolved in DMSO. The crude material was purified via preparative LC/MS with the following conditions: Column: XBridge C18, 19×200 mm, 5-km particles; Mobile Phase A: 5:95 acetonitrile: water with 0.1% trifluoroacetic acid; Mobile Phase B: 95:5 acetonitrile: water with 0.1% trifluoroacetic acid; Gradient: 20-60% B over 25 min, then a 4-minute hold at 100% B; Flow: 20 mL/min. Fractions containing the desired product were combined and dried via centrifugal evaporation. 5-{2-acetamido-3-methylimidazo[1,2-b]pyridazin-6-yl}-N-{[2-fluoro-5-(trifluoromethoxy)phenyl]methyl}-2-methoxypyridine-3-carboxamide (6.3 mg, 9.7 μmol, 26.3%) was isolated.

MS ESI m/z 533.1 (M+H)

1H NMR (500 MHz, DMSO-d6) δ 10.18-9.87 (m, 1H), 9.00 (s, 1H), 8.96-8.87 (m, 1H), 8.71 (d, J=2.1 Hz, 1H), 8.12-7.96 (m, 1H), 7.76 (br d, J=8.9 Hz, 1H), 7.42 (br d, J=5.4 Hz, 1H), 7.36-7.27 (m, 2H), 4.60 (d, J=5.9 Hz, 2H), 4.08 (s, 3H), 2.47 (s, 3H), 2.09 (br s, 3H).

Example 7: 5-[2-(2-cyanoacetamido)imidazo[1,2-b]pyridazin-6-yl]-N-{[2-(cyclopropylmethoxy)-3,5-difluorophenyl]methyl}-2-methoxypyridine-3-carboxamide

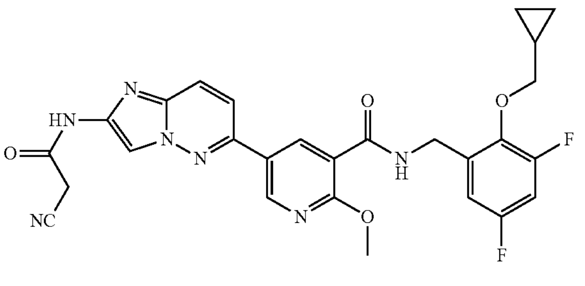 [SMILES: COc1ncc(-c2ccc3nc(NC(=O)CC#N)cn3n2)cc1C(=O)NCc1cc(F)cc(F)c1OCC1CC1]

7A: N-(6-Chloroimidazo[1,2-b]pyridazin-2-yl)-2-cyanoacetamide: A solution of 6-chloroimidazo[1,2-b]pyridazin-2-amine (250 mg, 1.483 mmol), 2-cyanoacetic acid (126 mg, 1.483 mmol), Hünig's base (1.295 mL, 7.41 mmol) and HATU (846 mg, 2.224 mmol) in DMF (8 mL) and was stirred at rt ON. The reaction mixture was diluted to 100 mL with EtOAc. The organics were washed with 10% lithium chloride solution (2×) and brine, dried over sodium sulfate, filtered and concentrated. The crude residue was loaded onto a 24 g ISCO column and purified by flash chromatography, eluting with 0-10% MeOH in DCM. N-(6-Chloroimidazo[1,2-b]pyridazin-2-yl)-2-cyanoacetamide (187 mg, 0.778 mmol, 52.4% yield) was isolated as an off-white solid.

MS ESI m/z 235.9 (M+H)

7B: Methyl 5-(2-(2-cyanoacetamido)imidazo[1,2-b]pyridazin-6-yl)-2-methoxynicotinate: A mixture of N-(6-chloroimidazo[1,2-b]pyridazin-2-yl)-2-cyanoacetamide (185 mg, 0.785 mmol), methyl 2-methoxy-5-(4,4,5,5-tetramethyl-1,3,2-dioxaborolan-2-yl)nicotinate (230 mg, 0.785 mmol) and 1,1'-bis(di-tert-butylphosphino)ferrocene palladium dichloride (20.47 mg, 0.031 mmol) in 1,4-dioxane (5 mL) was degassed by bubbling nitrogen though for 5 min. 2M $K_3PO_4$ (1.178 mL, 2.355 mmol) was added and the mixture stirred 75 min at 100° C. The reaction mixture was concentrated onto Celite and purified by flash chromatography using a 24 g ISCO column, eluting with 0-100% EtOAc followed by 0-10% MeOH in DCM to afford methyl 5-(2-(2-cyanoacetamido)imidazo[1,2-b]pyridazin-6-yl)-2-methoxynicotinate (52 mg, 0.139 mmol, 17.72% yield).

MS ESI m/z 367.2 (M+H)

7C: 5-(2-(2-Cyanoacetamido)imidazo[1,2-b]pyridazin-6-yl)-2-methoxynicotinic acid, lithium salt: To a mixture of methyl 5-(2-(2-cyanoacetamido)imidazo[1,2-b]pyridazin-6-yl)-2-methoxynicotinate (52 mg, 0.142 mmol) in tetrahydrofuran (2 mL) was added a solution of lithium hydroxide monohydrate (7.15 mg, 0.170 mmol) in water (1 mL) and the resulting mixture was stirred ON at rt. The reaction mixture was concentrated to a solid to afford 5-(2-(2-cyanoacetamido)imidazo[1,2-b]pyridazin-6-yl)-2-methoxynicotinic acid, lithium salt (49 mg, 0.128 mmol, 90% yield) as a beige solid. Material was used as is in subsequent chemistry.

MS ESI m/z 353.1 (M+H)

7: A mixture of 5-(2-(2-cyanoacetamido)imidazo[1,2-b]pyridazin-6-yl)-2-methoxynicotinic acid, lithium salt (16 mg, 0.045 mmol), BOP (30.1 mg, 0.068 mmol), (2-(cyclopropylmethoxy)-3,5-difluorophenyl)methanamine (9.68 mg, 0.045 mmol) and Hünig's base (0.040 mL, 0.227 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 min, then a 4-minute hold at 100% B; Flow: 20 mL/min. Fractions containing the desired product were combined and dried via centrifugal evaporation. 5-[2-(2-Cyanoacetamido)imidazo[1,2-b]pyridazin-6-yl]-N-{[2-(cyclopropylmethoxy)-3,5-difluorophenyl]methyl}-2-methoxypyridine-3-carboxamide (1.9 mg, 3.5 μmol, 7.7%) was isolated.

MS ESI m/z 548.1 (M+H)

$^1$H NMR (500 MHz, DMSO-$d_6$) δ 9.03-8.89 (m, 2H), 8.71 (br s, 1H), 8.31 (s, 1H), 8.08 (br d, J=9.5 Hz, 1H), 7.85 (br d, J=9.5 Hz, 1H), 7.18 (br t, J=8.5 Hz, 2H), 6.98 (br d, J=8.9 Hz, 2H), 4.60 (br d, J=5.5 Hz, 2H), 4.07 (s, 3H), 3.97 (s, 1H), 3.87 (br d, J=7.0 Hz, 2H), 1.24 (br s, 1H), 0.56 (br d, J=7.0 Hz, 2H), 0.29 (br d, J=4.0 Hz, 2H).

Example 8: 5-[2-(2-cyano-2,2-dimethylacetamido)imidazo[1,2-b]pyridazin-6-yl]-N-({[2-(chloropyl-methoxy)-3,5-difluorophenyl]methyl}-2-methoxy-pyridine-3-carboxamide

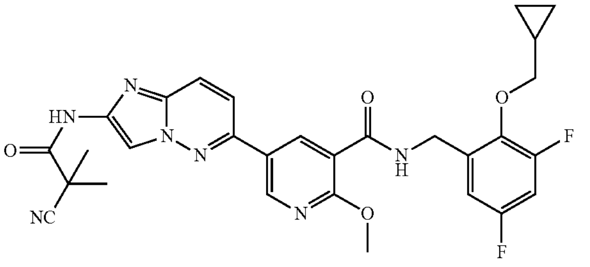 [SMILES: COc1ncc(-c2ccc3nc(NC(=O)C(C)(C)C#N)cn3n2)cc1C(=O)NCc1cc(F)cc(F)c1OCC1CC1]

8A: N-(6-Chloroimidazo[1,2-b]pyridazin-2-yl)-2-cyano-2-methylpropanamide: A solution of 6-chloroimidazo[1,2-b]pyridazin-2-amine (257 mg, 1.524 mmol), 2-cyano-2-methylpropanoic acid (259 mg, 2.287 mmol), HATU (869 mg, 2.287 mmol) and Hünig's base (1.331 mL, 7.62 mmol) in DMF (8 mL) was stirred at rt ON. The reaction mixture was diluted to a total volume of 100 mL with EtOAc. The organic layer was washed with 10% lithium chloride solution (2×) and brine, dried over sodium sulfate, filtered and concentrated. The crude residue was loaded onto a 24 g ISCO column and purified by flash chromatography, eluting with 0-10% MeOH in DCM. Afforded N-(6-chloroimidazo[1,2-b]pyridazin-2-yl)-2-cyano-2-methylpropanamide (388 mg, 1.398 mmol, 92% yield) as a yellow solid.

MS ESI m/z 264.1 (M+H)

8B: Methyl 5-(2-(2-cyano-2-methylpropanamido)imidazo[1,2-b]pyridazin-6-yl)-2-methoxynicotinate: A mixture of N-(6-chloroimidazo[1,2-b]pyridazin-2-yl)-2-cyano-2-methylpropanamide (190 mg, 0.721 mmol), methyl 2-methoxy-5-(4,4,5,5-tetramethyl-1,3,2-dioxaborolan-2-yl)nicotinate (211 mg, 0.721 mmol), and 1,1'-bis(di-tert-butylphosphino)ferrocene palladium dichloride (23.48 mg, 0.036 mmol) in 1,4-dioxane (5 mL) was degassed by bubbling nitrogen through for 5 min. 2M $K_3PO_4$ (1.081 mL, 2.162 mmol) was added and the mixture stirred 20 min at 100° C. The reaction mixture was partitioned between EtOAc (100 mL) and water (10 mL). The organic layer was washed with brine, dried over sodium sulfate, filtered and concentrated in vacuo. The crude residue was loaded onto a 12 g ISCO column, eluting with 0-100% EtOAc and then 0-10% MeOH in DCM to afford methyl 5-(2-(2-cyano-2-methylpropanamido)imidazo[1,2-b]pyridazin-6-yl)-2-methoxynicotinate (158 mg, 0.393 mmol, 54.5% yield).

MS ESI m/z 395.2 (M+H)

8C: 5-(2-(2-cyano-2-methylpropanamido)imidazo[1,2-b]pyridazin-6-yl)-2-methoxynicotinic acid, lithium salt: To a mixture of methyl 5-(2-(2-cyano-2-methylpropanamido)imidazo[1,2-b]pyridazin-6-yl)-2-methoxynicotinate (158 mg, 0.401 mmol) in tetrahydrofuran (3 mL) was added a solution of lithium hydroxide monohydrate (20.17 mg, 0.481 mmol) in water (1.5 mL), and the resulting mixture was stirred ON at rt. The reaction mixture was concentrated providing 5-(2-(2-cyano-2-methylpropanamido)imidazo[1,2-b]pyridazin-6-yl)-2-methoxynicotinic acid, lithium salt (144 mg, 0.360 mmol, 90% yield) as a beige solid. Used as is in the next step.

MS ESI m/z 381.2 (M+H)

8: A mixture of 5-(2-(2-cyano-2-methylpropanamido)imidazo[1,2-b]pyridazin-6-yl)-2-methoxynicotinic acid, lithium salt (20 mg, 0.053 mmol), BOP (34.9 mg, 0.079 mmol), (2-(cyclopropylmethoxy)-3,5-difluorophenyl)methanamine (11.21 mg, 0.053 mmol) and Hünig's base (0.046 mL, 0.263 mmol) in DMF (1.0 mL) was stirred at rt over the weekend. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 25 min, then a 5-minute hold at 100% B; Flow: 20 mL/min. Fractions containing the desired product were combined and dried via centrifugal evaporation. 5-[2-(2-Cyano-2,2-dimethylacetamido)imidazo[1,2-b]pyridazin-6-yl]-N-{[2-(cyclopropylmethoxy)-3,5-difluorophenyl]methyl}-2-methoxypyridine-3-carboxamide (11.9 mg, 20.7 μmol, 39%) was isolated.

MS ESI m/z 576 (M+H)

$^1$H NMR (500 MHz, DMSO-d6) δ 11.32-11.27 (m, 1H), 9.00-8.97 (m, 1H), 8.94 (t, J=6.6 Hz, 1H), 8.72 (d, J=2.4 Hz, 1H), 8.35 (s, 1H), 8.11 (d, J=9.5 Hz, 1H), 7.87 (d, J=9.8 Hz, 1H), 7.19 (br t, J=8.9 Hz, 1H), 6.99 (br d, J=8.9 Hz, 1H), 4.61 (br d, J=5.8 Hz, 2H), 4.07 (s, 3H), 3.88 (d, J=7.3 Hz, 2H), 1.69 (s, 6H), 1.29-1.16 (m, 1H), 0.57 (br d, J=6.7 Hz, 2H), 0.30 (br d, J=4.6 Hz, 2H).

Example 9: 5-{2-acetamidoimidazo[1,2-b]pyridazin-6-yl}-N-[(1R)-1-[2-fluoro-5-(trifluoromethoxy)phenyl]ethyl]-2-methylpyridine-3-carboxamide

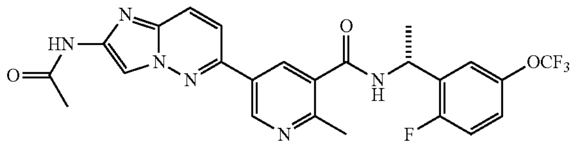

9A: ethyl 5-(2-acetamidoimidazo[1,2-b]pyridazin-6-yl)-2-methylnicotinate: A mixture of N-(6-chloroimidazo[1,2-b]pyridazin-2-yl)acetamide (310 mg, 1.472 mmol), 4,4,4',4',5,5,5',5'-octamethyl-2,2'-bi(1,3,2-dioxaborolane) (598 mg, 2.355 mmol), $PdCl_2(dppf)-CH_2Cl_2$ adduct (120 mg, 0.147 mmol) and potassium acetate (433 mg, 4.42 mmol) in 1,4-dioxane (8 mL) was heated to 100° C. for 2 h. To this crude mixture was added ethyl 5-bromo-2-methylnicotinate (320 mg, 1.311 mmol), and 1,1'-bis(di-tert-butylphosphino)ferrocene palladium dichloride (42.7 mg, 0.066 mmol) in 1,4-dioxane (9 mL). The reaction mixture was degassed by bubbling nitrogen through for 5 min. 2M $K_3PO_4$ (1.967 mL, 3.93 mmol) was added and the mixture stirred 15 min at 100° C. After 15 min, the reaction is cooled to rt and partitioned between EtOAc (100 mL) and water (10 mL). The organic layer was washed with brine, dried over sodium sulfate, filtered and concentrated. The crude residue was loaded onto a 24 g ISCO cartridge and purified using an ISCO system, eluting with 0-10% MeOH in DCM. Afforded ethyl 5-(2-acetamidoimidazo[1,2-b]pyridazin-6-yl)-2-methylnicotinate (363 mg, 1.016 mmol, 78% yield) as a yellow solid.

9B: 5-(2-acetamidoimidazo[1,2-b]pyridazin-6-yl)-2-methylnicotinic acid, lithium salt: To a mixture of ethyl 5-(2-acetamidoimidazo[1,2-b]pyridazin-6-yl)-2-methylnicotinate (363 mg, 1.070 mmol) in tetrahydrofuran (7 mL) was added a solution of lithium hydroxide monohydrate (53.9 mg, 1.284 mmol) in 1.5 mL water, and the resulting mixture was stirred overnight at room temperature. After stirring overnight, LC-MS indicated complete conversion. Concentrated to a solid, used as-is in the next step. Afforded 5-(2-acetamidoimidazo[1,2-b]pyridazin-6-yl)-2-methylnicotinic acid (299 mg, 0.864 mmol, 81% yield), a beige solid.

9: A mixture of 5-(2-acetamidoimidazo[1,2-b]pyridazin-6-yl)-2-methylnicotinic acid (35 mg, 0.112 mmol), 1-(2-fluoro-5-(trifluoromethoxy)phenyl)ethanamine (50.2 mg, 0.225 mmol), Hünig's base (0.098 mL, 0.562 mmol) and BOP (74.6 mg, 0.169 mmol) in DMF (1.0 mL) was stirred at rt ON. Purification afforded the racemate 5-(2-acetamidoimidazo[1,2-b]pyridazin-6-yl)-N-(1-(2-fluoro-5-(trifluoromethoxy)phenyl)ethyl)-2-methylnicotinamide (16.0 mg, 0.031 mmol, 27.3% yield). The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 17-57% B over 20 min, then a 5-minute hold at 100% B; Flow: 20 mL/min. Fractions containing the desired product were combined and dried via centrifugal evaporation. Subsequent chiral separation afforded 5-(2-acetamidoimidazo[1,2-b]pyridazin-6-yl)-N-(1-(2-fluoro-5-(trifluoromethoxy)phenyl)ethyl)-2-methylnicotinamide (6.1 mg, 0.011 mmol, 10.09% yield) and 5-(2-acetamidoimidazo[1,2-b]pyridazin-6-yl)-N-(1-(2-fluoro-5-(trifluoromethoxy)phenyl)ethyl)-2-methylnicotinamide (5.9 mg, 10.97 μmol, 9.75% yield).

MS ESI m/z 517.2 (M+H)

9-1 (first eluting): 1H NMR (500 MHz, DMSO-d6) δ 10.95 (s, 1H), 9.23-9.07 (m, 2H), 8.44-8.27 (m, 2H), 8.14 (d, J=9.5 Hz, 1H), 7.90 (d, J=9.5 Hz, 1H), 7.50 (br s, 1H), 7.45-7.31 (m, 2H), 5.38 (br t, J=7.2 Hz, 1H), 2.13 (s, 3H), 1.49 (br d, J=7.0 Hz, 3H), 1.24 (s, 3H).

9-2 (second eluting): 1H NMR (500 MHz, DMSO-d6) δ 10.96 (s, 1H), 9.24-9.05 (m, 2H), 8.47-8.29 (m, 2H), 8.15 (d, J=9.5 Hz, 1H), 7.92 (d, J=9.5 Hz, 1H), 7.52 (br s, 1H), 7.45-7.30 (m, 2H), 5.38 (br t, J=7.2 Hz, 1H), 2.15 (s, 3H), 1.49 (br d, J=7.0 Hz, 3H), 1.25 (s, 3H).

9-2 chiral synthesis: A mixture of 5-(2-acetamidoimidazo[1,2-b]pyridazin-6-yl)-2-methylnicotinic acid (45 mg, 0.145 mmol) and BOP (96 mg, 0.217 mmol), (R)-1-(2-fluoro-5-(trifluoromethoxy)phenyl)ethan-1-amine (35.5 mg, 0.159 mmol) and Hünig's Base (0.126 mL, 0.723 mmol) in DMF (1.5 mL) was stirred at rt over the weekend. Diluted to 100 mL with EtOAc, then washed 2×10% aq. LiCl, lx brine. Dried over sodium sulfate, then filtered and concentrated. Loaded onto a 12 g ISCO column, purified by flash chromatography eluting with 0-100% EtOAc in hexanes and then 0-10% MeOH in DCM. Afforded 25 mg of the product, somewhat less pure than optimal. Triturated 2×1:1 hexanes: diethyl ether and dried. Afforded (R)-5-(2-acetamidoimidazo[1,2-b]pyridazin-6-yl)-N-(1-(2-fluoro-5-(trifluoromethoxy)phenyl)ethyl)-2-methylnicotinamide (19 mg, 0.035 mmol, 24.18% yield)

MS ESI m/z (M+H)

1H NMR (400 MHz, DMSO-d6) δ 10.95 (s, 1H), 9.24-9.16 (m, 2H), 8.36 (s, 1H), 8.34 (s, 1H), 8.14 (d, J=9.4 Hz, 1H), 7.91 (d, J=9.4 Hz, 1H), 7.50 (br d, J=4.3 Hz, 1H), 7.42-7.34 (m, 2H), 5.38 (quin, J=7.1 Hz, 1H), 2.53 (s, 3H), 2.12 (s, 3H), 1.49 (d, J=7.0 Hz, 3H).

Example 10: N-{[2-fluoro-5-(trifluoromethoxy)phenyl]methyl}-2-methoxy-5-{2-propanamidoimidazo[1,2-b] pyridazin-6-yl}pyridine-3-carboxamide

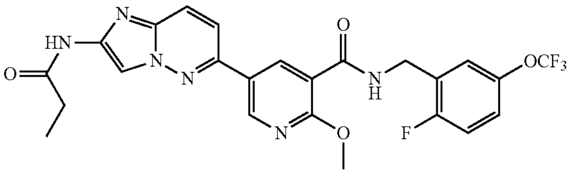 [SMILES: CCC(=O)Nc1cn2nc(-c3cnc(OC)c(C(=O)NCc4cc(OC(F)(F)F)ccc4F)c3)ccc2n1]

10A: Methyl 5-(2-aminoimidazo[1,2-b]pyridazin-6-yl)-2-methoxynicotinate: A mixture of 6-chloroimidazo[1,2-b]pyridazin-2-amine (202 mg, 1.201 mmol), methyl 2-methoxy-5-(4,4,5,5-tetramethyl-1,3,2-dioxaborolan-2-yl)nicotinate (320 mg, 1.092 mmol) and 1,1'-bis(di-tert-butylphosphino)ferrocene palladium dichloride (21.35 mg, 0.033 mmol) in 1,4-dioxane (6 mL) was degassed by bubbling $N_2$ though for 5 min. 2M $K_3PO_4$ (1.638 mL, 3.28 mmol) was added and the mixture was stirred 30 min at 100° C. The reaction mixture was concentrated directly onto Celite. Using a 24 g ISCO column, the crude material was purified by flash chromatography eluting with 0-10% MeOH in DCM to afford methyl 5-(2-aminoimidazo[1,2-b]pyridazin-6-yl)-2-methoxynicotinate (223 mg, 0.730 mmol, 66.9% yield) as a white solid.

MS ESI m/z 300.2 (M+H)

10B: 5-(2-Aminoimidazo[1,2-b]pyridazin-6-yl)-2-methoxynicotinic acid, lithium salt: To a mixture of methyl 5-(2-aminoimidazo[1,2-b]pyridazin-6-yl)-2-methoxynicotinate (223 mg, 0.745 mmol) in tetrahydrofuran (5 mL) was added a solution of lithium hydroxide monohydrate (37.5 mg, 0.894 mmol) in water (1.5 mL), and the resulting mixture was stirred ON at rt. The reaction mixture was concentrated to a solid to afford 5-(2-aminoimidazo[1,2-b]pyridazin-6-yl)-2-methoxynicotinic acid, lithium salt (210 mg, 0.699 mmol, 94% yield) as a beige solid which was used as is in subsequent chemistry.

MS ESI m/z 286.0 (M+H)

10C: 5-(2-Aminoimidazo[1,2-b]pyridazin-6-yl)-N-(2-fluoro-5-(trifluoromethoxy)benzyl)-2-methoxynicotinamide: A mixture of 5-(2-aminoimidazo[1,2-b]pyridazin-6-yl)-2-methoxynicotinic acid, lithium salt (210 mg, 0.736 mmol), BOP (488 mg, 1.104 mmol) (2-fluoro-5-(trifluoromethoxy)phenyl)methanamine (192 mg, 0.920 mmol), and Hünig's base (0.643 mL, 3.68 mmol) in DMF (5 mL) was stirred at rt ON. The reaction mixture was concentrated directly onto Celite and purified by flash chromatography, eluting with 0-10% MeOH in DCM. 5-(2-Aminoimidazo[1,2-b]pyridazin-6-yl)-N-(2-fluoro-5-(trifluoromethoxy)benzyl)-2-methoxynicotinamide (282 mg, 0.533 mmol, 72.4% yield) was isolated as a brown oil.

MS ESI m/z 477.2 (M+H)

10: A solution of 5-(2-aminoimidazo[1,2-b]pyridazin-6-yl)-N-(2-fluoro-5-(trifluoromethoxy)benzyl)-2-methoxynicotinamide (22 mg, 0.046 mmol), propionic acid (10.26 mg, 0.139 mmol), 1-propanephosphonic anhydride (58.8 mg, 0.092 mmol) and Hünig's base (0.056 mL, 0.323 mmol) in DMF (1 mL) and was stirred at rt ON. The reaction mixture was warmed to 80° C. and stirred ON. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 20 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 min, then a 5-minute hold at 100% B; Flow: 20 mL/min. Fractions containing the desired product were combined and dried via centrifugal evaporation. N-{[2-fluoro-5-(trifluoromethoxy)phenyl]methyl}-2-methoxy-5-{2-propanamidoimidazo[1,2-b]pyridazin-6-yl}pyridine-3-carboxamide (3.9 mg, 7.3 μmol, 15.9%) was isolated.

MS ESI m/z 533.2 (M+H)

$^1$H NMR (500 MHz, DMSO-d6) δ 10.85 (s, 1H), 9.03 (t, J=6.4 Hz, 1H), 8.98 (s, 1H), 8.68 (d, J=2.4 Hz, 1H), 8.32 (s, 1H), 8.06 (d, J=9.5 Hz, 1H), 7.83 (d, J=9.5 Hz, 1H), 7.44-7.32 (m, 3H), 4.59 (br d, J=5.8 Hz, 2H), 4.07 (s, 3H), 2.48-2.35 (m, 2H), 1.10 (t, J=7.5 Hz, 3H).

Example 11: N-{[2-fluoro-5-(trifluoromethoxy)phenyl]methyl}-2-methoxy-5-[2-(2-methylpropanamido)imidazo[1,2-b]pyridazin-6-yl]pyridine-3-carboxamide

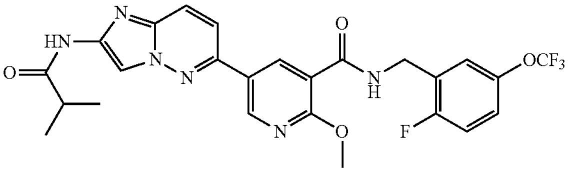 [SMILES: COc1ncc(-c2ccc3nc(NC(=O)C(C)C)cn3n2)cc1C(=O)NCc1cc(OC(F)(F)F)ccc1F]

A solution of 5-(2-aminoimidazo[1,2-b]pyridazin-6-yl)-N-(2-fluoro-5-(trifluoromethoxy)benzyl)-2-methoxynicotinamide (20 mg, 0.042 mmol), isobutyric acid (11.10 mg, 0.126 mmol), BOP (27.9 mg, 0.063 mmol) and Hünig's base (0.051 mL, 0.294 mmol) in DMF (1 mL) was stirred at rt ON. The reaction mixture was warmed to 55° C. ON. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 25 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-70% B over 25 min, then a 2-minute hold at 70% B; Flow: 20 mL/min. Fractions containing the desired product were combined and dried via centrifugal evaporation. N-{[2-fluoro-5-(trifluoromethoxy)phenyl]methyl}-2-methoxy-5-[2-(2-methylpropanamido)imidazo[1,2-b]pyridazin-6-yl]pyridine-3-carboxamide (0.8 mg, 1.5 μmol, 3.5%) was isolated.

MS ESI m/z 547.2 (M+H)

$^1$H NMR (500 MHz, DMSO-d6) δ 10.86 (s, 1H), 9.09-8.94 (m, 2H), 8.69 (s, 1H), 8.34 (s, 1H), 8.08 (d, J=9.5 Hz,

1H), 7.85 (d, J=9.5 Hz, 1H), 7.46-7.32 (m, 3H), 4.60 (br d, J=5.8 Hz, 2H), 4.08 (s, 3H), 2.90-2.71 (m, 1H), 1.13 (br d, J=6.7 Hz, 6H).

Example 12: 2-chloro-5-{2-acetamidoimidazo[1,2-b]pyridazin-6-yl}-N-{[2-fluoro-5-(trifluoromethoxy)phenyl]methyl}pyridine-3-carboxamide

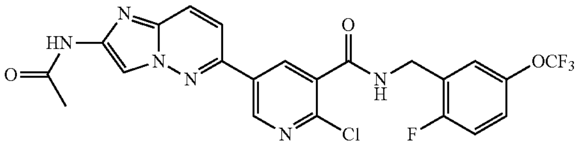 [SMILES: CC(=O)Nc1cn2nc(-c3cnc(Cl)c(C(=O)NCc4cc(OC(F)(F)F)ccc4F)c3)ccc2n1]

12A: Methyl 5-(2-acetamidoimidazo[1,2-]pyridazin-6-yl)-2-chloronicotinate: A mixture of N-(6-chloroimidazo[1,2-b]pyridazin-2-yl)acetamide (300 mg, 1.424 mmol), 4,4,4',4',5,5,5',5'-octamethyl-2,2'-bi(1,3,2-dioxaborolane) (579 mg, 2.279 mmol), $PdCl_2(dppf)-CH_2Cl_2$ adduct (116 mg, 0.142 mmol) and potassium acetate (419 mg, 4.27 mmol) in dioxane (8 mL) was heated to 100° C. for 6 h. The reaction mixture was allowed to cool to rt. To the stirred crude mixture was added methyl 5-bromo-2-chloronicotinate (392 mg, 1.565 mmol) and $PdCl_2(dppf)-CH_2Cl_2$ adduct (58.1 mg, 0.071 mmol) and the mixture was degassed by bubbling nitrogen though the mixture for 5 min. Potassium carbonate (393 mg, 2.85 mmol) was quickly added and the reaction mixture heated at 100° C. for 4 h. An additional 1/2 equivalent of bromide, catalyst and base were added and heating to 100° C. was continued for 2 h. The reaction mixture was partitioned between EtOAc (75 mL) and water (75 mL). The organic layer was washed with brine (50 mL), dried ($Na_2SO_4$) and concentrated to a residue that was chromatographed on a 40 gm ISCO silica gel cartridge, eluting with a 0-10% MeOH/DCM gradient. The pure fractions were concentrated to afford methyl 5-(2-acetamidoimidazo[1,2-b]pyridazin-6-yl)-2-chloronicotinate (275 mg, 0.795 mmol, 55.9% yield) as a yellow solid.

MS ESI m/z 346.1/348.1 (M+H)

$^1$H NMR (500 MHz, DMSO-$d_6$) δ 10.97 (s, 1H), 9.24 (d, J=2.2 Hz, 1H), 8.85 (d, J=2.5 Hz, 1H), 8.36 (s, 1H), 8.14 (d, J=8.8 Hz, 1H), 7.92 (d, J=9.4 Hz, 1H), 3.94 (s, 3H), 2.12 (s, 3H).

12B: 5-(2-Acetamidoimidazo[1,2-b]pyridazin-6-yl)-2-chloronicotinic acid, 1.25 lithium salt: To a suspension of methyl 5-(2-acetamidoimidazo[1,2-b]pyridazin-6-yl)-2-chloronicotinate (267 mg, 0.772 mmol) in THF (6 mL) at rt was added lithium hydroxide monohydrate (40.5 mg, 0.965 mmol) as a solution in water (1 mL). The reaction mixture was allowed to stir at rt for 16 h. Concentration and drying afforded 5-(2-acetamidoimidazo[1,2-b]pyridazin-6-yl)-2-chloronicotinic acid, 1.25 lithium salt (263 mg, 0.773 mmol, 100% yield) as a yellow solid.

MS ESI m/z 332.1/334.1 (M+H).

12: A mixture of 5-(2-acetamidoimidazo[1,2-b]pyridazin-6-yl)-2-chloronicotinic acid, 1.25 lithium salt (15 mg, 0.044 mmol), (2-fluoro-5-(trifluoromethoxy)phenyl)methanamine (13.82 mg, 0.066 mmol), BOP (21.44 mg, 0.048 mmol) and $Et_3N$ (0.018 mL, 0.132 mmol) in DMF at rt was agitated for 4 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate;

Gradient: 20-60% B over 20 min, then a 4-minute hold at 100% B; Flow: 20 mL/min. Fractions containing the desired product were combined and dried via centrifugal evaporation. 2-chloro-5-{2-acetamidoimidazo[1,2-b]pyridazin-6-yl}-N-{[2-fluoro-5-(trifluoromethoxy)phenyl]methyl}pyridine-3-carboxamide (2.5 mg, 4.8 μmol, 10.9%) was isolated.

MS ESI m/z 523.1 (M+H)

$^1$H NMR (500 MHz, DMSO-d6) δ 10.95 (s, 1H), 9.36 (br t, J=5.8 Hz, 1H), 9.13 (d, J=2.5 Hz, 1H), 8.51 (d, J=2.5 Hz, 1H), 8.33 (s, 1H), 8.10 (d, J=9.4 Hz, 1H), 7.88 (d, J=9.6 Hz, 1H), 7.46 (br d, J=5.5 Hz, 1H), 7.37 (br d, J=6.6 Hz, 2H), 4.56 (br d, J=5.8 Hz, 2H), 2.11 (s, 3H).

Example 13: 5-{2-acetamidoimidazo[1,2-b]pyridazin-6-yl}-2-($D_3$)methoxy-6-methyl-N-{1-[2-(trifluoromethoxy)phenyl] ethyl}pyridine-3-carboxamide

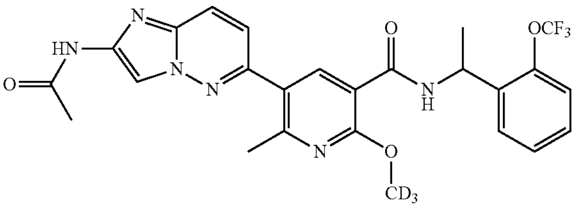 [SMILES: [2H]C([2H])([2H])Oc1nc(C)c(-c2ccc3nc(NC(C)=O)cn3n2)cc1C(=O)NC(C)c1ccccc1OC(F)(F)F]

13A: Methyl-$D_3$ 5-bromo-2-(methoxy-$D_3$)-6-methylnicotinate: To a rapidly stirring mixture of 5-bromo-2-hydroxy-6-methylnicotinic acid (1.20 g, 5.17 mmol) and iodomethane-$D_3$ (1.931 mL, 31.0 mmol) in chloroform (100 mL) was added silver carbonate (7.13 g, 25.9 mmol) and the resulting mixture was stirred in the dark [aluminum foil wrap] for 4 d. The reaction mixture was filtered though Celite, then concentrated to an oil. The crude residue was loaded onto a 40 g ISCO column and purified by flash chromatography, eluting with 0-75% EtOAc in hexanes. Methyl-$D_3$ 5-bromo-2-(methoxy-$D_3$)-6-methylnicotinate (732 mg, 2.64 mmol, 51.1% yield) as a white solid.

MS ESI m/z 266.0 (M+H)

13B: Methyl-$D_3$ 5-(2-acetamidoimidazo[1,2-b]pyridazin-6-yl)-2-(methoxy-$D_3$)-6-methylnicotinate: A degassed solution of methyl-$D_3$ 5-bromo-2-(methoxy-$D_3$)-6-methylnicotinate (300 mg, 1.127 mmol), 4,4,4',4',5,5,5',5'-octamethyl-2,2'-bi(1,3,2-dioxaborolane) (401 mg, 1.578 mmol), potassium acetate (171 mg, 1.747 mmol) and $PdCl_2(dppf)-CH_2Cl_2$ adduct (73.6 mg, 0.090 mmol) in dioxane (7 mL) was heated to 65° C. with vigorous mixing ON. To the crude reaction mixture was added N-(6-chloroimidazo[1,2-b]pyridazin-2-yl)acetamide (240 mg, 1.141 mmol), and 1,1'-bis(di-tert-butylphosphino)ferrocene palladium dichloride (20.29 mg, 0.031 mmol). The mixture was degassed by bubbling $N_2$ though for 5 min. 2M $K_3PO_4$ (1.557 mL, 3.11 mmol) was added and the reaction mixture was stirred 15 min at 100° C. The reaction mixture was concentrated directly onto Celite. Using a 24 g ISCO column, the material was purified by flash chromatography eluting with 0-10% MeOH in DCM to afford methyl-$D_3$ 5-(2-acetamidoimidazo[1,2-b]pyridazin-6-yl)-2-(methoxy-$D_3$)-6-methylnicotinate (195 mg, 0.529 mmol, 51.0% yield) as a white solid.

MS ESI m/z 362.2 (M+H)

13C: 5-(2-Acetamidoimidazo[1,2-b]pyridazin-6-yl)-2-(methoxy-$D_3$)-6-methylnicotinic acid, lithium salt: To a mixture of methyl-$D_3$ 5-(2-acetamidoimidazo[1,2-b]

pyridazin-6-yl)-2-(methoxy-$D_3$)-6-methylnicotinate (195 mg, 0.540 mmol) in tetrahydrofuran (6 mL) was added a solution of lithium hydroxide monohydrate (27.2 mg, 0.648 mmol) in water (1.5 mL), and the resulting mixture was stirred ON at rt. The reaction mixture was concentrated to a solid to afford 5-(2-acetamidoimidazo[1,2-b]pyridazin-6-yl)-2-(methoxy-$D_3$)-6-methylnicotinic acid, lithium salt (180 mg, 0.497 mmol, 92% yield) as a yellow solid. The material was used as is in subsequent chemistry.

MS ESI m/z 345.2 (M+H)

13: A mixture of 5-(2-acetamidoimidazo[1,2-b]pyridazin-6-yl)-2-(methoxy-d3)-6-methylnicotinic acid, lithium salt (30 mg, 0.087 mmol), BOP (57.8 mg, 0.131 mmol), 1-(2-(trifluoromethoxy)phenyl)ethanamine (23.24 mg, 0.113 mmol) and Hünig's base (0.076 mL, 0.436 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-75% B over 20 min, then a 3-minute hold at 100% B; Flow: 20 mL/min. Fractions containing the desired product were combined and dried via centrifugal evaporation to afford the racemate 5-(2-acetamidoimidazo[1,2-b]pyridazin-6-yl)-2-(methoxy-d3)-6-methyl-N-(1-(2-(trifluoromethoxy)phenyl)ethyl)nicotinamide (24.2 mg, 0.045 mmol, 51.7% yield). This material was subsequently submitted for chiral separation, affording 5-(2-acetamidoimidazo[1,2-b]pyridazin-6-yl)-2-(methoxy-d3)-6-methyl-N-(1-(2-(trifluoromethoxy)phenyl)ethyl)nicotinamide (7.7 mg, 0.014 mmol, 16.46% yield) and 5-(2-acetamidoimidazo[1,2-b]pyridazin-6-yl)-2-(methoxy-d3)-6-methyl-N-(1-(2-(trifluoromethoxy)phenyl)ethyl) nicotinamide (7.6 mg, 0.014 mmol, 16.25% yield).

MS ESI m/z 532 (M+H)

13-1 (first eluting): 1H NMR (500 MHz, DMSO-d6) δ 10.91 (s, 1H), 8.67 (d, J=7.6 Hz, 1H), 8.28 (s, 1H), 8.11 (s, 1H), 8.04 (d, J=9.2 Hz, 1H), 7.68-7.59 (m, 1H), 7.44-7.37 (m, 3H), 7.35 (br s, 1H), 5.40 (quin, J=7.1 Hz, 1H), 2.55 (s, 3H), 2.11 (s, 3H), 1.46 (d, J=7.0 Hz, 3H).

13-2 (second eluting): $^1H$ NMR (500 MHz, DMSO-$d_6$) δ 10.91 (s, 1H), 8.67 (d, J=7.6 Hz, 1H), 8.28 (s, 1H), 8.11 (s, 1H), 8.04 (d, J=9.5 Hz, 1H), 7.64 (dd, J=5.6, 3.5 Hz, 1H), 7.44-7.37 (m, 3H), 7.35 (br s, 1H), 5.40 (quin, J=7.2 Hz, 1H), 2.57-2.54 (m, 3H), 2.11 (s, 3H), 1.46 (d, J=7.0 Hz, 3H)

Example 14: 5-{2-acetamidoimidazo[1,2-b]pyridazin-6-yl}-2-($D_3$)methoxy-N-{[2-trifluoromethoxy)phenyl]methyl}pyridine-3-carboxamide

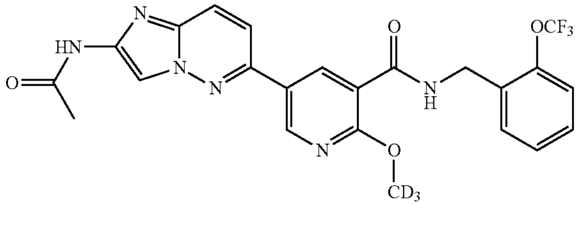 [SMILES: [2H]C([2H])([2H])Oc1ncc(-c2ccc3nc(NC(C)=O)cn3n2)cc1C(=O)NCc1ccccc1OC(F)(F)F]

14A: Methyl-$D_3$ 5-(2-acetamidoimidazo[1,2-b]pyridazin-6-yl)-2-(methoxy-$D_3$)nicotinate: A mixture of (2-acetamidoimidazo[1,2-b]pyridazin-6-yl)boronic acid (240 mg, 1.091 mmol), methyl-$D_3$ 5-bromo-2-(methoxy-$D_3$)nicotinate (250 mg, 0.992 mmol) (which can be prepared using the procedure described in Example of U.S. Patent Application No. 62/458,144), and 1,1'-bis(di-tert-butylphosphino)ferrocene palladium dichloride (32.3 mg, 0.050 mmol) in 1,4-dioxane (9 mL) was degassed by bubbling nitrogen though for 5 min. 2M $K_3PO_4$ (1.488 mL, 2.98 mmol) was added and the mixture stirred 15 min at 100° C. The reaction mixture was concentrated directly onto Celite. The mixture was purified by column chromatography on the Isco system (24 g, 0-10% MeOH/DCM to afford methyl-$D_3$ 5-(2-acetamidoimidazo[1,2-b]pyridazin-6-yl)-2-(methoxy-$D_3$)nicotinate (350 mg, 0.907 mmol, 91% yield) as a yellow solid.

MS ESI m/z 359.2 (M+H)

14B: 5-(2-Acetamidoimidazo[1,2-b]pyridazin-6-yl)-2-(methoxy-$D_3$)nicotinic acid, lithium salt: To a mixture of methyl-$D_3$ 5-(2-acetamidoimidazo[1,2-b]pyridazin-6-yl)-2-(methoxy-$D_3$)nicotinate (350 mg, 1.008 mmol) in tetrahydrofuran (8 mL) was added a solution of lithium hydroxide monohydrate (50.7 mg, 1.209 mmol) in water (1.5 mL), and the resulting mixture was stirred 1 h at rt. The reaction mixture was concentrated to afford 5-(2-acetamidoimidazo[1,2-b]pyridazin-6-yl)-2-(methoxy-$D_3$)nicotinic acid, lithium salt (317 mg, 0.864 mmol, 86% yield) as a beige solid. Material was used as is in subsequent chemistry.

MS ESI m/z 331.1 (M+H)

14: A mixture of 5-(2-acetamidoimidazo[1,2-b]pyridazin-6-yl)-2-(methoxy-$D_3$)nicotinic acid, lithium salt (15 mg, 0.045 mmol), BOP (30.1 mg, 0.068 mmol), (2-(trifluoromethoxy)phenyl)methanamine (11.28 mg, 0.059 mmol) and Hünig's base (0.040 mL, 0.227 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 min, then a 5-minute hold at 100% B; Flow: 20 mL/min.

Fractions containing the desired product were combined and dried via centrifugal evaporation. 5-{2-acetamidoimidazo[1,2-b]pyridazin-6-yl}-2-($D_3$)methoxy-N-{[2-(trifluoromethoxy)phenyl]methyl}pyridine-3-carboxamide (12.5 mg, 24.8 μmol, 55.2%) was isolated.

MS ESI m/z 504.3 (M+H)

$^1H$ NMR (500 MHz, DMSO-d6) δ 10.90 (s, 1H), 9.05-8.86 (m, 2H), 8.73 (d, J=2.4 Hz, 1H), 8.30 (s, 1H), 8.05 (d, J=9.5 Hz, 1H), 7.82 (d, J=9.5 Hz, 1H), 7.51 (br d, J=8.2 Hz, 1H), 7.45-7.35 (m, 3H), 4.61 (br d, J=5.8 Hz, 2H), 2.11 (s, 3H).

Example 15: N-{[2-(cyclopropylmethoxy)-3-fluorophenyl]methyl}-5-[2-(2-hydroxy-2-methylpropanamido)imidazo[1,2-b]pyridazin-6-yl]-2-methoxypyridine-3-carboxamide

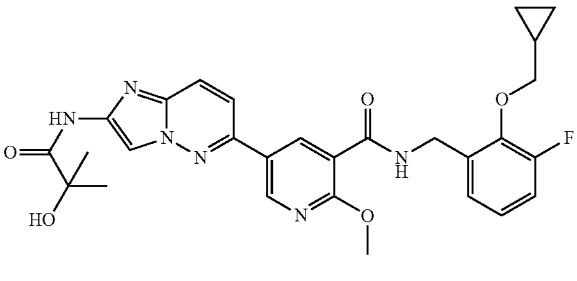 [SMILES: COc1ncc(-c2ccc3nc(NC(=O)C(C)(C)O)cn3n2)cc1C(=O)NCc1cccc(F)c1OCC1CC1]

15A: N-(6-chloroimidazo[1,2-b]pyridazin-2-yl)-2-hydroxy-2-methylpropanamide: A solution of 6-chloroimidazo

[1,2-b]pyridazin-2-amine (225 mg, 1.335 mmol), 2-hydroxy-2-methylpropanoic acid (153 mg, 1.468 mmol), DIEA (0.932 mL, 5.34 mmol) and BOP (885 mg, 2.002 mmol) in DMF (8 mL) and was stirred at rt ON. After stirring ON, the product was filtered off and dried to afford N-(6-chloroimidazo[1,2-b]pyridazin-2-yl)-2-hydroxy-2-methylpropanamide (500 mg, 0.864 mmol, 64.7% yield) as a yellow solid. Attempted purification was ineffective, so the ~40-50% clean material was used as-is in the subsequent steps.

MS ESI m/z 255.1 (M+H)

15B: Methyl 5-(2-(2-hydroxy-2-methylpropanamido)imidazo[1,2-b]pyridazin-6-yl)-2-methoxynicotinate: A mixture of N-(6-chloroimidazo[1,2-b]pyridazin-2-yl)-2-hydroxy-2-methylpropanamide (96 mg, 0.375 mmol), methyl 2-methoxy-5-(4,4,5,5-tetramethyl-1,3,2-dioxaborolan-2-yl) nicotinate (100 mg, 0.341 mmol) and 1,1'-bis(di-tert-butylphosphino)ferrocene palladium dichloride (6.67 mg, 10.23 μmol) in 1,4-dioxane (2.5 mL) was degassed by bubbling $N_2$ through for 5 min. 2M $K_3PO_4$ (0.512 mL, 1.023 mmol) was added and the reaction mixture stirred 15 min at 100° C. The reaction mixture was concentrated directly onto Celite. Using an Isco system, the crude material was purified by flash chromatography eluting with 0-10% MeOH in DCM. Afforded methyl 5-(2-(2-hydroxy-2-methylpropanamido)imidazo[1,2-b]pyridazin-6-yl)-2-methoxynicotinate (82 mg, 0.213 mmol, 62.4% yield) as a tan solid.

MS ESI m/z 386.2 (M+H)

15C: 5-(2-(2-hydroxy-2-methylpropanamido)imidazo[1,2-b]pyridazin-6-yl)-2-methoxynicotinic acid, lithium salt: To a mixture of methyl 5-(2-(2-hydroxy-2-methylpropanamido)imidazo[1,2-b]pyridazin-6-yl)-2-methoxynicotinate (82 mg, 0.213 mmol) in tetrahydrofuran (3 mL) was added a solution of lithium hydroxide monohydrate (10.71 mg, 0.255 mmol) in water (1.5 mL) and the resulting mixture was stirred at rt 90 min. The reaction mixture was concentrated to a solid, then azeotroped with toluene. Afforded 5-(2-(2-hydroxy-2-methylpropanamido)imidazo[1,2-b]pyridazin-6-yl)-2-methoxynicotinic acid, lithium salt (80 mg, 0.194 mmol, 91% yield) as a tan solid which could be used as is in subsequent chemistry.

MS ESI m/z 372.2 (M+H)

15: A mixture of 5-(2-(2-hydroxy-2-methylpropanamido)imidazo[1,2-b]pyridazin-6-yl)-2-methoxynicotinic acid (30 mg, 0.081 mmol), BOP (53.6 mg, 0.121 mmol), (2-(cyclopropylmethoxy)-3-fluorophenyl)methanamine (15.77 mg, 0.081 mmol) and Hünig's base (0.071 mL, 0.404 mmol) in DMF (1 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-90% B over 22 min, then a 5-minute hold at 100% B; Flow: 20 mL/min. Fractions containing the desired product were combined and dried via centrifugal evaporation. N-{[2-(cyclopropylmethoxy)-3-fluorophenyl]methyl}-5-[2-(2-hydroxy-2-methylpropanamido)imidazo[1,2-b]pyridazin-6-yl]-2-methoxypyridine-3-carboxamide (1.3 mg, 2.4 μmol, 2.9%) was isolated.

MS ESI m/z 549 (M+H)

$^1$H NMR (500 MHz, DMSO-d6) δ 9.00 (d, J=2.4 Hz, 1H), 8.90 (br s, 1H), 8.75 (d, J=2.4 Hz, 1H), 8.37 (s, 1H), 8.13 (d, J=9.5 Hz, 1H), 7.89 (d, J=9.5 Hz, 1H), 7.23-7.06 (m, 4H), 4.63 (br d, J=5.9 Hz, 2H), 4.08 (s, 3H), 3.93 (d, J=7.2 Hz, 2H), 1.71 (s, 1H), 1.39 (s, 6H), 1.36-1.15 (m, 1H), 0.66-0.50 (m, 2H), 0.41-0.25 (m, 2H).

Example 16: N-{[2-(cyclopropylmethoxy)-3,5-difluorophenyl]methyl}-5-{2-acetamidoimidazo[1,2-b]pyridazin-6-yl}-6-methylpyridine-3-carboxamide

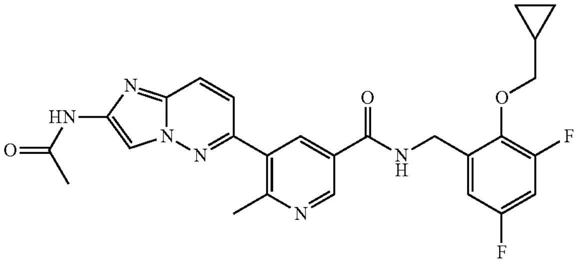 [SMILES: CC(=O)Nc1cn2nc(-c3cc(C(=O)NCc4cc(F)cc(F)c4OCC4CC4)cnc3C)ccc2n1]

16A: Ethyl 6-methyl-5-(4,4,5,5-tetramethyl-1,3,2-dioxaborolan-2-yl)nicotinate: A degassed solution of ethyl 5-bromo-6-methylnicotinate (600 mg, 2.458 mmol), 4,4,4',4',5,5,5',5'-octamethyl-2,2'-bi(1,3,2-dioxaborolane) (874 mg, 3.44 mmol), potassium acetate (374 mg, 3.81 mmol) and $PdCl_2$(dppf)-$CH_2Cl_2$ adduct (161 mg, 0.197 mmol) in dioxane (10 mL) was heated to 60° C. with vigorous mixing ON. The reaction mixture was concentrated onto Celite, then purified by flash chromatography utilizing a 40 g ISCO column and eluting with 0-90% EtOAc in hexanes. The pure fractions were concentrated to afford ethyl 6-methyl-5-(4,4,5,5-tetramethyl-1,3,2-dioxaborolan-2-yl)nicotinate (490 mg, 1.599 mmol, 65.0% yield) as a waxy white solid.

MS ESI m/z 291.8 (M+H)

16B: Ethyl 5-(2-acetamidoimidazo[1,2-b]pyridazin-6-yl)-6-methylnicotinate: A mixture of N-(6-chloroimidazo[1,2-b]pyridazin-2-yl)acetamide (226 mg, 1.074 mmol), ethyl 6-methyl-5-(4,4,5,5-tetramethyl-1,3,2-dioxaborolan-2-yl) nicotinate (272 mg, 0.934 mmol) and 1,1'-bis(di-tert-butylphosphino)ferrocene palladium dichloride (18.27 mg, 0.028 mmol) in 1,4-dioxane (6 mL) was degassed by bubbling $N_2$ through for 5 min. 2M $K_3PO_4$ (1.401 mL, 2.80 mmol) was added and the reaction mixture stirred 15 min at 100° C. The reaction mixture was diluted with ethyl acetate (100 mL) and washed sequentially with saturated aqueous ammonium chloride and brine. The organics were dried over sodium sulfate, filtered and concentrated. The crude residue was loaded onto a 24 g silica column and purified by flash chromatography, eluting with 0-10% MeOH in DCM to afford ethyl 5-(2-acetamidoimidazo[1,2-b]pyridazin-6-yl)-6-methylnicotinate (145 mg, 0.419 mmol, 44.8% yield) as a tan solid.

MS ESI m/z 339.8 (M+H)

16C: 5-(2-Acetamidoimidazo[1,2-b]pyridazin-6-yl)-6-methylnicotinic acid, lithium salt: To a solution of ethyl 5-(2-acetamidoimidazo[1,2-b]pyridazin-6-yl)-6-methylnicotinate (145 mg, 0.427 mmol) in tetrahydrofuran (3 mL) was added a solution of lithium hydroxide monohydrate (21.52 mg, 0.513 mmol) in water (1.5 mL), and the resulting mixture was stirred 1 h at rt. The reaction mixture was concentrated to a solid and azeotroped with toluene to afford 5-(2-acetamidoimidazo[1,2-b]pyridazin-6-yl)-6-methylnicotinic acid (127 mg, 0.388 mmol, 91% yield) as a yellow solid. Material was used as is in subsequent chemistry.

MS ESI m/z 311.8 (M+H)

16: A mixture of 5-(2-acetamidoimidazo[1,2-b]pyridazin-6-yl)-6-methylnicotinic acid (15 mg, 0.048 mmol), BOP (32.0 mg, 0.072 mmol), (2-(cyclopropylmethoxy)-3,5-difluorophenyl)methanamine (10.27 mg, 0.048 mmol) and Hünig's base (0.042 mL, 0.241 mmol) in DMF (1.0 mL) was stirred at rt for 6 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 min, then a 4-minute hold at 100% B; Flow: 20 mL/min. Fractions containing the desired product were combined and dried via centrifugal evaporation. N-{[2-(cyclopropylmethoxy)-3,5-difluorophenyl]methyl}-5-{2-acetamidoimidazo[1,2-b]pyridazin-6-yl}-6-methylpyridine-3-carboxamide (9.3 mg, 18.4 mol, 38.3%) was isolated.

MS ESI m/z 507.2 (M+H)

1H NMR (500 MHz, DMSO-d6) δ 10.89 (s, 1H), 9.24-9.17 (m, 1H), 8.98 (s, 1H), 8.28 (d, J=11.9 Hz, 2H), 8.04 (d, J=9.2 Hz, 1H), 7.44 (d, J=9.2 Hz, 1H), 7.18-7.07 (m, 1H), 6.90 (d, J=9.2 Hz, 1H), 4.53 (d, J=5.5 Hz, 2H), 3.80 (d, J=7.0 Hz, 2H), 2.57 (s, 3H), 2.07 (s, 3H), 1.17 (br. s., 1H), 0.49 (d, J=6.7 Hz, 2H), 0.22 (d, J=4.6 Hz, 2H).

Example 17: 5-{2-acetamidoimidazo[1,2-b]pyridazin-6-yl}-N-({2-[(1-hydroxypropan-2-yl)oxy]phenyl}methyl)-2-methoxy-6-methylpyridine-3-carboxamide

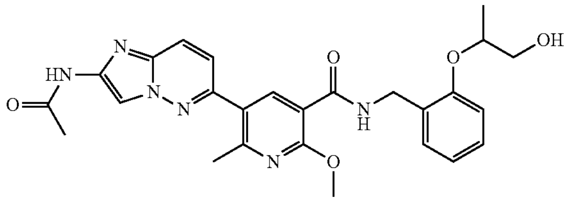 [SMILES: COc1nc(C)c(-c2ccc3nc(NC(C)=O)cn3n2)cc1C(=O)NCc1ccccc1OC(C)CO]

17A: 2-(Oxetan-3-yloxy)benzonitrile: To a solution of 2-hydroxybenzonitrile (300 mg, 2.52 mmol), oxetan-3-ol (224 mg, 3.02 mmol) and triphenylphosphine (925 mg, 3.53 mmol) in THF (10 mL) at 0° C. was added diisopropyl azodicarboxylate (0.734 mL, 3.78 mmol). The reaction mixture was allowed to warm to rt and stirred for 10 d. The volatiles were removed in vacuo and the residue was chromatographed on a 40 gm ISCO silica gel cartridge, eluting with a 0-50% EtOAc/Hex gradient. The pure fractions were concentrated to afford 2-(oxetan-3-yloxy)benzonitrile (203 mg, 1.159 mmol, 46.0% yield) as an amber oil. Material used as is in the next step.

$^1$H NMR (400 MHz, $CDCl_3$) δ 7.61 (dd, J=7.6, 1.7 Hz, 1H), 7.50 (td, J=8.0, 1.7 Hz, 1H), 7.06 (td, J=7.6, 0.7 Hz, 1H), 6.52 (d, J=8.4 Hz, 1H), 5.30 (quin, J=5.7 Hz, 1H), 5.00 (dd, J=7.5, 6.7 Hz, 2H), 4.90-4.80 (m, 2H).

17B: 2-(2-(Aminomethyl)phenoxy)propan-1-ol: To a suspension of LAH (240 mg, 6.32 mmol) in ether (15 mL) at 0° C. was added 2-(oxetan-3-yloxy)benzonitrile (193 mg, 1.102 mmol) as a solution in 2 mL of ether dropwise over 10 min. The reaction mixture was allowed to warm to rt and stir ON. The reaction mixture was re-cooled to 0° C. and water (0.25 mL) was added with extreme care to minimize gas evolution. NaOH (15%, 0.25 mL) was added followed by water (0.75 mL). The mixture was stirred 1 h. Anhydrous magnesium sulfate was added and stirring was continued as the mixture warmed to rt for 1 h. Filtration and concentration afforded 2-(2-(aminomethyl)phenoxy)propan-1-ol (140 mg, 0.772 mmol, 70.1% yield) as an orange oil. Material used as is in the next step.

MS ESI m/z 182.1 (M+H)

$^1$H NMR (400 MHz, $CDCl_3$) δ 7.23 (dd, J=7.7, 1.5 Hz, 1H), 7.15 (dd, J=7.4, 1.7 Hz, 1H), 6.98 (d, J=8.1 Hz, 1H), 6.90 (td, J=7.4, 1.0 Hz, 1H), 4.46 (quind, J=6.4, 2.8 Hz, 1H), 4.13 (d, J=11.7 Hz, 1H), 3.69-3.56 (m, 3H), 1.41 (d, J=6.5 Hz, 3H).

17C: methyl 2-methoxy-6-methyl-5-(4,4,5,5-tetramethyl-1,3,2-dioxaborolan-2-yl)nicotinate: A degassed solution of methyl 5-bromo-2-methoxy-6-methylnicotinate (650 mg, 2.499 mmol), 4,4,4',4',5,5,5',5'-octamethyl-2,2'-bi(1,3,2-dioxaborolane) (888 mg, 3.50 mmol), potassium acetate (380 mg, 3.87 mmol) and $PdCl_2$(dppf)-$CH_2Cl_2$ adduct (163 mg, 0.200 mmol) in dioxane (10 mL) was heated to 60° C. with vigorous mixing ON. The reaction mixture was concentrated onto Celite, then purified by flash chromatography utilizing an ISCO system eluting with 0-90% EtOAc in hexanes. The pure fractions were concentrated to afford methyl 2-methoxy-6-methyl-5-(4,4,5,5-tetramethyl-1,3,2-dioxaborolan-2-yl)nicotinate (599 mg, 1.911 mmol, 76% yield).

MS ESI m/z 308.3 (M+H)

17D: methyl 5-(2-acetamidoimidazo[1,2-b]pyridazin-6-yl)-2-methoxy-6-methylnicotinate: A mixture of N-(6-chloroimidazo[1,2-b]pyridazin-2-yl)acetamide (257 mg, 1.221 mmol), methyl 2-methoxy-6-methyl-5-(4,4,5,5-tetramethyl-1,3,2-dioxaborolan-2-yl)nicotinate (300 mg, 0.977 mmol) and 1,1'-bis(di-tert-butylphosphino)ferrocene palladium dichloride (19.10 mg, 0.029 mmol) in 1,4-dioxane (6 mL) was degassed by bubbling $N_2$ through for 5 min. 2M $K_3PO_4$ (1.465 mL, 2.93 mmol) was added and the mixture stirred 15 min at 100° C. The reaction mixture was concentrated directly onto Celite. Using an ISCO system, the crude product was purified by flash chromatography, eluting with 0-10% MeOH in DCM. Afforded methyl 5-(2-acetamidoimidazo[1,2-b]pyridazin-6-yl)-2-methoxy-6-methylnicotinate (242 mg, 0.674 mmol, 69.0% yield) as a tan solid.

MS ESI m/z 356.2 (M+H)

17E: 5-(2-acetamidoimidazo[1,2-b]pyridazin-6-yl)-2-methoxy-6-methylnicotinic acid, lithium salt: To a mixture of methyl 5-(2-acetamidoimidazo[1,2-b]pyridazin-6-yl)-2-methoxy-6-methylnicotinate (240 mg, 0.675 mmol) in tetrahydrofuran (5 mL) was added a solution of lithium hydroxide monohydrate (34.0 mg, 0.810 mmol) in water (1.5 mL). The resulting mixture was stirred ON at rt. The crude reaction mixture was concentrated to a solid to afford 5-(2-acetamidoimidazo[1,2-b]pyridazin-6-yl)-2-methoxy-6-methylnicotinic acid, lithium salt (222 mg, 0.618 mmol, 91% yield) as a tan solid.

MS ESI m/z 341.8 (M+H)

17: A mixture of 5-(2-acetamidoimidazo[1,2-b]pyridazin-6-yl)-2-methoxy-6-methylnicotinic acid, lithium salt (15 mg, 0.044 mmol), BOP (29.2 mg, 0.066 mmol), 2-(2-(aminomethyl)phenoxy)propan-1-ol (8.76 mg, 0.048 mmol) and Hünig's base (0.038 mL, 0.220 mmol) in DMF (1.0 mL) was stirred at rt 4 d. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-60% B over 20 min, then a 4-minute hold at 100% B; Flow: 20 mL/min. Fractions containing the desired product were combined and dried via centrifugal evaporation. 5-{2-acetamidoimidazo[1,2-b]pyridazin-6-yl}-N-({2-[(1-hydroxypropan-2-yl)oxy]phenyl}methyl)-2-methoxy-6-methylpyridine-3-carboxamide (9.8 mg, 19.4 μmol, 44.1%) was isolated.

MS ESI m/z 505.4 (M+H)

$^1$H NMR (500 MHz, DMSO-d6) δ 10.89 (br. s., 1H), 8.75-8.55 (m, 1H), 8.35-8.18 (m, 2H), 8.00 (br. s., 1H), 7.40 (d, J=6.7 Hz, 1H), 7.28-7.12 (m, 2H), 7.01 (d, J=7.9 Hz, 1H), 6.92-6.83 (m, 1H), 4.47 (d, J=5.2 Hz, 3H), 4.04 (s, 3H), 3.72 (br. s., 2H), 3.67 (br. s., 1H), 3.55 (d, J=14.0 Hz, 1H), 2.53 (d, J=4.0 Hz, 3H), 2.10 (br. s., 2H), 1.27-1.19 (m, 3H).

Example 18: 5-{2-acetamidoimidazo[1,2-b]pyridazin-6-yl}-N-{[2-fluoro-5-(trifluoromethoxy)phenyl] methyl}-2-(trifluoromethyl)pyridine-3-carboxamide

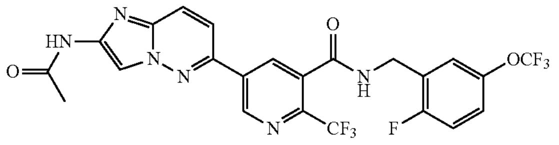 [SMILES: CC(=O)Nc1cn2nc(-c3cnc(C(F)(F)F)c(C(=O)NCc4cc(OC(F)(F)F)ccc4F)c3)ccc2n1]

18A: Ethyl 5-(2-acetamidoimidazo[1,2-b]pyridazin-6-yl)-2-(trifluoromethyl)nicotinate: A mixture of ethyl 5-bromo-2-(trifluoromethyl)nicotinate (300 mg, 1.007 mmol), 4,4,4',4',5,5,5',5'-octamethyl-2,2'-bi(1,3,2-dioxaborolane) (383 mg, 1.510 mmol), 1,1'-bis(diphenyllphosphino)ferrocene palladium dichloride—$CH_2Cl_2$ adduct (82 mg, 0.101 mmol) and potassium acetate (198 mg, 2.013 mmol) in dioxane (8 mL) was degassed by bubbling nitrogen though the reaction mixture for 1 min. The reaction mixture was heated to 100° C. for 3 h. After cooling to rt, N-(6-chloroimidazo[1,2-b]pyridazin-2-yl)acetamide (255 mg, 1.209 mmol) and 1,1'-bis(diphenyllphosphino)ferrocene palladium dichloride—$CH_2Cl_2$ adduct (41.1 mg, 0.050 mmol) were added. Following degassing by bubbling nitrogen though the mixture for 5 min, 2M $K_3PO_4$ (aq) (1.512 mL, 3.02 mmol) was quickly added and the reaction mixture heated to 100° C. for 1.5 h. After cooling to rt, the reaction mixture was partitioned between EtOAc (50 mL) and brine (30 mL). The organic layer was dried over anhydrous sodium sulfate. Filtration and concentration afforded a dark residue that was chromatographed on a 24 gm ISCO silica gel cartridge, eluting with a 1-10% MeOH/DCM gradient. The pure fractions were concentrated to afford a dark yellow solid that was triturated with ether and dried to afford ethyl 5-(2-acetamidoimidazo[1,2-b]pyridazin-6-yl)-2-(trifluoromethyl)nicotinate (367 mg, 0.933 mmol, 93% yield) as a yellow solid.

MS ESI m/z 394.2 (M+H)

$^1$H NMR (500 MHz, DMSO-$d_6$) δ 11.02 (br. s., 1H), 9.52 (s, 1H), 8.88 (s, 1H), 8.38 (s, 1H), 8.18 (d, J=9.5 Hz, 1H), 7.99 (d, J=9.5 Hz, 1H), 4.41 (q, J=7.1 Hz, 2H), 2.12 (s, 3H), 1.34 (t, J=7.1 Hz, 3H).

18B: 5-(2-Acetamidoimidazo[1,2-b]pyridazin-6-yl)-2-(trifluoromethyl)nicotinic acid, 1.5 lithium salt: Lithium hydroxide monohydrate (58.5 mg, 1.392 mmol) as a solution in water (2 mL) was added to ethyl 5-(2-acetamidoimidazo[1,2-b]pyridazin-6-yl)-2-(trifluoromethyl)nicotinate (365 mg, 0.928 mmol) in THF (8 mL) at rt and the resulting mixture was stirred at rt for 18 h. The volatiles were removed in vacuo and the residue was dried to afford 5-(2-acetamidoimidazo[1,2-b]pyridazin-6-yl)-2-(trifluoromethyl)nicotinic acid, 1.5 lithium salt (349 mg, 0.929 mmol, 100% yield) as a yellow solid.

MS ESI m/z 366.1 (M+H)

18: A mixture of 5-(2-acetamidoimidazo[1,2-b]pyridazin-6-yl)-2-(trifluoromethyl)nicotinic acid, lithium salt (12 mg, 0.033 mmol), (2-fluoro-5-(trifluoromethoxy)phenyl)methanamine (10.31 mg, 0.049 mmol) and $Et_3N$ (0.023 mL, 0.164 mmol) in DMF (0.25 mL) was agitated at rt for 16 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 min, then a 4-minute hold at 100% B; Flow: 20 mL/min. Fractions containing the desired product were combined and dried via centrifugal evaporation. 5-{2-acetamidoimidazo[1,2-b]pyridazin-6-yl}-N-{[2-fluoro-5-(trifluoromethoxy)phenyl]methyl}-2-(trifluoromethyl)pyridine-3-carboxamide (2.8 mg, 5 μmol, 15.2%) was isolated.

MS ESI m/z 557.1 (M+H)

1H NMR (500 MHz, DMSO-d6) δ 10.99 (s, 1H), 9.45 (d, J=1.7 Hz, 1H), 9.40 (t, J=5.8 Hz, 1H), 8.66 (d, J=1.7 Hz, 1H), 8.38 (s, 1H), 8.19 (d, J=9.6 Hz, 1H), 7.99 (d, J=9.6 Hz, 1H), 7.43 (d, J=5.5 Hz, 1H), 7.38 (d, J=6.9 Hz, 2H), 4.57 (d, J=5.8 Hz, 2H), 2.12 (s, 3H).

Example 19: 5-{2-acetamidoimidazo[1,2-b]pyridazin-6-yl}-2-methoxy-6-methyl-N-{[2-(trifluoromethoxy)phenyl]methyl}pyridine-3-carboxamide

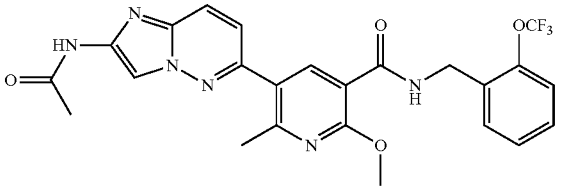 [SMILES: COc1nc(C)c(-c2ccc3nc(NC(C)=O)cn3n2)cc1C(=O)NCc1ccccc1OC(F)(F)F]

19: A mixture of 5-(2-acetamidoimidazo[1,2-b]pyridazin-6-yl)-2-methoxy-6-methylnicotinic acid (30 mg, 0.088 mmol), (2-(trifluoromethoxy)phenyl)methanamine (16.80 mg, 0.088 mmol), BOP (58.3 mg, 0.132 mmol) and Hünig's base (0.077 mL, 0.439 mmol) in DMF (1.0 mL) was stirred 3 d at rt. The reaction mixture was diluted with EtOAc (75 mL) and washed 10% lithium chloride solution and brine. The organics were dried over sodium sulfate, filtered and concentrated. The crude residue was loaded onto a 4 g ISCO column and purified by flash chromatography, eluting with 0-100% EtOAc in hexanes to afford 5-(2-acetamidoimidazo[1,2-b]pyridazin-6-yl)-2-methoxy-6-methyl-N-(2-(trifluoromethoxy)benzyl)nicotinamide (29 mg, 0.054 mmol, 61.6% yield) as an off-white solid.

MS ESI m/z 515.0 (M+H)

1H NMR (400 MHz, DMSO-d6) δ 10.90 (s, 1H), 8.84 (t, J=6.1 Hz, 1H), 8.28 (s, 1H), 8.25 (s, 1H), 8.05 (d, J=9.3 Hz, 1H), 7.50-7.46 (m, 1H), 7.45-7.34 (m, 4H), 4.60 (d, J=6.1 Hz, 2H), 4.07 (s, 3H), 2.57 (s, 3H), 2.13-2.09 (m, 3H).

Example 20: 5-{2-acetamidoimidazo[1,2-b]pyridazin-6-yl}-2-methyl-N-{[2-(propan-2-yloxy)phenyl]methyl}pyridine-3-carboxamide

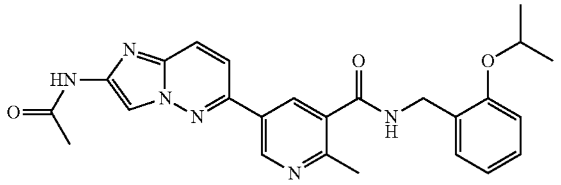 [SMILES: CC(=O)Nc1cn2nc(-c3cnc(C)c(C(=O)NCc4ccccc4OC(C)C)c3)ccc2n1]

20A: Ethyl 5-(2-acetamidoimidazo[1,2-b]pyridazin-6-yl)-2-methylnicotinate: A mixture of (2-acetamidoimidazo[1,2-b]pyridazin-6-yl)boronic acid (758 mg, 3.45 mmol), ethyl 5-bromo-2-methylnicotinate (765 mg, 3.13 mmol), and 1,1'-bis(di-tert-butylphosphino)ferrocene palladium dichloride (102 mg, 0.157 mmol) in 1,4-dioxane (9 mL) was degassed by bubbling nitrogen though for 5 min. 2M $K_3PO_4$ (4.70 mL, 9.40 mmol) was added and the mixture stirred 15 min at 100° C. The reaction mixture was concentrated directly onto Celite. Using a 40 g silica column, the material was eluted with 0-10% MeOH in DCM to afford ethyl 5-(2-acetamidoimidazo[1,2-b]pyridazin-6-yl)-2-methylnicotinate (852 mg, 2.385 mmol, 76% yield) as a yellow solid.

MS ESI m/z 340.1 (M+H)

20B: 5-(2-Acetamidoimidazo[1,2-b]pyridazin-6-yl)-2-methylnicotinic acid, lithium salt: To a mixture of ethyl 5-(2-acetamidoimidazo[1,2-b]pyridazin-6-yl)-2-methylnicotinate (852 mg, 2.51 mmol) in tetrahydrofuran (10 mL) was added a solution of lithium hydroxide monohydrate (126 mg, 3.01 mmol) in water (3 mL), and the resulting mixture was stirred 4 h at rt. A solution of lithium hydroxide monohydrate (20 mg) in water (1 mL) was added and the reaction mixture stirred ON. The reaction mixture was concentrated to afford 5-(2-acetamidoimidazo[1,2-b]pyridazin-6-yl)-2-methylnicotinic acid, lithium salt (750 mg, 2.168 mmol, 86% yield) as a beige solid.

MS ESI m/z 311.9 (M+H)

20: A mixture of 5-(2-acetamidoimidazo[1,2-b]pyridazin-6-yl)-2-methylnicotinic acid, lithium salt (10 mg, 0.032 mmol), BOP (21.31 mg, 0.048 mmol), (2-isopropoxyphenyl)methanamine (6.63 mg, 0.040 mmol) and Hünig's base (0.028 mL, 0.161 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 min, then a 5-minute hold at 100% B; Flow: 20 mL/min. Fractions containing the desired product were combined and dried via centrifugal evaporation. 5-{2-acetamidoimidazo[1,2-b]pyridazin-6-yl}-2-methyl-N-{[2-(propan-2-yloxy)phenyl]methyl}pyridine-3-carboxamide (4.3 mg, 9.4 μmol, 29.3%) was isolated.

MS ESI m/z 459.3 (M+H)

1H NMR (500 MHz, DMSO-d6) δ 10.93 (br. s., 1H), 9.14 (br. s., 1H), 8.88 (br. s., 1H), 8.41-8.28 (m, 2H), 8.09 (d, J=9.2 Hz, 1H), 7.86 (d, J=9.2 Hz, 1H), 7.29 (d, J=7.0 Hz, 1H), 7.23 (t, J=7.5 Hz, 1H), 7.02 (d, J=8.2 Hz, 1H), 6.92 (t, J=7.0 Hz, 1H), 4.72-4.60 (m, 1H), 4.45 (d, J=5.2 Hz, 2H), 2.61 (s, 3H), 2.11 (s, 3H), 1.43-1.19 (m, 6H).

Example 21: N-{[2-(cyclopentyloxy)phenyl]methyl}-5-{2-acetamidoimidazo[1,2-b]pyridazin-6-yl}pyridine-3-carboxamide

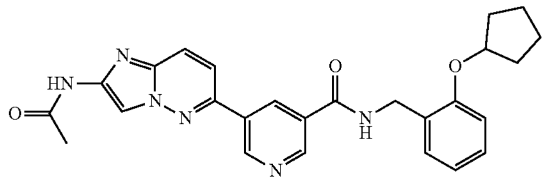 [SMILES: CC(=O)Nc1cn2nc(-c3cncc(C(=O)NCc4ccccc4OC4CCCC4)c3)ccc2n1]

21A: pyridazine-3,6-diol: To a 3 L 4-necked round bottom flask charged with furan-2,5-dione (150 g, 1530 mmol) in water (2000 mL) at rt was added hydrazine sulfate (219 g, 1683 mmol). The reaction mixture was heated to 100° C. and maintained for 8 h. The reaction mixture was cooled to rt and solid product was isolated by vacuum filtration, rinsing with water. The solid was dried under high vacuum at 50° C. to afford pyridazine-3,6-diol (126 g, 74%) as an off white solid.

MS ESI (m/z) 113.06 (M+H)

21B: 3,6-dichloropyridazine: To a 2 L round bottom flask under nitrogen charged with pyridazine-3,6-diol (125 g, 1115 mmol) was added $POCl_3$ (520 ml, 5576 mmol) at rt. The reaction mixture was heated at 80° C. ON. The reaction mixture was concentrated under high vacuum at 55-60° C. to obtain a thick mass which was diluted with EtOAc (1 L). The contents were slowly quenched into an ice-cold saturated solution of sodium bicarbonate to pH-8. The layers were separated and the aqueous layer was extracted with EtOAc (2×500 mL). The combined organic layers were washed with water (1 L), brine (1 L), dried over sodium sulfate, filtered and concentrated under vacuum. After drying under vacuum at 50° C., 3,6-dichloropyridazine (151 g, 85%) was isolated.

MS ESI (m/z) 150.2 (M+H)

21C: 6-chloropyridazin-3-amine: A 2 L autoclave reactor was charged with 3,6-dichloropyridazine (75 g, 503 mmol) and aqueous ammonia (1.25 L). The reaction mixture was heated at 100° C. ON. The reaction mixture was drained from the reactor and diluted with water (1 L). The solid was isolated by filtration, rinsing with water (500 mL). 6-Chloropyridazin-3-amine (44 g, 67%) was isolated as a brown solid.

MS ESI (m/z) 130.0 (M+H)

21D: N-(6-chloropyridazin-3-yl)-4-methylbenzenesulfonamide: A 2 L 4-necked round bottom flask was charged with 6-chloropyridazin-3-amine (90 g, 695 mmol) in pyridine (700 mL) at rt. p-Toluenesulfonyl chloride (146 g, 764 mmol) was added in 4 lots. After addition was complete, the reaction mixture was heated at 85° C. ON. The reaction mixture was cooled to rt and concentrated in vacuo. The crude residue was diluted with ethyl acetate and poured into ice cold 1 N HCl (1 L) with constant stirring. The aqueous layer was extracted with ethyl acetate (2×1 L). The combined organics were washed with water (1 L) and brine (1 L), dried over sodium sulfate, filtered and concentrated in vacuo. The crude residue was slurried with 10% EtOAc in MTBE (500 mL) and stirred for 10 min. The solids were isolated by filtration, washing with MTBE. N-(6-Chloropyridazin-3-yl)-4-methylbenzenesulfonamide (89 g, 38%) was isolated as a pale brown solid.

MS ESI (m/z) 284.1 (M+H)

21E: (Z)-2-(3-chloro-6-(tosylimino)pyridazin-1(6H)-yl) acetamide: A 2 L 4-necked round bottom flask was charged with N-(6-chloropyridazin-3-yl)-4-methylbenzenesulfonamide (89 g, 314 mmol) in DMF (400 mL). DIPEA (54.8 mL, 314 mmol) was added and the mixture was stirred 10 min at rt. Iodoacetamide (72.5 g, 392 mmol) was added the reaction mixture stirred 3 h at rt. The reaction mixture was quenched by slowly pouring into ice cold water (1 L) and stirring 15 min. The solid was isolated by vacuum filtration, washing with water (1 L) and MTBE (500 mL). (Z)-2-(3-chloro-6-(tosylimino)pyridazin-1(6H)-yl)acetamide (104 g, 85%) was isolated as a pale brown solid.

MS ESI (m/z) 339.0 (M−H)

21F: N-(6-chloroimidazo[1,2-b]pyridazin-2-yl)-2,2,2-trifluoroacetamide: To a 2 L 4-necked round bottom flask charged with (Z)-2-(3-chloro-6-(tosylimino)pyridazin-1(6H)-yl)acetamide (100 g, 293 mmol) in dichloromethane (1000 mL) was added trifluoroacetic anhydride (207 mL, 1467 mmol) at rt over 10 min. The reaction mixture was stirred at rt 2 h and concentrated in vacuo. The crude residue was slurried with dichloromethane (1 L) and concentrated in vacuo (2×). The crude material was diluted with water (500 ml) and treated with 10% aqueous sodium bicarbonate solution to pH-8. After stirring 30 min, the solid was isolated by filtration and washed with water (200 mL). Drying under vacuum ON yielded N-(6-chloroimidazo[1,2-b]pyridazin-2-yl)-2,2,2-trifluoroacetamide (74 g, 95%) as a brown solid.

MS ESI (m/z) 265.1 (M+H)

21G: 6-chloroimidazo[1,2-b]pyridazin-2-amine: A 2 L 4-necked round bottom flask was charged with N-(6-chloroimidazo[1,2-b]pyridazin-2-yl)-2,2,2-trifluoroacetamide (74 g, 280 mmol) in methanol (350 mL). Water (350 mL) was added, followed by potassium carbonate (38.7 g, 280 mmol) and the reaction mixture was heated at 85° C. ON. The reaction mixture was cooled to 0° C. and stirred 15 min. The solid product was isolated by vacuum filtration, rinsing with water (100 mL). Isolated 6-chloroimidazo[1,2-b]pyridazin-2-amine (20.2 g, 42%) as a brown solid. Additional material was isolated from the filtrate after partial concentration (15 g).

MS ESI (m/z) 169.2 (M+H)

21H: N-(6-chloroimidazo[1,2-b]pyridazin-2-yl)acetamide: To a round bottom flask charged with 6-chloroimidazo[1,2-b]pyridazin-2-amine (35 g, 208 mmol) in DMA (420 mL) was added acetyl chloride (16.24 mL, 228 mmol) dropwise over 10 min at rt. The reaction mixture was stirred at rt 2 h and a thick brown suspension was observed. The reaction mixture was poured into ice water (1 L) and stirred 10 min. The solid product was isolated by vacuum filtration, rinsing with water to yield N-(6-chloroimidazo[1,2-b]pyridazin-2-yl)acetamide (36.1 g, 82%) as a brown solid. 8. The reaction mass was quenched into ice water(1 L), stirred for 10 minutes.

MS ESI (m/z) 211.2 (M+H)

21I: N-(6-(4,4,5,5-tetramethyl-1,3,2-dioxaborolan-2-yl) imidazo[1,2-b]pyridazin-2-yl)acetamide: To a round bottom flask under nitrogen was added N-(6-chloroimidazo[1,2-b]pyridazin-2-yl)acetamide (20 g, 95 mmol) in dioxane (350 mL). 4,4,4',4',5,5,5',5'-Octamethyl-2,2'-bi(1,3,2-dioxaborolane) (36.2 g, 142 mmol), potassium acetate (28.0 g, 285 mmol), 1,1'-bis(diphenylphosphino)ferrocene-palladium(II) dichloride dichloromethane complex (4.65 g, 5.70 mmol) and dppf (2.106 g, 3.80 mmol) were added under constant nitrogen bubbling. After completion of addition, the contents were stirred and bubbled with nitrogen for 10 min. The reaction mixture was heated at 100° C. ON. The reaction mixture was cooled to rt and filtered through a pad of Celite, rinsing with methanol (500 mL). The filtrate was diluted with ethyl acetate (500 mL) and treated with charcoal (3 g). The slurry was heated to 50° C. for 10 min with stirring and was filtered through a pad of Celite. This was repeated twice and the solution was concentrated in vacuo. The crude residue was slurried with a 1:1 mix of EtOAc:DCM (300 mL) and stirred 15 min. The solid was isolated by filtration, rinsing with ethyl acetate (200 mL) to yield N-(6-(4,4,5,5-tetramethyl-1,3,2-dioxaborolan-2-yl)imidazo[1,2-b]pyridazin-2-yl)acetamide as a cream solid.

21J: Ethyl 5-(2-acetamidoimidazo[1,2-b]pyridazin-6-yl) nicotinate: In a sealed 40 mL tube, to the crude reaction mixture containing (2-acetamidoimidazo[1,2-b]pyridazin-6-yl)boronic acid (598 mg, 2.718 mmol) was added ethyl 5-bromonicotinate (414 mg, 1.800 mmol) and 1,1'-bis(di-tert-butylphosphino)ferrocene palladium dichloride (35.2 mg, 0.054 mmol). The mixture was degassed by bubbling $N_2$ through for 5 min. 2M $K_3PO_4$ (2.70 mL, 5.40 mmol) was added and the reaction mixture stirred 10 min at 100° C. Upon cooling to rt, the reaction mixture was diluted with ethyl acetate (150 mL). The organics were washed with saturated aqueous ammonium chloride and brine, dried over anhydrous sodium sulfate, filtered and concentrated in vacuo. The crude residue was loaded onto a 40 g silica column and purified by flash chromatography, eluting with 0-10% MeOH in DCM to afford ethyl 5-(2-acetamidoimidazo[1,2-b]pyridazin-6-yl)nicotinate (275 mg, 0.803 mmol, 44.6% yield).

MS ESI m/z 325.8 (M+H)

21K: 5-(2-Acetamidoimidazo[1,2-b]pyridazin-6-yl)nicotinic acid, lithium salt: To a solution of ethyl 5-(2-acetamidoimidazo[1,2-b]pyridazin-6-yl)nicotinate (275 mg, 0.845 mmol) in tetrahydrofuran (6 mL) was added a solution of lithium hydroxide monohydrate (42.6 mg, 1.014 mmol) in water (1.5 mL), and the resulting mixture was stirred 1 h at rt. The reaction mixture was concentrated to afford 5-(2-acetamidoimidazo[1,2-b]pyridazin-6-yl)nicotinic acid, lithium salt (242 mg, 0.733 mmol, 87% yield) as a tan solid. Material used as is in subsequent chemistry.

MS ESI m/z 298.5 (M+H)

21: A mixture of 5-(2-acetamidoimidazo[1,2-b]pyridazin-6-yl)nicotinic acid, lithium salt (12 mg, 0.040 mmol), BOP (26.8 mg, 0.061 mmol), (2-(cyclopentyloxy)phenyl)methanamine (9.65 mg, 0.050 mmol) and Hünig's base (0.035 mL, 0.202 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-55% B over 25 min, then a 2-minute hold at 55% B; Flow: 20 mL/min. Fractions containing the desired product were combined and dried via centrifugal evaporation. N-{[2-(cyclopentyloxy)phenyl]methyl}-5-{2-acetamidoimidazo[1,2-b]pyridazin-6-yl}pyridine-3-carboxamide (0.7 mg, 1.5 μmol, 3.7%) was isolated.

MS ESI m/z 471.3 (M+H)

1H NMR (500 MHz, DMSO-d6) δ 9.37 (s, 1H), 9.15 (s, 2H), 8.85 (s, 1H), 8.36 (s, 1H), 8.16 (d, J=9.5 Hz, 1H), 7.92

(d, J=9.3 Hz, 1H), 7.30-7.17 (m, 2H), 6.99 (d, J=8.1 Hz, 1H), 6.89 (t, J=7.4 Hz, 1H), 4.89 (br. s., 1H), 4.49 (d, J=5.4 Hz, 2H), 2.12 (s, 3H), 1.94-1.83 (m, 2H), 1.82-1.63 (m, 5H), 1.58 (br. s., 2H).

Example 22: N-{[2-(cyclopropylmethoxy)phenyl]methyl}-5-{2-acetamidoimidazo[1,2-b]pyridazin-6-yl}-2-methoxypyridine-3-carboxamide

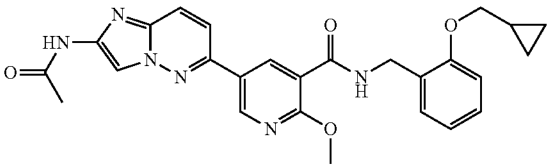 [SMILES: COc1ncc(-c2ccc3nc(NC(C)=O)cn3n2)cc1C(=O)NCc1ccccc1OCC1CC1]

22A: Methyl 5-(2-acetamidoimidazo[1,2-b]pyridazin-6-yl)-2-methoxynicotinate: To the crude reaction mixture containing (2-acetamidoimidazo[1,2-b]pyridazin-6-yl)boronic acid (516 mg, 2.347 mmol) was added methyl 5-bromo-2-methoxynicotinate (525 mg, 2.134 mmol), and 1,1'-bis(di-tert-butylphosphino)ferrocene palladium dichloride (69.5 mg, 0.107 mmol) and the resulting mixture was degassed by bubbling nitrogen through for 5 min. 2M $K_3PO_4$ (3.20 mL, 6.40 mmol) was added and the mixture stirred 15 min at 100° C. The reaction mixture was concentrated directly on to Celite. The material was purified by flash chromatography using a 24 g silica column, eluting with 0-10% MeOH in DCM to afford methyl 5-(2-acetamidoimidazo[1,2-b]pyridazin-6-yl)-2-methoxynicotinate (605 mg, 1.684 mmol, 79% yield) as a tan solid.

MS ESI m/z 342.1 (M+H)

22B: 5-(2-Acetamidoimidazo[1,2-b]pyridazin-6-yl)-2-methoxynicotinic acid, lithium salt: To a mixture of methyl 5-(2-acetamidoimidazo[1,2-b]pyridazin-6-yl)-2-methoxynicotinate (605 mg, 1.772 mmol) in tetrahydrofuran (10 mL) was added a solution of lithium hydroxide monohydrate (89 mg, 2.127 mmol) in water (1.5 mL), and the resulting mixture was stirred ON at rt. The reaction mixture was concentrated to afford 5-(2-acetamidoimidazo[1,2-b]pyridazin-6-yl)-2-methoxynicotinic acid, lithium salt (555 mg, 1.696 mmol, 96% yield) as a beige solid. Material was used as is in subsequent chemistry.

MS ESI m/z 328.1 (M+H)

22: A mixture of 5-(2-acetamidoimidazo[1,2-b]pyridazin-6-yl)-2-methoxynicotinic acid, lithium salt (11 mg, 0.034 mmol), BOP (22.30 mg, 0.050 mmol), (2-(cyclopropylmethoxy)phenyl)methanamine (7.45 mg, 0.042 mmol) and Hünig's base (0.029 mL, 0.168 mmol) in DMF (1.0 mL) was stirred at rt for 3 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 min, then a 4-minute hold at 100% B; Flow: 20 mL/min. Fractions containing the desired product were combined and dried via centrifugal evaporation. N-{[2-(cyclopropylmethoxy)phenyl]methyl}-5-{2-acetamidoimidazo[1,2-b]pyridazin-6-yl}-2-methoxypyridine-3-carboxamide (4.3 mg, 8.8 μmol, 26%) was isolated.

MS ESI m/z 487.3 (M+H)

1H NMR (500 MHz, DMSO-d6) δ 10.93 (s, 1H), 8.96 (s, 1H), 8.74 (br. s., 2H), 8.30 (s, 1H), 8.05 (d, J=9.3 Hz, 1H), 7.82 (d, J=9.5 Hz, 1H), 7.28-7.17 (m, 2H), 6.97 (d, J=8.2 Hz, 1H), 6.91 (t, J=7.4 Hz, 1H), 4.52 (d, J=5.8 Hz, 2H), 4.06 (s, 3H), 3.90 (d, J=6.8 Hz, 2H), 2.10 (s, 3H), 1.27 (br. s., 1H), 0.57 (d, J=7.3 Hz, 2H), 0.36 (d, J=4.5 Hz, 2H).

Example 23: N-[3-(4-chlorophenyl)-3-hydroxypropyl]-5-{2-acetamidoimidazo[1,2-b]pyridazin-6-yl}-2-methoxypyridine-3-carboxamide

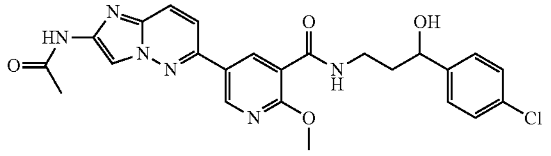 [SMILES: COc1ncc(-c2ccc3nc(NC(C)=O)cn3n2)cc1C(=O)NCCC(O)c1ccc(Cl)cc1]

23A: Methyl 5-(2-acetamidoimidazo[1,2-b]pyridazin-6-yl)-2-methoxynicotinate: To a vial charged with N-(6-(4,4,5,5-tetramethyl-1,3,2-dioxaborolan-2-yl)imidazo[1,2-b]pyridazin-2-yl)acetamide (0.5 g, 1.655 mmol), methyl 5-bromo-2-methoxynicotinate (0.370 g, 1.504 mmol) and $PdCl_2(dppf)-CH_2Cl_2$ adduct (0.123 g, 0.150 mmol) in dioxane (7.52 mL) and degassed by sparging for 5 min with nitrogen was added potassium phosphate tribasic 2M solution (2.257 mL, 4.51 mmol). The vial was capped and the reaction mixture heated to 90° C. 1 h. Water was added and the yellow solid isolated by vacuum filtration, washing with water. Methyl 5-(2-acetamidoimidazo[1,2-b]pyridazin-6-yl)-2-methoxynicotinate (0.3088 g, 0.905 mmol, 60.1% yield) was isolated as a yellow solid.

MS ESI m/z 342.1 (M+H)

23B: 5-(2-Acetamidoimidazo[1,2-b]pyridazin-6-yl)-2-methoxynicotinic acid, HCl: To a round bottom flask charged with methyl 5-(2-acetamidoimidazo[1,2-b]pyridazin-6-yl)-2-methoxynicotinate (0.3088 g, 0.905 mmol) in methanol (4.52 mL) was added 1 N sodium hydroxide (1.809 mL, 1.809 mmol). The reaction mixture was stirred at rt ON. Excess solvent was removed in vacuo. The residual slurry was acidified with 1 N HCl (~pH 3). A solid was isolated by vacuum filtration, however much of the solid stayed in the flask. The solid was washed with water. The batches of solid were combined and dried under vacuum. The solid was triturated with dichloromethane (3×). 5-(2-acetamidoimidazo[1,2-b]pyridazin-6-yl)-2-methoxynicotinic acid, HCl (0.1553 g, 0.427 mmol, 47.2% yield) was isolated as a yellow solid.

MS ESI m/z 328.0 (M+H)

23: Using a Bohdan Miniblock XT, 5-(2-acetamidoimidazo[1,2-b]pyridazin-6-yl)-2-methoxynicotinic acid hydrochloride (8.6 mg, 0.024 mmol) was dissolved in DMF (300 μL). PyBOP (14.76 mg, 0.028 mmol), Hünig's base (20.65 μl, 0.118 mmol) and 3-amino-1-(4-chlorophenyl)propan-1-ol (8.78 mg, 0.047 mmol) were added and the reaction mixture stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 min, then a 2-minute hold at 100% B; Flow: 20 mL/min. Fractions containing the desired product were combined and dried via centrifugal evaporation. N-[3-(4-chlorophenyl)-3-hydroxypropyl]-5-{2-acetamidoimidazo[1,2-b]pyridazin-6-yl}-2-methoxypyridine-3-carboxamide (5.9 mg, 11.9 μmol, 49.7%) was isolated.

MS ESI m/z 495.3 (M+H)

$^1$H NMR (500 MHz, DMSO-d6) δ 10.92 (s, 1H), 8.91 (s, 1H), 8.68 (s, 1H), 8.57 (br s, 1H), 8.29 (s, 1H), 8.03 (br d, J=9.3 Hz, 1H), 7.79 (br d, J=9.3 Hz, 1H), 7.37 (s, 5H), 4.69 (br s, 1H), 4.03 (s, 3H), 3.37 (br d, J=5.9 Hz, 2H), 2.10 (s, 3H), 1.96-1.76 (m, 2H).

Example 24: 2-fluoro-N-(6-{3-[(3-phenylbutyl)carbamoyl]phenyl}imidazo[1,2-b]pyridazin-2-yl)pyridine-4-carboxamide

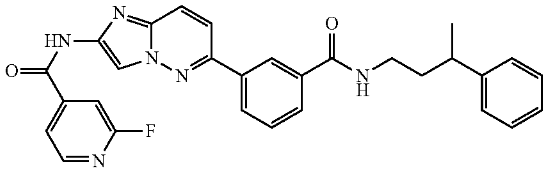 [SMILES: CC(CCNC(=O)c1cccc(-c2ccc3nc(NC(=O)c4ccnc(F)c4)cn3n2)c1)c1ccccc1]

24A: N-(3-phenylbutyl)-3-(4,4,5,5-tetramethyl-1,3,2-dioxaborolan-2-yl)benzamide: To a solution of 3-carboxyphenylboronic acid pinacol ester (1.0 g, 4.03 mmol), 3-phenylbutan-1-amine, HCl (0.749 g, 4.03 mmol) and Hünig's base (1.478 mL, 8.46 mmol) in DMF (12 mL) was added BOP (1.783 g, 4.03 mmol). The reaction mixture was stirred at rt over the weekend. The reaction mixture was diluted with EtOAc which was washed with 10% LiCl solution (3×) and brine. The organics were dried over anhydrous sodium sulfate and concentrated in vacuo. The crude product was purified by column chromatography on the Isco system (80 g, 0-20% EtOAc/$CH_2Cl_2$) to yield N-(3-phenylbutyl)-3-(4,4,5,5-tetramethyl-1,3,2-dioxaborolan-2-yl)benzamide (1.02 g, 2.69 mmol, 66.7% yield) as a clear, viscous oil.

MS ESI m/z 380.1 (M+H)

24: A vial containing a solution of N-(3-phenylbutyl)-3-(4,4,5,5-tetramethyl-1,3,2-dioxaborolan-2-yl)benzamide (19 mg, 0.050 mmol) in dioxane (1 mL) was degassed with nitrogen. A solution of tripotassium phosphate (31.9 mg, 0.150 mmol) in water (0.1 mL) and degassed with nitrogen was added. N-(6-Chloroimidazo[1,2-b]pyridazin-2-yl)-2-fluoroisonicotinamide (25 mg, 0.085 mmol and 2nd generation Xphos precatalyst (CAS #1310584-14-5) (1.971 mg, 2.505 μmol) were added. The vial was flushed with nitrogen and shaken at rt. Additional catalyst (1.971 mg, 2.505 μmol) was added and the reaction mixture heated to 60° C. with stirring. The vial contents were transferred to 6 mL PL-Thiol SPE cartridges (conditioned w/MeOH) and product was eluted with MeOH (4 mL). Samples were blown down in the Zymark tabletop dryer at 35° C. for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 min, then a 5-minute hold at 100% B; Flow: 20 mL/min. Fractions containing the desired product were combined and dried via centrifugal evaporation. 2-fluoro-N-(6-{3-[(3-phenylbutyl)carbamoyl]phenyl}imidazo[1,2-b]pyridazin-2-yl)pyridine-4-carboxamide (9.4 mg, 18.5 μmol, 37%) was isolated.

MS ESI m/z 509.1 (M+H)

$^1$H NMR (500 MHz, DMSO-$d_6$) δ 11.87 (s, 1H), 8.60 (t, J=5.5 Hz, 1H), 8.57 (s, 1H), 8.49-8.44 (m, 2H), 8.24-8.17 (m, 2H), 8.00-7.94 (m, 2H), 7.90 (d, J=9.5 Hz, 1H), 7.80 (s, 1H), 7.65 (t, J=7.7 Hz, 1H), 7.36-7.24 (m, 4H), 7.22-7.15 (m, 1H), 3.36-3.10 (m, 1H), 2.81 (sxt, J=6.8 Hz, 1H), 1.86 (q, J=7.3 Hz, 2H), 1.25 (d, J=7.0 Hz, 3H). Note: One CH between 3.36-3.10 not visible due to water suppression.

Example 25: 5-{2-acetamidoimidazo[1,2-b]pyridazin-6-yl}-2-methoxy-N-(3-phenylbutyl)pyridine-3-carboxamide

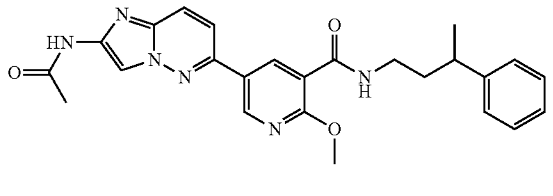 [SMILES: COc1ncc(-c2ccc3nc(NC(C)=O)cn3n2)cc1C(=O)NCCC(C)c1ccccc1]

25A: 5-Borono-2-methoxynicotinic acid, lithium salt and 2-methoxy-5-(4,4,5,5-tetramethyl-1,3,2-dioxaborolan-2-yl)nicotinate, lithium salt: To a round bottom flask charged with methyl 2-methoxy-5-(4,4,5,5-tetramethyl-1,3,2-dioxaborolan-2-yl)nicotinate (0.5 g, 1.706 mmol) in tetrahydrofuran (6.4 mL) and water (2.1 mL) was added lithium hydroxide monohydrate (0.215 g, 5.12 mmol). The reaction mixture was stirred at rt 4 h. The reaction mixture was concentrated in vacuo and dried ON under vacuum. Material used crude in next step.

MS ESI m/z 198.0 (M+H)

25B: (6-Methoxy-5-((3-phenylbutyl)carbamoyl)pyridine-3-yl)boronic acid and 2-methoxy-N-(3-phenylbutyl)-5-(4,4,5,5-tetramethyl-1,3,2-dioxaborolan-2-yl)nicotinamide: To a solution of 5-borono-2-methoxynicotinic acid, lithium salt (0.348 g, 1.706 mmol), 3-phenylbutan-1-amine, HCl (0.317 g, 1.706 mmol) and Hünig's base (0.626 mL, 3.58 mmol) in DMF (5.69 mL) was added BOP (0.755 g, 1.706 mmol). The reaction mixture was stirred at rt 6 h. The reaction mixture was diluted with EtOAc and washed with 10% LiCl solution (2×), water and brine. The organics were dried over anhydrous sodium sulfate and concentrated in vacuo. The material was dried under vacuum ON and used as is in subsequent chemistry.

MS ESI m/z 329.0 (M+H) and 411.1 (M+H)

25: A vial charged with N-(6-chloroimidazo[1,2-b]pyridazin-2-yl)acetamide (17.55 mg, 0.083 mmol), 2-methoxy-N-(3-phenylbutyl)-5-(4,4,5,5-tetramethyl-1,3,2-dioxaborolan-2-yl)nicotinamide (41.0 mg, 0.1 mmol) and $PdCl_2$(dppf)-$CH_2Cl_2$ adduct (6.81 mg, 8.33 μmol) in DMF (417 μl) was degassed by sparging for 5 min with nitrogen. Potassium phosphate tribasic 2M solution (125 μl, 0.250 mmol) was added, the vial was capped and the reaction mixture was heated to 100° C. for 2.5 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 min, then a 5-minute hold at 100% B; Flow: 20 mL/min. Fractions containing the desired product were combined and dried via centrifugal evaporation. 5-{2-acetamidoimidazo[1,2-b]pyridazin-6-yl}-2-methoxy-N-(3-phenylbutyl)pyridine-3-carboxamide (5.4 mg, 11.8 μmol, 14.2%) was isolated.

MS ESI m/z 459.2 (M+H)

$^1$H NMR (500 MHz, DMSO-d6) δ 10.91 (s, 1H), 8.89 (br s, 1H), 8.60 (s, 1H), 8.34 (br s, 1H), 8.28 (s, 1H), 8.02 (br d, J=9.3 Hz, 1H), 7.78 (br d, J=9.2 Hz, 1H), 7.32-7.21 (m, 4H), 7.20-7.12 (m, 1H), 4.01 (s, 3H), 3.26-3.12 (m, 2H), 2.78 (br d, J=6.6 Hz, 1H), 2.10 (s, 3H), 1.81 (br d, J=7.1 Hz, 2H), 1.22 (br d, J=6.7 Hz, 3H).

Example 26: 5-[2-(2-cyano-2,2-dimethylacetamido)imidazo[1,2-b]pyridazin-6-yl]-N-[(2-{[2-(hydroxymethyl)phenyl] sulfanyl}phenyl)methyl]-2-methylpyridine-3-carboxamide

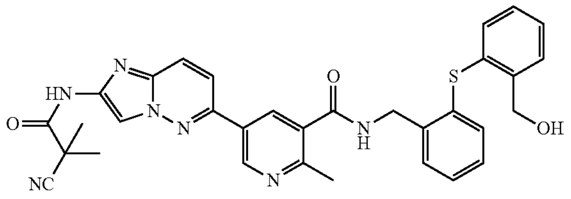 [SMILES: Cc1ncc(-c2ccc3nc(NC(=O)C(C)(C)C#N)cn3n2)cc1C(=O)NCc1ccccc1Sc1ccccc1CO]

26A: (2-(2-cyano-2-methylpropanamido)imidazo[1,2-b]pyridazin-6-yl)boronic acid: A mixture of N-(6-chloroimidazo[1,2-b]pyridazin-2-yl)-2-cyano-2-methylpropanamide (110 mg, 0.417 mmol), 4,4,4',4',5,5,5',5'-octamethyl-2,2'-bi(1,3,2-dioxaborolane) (169 mg, 0.667 mmol), $PdCl_2$(dppf)-$CH_2Cl_2$ adduct (34.1 mg, 0.042 mmol) and potassium acetate (123 mg, 1.251 mmol) in dioxane (2.5 mL) was heated to 100° C. for 1 h. The reaction mixture was cooled to rt and use as is in subsequent chemistry.

MS ESI (m/z) 274.1 (M+H).

26B: ethyl 5-(2-(2-cyano-2-methylpropanamido)imidazo[1,2-b]pyridazin-6-yl)-2-methylnicotinate: A mixture of (2-(2-cyano-2-methylpropanamido)imidazo[1,2-b]pyridazin-6-yl)boronic acid (111 mg, 0.406 mmol), ethyl 5-bromo-2-methylnicotinate (90 mg, 0.369 mmol), and 1,1'-bis(di-tert-butylphosphino)ferrocene palladium dichloride (12.02 mg, 0.018 mmol) in 1,4-dioxane (3 mL) was degassed by bubbling nitrogen through for 5 minutes. 2 M $K_3PO_4$ (0.553 mL, 1.106 mmol) was added and the mixture stirred 15 min at 100° C. After cooling to rt, the reaction mixture was partitioned between EtOAc (100 mL) and water (10 mL). The organic layer was washed with brine, dried over anhydrous sodium sulfate, filtered and concentrated in vacuo. The crude residue was loaded onto a 12 g ISCO column and purified, eluting with 0-10% MeOH in DCM. Afforded ethyl 5-(2-(2-cyano-2-methylpropanamido)imidazo[1,2-b]pyridazin-6-yl)-2-methylnicotinate (123 mg, 0.282 mmol, 77% yield) as a yellow solid.

MS ESI (m/z) 393.4 (M+H).

26C: 5-(2-(2-cyano-2-methylpropanamido)imidazo[1,2-b]pyridazin-6-yl)-2-methylnicotinic acid, lithium salt: To a mixture of ethyl 5-(2-(2-cyano-2-methylpropanamido)imidazo[1,2-b]pyridazin-6-yl)-2-methylnicotinate (123 mg, 0.313 mmol) in tetrahydrofuran (2.5 mL) was added a solution of lithium hydroxide monohydrate (15.78 mg, 0.376 mmol) in water (1.5 mL). The reaction mixture was stirred ON at rt. A solution of lithium hydroxide monohydrate (5 mg) in water (0.5 mL) was added and stirring continued ON. The reaction mixture was concentrated to a solid to afford 5-(2-(2-cyano-2-methylpropanamido)imidazo[1,2-b]pyridazin-6-yl)-2-methylnicotinic acid, lithium salt (120 mg, 0.296 mmol, 95% yield) as a beige solid.

Material was used as is in subsequent chemistry.

MS ESI (m/z) 365.1 (M+H). 26: A mixture of 5-(2-(2-cyano-2-methylpropanamido)imidazo[1,2-b]pyridazin-6-yl)-2-methylnicotinic acid, lithium salt (15 mg, 0.041 mmol), BOP (27.3 mg, 0.062 mmol), (2-((2-(aminomethyl)phenyl)thio)phenyl)methanol (12.12 mg, 0.049 mmol) and Hünig's base (0.036 mL, 0.206 mmol) in DMF (1 mL) was stirred at rt 3d. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 25 minutes, then a 6-minute hold at 100% B; Flow: 20 mL/min. Fractions containing the desired product were combined and dried via centrifugal evaporation. 5-[2-(2-Cyano-2,2-dimethylacetamido)imidazo[1,2-b]pyridazin-6-yl]-N-[(2-{[2-(hydroxymethyl)phenyl] sulfanyl}phenyl)methyl]-2-methylpyridine-3-carboxamide (12.6 mg, 17.9 Iμmol, 43.5%) was isolated.

MS ESI m/z 592.3 (M+H)

$^1$H NMR (500 MHz, DMSO-d6) δ 11.40 (s, 1H), 9.20 (br s, 1H), 9.14 (br t, J=5.5 Hz, 1H), 8.42 (br d, J=15.3 Hz, 2H), 8.20 (br d, J=9.3 Hz, 1H), 8.05-7.86 (m, 1H), 7.63-7.44 (m, 2H), 7.42-7.22 (m, 3H), 7.18-7.07 (m, 2H), 7.05 (s, 1H), 4.66-4.56 (m, 3H), 2.65 (s, 2H), 2.57-2.53 (m, 3H), 1.71 (s, 6H).

Example 27: 5-[2-(2-cyano-2,2-dimethylacetamido)imidazo[1,2-b]pyridazin-6-yl]-N-[(1R)-1-[2-fluoro-5-(trifluoromethoxy)phenyl] ethyl]-2-methylpyridine-3-carboxamide

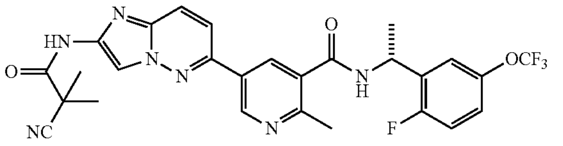 [SMILES: Cc1ncc(-c2ccc3nc(NC(=O)C(C)(C)C#N)cn3n2)cc1C(=O)N[C@H](C)c1cc(OC(F)(F)F)ccc1F]

A mixture of 5-(2-(2-cyano-2-methylpropanamido)imidazo[1,2-b]pyridazin-6-yl)-2-methylnicotinic acid (15 mg, 0.041 mmol), BOP (27.3 mg, 0.062 mmol), (R)-1-(2-fluoro-5-(trifluoromethoxy)phenyl)ethan-1-amine (11.02 mg, 0.049 mmol) and Hünig's base (0.036 mL, 0.206 mmol) in DMF (1 mL) was stirred at rt 3 d. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 27-67% B over 20 minutes, then a 4-minute hold at 100% B; Flow: 20 mL/min. Fractions containing the desired product were combined and dried via centrifugal evaporation. 5-[2-(2-Cyano-2,2-dimethylacetamido)imidazo[1,2-b]pyridazin-6-yl]-N-[(1R)-1-[2-fluoro-5-(trifluoromethoxy)phenyl] ethyl]-2-methylpyridine-3-carboxamide (8.6 mg, 15.1 μmol, 36.8%) was isolated.

MS ESI m/z 570.4 (M+H)

$^1$H NMR (500 MHz, DMSO-d6) δ 11.21 (s, 1H), 9.29-9.12 (m, 2H), 8.39 (s, 1H), 8.37 (s, 1H), 8.19 (d, J=9.5 Hz, 1H), 7.95 (d, J=9.5 Hz, 1H), 7.50 (br s, 1H), 7.46-7.31 (m, 2H), 5.47-5.31 (m, 1H), 2.56-2.53 (m, 3H), 1.72 (s, 6H), 1.50 (d, J=7.0 Hz, 3H).

Example 28: 5-[2-(2-cyano-2,2-dimethylacetamido)imidazo[1,2-b]pyridazin-6-yl]-N-{[2-fluoro-5-(trifluoromethoxy)phenyl]methyl}-2-methoxypyridine-3-carboxamide

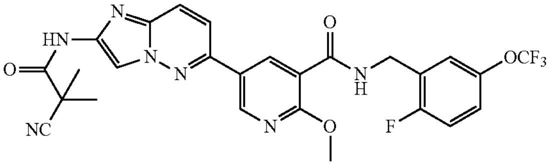 [SMILES: COc1ncc(-c2ccc3nc(NC(=O)C(C)(C)C#N)cn3n2)cc1C(=O)NCc1cc(OC(F)(F)F)ccc1F]

28A: N-(6-chloroimidazo[1,2-b]pyridazin-2-yl)-2-cyano-2-methylpropanamide: A solution of 6-chloroimidazo[1,2-b]pyridazin-2-amine (257 mg, 1.524 mmol), 2-cyano-2-methylpropanoic acid (259 mg, 2.287 mmol), DIEA (1.331 mL, 7.62 mmol) and HATU (869 mg, 2.287 mmol) in DMF (8 mL) was stirred at rt ON. The reaction mixture was diluted to a total volume of 100 mL with EtOAc. The organic layer was washed with 10% Li Cl solution (2×) and brine. The combined organics were dried over sodium sulfate, filtered and concentrated. The crude residue was loaded onto a 24 g ISCO column and purified by flash chromatography, eluting with 0-10% MeOH in DCM. Afforded N-(6-chloroimidazo[1,2-b]pyridazin-2-yl)-2-cyano-2-methylpropanamide (388 mg, 1.398 mmol, 92% yield) as a yellow solid.

MS ESI (m/z) 264.0 (M+H).

28B: methyl 5-(2-(2-cyano-2-methylpropanamido)imidazo[1,2-b]pyridazin-6-yl)-2-methoxynicotinate: A mixture of N-(6-chloroimidazo[1,2-b]pyridazin-2-yl)-2-cyano-2-methylpropanamide (190 mg, 0.721 mmol), methyl 2-methoxy-5-(4,4,5,5-tetramethyl-1,3,2-dioxaborolan-2-yl)nicotinate (211 mg, 0.721 mmol) and 1,1'-bis(di-tert-butylphosphino)ferrocene palladium dichloride (23.48 mg, 0.036 mmol) in 1,4-dioxane (5 mL) was degassed by bubbling nitrogen through for 5 min. 2 M $K_3PO_4$ (1.081 mL, 2.162 mmol) was added and the mixture stirred 20 min at 100° C. The reaction mixture was partitioned between EtOAc (100 mL) and water (10 mL). The organic layer was washed with brine, dried over anhydrous sodium sulfate, filtered and concentrated in vacuo. The crude residue was loaded onto a 12 g ISCO column and purified, eluting with 0-100% EtOAc followed by 0-10% MeOH in DCM. Afforded methyl 5-(2-(2-cyano-2-methylpropanamido)imidazo[1,2-b]pyridazin-6-yl)-2-methoxynicotinate (158 mg, 0.393 mmol, 54.5% yield).

MS ESI (m/z) 395.2 (M+H).

28C: 5-(2-(2-cyano-2-methylpropanamido)imidazo[1,2-b]pyridazin-6-yl)-2-methoxynicotinic acid, lithium salt: To a mixture of methyl 5-(2-(2-cyano-2-methylpropanamido)imidazo[1,2-b]pyridazin-6-yl)-2-methoxynicotinate (158 mg, 0.401 mmol) in tetrahydrofuran (3 mL) was added a solution of lithium hydroxide monohydrate (20.17 mg, 0.481 mmol) in water (1.5 mL) The mixture was stirred ON at rt. The reaction mixture was concentrated to a solid to yield 5-(2-(2-cyano-2-methylpropanamido)imidazo[1,2-b]pyridazin-6-yl)-2-methoxynicotinic acid, lithium salt (144 mg, 0.360 mmol, 90% yield) as a beige solid. Used as-is in the next step.

MS ESI (m/z) 381.2 (M+H).

28: A mixture of 5-(2-(2-cyano-2-methylpropanamido)imidazo[1,2-b]pyridazin-6-yl)-2-methoxynicotinic acid, lithium salt (20 mg, 0.053 mmol), BOP (34.9 mg, 0.079 mmol), (2-fluoro-5-(trifluoromethoxy)phenyl)methanamine (11.00 mg, 0.053 mmol) and Hünig's base (0.046 mL, 0.263 mmol) in DMF (1.0 mL) was stirred at rt 3 d. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 20 minutes, then a 4-minute hold at 100% B; Flow: 20 mL/min. Fractions containing the desired product were combined and dried via centrifugal evaporation. 5-[2-(2-Cyano-2,2-dimethylacetamido)imidazo[1,2-b]pyridazin-6-yl]-N-{[2-fluoro-5-(trifluoromethoxy)phenyl]methyl}-2-methoxypyridine-3-carboxamide (14.4 mg, 25.2 μmol, 47.5%) was isolated.

MS ESI m/z 572 (M+H)

$^1$H NMR (500 MHz, DMSO-d6) δ 11.31 (s, 1H), 9.06-8.96 (m, 2H), 8.70 (d, J=2.1 Hz, 1H), 8.36 (s, 1H), 8.12 (d, J=9.5 Hz, 1H), 7.89 (d, J=9.5 Hz, 1H), 7.44-7.33 (m, 2H), 7.30 (br d, J=7.6 Hz, 1H), 4.60 (br d, J=5.8 Hz, 2H), 4.07 (s, 3H), 1.70 (s, 6H).

Example 29: 5-[2-(2-cyano-2,2-dimethylacetamido)imidazo[1,2-b]pyridazin-6-yl]-N-{[5-(cyclopropylmethoxy)-2-fluorophenyl]methyl}-2-methoxypyridine-3-carboxamide

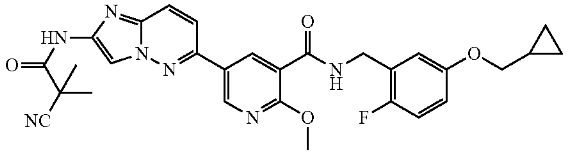 [SMILES: COc1ncc(-c2ccc3nc(NC(=O)C(C)(C)C#N)cn3n2)cc1C(=O)NCc1cc(OCC2CC2)ccc1F]

A mixture of 5-(2-(2-cyano-2-methylpropanamido)imidazo[1,2-b]pyridazin-6-yl)-2-methoxynicotinic acid (20 mg, 0.053 mmol), BOP (34.9 mg, 0.079 mmol), (5-(cyclopropylmethoxy)-2-fluorophenyl)methanamine (10.27 mg, 0.053 mmol) and Hünig's base (0.046 mL, 0.263 mmol) in DMF (1.0 mL) was stirred at rt 3 d. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 20 minutes, then a 4-minute hold at 100% B; Flow: 20 mL/min. Fractions containing the desired product were combined and dried via centrifugal evaporation. 5-[2-(2-Cyano-2,2-dimethylacetamido)imidazo[1,2-b]pyridazin-6-yl]-N-{[5-(cyclopropylmethoxy)-2-fluorophenyl]methyl}-2-methoxypyridine-3-carboxamide (6.8 mg, 12.2 μmol, 23%) was isolated.

MS ESI m/z 558.1 (M+H)

1H NMR (500 MHz, DMSO-d6) δ 11.31 (s, 1H), 8.99 (d, J=2.1 Hz, 1H), 8.91 (br t, J=5.8 Hz, 1H), 8.71 (d, J=2.1 Hz, 1H), 8.36 (s, 1H), 8.12 (d, J=9.5 Hz, 1H), 7.89 (d, J=9.5 Hz, 1H), 7.10 (t, J=9.3 Hz, 1H), 7.00-6.92 (m, 1H), 6.89-6.78 (m, 1H), 4.54 (br d, J=5.5 Hz, 2H), 4.08 (s, 3H), 3.77 (d, J=7.0 Hz, 2H), 1.70 (s, 6H), 1.21-1.14 (m, 1H), 0.54 (br d, J=7.0 Hz, 2H), 0.29 (br d, J=4.6 Hz, 2H).

Example 30: 5-{2-acetamidoimidazo[1,2-b]pyridazin-6-yl}-N-{[2-fluoro-5-(trifluoromethyl)phenyl]methyl}-2-(trifluoromethyl)pyridine-3-carboxamide

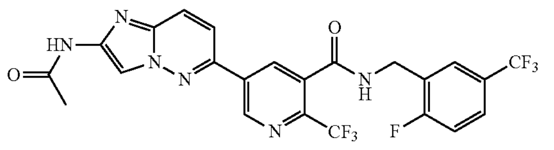

30A: N-(6-chloroimidazo[1,2-b]pyridazin-2-yl)acetamide: To a solution of 6-chloroimidazo[1,2-b]pyridazin-2-amine (320 mg, 1.898 mmol) in DCM (8 mL) was added triethylamine (0.291 mL, 2.088 mmol), DMAP (23.19 mg, 0.190 mmol) and acetic anhydride (0.197 mL, 2.088 mmol) sequentially at rt. The reaction mixture was stirred ON. The product was filtered off and dried to afford N-(6-chloroimidazo[1,2-b]pyridazin-2-yl)acetamide (194 mg, 0.912 mmol, 48.0% yield) as a tan solid. The remainder of the material remained in the mother liquor and was set aside.

MS ESI (m/z) 210.8 (M+H).

30B: (5-(ethoxycarbonyl)-6-(trifluoromethyl)pyridin-3-yl)boronic acid: A mixture of ethyl 5-bromo-2-(trifluoromethyl)nicotinate (300 mg, 1.007 mmol), 4,4,4',4',5,5,5',5'-octamethyl-2,2'-bi(1,3,2-dioxaborolane) (383 mg, 1.510 mmol), 1,1'-bis(diphenylphosphino)ferrocene palladium dichloride—$CH_2Cl_2$ adduct (82 mg, 0.101 mmol) and potassium acetate (198 mg, 2.013 mmol) in dioxane (100 mL) was degassed by bubbling nitrogen through the reaction mixture for 1 min. The reaction mixture was heated to 100° C. for 3 r. The reaction mixture was cooled to rt and used as is in the next step.

MS ESI (m/z) 264.1 (M+H).

30C: ethyl 5-(2-acetamidoimidazo[1,2-b]pyridazin-6-yl)-2-(trifluoromethyl)nicotinate: A stirred mixture of (5-(ethoxycarbonyl)-6-(trifluoromethyl)pyridin-3-yl)boronic acid (265 mg, 1.008 mmol), N-(6-chloroimidazo[1,2-b]pyridazin-2-yl)acetamide (255 mg, 1.209 mmol) and 1,1'-bis(diphenylphosphino)ferrocene-palladium(II)dichloride dichloromethane complex (41.1 mg, 0.050 mmol) in dioxane (8 mL) was degassed by bubbling nitrogen through the mixture for 5 min. Then 2M $K_3PO_4$ (aq) (1.512 mL, 3.02 mmol) was quickly added and the reaction mixture heated to 100° C. for 1.5 hr. After cooling to rt, the reaction mixture was partitioned between EtOAc (50 ml) and brine (30 ml). The organic layer was dried over anhydrous sodium sulfate. Filtration and concentration afforded a dark residue that was chromatographed on a 24 gm ISCO silica gel cartridge, eluting with a 1-10% MeOH/DCM gradient. The pure fractions were concentrated to afford a dark yellow solid that was triturated with ether and dried to afford ethyl 5-(2-acetamidoimidazo[1,2-b]pyridazin-6-yl)-2-(trifluoromethyl)nicotinate (367 mg, 0.933 mmol, 93% yield) as a yellow solid.

MS ESI (m/z) 394.2 (M+H).

30D: 5-(2-acetamidoimidazo[1,2-b]pyridazin-6-yl)-2-(trifluoromethyl)nicotinic acid, 1.5 lithium salt: LiOH, hydrate (58.5 mg, 1.392 mmol) as a solution in water (2 mL) was added to ethyl 5-(2-acetamidoimidazo[1,2-b]pyridazin-6-yl)-2-(trifluoromethyl)nicotinate (365 mg, 0.928 mmol) in THF (8 mL) at rt and the resulting mixture was stirred at rt for 18 h. The volatiles were removed in vacuo and the residue was dried to afford 5-(2-acetamidoimidazo[1,2-b]pyridazin-6-yl)-2-(trifluoromethyl)nicotinic acid, 1.5 lithium salt (349 mg, 0.929 mmol, 100% yield) as a yellow solid.

MS ESI (m/z) 366.1 (M+H). 30: A mixture of 5-(2-acetamidoimidazo[1,2-b]pyridazin-6-yl)-2-(trifluoromethyl)nicotinic acid, lithium salt (12 mg, 0.033 mmol), (2-fluoro-5-(trifluoromethyl)phenyl)methanamine (9.52 mg, 0.049 mmol), BOP (15.98 mg, 0.036 mmol) and $Et_3N$ (0.023 mL, 0.164 mmol) in DMF (0.25 mL) was agitated at rt for 16 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 4-minute hold at 100% B; Flow: 20 mL/min. Fractions containing the desired product were combined and dried via centrifugal evaporation to yield 5-{2-acetamidoimidazo[1,2-b]pyridazin-6-yl}-N-{[2-fluoro-5-(trifluoromethyl)phenyl]methyl}-2-(trifluoromethyl)pyridine-3-carboxamide (4 mg, 7.4 μmol, 22.4%).

MS ESI m/z 541.1 (M+H)

1H NMR (500 MHz, DMSO-d6) δ 11.00 (s, 1H), 9.45 (s, 1H), 9.43 (t, J=5.4 Hz, 1H), 8.67 (s, 1H), 8.38 (s, 1H), 8.19 (d, J=9.4 Hz, 1H), 7.99 (d, J=9.4 Hz, 1H), 7.82 (d, J=6.9 Hz, 1H), 7.76 (br. s., 1H), 7.48 (t, J=9.2 Hz, 1H), 4.62 (d, J=5.8 Hz, 2H), 2.12 (s, 3H).

Example 31: N-{[2-(cyclopropylmethoxy)-3,6-difluorophenyl]methyl}-5-{2-acetamidoimidazo[1,2-b]pyridazin-6-yl}-2-(trifluoromethyl)pyridine-3-carboxamide

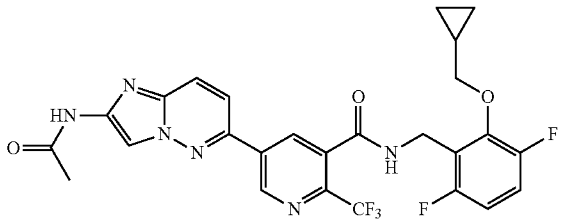 [SMILES: CC(=O)Nc1cn2nc(-c3cnc(C(F)(F)F)c(C(=O)NCc4c(F)ccc(F)c4OCC4CC4)c3)ccc2n1]

A mixture of 5-(2-acetamidoimidazo[1,2-b]pyridazin-6-yl)-2-(trifluoromethyl)nicotinic acid (15 mg, 0.041 mmol), (2-(cyclopropylmethoxy)-3,6-difluorophenyl)methanamine (8.76 mg, 0.041 mmol), BOP (19.98 mg, 0.041 mmol) and $Et_3N$ (0.029 mL, 0.205 mmol) in DMF (0.25 mL) was agitated at rt for 3 days. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 20 minutes, then a 4-minute hold at 100% B; Flow: 20 mL/min. Fractions containing the desired product were combined and dried via centrifugal evaporation to yield N-{[2-(cyclopropylmethoxy)-3,6-difluorophenyl]methyl}-5-{2-acetamidoimidazo[1,2-b]pyridazin-6-yl}-2-(trifluoromethyl)pyridine-3-carboxamide (2.6 mg, 3.9 μmol, 9.4%).

MS ESI m/z 561.22, 560.96 (M+H)

1H NMR (500 MHz, DMSO-d6) δ 10.98 (s, 1H), 9.39 (s, 1H), 9.23-8.81 (m, 1H), 8.50 (s, 1H), 8.36 (s, 1H), 8.14 (d, J=9.4 Hz, 1H), 7.93 (d, J=9.4 Hz, 1H), 7.32-7.22 (m, 1H), 6.99 (td, J=9.1, 3.4 Hz, 1H), 4.57 (br d, J=5.0 Hz, 2H), 3.94

(d, J=7.2 Hz, 2H), 2.11 (s, 3H), 1.30-1.24 (m, 1H), 0.55 (br d, J=6.6 Hz, 2H), 0.30 (br d, J=5.0 Hz, 2H).

Example 32: 5-[2-(2-cyanoacetamido)imidazo[1,2-b]pyridazin-6-yl]-2-methoxy-N-{[2-(trifluoromethoxy)phenyl]methyl}pyridine-3-carboxamide

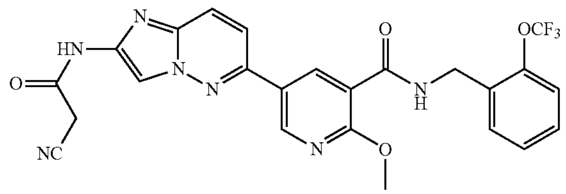 [SMILES: COc1ncc(-c2ccc3nc(NC(=O)CC#N)cn3n2)cc1C(=O)NCc1ccccc1OC(F)(F)F]

32A: N-(6-chloroimidazo[1,2-b]pyridazin-2-yl)-2-cyanoacetamide: A solution of 6-chloroimidazo[1,2-b]pyridazin-2-amine (250 mg, 1.483 mmol), 2-cyanoacetic acid (126 mg, 1.483 mmol), DIEA (1.295 mL, 7.41 mmol) and HATU (846 mg, 2.224 mmol) in DMF (8 mL) was stirred at rt ON. The reaction mixture was diluted to a total volume of 100 mL with EtOAc and washed with 10% LiCl solution (2×) and brine. The organics were dried over sodium sulfate, filtered and concentrated. Loaded onto a 24 g ISCO column, purified by flash chromatography eluting with 0-10% MeOH in DCM. Afforded N-(6-chloroimidazo[1,2-b]pyridazin-2-yl)-2-cyanoacetamide (187 mg, 0.778 mmol, 52.4% yield), an off-white solid.

MS ESI (m/z) 236.0 (M+H).

32B: methyl 5-(2-(2-cyanoacetamido)imidazo[1,2-b]pyridazin-6-yl)-2-methoxynicotinate: A mixture of N-(6-chloroimidazo[1,2-b]pyridazin-2-yl)-2-cyanoacetamide (185 mg, 0.785 mmol), methyl 2-methoxy-5-(4,4,5,5-tetramethyl-1,3,2-dioxaborolan-2-yl)nicotinate (230 mg, 0.785 mmol), and 1,1'-bis(di-tert-butylphosphino)ferrocene palladium dichloride (20.47 mg, 0.031 mmol) in 1,4-dioxane (5 mL) was degassed by bubbling nitrogen n through for 5 min. 2M $K_3PO_4$ (1.178 mL, 2.355 mmol) was added and the mixture stirred 75 min at 100° C. The reaction mixture was cooled and concentrated onto Celite, then purified by flash chromatography using a 24 g ISCO column, eluting with 0-100% EtOAc followed by 0-10% MeOH in DCM. Afforded methyl 5-(2-(2-cyanoacetamido)imidazo[1,2-b]pyridazin-6-yl)-2-methoxynicotinate (52 mg, 0.139 mmol, 17.72% yield).

MS ESI (m/z) 367.2 (M+H)

32C: 5-(2-(2-cyanoacetamido)imidazo[1,2-b]pyridazin-6-yl)-2-methoxynicotinic acid, lithium salt: To a mixture of methyl 5-(2-(2-cyanoacetamido)imidazo[1,2-b]pyridazin-6-yl)-2-methoxynicotinate (52 mg, 0.142 mmol) in tetrahydrofuran (2 mL) was added a solution of lithium hydroxide monohydrate (7.15 mg, 0.170 mmol) in water (1 mL). The reaction mixture was stirred at rt ON. The reaction mixture was concentrated to a solid to afford 5-(2-(2-cyanoacetamido)imidazo[1,2-b]pyridazin-6-yl)-2-methoxynicotinic acid, lithium salt (49 mg, 0.128 mmol, 90% yield) as a beige solid. Material was used as is in subsequent chemistry.

MS ESI (m/z) 353.1 (M+H)

32: A mixture of 5-(2-(2-cyanoacetamido)imidazo[1,2-b]pyridazin-6-yl)-2-methoxynicotinic acid, lithium salt (16 mg, 0.045 mmol), BOP (30.1 mg, 0.068 mmol), (2-(trifluoromethoxy)phenyl)methanamine (8.68 mg, 0.045 mmol) and Hünig's base (0.040 mL, 0.227 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 4-minute hold at 100% B; Flow: 20 mL/min. Fractions containing the desired product were combined and dried via centrifugal evaporation. 5-[2-(2-Cyanoacetamido)imidazo[1,2-b]pyridazin-6-yl]-2-methoxy-N-{[2-(trifluoromethoxy)phenyl]methyl}pyridine-3-carboxamide (2.8 mg, 5.3 μmol, 11.8%) was isolated.

MS ESI m/z 526 (M+H)

1H NMR (500 MHz, DMSO-d6) δ 11.30 (s, 1H), 8.96 (br d, J=2.1 Hz, 2H), 8.72 (d, J=2.1 Hz, 1H), 8.31 (s, 1H), 8.08 (br d, J=9.5 Hz, 1H), 7.84 (br d, J=9.5 Hz, 1H), 7.52-7.33 (m, 4H), 4.66-4.51 (m, 2H), 4.07 (s, 3H), 3.97 (d, J=5.2 Hz, 2H).

Example 33: 5-[2-(2-cyanoacetamido)imidazo[1,2-b]pyridazin-6-yl]-N-{[2-fluoro-5-(trifluoromethoxy)phenyl]methyl}-2-methoxypyridine-3-carboxamide

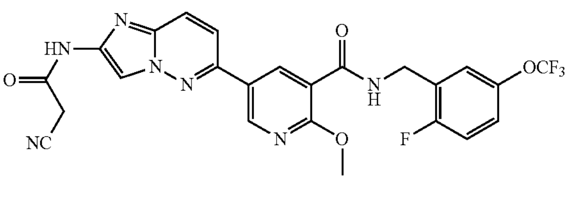 [SMILES: COc1ncc(-c2ccc3nc(NC(=O)CC#N)cn3n2)cc1C(=O)NCc1cc(OC(F)(F)F)ccc1F]

A mixture of 5-(2-(2-cyanoacetamido)imidazo[1,2-b]pyridazin-6-yl)-2-methoxynicotinic acid (16 mg, 0.045 mmol), BOP (30.1 mg, 0.068 mmol), (2-fluoro-5-(trifluoromethoxy)phenyl)methanamine (9.50 mg, 0.045 mmol) and Hünig's Base (0.040 mL, 0.227 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation. 5-[2-(2-Cyanoacetamido)imidazo[1,2-b]pyridazin-6-yl]-N-{[2-fluoro-5-(trifluoromethoxy)phenyl]methyl}-2-methoxypyridine-3-carboxamide (2.6 mg, 4.8 μmol, 10.6%) was isolated.

MS ESI m/z 543.8 (M+H)

$^1$H NMR (500 MHz, DMSO-d6) δ 9.05-8.85 (m, 2H), 8.68 (d, J=2.1 Hz, 1H), 8.31 (s, 1H), 8.08 (br d, J=9.2 Hz, 1H), 7.83 (d, J=9.5 Hz, 1H), 7.42 (br s, 1H), 7.34 (q, J=9.3 Hz, 2H), 4.67-4.52 (m, 2H), 4.08 (s, 3H), 3.44-3.38 (m, 3H).

Example 34: N-{[2-fluoro-5-(trifluoromethyl)phenyl]methyl}-5-[2-(2-hydroxyacetamido)imidazo[1,2-b]pyridazin-6-yl]-2-methoxypyridine-3-carboxamide

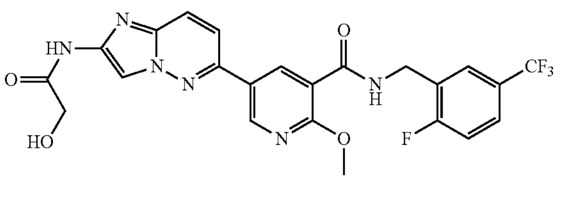 [SMILES: COc1ncc(-c2ccc3nc(NC(=O)CO)cn3n2)cc1C(=O)NCc1cc(C(F)(F)F)ccc1F]

34A: 2-(benzyloxy)-N-(6-chloroimidazo[1,2-b]pyridazin-2-yl)acetamide: A solution of 6-chloroimidazo[1,2-b]pyridazin-2-amine (250 mg, 1.483 mmol), 2-(benzyloxy)acetic acid (259 mg, 1.557 mmol), DIEA (1.295 mL, 7.41 mmol) and HATU (846 mg, 2.224 mmol) in DMF (6.5 mL) was stirred at rt ON. The reaction mixture was partitioned between EtOAc (125 mL) and water (20 mL). The organics were washed with 10% LiCl solution (2×) and brine, dried over anhydrous sodium sulfate, filtered and concentrated in vacuo. The crude residue was loaded onto a 24 g ISCO column and purified by flash chromatography, eluting with 0-100% EtOAc in hexanes followed by 0-10% MeOH in DCM. Afforded 2-(benzyloxy)-N-(6-chloroimidazo[1,2-b]pyridazin-2-yl)acetamide (428 mg, 1.284 mmol, 87% yield) as a pale yellow sold.

MS ESI (m/z) 317.4 (M+H).

34B: methyl 5-(2-(2-(benzyloxy)acetamido)imidazo[1,2-b]pyridazin-6-yl)-2-methoxynicotinate: A mixture of 2-(benzyloxy)-N-(6-chloroimidazo[1,2-b]pyridazin-2-yl)acetamide (210 mg, 0.663 mmol), methyl 2-methoxy-5-(4,4,5,5-tetramethyl-1,3,2-dioxaborolan-2-yl)nicotinate (214 mg, 0.729 mmol) and 1,1'-bis(di-tert-butylphosphino)ferrocene palladium dichloride (21.61 mg, 0.033 mmol) in 1,4-dioxane (5 mL) was degassed by bubbling nitrogen through for 5 min. Then 2M $K_3PO_4$ (0.994 mL, 1.989 mmol) was added and the mixture stirred 15 min at 100° C. The reaction mixture was partitioned between EtOAc (100 mL) and water (10 mL). The organics were washed with brine, dried over anhydrous sodium sulfate, filtered and concentrated in vacuo. The crude residue was loaded onto a 12 g ISCO column and purified by column chromatography, eluting with 0-10% MeOH in DCM. Afforded methyl 5-(2-(2-(benzyloxy)acetamido)imidazo[1,2-b]pyridazin-6-yl)-2-methoxynicotinate (159 mg, 0.355 mmol, 53.6% yield) as a yellow solid.

MS ESI (m/z) 448.1 (M+H).

34C: 5-(2-(2-(benzyloxy)acetamido)imidazo[1,2-b]pyridazin-6-yl)-2-methoxynicotinic acid, lithium salt: To a mixture of methyl 5-(2-(2-(benzyloxy)acetamido)imidazo[1,2-b]pyridazin-6-yl)-2-methoxynicotinate (159 mg, 0.355 mmol) in tetrahydrofuran (5 mL) was added a solution of lithium hydroxide monohydrate (17.89 mg, 0.426 mmol) in water (1.5 mL). The reaction mixture was stirred at rt 3 d. The mixture was concentrated to a solid to afford 5-(2-(2-(benzyloxy)acetamido)imidazo[1,2-b]pyridazin-6-yl)-2-methoxynicotinic acid, lithium salt (150 mg, 0.311 mmol, 88% yield) as a beige solid. Material used crude in the subsequent step.

MS ESI (m/z) 434.1 (M+H).

34D: 5-(2-(2-(benzyloxy)acetamido)imidazo[1,2-b]pyridazin-6-yl)-N-(2-fluoro-5-(trifluoromethyl)benzyl)-2-methoxynicotinamide: A mixture of 5-(2-(2-(benzyloxy)acetamido)imidazo[1,2-b]pyridazin-6-yl)-2-methoxynicotinic acid, lithium salt (22 mg, 0.051 mmol), BOP (33.7 mg, 0.076 mmol), (2-fluoro-5-(trifluoromethyl)phenyl)methanamine, HCl (11.65 mg, 0.051 mmol) and Hünig's base (0.044 mL, 0.254 mmol) in DMF (2.5 mL) was stirred at rt 3 d. The reaction mixture was diluted to a total volume of 75 mL with EtOAc. The organic layer was washed with 10% LiCl solution (2×) and brine, dried over anhydrous sodium sulfate, filtered and concentrated in vacuo to afford 5-(2-(2-(benzyloxy)acetamido)imidazo[1,2-b]pyridazin-6-yl)-N-(2-fluoro-5-(trifluoromethyl)benzyl)-2-methoxynicotinamide (30 mg, 0.044 mmol, 87% yield). Used as is in subsequent chemistry.

MS ESI (m/z) 609.3 (M+H).

34: A mixture of crude 5-(2-(2-(benzyloxy)acetamido)imidazo[1,2-b]pyridazin-6-yl)-N-(2-fluoro-5-(trifluoromethyl)benzyl)-2-methoxynicotinamide (30 mg, 0.049 mmol) and 10% Pd/C (2.62 mg, 2.465 μmol) in acetic acid (2 mL) was degassed by vacuum and flooded with hydrogen gas. The reaction mixture was stirred at rt 5 h. The reaction/mixture was filtered and concentrated to an oil. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford N-{[2-fluoro-5-(trifluoromethyl)phenyl]methyl}-5-[2-(2-hydroxyacetamido)imidazo[1,2-b]pyridazin-6-yl]-2-methoxypyridine-3-carboxamide (4.9 mg, 9.5 μmol, 19.3%).

MS ESI m/z 519.1 (M+H)

1H NMR (500 MHz, DMSO-d6) δ 10.39 (s, 1H), 9.08 (br t, J=5.9 Hz, 1H), 9.02 (d, J=2.4 Hz, 1H), 8.70 (d, J=2.4 Hz, 1H), 8.38 (s, 1H), 8.12 (d, J=9.4 Hz, 1H), 7.99-7.80 (m, 2H), 7.76 (br s, 1H), 7.49 (br t, J=9.2 Hz, 2H), 4.65 (br d, J=5.9 Hz, 2H), 4.11 (br d, J=5.7 Hz, 2H), 4.08 (s, 3H).

Example 35: N-{[2-fluoro-5-(trifluoromethoxy)phenyl]methyl}-5-[2-(2-hydroxyacetamido)imidazo[1,2-b]pyridazin-6-yl]-2-methoxypyridine-3-carboxamide

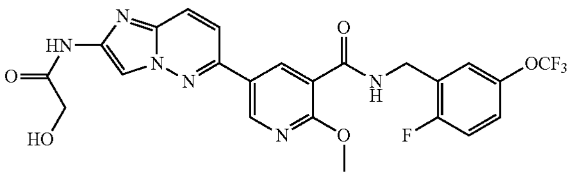

A mixture of 5-(2-(2-(benzyloxy)acetamido)imidazo[1,2-b]pyridazin-6-yl)-N-(2-fluoro-5-(trifluoromethoxy)benzyl)-2-methoxynicotinamide (28 mg, 0.045 mmol) and 10% Pd/C (2.386 mg, 2.242 μmol) in EtOH (1.5 mL) was degassed by vacuum and flooded with hydrogen gas. The reaction mixture was stirred ON at rt. Acetic acid (3 mL) and fresh 10% Pd/C catalyst (10 mg) were added. The reaction mixture was degassed and flooded with hydrogen and stirred ON at rt. The reaction mixture was filtered and concentrated to an oil. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 6-minute hold at 100% B; Flow: 20 mL/min. Fractions containing the desired product were combined and dried via centrifugal evaporation. N-{[2-Fluoro-5-(trifluoromethoxy)phenyl]methyl}-5-[2-(2-hydroxyacetamido)imidazo[1,2-b]pyridazin-6-yl]-2-methoxypyridine-3-carboxamide (5.6 mg, 10.5 μmol, 23.3%) was isolated.

MS ESI m/z 535.2 (M+H)

$^1$H NMR (500 MHz, DMSO-d6) δ 10.39 (s, 1H), 9.11-8.98 (m, 2H), 8.70 (d, J=2.4 Hz, 1H), 8.38 (s, 1H), 8.12 (d, J=9.5 Hz, 1H), 7.89 (d, J=9.5 Hz, 1H), 7.47-7.35 (m, 3H), 4.60 (br d, J=5.8 Hz, 2H), 4.15-4.10 (m, 2H), 4.09-4.05 (m, 3H), 3.18 (br s, 1H).

Example 36: N-{[2-fluoro-5-(trifluoromethoxy)phenyl]methyl}-5-[2-(2-hydroxy-2-methylpropanamido)imidazo[1,2-b]pyridazin-6-yl]-2-methoxypyridine-3-carboxamide

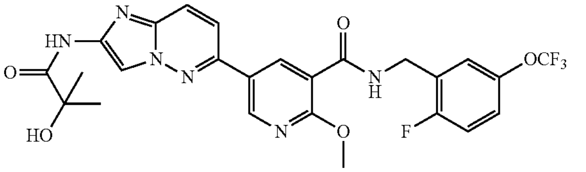 [SMILES: COc1ncc(-c2ccc3nc(NC(=O)C(C)(C)O)cn3n2)cc1C(=O)NCc1cc(OC(F)(F)F)ccc1F]

36A: N-(6-chloroimidazo[1,2-b]pyridazin-2-yl)-2-hydroxy-2-methylpropanamide: A solution of 6-chloroimidazo[1,2-b]pyridazin-2-amine (225 mg, 1.335 mmol), 2-hydroxy-2-methylpropanoic acid (153 mg, 1.468 mmol), and BOP (885 mg, 2.002 mmol) in DMF (8 mL) and DIEA (0.932 mL, 5.34 mmol) was stirred at rt ON. The product was filtered off and dried to afford N-(6-chloroimidazo[1,2-b]pyridazin-2-yl)-2-hydroxy-2-methylpropanamide (500 mg, 0.864 mmol, 64.7% yield) as a yellow solid. Attempted purification was ineffective, so the impure material (~50% purity) was used as is in subsequent chemistry.

36B: methyl 5-(2-(2-hydroxy-2-methylpropanamido)imidazo[1,2-b]pyridazin-6-yl)-2-methoxynicotinate: A mixture of N-(6-chloroimidazo[1,2-b]pyridazin-2-yl)-2-hydroxy-2-methylpropanamide (96 mg, 0.375 mmol), methyl 2-methoxy-5-(4,4,5,5-tetramethyl-1,3,2-dioxaborolan-2-yl)nicotinate (100 mg, 0.341 mmol) and 1,1'-bis(di-tert-butylphosphino)ferrocene palladium dichloride (6.67 mg, 10.23 µmol) in 1,4-dioxane (2.5 mL) was degassed by bubbling $N_2$ through for 5 min. 2M $K_3PO_4$ (0.512 mL, 1.023 mmol) was added and the reaction mixture stirred 15 min at 100° C. The crude reaction mixture was concentrated directly onto Celite and purified by flash column chromatography on an Isco system (24 g, 0-10% MeOH/$CH_2Cl_2$). Afforded methyl 5-(2-(2-hydroxy-2-methylpropanamido)imidazo[1,2-b]pyridazin-6-yl)-2-methoxynicotinate (82 mg, 0.213 mmol, 62.4% yield) as a tan solid, appears to be a mixture of acylated and non-acylated material which was used as is in subsequent chemistry.

MS ESI (m/z) 386.2 (M+H)

36C: 5-(2-(2-hydroxy-2-methylpropanamido)imidazo[1,2-b]pyridazin-6-yl)-2-methoxynicotinic acid: To a mixture of methyl 5-(2-(2-hydroxy-2-methylpropanamido)imidazo[1,2-b]pyridazin-6-yl-2-methoxynicotinate and methyl 5-(2-aminoimidazo[1,2-b]pyridazin-6-yl-2-methoxynicotinate (82 mg, 0.213 mmol) in tetrahydrofuran (3 mL) in water (1.5 mL). The reaction mixture was stirred 90 min at rt and concentrated to a solid. The solid was azeotroped with toluene to afford 5-(2-(2-hydroxy-2-methylpropanamido)imidazo[1,2-b]pyridazin-6-yl)-2-methoxynicotinic acid (80 mg, 0.194 mmol, 91% yield) a tan solid and a mixture with the non-acylated material. The crude material was used as is in subsequent chemistry.

MS ESI (m/z) 372.2 (M+H)

36: A mixture of 5-(2-(2-hydroxy-2-methylpropanamido)imidazo[1,2-b]pyridazin-6-yl)-2-methoxynicotinic acid (39 mg, 0.105 mmol), BOP (69.7 mg, 0.158 mmol), (2-fluoro-5-(trifluoromethoxy)phenyl)methanamine (21.96 mg, 0.105 mmol) and Hünig's base (0.092 mL, 0.525 mmol) in DMF (1 mL) was stirred at rt ON. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-80% B over 20 minutes, then a 4-minute hold at 100% B; Flow: 20 mL/min. Fractions containing the desired product were combined and dried via centrifugal evaporation to afford the desired product, N-(2-fluoro-5-(trifluoromethoxy)benzyl)-5-(2-(2-hydroxy-2-methylpropanamido)imidazo[1,2-b]pyridazin-6-yl)-2-methoxynicotinamide (13.9 mg, 0.024 mmol, 46.6% yield). Additionally, 5-(2-aminoimidazo[1,2-b]pyridazin-6-yl)-N-(2-fluoro-5-(trifluoromethoxy)benzyl)-2-methoxynicotinamide (13.2 mg, 0.027 mmol, 52.2% yield) [BMT-313951-01-001] was also isolated.

MS ESI m/z 563.2 (M+H)

$^1$H NMR (500 MHz, DMSO-$d_6$) δ 9.81 (s, 1H), 9.03 (br t, J=6.0 Hz, 1H), 8.96 (d, J=2.4 Hz, 1H), 8.67 (d, J=2.4 Hz, 1H), 8.34 (s, 1H), 8.07 (d, J=9.5 Hz, 1H), 7.84 (d, J=9.5 Hz, 1H), 7.43-7.29 (m, 4H), 4.58 (br d, J=5.8 Hz, 2H), 4.06 (s, 3H), 1.38 (s, 6H).

Example 37: 5-(2-acetamidoimidazo[1,2-b]pyridazin-6-yl)-N-(2-fluoro-5-methoxybenzyl)-2,6-dimethylnicotinamide

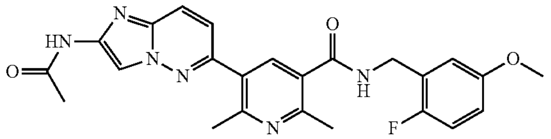 [SMILES: COc1ccc(F)c(CNC(=O)c2cc(-c3ccc4nc(NC(C)=O)cn4n3)c(C)nc2C)c1]

37A: ethyl (2Z,3E)-2-(1-aminoethylidene)-5-oxohex-3-enoate: To a solution of ethyl (Z)-3-aminobut-2-enoate (2 g, 15.48 mmol) in ethanol (175 mL) was added 4-(trimethylsilyl)but-3-yn-2-one (2.98 mL, 17.81 mmol) and the resulting solution was stirred at 50° C. over 2 nights. The crude reaction mixture was cooled to rt and concentrated to an oil [in a cold water bath]. The crude product was loaded onto a 40 g ISCO column and purified by column chromatography, eluting with 0-100% EtOAc in hexanes. The product eluted at 100% EtOAc [eluted last] and was a rather small peak with the detector set to 230 nM and 243 nM. Afforded the desired dieneone as a yellow crystalline solid, ethyl (2Z,3E)-2-(1-aminoethylidene)-5-oxohex-3-enoate (1.78 g, 8.12 mmol, 52.5% yield).

MS ESI (m/z) 198.3 (M+H)

37B: ethyl 5-bromo-2,6-dimethylnicotinate: NBS (1.928 g, 10.83 mmol) was added to a solution of ethyl (2Z,3E)-2-(1-aminoethylidene)-5-oxohex-3-enoate (1.78 g, 9.02 mmol) in ethanol (85 mL) and the resulting solution was stirred at 0° C. for 30 min. The crude reaction mixture was concentrated to an oil, loaded onto a 80 g ISCO column and purified by column chromatography, eluting with 0-100% EtOAc in hexanes. Afforded ethyl 5-bromo-2,6-dimethylnicotinate (1.92 g, 7.07 mmol, 78% yield) as a crystalline light yellow solid.

MS ESI (m/z) 259.9 (M+H)

37C: ethyl 5-(2-acetamidoimidazo[1,2-b]pyridazin-6-yl)-2,6-dimethylnicotinate: A mixture of N-(6-chloroimidazo[1,2-b]pyridazin-2-yl)acetamide (500 mg, 2.374 mmol), 4,4,4',4',5,5,5',5'-octamethyl-2,2'-bi(1,3,2-dioxaborolane) (965 mg, 3.80 mmol), $PdCl_2(dppf)-CH_2Cl_2$ adduct (194 mg, 0.237 mmol) and potassium acetate (699 mg, 7.12 mmol) in dioxane (11 mL) was heated to 100° C. for 2 h. The mixture was cooled to rt. Ethyl 5-bromo-2,6-dimethylnicotinate (550 mg, 2.131 mmol) and 1,1'-bis(di-tert-butylphosphino)ferrocene palladium, dichloride (69.4 mg, 0.107 mmol) in 1,4-dioxane (9 mL) was added and the mixture degassed by bubbling nitrogen through for 5 min. 2M $K_3PO_4$ (3.20 mL, 6.39 mmol) was added and the mixture stirred 15 min at 100° C. The reaction mixture was cooled and partitioned between EtOAc (100 mL) and water (10 mL) water. The organic layer was washed with brine, dried over sodium sulfate, filtered and concentrated in vacuo. The crude residue was loaded onto a 24 g ISCO column and purified by column chromatography, eluting with 0-10% MeOH in DCM. Afforded ethyl 5-(2-acetamidoimidazo[1,2-b]pyridazin-6-yl)-2,6-dimethylnicotinate (750 mg, 1.910 mmol, 90% yield) as a yellow solid.

MS ESI (m/z) 354.4 (M+H)

37D: 5-(2-acetamidoimidazo[1,2-b]pyridazin-6-yl)-2,6-dimethylnicotinic acid, lithium salt: To a mixture of ethyl 5-(2-acetamidoimidazo[1,2-b]pyridazin-6-yl)-2,6-dimethylnicotinate (750 mg, 2.122 mmol) in THF (10 mL) was added a solution of lithium hydroxide monohydrate (107 mg, 2.55 mmol) in water (1.5 mL). The mixture was stirred 1 h at rt and was left in the fridge for 3 d. Additional lithium hydroxide monohydrate (20 mg) in water (0.5 mL) was added and the reaction mixture stirred at rt ON. The reaction mixture was concentrated to a solid to afford 5-(2-acetamidoimidazo[1,2-b]pyridazin-6-yl)-2,6-dimethylnicotinic acid (655 mg, 1.812 mmol, 85% yield) as a yellow solid.

MS ESI (m/z) 326.2 (M+H)

37: A mixture of 5-(2-acetamidoimidazo[1,2-b]pyridazin-6-yl)-2,6-dimethylnicotinic acid (20 mg, 0.061 mmol), Hünig's base (0.054 mL, 0.307 mmol), (2-fluoro-5-methoxyphenyl)methanamine (9.54 mg, 0.061 mmol) and BOP (40.8 mg, 0.092 mmol) in DMF (1.0 mL) was stirred at rt 3 d. The crude reaction mixture was purified via preparative LC/MS with the following conditions: Column: XBridge C18, 30×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 9-49% B over 20 minutes, then a 2-minute hold at 100% B; Flow: 45 mL/min. Fractions containing the desired product were combined and dried via centrifugal evaporation to afford 5-(2-acetamidoimidazo[1,2-b]pyridazin-6-yl)-N-(2-fluoro-5-methoxybenzyl)-2,6-dimethylnicotinamide (11.3 mg, 0.024 mmol, 39.7% yield).

MS ESI (m/z) 463.2 (M+H)

$^1$H NMR (500 MHz, DMSO-$d_6$) δ 10.93 (s, 1H), 9.03 (br s, 1H), 8.29 (s, 1H), 8.07 (br d, J=9.5 Hz, 1H), 7.86 (s, 1H), 7.45 (br d, J=9.5 Hz, 1H), 7.12 (br t, J=9.3 Hz, 1H), 6.95 (br s, 1H), 6.86 (br d, J=8.9 Hz, 1H), 4.47 (br d, J=5.5 Hz, 2H), 3.66-3.59 (m, 3H), 2.57-2.54 (m, 6H), 2.12 (s, 3H).

Example 38: N-(2-fluoro-5-(trifluoromethoxy)benzyl)-5-(2-(2-hydroxyacetamido)imidazo[1,2-b]pyridazin-6-yl)-2,6-dimethylnicotinamide

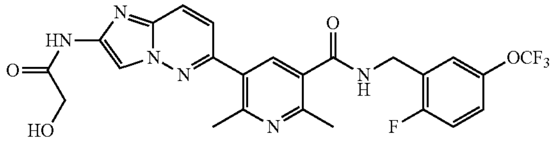 [SMILES: Cc1nc(C)c(-c2ccc3nc(NC(=O)CO)cn3n2)cc1C(=O)NCc1cc(OC(F)(F)F)ccc1F]

38A: 5-bromo-N-(2-fluoro-5-(trifluoromethoxy)benzyl)-2,6-dimethylnicotinamide: A mixture of 5-bromo-2,6-dimethylnicotinic acid (150 mg, 0.652 mmol), BOP (433 mg, 0.978 mmol), (2-fluoro-5-(trifluoromethoxy)phenyl)methanamine (150 mg, 0.717 mmol) and Hünig's Base (0.569 mL, 3.26 mmol) in DMF (4 mL) was stirred at rt ON. The reaction mixture was diluted to a total volume of 75 mL with ethyl acetate. The organics were washed with 10% aqueous lithium chloride solution and brine, dried over anhydrous sodium sulfate, filtered and concentrated in vacuo. The crude residue was loaded onto a 24 g ISCO column and purified by column chromatography, eluting with 0-100% EtOAc in hexanes. Afforded 5-bromo-N-(2-fluoro-5-(trifluoromethoxy)benzyl)-2,6-dimethylnicotinamide (199 mg, 0.463 mmol, 71.0% yield) as a white solid.

MS ESI (m/z) 421.2 (M+H)

38B: 2-((6-chloroimidazo[1,2-b]pyridazin-2-yl)amino)-2-oxoethyl acetate: A solution of 6-chloroimidazo[1,2-b]pyridazin-2-amine (800 mg, 4.75 mmol), 2-acetoxyacetic acid (588 mg, 4.98 mmol), DIEA (4.14 mL, 23.73 mmol) and BOP (3148 mg, 7.12 mmol) in DMF (18 mL) was stirred at rt ON. After stirring ON, the reaction mixture was partitioned between EtOAc (125 mL) and water (20 mL). The organics were washed with 10% LiCl solution (2×) and brine, dried over sodium sulfate, filtered and concentrated. The crude residue was loaded onto a 24 g ISCO column, purifying by flash chromatography eluting with 0-100% EtOAc in hexanes and then 0-10% MeOH in DCM. Afforded 2-((6-chloroimidazo[1,2-b]pyridazin-2-yl)amino)-2-oxoethyl acetate (1.079 g, 3.82 mmol, 80% yield) as a pale yellow sold.

MS ESI (m/z) 269.1 (M+H)

38C: 2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl acetate: A mixture of 2-((6-chloroimidazo[1,2-b]pyridazin-2-yl)amino)-2-oxoethyl acetate (54 mg, 0.201 mmol), 4,4,4',4',5,5,5',5'-octamethyl-2,2'-bi(1,3,2-dioxaborolane) (82 mg, 0.322 mmol), $PdCl_2$(dppf)-$CH_2Cl_2$ adduct (16.4 mg, 0.020 mmol) and potassium acetate (59.2 mg, 0.603 mmol) in dioxane (2 mL) was heated to 100° C. for 1 h. After cooling to rt, 5-bromo-N-(2-fluoro-5-(trifluoromethoxy)benzyl)-2,6-dimethylnicotinamide (64 mg, 0.152 mmol) and 1,1'-bis(di-tert-butylphosphino)ferrocene palladium dichloride (9.90 mg, 0.015 mmol) were added. The reaction mixture was degassed by bubbling nitrogen through for 5 min. 2M $K_3PO_4$ (0.228 mL, 0.456 mmol) was added and the mixture stirred 10 min at 100° C. The reaction mixture was concentrated directly onto Celite and loaded onto 12 g ISCO column for purification by column chromatography, eluting with 0-10% MeOH in DCM. Afforded 2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl acetate (78 mg, 0.122 mmol, 80% yield).

MS ESI (m/z) 575.4 (M+H)

38: To a mixture of 2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl acetate (78 mg, 0.136 mmol) in tetrahydrofuran (2 mL) was added a solution of lithium hydroxide monohydrate (6.84 mg, 0.163 mmol) in water (1.5 mL). The mixture was stirred 1 h at rt. The reaction mixture was concentrated onto Celite and purified by column chromatography on the Isco system, eluting with 0-15% MeOH in DCM. Afforded a yellow solid, N-(2-fluoro-5-(trifluoromethoxy)benzyl)-5-(2-(2-hydroxyacetamido)imidazo[1,2-b]pyridazin-6-yl)-2,6-dimethylnicotinamide (39 mg, 0.072 mmol, 52.9% yield).

MS ESI (m/z) 533.4 (M+H)

$^1$H NMR (400 MHz, DMSO-$d_6$) δ 10.37 (s, 1H), 9.09 (br t, J=5.7 Hz, 1H), 8.36 (s, 1H), 8.13 (d, J=9.3 Hz, 1H), 7.90 (s, 1H), 7.51-7.34 (m, 4H), 5.55 (br t, J=6.1 Hz, 1H), 4.53 (br d, J=5.6 Hz, 2H), 4.11 (d, J=6.0 Hz, 2H), 2.60-2.54 (m, 6H)

Example 39: N-{[2-fluoro-5-(trifluoromethoxy)phenyl]methyl}-5-[2-(2-hydroxyacetamido)imidazo[1,2-b]pyridazin-6-yl]-2-methylpyridine-3-carboxamide

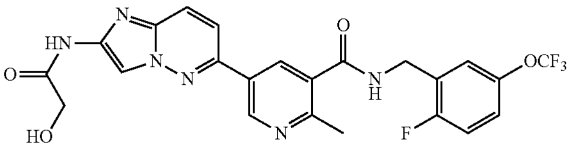 [SMILES: Cc1ncc(-c2ccc3nc(NC(=O)CO)cn3n2)cc1C(=O)NCc1cc(OC(F)(F)F)ccc1F]

39A: 2-(benzyloxy)-N-(6-chloroimidazo[1,2-b]pyridazin-2-yl)acetamide: A solution of 6-chloroimidazo[1,2-b]pyridazin-2-amine (250 mg, 1.483 mmol), 2-(benzyloxy)acetic acid (259 mg, 1.557 mmol), DIEA (1.295 mL, 7.41 mmol) and HATU (846 mg, 2.224 mmol) in DMF (6.5 mL) was stirred at rt ON. After stirring ON, the reaction mixture was partitioned between EtOAc (125 mL) and water (20 mL). The organic layer was washed with 10% LiCl solution (2×) and brine, dried over anhydrous sodium sulfate, filtered and concentrated in vacuo. The crude residue was loaded onto a 24 g ISCO column and purified by flash chromatography, eluting with 0-100% EtOAc in hexanes followed by 0-10% MeOH in DCM. Afforded 2-(benzyloxy)-N-(6-chloroimidazo[1,2-b]pyridazin-2-yl)acetamide (428 mg, 1.284 mmol, 87% yield) as a pale yellow sold.

MS ESI (m/z) 317.4 (M+H)

39B: ethyl 5-(2-(2-(benzyloxy)acetamido)imidazo[1,2-b]pyridazin-6-yl)-2-methylnicotinate: A mixture of 2-(benzyloxy)-N-(6-chloroimidazo[1,2-b]pyridazin-2-yl)acetamide (220 mg, 0.695 mmol), 4,4,4',4',5,5,5',5'-octamethyl-2,2'-bi(1,3,2-dioxaborolane) (282 mg, 1.111 mmol), $PdCl_2$(dppf)-$CH_2Cl_2$ adduct (56.7 mg, 0.069 mmol) and potassium acetate (204 mg, 2.084 mmol) in dioxane (5 mL) was heated to 100° C. for 1 h. Ethyl 5-bromo-2-methylnicotinate (150 mg, 0.615 mmol) and 1,1'-bis(di-tert-butylphosphino)ferrocene palladium dichloride (20.03 mg, 0.031 mmol) in 1,4-dioxane (5 mL) were added and the reaction mixture degassed by bubbling nitrogen through for 5 min. 2M $K_3PO_4$ (0.922 mL, 1.844 mmol) was added and the mixture stirred 15 min at 100° C. The reaction mixture was concentrated directly on to Celite and purified by flash chromatography using a 24 g ISCO column, eluting with 0-10% MeOH in DCM. Afforded ethyl 5-(2-(2-(benzyloxy)acetamido)imidazo[1,2-b]pyridazin-6-yl)-2-methylnicotinate (275 mg, 0.556 mmol, 90% yield) as a tan solid.

MS ESI (m/z) 446.5 (M+H)

39C: 5-(2-(2-(benzyloxy)acetamido)imidazo[1,2-b]pyridazin-6-yl)-2-methylnicotinic acid, lithium salt: To a mixture of ethyl 5-(2-(2-(benzyloxy)acetamido)imidazo[1,2-b]pyridazin-6-yl)-2-methylnicotinate (275 mg, 0.617 mmol) in tetrahydrofuran (4 mL) was added a solution of lithium hydroxide monohydrate (31.1 mg, 0.741 mmol) in water (1.5 mL). The mixture was stirred ON at rt. A a solution of LiOH monohydrate (5 mg) in water (0.5 mL) was added and the mixture stirred ON. The reaction mixture was concentrated to a solid to afford 5-(2-(2-(benzyloxy)acetamido)imidazo[1,2-b]pyridazin-6-yl)-2-methylnicotinic acid (250 mg, 0.539 mmol, 87% yield) as a beige solid.

MS ESI (m/z) 418.3

39D: 5-(2-(2-(benzyloxy)acetamido)imidazo[1,2-b]pyridazin-6-yl)-N-(2-fluoro-5-(trifluoromethoxy)benzyl)-2-methylnicotinamide: A mixture of 5-(2-(2-(benzyloxy)acetamido)imidazo[1,2-b]pyridazin-6-yl)-2-methylnicotinic acid (20 mg, 0.048 mmol), Hünig's Base (0.042 mL, 0.240 mmol), BOP (31.8 mg, 0.072 mmol) and (2-fluoro-5-(trifluoromethoxy)phenyl)methanamine, HCl (12.94 mg, 0.053 mmol) in DMF (2.5 mL) was stirred at rt ON. The reaction mixture was diluted with ethyl acetate (75 mL) and washed with 10% LiCl solution and brine. The organics were dried over anhydrous sodium sulfate, filtered and concentrated in vacuo. The crude residue was loaded onto a 4 g ISCO column and purified by column chromatography, eluting with 0-100% EtOAc in hexanes. Afforded 5-(2-(2-(benzyloxy)acetamido)imidazo[1,2-b]pyridazin-6-yl)-N-(2-fluoro-5-(trifluoromethoxy)benzyl)-2-methylnicotinamide (25 mg, 0.037 mmol, 77% yield).

MS ESI (m/z) 609.6 (M+H)

39: A mixture of 5-(2-(2-(benzyloxy)acetamido)imidazo[1,2-b]pyridazin-6-yl)-N-(2-fluoro-5-(trifluoromethoxy)benzyl)-2-methylnicotinamide (25 mg, 0.041 mmol) and 10% Pd/C (10.93 mg, 10.27 μmol) in acetic acid (2 mL) was degassed by vacuum and then flooded with hydrogen gas. The reaction mixture was stirred at rt ON. The reaction mixture was filtered and concentrated to an oil. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammoniumacetate; Gradient: 13-53% B over 20 minutes, then a 4-minute hold at 100% B; Flow: 20 mL/min. Fractions containing the desired product were combined and dried via centrifugal evaporation to afford N-(2-fluoro-5-(trifluoromethoxy)benzyl)-5-(2-(2-hydroxyacetamido)imidazo[1,2-b]pyridazin-6-yl)-2-methylnicotinamide (1.4 mg, 2.64 μmol, 6.44% yield).

MS ESI (m/z) 518.9 (M+H)

$^1$H NMR (500 MHz, DMSO-d6) δ 10.38 (s, 1H), 9.28-9.15 (m, 2H), 8.40 (s, 2H), 8.15 (d, J=9.5 Hz, 1H), 7.91 (d, J=9.5 Hz, 1H), 7.46 (br s, 1H), 7.40 (br d, J=7.3 Hz, 2H), 4.58 (br d, J=5.8 Hz, 2H), 4.12 (br s, 2H), 3.60-3.26 (m, 1H), 2.59 (s, 3H).

TABLE 1

Compounds in Table 1 were prepared by methods as described in Example 14.

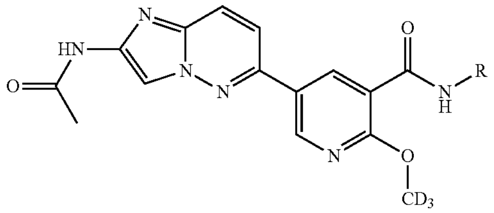

| Ex | Name | R | Obs. MS Ion | NMR Assignments |
|---|---|---|---|---|
| 40 | 5-{2-acetamidoimidazo[1,2-b]pyridazin-6-yl}-N-[(2-fluoro-5-methoxyphenyl)methyl]-2-($D_3$)methoxypyridine-3-carboxamide | 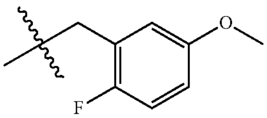 [SMILES: *Cc1cc(OC)ccc1F] | 468.2 | 1H NMR (500 MHz, DMSO-d6) δ 10.77 (br s, 1H), 8.97 (s, 1H), 8.86-8.75 (m, 1H), 8.71 (d, J = 2.2 Hz, 1H), 8.31 (s, 1H), 8.05 (d, J = 9.4 Hz, 1H), 7.81 (d, J = 9.4 Hz, 1H), 7.16-6.97 (m, 2H), 6.93-6.79 (m, 2H), 4.57 (br d, J = 5.8 Hz, 2H), 3.77-3.74 (m, 2H), 2.13 (s, 3H) |
| 41 | 5-{2-acetamidoimidazo[1,2-b]pyridazin-6-yl}-N-[(1S)-1-[2-fluoro-5-(trifluoromethoxy)phenyl]ethyl]-2-($D_3$)methoxypyridine-3-carboxamide | 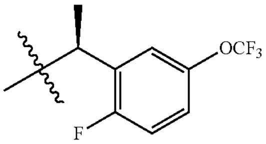 [SMILES: *[C@@H](C)c1cc(OC(F)(F)F)ccc1F] | 536.1 | 1H NMR (400 MHz, DMSO-d6) δ 10.91 (s, 1H), 8.99 (d, J = 2.4 Hz, 1H), 8.93 (d, J = 7.7 Hz, 1H), 8.56 (d, J = 2.4 Hz, 1H), 8.31 (s, 1H), 8.09 (d, J = 9.4 Hz, 1H), 7.91-7.79 (m, 1H), 7.57 (br d, J = 4.3 Hz, 1H), 7.42-7.32 (m, 2H), 5.38 (quin, J = 7.1 Hz, 1H), 2.17-2.07 (m, 3H), 1.52-1.47 (m, 3H). |
| 42 | 5-{2-acetamidoimidazo[1,2-b]pyridazin-6-yl}-N-{[2-fluoro-6-(2,2,2-trifluoroethoxy)phenyl]methyl}-2-($D_3$)methoxypyridine-3-carboxamide | 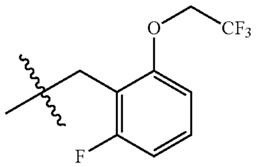 [SMILES: *Cc1c(F)cccc1OCC(F)(F)F] | 535.9 | 1H NMR (500 MHz, DMSO-d6) d 10.91 (br s, 1H), 9.07-8.87 (m, 1H), 8.84-8.67 (m, 1H), 8.46 (br s, 1H), 8.31 (br s, 1H), 8.08 (br d, J = 8.5 Hz, 1H), 7.93-7.78 (m, 1H), 7.43-7.28 (m, 1H), 7.04 (br d, J = 8.2 Hz, 1H), 6.96 (br t, J = 8.7 Hz, 1H), 4.96-4.75 (m, 2H), 4.61 (br d, J = 4.9 Hz, 2H), 2.17-2.09 (m, 3H). |
| 43 | N-{[3,5-difluoro-2-(oxan-3-yloxy)phenyl]methyl}-5-{2-acetamidoimidazo[1,2-b]pyridazin-6-yl}-2-($D_3$)methoxypyridine-3-carboxamide | 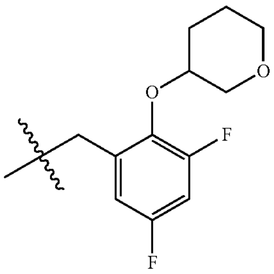 [SMILES: *Cc1cc(F)cc(F)c1OC1CCCOC1] | 556.2 | 1H NMR (500 MHz, DMSO-d6) d 11.10-10.65 (m, 1H), 8.98 (s, 1H), 8.92 (br t, J = 5.8 Hz, 1H), 8.73 (s, 1H), 8.34 (br s, 1H), 8.06 (br s, 1H), 7.84 (br d, J = 8.5 Hz, 1H), 7.22 (br t, J = 8.7 Hz, 1H), 7.02 (br d, J = 8.9 Hz, 1H), 4.70-4.53 (m, 2H), 4.17 (br s, 1H), 3.77 (br d, J = 11.9 Hz, 1H), 3.67-3.52 (m, 1H), 3.18 (d, J = 4.9 Hz, 1H), 2.58-2.54 (m, 2H), 2.12 (br s, 2H), 2.05-1.96 (m, 1H), 1.95-1.79 (m, 2H), 1.52 (br d, J = 5.2 Hz, 1H). |
| 44 | N-({3,5-difluoro-2-[(3R)-oxolan-3-yloxy]phenyl}methyl)-5-{2-acetamidoimidazo[1,2-b]pyridazin-6-yl}-2-($D_3$)methoxypyridine-3-carboxamide | 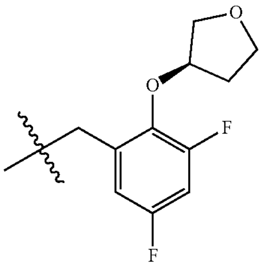 [SMILES: *Cc1cc(F)cc(F)c1O[C@@H]1CCOC1] | 542.0 | 1H NMR (500 MHz, DMSO-d6) δ 10.91 (s, 1H), 9.00 (d, J = 2.1 Hz, 1H), 8.92 (br t, J = 5.8 Hz, 1H), 8.74 (d, J = 2.1 Hz, 1H), 8.32 (s, 1H), 8.09 (d, J = 9.5 Hz, 1H), 7.86 (d, J = 9.5 Hz, 1H), 7.26 (br t, J = 8.7 Hz, 1H), 7.03 (br d, J = 9.2 Hz, 1H), 5.01 (br s, 1H), 4.62-4.49 (m, 2H), 4.02-3.90 (m, 2H), 3.87-3.79 (m, 1H), 3.75 (dd, J = 10.4, 3.7 Hz, 1H), 2.21-2.13 (m, 2H), 2.14-2.10 (m, 3H). |
| 45 | N-({3,5-difluoro-2-[(3S)-oxolan-3-yloxy]phenyl}methyl)-5-{2-acetamidoimidazo[1,2-b]pyridazin-6-yl}-2-($D_3$)methoxypyridine-3-carboxamide | 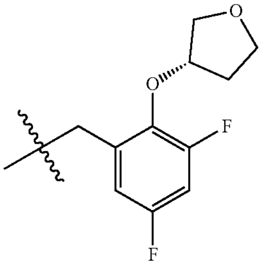 [SMILES: *Cc1cc(F)cc(F)c1O[C@H]1CCOC1] | 541.9 | 1H NMR (500 MHz, DMSO-d6) δ 10.78 (br s, 1H), 8.98 (d, J = 2.1 Hz, 1H), 8.81 (br t, J = 5.7 Hz, 1H), 8.73 (d, J = 2.3 Hz, 1H), 8.31 (s, 1H), 8.06 (d, J = 9.4 Hz, 1H), 7.82 (d, J = 9.4 Hz, 1H), 7.32-7.12 (m, 1H), 7.04 (br d, J = 9.3 Hz, 1H), 5.01 (br s, 1H), 4.67-4.48 (m, 2H), 4.04-3.89 (m, 2H), 3.89-3.71 (m, 2H), 3.29 (br s, 1H), 2.20-2.16 (m, 1H), 2.13 (s, 3H). |

TABLE 1-continued

Compounds in Table 1 were prepared by methods as described in Example 14.

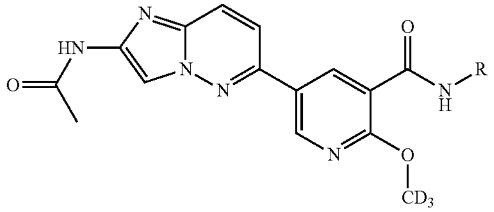

| Ex | Name | R | Obs. MS Ion | NMR Assignments |
|---|---|---|---|---|
| 46 | N-{[3,5-difluoro-2-(oxan-4-yloxy)phenyl](deutero)methyl}-5-{2-acetamidoimidazo[1,2-b]pyridazin-6-yl}-2-($D_3$)methoxypyridine-3-carboxamide | 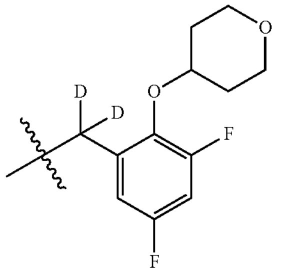 [SMILES: *C([2H])([2H])c1cc(F)cc(F)c1OC1CCOCC1] | 558.2 | 1H NMR (500 MHz, DMSO-d6) δ 10.91 (s, 1H), 8.99 (d, J = 2.1 Hz, 1H), 8.93 (s, 1H), 8.73 (d, J = 2.4 Hz, 1H), 8.31 (s, 1H), 8.08 (d, J = 9.5 Hz, 1H), 7.85 (d, J = 9.5 Hz, 1H), 7.31-7.16 (m, 1H), 7.03 (br d, J = 9.2 Hz, 1H), 4.31 (dt, J = 9.1, 4.8 Hz, 1H), 3.96-3.87 (m, 2H), 2.57-2.56 (m, 2H), 2.12 (s, 3H), 1.98 (br d, J = 11.6 Hz, 2H), 1.77-1.68 (m, 2H). |
| 47 | 5-{2-acetamidoimidazo[1,2-b]pyridazin-6-yl}-N-[(1R)-1-[2-fluoro-5-(trifluoromethoxy)phenyl]ethyl]-2-($D_3$)methoxypyridine-3-carboxamide | 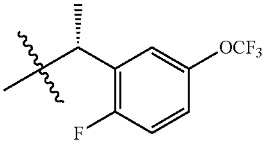 [SMILES: *[C@H](C)c1cc(OC(F)(F)F)ccc1F] | 536.1 | 1H NMR (400 MHz, DMSO-d6) δ 10.91 (s, 1H), 8.99 (d, J = 2.6 Hz, 1H), 8.93 (d, J = 7.7 Hz, 1H), 8.55 (d, J = 2.6 Hz, 1H), 8.31 (s, 1H), 8.09 (d, J = 9.9 Hz, 1H), 7.86 (d, J = 9.5 Hz, 1H), 7.56 (br d, J = 3.9 Hz, 1H), 7.42-7.33 (m, 2H), 5.38 (quin, J = 7.2 Hz, 1H), 2.16-2.08 (m, 3H), 1.49 (d, J = 7.1 Hz, 3H). |
| 48 | N-{[3,5-difluoro-2-(oxetan-3-yloxy)phenyl]methyl}-5-{2-acetamidoimidazo[1,2-b]pyridazin-6-yl}-2-(D3)methoxypyridine-3-carboxamide | 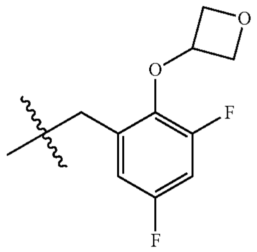 [SMILES: *Cc1cc(F)cc(F)c1OC1COC1] | 528.3 | 1H NMR (500 MHz, DMSO-d6) δ 10.90 (s, 1H), 9.00-8.90 (m, 2H), 8.70 (d, J = 2.1 Hz, 1H), 8.30 (s, 1H), 8.05 (d, J = 9.5 Hz, 1H), 7.82 (d, J = 9.5 Hz, 1H), 7.29-7.15 (m, 1H), 7.01 (br d, J = 8.9 Hz, 1H), 5.16 (br d, J = 6.1 Hz, 1H), 4.83 (t, J = 6.9 Hz, 2H), 4.74 (br t, J = 6.1 Hz, 2H), 4.56 (br d, J = 6.1 Hz, 2H), 2.11 (s, 3H). |
| 49 | N-({2-[cyclopropyl(deutero)methoxy]-3,5-difluorophenyl}methyl)-5-{2-acetamidoimidazo[1,2-b]pyridazin-6-yl}-2-($D_3$)methoxypyridine-3-carboxamide | 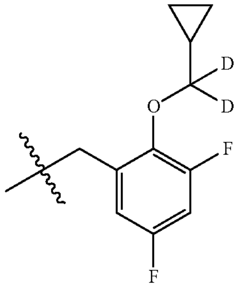 [SMILES: *Cc1cc(F)cc(F)c1OC([2H])([2H])C1CC1] | 528.0 | 1H NMR (500 MHz, DMSO-d6) δ 10.91 (br s, 1H), 8.99 (br s, 1H), 8.93 (br s, 1H), 8.72 (br s, 1H), 8.31 (s, 1H), 8.08 (br d, J = 9.5 Hz, 1H), 7.85 (br d, J = 9.5 Hz, 1H), 7.21 (br t, J = 8.4 Hz, 1H), 7.01 (br d, J = 9.5 Hz, 1H), 4.62 (br d, J = 5.8 Hz, 2H), 2.12 (s, 3H), 1.25 (br s, 1H), 0.58 (br d, J = 7.3 Hz, 2H), 0.32 (br d, J = 4.0 Hz, 2H). |
| 50 | N-{[3,5-difluoro-2-(oxan-4-yloxy)phenyl]methyl}-5-{2-acetamidoimidazo[1,2-b]pyridazin-6-yl}-2-($D_3$)methoxypyridine-3-carboxamide | 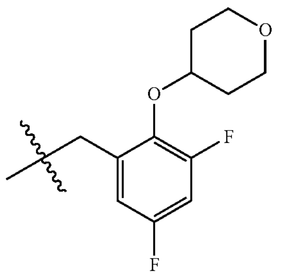 [SMILES: *Cc1cc(F)cc(F)c1OC1CCOCC1] | 556.2 | 1H NMR (500 MHz, DMSO-d6) δ 10.93 (br s, 1H), 8.97 (br d, J = 6.4 Hz, 2H), 8.70 (br s, 1H), 8.30 (s, 1H), 8.07-8.02 (m, 1H), 7.84-7.79 (m, 1H), 7.21 (br s, 1H), 6.99 (br d, J = 9.0 Hz, 1H), 4.57 (br d, J = 5.4 Hz, 2H), 4.29 (br s, 1H), 3.44-3.33 (m, 2H), 2.11 (s, 3H), 1.96 (br d, J = 12.0 Hz, 2H), 1.70 (br d, J = 9.5 Hz, 2H), 1.21 (br s, 2H). |

TABLE 1-continued

Compounds in Table 1 were prepared by methods as described in Example 14.

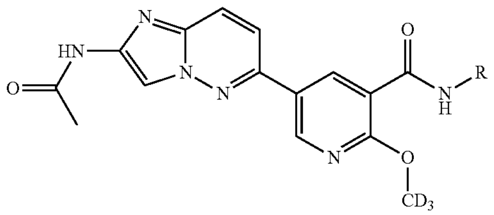

| Ex | Name | R | Obs. MS Ion | NMR Assignments |
|---|---|---|---|---|
| 51 | 5-{2-acetamidoimidazo[1,2-b]pyridazin-6-yl}-N-{1-[2-fluoro-5-(trifluoromethyl)phenyl]ethyl}-2-($D_3$)methoxypyridine-3-carboxamide | 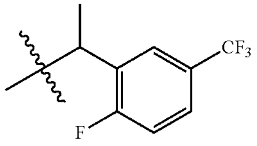 [SMILES: *C(C)c1cc(C(F)(F)F)ccc1F] | 520.1 | 1H NMR (500 MHz, DMSO-d6) δ 10.91 (s, 1H), 9.05-8.92 (m, 2H), 8.55 (d, J = 2.1 Hz, 1H), 8.31 (s, 1H), 8.08 (d, J = 9.5 Hz, 1H), 7.96 (br d, J = 5.5 Hz, 1H), 7.85 (d, J = 9.5 Hz, 1H), 7.74 (br s, 1H), 7.48 (br t, J = 9.3 Hz, 1H), 5.43 (br t, J = 7.2 Hz, 1H), 2.12 (s, 3H), 1.50 (br d, J = 7.0 Hz, 3H). |
| 52 | 5-{2-acetamidoimidazo[1,2-b]pyridazin-6-yl}-N-{1-[2-fluoro-5-(trifluoromethyl)phenyl]ethyl}-2-($D_3$)methoxypyridine-3-carboxamide | 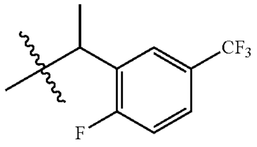 | 520.2 | 1H NMR (500 MHz, DMSO-d6) δ 10.91 (s, 1H), 9.05-8.92 (m, 2H), 8.55 (d, J = 2.1 Hz, 1H), 8.31 (s, 1H), 8.08 (d, J = 9.5 Hz, 1H), 7.96 (br d, J = 5.5 Hz, 1H), 7.85 (d, J = 9.5 Hz, 1H), 7.74 (br s, 1H), 7.48 (br t, J = 9.3 Hz, 1H), 5.43 (br t, J = 7.2 Hz, 1H), 2.12 (s, 3H), 1.50 (br d, J = 7.0 Hz, 3H). |
| 53 | N-{[2-(cyclopropylmethoxy)-3,4-difluorophenyl]methyl}-5-{2-acetamidoimidazo[1,2-b]pyridazin-6-yl}-2-($D_3$)methoxypyridine-3-carboxamide | 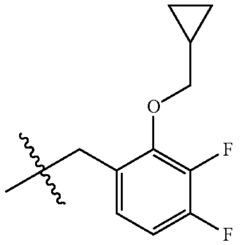 [SMILES: *Cc1ccc(F)c(F)c1OCC1CC1] | 526.1 | 1H NMR (500 MHz, DMSO-d6) δ 10.91 (s, 1H), 8.97 (br d, J = 2.1 Hz, 1H), 8.87 (br s, 1H), 8.72 (s, 1H), 8.31 (s, 1H), 8.07 (br d, J = 9.2 Hz, 1H), 7.83 (br d, J = 9.5 Hz, 1H), 7.15 (br d, J = 7.3 Hz, 2H), 4.57 (br d, J = 5.8 Hz, 2H), 3.99 (br d, J = 7.0 Hz, 2H), 2.11 (s, 3H), 1.29 (br s, 1H), 0.64-0.45 (m, 2H), 0.33 (br d, J = 4.0 Hz, 2H) |
| 54 | 5-{2-acetamidoimidazo[1,2-b]pyridazin-6-yl}-2-($D_3$)methoxy-N-{1-[2-(trifluoromethoxy)phenyl]ethyl}pyridine-3-carboxamide | 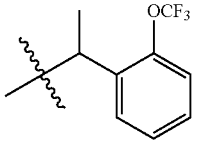 [SMILES: *C(C)c1ccccc1OC(F)(F)F] | 518 | 1H NMR (500 MHz, DMSO-d6) δ 10.90 (s, 1H), 8.96 (d, J = 2.4 Hz, 1H), 8.81 (d, J = 7.6 Hz, 1H), 8.58 (d, J = 2.4 Hz, 1H), 8.30 (s, 1H), 8.07 (d, J = 9.5 Hz, 1H), 7.83 (d, J = 9.5 Hz, 1H), 7.74-7.59 (m, 1H), 7.48-7.32 (m, 3H), 5.43 (quin, J = 7.1 Hz, 1H), 2.11 (s, 3H), 1.47 (d, J = 7.0 Hz, 3H). |
| 55 | N-{[2-(cyclopropylmethoxy)-3,5-difluorophenyl]methyl}-5-{2-acetamidoimidazo[1,2-b]pyridazin-6-yl}-2-($D_3$)methoxypyridine-3-carboxamide, TFA | 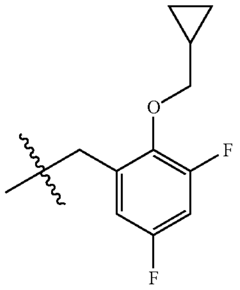 [SMILES: *Cc1cc(F)cc(F)c1OCC1CC1] | 526.5 | 1H NMR (500 MHz, DMSO-d6) δ 10.93 (br s, 1H), 8.97 (br s, 2H), 8.71 (d, J = 2.1 Hz, 1H), 8.30 (s, 1H), 8.06 (br d, J = 9.4 Hz, 1H), 7.83 (br d, J = 9.4 Hz, 1H), 7.20 (br t, J = 8.7 Hz, 1H), 6.99 (br d, J = 9.0 Hz, 1H), 4.60 (br d, J = 5.7 Hz, 2H), 3.95-3.84 (m, 2H), 2.11 (s, 3H), 1.25 (br s, 1H), 0.57 (br d, J = 6.8 Hz, 2H), 0.30 (br d, J = 4.6 Hz, 2H). |
| 56 | N-{[5-(cyclopropylmethoxy)-2-fluorophenyl]methyl}-5-{2-acetamidoimidazo[1,2-b]pyridazin-6-yl}-2-($D_3$)methoxypyridine-3-carboxamide, TFA | 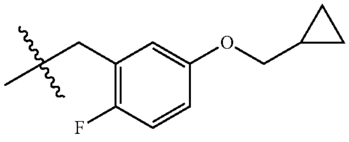 [SMILES: *Cc1cc(OCC2CC2)ccc1F] | 508.4 | 1H NMR (500 MHz, DMSO-d6) δ 10.91 (s, 1H), 8.97 (d, J = 2.4 Hz, 1H), 8.91 (br t, J = 6.0 Hz, 1H), 8.69 (d, J = 2.4 Hz, 1H), 8.31 (s, 1H), 8.06 (d, J = 9.5 Hz, 1H), 7.83 (d, J = 9.5 Hz, 1H), 7.10 (t, J = 9.5 Hz, 1H), 6.95 (d, J = 6.7 Hz, 1H), 6.89-6.74 (m, 1H), 4.53 (br d, J = 5.8 Hz, 2H), 3.77 (d, J = 7.0 Hz, 2H), 2.11 (s, 3H), 1.00 (d, J = 6.1 Hz, 1H), 0.60-0.47 (m, 2H), 0.28 (br d, J = 4.9 Hz, 2H). |

TABLE 1-continued

Compounds in Table 1 were prepared by methods as described in Example 14.

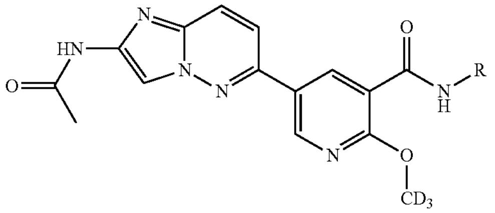

| Ex | Name | R | Obs. MS Ion | NMR Assignments |
|---|---|---|---|---|
| 57 | 5-{2-acetamidoimidazo[1,2-b]pyridazin-6-yl}-2-($D_3$)methoxy-N-{1-[2-(trifluoromethoxy)phenyl]ethyl}pyridine-3-carboxamide | 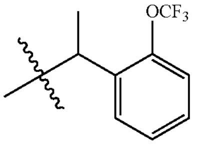 [SMILES: *C(C)c1ccccc1OC(F)(F)F] | 518.4 | 1H NMR (500 MHz, DMSO-d6) δ 10.90 (s, 1H), 8.96 (d, J = 2.4 Hz, 1H), 8.81 (d, J = 7.6 Hz, 1H), 8.58 (d, J = 2.4 Hz, 1H), 8.30 (s, 1H), 8.07 (d, J = 9.5 Hz, 1H), 7.83 (d, J = 9.5 Hz, 1H), 7.74-7.59 (m, 1H), 7.48-7.32 (m, 3H), 5.43 (quin, J = 7.1 Hz, 1H), 2.11 (s, 3H), 1.47 (d, J = 7.0 Hz, 3H). |
| 58 | 5-{2-acetamidoimidazo[1,2-b]pyridazin-6-yl}-N-{[2-fluoro-5-(trifluoromethoxy)phenyl]methyl}-2-($D_3$)methoxypyridine-3-carboxamide | 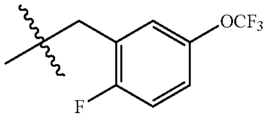 [SMILES: *Cc1cc(OC(F)(F)F)ccc1F] | 522.4 | 1H NMR (500 MHz, DMSO-d6) δ 10.91 (s, 1H), 9.03 (t, J = 6.4 Hz, 1H), 8.98 (s, 1H), 8.67 (d, J = 2.1 Hz, 1H), 8.30 (s, 1H), 8.06 (d, J = 9.5 Hz, 1H), 7.83 (d, J = 9.5 Hz, 1H), 7.45-7.30 (m, 3H), 4.59 (br d, J = 5.8 Hz, 2H), 2.11 (s, 3H). |

TABLE 2

Compounds in Table 2 were prepared by methods as described in Example 37.

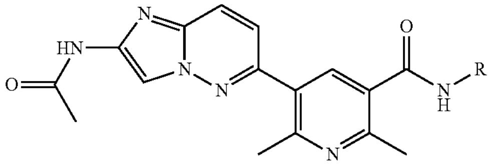

| Ex | Name | R | Obs. MS Ion | NMR Assignments |
|---|---|---|---|---|
| 59 | N-{[3,5-difluoro-2-(oxan-3-yloxy)phenyl]methyl}-5-{2-acetamidoimidazo[1,2-b]pyridazin-6-yl}-2,6-dimethylpyridine-3-carboxamide | 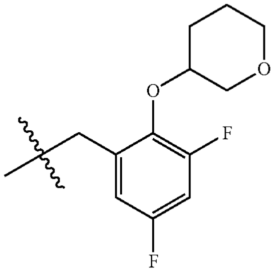 [SMILES: *Cc1cc(F)cc(F)c1OC1CCCOC1] | 551 | 1H NMR (500 MHz, DMSO-d6) δ 10.93 (s, 1H), 8.96 (br t, J = 5.6 Hz, 1H), 8.30 (s, 1H), 8.09 (d, J = 9.2 Hz, 1H), 7.93 (s, 1H), 7.46 (d, J = 9.2 Hz, 1H), 7.22 (br t, J = 8.7 Hz, 1H), 7.00 (br d, J = 8.5 Hz, 1H), 4.61-4.49 (m, 2H), 4.12 (br s, 1H), 3.76 (br d, J = 11.3 Hz, 1H), 3.61-3.49 (m, 1H), 2.60 (s, 3H), 2.57 (s, 3H), 2.12 (s, 3H), 2.03-1.91 (m, 1H), 1.91-1.77 (m, 2H), 1.49 (br d, J = 5.8 Hz, 1H). |
| 60 | N-({3,5-difluoro-2-[(3S)-oxolan-3-yloxy]phenyl}methyl)-5-{2-acetamidoimidazo[1,2-b]pyridazin-6-yl}-2,6-dimethylpyridine-3-carboxamide | 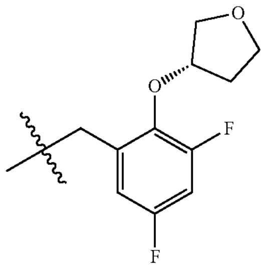 [SMILES: *Cc1cc(F)cc(F)c1O[C@H]1CCOC1] | 537.4 | 1H NMR (500 MHz, DMSO-d6) δ 10.79 (br s, 1H), 8.83 (br t, J = 5.6 Hz, 1H), 8.30 (s, 1H), 8.06 (d, J = 9.3 Hz, 1H), 7.92 (s, 1H), 7.44 (d, J = 9.3 Hz, 1H), 7.19 (br t, J = 9.0 Hz, 1H), 7.01 (br d, J = 9.2 Hz, 1H), 4.96 (br s, 1H), 4.57-4.44 (m, 2H), 4.00-3.87 (m, 2H), 3.84-3.72 (m, 2H), 2.64-2.54 (m, 6H), 2.21-2.06 (m, 5H). |

TABLE 2-continued

Compounds in Table 2 were prepared by methods as described in Example 37.

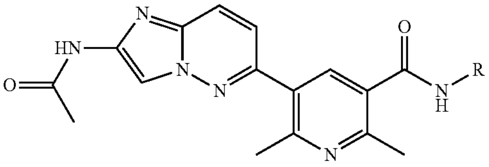

| Ex | Name | R | Obs. MS Ion | NMR Assignments |
|---|---|---|---|---|
| 61 | N-({3,5-difluoro-2-[(3R)-oxolan-3-yloxy]phenyl}methyl)-5-{2-acetamidoimidazo[1,2-b]pyridazin-6-yl}-2,6-dimethylpyridine-3-carboxamide | 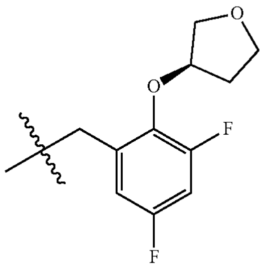 [SMILES: *Cc1cc(F)cc(F)c1O[C@@H]1CCOC1] | 537.0 | 1H NMR (500 MHz, DMSO-d6) δ 10.80 (br s, 1H), 8.84 (br s, 1H), 8.30 (s, 1H), 8.07 (d, J = 9.3 Hz, 1H), 7.93 (s, 1H), 7.44 (d, J = 9.3 Hz, 1H), 7.20 (br t, J = 8.6 Hz, 1H), 7.02 (br d, J = 8.9 Hz, 1H), 4.97 (br s, 1H), 4.60-4.44 (m, 2H), 4.01-3.86 (m, 2H), 3.85-3.72 (m, 2H), 2.61 (s, 3H), 2.58 (s, 3H), 2.27-2.03 (m, 5H). |
| 62 | N-({3,5-difluoro-2-[(2-methyloxan-4-yl)oxy]phenyl}methyl)-5-{2-acetamidoimidazo[1,2-b]pyridazin-6-yl}-2,6-dimethylpyridine-3-carboxamide | 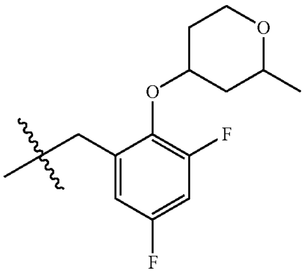 [SMILES: *Cc1cc(F)cc(F)c1OC1CCOC(C)C1] | 565.3 | 1H NMR (500 MHz, DMSO-d6) δ 10.94 (s, 1H), 8.99 (br t, J = 5.5 Hz, 1H), 8.31 (s, 1H), 8.11 (d, J = 9.5 Hz, 1H), 7.95 (s, 1H), 7.48 (d, J = 9.5 Hz, 1H), 7.24 (br t, J = 8.7 Hz, 1H), 7.04 (br d, J = 8.2 Hz, 1H), 4.58-4.49 (m, 3H), 3.97-3.81 (m, 2H), 3.80-3.73 (m, 1H), 2.61 (s, 3H), 2.56 (s, 3H), 2.13 (s, 3H), 1.91 (br d, J = 12.5 Hz, 1H), 1.78 (br s, 2H), 1.63-1.46 (m, 1H), 1.10 (d, J = 6.4 Hz, 3H). |
| 63 | N-[(2-{[(2R,6S)-2,6-dimethyloxan-4-yl]oxy}-3-fluorophenyl)methyl]-5-{2-acetamidoimidazo[1,2-b]pyridazin-6-yl}-2,6-dimethylpyridine-3-carboxamide | 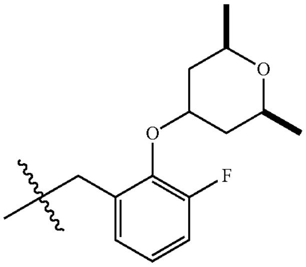 [SMILES: *Cc1cccc(F)c1OC1C[C@@H](C)O[C@@H](C)C1] | 561.2 | 1H NMR (500 MHz, DMSO-d6) δ 10.94 (s, 1H), 8.95 (br t, J = 5.5 Hz, 1H), 8.31 (s, 1H), 8.10 (br d, J = 9.2 Hz, 1H), 7.98-7.84 (m, 1H), 7.47 (d, J = 8.9 Hz, 1H), 7.23-7.13 (m, 2H), 7.13-7.04 (m, 1H), 4.59 (br s, 1H), 4.53 (br d, J = 5.5 Hz, 2H), 3.97 (br dd, J = 10.8, 6.0 Hz, 2H), 2.62-2.54 (m, 6H), 2.13 (s, 3H), 1.89 (br d, J = 14.0 Hz, 2H), 1.41 (br t, J = 11.9 Hz, 2H), 1.16-1.05 (m, 6H). |
| 64 | N-({2-[(2,6-dimethyloxan-4-yl)oxy]-3,5-difluorophenyl}methyl)-5-{2-acetamidoimidazo[1,2-b]pyridazin-6-yl}-2,6-dimethylpyridine-3-carboxamide | 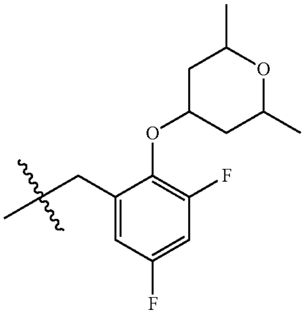 [SMILES: *Cc1cc(F)cc(F)c1OC1CC(C)OC(C)C1] | 579.2 | 1H NMR (500 MHz, DMSO-d6) δ 10.94 (br s, 1H), 9.03-8.92 (m, 1H), 8.31 (s, 1H), 8.11 (br d, J = 9.2 Hz, 1H), 7.98-7.90 (m, 1H), 7.48 (br d, J = 9.2 Hz, 1H), 7.24 (br t, J = 8.9 Hz, 1H), 7.04 (br d, J = 8.9 Hz, 1H), 4.58-4.46 (m, 3H), 3.97 (br dd, J = 11.0, 6.1 Hz, 1H), 2.63-2.60 (m, 3H), 2.59-2.57 (m, 3H), 2.13 (s, 3H), 2.01 (br d, J = 12.8 Hz, 1H), 1.89 (br d, J = 13.7 Hz, 2H), 1.40 (br t, J = 11.9 Hz, 1H), 1.33-1.18 (m, 1H), 1.16-1.06 (m, 6H). |
| 65 | 5-{2-acetamidoimidazo[1,2-b]pyridazin-6-yl}-2,6-dimethyl-N-{[3-(2,2,2-trifluoroethoxy)pyridin-2-yl]methyl}pyridine-3-carboxamide | 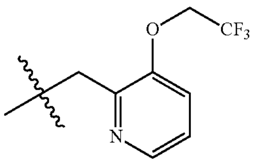 [SMILES: *Cc1ncccc1OCC(F)(F)F] | 514.2 | 1H NMR (500 MHz, DMSO-d6) δ 10.93 (s, 1H), 8.79 (br t, J = 5.3 Hz, 1H), 8.31 (s, 1H), 8.21 (d, J = 4.3 Hz, 1H), 8.09 (d, J = 9.2 Hz, 1H), 7.91 (s, 1H), 7.57 (d, J = 8.2 Hz, 1H), 7.47 (d, J = 9.5 Hz, 1H), 7.35 (dd, J = 8.2, 4.9 Hz, 1H), 4.89 (q, J = 8.9 Hz, 2H), 4.60 (d, J = 5.2 Hz, 2H), 2.62 (s, 3H), 2.57 (s, 3H), 2.13 (s, 3H). |

TABLE 2-continued

Compounds in Table 2 were prepared by methods as described in Example 37.

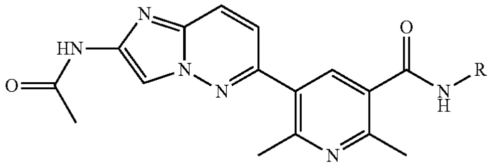

| Ex | Name | R | Obs. MS Ion | NMR Assignments |
|---|---|---|---|---|
| 66 | N-{[3,5-difluoro-2-(oxan-4-yloxy)phenyl](deutero)methyl}-5-{2-acetamidoimidazo[1,2-b]pyridazin-6-yl}-2,6-dimethylpyridine-3-carboxamide | 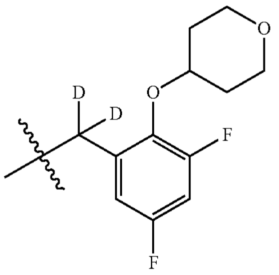 [SMILES: *C([2H])([2H])c1cc(F)cc(F)c1OC1CCOCC1] | 553.2 | 1H NMR (500 MHz, DMSO-d6) δ 10.94 (s, 1H), 8.96 (s, 1H), 8.31 (s, 1H), 8.10 (d, J = 9.5 Hz, 1H), 7.93 (s, 1H), 7.47 (d, J = 9.5 Hz, 1H), 7.34-7.15 (m, 1H), 7.04 (br d, J = 8.2 Hz, 1H), 4.37-4.20 (m, 1H), 3.94-3.84 (m, 2H), 2.62-2.55 (m, 8H), 2.13 (s, 3H), 1.95 (br d, J = 11.0 Hz, 2H), 1.70 (q, J = 9.2 Hz, 2H). |
| 67 | 5-{2-acetamidoimidazo[1,2-b]pyridazin-6-yl}-N-[(1R)-1-[2-fluoro-5-(trifluoromethyl)phenyl](2,2,2-deutero)ethyl]-2,6-dimethylpyridine-3-carboxamide | 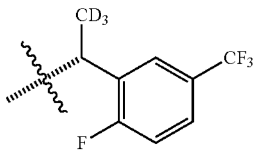 [SMILES: *[C@@H](c1cc(C(F)(F)F)ccc1F)C([2H])([2H])[2H]] | 518.2 | 1H NMR (500 MHz, DMSO-d6) δ 10.95 (s, 1H), 9.10 (br d, J = 7.3 Hz, 1H), 8.32 (s, 1H), 8.11 (d, J = 9.2 Hz, 1H), 7.88 (s, 1H), 7.85 (d, J = 7.1 Hz, 1H), 7.74 (br s, 1H), 7.55-7.40 (m, 2H), 5.38 (br d, J = 7.3 Hz, 1H), 2.59-2.54 (m, 6H), 2.13 (s, 3H). |
| 68 | 5-{2-acetamidoimidazo[1,2-b]pyridazin-6-yl}-2,6-dimethyl-N-{[2-(2,2,2-trifluoroethoxy)phenyl]methyl}pyridine-3-carboxamide | 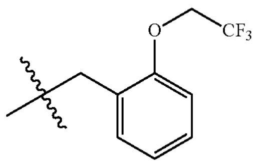 [SMILES: *Cc1ccccc1OCC(F)(F)F] | 513.2 | 1H NMR (500 MHz, DMSO-d6) δ 10.93 (s, 1H), 8.87 (br t, J = 5.6 Hz, 1H), 8.32 (br s, 1H), 8.11 (br d, J = 9.5 Hz, 1H), 7.92 (s, 1H), 7.48 (d, J = 9.2 Hz, 1H), 7.37-7.26 (m, 2H), 7.13 (d, J = 7.9 Hz, 1H), 7.06 (t, J = 7.5 Hz, 1H), 4.81 (q, J = 8.7 Hz, 2H), 4.48 (br d, J = 5.5 Hz, 2H), 2.61 (s, 3H), 2.58 (s, 3H), 2.13 (s, 3H). |
| 69 | 5-{2-acetamidoimidazo[1,2-b]pyridazin-6-yl}-N-[(1R)-1-[2-fluoro-5-(trifluoromethyl)phenyl]ethyl]-2,6-dimethylpyridine-3-carboxamide | 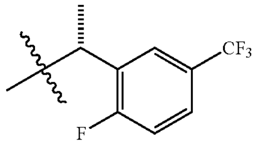 [SMILES: *[C@H](C)c1cc(C(F)(F)F)ccc1F] | 515.1 | 1H NMR (500 MHz, DMSO-d6) δ 10.95 (s, 1H), 9.10 (br d, J = 7.3 Hz, 1H), 8.32 (s, 1H), 8.11 (d, J = 9.5 Hz, 1H), 7.88 (s, 1H), 7.87-7.84 (m, 1H), 7.74 (br s, 1H), 7.54-7.42 (m, 2H), 5.39 (br t, J = 7.2 Hz, 1H), 2.59-2.54 (m, 6H), 2.13 (s, 3H), 1.49 (br d, J = 7.0 Hz, 3H). |
| 70 | 5-{2-acetamidoimidazo[1,2-b]pyridazin-6-yl}-N-[(1R)-1-[2-fluoro-5-(trifluoromethoxy)phenyl](2,2,2-deutero)ethyl]-2,6-dimethylpyridine-3-carboxamide | 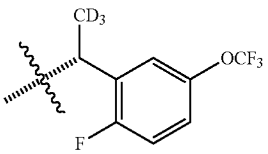 [SMILES: *[C@@H](c1cc(OC(F)(F)F)ccc1F)C([2H])([2H])[2H]] | 534.2 | 1H NMR (500 MHz, DMSO-d6) δ 10.94 (s, 1H), 9.06 (br d, J = 7.6 Hz, 1H), 8.31 (s, 1H), 8.11 (d, J = 9.2 Hz, 1H), 7.87 (s, 1H), 7.51-7.43 (m, 2H), 7.43-7.29 (m, 2H), 5.33 (br d, J = 7.3 Hz, 1H), 2.55 (s, 6H), 2.13 (s, 3H). |
| 71 | 5-{2-acetamidoimidazo[1,2-b]pyridazin-6-yl}-N-[(1R)-1-[2-fluoro-5-(trifluoromethoxy)phenyl]ethyl]-2,6-dimethylpyridine-3-carboxamide | 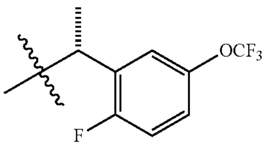 | 531.2 | 1H NMR (500 MHz, DMSO-d6) δ 10.94 (s, 1H), 9.08 (br d, J = 7.3 Hz, 1H), 8.31 (s, 1H), 8.10 (d, J = 9.5 Hz, 1H), 7.86 (s, 1H), 7.49-7.42 (m, 2H), 7.42-7.28 (m, 2H), 5.34 (br t, J = 7.2 Hz, 1H), 2.59-2.55 (m, 3H), 2.51-2.49 (m, 3H), 2.13 (s, 3H), 1.46 (d, J = 7.0 Hz, 3H). |
| 72 | 5-{2-acetamidoimidazo[1,2-b]pyridazin-6-yl}-N-{[5-fluoro-2-(2,2,2-trifluoroethoxy)phenyl]methyl}-2,6-dimethylpyridine-3-carboxamide, TFA | 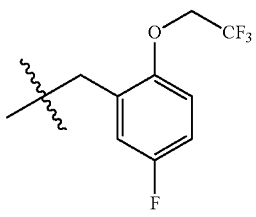 [SMILES: *Cc1cc(F)ccc1OCC(F)(F)F] | 531.2 | 1H NMR (500 MHz, DMSO-d6) δ 11.06-10.58 (m, 1H), 8.94 (s, 1H), 7.99 (s, 1H), 7.50 (br s, 1H), 7.29-7.01 (m, 4H), 4.80 (q, J = 8.7 Hz, 2H), 4.47 (br d, J = 5.5 Hz, 2H), 2.64-2.56 (m, 6H), 2.22-2.22 (m, 1H), 1.01 (d, J = 6.4 Hz, 3H). |

TABLE 2-continued

Compounds in Table 2 were prepared by methods as described in Example 37.

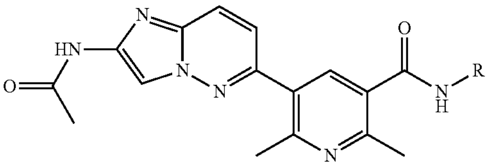

| Ex | Name | R | Obs. MS Ion | NMR Assignments |
|---|---|---|---|---|
| 73 | 5-{2-acetamidoimidazo[1,2-b]pyridazin-6-yl}-2,6-dimethyl-N-{[3-(2,2,2-trifluoroethoxy)phenyl]methyl}pyridine-3-carboxamide | 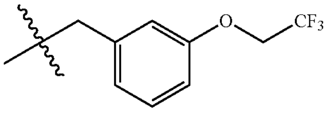 [SMILES: *Cc1cccc(OCC(F)(F)F)c1] | 512.9 | 1H NMR (500 MHz, DMSO-d6) δ 10.93 (s, 1H), 9.01 (br t, J = 5.6 Hz, 1H), 8.31 (s, 1H), 8.10 (d, J = 9.5 Hz, 1H), 7.90 (s, 1H), 7.47 (d, J = 9.2 Hz, 1H), 7.33 (br t, J = 8.1 Hz, 1H), 7.05 (br s, 2H), 6.97 (br d, J = 7.9 Hz, 1H), 4.75 (q, J = 8.9 Hz, 2H), 4.47 (br d, J = 5.8 Hz, 2H), 2.60 (s, 3H), 2.57 (s, 3H), 2.13 (s, 3H) |
| 74 | 5-{2-acetamidoimidazo[1,2-b]pyridazin-6-yl}-2,6-dimethyl-N-{[3-(trifluoro-methyl)phenyl](deutero)methyl}pyridine-3-carboxamide, TFA | 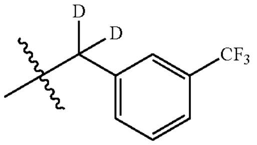 [SMILES: *C([2H])([2H])c1cccc(C(F)(F)F)c1] | 485 | 1H NMR (500 MHz, DMSO-d6) δ 10.94 (s, 1H), 9.13 (s, 1H), 8.31 (s, 1H), 8.13-8.07 (m, 1H), 7.93 (s, 1H), 7.74-7.66 (m, 2H), 7.62 (dt, J = 15.0, 7.6 Hz, 2H), 7.50-7.45 (m, 1H), 7.25-6.99 (m, 1H), 2.64-2.55 (m, 6H), 2.13 (s, 3H). |
| 75 | 5-{2-acetamidoimidazo[1,2-b]pyridazin-6-yl}-N-{[2-fluoro-5-(trifluoromethyl)phenyl](deutero)methyl}-2,6-dimethylpyridine-3-carboxamide | 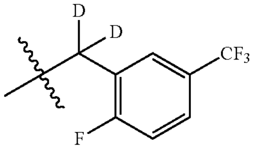 [SMILES: *C([2H])([2H])c1cc(C(F)(F)F)ccc1F] | 503.3 | 1H NMR (500 MHz, DMSO-d6) δ 10.93 (s, 1H), 9.09 (s, 1H), 8.30 (s, 1H), 8.09 (d, J = 9.2 Hz, 1H), 7.88 (s, 1H), 7.81 (br d, J = 6.7 Hz, 1H), 7.75 (br s, 1H), 7.53-7.39 (m, 2H), 2.60-2.54 (m, 6H), 2.12 (s, 3H). |
| 76 | 5-{2-acetamidoimidazo[1,2-b]pyridazin-6-yl}-N-{[2-fluoro-5-(trifluorometh-oxy)phenyl](deutero)methyl}-2,6-dimethylpyridine-3-carboxamide | 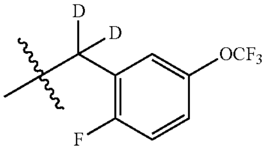 [SMILES: *C([2H])([2H])c1cc(OC(F)(F)F)ccc1F] | 519.3 | 1H NMR (500 MHz, DMSO-d6) δ 10.93 (s, 1H), 9.08 (s, 1H), 8.29 (s, 1H), 8.08 (d, J = 9.2 Hz, 1H), 7.88 (s, 1H), 7.45 (d, J = 8.8 Hz, 1H), 7.42 (d, J = 6.6 Hz, 1H), 7.36 (br d, J = 7.3 Hz, 2H), 2.59-2.53 (m, 6H), 2.12 (s, 3H). |
| 77 | N-{[3,5-difluoro-2-(oxetan-3-yloxy)phenyl]methyl}-5-{2-acetamidoimidazo[1,2-b]pyridazin-6-yl}-2,6-dimethylpyridine-3-carboxamide | 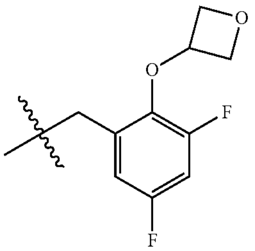 [SMILES: *Cc1cc(F)cc(F)c1OC1COC1] | 523.3 | 1H NMR (500 MHz, DMSO-d6) δ 10.93 (s, 1H), 8.98 (br t, J = 5.6 Hz, 1H), 8.30 (s, 1H), 8.09 (d, J = 9.2 Hz, 1H), 7.92 (s, 1H), 7.46 (d, J = 9.2 Hz, 1H), 7.24 (br t, J = 8.4 Hz, 1H), 7.02 (br d, J = 8.2 Hz, 1H), 5.15 (br s, 1H), 4.81 (t, J = 6.9 Hz, 2H), 4.72 (br t, J = 6.1 Hz, 2H), 4.50 (br d, J = 5.5 Hz, 2H), 2.61-2.53 (m, 6H), 2.12 (s, 3H). |
| 78 | N-{[3,5-difluoro-2-(oxan-4-yloxy)phenyl]methyl}-5-{2-acetamidoimidazo[1,2-b]pyridazin-6-yl}-2,6-dimethylpyridine-3-carboxamide | 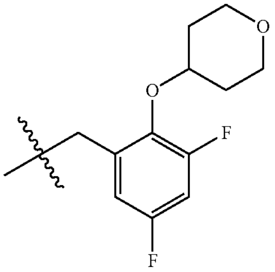 [SMILES: *Cc1cc(F)cc(F)c1OC1CCOCC1] | 551.3 | 1H NMR (500 MHz, DMSO-d6) δ 10.93 (s, 1H), 8.99 (br t, J = 5.5 Hz, 1H), 8.29 (s, 1H), 8.07 (d, J = 9.5 Hz, 1H), 7.91 (s, 1H), 7.45 (d, J = 9.5 Hz, 1H), 7.34-7.13 (m, 1H), 7.01 (br d, J = 8.2 Hz, 1H), 4.52 (br d, J = 5.5 Hz, 2H), 3.92-3.82 (m, 2H), 3.37 (br t, J = 10.1 Hz, 1H), 2.59 (s, 3H), 2.55 (s, 3H), 2.12 (s, 3H), 1.93 (br d, J = 12.5 Hz, 2H), 1.68 (q, J = 9.4 Hz, 2H), 1.22 (s, 2H). |

TABLE 2-continued

Compounds in Table 2 were prepared by methods as described in Example 37.

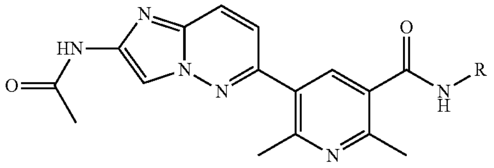

| Ex | Name | R | Obs. MS Ion | NMR Assignments |
|---|---|---|---|---|
| 79 | 5-{2-acetamidoimidazo[1,2-b]pyridazin-6-yl}-N-{[3-fluoro-5-(trifluoromethoxy)phenyl]methyl}-2,6-dimethylpyridine-3-carboxamide, TFA | 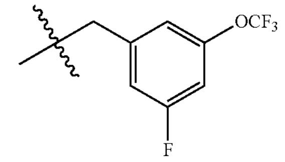 [SMILES: *Cc1cc(F)cc(OC(F)(F)F)c1] | 516.8 | 1H NMR (500 MHz, DMSO-d6) δ 10.93 (s, 1H), 9.14 (br t, J = 5.6 Hz, 1H), 8.29 (s, 1H), 8.07 (d, J = 9.2 Hz, 1H), 7.91 (s, 1H), 7.45 (d, J = 9.5 Hz, 1H), 7.29-7.14 (m, 3H), 4.52 (br d, J = 5.8 Hz, 2H), 2.60-2.53 (m, 6H), 2.12 (s, 3H). |
| 80 | 5-{2-acetamidoimidazo[1,2-b]pyridazin-6-yl}-N-{[2-fluoro-5-(trifluoromethyl)phenyl]methyl}-2,6-dimethylpyridine-3-carboxamide | 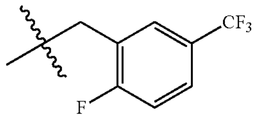 [SMILES: *Cc1cc(C(F)(F)F)ccc1F] | 501.1 | 1H NMR (500 MHz, DMSO-d6) δ 10.91 (s, 1H), 9.14 (br t, J = 5.6 Hz, 1H), 8.28 (s, 1H), 8.04 (d, J = 9.2 Hz, 1H), 7.85 (s, 1H), 7.79-7.69 (m, 2H), 7.51-7.36 (m, 2H), 4.55 (br d, J = 5.5 Hz, 2H), 2.56-2.53 (m, 6H), 2.11 (s, 3H). |
| 81 | 5-{2-acetamidoimidazo[1,2-b]pyridazin-6-yl}-N-{[2-fluoro-5-(trifluoromethoxy)phenyl]methyl}-2,6-dimethylpyridine-3-carboxamide | 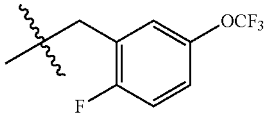 [SMILES: *Cc1cc(OC(F)(F)F)ccc1F] | 517.2 | 1H NMR (500 MHz, DMSO-d6) δ 10.93 (s, 1H), 9.09 (br t, J = 5.6 Hz, 1H), 8.30 (s, 1H), 8.09 (d, J = 9.2 Hz, 1H), 7.88 (s, 1H), 7.47-7.32 (m, 4H), 4.52 (br d, J = 5.8 Hz, 2H), 2.59-2.53 (m, 6H), 2.12 (s, 3H). |
| 82 | N-[(3S)-3-(4-chlorophenyl)-3-hydroxypropyl]-5-{2-acetamidoimidazo[1,2-b]pyridazin-6-yl}-2,6-dimethylpyridine-3-carboxamide | 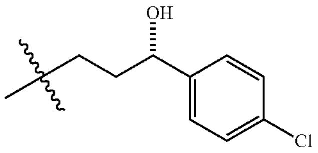 [SMILES: *CC[C@H](O)c1ccc(Cl)cc1] | 493.4 | 1H NMR (500 MHz, DMSO-d6) δ 10.92 (s, 1H), 8.44 (br t, J = 5.3 Hz, 1H), 8.30 (s, 1H), 8.08 (d, J = 9.5 Hz, 1H), 7.78 (s, 1H), 7.44 (d, J = 9.2 Hz, 1H), 7.37 (s, 4H), 4.72-4.58 (m, 1H), 3.72-2.62 (m, 3H), 2.56-2.54 (m, 6H), 2.12 (s, 3H), 1.84 (q, J = 6.8 Hz, 2H). |
| 83 | N-{[2-(cyclopropylmethoxy)phenyl]methyl}-5-{2-acetamidoimidazo[1,2-b]pyridazin-6-yl}-2,6-dimethylpyridine-3-carboxamide | 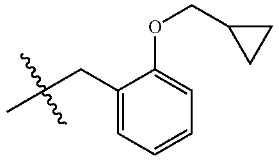 [SMILES: *Cc1ccccc1OCC1CC1] | 484.9 | 1H NMR (500 MHz, DMSO-d6) δ 10.92 (s, 1H), 8.81 (br t, J = 5.6 Hz, 1H), 8.28 (s, 1H), 8.06 (d, J = 9.5 Hz, 1H), 7.88 (s, 1H), 7.44 (d, J = 9.5 Hz, 1H), 7.26-7.18 (m, 2H), 6.95 (d, J = 8.0 Hz, 1H), 6.90 (t, J = 7.4 Hz, 1H), 4.45 (br d, J = 5.5 Hz, 2H), 3.85 (d, J = 6.7 Hz, 2H), 2.58 (s, 3H), 2.56-2.54 (m, 3H), 2.11 (s, 3H), 1.21 (m, 1H), 0.52 (br d, J = 7.0 Hz, 2H), 0.32 (br d, J = 4.3 Hz, 2H) |
| 84 | N-{[2-(cyclopentylmethoxy)pyridin-3-yl]methyl}-5-{2-acetamidoimidazo[1,2-b]pyridazin-6-yl}-2,6-dimethylpyridine-3-carboxamide | 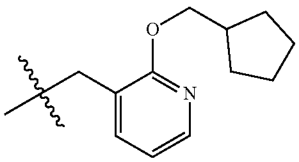 [SMILES: *Cc1cccnc1OCC1CCCC1] | 514.2 | 1H NMR (500 MHz, DMSO-d6) δ 10.92 (s, 1H), 8.86 (br t, J = 5.3 Hz, 1H), 8.29 (s, 1H), 8.07 (d, J = 8.5 Hz, 1H), 8.03 (d, J = 5.5 Hz, 1H), 7.90 (s, 1H), 7.62 (br d, J = 7.0 Hz, 1H), 7.45 (d, J = 9.5 Hz, 1H), 6.95 (t, J = 6.2 Hz, 1H), 4.39 (br d, J = 5.2 Hz, 2H), 4.17 (d, J = 6.7 Hz, 2H), 2.59 (s, 3H), 2.55 (s, 3H), 2.31 (dt, J = 14.9, 7.4 Hz, 1H), 2.11 (s, 3H), 1.73 (br d, J = 7.6 Hz, 2H), 1.55 (br d, J = 6.7 Hz, 2H), 1.52-1.43 (m, 2H), 1.32 (br dd, J = 12.4, 6.9 Hz, 2H) |
| 85 | N-{[2-(cyclopentylmethoxy)phenyl]methyl}-5-{2-acetamidoimidazo[1,2-b]pyridazin-6-yl}-2,6-dimethylpyridine-3-carboxamide | 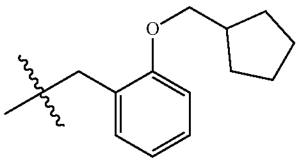 [SMILES: *Cc1ccccc1OCC1CCCC1] | 513.0 | 1H NMR (500 MHz, DMSO-d6) δ 10.93 (s, 1H), 8.78 (br t, J = 5.5 Hz, 1H), 8.30 (s, 1H), 8.09 (d, J = 9.5 Hz, 1H), 7.89 (s, 1H), 7.46 (d, J = 9.2 Hz, 1H), 7.27-7.21 (m, 2H), 6.98 (br d, J = 7.9 Hz, 1H), 6.91 (br t, J = 7.3 Hz, 1H), 4.45 (br d, J = 5.5 Hz, 2H), 3.89 (br d, J = 6.4 Hz, 2H), 2.61 (s, 3H), 2.57 (s, 3H), 2.32 (dq, J = 14.8, 7.6 Hz, 1H), 2.12 (s, 3H), 1.78 (br d, J = 7.3 Hz, 2H), 1.62-1.48 (m, 4H), 1.37 (br dd, J = 12.1, 6.9 Hz, 2H) |

TABLE 2-continued

Compounds in Table 2 were prepared by methods as described in Example 37.

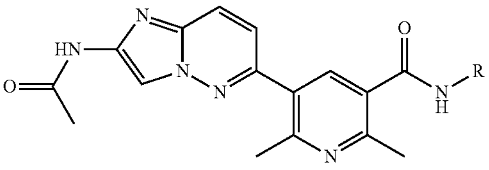

| Ex | Name | R | Obs. MS Ion | NMR Assignments |
|---|---|---|---|---|
| 86 | N-{[2-(cyclobutylmethoxy)pyridin-3-yl]methyl}-5-{2-acetamidoimidazo[1,2-b]pyridazin-6-yl}-2,6-dimethylpyridine-3-carboxamide | 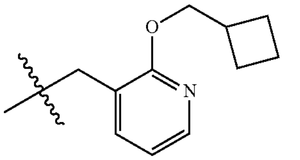 [SMILES: *Cc1cccnc1OCC1CCC1] | 499.9 | 1H NMR (500 MHz, DMSO-d6) δ 10.91 (s, 1H), 8.87 (br t, J = 5.3 Hz, 1H), 8.28 (s, 1H), 8.05-8.00 (m, 2H), 7.87 (s, 1H), 7.61 (br d, J = 7.3 Hz, 1H), 7.42 (d, J = 9.5 Hz, 1H), 6.94 (t, J = 6.4 Hz, 1H), 4.37 (br d, J = 5.2 Hz, 2H), 4.24 (d, J = 6.7 Hz, 2H), 2.69 (br d, J = 6.4 Hz, 1H), 2.55-2.52 (m, 6H), 2.11 (s, 3H), 2.03-1.96 (m, 2H), 1.80 (br s, 4H) |
| 87 | N-{[2-(cyclopropylmethoxy)-3,5-difluorophenyl]methyl}-5-{2-acetamidoimidazo[1,2-b]pyridazin-6-yl}-2,6-dimethylpyridine-3-carboxamide | 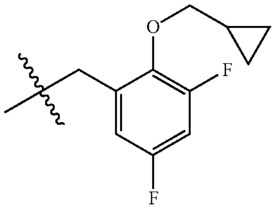 [SMILES: *Cc1cc(F)cc(F)c1OCC1CC1] | 521.3 | 1H NMR (500 MHz, DMSO-d6) δ 10.93 (s, 1H), 8.98 (br t, J = 5.5 Hz, 1H), 8.29 (s, 1H), 8.08 (br d, J = 9.2 Hz, 1H), 7.92 (s, 1H), 7.45 (br d, J = 9.2 Hz, 1H), 7.19 (br t, J = 8.7 Hz, 1H), 6.99 (d, J = 8.6 Hz, 1H), 4.54 (br d, J = 5.5 Hz, 2H), 3.89-3.82 (m, 2H), 2.57-2.53 (m, 6H), 2.11 (s, 3H), 1.26-1.18 (m, 1H), 0.53 (br d, J = 6.7 Hz, 2H), 0.27 (br d, J = 4.3 Hz, 2H) |
| 88 | 5-{2-acetamidoimidazo[1,2-b]pyridazin-6-yl}-2,6-dimethyl-N-{[3-(trifluoromethoxy)phenyl]methyl}pyridine-3-carboxamide | 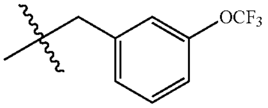 [SMILES: *Cc1cccc(OC(F)(F)F)c1] | 499.2 | 1H NMR (500 MHz, DMSO-d6) δ 10.92 (s, 1H), 9.14 (br s, 1H), 8.29 (s, 1H), 8.06 (br d, J = 9.2 Hz, 1H), 7.87 (s, 1H), 7.48 (t, J = 8.0 Hz, 1H), 7.44 (d, J = 8.9 Hz, 1H), 7.38 (br d, J = 7.3 Hz, 1H), 7.31 (br s, 1H), 7.24 (br d, J = 7.9 Hz, 1H), 4.51 (br d, J = 5.8 Hz, 2H), 2.58-2.55 (m, 6H), 2.12 (s, 3H) |
| 89 | 5-{2-acetamidoimidazo[1,2-b]pyridazin-6-yl}-2,6-dimethyl-N-{[2-(trifluoromethoxy)phenyl]methyl}pyridine-3-carboxamide | 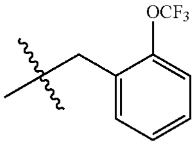 [SMILES: *Cc1ccccc1OC(F)(F)F] | 499.1 | 1H NMR (500 MHz, DMSO-d6) δ 10.93 (s, 1H), 9.04 (br t, J = 5.5 Hz, 1H), 8.30 (s, 1H), 8.08 (d, J = 9.5 Hz, 1H), 7.90 (s, 1H), 7.52 (br d, J = 7.3 Hz, 1H), 7.47-7.35 (m, 4H), 4.54 (br d, J = 5.5 Hz, 2H), 2.59 (s, 3H), 2.56 (s, 3H), 2.12 (s, 3H) |
| 90 | N-{[2-(cyclopentylmethoxy)-3,5-difluorophenyl]methyl}-5-{2-acetamidoimidazo[1,2-b]pyridazin-6-yl}-2,6-dimethylpyridine-3-carboxamide | 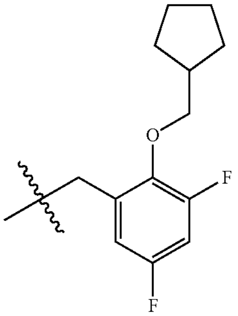 [SMILES: *Cc1cc(F)cc(F)c1OCC1CCCC1] | 549.4 | 1H NMR (500 MHz, DMSO-d6) δ 10.92 (s, 1H), 8.97 (br t, J = 5.5 Hz, 1H), 8.28 (s, 1H), 8.06 (d, J = 9.2 Hz, 1H), 7.90 (s, 1H), 7.44 (d, J = 9.2 Hz, 1H), 7.19 (br t, J = 8.5 Hz, 1H), 6.98 (br d, J = 8.9 Hz, 1H), 4.49 (br d, J = 5.5 Hz, 2H), 3.87 (br d, J = 7.0 Hz, 2H), 2.58 (s, 3H), 2.54 (s, 3H), 2.33-2.28 (m, 1H), 2.11 (s, 3H), 1.75 (br d, J = 7.3 Hz, 2H), 1.59-1.48 (m, 4H), 1.34 (br dd, J = 12.2, 6.4 Hz, 2H) |

TABLE 3

Compounds in Table 3 were prepared by methods as described in Example 38.

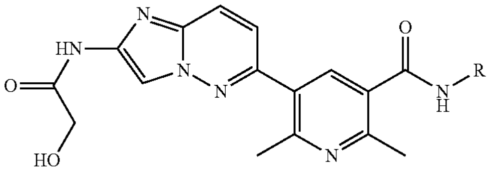

| Ex | Name | R | Obs. MS Ion | NMR Assignments |
|---|---|---|---|---|
| 91 | N-({3,5-difluoro-2-[(3S)-oxolan-3-yloxy]phenyl}methyl)-5-[2-(2-hydroxy-acetamido)imidazo[1,2-b]pyridazin-6-yl]-2,6-dimethylpyridine-3-carboxamide, TFA | 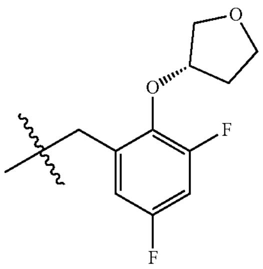 [SMILES: *Cc1cc(F)cc(F)c1O[C@H]1CCOC1] | 553.2 | 1H NMR (500 MHz, DMSO-d6) δ 10.18 (s, 1H), 8.86 (br t, J = 5.6 Hz, 1H), 8.36 (s, 1H), 8.10 (d, J = 9.3 Hz, 1H), 7.94 (s, 1H), 7.47 (d, J = 9.3 Hz, 1H), 7.25-7.15 (m, 2H), 7.04-6.97 (m, 1H), 4.97 (br s, 1H), 4.60-4.40 (m, 2H), 4.12 (s, 2H), 4.01-3.86 (m, 2H), 3.85-3.70 (m, 2H), 2.61 (s, 3H), 2.58 (s, 3H), 2.21-2.06 (m, 2H). |
| 92 | N-[(1R)-1-[2-fluoro-5-(trifluoromethyl)phenyl]ethyl]-5-[2-(2-hydroxyacet-amido)imidazo[1,2-b]pyridazin-6-yl]-2,6-dimethylpyridine-3-carboxamide | 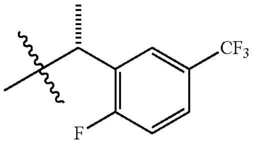 [SMILES: *[C@H](C)c1cc(C(F)(F)F)ccc1F] | 531.1 | 1H NMR (500 MHz, DMSO-d6) δ 10.37 (s, 1H), 9.11 (br d, J = 7.3 Hz, 1H), 8.37 (s, 1H), 8.13 (d, J = 9.5 Hz, 1H), 7.88 (s, 1H), 7.84 (d, J = 6.7 Hz, 1H), 7.73 (br s, 1H), 7.55-7.41 (m, 2H), 5.38 (quin, J = 7.2 Hz, 1H), 4.12 (s, 2H), 3.20-2.96 (m, 1H), 2.57 (s, 3H), 2.50-2.47 (m, 3H), 1.48 (d, J = 7.0 Hz, 3H). |
| 93 | N-{[2-fluoro-5-(trifluoro-methyl)phenyl](deutero)methyl}-5-[2-(2-hydroxy-acetamido)imidazo[1,2-b]pyridazin-6-yl]-2,6-dimethylpyridine-3-carboxamide | 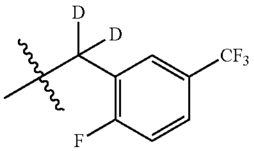 [SMILES: *C([2H])([2H])c1cc(C(F)(F)F)ccc1F] | 519.2 | 1H NMR (500 MHz, DMSO-d6) δ 10.34-9.83 (m, 1H), 8.98 (s, 1H), 8.35 (s, 1H), 8.09 (d, J = 9.3 Hz, 1H), 7.88 (s, 1H), 7.81 (br d, J = 6.5 Hz, 1H), 7.73 (br s, 1H), 7.52-7.40 (m, 2H), 4.12 (br d, J = 5.0 Hz, 2H), 3.26 (s, 1H), 2.62-2.54 (m, 6H). |
| 94 | N-{[2-fluoro-5-(trifluoromethyl)phenyl]methyl}-5-[2-(2-hydroxyacet-amido)imidazo[1,2-b]pyridazin-6-yl]-2,6-dimethylpyridine-3-carboxamide | 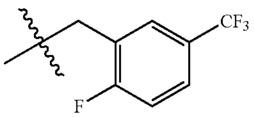 [SMILES: *Cc1cc(C(F)(F)F)ccc1F] | 517.3 | 1H NMR (500 MHz, DMSO-d6) δ 9.07-8.81 (m, 1H), 8.34 (s, 1H), 8.06 (d, J = 9.3 Hz, 1H), 7.85 (s, 1H), 7.78 (br d, J = 5.2 Hz, 1H), 7.72 (br s, 1H), 7.54-7.33 (m, 2H), 4.57 (br d, J = 5.6 Hz, 2H), 4.11 (br s, 2H), 3.72 (m, 2H), 2.58-2.54 (m, 6H). |
| 95 | N-[(1R)-1-[2-fluoro-5-(trifluoromethoxy)phenyl]ethyl]-5-[2-(2-hydroxyacet-amido)imidazo[1,2-b]pyridazin-6-yl]-2,6-dimethylpyridine-3-carboxamide | 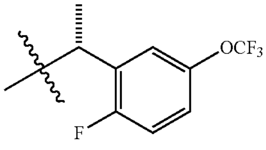 [SMILES: *[C@H](C)c1cc(OC(F)(F)F)ccc1F] | 547.2 | 1H NMR (500 MHz, DMSO-d6) δ 10.36 (br s, 1H), 9.07 (br d, J = 7.3 Hz, 1H), 8.38 (br s, 1H), 8.12 (br d, J = 9.2 Hz, 1H), 7.87 (s, 1H), 7.52-7.42 (m, 2H), 7.40-7.28 (m, 2H), 5.34 (quin, J = 7.0 Hz, 1H), 4.12 (br d, J = 5.5 Hz, 2H), 3.00 (s, 1H), 2.57 (s, 3H), 2.50 (br s, 3H), 1.45 (d, J = 7.0 Hz, 3H). |

TABLE 4

Compounds in Table 4 were prepared by methods as described in Examples 22, 23, and 25. For examples containing tertiary amides, the compounds are of formula (4A) and R* is as indicated in the table.

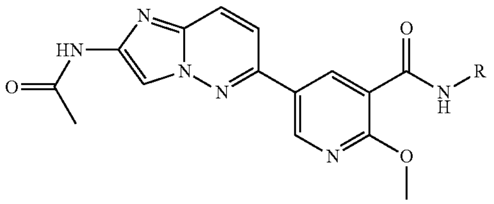

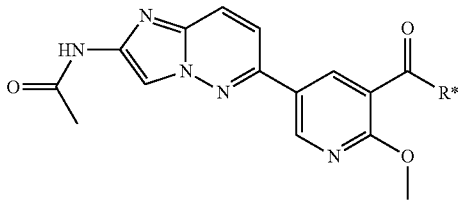

4A

| Ex | Name | R | Obs. MS Ion | NMR Assignments |
|---|---|---|---|---|
| 96 | N-({3,5-difluoro-2-[(2-methyloxan-4-yl)oxy]phenyl}methyl)-5-{2-acetamidoimidazo[1,2-b]pyridazin-6-yl}-2-methoxypyridine-3-carboxamide | 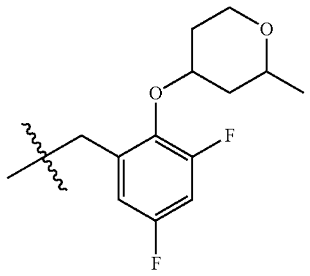 [SMILES: *Cc1cc(F)cc(F)c1OC1CCOC(C)C1] | 567.2 | 1H NMR (500 MHz, DMSO-d6) δ 10.91 (s, 1H), 9.01-8.91 (m, 2H), 8.70 (d, J = 2.4 Hz, 1H), 8.30 (s, 1H), 8.05 (d, J = 9.2 Hz, 1H), 7.82 (d, J = 9.5 Hz, 1H), 7.20 (br t, J = 8.5 Hz, 1H), 7.01 (br d, J = 8.5 Hz, 1H), 4.59 (br d, J = 5.8 Hz, 2H), 4.54 (br s, 1H), 4.08 (s, 3H), 3.97-3.81 (m, 2H), 3.81-3.73 (m, 1H), 2.12 (s, 3H), 1.92 (br d, J = 13.7 Hz, 1H), 1.79 (br s, 2H), 1.52 (br t, J = 11.4 Hz, 1H), 1.12 (d, J = 6.1 Hz, 3H). |
| 97 | N-{[2-(cyclobutylmethoxy)-3,5-difluorophenyl]methyl}-5-{2-acetamidoimidazo[1,2-b]pyridazin-6-yl}-2-methoxypyridine-3-carboxamide | 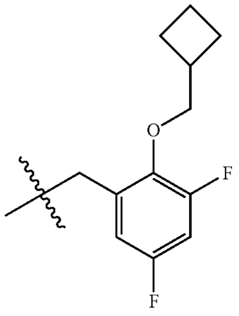 [SMILES: *Cc1cc(F)cc(F)c1OCC1CCC1] | 536.9 | 1H NMR (500 MHz, DMSO-d6) δ 10.93 (br. s., 1H), 9.03-8.89 (m, 2H), 8.71 (d, J = 2.0 Hz, 1H), 8.29 (s, 1H), 8.06 (d, J = 9.3 Hz, 1H), 7.83 (d, J = 9.3 Hz, 1H), 7.32-7.10 (m, 1H), 6.98 (d, J = 8.8 Hz, 1H), 4.55 (d, J = 5.8 Hz, 2H), 4.07 (s, 3H), 4.01 (d, J = 6.6 Hz, 2H), 2.79-2.68 (m, 1H), 2.10 (s, 3H), 2.08 (d, J = 6.2 Hz, 2H), 1.97-1.80 (m, 4H). |
| 98 | N-({3,5-difluoro-2-[(3S)-oxolan-3-yloxy]phenyl}methyl)-5-{2-acetamidoimidazo[1,2-b]pyridazin-6-yl}-2-methoxypyridine-3-carboxamide | 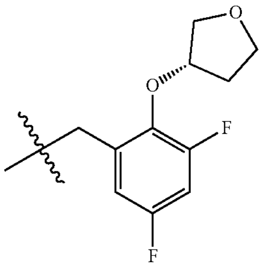 [SMILES: *Cc1cc(F)cc(F)c1O[C@H]1CCOC1] | 539.0 | 1H NMR (500 MHz, DMSO-d6) δ 10.91 (s, 1H), 9.01-8.90 (m, 2H), 8.72 (d, J = 2.4 Hz, 1H), 8.31 (s, 1H), 8.06 (d, J = 9.5 Hz, 1H), 7.83 (d, J = 9.5 Hz, 1H), 7.23 (br t, J = 8.7 Hz, 1H), 7.01 (br d, J = 8.2 Hz, 1H), 5.00 (br s, 1H), 4.64-4.48 (m, 2H), 4.09 (s, 3H), 4.04-3.89 (m, 2H), 3.87-3.78 (m, 1H), 3.74 (dd, J = 10.4, 4.0 Hz, 1H), 3.56 (br s, 1H), 2.19-2.13 (m, 1H), 2.11 (s, 3H). |
| 99 | N-{[3,5-difluoro-2-(oxan-3-yloxy)phenyl]methyl}-5-{2-acetamidoimidazo[1,2-b]pyridazin-6-yl}-2-methoxypyridme-3-carboxamide | 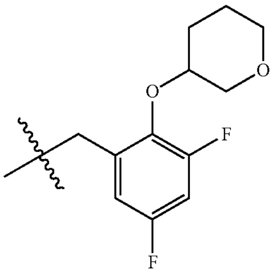 [SMILES: *Cc1cc(F)cc(F)c1OC1CCCOC1] | 552.9 | 1H NMR (500 MHz, DMSO-d6) δ 10.76 (br s, 1H), 8.95 (d, J = 2.4 Hz, 1H), 8.88-8.76 (m, 1H), 8.71 (d, J = 2.4 Hz, 1H), 8.30 (s, 1H), 8.03 (d, J = 9.3 Hz, 1H), 7.79 (d, J = 9.3 Hz, 1H), 7.16 (br t, J = 8.7 Hz, 1H), 7.02 (br d, J = 9.2 Hz, 1H), 4.62 (br t, J = 6.2 Hz, 2H), 4.17 (br s, 1H), 4.09 (s, 3H), 2.55 (s, 3H), 2.12 (s, 3H), 2.08-1.97 (m, 1H), 1.95-1.78 (m, 2H), 1.61-1.42 (m, 1H). |

TABLE 4-continued

Compounds in Table 4 were prepared by methods as described in Examples 22, 23, and 25. For examples containing tertiary amides, the compounds are of formula (4A) and R* is as indicated in the table.

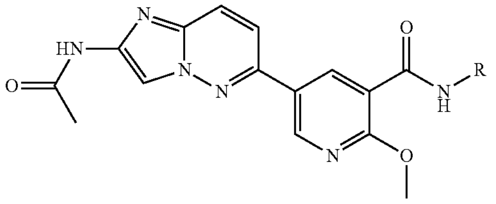

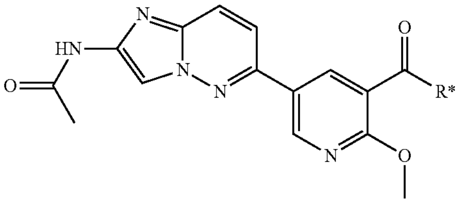

4A

| Ex | Name | R | Obs. MS Ion | NMR Assignments |
|---|---|---|---|---|
| 100 | 5-{2-acetamidoimidazo[1,2-b]pyridazin-6-yl}-N-[(2-fluoro-5-methoxyphenyl)methyl]-2-methoxypyridine-3-carboxamide | 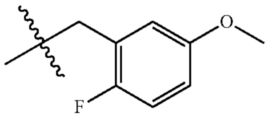 [SMILES: *Cc1cc(OC)ccc1F] | 465.0 | 1H NMR (500 MHz, DMSO-d6) δ 10.78 (br s, 1H), 8.97 (s, 1H), 8.79 (br s, 1H), 8.71 (s, 1H), 8.31 (s, 1H), 8.05 (br d, J = 9.3 Hz, 1H), 7.81 (br d, J = 9.4 Hz, 1H), 7.19-7.02 (m, 2H), 7.00 (br s, 1H), 6.92-6.79 (m, 2H), 4.57 (br d, J = 5.7 Hz, 2H), 4.09 (s, 3H), 2.55 (s, 1H), 2.13 (s, 3H) |
| 101 | 5-{2-acetamidoimidazo[1,2-b]pyridazin-6-yl}-2-methoxy-N-{[3-(2,2,2-trifluoroethoxy)pyridin-2-yl]methyl}pyridine-3-carboxamide, 2 TFA | 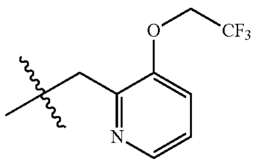 [SMILES: *Cc1ncccc1OCC(F)(F)F] | 516.2 | 1H NMR (500 MHz, DMSO-d6) δ 10.92 (s, 1H), 9.35-9.24 (m, 1H), 9.03 (d, J = 2.4 Hz, 1H), 8.92 (d, J = 2.1 Hz, 1H), 8.33 (s, 1H), 8.31 (s, 1H), 8.10 (d, J = 9.5 Hz, 1H), 7.86 (d, J = 9.5 Hz, 1H), 7.64 (d, J = 8.2 Hz, 1H), 7.42 (dd, J = 8.2, 4.9 Hz, 1H), 4.95 (q, J = 8.5 Hz, 2H), 4.69 (br d, J = 4.9 Hz, 2H), 4.17 (s, 3H), 2.13 (s, 3H). |
| 102 | 5-{2-acetamidoimidazo[1,2-b]pyridazin-6-yl}-N-{[2-fluoro-6-(2,2,2-trifluoroethoxy)phenyl]methyl}-2-methoxypyridine-3-carboxamide | 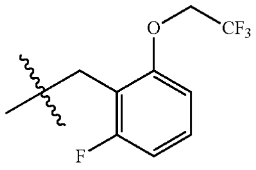 [SMILES: *Cc1c(F)cccc1OCC(F)(F)F] | 533.1 | 1H NMR (500 MHz, DMSO-d6) δ 10.92 (br s, 1H), 9.07-8.90 (m, 1H), 8.82-8.69 (m, 1H), 8.46 (br s, 1H), 8.31 (br s, 1H), 8.08 (br d, J = 9.5 Hz, 1H), 7.92-7.73 (m, 1H), 7.44-7.23 (m, 1H), 7.05 (br d, J = 8.2 Hz, 1H), 6.96 (br t, J = 8.9 Hz, 1H), 4.97-4.82 (m, 2H), 4.56 (br d, J = 5.2 Hz, 1H), 4.09 (s, 1H), 4.04 (s, 3H), 2.12 (s, 3H). |
| 103 | N-({2-[(2,6-dimethyloxan-4-yl)oxy]-3,5-difluorophenyl}methyl)-5-{2-acetamidoimidazo[1,2-b]pyridazin-6-yl}-2-methoxypyridine-3-carboxamide | 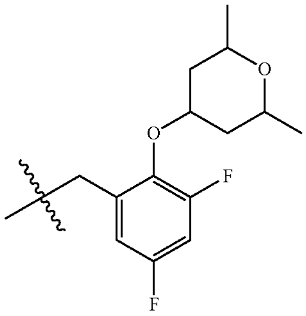 [SMILES: *Cc1cc(F)cc(F)c1OC1CC(C)OC(C)C1] | 581.2 | 1H NMR (500 MHz, DMSO-d6) δ 10.92 (s, 1H), 9.00 (s, 1H), 8.97-8.88 (m, 1H), 8.72 (s, 1H), 8.32 (s, 1H), 8.08 (d, J = 9.5 Hz, 1H), 7.85 (d, J = 9.2 Hz, 1H), 7.23 (br t, J = 8.7 Hz, 1H), 7.03 (br d, J = 8.9 Hz, 1H), 4.64-4.52 (m, 3H), 4.09 (s, 3H), 3.98 (br dd, J = 11.3, 6.1 Hz, 1H), 2.60-2.54 (m, 1H), 2.12 (s, 3H), 1.96-1.85 (m, 2H), 1.43 (br t, J = 12.1 Hz, 1H), 1.29 (q, J = 11.3 Hz, 1H), 1.18-1.09 (m, 6H). |
| 104 | 5-{2-acetamidoimidazo[1,2-b]pyridazin-6-yl}-2-methoxy-N-[(1R)-1-[2-(trifluoromethyl)phenyl]ethyl]pyridine-3-carboxamide | 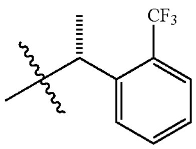 [SMILES: *[C@H](C)c1ccccc1C(F)(F)F] | 499.2 | 1H NMR (500 MHz, DMSO-d6) δ 10.91 (s, 1H), 8.99-8.88 (m, 2H), 8.55 (d, J = 2.4 Hz, 1H), 8.30 (s, 1H), 8.05 (d, J = 9.5 Hz, 1H), 7.88-7.78 (m, 2H), 7.76-7.68 (m, 2H), 7.49 (t, J = 7.5 Hz, 1H), 5.45 (br t, J = 6.9 Hz, 1H), 4.07 (s, 3H), 2.12 (s, 3H), 1.48 (d, J = 6.7 Hz, 3H) |
| 105 | 5-{2-acetamidoimidazo[1,2-b]pyridazin-6-yl}-N-{[5-fluoro-2-(2,2,2-trifluoroethoxy)phenyl]methyl}-2-methoxypyridine-3-carboxamide | 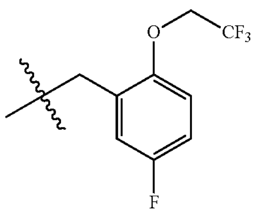 [SMILES: *Cc1cc(F)ccc1OCC(F)(F)F] | 533.2 | 1H NMR (500 MHz, DMSO-d6) δ 10.92 (s, 1H), 9.00 (d, J = 2.4 Hz, 1H), 8.86 (br t, J = 6.0 Hz, 1H), 8.75 (d, J = 2.1 Hz, 1H), 8.32 (s, 1H), 8.08 (d, J = 9.5 Hz, 1H), 7.85 (d, J = 9.8 Hz, 1H), 7.23-7.09 (m, 3H), 4.84 (q, J = 8.9 Hz, 2H), 4.53 (br d, J = 5.8 Hz, 2H), 4.10 (s, 3H), 2.13 (s, 3H). |

TABLE 4-continued

Compounds in Table 4 were prepared by methods as described in Examples 22, 23, and 25. For examples containing tertiary amides, the compounds are of formula (4A) and R* is as indicated in the table.

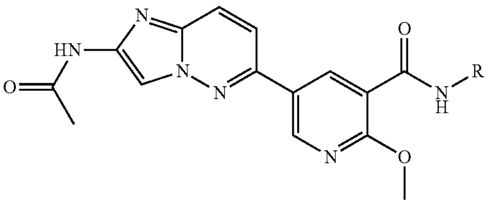

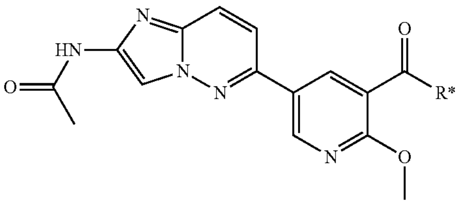

4A

| Ex | Name | R | Obs. MS Ion | NMR Assignments |
|---|---|---|---|---|
| 106 | 5-{2-acetamidoimidazo[1,2-b]pyridazin-6-yl}-N-[(1S)-1-[2-fluoro-5-(trifluoromethyl)phenyl](2,2,2-deutero)ethyl]-2-methoxypyridine-3-carboxamide | 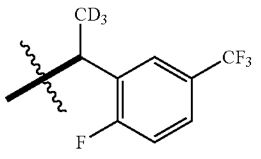 [SMILES: *[C@H](c1cc(C(F)(F)F)ccc1F)C([2H])([2H])[2H]] | 520.3 | 1H NMR (500 MHz, DMSO-d6) δ 10.77 (br s, 1H), 8.96 (d, J = 2.4 Hz, 1H), 8.86 (br d, J = 7.6 Hz, 1H), 8.56 (d, J = 2.4 Hz, 1H), 8.31 (s, 1H), 8.05 (d, J = 9.4 Hz, 1H), 7.95 (br d, J = 5.2 Hz, 1H), 7.81 (d, J = 9.4 Hz, 1H), 7.77-7.69 (m, 1H), 7.46 (t, J = 9.3 Hz, 1H), 5.44 (br d, J = 7.7 Hz, 1H), 4.08 (s, 3H), 2.13 (s, 3H). |
| 107 | 5-{2-acetamidoimidazo[1,2-b]pyridazin-6-yl}-N-[(1R)-1-[2-fluoro-5-(trifluoromethyl)phenyl](2,2,2-deutero)ethyl]-2-methoxypyridine-3-carboxamide | 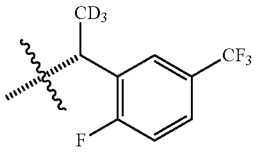 [SMILES: *[C@@H](c1cc(C(F)(F)F)ccc1F)C([2H])([2H])[2H]] | 520.3 | 1H NMR (500 MHz, DMSO-d6) δ 10.77 (br s, 1H), 8.96 (d, J = 2.4 Hz, 1H), 8.86 (br d, J = 7.6 Hz, 1H), 8.56 (d, J = 2.4 Hz, 1H), 8.30 (s, 1H), 8.05 (d, J = 9.4 Hz, 1H), 7.94 (br d, J = 6.6 Hz, 1H), 7.81 (d, J = 9.4 Hz, 1H), 7.73 (br s, 1H), 7.46 (t, J = 9.4 Hz, 1H), 5.44 (br d, J = 7.7 Hz, 1H), 4.08 (s, 3H), 2.13 (s, 3H). |
| 108 | 5-{2-acetamidoimidazo[1,2-b]pyridazin-6-yl}-2-methoxy-N-{[2-(2,2,2-trifluoroethoxy)phenyl]methyl}pyridine-3-carboxamide | 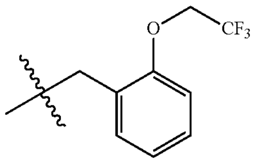 [SMILES: *Cc1ccccc1OCC(F)(F)F] | 515.3 | 1H NMR (500 MHz, DMSO-d6) δ 10.92 (s, 1H), 9.00 (d, J = 2.1 Hz, 1H), 8.83-8.71 (m, 2H), 8.32 (s, 1H), 8.09 (d, J = 9.5 Hz, 1H), 7.86 (d, J = 9.5 Hz, 1H), 7.40-7.26 (m, 2H), 7.15 (d, J = 7.9 Hz, 1H), 7.07 (t, J = 7.5 Hz, 1H), 4.85 (q, J = 8.9 Hz, 2H), 4.56 (br d, J = 6.1 Hz, 2H), 4.09 (s, 3H), 2.13 (s, 3H). |
| 109 | 5-{2-acetamidoimidazo[1,2-b]pyridazin-6-yl}-N-[(1R)-1-[2-fluoro-5-(trifluoromethoxy)phenyl](2,2,2-deutero)ethyl]-2-methoxypyridine-3-carboxamide | 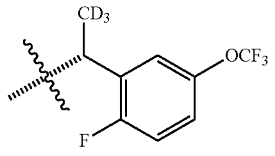 [SMILES: *[C@@H](c1cc(OC(F)(F)F)ccc1F)C([2H])([2H])[2H]] | 536.3 | 1H NMR (500 MHz, DMSO-d6) δ 10.92 (s, 1H), 8.99 (d, J = 2.4 Hz, 1H), 8.93 (br d, J = 7.6 Hz, 1H), 8.55 (d, J = 2.4 Hz, 1H), 8.31 (s, 1H), 8.08 (d, J = 9.5 Hz, 1H), 7.85 (d, J = 9.5 Hz, 1H), 7.55 (br s, 1H), 7.48-7.28 (m, 2H), 5.36 (br d, J = 7.6 Hz, 1H), 4.06 (s, 3H), 2.12 (s, 3H). |
| 110 | 5-{2-acetamidoimidazo[1,2-b]pyridazin-6-yl}-2-methoxy-N-{[3-(trifluoromethyl)phenyl](deutero)methyl}pyridine-3-carboxamide | 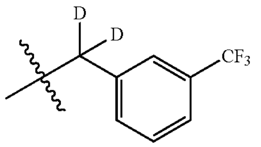 [SMILES: *C([2H])([2H])c1cccc(C(F)(F)F)c1] | 487.1 | 1H NMR (500 MHz, DMSO-d6) δ 10.92 (s, 1H), 9.05 (s, 1H), 9.00 (d, J = 2.4 Hz, 1H), 8.72 (d, J = 2.4 Hz, 1H), 8.32 (s, 1H), 8.09 (d, J = 9.5 Hz, 1H), 7.86 (d, J = 9.2 Hz, 1H), 7.76 (s, 1H), 7.73-7.59 (m, 3H), 4.09 (s, 3H), 2.13 (s, 3H). |
| 111 | 5-{2-acetamidoimidazo[1,2-b]pyridazin-6-yl}-N-{[2-fluoro-5-(trifluoromethyl)phenyl](deutero)methyl}-2-methoxypyridine-3-carboxamide | 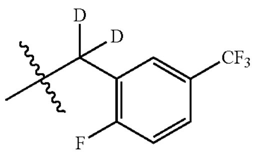 [SMILES: *C([2H])([2H])c1cc(C(F)(F)F)ccc1F] | 505.4 | 1H NMR (500 MHz, DMSO-d6) δ 10.91 (s, 1H), 9.04 (s, 1H), 8.98 (s, 1H), 8.67 (s, 1H), 8.30 (s, 1H), 8.06 (d, J = 9.5 Hz, 1H), 7.83 (br d, J = 9.2 Hz, 2H), 7.75 (br s, 1H), 7.47 (br t, J = 9.2 Hz, 1H), 4.07 (s, 3H), 2.11 (s, 3H). |
| 112 | 5-{2-acetamidoimidazo[1,2-b]pyridazin-6-yl}-2-methoxy-N-[(1R)-1-[3-(trifluoromethoxy)phenyl](2,2,2-deutero)ethyl]pyridine-3-carboxamide | 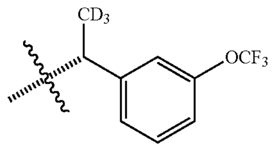 [SMILES: *[C@@H](c1cccc(OC(F)(F)F)c1)C([2H])([2H])[2H]] | 518.2 | 1H NMR (500 MHz, DMSO-d6) δ 10.91 (s, 1H), 9.02-8.91 (m, 1H), 8.82 (br d, J = 7.9 Hz, 1H), 8.63-8.48 (m, 1H), 8.30 (s, 1H), 8.07 (d, J = 9.5 Hz, 1H), 7.84 (d, J = 9.5 Hz, 1H), 7.55-7.40 (m, 3H), 7.26 (br d, J = 7.3 Hz, 1H), 5.20 (br d, J = 7.6 Hz, 1H), 4.05 (s, 3H), 2.12 (s, 3H). |

TABLE 4-continued

Compounds in Table 4 were prepared by methods as described in Examples 22, 23, and 25. For examples containing tertiary amides, the compounds are of formula (4A) and R* is as indicated in the table.

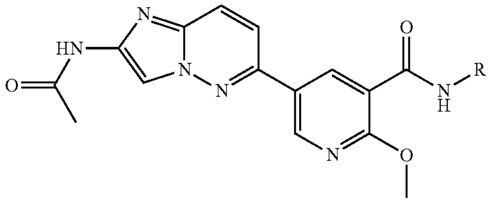

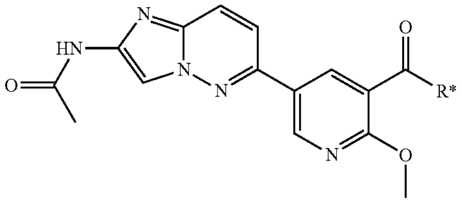

4A

| Ex | Name | R | Obs. MS Ion | NMR Assignments |
|---|---|---|---|---|
| 113 | 5-{2-acetamidoimidazo[1,2-b]pyridazin-6-yl}-2-methoxy-N-({2-[(morpholin-4-yl)methyl]phenyl}methyl)pyridine-3-carboxamide, 2 TFA | 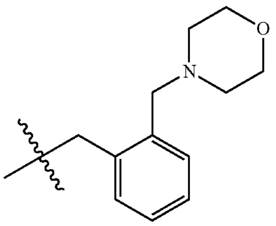 [SMILES: *Cc1ccccc1CN1CCOCC1] | 516.1 | 1H NMR (500 MHz, DMSO-d6) δ 10.92 (s, 1H), 9.34 (br s, 1H), 8.99 (s, 1H), 8.70 (d, J = 1.8 Hz, 1H), 8.29 (s, 1H), 8.08 (d, J = 9.5 Hz, 1H), 7.82 (d, J = 9.5 Hz, 1H), 7.58 (br d, J = 7.3 Hz, 1H), 7.54-7.48 (m, 2H), 7.45-7.34 (m, 1H), 7.29-7.03 (m, 1H), 4.67 (br d, J = 5.5 Hz, 2H), 4.57 (br s, 2H), 4.09 (s, 3H), 2.56-2.53 (m, 7H), 2.11 (s, 3H) |
| 114 | 5-{2-acetamidoimidazo[1,2-b]pyridazin-6-yl}-2-methoxy-N-({2-[(propan-2-yloxy)methyl]phenyl}methyl)pyridine-3-carboxamide, TFA | 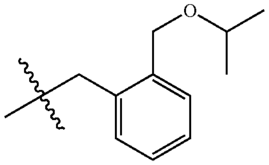 [SMILES: *Cc1ccccc1COC(C)C] | 489.3 | 1H NMR (500 MHz, DMSO-d6) δ 10.91 (s, 1H), 8.97 (d, J = 2.1 Hz, 1H), 8.78 (brt, J = 5.8 Hz, 1H), 8.72 (d, J = 2.1 Hz, 1H), 8.31 (s, 1H), 8.07 (d, J = 9.5 Hz, 1H), 7.84 (d, J = 9.5 Hz, 1H), 7.38 (t, J = 6.9 Hz, 2H), 7.31 (t, J = 7.3 Hz, 1H), 7.26 (d, J = 7.7 Hz, 1H), 4.65-4.55 (m, 4H), 4.06 (s, 3H), 3.71 (dt, J = 122, 6.1 Hz, 1H), 2.12 (s, 3H), 1.18 (d, J = 6.1 Hz, 6H). |
| 115 | N-{[3,5-difluoro-2-(oxetan-3-yloxy)phenyl]methyl}-5-{2-acetamidoimidazo[1,2-b]pyridazin-6-yl}-2-methoxypyridine-3-carboxamide | 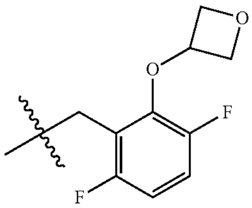 [SMILES: *Cc1c(F)ccc(F)c1OC1COC1] | 525.2 | 1H NMR (500 MHz, DMSO-d6) δ 10.91 (s, 1H), 9.02-8.88 (m, 2H), 8.71 (d, J = 2.1 Hz, 1H), 8.31 (s, 1H), 8.07 (d, J = 9.5 Hz, 1H), 7.84 (d, J = 9.5 Hz, 1H), 7.24 (br t, J = 8.5 Hz, 1H), 7.03 (br d, J = 8.9 Hz, 1H), 5.17 (br d, J = 4.6 Hz, 1H), 4.84 (t, J = 6.7 Hz, 2H), 4.74 (br t, J = 6.1 Hz, 2H), 4.56 (br d, J = 5.8 Hz, 2H), 4.09 (s, 3H), 2.11 (s, 3H). |
| 116 | N-{[3,5-difluoro-2-(2-methylpropoxy)phenyl]methyl}-5-{2-acetamidoimidazo[1,2-b]pyridazin-6-yl}-2-methoxypyridine-3-carboxamide | 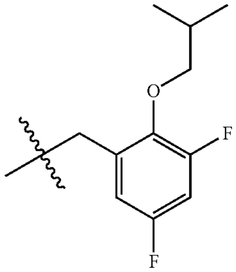 [SMILES: *Cc1cc(F)cc(F)c1OCC(C)C] | 525.4 | 1H NMR (500 MHz, DMSO-d6) δ 10.93 (s, 1H), 9.00 (br s, 1H), 8.93 (br t, J = 5.8 Hz, 1H), 8.73 (s, 1H), 8.31 (s, 1H), 8.09 (br d, J = 9.3 Hz, 1H), 7.86 (br d, J = 9.4 Hz, 1H), 7.29-7.17 (m, 1H), 7.01 (br d, J = 9.1 Hz, 1H), 4.59 (br d, J = 5.7 Hz, 2H), 4.09 (s, 3H), 3.83 (br d, J = 6.2 Hz, 2H), 2.14-2.10 (m, 3H), 2.10-2.03 (m, 1H), 1.04 (br d, J = 6.6 Hz, 6H). |
| 117 | 5-{2-acetamidoimidazo[1,2-b]pyridazin-6-yl}-2-methoxy-N-{[2-(2-methylpropoxy)phenyl]methyl}pyridine-3-carboxamide | 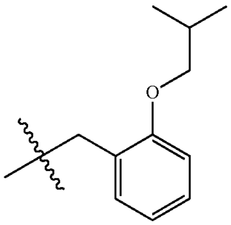 [SMILES: *Cc1ccccc1OCC(C)C] | 489.1 | 1H NMR (500 MHz, DMSO-d6) δ 10.93 (s, 1H), 8.99 (d, J = 2.3 Hz, 1H), 8.76 (d, J = 2.3 Hz, 1H), 8.70 (br t, J = 5.9 Hz, 1H), 8.32 (s, 1H), 8.09 (d, J = 9.4 Hz, 1H), 7.85 (d, J = 9.4 Hz, 1H), 7.32-7.22 (m, 2H), 7.00 (d, J = 8.1 Hz, 1H), 6.93 (t, J = 7.4 Hz, 1H), 4.54 (br d, J = 5.8 Hz, 2H), 4.08 (s, 3H), 3.83 (d, J = 6.3 Hz, 2H), 2.12 (s, 3H), 2.11-2.04 (m, 1H), 1.05 (d, J = 6.6 Hz, 6H). |

TABLE 4-continued

Compounds in Table 4 were prepared by methods as described in Examples 22, 23, and 25. For examples containing tertiary amides, the compounds are of formula (4A) and R* is as indicated in the table.

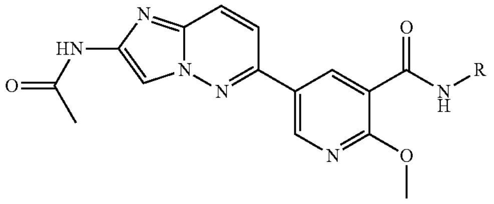

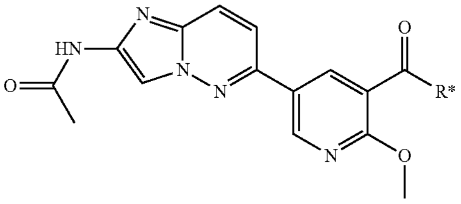

4A

| Ex | Name | R | Obs. MS Ion | NMR Assignments |
|---|---|---|---|---|
| 118 | N-[(2-cyclopropoxy-3,5-difluorophenyl)methyl]-5-{2-acetamidoimidazo[1,2-b]pyridazin-6-yl}-2-methoxypyridine-3-carboxamide | 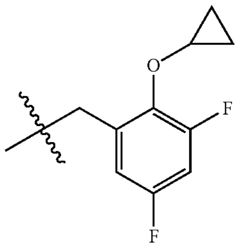 [SMILES: *Cc1cc(F)cc(F)c1OC1CC1] | 509.1 | 1H NMR (500 MHz, DMSO-d6) δ 10.91 (s, 1H), 8.98 (d, J = 2.1 Hz, 1H), 8.92 (br t, J = 6.0 Hz, 1H), 8.72 (d, J = 2.1 Hz, 1H), 8.31 (s, 1H), 8.07 (d, J = 9.5 Hz, 1H), 7.84 (d, J = 9.5 Hz, 1H), 7.25 (br t, J = 8.7 Hz, 1H), 7.00 (br d, J = 8.9 Hz, 1H), 4.48 (br d, J = 6.1 Hz, 2H), 4.23 (br d, J = 2.7 Hz, 1H), 4.08 (s, 3H), 2.11 (s, 3H), 0.85 (br s, 2H), 0.73-0.57 (m, 2H). |
| 119 | N-[(3S)-3-(4-chlorophenyl)-3-hydroxypropyl]-5-{2-acetamidoimidazo[1,2-b]pyridazin-6-yl}-2-methoxypyridine-3-carboxamide | 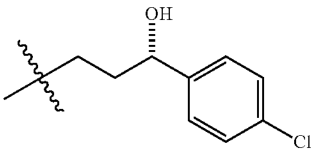 [SMILES: *CC[C@H](O)c1ccc(Cl)cc1] | 495.2 | 1H NMR (500 MHz, DMSO-d6) Shift 10.92 (s, 1H), 8.99-8.91 (m, 1H), 8.71 (d, J = 2.3 Hz, 1H), 8.56 (br t, J = 5.3 Hz, 1H), 8.31 (s, 1H), 8.07 (d, J = 9.4 Hz, 1H), 7.82 (d, J = 9.4 Hz, 1H), 7.44-7.35 (m, 4H), 5.57 (br s, 1H), 4.76-4.67 (m, 1H), 4.05 (s, 3H), 3.49 (br s, 2H), 2.12 (s, 3H), 1.99-1.81 (m, 2H) |
| 120 | 5-{2-acetamidoimidazo[1,2-b]pyridazin-6-yl}-N-{[4-fluoro-2-(trifluoromethoxy)phenyl]methyl}-2-methoxypyridine-3-carboxamide | 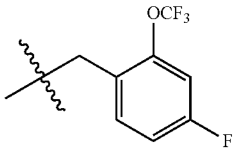 [SMILES: *Cc1ccc(F)cc1OC(F)(F)F] | 519.2 | 1H NMR (500 MHz, DMSO-d6) δ 10.92 (s, 1H), 9.03-8.91 (m, 2H), 8.81-8.66 (m, 1H), 8.31 (s, 1H), 8.08 (br d, J = 9.5 Hz, 1H), 7.84 (br d, J = 9.5 Hz, 1H), 7.57 (br t, J = 7.5 Hz, 1H), 7.43-7.27 (m, 2H), 4.58 (br d, J = 5.5 Hz, 2H), 4.08 (s, 3H), 2.12 (s, 3H). |
| 121 | N-({2-[cyclopropyl(deutero)methoxy]-3,5-difluorophenyl}methyl)-5-{2-acetamidoimidazo[1,2-b]pyridazin-6-yl}-2-methoxypyridine-3-carboxamide | 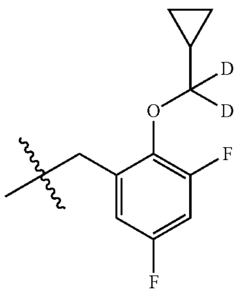 [SMILES: *Cc1cc(F)cc(F)c1OC([2H])([2H])C1CC1] | 525.1 | 1H NMR (500 MHz, DMSO-d6) δ 10.90 (s, 1H), 9.01-8.87 (m, 2H), 8.70 (d, J = 2.1 Hz, 1H), 8.29 (s, 1H), 8.05 (br d, J = 9.5 Hz, 1H), 7.82 (br d, J = 9.5 Hz, 1H), 7.18 (br t, J = 8.5 Hz, 1H), 6.98 (br d, J = 8.5 Hz, 1H), 4.60 (br d, J = 5.8 Hz, 2H), 4.07 (s, 3H), 2.10 (s, 3H), 1.21 (br s, 1H), 0.56 (br d, J = 6.7 Hz, 2H), 0.29 (br d, J = 4.6 Hz, 2H). |
| 122 | N-{1-[2-(cyclopropylmethoxy)-6-fluorophenyl]ethyl}-5-{2-acetamidoimidazo[1,2-b]pyridazin-6-yl}-2-methoxypyridine-3-carboxamide, TFA | 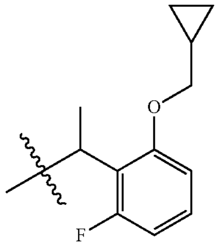 [SMILES: *C(C)c1c(F)cccc1OCC1CC1] | 519 | 1H NMR (500 MHz, DMSO-d6) δ 10.91 (s, 1H), 8.99 (d, J = 2.1 Hz, 1H), 8.90-8.79 (m, 2H), 8.31 (s, 1H), 8.07 (br d, J = 9.5 Hz, 1H), 7.83 (d, J = 9.5 Hz, 1H), 7.34-7.20 (m, 1H), 6.90 (br d, J = 8.2 Hz, 1H), 6.82 (br t, J = 9.3 Hz, 1H), 5.84-5.74 (m, 1H), 4.11 (s, 4H), 3.90 (dd, J = 10.2, 7.5 Hz, 1H), 2.12 (s, 3H), 1.54 (br d, J = 7.0 Hz, 3H), 1.32 (br s, 1H), 0.67-0.55 (m, 2H), 0.39 (br d, J = 4.6 Hz, 2H). |

TABLE 4-continued

Compounds in Table 4 were prepared by methods as described in Examples 22, 23, and 25. For examples containing tertiary amides, the compounds are of formula (4A) and R* is as indicated in the table.

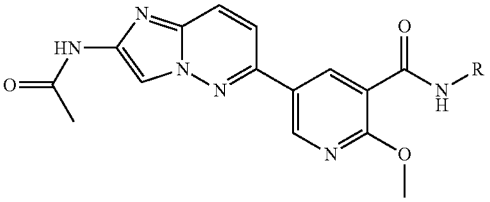

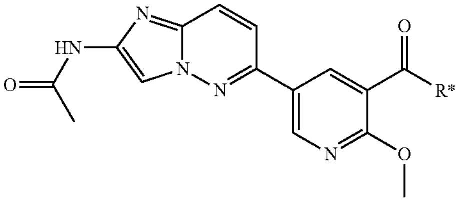

4A

| Ex | Name | R | Obs. MS Ion | NMR Assignments |
|---|---|---|---|---|
| 123 | 5-{2-acetamidoimidazo[1,2-b]pyridazin-6-yl}-2-methoxy-N-{1-[3-(trifluoro-methoxy)phenyl]ethyl}pyridine-3-carboxamide | 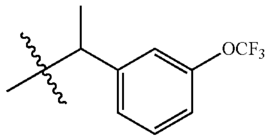 [SMILES: *C(C)c1cccc(OC(F)(F)F)c1] | 515.1 | 1H NMR (500 MHz, DMSO-d6) δ 10.91 (br s, 1H), 8.96 (s, 1H), 8.83 (br d, J = 7.9 Hz, 1H), 8.55 (s, 1H), 8.30 (s, 1H), 8.06 (br d, J = 9.2 Hz, 1H), 7.83 (br d, J = 9.5 Hz, 1H), 7.54-7.41 (m, 3H), 7.25 (br d, J = 7.0 Hz, 1H), 5.21 (br t, J = 7.3 Hz, 1H), 4.05 (s, 3H), 2.12 (s, 3H), 1.49 (br d, J = 7.0 Hz, 3H). |
| 124 | N-{1-[2-(cyclopropylmethoxy)-6-fluorophenyl]ethyl}-5-{2-acetamidoimidazo[1,2-b]pyridazin-6-yl}-2-methoxypyridine-3-carboxamide, TFA | 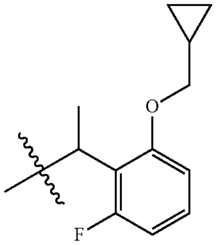 [SMILES: *C(C)c1c(F)cccc1OCC1CC1] | 519.2 | 1H NMR (500 MHz, DMSO-d6) δ 10.91 (s, 1H), 8.99 (d, J = 2.1 Hz, 1H), 8.90-8.79 (m, 2H), 8.31 (s, 1H), 8.07 (br d, J = 9.5 Hz, 1H), 7.83 (d, J = 9.5 Hz, 1H), 7.34-7.20 (m, 1H), 6.90 (br d, J = 8.2 Hz, 1H), 6.82 (br t, J = 9.3 Hz, 1H), 5.84-5.74 (m, 1H), 4.11 (s, 4H), 3.90 (dd, J = 10.2, 7.5 Hz, 1H), 2.12 (s, 3H), 1.54 (br d, J = 7.0 Hz, 3H), 1.32 (br s, 1H), 0.67-0.55 (m, 2H), 0.39 (br d, J = 4.6 Hz, 2H). |
| 125 | 5-{2-acetamidoimidazo[1,2-b]pyridazin-6-yl}-2-methoxy-N-{1-[3-(trifluoro-methoxy)phenyl]ethyl}pyridine-3-carboxamide | 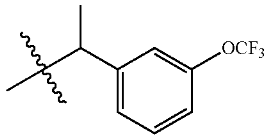 [SMILES: *C(C)c1cccc(OC(F)(F)F)c1] | 515.2 | 1H NMR (500 MHz, DMSO-d6) δ 10.91 (br s, 1H), 8.96 (s, 1H), 8.83 (br d, J = 7.9 Hz, 1H), 8.55 (s, 1H), 8.30 (s, 1H), 8.06 (br d, J = 9.2 Hz, 1H), 7.83 (br d, J = 9.5 Hz, 1H), 7.54-7.41 (m, 3H), 7.25 (br d, J = 7.0 Hz, 1H), 5.21 (br t, J = 7.3 Hz, 1H), 4.05 (s, 3H), 2.12 (s, 3H), 1.49 (br d, J = 7.0 Hz, 3H). |
| 126 | 5-{2-acetamidoimidazo[1,2-b]pyridazin-6-yl}-2-methoxy-N-{[3-(trifluoro-methoxy)phenyl]methyl}pyridine-3-carboxamide | 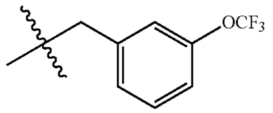 [SMILES: *Cc1cccc(OC(F)(F)F)c1] | 501.1 | 1H NMR (500 MHz, DMSO-d6) δ 10.91 (s, 1H), 9.08-8.93 (m, 2H), 8.71 (d, J = 2.1 Hz, 1H), 8.31 (s, 1H), 8.08 (d, J = 9.2 Hz, 1H), 7.85 (d, J = 9.5 Hz, 1H), 7.56-7.46 (m, 1H), 7.41 (d, J = 7.6 Hz, 1H), 7.38-7.36 (m, 1H), 7.26 (br d, J = 7.9 Hz, 1H), 4.59 (br d, J = 5.8 Hz, 2H), 4.07 (s, 3H), 2.12 (s, 3H). |
| 127 | N-{[2-(cyclopropylmethoxy)-3,6-difluorophenyl]methyl}-5-{2-acetamidoimidazo[1,2-b]pyridazin-6-yl}-2-methoxypyridine-3-carboxamide | 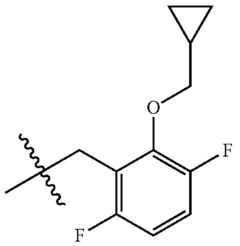 [SMILES: *Cc1c(F)ccc(F)c1OCC1CC1] | 522.9 | 1H NMR (500 MHz, DMSO-d6) δ 10.66 (s, 1H), 8.79-8.62 (m, 1H), 8.51-8.36 (m, 2H), 8.06 (s, 1H), 7.82 (d, J = 9.5 Hz, 1H), 7.66-7.51 (m, 1H), 7.08-6.89 (m, 1H), 6.76 (td, J = 9.1, 3.5 Hz, 1H), 4.40 (br d, J = 5.2 Hz, 2H), 3.80 (s, 3H), 3.74 (br d, J = 7.0 Hz, 2H), 1.87 (s, 3H), 1.06 (br s, 1H), 0.33 (br d, J = 6.4 Hz, 2H), 0.10 (br d, J = 4.0 Hz, 2H). |
| 128 | 5-{2-acetamidoimidazo[1,2-b]pyridazin-6-yl}-N-{[2-fluoro-6-(oxan-4-yloxy)phenyl]methyl}-2-methoxypyridine-3-carboxamide, TFA | 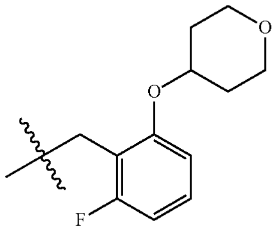 [SMILES: *Cc1c(F)cccc1OC1CCOCC1] | 535.2 | 1H NMR (500 MHz, DMSO-d6) δ 10.91 (s, 1H), 8.96 (d, J = 2.1 Hz, 1H), 8.72 (d, J = 2.4 Hz, 1H), 8.46 (br s, 1H), 8.30 (s, 1H), 8.06 (d, J = 9.5 Hz, 1H), 7.82 (d, J = 9.5 Hz, 1H), 7.14 (s, 1H), 7.04 (s, 1H), 6.97 (br d, J = 8.5 Hz, 1H), 4.77-4.66 (m, 1H), 4.60 (br d, J = 5.2 Hz, 2H), 4.05 (s, 3H), 3.94-3.82 (m, 2H), 2.12 (s, 3H), 2.00 (br d, J = 12.5 Hz, 2H), 1.77-1.64 (m, 2H), 1.23 (s, 2H). |

TABLE 4-continued

Compounds in Table 4 were prepared by methods as described in Examples 22, 23, and 25. For examples containing tertiary amides, the compounds are of formula (4A) and R* is as indicated in the table.

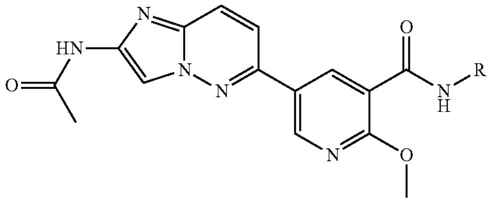

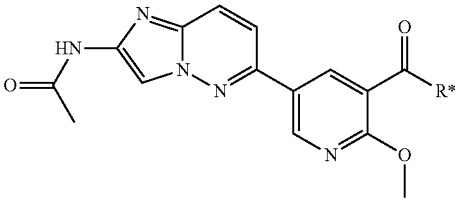

4A

| Ex | Name | R | Obs. MS Ion | NMR Assignments |
|---|---|---|---|---|
| 129 | N-{[3,5-difluoro-2-(oxan-4-yloxy)phenyl]methyl}-5-{2-acetamidoimidazo[1,2-b]pyridazin-6-yl}-2-methoxypyridine-3-carboxamide, TFA | 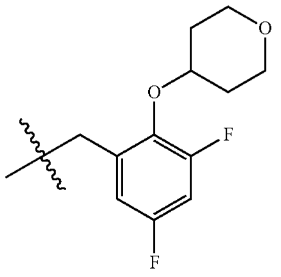 [SMILES: *Cc1cc(F)cc(F)c1OC1CCOCC1] | 553.3 | 1H NMR (500 MHz, DMSO-d6) δ 10.90 (s, 1H), 9.04-8.87 (m, 2H), 8.76-8.65 (m, 1H), 8.30 (s, 1H), 8.05 (d, J = 9.5 Hz, 1H), 7.82 (d, J = 9.5 Hz, 1H), 7.27-7.13 (m, 1H), 7.09-6.92 (m, 1H), 4.58 (br d, J = 5.8 Hz, 2H), 4.37-4.21 (m, 1H), 4.07 (s, 3H), 3.90 (br d, J = 11.6 Hz, 1H), 3.62-3.48 (m, 1H), 3.39 (br t, J = 10.1 Hz, 1H), 2.11 (s, 3H), 1.96 (br d, J = 11.6 Hz, 2H), 1.77-1.63 (m, 2H). |
| 130 | N-{1-[2-(cyclopropylmethoxy)-3,5-difluorophenyl]ethyl}-5-{2-acetamidoimidazo[1,2-b]pyridazin-6-yl}-2-methoxypyridine-3-carboxamide | 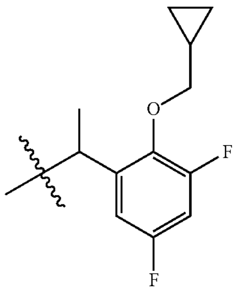 [SMILES: *C(C)c1cc(F)cc(F)c1OCC1CC1] | 537 | 1H NMR (500 MHz, DMSO-d6) δ 10.91 (s, 1H), 8.97 (d, J = 2.1 Hz, 1H), 8.81 (br d, J = 7.6 Hz, 1H), 8.57 (d, J = 2.1 Hz, 1H), 8.31 (s, 1H), 8.07 (d, J = 9.5 Hz, 1H), 7.84 (d, J = 9.5 Hz, 1H), 7.23-7.14 (m, 2H), 5.51 (br t, J = 7.2 Hz, 1H), 4.07 (s, 3H), 4.00-3.86 (m, 2H), 2.11 (s, 3H), 1.44 (br d, J = 7.0 Hz, 3H), 1.31 (br s, 1H), 0.60 (br d, J = 7.6 Hz, 2H), 0.35 (br d, J = 15.6 Hz, 2H). |
| 131 | N-{[2-(1-cyclopropylethoxy)-3,4-difluorophenyl]methyl}-5-{2-acetamidoimidazo[1,2-b]pyridazin-6-yl}-2-methoxypyridine-3-carboxamide | 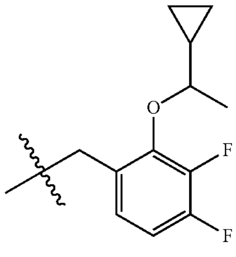 [SMILES: *Cc1ccc(F)c(F)c1OC(C)C1CC1] | 537.3 | 1H NMR (500 MHz, DMSO-d6) δ 10.89 (s, 1H), 8.94 (d, J = 2.4 Hz, 1H), 8.83 (br t, J = 6.0 Hz, 1H), 8.70 (d, J = 2.4 Hz, 1H), 8.29 (s, 1H), 8.04 (d, J = 9.5 Hz, 1H), 7.80 (d, J = 9.5 Hz, 1H), 7.17-7.07 (m, 2H), 4.56 (br d, J = 6.1 Hz, 2H), 4.05 (s, 3H), 3.80-3.63 (m, 1H), 2.10 (s, 3H), 1.40 (d, J = 6.1 Hz, 3H), 1.12 (br d, J = 7.9 Hz, 1H), 0.46 (q, J = 7.0 Hz, 2H), 0.31-0.16 (m, 1H), 0.16-0.09 (m, 1H). |
| 132 | N-{[2-(1-cyclopropylethoxy)-3,4-difluorophenyl]methyl}-5-{2-acetamidoimidazo[1,2-b]pyridazin-6-yl}-2-methoxypyridine-3-carboxamide | 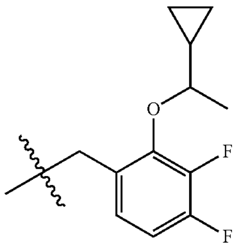 [SMILES: *Cc1ccc(F)c(F)c1OC(C)C1CC1] | 537.2 | 1H NMR (500 MHz, DMSO-d6) δ 10.89 (s, 1H), 8.94 (d, J = 2.4 Hz, 1H), 8.83 (br t, J = 6.0 Hz, 1H), 8.70 (d, J = 2.4 Hz, 1H), 8.29 (s, 1H), 8.04 (d, J = 9.5 Hz, 1H), 7.80 (d, J = 9.5 Hz, 1H), 7.17-7.07 (m, 2H), 4.56 (br d, J = 6.1 Hz, 2H), 4.05 (s, 3H), 3.80-3.63 (m, 1H), 2.10 (s, 3H), 1.40 (d, J = 6.1 Hz, 3H), 1.12 (br d, J = 7.9 Hz, 1H), 0.46 (q, J = 7.0 Hz, 2H), 0.31-0.16 (m, 1H), 0.16-0.09 (m, 1H). |

TABLE 4-continued

Compounds in Table 4 were prepared by methods as described in Examples 22, 23, and 25. For examples containing tertiary amides, the compounds are of formula (4A) and R* is as indicated in the table.

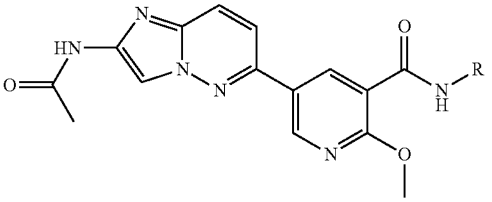

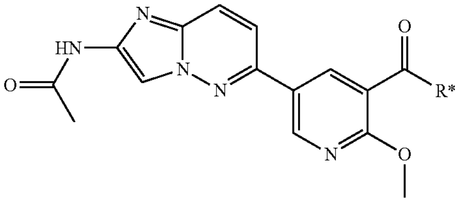

4A

| Ex | Name | R | Obs. MS Ion | NMR Assignments |
|---|---|---|---|---|
| 133 | N-{1-[2-(cyclopropylmethoxy)-3,5-difluorophenyl]ethyl}-5-{2-acetamidoimidazo[1,2-b]pyridazin-6-yl}-2-methoxypyridine-3-carboxamide | 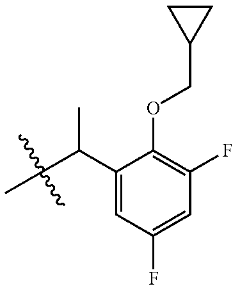 [SMILES: *C(C)c1cc(F)cc(F)c1OCC1CC1] | 537.3 | 1H NMR (500 MHz, DMSO-d6) δ 10.91 (s, 1H), 8.97 (d, J = 2.1 Hz, 1H), 8.81 (br d, J = 7.6 Hz, 1H), 8.57 (d, J = 2.1 Hz, 1H), 8.31 (s, 1H), 8.07 (d, J = 9.5 Hz, 1H), 7.84 (d, J = 9.5 Hz, 1H), 7.23-7.14 (m, 2H), 5.51 (br t, J = 7.2 Hz, 1H), 4.07 (s, 3H), 4.00-3.86 (m, 2H), 2.11 (s, 3H), 1.44 (br d, J = 7.0 Hz, 3H), 1.31 (br s, 1H), 0.60 (br d, J = 7.6 Hz, 2H), 0.35 (br d, J = 15.6 Hz, 2H). |
| 134 | N-{[2-(1-cyclopropylethoxy)-3-fluorophenyl]methyl}-5-{2-acetamidoimidazo[1,2-b]pyridazin-6-yl}-2-methoxypyridine-3-carboxamide | 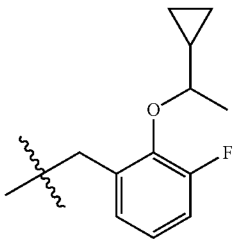 [SMILES: *Cc1cccc(F)c1OC(C)C1CC1] | 519.1 | 1H NMR (500 MHz, DMSO-d6) δ 10.77 (s, 1H), 8.84 (d, J = 2.1 Hz, 1H), 8.70 (br t, J = 6.0 Hz, 1H), 8.60 (d, J = 2.4 Hz, 1H), 8.17 (s, 1H), 7.93 (d, J = 9.2 Hz, 1H), 7.70 (d, J = 9.5 Hz, 1H), 7.06-6.90 (m, 3H), 4.50 (br d, J = 6.1 Hz, 2H), 3.94 (s, 3H), 3.61-3.42 (m, 1H), 1.97 (s, 3H), 1.25 (d, J = 6.1 Hz, 3H), 0.99 (br d, J = 7.0 Hz, 1H), 0.41-0.24 (m, 2H), 0.07 (br d, J = 8.5 Hz, 1H), −0.01 (br d, J = 8.9 Hz, 1H). |
| 135 | N-{[2-(1-cyclopropylethoxy)-3-fluorophenyl]methyl}-5-{2-acetamidoimidazo[1,2-b]pyridazin-6-yl}-2-methoxypyridine-3-carboxamide | 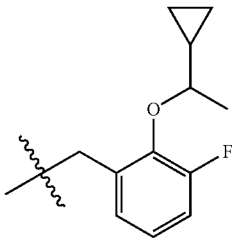 [SMILES: *Cc1cccc(F)c1OC(C)C1CC1] | 519.1 | 1H NMR (500 MHz, DMSO-d6) δ 10.77 (s, 1H), 8.84 (d, J = 2.1 Hz, 1H), 8.70 (br t, J = 6.0 Hz, 1H), 8.60 (d, J = 2.4 Hz, 1H), 8.17 (s, 1H), 7.93 (d, J = 9.2 Hz, 1H), 7.70 (d, J = 9.5 Hz, 1H), 7.06-6.90 (m, 3H), 4.50 (br d, J = 6.1 Hz, 2H), 3.94 (s, 3H), 3.61-3.42 (m, 1H), 1.97 (s, 3H), 1.25 (d, J = 6.1 Hz, 3H), 0.99 (br d, J = 7.0 Hz, 1H), 0.41-0.24 (m, 2H), 0.07 (br d, J = 8.5 Hz, 1H), −0.01 (br d, J = 8.9 Hz, 1H). |
| 136 | N-{[3-(1-cyclopropylethoxy)pyridin-2-yl]methyl}-5-{2-acetamidoimidazo[1,2-b]pyridazin-6-yl}-2-methoxypyridine-3-carboxamide | 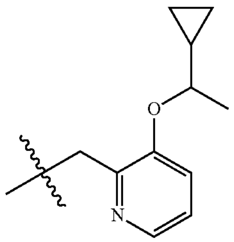 [SMILES: *Cc1ncccc1OC(C)C1CC1] | 501.9 | 1H NMR (500 MHz, DMSO-d6) δ 10.91 (s, 1H), 9.42-9.25 (m, 1H), 9.01 (d, J = 2.4 Hz, 1H), 8.92 (d, J = 2.1 Hz, 1H), 8.32 (s, 1H), 8.17 (d, J = 4.6 Hz, 1H), 8.08 (d, J = 9.5 Hz, 1H), 7.85 (d, J = 9.5 Hz, 1H), 7.48 (d, J = 8.2 Hz, 1H), 7.31 (dd, J = 8.1, 4.7 Hz, 1H), 4.64 (br d, J = 4.6 Hz, 2H), 4.18 (s, 3H), 4.15-4.08 (m, 1H), 2.12 (s, 3H), 1.35 (d, J = 5.8 Hz, 3H), 1.00 (d, J = 6.4 Hz, 1H), 0.52 (br d, J = 8.2 Hz, 2H), 0.43-0.25 (m, 2H) |
| 137 | 5-{2-acetamidoimidazo[1,2-b]pyridazin-6-yl}-2-methoxy-N-{1-[2-(trifluoromethoxy)phenyl]ethyl}pyridine-3-carboxamide | 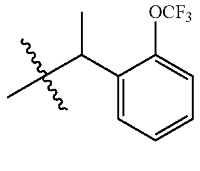 [SMILES: *C(C)c1ccccc1OC(F)(F)F] | 514.9 | 1H NMR (500 MHz, DMSO-d6) δ 10.90 (s, 1H), 8.95 (d, J = 2.4 Hz, 1H), 8.81 (d, J = 7.6 Hz, 1H), 8.58 (d, J = 2.4 Hz, 1H), 8.30 (s, 1H), 8.06 (d, J = 9.5 Hz, 1H), 7.82 (d, J = 9.5 Hz, 1H), 7.72-7.59 (m, 1H), 7.48-7.32 (m, 3H), 5.42 (quin, J = 7.2 Hz, 1H), 4.06 (s, 3H), 2.11 (s, 3H), 1.47 (d, J = 7.0 Hz, 3H). |

TABLE 4-continued

Compounds in Table 4 were prepared by methods as described in Examples 22, 23, and 25. For examples containing tertiary amides, the compounds are of formula (4A) and R* is as indicated in the table.

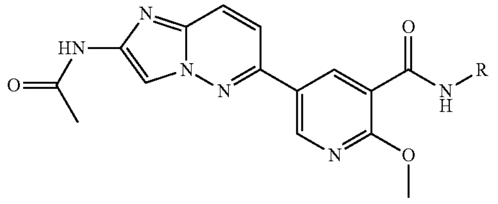

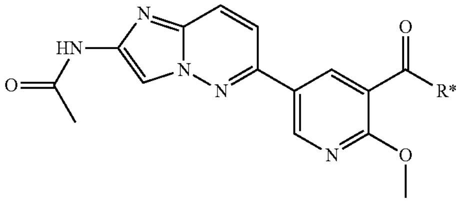

4A

| Ex | Name | R | Obs. MS Ion | NMR Assignments |
|---|---|---|---|---|
| 138 | 5-{2-acetamidoimidazo[1,2-b]pyridazin-6-yl}-N-{[3-fluoro-5-(trifluoromethoxy)phenyl]methyl}-2-methoxypyridine-3-carboxamide | 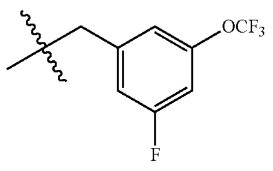 [SMILES: *Cc1cc(F)cc(OC(F)(F)F)c1] | 519.3 | 1H NMR (500 MHz, DMSO-d6) δ 10.93 (br s, 1H), 9.11 (br s, 1H), 8.95 (br s, 1H), 8.68 (s, 1H), 8.29 (s, 1H), 8.04 (br d, J = 9.3 Hz, 1H), 7.81 (br d, J = 9.3 Hz, 1H), 4.57 (br d, J = 5.9 Hz, 2H), 4.06 (s, 3H), 2.55 (s, 3H), 2.11 (s, 3H). |
| 139 | 5-{2-acetamidoimidazo[1,2-b]pyridazin-6-yl}-2-methoxy-N-{1-[2-(trifluoro-methoxy)phenyl]ethyl}pyridine-3-carboxamide | 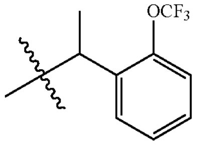 [SMILES: *C(C)c1ccccc1OC(F)(F)F] | 515.4 | 1H NMR (500 MHz, DMSO-d6) δ 10.90 (s, 1H), 8.95 (d, J = 2.4 Hz, 1H), 8.81 (d, J = 7.6 Hz, 1H), 8.58 (d, J = 2.4 Hz, 1H), 8.30 (s, 1H), 8.06 (d, J = 9.5 Hz, 1H), 7.82 (d, J = 9.5 Hz, 1H), 7.72-7.59 (m, 1H), 7.48-7.32 (m, 3H), 5.42 (quin, J = 7.2 Hz, 1H), 4.06 (s, 3H), 2.11 (s, 3H), 1.47 (d, J = 7.0 Hz, 3H). |
| 140 | N-{[3-(cyclopropylmethoxy)-5-fluorophenyl]methyl}-5-{2-acetamidoimidazo[1,2-b]pyridazin-6-yl}-2-methoxypyridine-3-carboxamide | 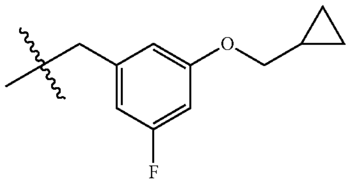 [SMILES: *Cc1cc(F)cc(OCC2CC2)c1] | 505.4 | 1H NMR (500 MHz, DMSO-d6) δ 10.91 (s, 1H), 9.05-8.84 (m, 2H), 8.71 (d, J = 2.1 Hz, 1H), 8.31 (s, 1H), 8.08 (d, J = 9.5 Hz, 1H), 7.85 (d, J = 9.5 Hz, 1H), 6.88-6.72 (m, 2H), 6.68 (br d, J = 11.0 Hz, 1H), 4.50 (br d, J = 6.1 Hz, 2H), 4.08 (s, 3H), 3.83 (d, J = 7.0 Hz, 2H), 2.12 (s, 3H), 1.21 (br s, 1H), 0.65-0.47 (m, 2H), 0.31 (br d, J = 4.9 Hz, 2H). |
| 141 | N-[(3,6-difluoro-2-methoxyphenyl)methyl]-5-{2-acetamidoimidazo[1,2-b]pyridazin-6-yl}-2-methoxypyridine-3-carboxamide | 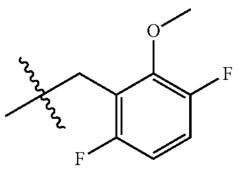 [SMILES: *Cc1c(F)ccc(F)c1OC] | 483.3 | 1H NMR (500 MHz, DMSO-d6) δ 10.90 (s, 1H), 8.96 (d, J = 2.1 Hz, 1H), 8.69 (br d, J = 2.4 Hz, 2H), 8.30 (s, 1H), 8.06 (d, J = 9.5 Hz, 1H), 7.82 (d, J = 9.5 Hz, 1H), 7.29 (td, J = 10.1, 5.3 Hz, 1H), 7.00 (td, J = 9.2, 3.7 Hz, 1H), 4.59 (br d, J = 5.5 Hz, 2H), 4.05 (s, 3H), 3.98 (s, 3H), 2.11 (s, 3H) |
| 142 | N-{[3-(cyclopropylmethoxy)-4-fluorophenyl]methyl}-5-{2-acetamidoimidazo[1,2-b]pyridazin-6-yl}-2-methoxypyridine-3-carboxamide | 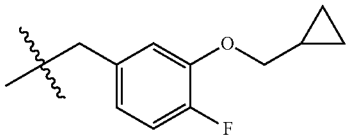 [SMILES: *Cc1ccc(F)c(OCC2CC2)c1] | 505.2 | 1H NMR (500 MHz, DMSO-d6) δ 10.91 (s, 1H), 8.96 (d, J = 2.1 Hz, 1H), 8.90 (br t, J = 6.0 Hz, 1H), 8.69 (d, J = 2.1 Hz, 1H), 8.31 (s, 1H), 8.06 (d, J = 9.5 Hz, 1H), 7.83 (d, J = 9.5 Hz, 1H), 7.26-7.06 (m, 2H), 6.93 (br s, 1H), 4.48 (br d, J = 5.8 Hz, 2H), 4.06 (s, 3H), 3.89 (d, J = 6.7 Hz, 2H), 2.11 (s, 3H), 1.24 (br s, 1H), 0.57 (br d, J = 7.0 Hz, 2H), 0.33 (br d, J = 5.2 Hz, 2H). |
| 143 | 5-{2-acetamidoimidazo[1,2-b]pyridazin-6-yl}-2-methoxy-N-methyl-N-{[3-(trifluoromethoxy)phenyl]meth-yl}pyridine-3-carboxamide | R* is 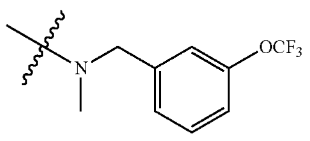 | 515.4 | 1H NMR (500 MHz, DMSO-d6) δ 11.01-10.81 (m, 1H), 8.94 (d, J = 2.4 Hz, 1H), 8.37 (d, J = 2.4 Hz, 1H), 8.33-8.21 (m, 2H), 8.16-7.94 (m, 1H), 7.84 (d, J = 9.5 Hz, 1H), 7.56 (t, J = 7.9 Hz, 1H), 7.42 (br d, J = 7.6 Hz, 1H), 7.37-7.28 (m, 2H), 7.24 (br d, J = 7.9 Hz, 1H), 4.46 (br s, 1H), 4.02 (s, 3H), 2.80 (s, 2H), 2.11 (s, 3H) |

TABLE 4-continued

Compounds in Table 4 were prepared by methods as described in Examples 22, 23, and 25. For examples containing tertiary amides, the compounds are of formula (4A) and R* is as indicated in the table.

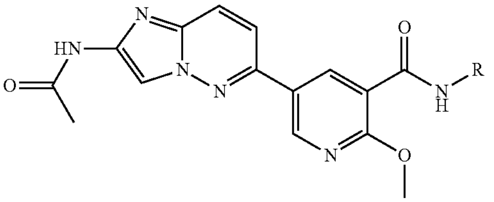

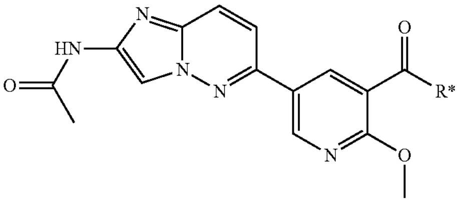

4A

| Ex | Name | R | Obs. MS Ion | NMR Assignments |
|---|---|---|---|---|
| 144 | N-{[2-(1-cyclopropylethoxy)-3-fluorophenyl]methyl}-5-{2-acetamidoimidazo[1,2-b]pyridazin-6-yl}-2-methoxypyridine-3-carboxamide | 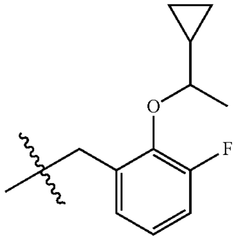 [SMILES: *Cc1cccc(F)c1OC(C)C1CC1] | 519.4 | 1H NMR (500 MHz, DMSO-d6) δ 10.77 (s, 1H), 8.84 (d, J = 2.1 Hz, 1H), 8.70 (br t, J = 6.0 Hz, 1H), 8.60 (d, J = 2.4 Hz, 1H), 8.17 (s, 1H), 7.93 (d, J = 9.2 Hz, 1H), 7.70 (d, J = 9.5 Hz, 1H), 7.06-6.90 (m, 3H), 4.50 (br d, J = 6.1 Hz, 2H), 3.94 (s, 3H), 3.61-3.42 (m, 1H), 1.97 (s, 3H), 1.25 (d, J = 6.1 Hz, 3H), 0.99 (br d, J = 7.0 Hz, 1H), 0.41-0.24 (m, 2H), 0.07 (br d, J = 8.5 Hz, 1H), −0.01 (br d, J = 8.9 Hz, 1H). |
| 145 | 5-{2-acetamidoimidazo[1,2-b]pyridazin-6-yl}-N-{[2-fluoro-5-(trifluoro-methoxy)phenyl](deutero)methyl}-2-methoxypyridine-3-carboxamide | 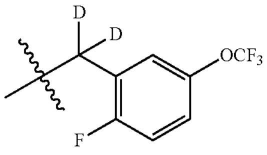 [SMILES: *C([2H])([2H])c1cc(OC(F)(F)F)ccc1F] | 520.9 | 1H NMR (500 MHz, DMSO-d6) δ 11.03-10.82 (m, 1H), 9.14-8.86 (m, 2H), 8.77-8.59 (m, 1H), 8.35-8.20 (m, 1H), 8.08-7.96 (m, 1H), 7.89-7.74 (m, 1H), 7.45-7.20 (m, 3H), 4.08-3.98 (m, 3H), 2.19-2.01 (m, 3H). |
| 146 | 5-{2-acetamidoimidazo[1,2-b]pyridazin-6-yl}-N-{[2-fluoro-5-(trifluoromethyl)phenyl]methyl}-2-methoxypyridine-3-carboxamide | 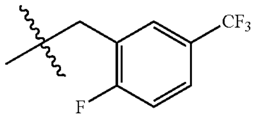 | 506.2 | 1H NMR (500 MHz, DMSO-d6) δ 10.91 (s, 1H), 9.05 (br t, J = 5.8 Hz, 1H), 8.99 (s, 1H), 8.75-8.62 (m, 1H), 8.31 (s, 1H), 8.08 (d, J = 9.5 Hz, 1H), 7.89-7.79 (m, 2H), 7.75 (br s, 1H), 7.48 (br t, J = 9.2 Hz, 1H), 4.64 (br d, J = 5.8 Hz, 2H), 2.12 (s, 3H). |
| 147 | N-{[2-chloro-5-(trifluoromethyl)phenyl]methyl}-5-{2-acetamidoimidazo[1,2-b]pyridazin-6-yl}-2-methoxypyridine-3-carboxamide | 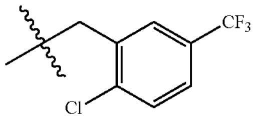 | 519.3 | 1H NMR (500 MHz, DMSO-d6) δ 10.91 (s, 1H), 9.10 (br t, J = 5.8 Hz, 1H), 9.00 (s, 1H), 8.73-8.62 (m, 1H), 8.31 (s, 1H), 8.07 (br d, J = 9.8 Hz, 2H), 7.88-7.69 (m, 3H), 4.66 (br d, J = 5.5 Hz, 2H), 4.08 (s, 3H), 2.11 (s, 3H). |
| 148 | N-{[2-(1-cyclopropylethoxy)-3,5-difluorophenyl]methyl}-5-(2-acetamidoimidazo[1,2-b]pyridazin-6-yl}-2-methoxypyridine-3-carboxamide | 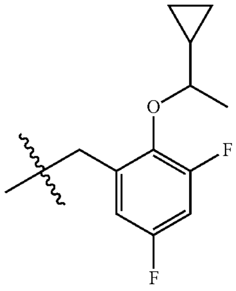 [SMILES: *Cc1cc(F)cc(F)c1OC(C)C1CC1] | 537.4 | 1H NMR (500 MHz, DMSO-d6) δ 10.79 (s, 1H), 8.89-8.76 (m, 2H), 8.59 (d, J = 2.1 Hz, 1H), 8.18 (s, 1H), 7.92 (d, J = 9.5 Hz, 1H), 7.69 (d, J = 9.2 Hz, 1H), 7.09-6.99 (m, 1H), 6.87 (br d, J = 8.5 Hz, 1H), 4.51 (br d, J = 6.1 Hz, 2H), 3.96 (s, 3H), 3.67-3.45 (m, 1H), 2.01 (s, 3H), 1.27 (d, J = 6.1 Hz, 3H), 1.07-0.95 (m, 1H), 0.36 (br d, J = 7.9 Hz, 2H), 0.11-0.03 (m, 1H), 0.03--0.04 (m, 1H) |
| 149 | N-{[5-(cyclopropylmethoxy)-2-fluorophenyl]methyl}-5-{2-acetamidoimidazo[1,2-b]pyridazin-6-yl}-2-methoxypyridine-3-carboxamide | 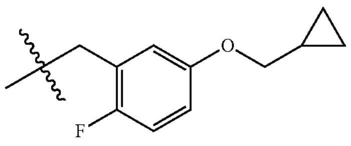 [SMILES: *Cc1cc(OCC2CC2)ccc1F] | 505.2 | 1H NMR (500 MHz, DMSO-d6) δ 10.92 (br. s., 1H), 8.94 (d, J = 2.3 Hz, 2H), 8.66 (d, J = 2.4 Hz, 1H), 8.28 (s, 1H), 8.03 (d, J = 9.4 Hz, 1H), 7.80 (d, J = 9.4 Hz, 1H), 7.08 (t, J = 9.3 Hz, 1H), 6.91 (dd, J = 5.8, 3.0 Hz, 1H), 6.81 (dd, J = 8.0, 4.3 Hz, 1H), 4.51 (d, J = 5.8 Hz, 2H), 4.04 (s, 3H), 3.70 (s, 1H), 2.10 (s, 3H), 1.15 (t, J = 7.3 Hz, 1H), 0.57-0.45 (m, 2H), 0.25 (q, J = 4.7 Hz, 3H). |

TABLE 4-continued

Compounds in Table 4 were prepared by methods as described in Examples 22, 23, and 25. For examples containing tertiary amides, the compounds are of formula (4A) and R* is as indicated in the table.

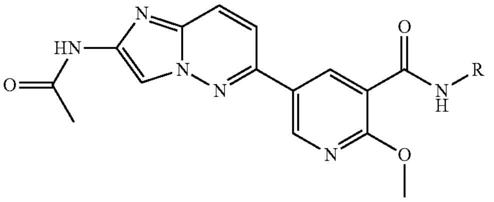

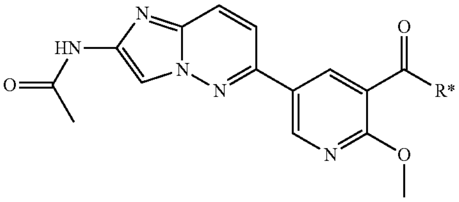

4A

| Ex | Name | R | Obs. MS Ion | NMR Assignments |
|---|---|---|---|---|
| 150 | N-{[2-(cyclopropylmethoxy)-4,6-difluorophenyl]methyl}-5-{2-acetamidoimidazo[1,2-b]pyridazin-6-yl}-2-methoxypyridine-3-carboxamide | 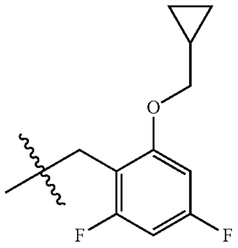 [SMILES: *Cc1c(F)cc(F)cc1OCC1CC1] | 523.4 | 1H NMR (500 MHz, DMSO-d6) δ 10.93 (br s, 1H), 8.94 (br s, 1H), 8.70 (br s, 1H), 8.48 (br s, 1H), 8.30 (s, 1H), 8.05 (br d, J = 9.8 Hz, 1H), 7.81 (br d, J = 9.3 Hz, 1H), 6.89-6.69 (m, 2H), 4.52 (br d, J = 4.8 Hz, 2H), 4.03 (s, 3H), 2.72-2.54 (m, 2H), 2.11 (s, 3H), 1.27 (br s, 1H), 0.58 (br d, J = 6.6 Hz, 2H), 0.36 (br d, J = 4.1 Hz, 2H) |
| 151 | N-{[2-(cyclopropylmethoxy)-3-fluorophenyl]methyl}-5-{2-acetamidoimidazo[1,2-b]pyridazin-6-yl}-2-methoxypyridine-3-carboxamide, TFA | 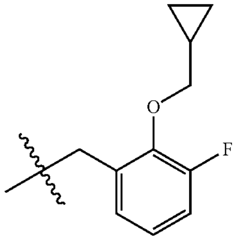 [SMILES: *Cc1cccc(F)c1OCC1CC1] | 505.1 | 1H NMR (500 MHz, DMSO-d6) δ 11.06-10.56 (m, 1H), 8.97 (br s, 2H), 8.89 (br s, 1H), 8.72 (br s, 1H), 7.86 (br s, 2H), 7.26-7.06 (m, 3H), 4.62 (br d, J = 5.8 Hz, 2H), 4.07 (s, 3H), 3.92 (br d, J = 7.1 Hz, 2H), 2.16 (br s, 3H), 1.27 (br s, 1H), 0.57 (br d, J = 7.7 Hz, 2H), 0.31 (br d, J = 4.5 Hz, 2H) |
| 152 | 5-{2-acetamidoimidazo[1,2-b]pyridazin-6-yl}-N-{[4-fluoro-2-(oxan-4-yloxy)phenyl]methyl}-2-methoxypyridine-3-carboxamide | 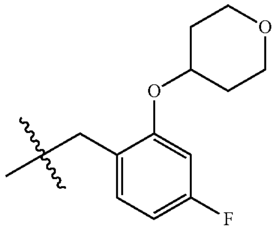 [SMILES: *Cc1ccc(F)cc1OC1CCOCC1] | 535.2 | 1H NMR (500 MHz, DMSO-d6) δ 10.93 (br s, 1H), 8.97 (s, 1H), 8.73 (br s, 2H), 8.30 (s, 1H), 8.07 (br d, J = 9.3 Hz, 1H), 7.83 (br d, J = 9.3 Hz, 1H), 7.29 (br t, J = 7.7 Hz, 1H), 7.02 (br d, J = 11.2 Hz, 1H), 6.74 (t, J = 8.3 Hz, 1H), 4.71 (br s, 1H), 4.47 (br d, J = 5.6 Hz, 2H), 4.07 (s, 3H), 3.91-3.70 (m, 3H), 3.17 (br d, J = 5.0 Hz, 1H), 2.11 (s, 3H), 1.99 (br d, J = 11.1 Hz, 2H), 1.83-1.62 (m, 2H) |
| 153 | 5-(2-acetamidoimidazo[1,2-b]pyridazin-6-yl)-N-((3,5-difluoro-2-((tetrahydro-2H-pyran-4-yl)oxy)phenyl)methyl-d2)-2-methoxynicotinamide | 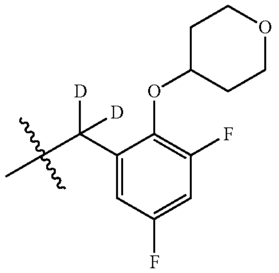 [SMILES: *C([2H])([2H])c1cc(F)cc(F)c1OC1CCOCC1] | 555.2 | $^{1}$H NMR (500 MHz, DMSO-d6) δ 10.92 (s, 1H), 9.00 (d, J = 2.1 Hz, 1H), 8.93 (s, 1H), 8.73 (d, J = 2.4 Hz, 1H), 8.32 (s, 1H), 8.08 (d, J = 9.2 Hz, 1H), 7.85 (d, J = 9.5 Hz, 1H), 7.32-7.13 (m, 1H), 7.03 (br d, J = 8.9 Hz, 1H), 4.36-4.23 (m, 1H), 4.09 (s, 3H), 3.97-3.86 (m, 2H), 2.12 (s, 3H), 1.98 (br d, J = 11.6 Hz, 2H), 1.80-1.65 (m, 2H)<br>2 protons short (water suppression) |
| 154 | 5-{2-acetamidoimidazo[1,2-b]pyridazin-6-yl}-N-{[2-fluoro-5-(trifluoromethoxy)phenyl]methyl}-2-methoxypyridine-3-carboxamide | 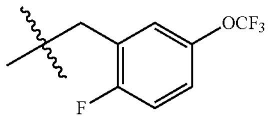 [SMILES: *Cc1cc(OC(F)(F)F)ccc1F] | 519.3 | 1H NMR (500 MHz, DMSO-d6) δ 10.90 (s, 1H), 9.03 (br t, J = 5.8 Hz, 1H), 8.97 (d, J = 2.1 Hz, 1H), 8.67 (d, J = 2.1 Hz, 1H), 8.30 (s, 1H), 8.05 (d, J = 9.5 Hz, 1H), 7.82 (d, J = 9.5 Hz, 1H), 7.43-7.33 (m, 3H), 4.59 (br d, J = 5.8 Hz, 2H), 4.06 (s, 3H), 2.11 (s, 3H) |

TABLE 4-continued

Compounds in Table 4 were prepared by methods as described in Examples 22, 23, and 25. For examples containing tertiary amides, the compounds are of formula (4A) and R* is as indicated in the table.

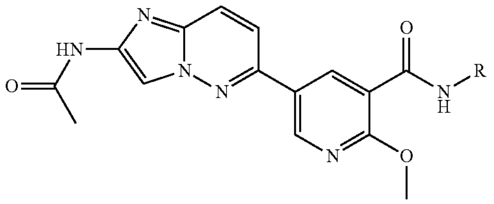

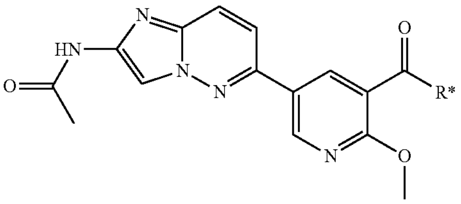

4A

| Ex | Name | R | Obs. MS Ion | NMR Assignments |
|---|---|---|---|---|
| 155 | N-{[2-(cyclobutylmethoxy)phenyl]methyl}-5-{2-acetamidoimidazo[1,2-b]pyridazin-6-yl}-2-methoxypyridine-3-carboxamide | 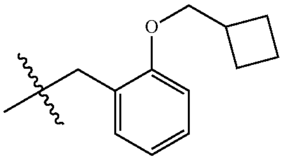 [SMILES: *Cc1ccccc1OCC1CCC1] | 501.1 | 1H NMR (500 MHz, DMSO-d6) δ 10.91 (s, 1H), 8.98 (d, J = 2.1 Hz, 1H), 8.76 (d, J = 2.1 Hz, 1H), 8.68 (br t, J = 5.8 Hz, 1H), 8.47-8.42 (m, 1H), 8.31 (s, 1H), 8.26 (br d, J = 7.6 Hz, 1H), 8.08 (d, J = 9.5 Hz, 1H), 7.95-7.81 (m, 2H), 7.29-7.22 (m, 2H), 7.01 (d, J = 7.9 Hz, 1H), 6.93 (t, J = 7.5 Hz, 1H), 4.53 (br d, J = 5.8 Hz, 2H), 4.08 (s, 3H), 4.05-3.97 (m, 2H), 2.78 (br s, 1H), 2.45-2.34 (m, 1H), 2.29-2.16 (m, 1H), 2.14-2.07 (m, 4H) |
| 156 | N-{[2-(cyclopentyloxy)-6-fluorophenyl]methyl}-5-{2-acetamidoimidazo[1,2-b]pyridazin-6-yl}-2-methoxypyridine-3-carboxamide | 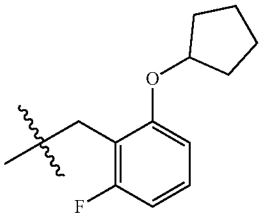 [SMILES: *Cc1c(F)cccc1OC1CCCC1] | 519.2 | 1H NMR (500 MHz, DMSO-d6) δ 10.94 (s, 1H), 8.96 (br s, 1H), 8.72 (br s, 1H), 8.40 (br s, 1H), 8.30 (s, 1H), 8.08 (br d, J = 9.5 Hz, 1H), 7.84 (br d, J = 9.6 Hz, 1H), 7.30 (br d, J = 6.9 Hz, 1H), 6.88 (br d, J = 8.4 Hz, 1H), 6.79 (br s, 1H), 4.94 (br s, 1H), 4.53 (br s, 2H), 4.04 (s, 3H), 2.11 (s, 3H), 1.94 (br s, 2H), 1.84-1.67 (m, 4H), 1.59 (br s, 2H) |
| 157 | 5-{2-acetamidoimidazo[1,2-b]pyridazin-6-yl}-2-methoxy-N-{[2-(trifluoromethoxy)phenyl]methyl}pyridine-3-carboxamide | 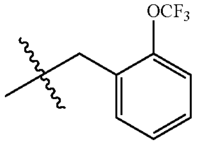 [SMILES: *Cc1ccccc1OC(F)(F)F] | 501 | 1H NMR (500 MHz, DMSO-d6) δ 10.93 (s, 1H), 9.00-8.93 (m, 2H), 8.73 (s, 1H), 8.30 (s, 1H), 8.07 (br d, J = 9.4 Hz, 1H), 7.83 (br d, J = 9.4 Hz, 1H), 7.51 (br d, J = 6.7 Hz, 1H), 7.42 (s, 2H), 7.40-7.36 (m, 1H), 4.61 (br d, J = 5.6 Hz, 2H), 4.07 (s, 3H), 2.11 (s, 3H) |
| 158 | N-{[2-(cyclopropanesulfonyl)phenyl]methyl}-5-{2-acetamidoimidazo[1,2-b]pyridazin-6-yl}-2-methoxypyridine-3-carboxamide | 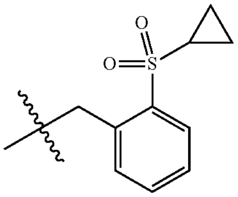 [SMILES: *Cc1ccccc1S(=O)(=O)C1CC1] | 521.1 | 1H NMR (500 MHz, DMSO-d6) δ 10.93 (s, 1H), 9.14 (br t, J = 6.1 Hz, 1H), 9.00 (d, J = 2.4 Hz, 1H), 8.81 (d, J = 2.3 Hz, 1H), 8.31 (s, 1H), 8.08 (d, J = 9.4 Hz, 1H), 7.91-7.88 (m, 1H), 7.85 (d, J = 8.9 Hz, 1H), 7.74 (t, J = 7.4 Hz, 1H), 7.68 (br d, J = 7.7 Hz, 1H), 7.56 (t, J = 7.4 Hz, 1H), 5.00 (br d, J = 6.1 Hz, 2H), 4.10 (s, 3H), 3.21-3.16 (m, 1H), 2.11 (s, 3H), 1.19-1.11 (m, 4H) |
| 159 | N-{[2-(cyclopentyloxy)phenyl]methyl}-5-{2-acetamidoimidazo[1,2-b]pyridazin-6-yl}-2-methoxypyridine-3-carboxamide | 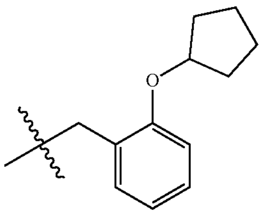 | 501.1 | 1H NMR (500 MHz, DMSO-d6) δ 10.93 (s, 1H), 8.97 (d, J = 2.4 Hz, 1H), 8.78-8.72 (m, 1H), 8.65 (t, J = 5.9 Hz, 1H), 8.30 (s, 1H), 8.07 (d, J = 9.4 Hz, 1H), 7.83 (d, J = 9.4 Hz, 1H), 7.30-7.18 (m, 2H), 6.99 (d, J = 8.2 Hz, 1H), 6.89 (t, J = 7.4 Hz, 1H), 4.93-4.86 (m, 1H), 4.46 (d, J = 5.9 Hz, 2H), 4.06 (s, 3H), 2.11 (s, 3H), 1.98-1.86 (m, 2H), 1.83-1.68 (m, 4H), 1.60 (br. s., 2H). |

TABLE 4-continued

Compounds in Table 4 were prepared by methods as described in Examples 22, 23, and 25. For examples containing tertiary amides, the compounds are of formula (4A) and R* is as indicated in the table.

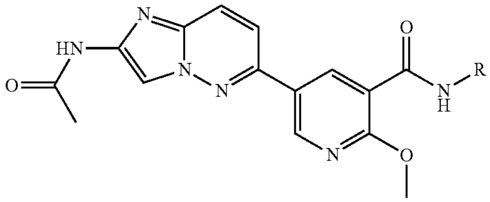

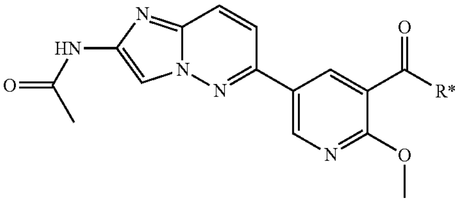

4A

| Ex | Name | R | Obs. MS Ion | NMR Assignments |
|---|---|---|---|---|
| 160 | 5-{2-acetamidoimidazo[1,2-b]pyridazin-6-yl}-2-methoxy-N-{[2-(1H-pyrrol-1-yl)phenyl]methyl}pyridine-3-carboxamide | 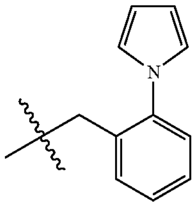 [SMILES: *Cc1ccccc1-n1cccc1] | 482.3 | 1H NMR (500 MHz, DMSO-d6) δ 10.92 (s, 1H), 8.93 (br s, 1H), 8.80-8.71 (m, 1H), 8.66 (br s, 1H), 8.29 (s, 1H), 8.03 (br d, J = 9.3 Hz, 1H), 7.79 (br d, J = 9.5 Hz, 1H), 7.51 (br d, J = 6.8 Hz, 1H), 7.46-7.35 (m, 2H), 7.29 (br d, J = 7.3 Hz, 1H), 7.00 (br s, 2H), 6.28 (br s, 2H), 4.42 (br d, J = 5.5 Hz, 2H), 4.03 (s, 3H), 2.10 (s, 3H) |
| 161 | 5-{2-acetamidoimidazo[1,2-b]pyridazin-6-yl}-N-{[(1S,2S)-2-(4-fluorophenyl)cyclopropyl]methyl}-2-methoxypyridine-3-carboxamide | 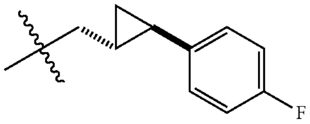 | 475.3 | 1H NMR (500 MHz, DMSO-d6) δ 10.91 (s, 1H), 8.90 (br s, 1H), 8.70-8.57 (m, 2H), 8.29 (s, 1H), 8.02 (br d, J = 9.2 Hz, 1H), 7.78 (br d, J = 9.5 Hz, 1H), 7.09 (br d, J = 5.5 Hz, 2H), 7.06-7.01 (m, 2H), 4.01 (s, 3H), 3.49-3.35 (m, 1H), 3.34-3.21 (m, 1H), 2.11 (s, 3H), 1.93 (br d, J = 3.5 Hz, 1H), 1.32 (br s, 1H), 0.97 (br d, J = 4.8 Hz, 1H), 0.89 (br d, J = 8.0 Hz, 1H) |
| 162 | 5-{2-acetamidoimidazo[1,2-b]pyridazin-6-yl}-2-methoxy-N-{[2-(morpholin-4-yl)phenyl]methyl}pyridine-3-carboxamide | 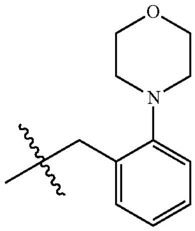 [SMILES: *Cc1ccccc1N1CCOCC1] | 502.3 | 1H NMR (500 MHz, DMSO-d6) δ 10.92 (s, 1H), 8.96 (s, 1H), 8.83 (br t, J = 5.6 Hz, 1H), 8.71 (s, 1H), 8.30 (s, 1H), 8.06 (br d, J = 9.4 Hz, 1H), 7.83 (d, J = 9.4 Hz, 1H), 7.34 (br d, J = 7.4 Hz, 1H), 7.29-7.21 (m, 1H), 7.16 (br d, J = 7.8 Hz, 1H), 7.10 (br t, J = 7.3 Hz, 1H), 4.63 (br d, J = 5.6 Hz, 2H), 4.04 (s, 3H), 3.76 (br s, 4H), 2.87 (br s, 4H), 2.10 (s, 3H) |
| 163 | N-{[3-(cyclopentyloxy)pyridin-2-yl]methyl}-5-{2-acetamidoimidazo[1,2-b]pyridazin-6-yl}-2-methoxypyridine-3-carboxamide | 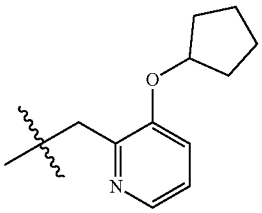 | 502.1 | 1H NMR (500 MHz, DMSO-d6) δ 11.00-10.88 (m, 1H), 9.26 (br s, 1H), 9.00 (d, J = 2.1 Hz, 1H), 8.90 (d, J = 2.1 Hz, 1H), 8.32 (s, 1H), 8.16 (br d, J = 4.6 Hz, 1H), 8.08 (br d, J = 9.5 Hz, 1H), 7.84 (d, J = 9.5 Hz, 1H), 7.45 (br d, J = 8.2 Hz, 1H), 7.32 (br dd, J = 7.9, 4.9 Hz, 1H), 4.96 (br s, 1H), 4.60 (br d, J = 4.6 Hz, 2H), 4.15 (s, 3H), 2.12 (s, 3H), 1.95 (br s, 2H), 1.78 (br d, J = 14.3 Hz, 4H), 1.67-1.59 (m, 2H) |
| 164 | N-{[2-(cyclopentylmethoxy)phenyl]methyl}-5-{2-acetamidoimidazo[1,2-b]pyridazin-6-yl}-2-methoxypyridine-3-carboxamide | 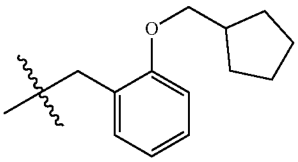 [SMILES: *Cc1ccccc1OCC1CCCC1] | 515.2 | 1H NMR (500 MHz, DMSO-d6) δ 10.94 (s, 1H), 8.98 (s, 1H), 8.75 (s, 1H), 8.69 (br t, J = 5.8 Hz, 1H), 8.31 (s, 1H), 8.08 (d, J = 9.3 Hz, 1H), 7.85 (d, J = 9.4 Hz, 1H), 7.28-7.22 (m, 2H), 7.00 (br d, J = 8.1 Hz, 1H), 6.92 (t, J = 7.3 Hz, 1H), 4.52 (br d, J = 5.6 Hz, 2H), 4.07 (s, 3H), 3.93 (br d, J = 6.6 Hz, 2H), 2.37 (dt, J = 14.6, 7.4 Hz, 1H), 2.11 (s, 3H), 1.82 (br d, J = 6.8 Hz, 2H), 1.66-1.52 (m, 4H), 1.44-1.37 (m, 2H) |

TABLE 4-continued

Compounds in Table 4 were prepared by methods as described in Examples 22, 23, and 25. For examples containing tertiary amides, the compounds are of formula (4A) and R* is as indicated in the table.

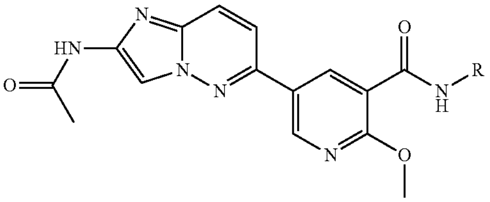

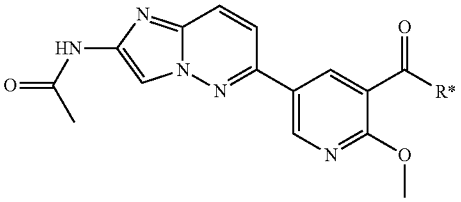

4A

| Ex | Name | R | Obs. MS Ion | NMR Assignments |
|---|---|---|---|---|
| 165 | 5-{2-acetamidoimidazo[1,2-b]pyridazin-6-yl}-2-methoxy-N-{[2-(propan-2-yloxy)phenyl]methyl}pyridine-3-carboxamide | 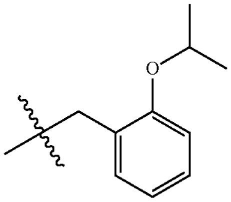 [SMILES: *Cc1ccccc1OC(C)C] | 475.1 | 1H NMR (500 MHz, DMSO-d6) δ 10.93 (s, 1H), 8.98 (s, 1H), 8.76 (s, 1H), 8.69 (t, J = 5.7 Hz, 1H), 8.30 (s, 1H), 8.08 (d, J = 9.4 Hz, 1H), 7.84 (d, J = 9.3 Hz, 1H), 7.30-7.17 (m, 2H), 7.02 (d, J = 8.2 Hz, 1H), 6.90 (t, J = 7.4 Hz, 1H), 4.67 (dt, J = 12.1, 6.0 Hz, 1H), 4.48 (d, J = 5.8 Hz, 2H), 4.13-4.04 (m, 3H), 2.11 (s, 3H), 1.32 (d, J = 6.0 Hz, 6H). |
| 166 | N-{[2-(cyclopentyloxy)-5-fluorophenyl]methyl}-5-{2-acetamidoimidazo[1,2-b]pyridazin-6-yl}-2-methoxypyridine-3-carboxamide | 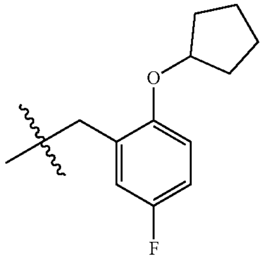 [SMILES: *Cc1cc(F)ccc1OC1CCCC1] | 519.1 | 1H NMR (500 MHz, DMSO-d6) δ 10.93 (s, 1H), 8.98 (s, 1H), 8.81-8.66 (m, 2H), 8.30 (s, 1H), 8.08 (d, J = 9.3 Hz, 1H), 7.84 (d, J = 9.4 Hz, 1H), 7.13-6.94 (m, 3H), 4.87 (br. s., 1H), 4.44 (d, J = 5.8 Hz, 2H), 4.07 (s, 3H), 2.14-2.07 (m, 3H), 1.90 (br. s., 2H), 1.82-1.65 (m, 4H), 1.60 (br. s., 2H). |

TABLE 5

Compounds in Table 5 were prepared by methods as described in Example 13.

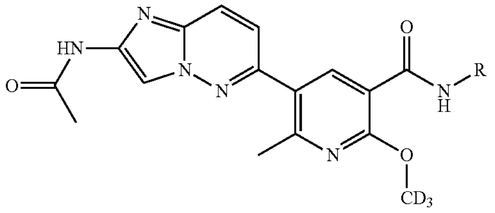

| Ex | Name | R | Obs. MS Ion | NMR Assignments |
|---|---|---|---|---|
| 167 | N-({2-[(2,6-dimethyloxan-4-yl)oxy]-3,5-difluorophenyl}methyl)-5-{2-acetamidoimidazo[1,2-b]pyridazin-6-yl}-2-(deutero)methoxy-6-methylpyridine-3-carboxamide | 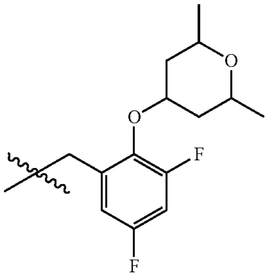 [SMILES: *Cc1cc(F)cc(F)c1OC1CC(C)OC(C)C1] | 597.9 | 1H NMR (500 MHz, DMSO-d6) δ 10.94 (br s, 1H), 8.86 (t, J = 6.9 Hz, 1H), 8.30 (s, 1H), 8.23 (s, 1H), 8.06 (br d, J = 9.3 Hz, 1H), 7.44 (d, J = 9.3 Hz, 1H), 7.22 (br t, J = 8.8 Hz, 1H), 6.97 (br d, J = 9.3 Hz, 1H), 4.63-4.48 (m, 3H), 3.99-3.88 (m, 2H), 2.57 (s 3H), 2.12 (s, 3H), 1.88 (br d, J = 13.5 Hz, 2H), 1.41 (br t, J = 11.7 Hz, 1H), 1.27 (q, J = 11.6 Hz, 1H), 1.17-1.06 (m,6H) |

TABLE 5-continued

Compounds in Table 5 were prepared by methods as described in Example 13.

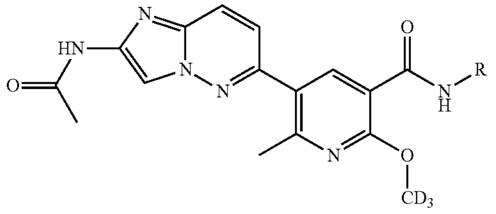

| Ex | Name | R | Obs. MS Ion | NMR Assignments |
|---|---|---|---|---|
| 168 | N-[(2-{[(2R,6S)-2,6-dimethyloxan-4-yl]oxy}-3-fluorophenyl)methyl]-5-{2-acetamidoimidazo[1,2-b]pyridazin-6-yl}-2-(deutero)methoxy-6-methylpyridine-3-carboxamide | 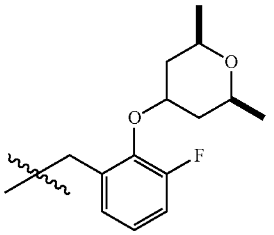 [SMILES: *Cc1cccc(F)c1OC1C[C@@H](C)O[C@@H](C)C1] | 580.0 | 1H NMR (500 MHz, DMSO-d6) δ 10.93 (s, 1H), 8.87-8.67 (m, 1H), 8.30 (s, 1H), 8.26 (s, 1H), 8.07 (d, J = 9.5 Hz, 1H), 7.45 (d, J = 9.2 Hz, 1H), 7.22-7.05 (m, 3H), 4.66-4.54 (m, 3H), 3.98 (br dd, J = 10.8, 6.0 Hz, 1H), 2.61-2.55 (m, 3H), 2.13 (s, 3H), 2.04 (br d, J = 10.4 Hz, 1H), 1.91 (br d, J = 14.0 Hz, 2H), 1.44 (br t, J = 12.5 Hz, 2H), 1.18-1.08 (m, 6H). |
| 169 | N-({3,5-difluoro-2-[(3R)-oxolan-3-yloxy]phenyl}methyl)-5-{2-acetamidoimidazo[1,2-b]pyridazin-6-yl}-2-(deutero)methoxy-6-methylpyridine-3-carboxamide | 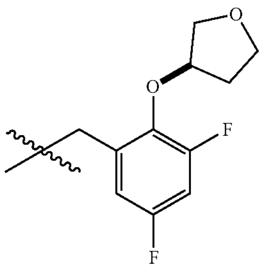 [SMILES: *Cc1cc(F)cc(F)c1O[C@@H]1CCOC1] | 556.2 | 1H NMR (500 MHz, DMSO-d6) δ 10.91 (br s, 1H), 9.07-8.87 (m, 1H), 8.84-8.67 (m, 1H), 8.46 (br s, 1H), 8.31 (br s, 1H), 8.08 (br d, J = 8.5 Hz, 1H), 7.93-7.78 (m, 1H), 7.43-7.28 (m, 1H), 7.04 (br d, J = 8.2 Hz, 1H), 6.96 (br t, J = 8.7 Hz, 1H), 4.96-4.75 (m, 2H), 4.61 (br d, J = 4.9 Hz, 2H), 2.17-2.09 (m, 3H). |
| 170 | N-{[3,5-difluoro-2-(oxan-3-yloxy)phenyl]methyl}-5-{2-acetamidoimidazo[1,2-b]pyridazin-6-yl}-2-(deutero)methoxy-6-methylpyridine-3-carboxamide | 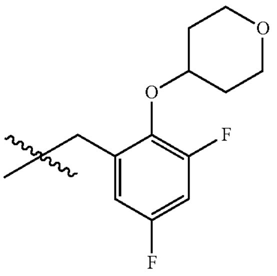 [SMILES: *Cc1cc(F)cc(F)c1OC1CCOCC1] | 570.3 | 1H NMR (500 MHz, DMSO-d6) δ 10.91 (s, 1H), 8.83 (brt, J = 6.0 Hz, 1H), 8.29 (s, 1H), 8.25 (s, 1H), 8.05 (d, J = 9.2 Hz, 1H), 7.43 (d, J = 9.2 Hz, 1H), 7.30-7.12 (m, 1H), 6.98 (br d, J = 9.2 Hz, 1H), 4.66-4.54 (m, 2H), 4.16 (br s, 1H), 3.76 (br d, J = 13.4 Hz, 1H), 3.64-3.54 (m, 2H), 2.57 (s, 3H), 2.56-2.55 (m, 1H), 2.12 (s, 3H), 2.05-1.97 (m, 1H), 1.93-1.77 (m, 2H), 1.51 (br dd, J = 10.4, 4.9 Hz, 1H). |
| 171 | N-({3,5-difluoro-2-[(3S)-oxolan-3-yloxy]phenyl}methyl)-5-{2-acetamidoimidazo[1,2-b]pyridazin-6-yl}-2-(deutero)methoxy-6-methylpyridine-3-carboxamide | 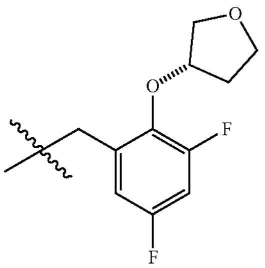 [SMILES: *Cc1cc(F)cc(F)c1O[C@H]1CCOC1] | 556.2 | 1H NMR (500 MHz, DMSO-d6) δ 10.77 (br s, 1H), 8.72 (br t, J = 5.8 Hz, 1H), 8.28 (s, 1H), 8.23 (s, 1H), 8.02 (d, J = 9.3 Hz, 1H), 7.40 (d, J = 9.3 Hz, 1H), 7.18 (br t, J = 8.6 Hz, 1H), 6.98 (br d, J = 9.4 Hz, 1H), 4.99 (br s, 1H), 4.65-4.48 (m, 2H), 4.06-3.87 (m, 2H), 3.85-3.64 (m, 2H), 2.60-2.54 (m, 3H), 2.14-2.10 (m, 5H). |
| 172 | N-({3,5-difluoro-2-[(2-methyloxan-4-yl)oxy]phenyl}methyl)-5-{2-acetamidoimidazo[1,2-b]pyridazin-6-yl}-2-(deutero)methoxy-6-methylpyridine-3-carboxamide | 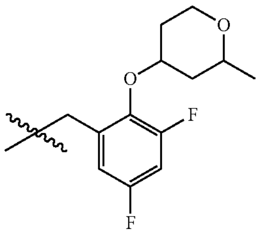 [SMILES: *Cc1cc(F)cc(F)c1OC1CCOC(C)C1] | 584.2 | 1H NMR (500 MHz, DMSO-d6) δ 10.91 (s, 1H), 8.87 (br t, J = 6.0 Hz, 1H), 8.28 (s, 1H), 8.23 (s, 1H), 8.03 (d, J = 9.2 Hz, 1H), 7.42 (d, J = 9.2 Hz, 1H), 7.19 (brt, J = 8.7 Hz, 1H), 6.96 (br d, J = 8.9 Hz, 1H), 4.57 (br d, J = 5.8 Hz, 2H), 4.53 (br s, 1H), 4.02-3.64 (m, 3H), 2.56 (s, 3H), 2.12 (s, 3H), 1.90 (br d, J = 14.3 Hz, 1H), 1.78 (br s, 2H), 1.51 (brt, J = 11.6 Hz, 1H), 1.10 (d, J = 6.1 Hz, 3H). |

TABLE 5-continued

Compounds in Table 5 were prepared by methods as described in Example 13.

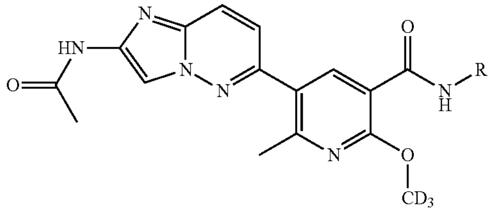

| Ex | Name | R | Obs. MS Ion | NMR Assignments |
|---|---|---|---|---|
| 173 | 5-{2-acetemidoimidazo[1,2-b] pyridazin-6-yl}-N-{[2-fluoro-6-(2,2,2-trifluoroethoxy)phenyl]methyl}-2-(deutero)methoxy-6-methylpyridine-3-carboxamide | 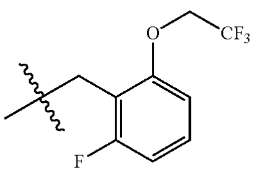 [SMILES: *Cc1c(F)cccc1OCC(F)(F)F] | 550.2 | 1H NMR (500 MHz, DMSO-d6) δ 10.92 (s, 1H), 8.55-8.34 (m, 1H), 8.33-8.23 (m, 2H), 8.05 (br d, J = 9.2 Hz, 1H), 7.49-7.34 (m, 2H), 7.31 (br d, J = 7.6 Hz, 1H), 7.04 (d, J = 8.2 Hz, 1H), 6.95 (br t, J = 8.9 Hz, 1H), 4.93-4.74 (m, 2H), 4.60 (br d, J = 5.2 Hz, 1H), 2.56 (s, 3H), 2.12 (s, 3H). |
| 174 | N-({2-[cyclopropyl(deutero)methoxy]-3,5-difluorophenyl}methyl)-5-{2-acetamidoimidazo[1,2-b]pyridazin-6-yl}-2-(deutero)methoxy-6-methylpyridine-3-carboxamide | 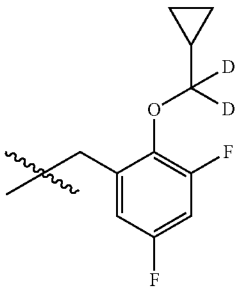 [SMILES: *Cc1cc(F)cc(F)c1OC([2H])([2H])C1CC1] | 542.3 | 1H NMR (500 MHz, DMSO-d6) δ 10.90 (br s, 1H), 8.83 (br t, J = 6.0 Hz, 1H), 8.30 (br s, 1H), 8.22 (s, 1H), 8.02 (br s, 1H), 7.42 (br d, J = 8.9 Hz, 1H), 7.17 (br t, J = 8.4 Hz, 1H), 6.94 (br d, J = 9.2 Hz, 1H), 4.59 (br d, J = 6.1 Hz, 2H), 2.56 (s, 3H), 2.11 (s, 3H), 1.22 (br s, 1H), 0.55 (br d, J = 6.7 Hz, 2H), 0.28 (br d, J = 4.9 Hz, 2H). |
| 175 | 5-{2-acetamidoimidazo[1,2-b] pyridazin-6-yl}-N-{[2-fluoro-5-(trifluoromethoxy)phenyl](deutero) methyl}-2-(deutero)methoxy-6-methylpyridine-3-carboxamide | 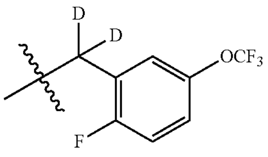 [SMILES: *C([2H])([2H])c1cc(OC(F)(F)F)ccc1F] | 538.3 | 1H NMR (500 MHz. DMSO-d6) δ 10.91 (s, 1H), 8.91 (s, 1H), 8.28 (s, 1H), 8.19 (s, 1H), 8.03 (br d, J = 9.5 Hz, 1H), 7.46-7.30 (m, 4H), 2.56 (s, 3H), 2.11 (s, 3H). |
| 176 | N-{[2-(cyclopropylmethoxy)-3,4-difluorophenyl]methyl}-5-{2-acetamidoimidazo[1,2-b]pyridazin-6-yl}-2-(deutero)methoxy-6-methylpyridine-3-carboxamide | 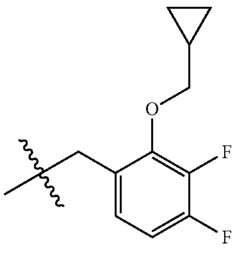 [SMILES: *Cc1ccc(F)c(F)c1OCC1CC1] | 540.4 | 1H NMR (500 MHz, DMSO-d6) δ 10.91 (s, 1H), 8.78 (br t, J = 5.8 Hz, 1H), 8.28 (s, 1H), 8.23 (s, 1H), 8.03 (d, J = 9.2 Hz, 1H), 7.41 (d, J = 9.5 Hz, 1H), 7.11 (br d, J = 6.7 Hz, 2H), 4.55 (br d, J = 5.8 Hz, 2H), 3.98 (s, 1H), 3.97 (s, 1H), 2.57-2.53 (m, 3H), 2.11 (s, 3H), 1.27 (br s, 1H), 0.64-0.49 (m, 2H), 0.31 (br d, J = 5.2 Hz, 2H). |
| 177 | N-{[2-(cyclopropylmethoxy)-3,5-difluorophenyl]methyl}-5-{2-acetamidoimidazo[1,2-b]pyridazin-6-yl}-2-(deutero)methoxy-6-methylpyridine-3-carboxamide | 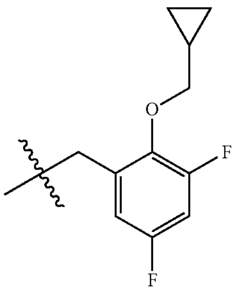 [SMILES: *Cc1cc(F)cc(F)c1OCC1CC1] | 540.4 | 1H NMR (500 MHz, DMSO-d6) δ 10.91 (s, 1H), 8.84 (t, J = 6.0 Hz, 1H), 8.28 (s, 1H), 8.23 (s, 1H), 8.04 (d, J = 9.2 Hz, 1H), 7.43 (d, J = 9.5 Hz, 1H), 7.27-7.10 (m, 1H), 6.96 (br d, J = 9.5 Hz, 1H), 4.60 (d, J = 5.8 Hz, 2H), 3.88 (d, J = 7.3 Hz, 2H), 2.56 (s, 3H), 2.11 (s, 3H), 1.33-1.17 (m, 1H), 0.62-0.51 (m. 2H), 0.36-0.25 (m, 2H). |

TABLE 5-continued

Compounds in Table 5 were prepared by methods as described in Example 13.

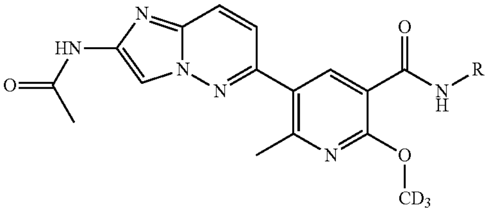

| Ex | Name | R | Obs. MS Ion | NMR Assignments |
|---|---|---|---|---|
| 178 | 5-{2-acetamidoimidazo[1,2-b]pyridazin-6-yl}-2-(deutero)methoxy-6-methyl-N-{[2-(trifluoromethoxy)phenyl]methyl}pyridine-3-carboxamide | 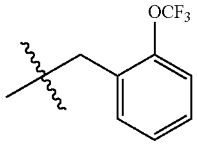 [SMILES: *Cc1ccccc1OC(F)(F)F] | 518.4 | 1H NMR (500 MHz, DMSO-d6) δ 10.91 (s, 1H), 8.85 (t, J = 6.0 Hz, 1H), 8.28 (s, 1H), 8.25 (s, 1H), 8.04 (d, J = 9.5 Hz, 1H), 7.49-7.35 (m, 5H), 4.60 (d, J = 6.1 Hz, 2H), 2.56 (s, 3H), 2.11 (s, 3H). |
| 179 | 5-{2-acetamidoimidazo[1,2-b]pyridazin-6-yl}-N-{[2-fluoro-5-(trifluoromethoxy)phenyl]methyl}-2-(deutero)methoxy-6-methylpyridine-3-carboxamide | 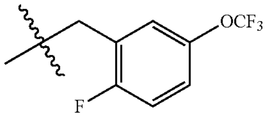 [SMILES: *Cc1cc(OC(F)(F)F)ccc1F] | 536.1 | 1H NMR (400 MHz, DMSO-d6) δ 10.92 (s, 1H), 8.91 (t, J = 6.1 Hz, 1H), 8.29 (s, 1H), 8.21 (s, 1H), 8.06 (d, J = 9.3 Hz, 1H), 7.46-7.31 (m. 4H), 4.59 (d, J = 6.1 Hz, 2H), 2.58 (s, 3H), 2.1s (s, 3H). |
| 180 | N-{[5-(cyclopropyhnethoxy)-2-fluorophenyl]methyl}-5-{2-acetamidoimidazo[1,2-b]pyridazin-6-yl}-2-(deutero)methoxy-6-methylpyridine-3-carboxamide | 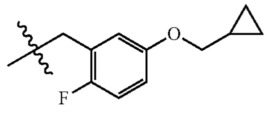 [SMILES: *Cc1cc(OCC2CC2)ccc1F] | 522.1 | 1H NMR (500 MHz, DMSO-d6) δ 10.91 (s, 1H), 8.81 (br t, J = 5.8 Hz, 1H), 8.28 (s, 1H), 8.21 (s, 1H), 8.04 (d, J = 9.5 Hz, 1H), 7.43 (d, J = 9.5 Hz, 1H), 7.09 (t, J = 9.3 Hz, 1H), 6.99-6.87 (m, 1H), 6.86-6.65 (m, 1H), 4.52 (br d, J = 5.8 Hz, 2H), 3.75 (d, J = 7.0 Hz, 2H), 2.58-2.54 (m, 3H), 2.11 (s, 3H), 1.17 (br d, J = 4.9 Hz, 1H), 0.61-0.44 (m, 2H), 0.27 (br d, J = 4.9 Hz, 2H). |

TABLE 6

Compounds in Table 6 were prepared by methods as described in Example 39.

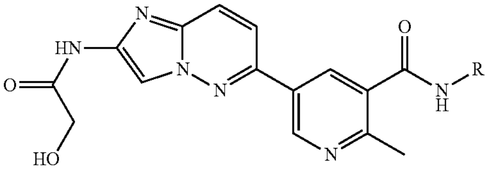

| Ex | Name | R | Obs. MS Ion | NMR Assignments |
|---|---|---|---|---|
| 181 | N-[(1S)-1-[2-fluoro-5-(trifluoromethoxy)phenyl]ethyl]-5-[2-(2-hydroxyacetamido)imidazo[1,2-b]pyridazin-6-yl]-2-methylpyridine-3-carboxamide | 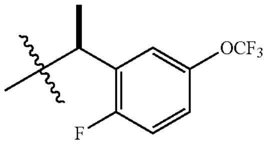 [SMILES: *[C@@H](C)c1cc(OC(F)(F)F)ccc1F] | 533.2 | 1H NMR (500 MHz, DMSO-d6) δ 10.39 (s, 1H), 9.21 (s, 1H), 9.20 (d, J = 6.3 Hz, 1H), 8.41 (s, 1H), 8.38 (s, 1H), 8.17 (d, J = 9.5 Hz, 1H), 7.93 (d, J = 9.5 Hz, 1H), 7.51 (br d, J = 3.7 Hz, 1H), 7.45-7.32 (m, 2H), 5.39 (quin, J = 7.0 Hz, 1H), 4.12 (br s, 2H), 2.55 (s, 3H), 1.50 (d, J = 7.0 Hz, 3H), 1.24 (s, 1H). |
| 182 | N-[(1R)-1-[2-fluoro-5-(trifluoromethyl)phenyl]ethyl]-5-[2-(2-hydroxyacetamido)imidazo[1,2-b]pyridazin-6-yl]-2-methylpyridine-3-carboxamide, TFA | 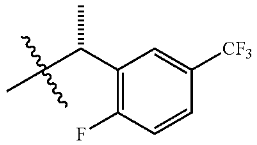 | 517.2 | 1H NMR (500 MHz, DMSO-d6) δ 10.39 (s, 1H), 9.27 (br d, J = 7.6 Hz, 1H), 9.23-9.15 (m, 1H), 8.46-8.32 (m, 2H), 8.15 (d, J = 9.5 Hz, 1H), 7.99-7.83 (m, 2H), 7.76 (br s, 1H), 7.49 (br t, J = 9.2 Hz, 1H), 5.43 (br t, J = 7.2 Hz, 1H), 4.12 (br d, J = 4.9 Hz, 2H), 2.56 (s, 3H), 1.52 (d, J = 7.0 Hz, 3H). |
| 183 | N-{[2-fluoro-5-(trifluoromethyl)phenyl]methyl}-5-[2-(2-hydroxyacetamido)imidazo[1,2-b]pyridazin-6-yl]-2-methylpyridine-3-carboxamide | 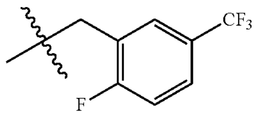 [SMILES: *Cc1cc(C(F)(F)F)ccc1F] | 503.2 | 1H NMR (500 MHz, DMSO-d6) δ 10.38 (br s, 1H), 9.27-9.23 (m, 1H), 9.19 (s, 1H), 8.40 (s, 2H), 8.15 (br d, J = 9.2 Hz, 1H), 7.91 (d, J = 9.5 Hz, 1H), 7.85 (br d, J = 6.4 Hz, 1H), 7.78 (br s, 1H), 7.50 (br t, J = 9.2 Hz, 1H), 5.62 (br t, J = 6.3 Hz, 1H), 4.63 (br d, J = 5.5 Hz, 2H), 4.12 (br d, J = 5.8 Hz, 2H), 2.59 (s, 3H). |

TABLE 6-continued

Compounds in Table 6 were prepared by methods as described in Example 39.

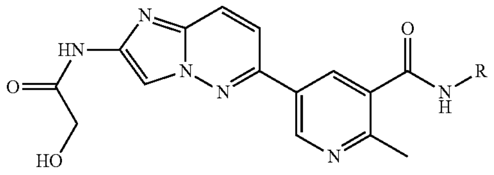

| Ex | Name | R | Obs. MS Ion | NMR Assignments |
|---|---|---|---|---|
| 184 | N-{[3,5-difluoro-2-(oxan-4-yloxy)phenyl](deutero)methyl}-5-[2-(2-hydroxyacetamido)imidazo[1,2-b]pyridazin-6-yl]-2-methylpyridine-3-carboxamide | 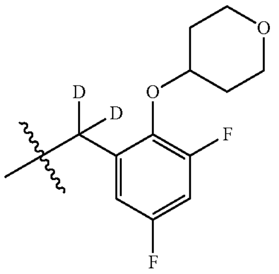 [SMILES: *C([2H])([2H])c1cc(F)cc(F)c1OC1CCOCC1] | 555 | 1H NMR (500 MHz, DMSO-d6) δ 10.48-10.33 (m, 1H), 9.20 (s, 1H), 9.09 (s, 1H), 8.44 (s, 1H), 8.40 (br s, 1H), 8.16 (d, J = 9.5 Hz, 1H), 7.93 (d, J = 9.5 Hz, 1H), 7.27 (br t, J = 8.5 Hz, 1H), 7.09 (br d, J = 8.2 Hz, 1H), 4.30 (dt, J = 9.2, 4.9 Hz, 1H), 4.12 (s, 2H), 3.97-3.86 (m, 2H), 2.63 (s, 3H), 2.57-2.56 (m, 3H), 1.98 (br d, J = 11.6 Hz, 2H), 1.78-1.67 (m, 2H) |
| 185 | N-[(1R)-1-[2-fluoro-5-(trifluoromethoxy)phenyl]ethyl]-5-[2-(2-hydroxyacetamido)imidazo[1,2-b]pyridazin-6-yl]-2-methylpyridine-3-carboxamide | 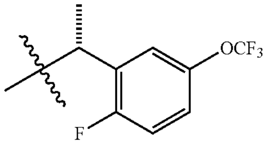 | 533.1 | 1H NMR (500 MHz, DMSO-d6) δ 9.22 (br d, J = 2.1 Hz, 2H), 8.41 (s, 1H), 8.39 (br s, 1H), 8.18 (d, J = 9.2 Hz, 1H), 7.95 (d, J = 9.5 Hz, 1H), 7.52 (br s, 1H), 7.47-7.29 (m, 3H), 5.47-5.31 (m, 1H), 4.13 (s, 2H), 2.57-2.54 (m, 3H), 1.86-1.69 (m, 1H), 1.58-1.45 (m, 3H). |

TABLE 7

Compounds in Table 7 were prepared by methods as described in Example 9 and 20.

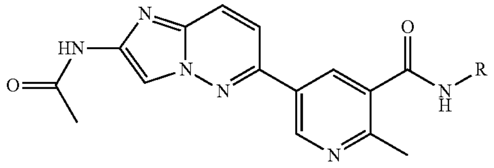

| Ex | Name | R | Obs. MS Ion | NMR Assignments |
|---|---|---|---|---|
| 186 | N-{[3,5-difluoro-2-(oxan-3-yloxy)phenyl]methyl}-5-{2-acetamidoimidazo[1,2-b]pyridazin-6-yl}-2-methylpyridine-3-carboxamide | 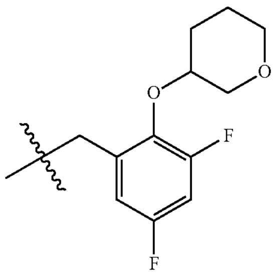 [SMILES: *Cc1cc(F)cc(F)c1OC1CCCOC1] | 537.0 | 1H NMR (500 MHz, DMSO-d6) δ 10.81 (br s, 1H), 9.22-9.14 (m, 1H), 8.95 (brt, J = 5.5 Hz, 1H), 8.41 (s, 1H), 8.34 (s, 1H), 8.10 (br d, J = 9.4 Hz, 1H), 7.86 (d, J = 9.4 Hz, 1H), 7.21 (br t, J = 8.5 Hz, 1H), 7.07 (br d, J = 8.8 Hz, 1H), 4.71-4.55 (m, 2H), 4.17 (br s, 1H), 3.81 (br d, J = 11.5 Hz, 1H), 3.67-3.53 (m, 2H), 2.64 (s, 3H), 2.13 (s, 3H), 2.05 (br dd, J = 11.3, 7.1 Hz, 1H), 1.95-1.82 (m, 2H), 1.60-1.46 (m, 1H), 1.32-1.11 (m, 1H). |

TABLE 7-continued

Compounds in Table 7 were prepared by methods as described in Example 9 and 20.

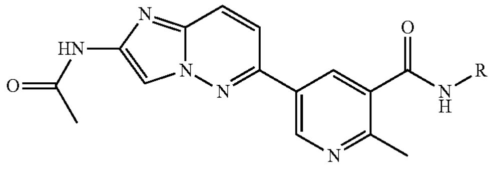

| Ex | Name | R | Obs. MS Ion | NMR Assignments |
|---|---|---|---|---|
| 187 | N-({3,5-difluoro-2-[(3S)-oxolan-3-yloxy]phenyl}methyl)-5-{2-acetamidoimidazo[1,2-b]pyridazin-6-yl}-2-methylpyridine-3-carboxamide | 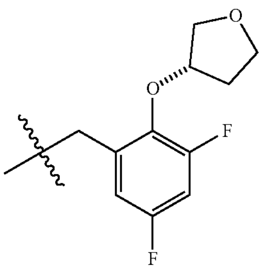 | 523.1 | 1H NMR (500 MHz, DMSO-d6) δ 10.80 (br s, 1H), 9.16 (d, J = 1.8 Hz, 1H), 8.96 (br t, J = 5.6 Hz, 1H), 8.40 (d, J = 1.9 Hz, 1H), 8.33 (s, 1H), 8.09 (d, J = 9.4 Hz, 1H), 7.85 (d, J = 9.5 Hz, 1H), 7.30-7.15 (m, 1H), 7.06 (br d, J = 8.5 Hz, 1H), 4.99 (br s, 1H), 4.60-4.44 (m, 2H), 4.03-3.87 (m, 2H), 3.85-3.64 (m, 2H), 3.51 (br s, 2H), 2.62 (s, 3H), 2.13 (s, 3H) |
| 188 | N-({3,5-difluoro-2-[(2-methyloxan-4-yl)oxy]phenyl}methyl)-5-{2-acetamidoimidazo[1,2-b]pyridazin-6-yl}-2-methylpyridine-3-carboxamide | 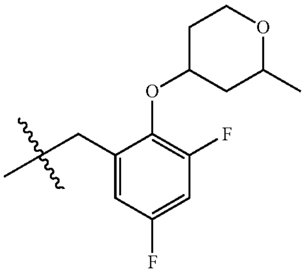 [SMILES: *Cc1cc(F)cc(F)c1OC1CCOC(C)C1] | 551.0 | 1H NMR (500 MHz, DMSO-d6) δ 10.95 (s, 1H), 9.20 (s, 1H), 9.11 (br t, J = 5.5 Hz, 1H), 8.50-8.39 (m, 1H), 8.34 (s, 1H), 8.14 (d, J = 9.5 Hz, 1H), 7.91 (d, J = 9.5 Hz, 1H), 7.78-7.64 (m, 1H), 7.27 (br t, J = 8.7 Hz, 1H), 7.09 (br d, J = 7.9 Hz, 1H), 4.62-4.57 (m, 2H), 4.29 (q, J = 7.1 Hz, 1H), 4.01-3.83 (m, 2H), 2.63 (s, 3H), 2.13 (s, 3H), 1.94 (br d, J = 14.0 Hz, 1H), 1.52 (br t, J = 11.4 Hz, 1H), 1.37-1.20 (m, 2H), 1.12 (d, J = 6.4 Hz, 3H). |
| 189 | N-({2-[(2,6-dimethyloxan-4-yl)oxy]-3,5-difluorophenyl}methyl)-5-{2-acetamidoimidazo[1,2-b]pyridazin-6-yl}-2-methylpyridine-3-carboxamide | 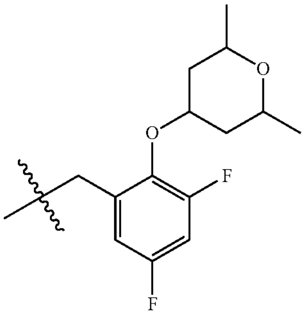 [SMILES: *Cc1cc(F)cc(F)c1OC1CC(C)OC(C)C1] | 565.2 | 1H NMR (500 MHz, DMSO-d6) δ 10.96 (br s, 1H), 9.20 (s, 1H), 9.15-8.95 (m, 1H), 8.49-8.39 (m, 1H), 8.35 (s, 1H), 8.15 (br d, J = 9.5 Hz, 1H), 7.91 (br d, J = 9.5 Hz, 1H), 7.34-7.20 (m, 1H), 7.10 (br d, J = 7.6 Hz, 1H), 4.64-4.49 (m, 3H), 4.00 (br dd, J = 11.0, 6.1 Hz, 1H), 2.64 (s, 3H), 2.14 (s, 3H), 2.11-2.00 (m, 1H), 1.92 (br d, J = 13.1 Hz, 2H), 1.43 (br t, J = 11.9 Hz, 1H), 1.30 (q, J = 11.5 Hz, 1H), 1.19-1.08 (m, 6H). |
| 190 | 5-{2-acetamidoimidazo[1,2-b]pyridazin-6-yl}-N-{[2-fluoro-6-(2,2,2-trifluoroethoxy)phenyl]methyl}-2-methylpyridine-3-carboxamide | 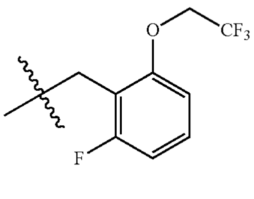 [SMILES: *Cc1c(F)cccc1OCC(F)(F)F] | 517.3 | 1H NMR (500 MHz, DMSO-d6) δ 11.01-10.89 (m, 1H), 9.19-9.11 (m, 1H), 8.74 (br s, 1H), 8.36-8.30 (m, 1H), 8.27 (d, J = 1.8 Hz, 1H), 8.18-8.04 (m, 1H), 7.97-7.77 (m, 1H), 7.45-7.35 (m, 1H), 7.11-7.02 (m, 1H), 6.97 (t, J = 8.9 Hz, 1H), 4.92-4.78 (m, 2H), 4.61-4.47 (m, 2H), 2.56 (s, 3H), 2.13 (s, 3H). |
| 191 | 5-{2-acetamidoimidazo[1,2-b]pyridazin-6-yl}-2-methyl-N-{[4-(trifluoromethyl)pyridin-2-yl]methyl}pyridine-3-carboxamide | 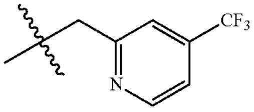 [SMILES: *Cc1cc(C(F)(F)F)ccn1] | 470.1 | 1H NMR (500 MHz, DMSO-d6) δ 10.95 (s, 1H), 9.31 (br t, J = 5.8 Hz, 1H), 9.20 (s, 1H), 8.87 (br d, J = 4.9 Hz, 1H), 8.45 (s, 1H), 8.35 (s, 1H), 8.14 (d, J = 9.5 Hz, 1H), 7.91 (d, J = 9.5 Hz, 1H), 7.78 (s, 1H), 7.72 (br d, J = 5.2 Hz, 1H), 4.73 (br d, J = 5.8 Hz, 2H), 2.56 (s, 3H), 2.13 (s, 3H). |

TABLE 7-continued

Compounds in Table 7 were prepared by methods as described in Example 9 and 20.

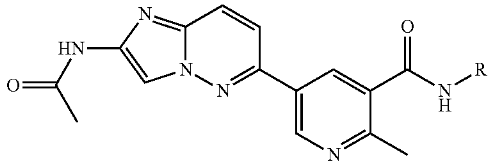

| Ex | Name | R | Obs. MS Ion | NMR Assignments |
| --- | --- | --- | --- | --- |
| 192 | N-{[3,5-difluoro-2-(oxan-4-yloxy)phenyl](deutero)methyl}-5-{2-acetamidoimidazo[1,2-b]pyridazin-6-yl}-2-methylpyridine-3-carboxamide | 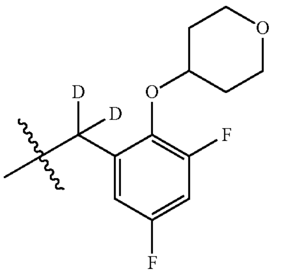 [SMILES: *C([2H])([2H])c1cc(F)cc(F)c1OC1CCOCC1] | 538.9 | 1H NMR (500 MHz, DMSO-d6) δ 10.95 (s, 1H), 9.20 (s, 1H), 9.09 (s, 1H), 8.43 (s, 1H), 8.35 (s, 1H), 8.14 (d, J = 9.5 Hz, 1H), 7.91 (d, J = 9.2 Hz, 1H), 7.27 (br t, J = 8.5 Hz, 1H), 7.10 (br d, J = 8.2 Hz, 1H), 4.30 (dt, J = 9.2,4.7 Hz, 1H), 3.99-3.85 (m, 2H), 2.63 (s, 3H), 2.57-2.55 (m, 2H), 2.13 (s, 3H), 1.98 (br d, J = 12.5 Hz, 2H), 1.73 (q, J = 9.5 Hz, 2H). |
| 193 | 5-{2-acetamidoimidazo[1,2-b]pyridazin-6-yl}-2-methyl-N-{[2-(2,2,2-trifluoroethoxy)phenyl]methyl}pyridine-3-carboxamide | 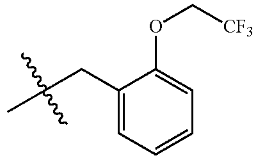 [SMILES: *Cc1ccccc1OCC(F)(F)F] | 499.3 | 1H NMR (500 MHz, DMSO-d6) δ 10.95 (s, 1H), 9.18 (d, J = 1.8 Hz, 1H), 8.98 (br t, J = 5.6 Hz, 1H), 8.41 (d, J = 1.8 Hz, 1H), 8.34 (s, 1H), 8.13 (d, J = 9.5 Hz, 1H), 7.89 (d, J = 9.5 Hz, 1H), 7.39 (br d, J = 7.3 Hz, 1H), 7.32 (t, J = 8.0 Hz, 1H), 7.16 (d, J = 8.2 Hz, 1H), 7.09 (t, J = 7.5 Hz, 1H), 4.83 (q, J = 8.9 Hz, 2H), 4.52 (br d, J = 5.5 Hz, 2H), 2.63 (s, 3H), 2.13 (s, 3H). |
| 194 | 5-{2-acetamidoimidazo[1,2-b]pyridazin-6-yl}-2-methyl-N-{[3-(2,2,2-trifluoroethoxy)phenyl]methyl}pyridine-3-carboxamide | 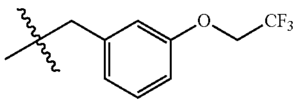 [SMILES: *Cc1cccc(OCC(F)(F)F)c1] | 499.2 | 1H NMR (500 MHz, DMSO-d6) δ 10.94 (s, 1H), 9.25-9.07 (m, 2H), 8.39 (d, J = 1.8 Hz, 1H), 8.34 (s, 1H), 8.12 (d, J = 9.5 Hz, 1H), 7.89 (d, J = 9.5 Hz, 1H), 7.36 (t, J = 8.1 Hz, 1H), 7.13-7.04 (m, 2H), 6.99 (br d, J = 9.2 Hz, 1H), 4.76 (q, J = 8.9 Hz, 2H), 4.51 (br d, J = 5.8 Hz, 2H), 2.62 (s, 3H), 2.13 (s, 3H). |
| 195 | 5-{2-acetamidoimidazo[1,2-b]pyridazin-6-yl}-N-{[5-fluoro-2-(2,2,2-trifluoroethoxy)phenyl]methyl}-2-methylpyridine-3-carboxamide | 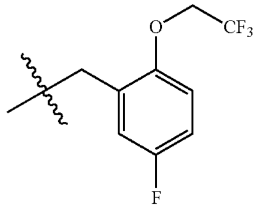 [SMILES: *Cc1cc(F)ccc1OCC(F)(F)F] | 517.2 | 1H NMR (500 MHz, DMSO-d6) δ 10.81 (br s, 1H), 9.17 (d, J = 2.1 Hz, 1H), 8.91 (br t, J = 5.6 Hz, 1H), 8.41 (d, J = 2.1 Hz, 1H), 8.34 (s, 1H), 8.10 (d, J = 9.4 Hz, 1H), 7.86 (d, J = 9.4 Hz, 1H), 7.25-7.10 (m, 3H), 4.80 (q, J = 8.8 Hz, 2H), 4.53 (d, J = 5.6 Hz, 2H), 2.64 (s, 3H), 2.13 (s, 3H). |
| 196 | 5-{2-acetamidoimidazo[1,2-b]pyridazin-6-yl}-N-[(1S)-1-[2-fluoro-5-(trifluoromethyl)phenyl](2,2,2-deutero)ethyl]-2-methylpyridine-3-carboxamide | 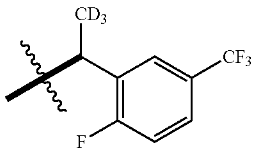 [SMILES: *[C@H](c1cc(C(F)(F)F)ccc1F)C([2H])([2H])[2H]] | 504.2 | 1H NMR (500 MHz, DMSO-d6) δ 10.95 (s, 1H), 9.30-9.16 (m, 2H), 8.43-8.32 (m, 2H), 8.13 (d, J = 9.5 Hz, 1H), 7.90 (br d, J = 9.2 Hz, 2H), 7.76 (br s, 1H), 7.49 (br t, J = 9.2 Hz, 1H), 5.42 (br d, J = 7.3 Hz, 1H), 2.56 (s, 3H), 2.13 (s, 3H). |
| 197 | 5-{2-acetamidoimidazo[1,2-b]pyridazin-6-yl}-N-[(1R)-1-[2-fluoro-5-(trifluoromethyl)phenyl](2,2,2-deutero)ethyl]-2-methylpyridine-3-carboxamide | 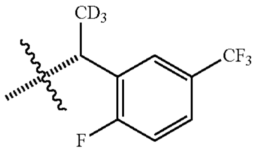 [SMILES: *[C@@H](c1cc(C(F)(F)F)ccc1F)C([2H])([2H])[2H]] | 504.4 | 1H NMR (500 MHz, DMSO-d6) δ 10.95 (s, 1H), 9.34-9.14 (m, 2H), 8.44-8.33 (m, 2H), 8.14 (d, J = 9.5 Hz, 1H), 7.91 (br d, J = 9.2 Hz, 2H), 7.76 (br s, 1H), 7.50 (br t, J = 9.3 Hz, 1H), 5.42 (br d, J = 7.6 Hz, 1H), 2.58 (s, 3H), 2.13 (s, 3H). |
| 198 | 5-{2-acetamidoimidazo[1,2-b]pyridazin-6-yl}-N-[(1S)-1-[2-fluoro-5-(trifluoromethoxy)phenyl](2,2,2-deutero)ethyl]-2-methylpyridine-3-carboxamide | 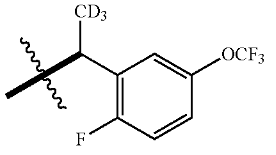 [SMILES: *[C@H](c1cc(OC(F)(F)F)ccc1F)C([2H])([2H])[2H]] | 520.1 | 1H NMR (500 MHz, DMSO-d6) δ 10.95 (s, 1H), 9.23-9.08 (m, 2H), 8.42-8.32 (m, 2H), 8.17-8.12 (m, 1H), 7.91 (d, J = 9.5 Hz, 1H), 7.50 (br d, J = 4.0 Hz, 1H), 7.43-7.36 (m, 2H), 5.37 (br d, J = 7.3 Hz, 1H), 2.53 (br s, 3H), 2.13 (s, 3H). |

TABLE 7-continued

Compounds in Table 7 were prepared by methods as described in Example 9 and 20.

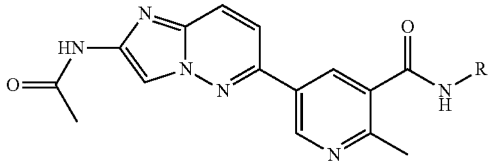

| Ex | Name | R | Obs. MS Ion | NMR Assignments |
|---|---|---|---|---|
| 199 | 5-{2-acetamidoimidazo[1,2-b] pyridazin-6-yl}-N-[(1R)-1-[2-fluoro-5-(trifluoromethoxy) phenyl](2,2,2-deutero)ethyl]-2-methylpyridine-3-carboxamide | 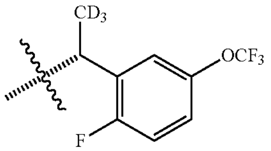 [SMILES: *[C@@H](c1cc(OC(F)(F)F)ccc1F)C([2H])([2H])[2H]] | 520.2 | 1H NMR (500 MHz, DMSO-d6) δ 10.97-10.93 (m, 1H), 9.23-9.16 (m, 2H), 8.36 (br d, J = 7.3 Hz, 2H), 8.16-8.11 (m, 1H), 7.93-7.88 (m, 1H), 7.41-7.33 (m, 2H), 5.37 (br d, J = 7.6 Hz, 1H), 3.18 (br d, J = 4.9 Hz, 1H), 2.54 (s, 3H), 2.13 (s, 3H) |
| 200 | 5-{2-acetamidoimidazo[1,2-b] pyridazin-6-yl}-N-{[2-fluoro-5-(trifluoromethyl)phenyl] (deutero)methyl}-2-methylpyridine-3-carboxamide | 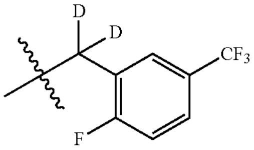 [SMILES: *C([2H])([2H])c1cc(C(F)(F)F)ccc1F] | 489.1 | 1H NMR (500 MHz, DMSO-d6) δ 10.94 (s, 1H), 9.22 (s, 1H), 9.18 (br s, 1H), 8.38 (s, 1H), 8.33 (s, 1H), 8.11 (d, J = 9.5 Hz, 1H), 7.93-7.81 (m, 2H), 7.77 (br s, 1H), 7.49 (br t, J = 9.2 Hz, 1H), 2.58 (s, 3H), 2.12 (s, 3H). |
| 201 | N-{[3,5-difluoro-2-(oxan-4-yloxy)phenyl]methyl}-5-{2-acetamidoimidazo[1,2-b] pyridazin-6-yl}-2-methylpyridine-3-carboxamide | 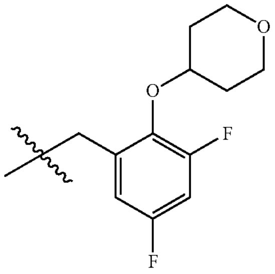 [SMILES: *Cc1cc(F)cc(F)c1OC1CCOCC1] | 537.3 | 1H NMR (500 MHz, DMSO-d6) δ 10.95 (br s, 1H), 9.21-9.06 (m, 2H), 8.44-8.35 (m, 1H), 8.31 (s, 1H), 8.14-8.05 (m, 1H), 7.86 (br d, J = 9.4 Hz, 1H), 7.23 (br s, 1H), 7.05 (br d, J = 8.4 Hz, 1H), 4.54 (br d, J = 5.3 Hz, 2H), 4.27 (br s, 1H), 3.94-3.84 (m, 2H), 3.37 (br t, J = 10.9 Hz, 2H), 2.60 (s, 3H), 2.10 (s, 3H), 1.94 (br d, J = 11.6 Hz, 2H), 1.69 (br d, J = 9.3 Hz, 2H). |
| 202 | 5-{2-acetamidoimidazo[1,2-b] pyridazin-6-yl}-2-methyl-N-{1-[2-(trifluoromethoxy) phenyl]ethyl}pyridine-3-carboxamide | 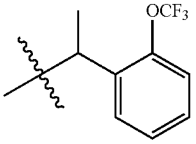 [SMILES: *C(C)c1ccccc1OC(F)(F)F] | 499.3 | 1H NMR (500 MHz, DMSO-d6) δ 10.94 (s, 1H), 9.26-9.04 (m, 2H), 8.33 (br d, J = 9.5 Hz, 2H), 8.12 (d, J = 9.2 Hz, 1H), 7.88 (d, J = 9.5 Hz, 1H), 7.64 (br d, J = 6.1 Hz, 1H), 7.47-7.40 (m, 2H), 7.38 (br s, 1H), 5.54-5.34 (m, 1H), 2.56-2.53 (m, 3H), 1.47 (br d, J = 7.0 Hz, 3H), 1.23 (s, 3H). |
| 203 | 5-{2-acetamidoimidazo[1,2-b] pyridazin-6-yl}-2-methyl-N-{1-[2-(trifluoromethoxy) phenyl]ethyl}pyridine-3-carboxamide | 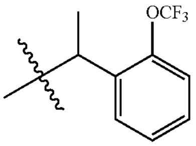 [SMILES: *C(C)c1ccccc1OC(F)(F)F] | 499.2 | 1H NMR (500 MHz, DMSO-d6) δ 10.94 (s, 1H), 9.21-9.09 (m, 2H), 8.38-8.28 (m, 2H), 8.12 (d, 9.2 Hz, 1H), 7.88 (d, J = 9.5 Hz, 1H), 7.70-7.61 (m, 1H), 7.48-7.32 (m, 3H), 5.44 (quin, J = 6.9 Hz, 1H), 2.54 (d, J = 10.1 Hz, 3H), 2.13 (s, 3H), 1.47 (br d, J = 7.0 Hz, 3H) |
| 204 | 5-{2-acetamidoimidazo[1,2-b] pyridazin-6-yl}-N-{1-[2-fluoro-5-(trifluoromethyl)phenyl] ethyl}-2-methylpyridine-3-carboxamide | 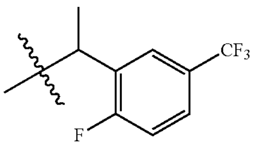 [SMILES: *C(C)c1cc(C(F)(F)F)ccc1F] | 501.1 | 1H NMR (500 MHz, DMSO-d6) δ 10.93 (s, 1H), 9.27 (br d, J = 7.6 Hz, 1H), 9.16 (s, 1H), 8.34 (br d, J = 2.7 Hz, 2H), 8.09 (br d, J = 9.5 Hz, 1H), 7.86 (br d, J = 9.5 Hz, 2H), 7.73 (br s, 1H), 7.47 (br t, J = 8.9 Hz, 1H), 5.52-5.31 (m, 1H), 2.12 (s, 3H), 1.50 (br d, J = 7.0 Hz, 3H), 1.21 (s, 3H). |
| 205 | 5-{2-acetamidoimidazo[1,2-b] pyridazin-6-yl}-N-{1-[2-fluoro-5-(trifluoromethyl)phenyl] ethyl}-2-methylpyridine-3-carboxamide | 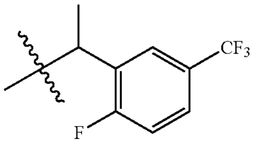 [SMILES: *C(C)c1cc(C(F)(F)F)ccc1F] | 501.1 | 1H NMR (500 MHz, DMSO-d6) δ 10.93 (s, 1H), 9.27 (br d, J = 7.6 Hz, 1H), 9.16 (s, 1H), 8.34 (br d, J = 2.7 Hz, 2H), 8.09 (br d, J = 9.5 Hz, 1H), 7.86 (br d, J = 9.5 Hz, 2H), 7.73 (br s, 1H), 7.47 (br t, J = 8.9 Hz, 1H), 5.52-5.31 (m, 1H), 2.12 (s, 3H), 1.50 (br d, J = 7.0 Hz, 3H), 1.21 (s, 3H). |
| 206 | 5-{2-acetamidoimidazo[1,2-b] pyridazin-6-yl}-N-{[2-fluoro-5-(trifluoromethyl)phenyl] methyl}-2-methylpyridine-3-carboxamide, TFA | 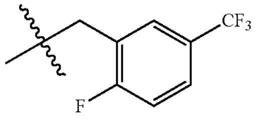 | 487.0 | 1H NMR (500 MHz, DMSO-d6) δ 10.94 (s, 1H), 9.24 (br s, 1H), 9.18 (s, 1H), 8.38 (s, 1H), 8.33 (s, 1H), 8.11 (br d, J = 9.2 Hz, 1H), 7.92-7.80 (m, 2H), 7.77 (br s, 1H), 7.49 (br t, J = 9.0 Hz, 1H), 4.62 (br d, J = 5.5 Hz, 2H), 2.61-2.53 (m, 3H), 2.12 (s, 3H). |

TABLE 7-continued

Compounds in Table 7 were prepared by methods as described in Example 9 and 20.

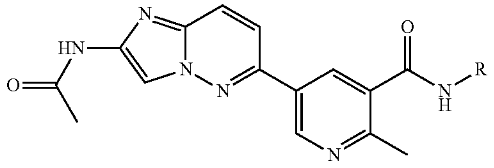

| Ex | Name | R | Obs. MS Ion | NMR Assignments |
|---|---|---|---|---|
| 207 | 5-{2-acetamidoimidazo[1,2-b]pyridazin-6-yl}-N-{[3-fluoro-5-(trifluoromethoxy)phenyl]methyl}-2-methylpyridine-3-carboxamide, TFA | 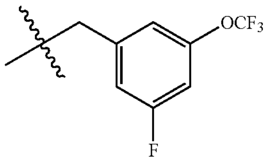 [SMILES: *Cc1cc(F)cc(OC(F)(F)F)c1] | 503.0 | 1H NMR (500 MHz, DMSO-d6) δ 10.94 (s, 1H), 9.28-9.15 (m, 2H), 8.42 (s, 1H), 8.33 (s, 1H), 8.13 (d, J = 9.5 Hz, 1H), 7.90 (d, J = 9.5 Hz, 1H), 7.37-7.23 (m, 3H), 4.57 (br d, J = 5.8 Hz, 2H), 2.60 (s, 3H), 2.12 (s, 3H). |
| 208 | 5-{2-acetamidoimidazo[1,2-b]pyridazin-6-yl}-N-{[2-fluoro-5-(trifluoromethoxy)phenyl](deutero)methyl}-2-methylpyridine-3-carboxamide | 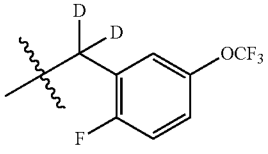 [SMILES: *C([2H])([2H])c1cc(OC(F)(F)F)ccc1F] | 505.3 | 1H NMR (500 MHz, DMSO-d6) δ 10.94 (s, 1H), 9.23-9.14 (m, 2H), 8.38 (d, J = 2.1 Hz, 1H), 8.33 (s, 1H), 8.11 (d, J = 9.5 Hz, 1H), 7.88 (d, J = 9.5 Hz, 1H), 7.46 (br d, J = 5.2 Hz, 1H), 7.43-7.33 (m, 2H), 2.57 (s, 3H), 2.12 (s, 3H). |
| 209 | N-{[2-(cyclopropylmethoxy)-3,4-difluorophenyl]methyl}-5-{2-acetamidoimidazo[1,2-b]pyridazin-6-yl}-2-methylpyridine-3-carboxamide | 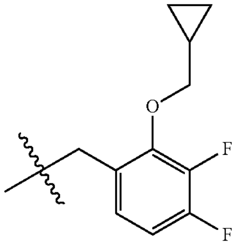 [SMILES: *Cc1ccc(F)c(F)c1OCC1CC1] | 507.5 | 1H NMR (500 MHz, DMSO-d6) δ 10.97 (br s, 1H), 9.16 (s, 1H), 9.08 (br s, 1H), 8.37 (s, 1H), 8.33 (s, 1H), 8.11 (br d, J = 9.4 Hz, 1H), 7.88 (br d, J = 9.4 Hz, 1H), 7.26-7.13 (m, 2H), 4.54 (br d, J = 5.3 Hz, 2H), 3.98.(br d, J = 7.2 Hz, 2H), 2.60 (s, 3H), 2.12 (s, 3H), 1.28 (br s, 1H), 0.57 (br d, J = 6.9 Hz, 2H), 0.32 (br d, J = 4.5 Hz, 2H). |
| 210 | N-{[2-(cyclobutylmethoxy)-3,5-difluorophenyl]methyl}-5-{2-acetamidoimidazo[1,2-b]pyridazin-6-yl}-2-methylpyridine-3-carboxamide, TFA | 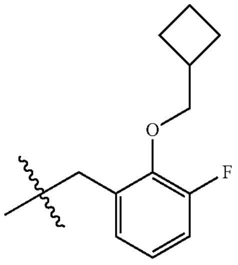 [SMILES: *Cc1cccc(F)c1OCC1CCC1] | 521.5 | 1H NMR (500 MHz, DMSO-d6) δ 10.90 (s, 1H), 9.14 (d, J = 1.8 Hz, 1H), 9.04 (t, J = 5.5 Hz, 1H), 8.38 (s, 1H), 8.29 (s, 1H), 8.08 (d, J = 9.2 Hz, 1H), 7.85 (d, J = 9.5 Hz, 1H), 7.24-7.16 (m, 1H), 7.01-6.88 (m, 2H), 4.51 (d, J = 5.5 Hz, 2H), 3.98 (d, J = 6.7 Hz, 2H), 2.57 (s, 3H), 2.08 (s, 3H), 2.07-1.96 (m, 2H), 1.91-1.77 (m, 4H). |
| 211 | N-[(3R)-3-(4-chlorophenyl)-3-hydroxypropyl]-5-{2-acetamidoimidazo[1,2-b]pyridazin-6-yl}-2-methylpyridine-3-carboxamide | 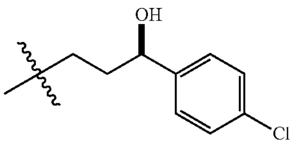 [SMILES: *CC[C@@H](O)c1ccc(Cl)cc1] | 479.4 | 1H NMR (500 MHz, DMSO-d6) δ 10.93 (br. s., 1H), 9.13 (s, 1H), 8.57 (br. s., 1H), 8.32 (s, 1H), 8.26 (s, 1H), 8.09 (d, J = 9.5 Hz, 1H), 7.85 (d, J = 9.5 Hz, 1H), 7.38 (s, 4H), 4.73-4.62 (m, 1H), 3.60 (br. s., 3H), 2.58 (s, 3H), 2.11 (s, 3H), 1.86 (q, J = 7.0 Hz, 2H). |
| 212 | N-{[2-(cyclopropylmethoxy)-3-fluorophenyl]methyl}-5-{2-acetamidoimidazo[1,2-b]pyridazin-6-yl}-2-methylpyridine-3-carboxamide | 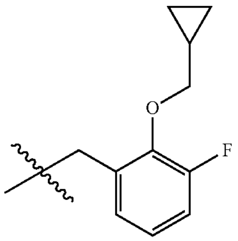 [SMILES: *Cc1cccc(F)c1OCC1CC1] | 489.3 | 1H NMR (500 MHz, DMSO-d6) δ 10.97 (br. s., 1H), 9.17 (s, 1H), 9.08 (br. s., 1H), 8.38 (s, 1H), 8.33 (s, 1H), 8.12 (d, J = 9.2 Hz, 1H), 7.89 (d, J = 9.4 Hz, 1H), 7.24-7.08 (m, 3H), 4.59 (d, J = 5.6 Hz, 2H), 3.91 (d, J = 7.2 Hz, 2H), 2.61 (s, 3H), 2.16-2.07 (m, 3H), 1.26 (br. s., 1H), 0.59-0.53 (m, 2H), 0.31 (d, J = 4.6 Hz, 2H). |

TABLE 7-continued

Compounds in Table 7 were prepared by methods as described in Example 9 and 20.

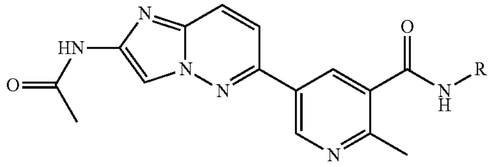

| Ex | Name | R | Obs. MS Ion | NMR Assignments |
|---|---|---|---|---|
| 213 | 5-{2-acetamidoimidazo[1,2-b] pyridazin-6-yl}-N-{[2-fluoro-5-(trifluoromethoxy)phenyl] methyl}-2-methylpyridine-3-carboxamide | 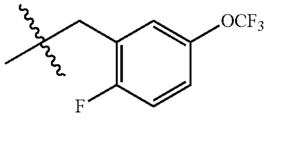 [SMILES: *Cc1cc(OC(F)(F)F)ccc1F] | 503.0 | 1H NMR (500 MHz, DMSO-d6) δ 10.96 (br. s., 1H), 9.24 (br. s., 1H), 9.16 (s, 1H), 8.36 (s, 1H), 8.31 (s, 1H), 8.10 (d, J = 9.4 Hz, 1H), 7.86 (d, J = 9.4 Hz, 1H), 7.44 (d, J = 4.5 Hz, 1H), 7.37 (d, J = 7.2 Hz, 2H), 4.55 (d, J = 5.6 Hz, 2H), 2.56 (s, 3H), 2.11 (s, 3H). |
| 214 | N-{[2-(cyclopropylmethoxy)-3,5-difluorophenyl]methyl}-5-{2-acetamidoimidazo[1,2-b] pyridazin-6-yl}-2-methylpyridine-3-carboxamide | 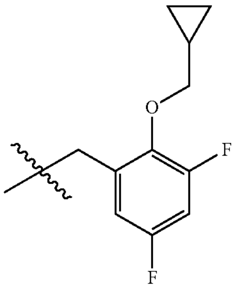 [SMILES: *Cc1cc(F)cc(F)c1OCC1CC1] | 507.0 | 1H NMR (500 MHz, DMSO-d6) δ 10.97 (br. s., 1H), 9.18 (s, 1H), 9.12 (br. s., 1H), 8.42 (s,-1H), 8.34 (s, 1H), 8.13 (d, J = 9.4 Hz, 1H), 7.90 (d, J = 9.4 Hz, 1H), 7.25 (t, J = 8.9 Hz, 1H), 7.06 (d, J = 9.0 Hz, 1H), 4.59 (d, J = 5.6 Hz, 2H), 3.88 (d, J = 7.2 Hz, 2H), 2.61 (s, 3H), 2.16-2.07 (m, 3H), 1.26 (br. s., 1H), 0.62-0.53 (m, 2H), 0.31 (d, J = 4.9 Hz, 2H). |
| 215 | N-{[5-(cyclopropylmethoxy)-2-fluorophenyl]methyl}-5-{2-acetamidoimidazo[1,2-b] pyridazin-6-yl}-2-methylpyridine-3-carboxamide | 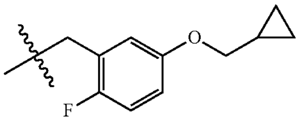 [SMILES: *Cc1cc(OCC2CC2)ccc1F] | 489.3 | 1H NMR (500 MHz, DMSO-d6) δ 10.97 (br. s., 1H), 9.20-9.12 (m, 2H), 8.34 (d, J = 16.2 Hz, 2H), 8.11 (d, J = 9.3 Hz, 1H), 7.88 (d, J = 9.6 Hz, 1H), 7.12 (t, J = 9.2 Hz, 1H), 6.98 (br. s., 1H), 6.90-6.79 (m, 1H), 4.50 (d, J = 5.6 Hz, 2H), 3.78 (d, J = 6.9 Hz, 2H), 2.59 (s, 3H), 2.11 (s, 3H), 1.20 (br. s., 1H), 0.54 (d, J = 7.0 Hz, 2H), 0.28 (d, J = 4.5 Hz, 2H). |
| 216 | N-[(3S)-3-(4-chlorophenyl)-3-hydroxypropyl]-5-{2-acetamidoimidazo[1,2-b] pyridazin-6-yl}-2-methylpyridine-3-carboxamide | 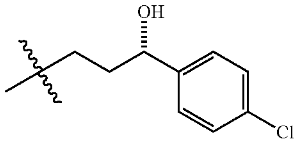 [SMILES: *CC[C@H](O)c1ccc(Cl)cc1] | 479.0 | 1H NMR (500 MHz, DMSO-d6) δ 10.95 (br. s., 1H), 9.12 (br. s., 1H), 8.60 (br. s., 1H), 8.32 (s, 1H), 8.25 (br. s., 1H), 8.08 (d, J = 9.3 Hz, 1H), 7.84 (d, J = 9.3 Hz, 1H), 7.38 (s, 4H), 4.66 (d, J = 4.7 Hz, 1H), 3.60 (br. s., 1H), 3.33 (d, J = 7.1 Hz, 2H), 2.56 (s, 3H), 2.10 (s, 3H), 1.91-1.79 (m, 2H). |
| 217 | N-{[2-(cyclopentylmethoxy) pyridin-3-yl]methyl}-5-{2-acetamidoimidazo [1,2-b]pyridazin-6-yl}-2-methylpyridine-3-carboxamide | 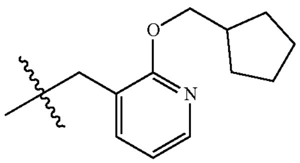 [SMILES: *Cc1cccnc1OCC1CCCC1] | 500.1 | 1H NMR (500 MHz, DMSO-d6) δ 10.94 (s, 1H), 9.16 (s, 1H), 8.96 (t, J = 5.9 Hz, 1H), 8.40 (s, 1H), 8.33 (s, 1H), 8.11 (br d, J = 9.5 Hz, 1H), 8.06 (br d, J = 4.0 Hz, 1H), 7.88 (d, J = 9.2 Hz, 1H), 7.67 (br d, J = 6.7 Hz, 1H), 6.99 (t, J = 6.4 Hz, 1H), 4.44 (br d, J = 5.5 Hz, 2H), 4.21 (d, J = 6.7 Hz, 2H), 2.62 (s, 3H), 2.35 (dt, J = 15.0, 7.5 Hz, 1H), 2.12 (s, 3H), 1.81-1.74 (m, 2H), 1.63-1.48 (m, 4H), 1.37 (br dd, J = 12.2, 6.7 Hz, 2H) |
| 218 | N-{[2-(cyclopentylmethoxy)-5-fluorophenyl]methyl}-5-{2-acetamidoimidazo[1,2-b] pyridazin-6-yl}-2-methylpyridine-3-carboxamide | 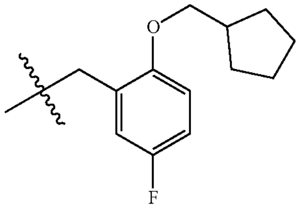 [SMILES: *Cc1cc(F)ccc1OCC1CCCC1] | 517.0 | 1H NMR (500 MHz, DMSO-d6) δ 10.94 (br. s., 1H), 9.17 (s, 1H), 8.96 (br. s., 1H), 8.41 (s, 1H), 8.33 (s, 1H), 8.12 (d, J = 9.5 Hz, 1H), 7.89 (d, J = 9.5 Hz, 1H), 7.16-6.96 (m, 3H), 4.48 (d, J = 5.2 Hz, 2H), 3.90 (d, J = 6.4 Hz, 2H), 2.62 (s, 3H), 2.41-2.30 (m, 1H), 2.12 (s, 3H), 1.80 (d, J = 6.4 Hz, 2H), 1.66-1.49 (m, 4H), 1.39 (dd, J = 12.5, 6.1 Hz, 2H). |
| 219 | N-{[2-(cyclobutylmethoxy)-6-fluorophenyl]methyl}-5-{2-acetamidoimidazo[1,2-b] pyridazin-6-yl}-2-methylpyridine-3-carboxamide | 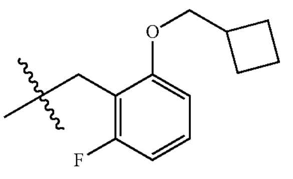 [SMILES: *Cc1c(F)cccc1OCC1CCC1] | 503.2 | 1H NMR (500 MHz, DMSO-d6) δ 10.96 (s, 1H), 9.13 (s, 1H), 8.68 (br. s., 1H), 8.31 (s, 1H), 8.26 (s, 1H), 8.11 (d, J = 9.4 Hz, 1H), 7.86 (d, J = 9.4 Hz, 1H), 7.32 (q, J = 7.8 Hz, 1H), 6.90 (d, J = 8.2 Hz, 1H), 6.82 (t, J = 8.8 Hz, 1H), 4.52 (d, J = 3.9 Hz, 2H), 4.02 (d, J = 6.2 Hz, 2H), 2.81-2.72 (m, 1H), 2.57 (s, 3H), 2.12 (s, 3H), 2.06 (br. s., 2H), 1.96-1.82 (m, 4H). |

TABLE 7-continued

Compounds in Table 7 were prepared by methods as described in Example 9 and 20.

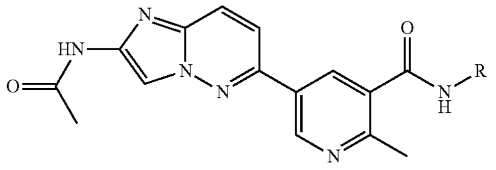

| Ex | Name | R | Obs. MS Ion | NMR Assignments |
|---|---|---|---|---|
| 220 | 5-{2-acetamidoimidazo[1,2-b]pyridazin-6-yl}-2-methyl-N-{[2-(trifluoromethoxy)phenyl]methyl}pyridine-3-carboxamide | 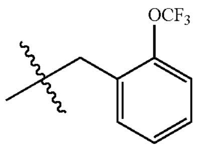 [SMILES: *Cc1ccccc1OC(F)(F)F] | 485.2 | 1H NMR (500 MHz, DMSO-d6) δ 10.94 (s, 1H), 9.20-9.11 (m, 2H), 8.38 (s, 1H), 8.32 (s, 1H), 8.11 (d, J = 9.5 Hz, 1H), 7.87 (d, J = 9.5 Hz, 1H), 7.57 (d, J = 7.0 Hz, 1H), 7.48-7.35 (m, 3H), 4.58 (d, J = 5.8 Hz, 2H), 2.60 (s, 3H), 2.12 (s, 3H). |
| 221 | 5-{2-acetamidoimidazo[1,2-b]pyridazin-6-yl}-2-methyl-N-{[3-(trifluoromethoxy)phenyl]methyl}pyridine-3-carboxamide, TFA | 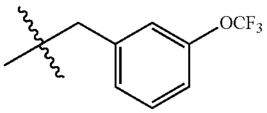 [SMILES: *Cc1cccc(OC(F)(F)F)c1] | 485.1 | 1H NMR (500 MHz, DMSO-d6) δ 10.94 (br. s., 1H), 9.23 (t, J = 5.8 Hz, 1H), 9.18 (br. s., 1H), 8.39 (s, 1H), 8.35 (br. s., 1H), 8.12 (d, J = 9.2 Hz, 1H), 7.89 (d, J = 9.5 Hz, 1H), 7.56-7.46 (m, 1H), 7.43 (d, J = 7.6 Hz, 1H), 7.37 (br. s., 1H), 7.28 (d, J = 7.6 Hz, 1H), 4.56 (d, J = 5.8 Hz, 2H), 2.60 (s, 3H), 2.13 (s, 3H). |
| 222 | N-{[2-(cyclopentyloxy)-5-fluorophenyl]methyl}-5-{2-acetamidoimidazo[1,2-b]pyridazin-6-yl}-2-methylpyridine-3-carboxamide | 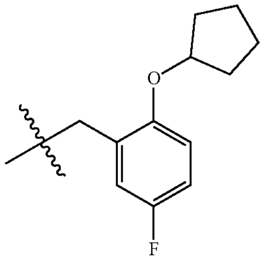 [SMILES: *Cc1cc(F)ccc1OC1CCCC1] | 503.1 | 1H NMR (500 MHz, DMSO-d6) δ 10.95 (s, 1H), 9.17 (s, 1H), 8.93 (t, J = 5.5 Hz, 1H), 8.39 (s, 1H), 8.33 (s, 1H), 8.12 (d, J = 9.5 Hz, 1H), 7.89 (d, J = 9.5 Hz, 1H), 7.16-6.97 (m, 3H), 4.86 (br. s., 1H), 4.43 (d, J = 5.2 Hz, 2H), 2.62 (s, 3H), 2.12 (s, 3H), 1.91 (br. s., 2H), 1.83-1.68 (m, 4H), 1.60 (br. s., 2H). |
| 223 | N-{[2-(cyclopentyloxy)-6-fluorophenyl]methyl}-5-{2-acetamidoimidazo[1,2-b]pyridazin-6-yl}-2-methylpyridine-3-carboxamide | 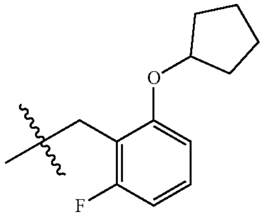 [SMILES: *Cc1c(F)cccc1OC1CCCC1] | 503.2 | 1H NMR (500 MHz, DMSO-d6) δ 10.93 (s, 1H), 9.12 (s, 1H), 8.63 (br. s., 1H), 8.29 (s, 1H), 8.24 (s, 1H), 8.09 (d, J = 9.5 Hz, 1H), 7.84 (d, J = 9.5 Hz, 1H), 7.29 (q, J = 7.4 Hz, 1H), 6.87 (d, J = 8.2 Hz, 1H), 6.78 (t, J = 8.9 Hz, 1H), 4.90 (br. s., 1H), 4.47 (d, J = 4.0 Hz, 2H), 2.57 (s, 3H), 2.11 (s, 3H), 1.98-1.86 (m, 2H), 1.84-1.66 (m, 4H), 1.56 (br. s., 2H). |
| 224 | 5-{2-acetamidoimidazo[1,2-b]pyridazin-6-yl}-2-methyl-N-{[2-(oxolan-3-yloxy)phenyl]methyl}pyridine-3-carboxamide | 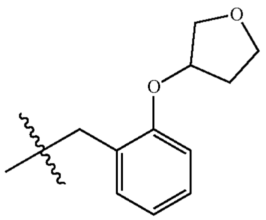 [SMILES: *Cc1ccccc1OC1CCOC1] | 487.0 | 1H NMR (500 MHz, DMSO-d6) δ 10.94 (s, 1H), 9.15 (s, 1H), 8.89 (t, J = 5.3 Hz, 1H), 8.34 (d, J = 12.8 Hz, 2H), 8.10 (d, J = 9.5 Hz, 1H), 7.87 (d, J = 9.5 Hz, 1H), 7.33 (d, J = 7.3 Hz, 1H), 7.27 (t, J = 7.6 Hz, 1H), 7.04-6.92 (m, 2H), 5.09 (br. s., 1H), 4.46 (d, J = 5.5 Hz, 2H), 3.97-3.91 (m, 1H), 3.90-3.81 (m, 2H), 3.80-3.74 (m, 1H), 2.61 (s, 3H), 2.30-2.19 (m, 1H), 2.12 (s, 3H), 2.08-2.00 (m, 1H). |
| 225 | N-{[2-(cyclopentyloxy)phenyl]methyl}-5-{2-acetamidoimidazo[1,2-b]pyridazin-6-yl}-2-methylpyridine-3-carboxamide | 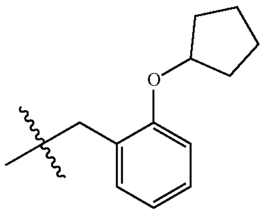 [SMILES: *Cc1ccccc1OC1CCCC1] | 485.2 | 1H NMR (500 MHz, DMSO-d6) δ 10.94 (s, 1H), 9.15 (s, 1H), 8.86 (br. s., 1H), 8.35 (s, 1H), 8.32 (s, 1H), 8.11 (d, J = 9.2 Hz, 1H), 7.87 (d, J = 9.5 Hz, 1H), 7.30 (d, J = 7.6 Hz, 1H), 7.25 (t, J = 7.5 Hz, 1H), 7.00 (d, J = 8.2 Hz, 1H), 6.92 (t, J = 7.5 Hz, 1H), 4.89 (br. s., 1H), 4.44 (d, J = 5.5 Hz, 2H), 2.61 (s, 3H), 2.12 (s, 3H), 1.92 (br. s., 2H), 1.84-1.69 (m, 4H), 1.59 (br. s., 2H). |

TABLE 7-continued

Compounds in Table 7 were prepared by methods as described in Example 9 and 20.

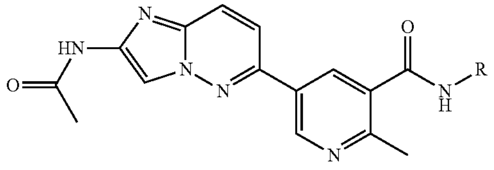

| Ex | Name | R | Obs. MS Ion | NMR Assignments |
|---|---|---|---|---|
| 226 | N-{[2-(cyclopropylmethoxy)-6-fluorophenyl]methyl}-5-{2-acetamidoimidazo[1,2-b]pyridazin-6-yl}-2-methylpyridine-3-carboxamide | 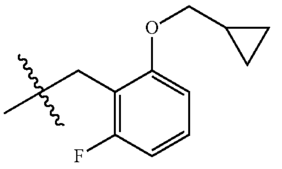 [SMILES: *Cc1c(F)cccc1OCC1CC1] | 489.4 | 1H NMR (500 MHz, DMSO-d6) δ 10.93 (br s, 1H), 9.12 (br s, 1H), 8.69 (br s, 1H), 8.31 (s, 1H), 8.27 (br s, 1H), 8.09 (br d, J = 9.5 Hz, 1H), 7.85 (br d, J = 9.5 Hz, 1H), 7.30 (br d, J = 7.3 Hz, 1H), 6.97-6.76 (m, 2H), 4.53 (br s, 2H), 3.92 (br d, J = 6.7 Hz, 2H), 2.58 (br s, 3H), 2.12 (br s, 2H), 1.25 (br d, J = 18.6 Hz, 2H), 0.56 (br d, J = 6.7 Hz, 2H), 0.36 (br s, 2H) |
| 227 | N-{[2-(cyclopropylmethoxy) phenyl]methyl}-5-{2-acetamidoimidazo [1,2-b]pyridazin-6-yl}-2-methylpyridine-3-carboxamide | 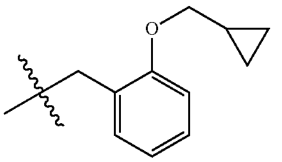 [SMILES: *Cc1ccccc1OCC1CC1] | 471.3 | 1H NMR (500 MHz, DMSO-d6) δ 10.96 (s, 1H), 9.15 (s, 1H), 8.94 (t, J = 5.5 Hz, 1H), 8.39 (s, 1H), 8.33 (s, 1H), 8.11 (d, J = 9.4 Hz, 1H), 7.88 (d, J = 9.3 Hz, 1H), 7.30 (d, J = 7.3 Hz, 1H), 7.24 (t, J = 7.6 Hz, 1H), 7.02-6.91 (m, 2H), 4.50 (d, J = 5.3 Hz, 2H), 3.89 (d, J = 6.6 Hz, 2H), 2.62 (s, 3H), 2.12 (s, 3H), 1.27 (br. s., 1H), 0.57 (d, J = 7.7 Hz, 2H), 0.36 (d, J = 4.6 Hz, 2H). |

TABLE 8

Compounds in Table 8 were prepared by methods as described in Example 16.

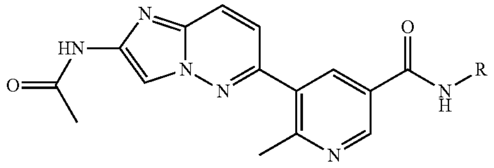

| Ex | Name | R | Obs. MS Ion | NMR Assignments |
|---|---|---|---|---|
| 228 | 5-{2-acetamidoimidazo[1,2-b]pyridazin-6-yl}-N-[(1S)-1-[2-fluoro-5-(trifluoromethoxy)phenyl]ethyl]-6-methylpyridine-3-carboxamide | 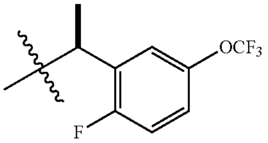 [SMILES: *[C@@H](C)c1cc(OC(F)(F)F)ccc1F] | 517.2 | 1H NMR (500 MHz, DMSO-d6) δ 10.95 (s, 1H), 9.16 (br d, J = 7.3 Hz, 1H), 9.03 (s, 1H), 8.34 (br d, J = 4.3 Hz, 2H), 8.13 (d, J = 9.5 Hz, 1H), 7.51 (d, J = 9.0 Hz, 1H), 7.49-7.46 (m, 1H), 7.39-7.28 (m, 2H), 5.40 (br t, J = 7.0 Hz, 1H), 2.63 (s, 3H), 2.13 (s, 3H), 1.51 (d, J = 7.0 Hz, 3H). |
| 229 | 5-{2-acetamidoimidazo[1,2-b]pyridazin-6-yl}-N-[(1R)-1-[2-fluoro-5-(trifluoromethoxy)phenyl] (2,2,2-deutero)ethyl]-6-methylpyridine-3-carboxamide | 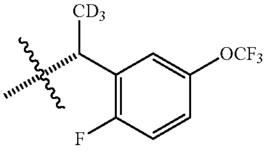 [SMILES: *[C@@H](c1cc(OC(F)(F)F)ccc1F)C([2H])([2H])[2H]] | 520.2 | 1H NMR (500 MHz, DMSO-d6) δ 10.95 (s, 1H), 9.15 (br d, J = 7.6 Hz, 1H), 9.08-8.98 (m, 1H), 8.40-8.29 (m, 2H), 8.13 (d, J = 9.2 Hz, 1H), 7.54-7.44 (m, 2H), 7.39-7.29 (m, 2H), 5.39 (br d, J = 7.3 Hz, 1H), 2.63 (s, 3H), 2.13 (s, 3H). |
| 230 | 5-{2-acetamidoimidazo[1,2-b]pyridazin-6-yl}-N-{[2-fluoro-5-(trifluoromethoxy)phenyl](deutero)methyl}-6-methylpyridine-3-carboxamide | 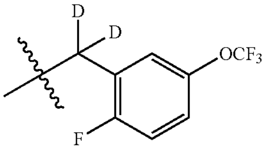 [SMILES: *C([2H])([2H])c1cc(OC(F)(F)F)ccc1F] | 505.2 | 1H NMR (500 MHz, DMSO-d6) δ 10.95 (s, 1H), 9.31 (s, 1H), 9.05 (s, 1H), 8.34 (d, J = 8.5 Hz, 2H), 8.12 (d, J = 9.2 Hz, 1H), 7.51 (d, J = 9.2 Hz, 1H), 7.46-7.32 (m, 3H), 2.64 (s, 3H), 2.13 (s, 3H). |
| 231 | 5-{2-acetamidoimidazo[1,2-b]pyridazin-6-yl}-6-methyl-N-(3-phenylbutyl)pyridine-3-carboxamide | 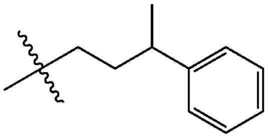 [SMILES: *CCC(C)c1ccccc1] | 442.9 | 1H NMR (500 MHz, DMSO-d6) δ 10.94 (s, 1H), 8.93 (s, 1H), 8.66 (br s, 1H), 8.31 (s, 1H), 8.21 (s, 1H), 8.08 (br d, J = 9.5 Hz, 1H), 7.46 (d, J = 9.2 Hz, 1H), 7.31-7.20 (m, 4H), 7.20-7.10 (m, 1H), 2.85-2.67 (m, 1H), 2.59 (s, 3H), 2.12 (s, 3H), 1.82 (q, J = 7.3 Hz, 2H), 1.21 (d, J = 7.0 Hz, 3H). |

TABLE 8-continued

Compounds in Table 8 were prepared by methods as described in Example 16.

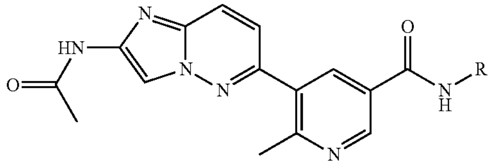

| Ex | Name | R | Obs. MS Ion | NMR Assignments |
|---|---|---|---|---|
| 232 | N-{[2-(cyclopropylmethoxy)-3-fluorophenyl]methyl}-5-{2-acetamidoimidazo[1,2-b]pyridazin-6-yl}-6-methylpyridine-3-carboxamide | 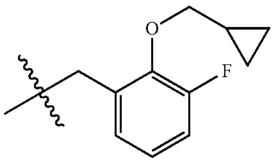 [SMILES: *Cc1cccc(F)c1OCC1CC1] | 489.2 | 1H NMR (500 MHz, DMSO-d6) δ 10.98-10.59 (m, 1H), 9.26-9.15 (m, 1H), 9.06-8.97 (m, 1H), 8.38-8.24 (m, 2H), 8.14-8.03 (m, 1H), 7.52-7.43 (m, 1H), 7.20-7.02 (m, 3H), 4.59 (br d, J = 5.5 Hz, 2H), 3.91-3.85 (m, 2H), 2.61 (s, 3H), 2.12 (s, 3H), 1.28-1.20 (m, 1H), 0.59-0.50 (m, 2H), 0.31-0.22 (m,2H). |
| 233 | 5-{2-acetamidoimidazo[1,2-b]pyridazin-6-yl}-6-methyl-N-{[2-(trifluoromethoxy)phenyl]methyl}pyridine-3-carboxamide | 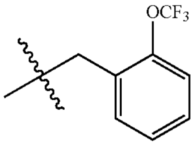 [SMILES: *Cc1ccccc1OC(F)(F)F] | 485.1 | 1H NMR (500 MHz, DMSO-d6) δ 10.89 (s, 1H), 9.24 (br t, J = 5.5 Hz, 1H), 8.98 (s, 1H), 8.27 (br d, J = 8.5 Hz, 2H), 8.04 (d, J = 9.5 Hz, 1H), 7.46-7.29 (m, 5H), 4.53 (br d, J = 5.8 Hz, 2H), 2.57 (s, 3H), 2.07 (s, 3H). |
| 234 | 5-{2-acetamidoimidazo[1,2-b]pyridazin-6-yl}-N-{[2-fluoro-5-(trifluoromethoxy)phenyl]methyl}-6-methylpyridine-3-carboxamide | 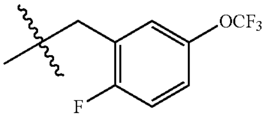 [SMILES: *Cc1cc(OC(F)(F)F)ccc1F] | 503.1 | 1H NMR (500 MHz, DMSO-d6) δ 11.01-10.88 (m, 1H), 9.43-9.27 (m, 1H), 9.05-8.95 (m, 1H), 8.40-8.24 (m, 2H), 8.13-7.98 (m, 1H), 7.56-7.42 (m, 1H), 7.40-7.23 (m, 3H), 4.62-4.50 (m, 2H), 2.61 (s, 3H), 2.17-2.07 (m, 3H). |

TABLE 9

Compounds in Table 9 were prepared by methods as described in Example 21.

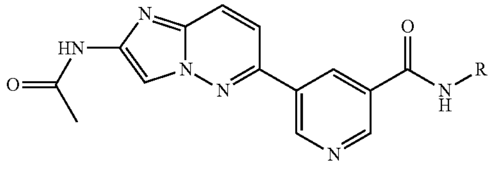

| Ex | Name | R | Obs. MS Ion | NMR Assignments |
|---|---|---|---|---|
| 235 | 5-{2-acetamidoimidazo[1,2-b]pyridazin-6-yl}-N-[(1R)-1-[2-fluoro-5-(trifluoromethoxy)phenyl]ethyl]pyridine-3-carboxamide | 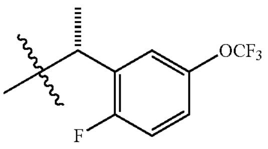 [SMILES: *[C@H](C)c1cc(OC(F)(F)F)ccc1F] | 503.2 | 1H NMR (500 MHz, DMSO-d6) δ 10.97 (s, 1H), 9.39 (s, 1H), 9.30 (br d, J = 7.3 Hz, 1H), 9.14 (s, 1H), 8.82 (s, 1H), 8.38 (s, 1H), 8.17 (d, J = 9.5 Hz, 1H), 7.93 (d, J = 9.5 Hz, 1H), 7.52 (br s, 1H), 7.41-7.32 (m, 2H), 5.44 (br t, J = 7.0 Hz, 1H), 2.13 (s, 3H), 1.55 (br d, J = 7.0 Hz, 3H). |
| 236 | N-{[5-(cyclopropylmethoxy)-2-fluorophenyl]methyl}-5-{2-acetamidoimidazo[1,2-b]pyridazin-6-yl}pyridine-3-carboxamide | 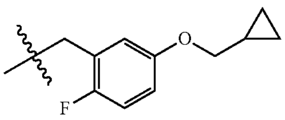 [SMILES: *Cc1cc(OCC2CC2)ccc1F] | 475.2 | 1H NMR (500 MHz, DMSO-d6) δ 10.96 (s, 1H), 9.44-9.29 (m, 2H), 9.14 (s, 1H), 8.84 (s, 1H), 8.36 (s, 1H), 8.14 (d, J = 9.5 Hz, 1H), 7.91 (d, J = 9.5 Hz, 1H), 7.11 (t, J = 9.3 Hz, 1H), 6.95 (dd, J = 6.1, 3.1 Hz, 1H), 6.90-6.79 (m, 1H), 4.54 (br d, J = 5.5 Hz, 2H), 3.76 (d, J = 7.0 Hz, 2H), 2.12 (s, 3H), 1.17 (br s, 1H), 0.61-0.45 (m, 2H), 0.36-0.20 (m, 2H). |
| 237 | 5-{2-acetamidoimidazo[1,2-b]pyridazin-6-yl}-N-{[2-fluoro-5-(trifluoromethoxy)phenyl]methyl}pyridine-3-carboxamide | 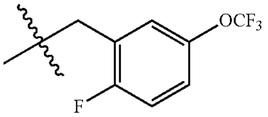 [SMILES: *Cc1cc(OC(F)(F)F)ccc1F] | 489.4 | 1H NMR (500 MHz, DMSO-d6) δ 10.96 (s, 1H), 9.46 (br t, J = 5.6 Hz, 1H), 9.37 (d, J = 1.8 Hz, 1H), 9.20-9.05 (m, 1H), 8.83 (s, 1H), 8.36 (s, 1H), 8.13 (d, J = 9.5 Hz, 1H), 7.89 (d, J = 9.5 Hz, 1H), 7.45-7.33 (m, 3H), 4.60 (br d, J = 5.5 Hz, 2H), 2.12 (s, 3H). |

TABLE 9-continued

Compounds in Table 9 were prepared by methods as described in Example 21.

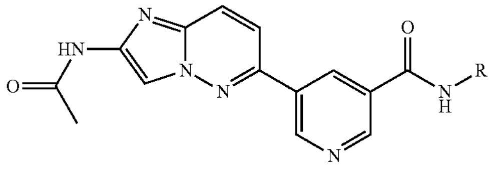

| Ex | Name | R | Obs. MS Ion | NMR Assignments |
|---|---|---|---|---|
| 238 | 5-{2-acetamidoimidazo[1,2-b] pyridazin-6-yl}-N-(3-phenylbutyl) pyridine-3-carboxamide | 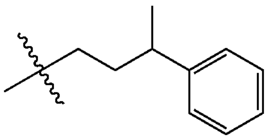 [SMILES: *CCC(C)c1ccccc1] | 429.2 | 1H NMR (500MHz, DMSO-d6) δ 10.97 (s, 1H), 9.32 (s, 1H), 9.04 (s, 1H), 8.80 (br. s., 1H), 8.72 (s, 1H), 8.35 (s, 1H), 8.12 (d, J = 9.4 Hz, 1H), 7.87 (d, J = 9.4 Hz, 1H), 7.35-7.21 (m, 4H), 7.20-7.10 (m, 1H), 3.31-3.09 (m, 2H), 2.85-2.75 (m, 1H), 2.11 (s, 3H), 1.85 (q, J = 7.2 Hz, 2H), 1.23 (d, J = 6.9 Hz, 3H). |
| 239 | N-{[2-(cyclopropylmethoxy)phenyl] methyl}-5-{2-acetamidoimidazo [1,2-b]pyridazin-6-yl}pyridine-3-carboxamide | 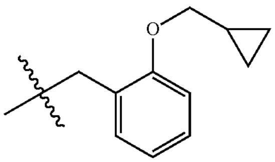 [SMILES: *Cc1ccccc1OCC1CC1] | 457.1 | 1H NMR (500MHz, DMSO-d6) δ 10.98 (s, 1H), 9.37 (s, 1H), 9.27-9.19 (m, 1H), 9.16 (s, 1H), 8.86 (br. s., 1H), 8.36 (s, 1H), 8.15 (d, J = 9.4 Hz, 1H), 7.92 (d, J = 9.4 Hz, 1H), 7.32-7.16 (m, 2H), 6.98 (d, J = 8.1 Hz, 1H), 6.91 (t, J = 7.4 Hz, 1H), 4.55 (d, J = 5.4 Hz, 2H), 3.90 (d, J = 6.7 Hz, 2H), 2.18-2.07 (m, 3H), 1.26 (br. s., 1H), 0.56 (d, J = 7.4 Hz, 2H), 0.35 (d, J = 4.5 Hz, 2H). |
| 240 | N-{[2-(cyclopentyloxy)-6-fluorophenyl]methyl}-5-{2-acetamidoimidazo[1,2-b]pyridazin-6-yl}pyridine-3-carboxamide | 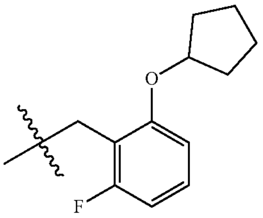 [SMILES: *Cc1c(F)cccc1OC1CCCC1] | 489.1 | 1H NMR (500MHz, DMSO-d6) δ 10.97 (s, 1H), 9.32 (s, 1H), 9.06 (s, 1H), 8.85 (br. s., 1H), 8.76 (s, 1H), 8.33 (s, 1H), 8.13 (d, J = 9.4 Hz, 1H), 7.87 (d, J = 9.3 Hz, 1H), 7.29 (q, J = 7.9 Hz, 1H), 6.90-6.82 (m, 1H), 6.78 (t, J = 8.8 Hz, 1H), 4.88 (br. s., 1H), 4.51 (d, J = 4.1 Hz, 2H), 2.11 (s, 3H), 1.91-1.80 (m, 2H), 1.74 (br. s., 2H), 1.63 (d, J = 4.6 Hz, 2H), 1.50 (br. s., 2H). |
| 241 | N-{[3-(cyclopentyloxy)pyridin-2-yl]methyl}-5-{2-acetamidoimidazo [1,2-b]pyridazin-6-yl}pyridine-3-carboxamide | 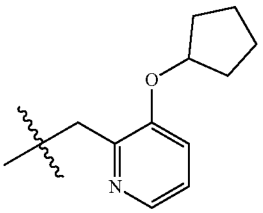 [SMILES: *Cc1ncccc1OC1CCCC1] | 472.1 | 1H NMR (500MHz, DMSO-d6) δ 10.98 (s, 1H), 9.37 (s, 1H), 9.19-9.06 (m, 2H), 8.86 (s, 1H), 8.36 (s, 1H), 8.16 (d, J = 9.4 Hz, 1H), 8.07 (d, J = 4.5 Hz, 1H), 7.92 (d, J = 9.5 Hz, 1H), 7.42 (d, J = 8.2 Hz, 1H), 7.28 (dd, J = 8.1, 4.7 Hz, 1H), 4.93 (br. s., 1H), 4.63 (d, J = 5.4 Hz, 2H), 2.12 (s, 3H), 1.90 (d, J = 6.6 Hz, 2H), 1.81-1.65 (m, 4H), 1.58 (br. s., 2H). |
| 242 | N-{[2-(cyclopentyloxy)-5-fluorophenyl]methyl}-5-{2-acetamidoimidazo[1,2-b]pyridazin-6-yl}pyridine-3-carboxamide | 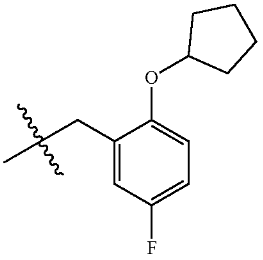 [SMILES: *Cc1cc(F)ccc1OC1CCCC1] | 489 | 1H NMR (500 MHz, DMSO-d6) δ 10.99 (br s, 1H), 9.41 (br s, 1H), 9.31-9.10 (m, 2H), 8.85 (s, 1H), 8.37 (br s, 1H), 8.16 (br d, J = 9.3 Hz, 1H), 7.92 (br d, J = 9.3 Hz, 1H), 7.12-6.96 (m, 3H), 4.86 (br s, 1H), 4.47 (br d, J = 5.4 Hz, 2H), 2.12 (s, 3H), 1.87 (br d, J = 5.5 Hz, 2H), 1.75 (br d, J = 13.9 Hz, 4H), 1.58 (br s, 2H) |

TABLE 10

Compounds in Table 10 were prepared by methods as described in Examples 4 and 10.

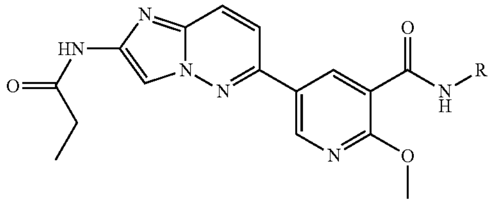

| Ex | Name | R | Obs. MS Ion | NMR Assignments |
|---|---|---|---|---|
| 243 | N-({2-[cyclopropyl(deutero)methoxy]-3,5-difluorophenyl}methyl)-2-methoxy-5-{2-propanamidoimidazo[1,2-b]pyridazin-6-yl}pyridine-3-carboxamide | 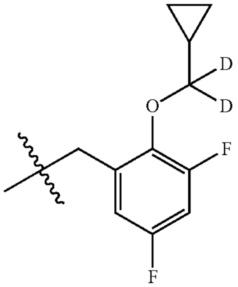 [SMILES: *Cc1cc(F)cc(F)c1OC([2H])([2H])C1CC1] | 539.3 | 1H NMR (500 MHz, DMSO-d6) δ 10.85 (hr s, 1H), 9.00-8.91 (m, 2H), 8.72 (d, J = 2.4 Hz, 1H), 8.35 (br s, 1H), 8.05 (br s, 1H), 7.83 (br d, J = 9.2 Hz, 1H), 7.27-7.12 (m, 1H), 7.00 (br d, J = 8.9 Hz, 1H), 4.62 (br d, J = 6.1 Hz, 2H), 4.08 (s, 3H), 2.48-2.36 (m, 2H), 1.31-1.22 (m, 1H), 1.11 (br t, J = 7.5 Hz, 3H), 0.62-0.52 (m, 2H), 0.31 (q, J = 4.8 Hz, 2H). |
| 244 | N-{[2-fluoro-5-(trifluoromethoxy)phenyl](deutero)methyl}-2-methoxy-5-{2-propanamidoimidazo[1,2-b]pyridazin-6-yl}pyridine-3-carboxamide | 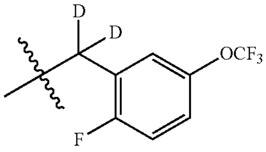 [SMILES: *C([2H])([2H])c1cc(OC(F)(F)F)ccc1F] | 535.2 | 1H NMR (500 MHz, DMSO-d6) δ 10.86 (br s, 1H), 9.00 (br s, 2H), 8.70 (d, J = 2.1 Hz, 1H), 8.38 (br s, 1H), 8.09 (br s, 1H), 7.86 (br d, J = 7.0 Hz, 1H), 7.54-7.34 (m, 3H), 4.08 (s, 3H), 2.49-2.31 (m, 2H), 1.12 (brt, J = 7.2 Hz, 3H). |
| 245 | N-[(1R)-1-[2-fluoro-5-(trifluoromethoxy)phenyl]ethyl]-2-methoxy-5-{2-propanamidoimidazo[1,2-b]pyridazin-6-yl}pyridine-3-carboxamide | 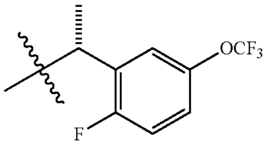 [SMILES: *[C@H](C)c1cc(OC(F)(F)F)ccc1F] | 547.0 | NA |
| 246 | N-[(3S)-3-(4-chlorophenyl)-3-hydroxypropyl]-2-methoxy-5-{2-propanamidoimidazo[1,2-b]pyridazin-6-yl}pyridine-3-carboxamide | 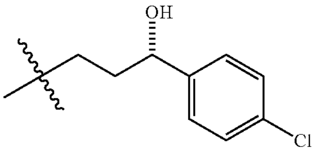 [SMILES: *CC[C@H](O)c1ccc(Cl)cc1] | 509.1 | 1H NMR (500 MHz, DMSO-d6) δ 10.86 (s, 1H), 8.96 (d, J = 2.1 Hz, 1H), 8.72 (d, J = 2.1 Hz, 1H), 8.55 (brs, 1H), 8.34 (s, 1H), 8.07 (d, J = 9.5 Hz, 1H), 7.83 (d, J = 9.5 Hz, 1H), 7.40 (s, 4H), 4.71 (br d, J = 3.7 Hz, 1H), 4.06 (s, 3H), 3.41 (br s, 1H), 2.49-2.28 (m, 2H), 1.95-1.80 (m, 2H), 1.26-1.21 (m, 1H), 1.11 (t, J = 7.5 Hz, 3H), 1.00 (d, J = 6.1 Hz, 1H). |
| 247 | N-{[3,5-difluoro-2-(oxan-4-yloxy)phenyl]methyl}-2-methoxy-5-{2-propanamidoimidazo[1,2-b]pyridazin-6-yl}pyridine-3-carboxamide | 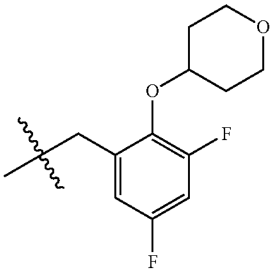 [SMILES: *Cc1cc(F)cc(F)c1OC1CCOCC1] | 567.2 | 1H NMR (500 MHz, DMSO-d6) δ 10.88 (s, 1H), 9.05-8.90 (m, 2H), 8.72 (d, J = 2.2 Hz, 1H), 8.33 (s, 1H), 8.08 (d, J = 9.4 Hz, 1H), 7.85 (d, J = 9.4 Hz, 1H), 7.31-7.16 (m, 1H), 7.02 (br d, J = 9.3 Hz, 1H), 4.59 (br d, J = 5.9 Hz, 2H), 4.30 (td, J = 9.4, 5.1 Hz, 1H), 4.09 (s, 3H), 3.94-3.88 (m, 2H), 3.67-3.43 (m, 2H), 2.48-2.28 (m, 2H), 1.97 (br d, J = 11.2 Hz, 2H), 1.78-1.60 (m, 2H), 1.11 (t, J = 7.5 Hz, 3H). |
| 248 | 2-methoxy-5-{2-propanamidoimidazo[1,2-b]pyridazin-6-yl}-N-{[2-(trifluoromethoxy)phenyl]methyl}pyridine-3-carboxamide, TFA | 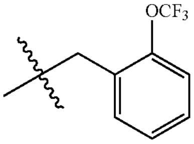 [SMILES: *Cc1ccccc1OC(F)(F)F] | 515.1 | 1H NMR (500 MHz, DMSO-d6) δ 10.88 (s, 1H), 9.04-8.91 (m, 2H), 8.74 (d, J = 2.4 Hz, 1H), 8.33 (s, 1H), 8.07 (d, J = 9.4 Hz, 1H), 7.84 (d, J = 9.4 Hz, 1H), 7.51 (d, J = 7.2 Hz, 1H), 7.46-7.36 (m, 3H), 4.62 (d, J = 5.9 Hz, 2H), 4.08 (s, 3H), 2.49-2.28 (m, 2H), 1.10 (t, J = 7.6 Hz, 3H). |

TABLE 10-continued

Compounds in Table 10 were prepared by methods as described in Examples 4 and 10.

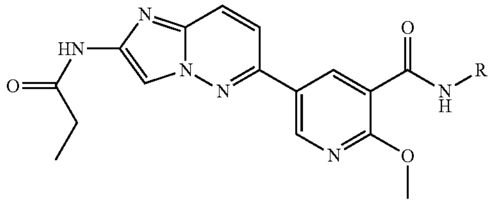

| Ex | Name | R | Obs. MS Ion | NMR Assignments |
|---|---|---|---|---|
| 249 | N-{[2-(cyclopropylmethoxy)-3,4-difluorophenyl]methyl}-2-methoxy-5-{2-propanamidoimidazo[1,2-b]pyridazin-6-yl}pyridine-3-carboxamide | 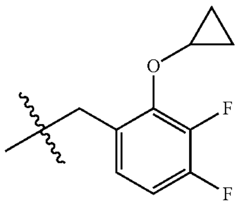 [SMILES: *Cc1ccc(F)c(F)c1OC1CC1] | 537.2 | 1H NMR (500 MHz, DMSO-d6) δ 10.89 (br s, 1H), 8.99 (br s, 1H), 8.90 (br s, 1H), 8.73 (br s, 1H), 8.34 (br s, 1H), 8.08 (br d, J = 8.2 Hz, 1H), 7.85 (br d, J = 8.7 Hz, 1H), 7.16 (br d, J = 5.3 Hz, 2H), 4.57 (br s, 2H), 4.08 (br s, 3H), 3.94 (m, 2H), 2.47-2.31 (m, 2H), 1.24 (br s, 3H), 0.86 (br s, 1H), 0.59 (br s, 2H), 0.34 (br s, 2H). |
| 250 | N-{[5-(cyclopropylmethoxy)-2-fluorophenyl]methyl}-2-methoxy-5-{2-propanamidoimidazo[1,2-b]pyridazin-6-yl}pyridine-3-carboxamide | 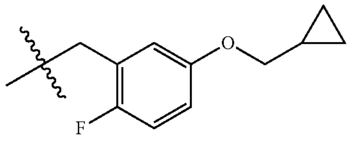 [SMILES: *Cc1cc(OCC2CC2)ccc1F] | 519.1 | 1H NMR (500 MHz, DMSO-d6) δ 10.85 (s, 1H), 9.02-8.85 (m, 2H), 8.69 (d, J = 2.4 Hz, 1H), 8.32 (s, 1H), 8.05 (d, J = 9.5 Hz, 1H), 7.82 (d, J = 9.5 Hz, 1H), 7.10 (t, J = 9.3 Hz, 1H), 7.00-6.90 (m, 1H), 6.88-6.77 (m, 1H), 4.53 (br d, J = 5.5 Hz, 2H), 4.07 (s, 3H), 3.76 (d, J = 7.0 Hz, 2H), 2.41 (q, J = 7.4 Hz, 2H), 1.21-1.14 (m, 1H), 1.10 (t, J = 7.5 Hz, 3H), 0.53 (br d, J = 6.7 Hz, 2H), 0.28 (br d, J = 4.6 Hz, 2H). |

TABLE 11

Compounds in Table 11 were prepared by methods as described in Examples 6, 9, and 20.

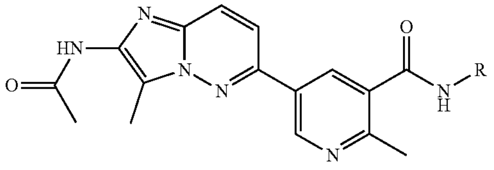

| Ex | Name | R | Obs. MS Ion | NMR Assignments |
|---|---|---|---|---|
| 251 | 5-{2-acetamido-3-methylimidazo[1,2-b]pyridazin-6-yl}-2-methyl-N-{[3-(trifluoromethoxy)phenyl]methyl}pyridine-3-carboxamide | 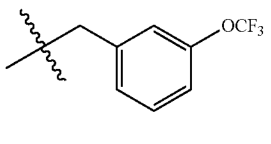 [SMILES: *Cc1cccc(OC(F)(F)F)c1] | 499.3 | 1H NMR (500 MHz, DMSO-d6) δ 10.21 (br s, 1H), 9.26-9.19 (m, 2H), 8.42 (d, J = 2.2 Hz, 1H), 8.13 (d, J = 9.1 Hz, 1H), 7.85 (d, J = 9.4 Hz, 1H), 7.55-7.48 (m, 1H), 7.43 (d, J = 7.7 Hz, 1H), 7.37 (s, 1H), 7.28 (br d, J = 8.3 Hz, 1H), 4.56 (d, J = 6.1 Hz, 2H), 2.59 (s, 3H), 2.48 (s, 3H), 2.09 (s, 3H). |
| 252 | 5-{2-acetamido-3-methylimidazo[1,2-b]pyridazin-6-yl}-N-{[2-fluoro-5-(trifluoromethyl)phenyl]methyl}-2-methylpyridine-3-carboxamide | 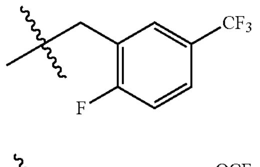 | 501.3 | 1H NMR (500 MHz, DMSO-d6) δ 10.22 (br s, 1H), 9.50-9.06 (m, 2H), 8.42 (s, 1H), 8.13 (br d, J = 9.6 Hz, 1H), 7.89-7.81 (m, 2H), 7.80-7.73 (m, 1H), 7.55-7.46 (m, 1H), 4.62 (br d, J = 5.5 Hz, 2H), 2.58 (s, 3H), 2.48 (s, 3H), 2.09 (s, 3H). |
| 253 | 5-{2-acetamido-3-methylimidazo[1,2-b]pyridazin-6-yl}-N-{[2-fluoro-5-(trifluoromethoxy)phenyl]methyl}-2-methylpyridine-3-carboxamide | 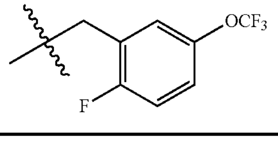 | 517.3 | 1H NMR (500 MHz, DMSO-d6) δ 10.21 (br s, 1H), 9.31-9.07 (m, 3H), 8.40 (d, J = 1.9 Hz, 1H), 8.12 (br d, J = 9.1 Hz, 1H), 7.84 (s, 1H), 7.37 (br d, J = 7.2 Hz, 2H), 4.56 (br d, J = 5.5 Hz, 2H), 2.57 (s, 3H), 2.47 (s, 3H), 2.08 (s, 3H). |

TABLE 12

Compounds in Table 12 were prepared by methods as described in Example 6.

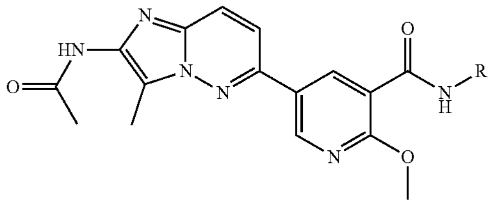

| Ex | Name | R | Obs. MS Ion | NMR Assignments |
|---|---|---|---|---|
| 254 | 5-{2-acetamido-3-methylimidazo[1,2-b]pyridazin-6-yl}-N-{[2-fluoro-5-(trifluoromethyl)phenyl]methyl}-2-methoxypyridine-3-carboxamide | 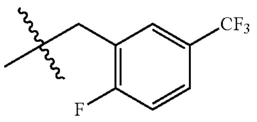 [SMILES: *Cc1cc(C(F)(F)F)ccc1F] | 517.1 | 1H NMR (500 MHz, DMSO-d6) δ 10.18 (br s, 1H), 9.10-9.04 (m, 1H), 9.03 (d, J = 2.5 Hz, 1H), 8.71 (d, J = 2.5 Hz, 1H), 8.09 (br d, J = 9.6 Hz, 1H), 7.86-7.78 (m, 2H), 7.74 (br d, J = 4.4 Hz, 1H), 7.47 (br t, J = 9.2 Hz, 1H), 4.77-4.49 (m, 2H), 4.07 (s, 3H), 2.46 (s, 3H), 2.08 (s, 3H). |
| 255 | 5-{2-acetamido-3-methylimidazo[1,2-b]pyridazin-6-yl}-N-{[4-fluoro-3-(trifluoromethoxy)phenyl]methyl}-2-methoxypyridine-3-carboxamide | 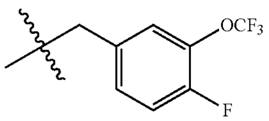 [SMILES: *Cc1ccc(F)c(OC(F)(F)F)c1] | 533.2 | 1H NMR (500 MHz, DMSO-d6) δ 10.18 (dd, J = 4.5, 3.2 Hz, 1H), 9.03 (br d, J = 2.8 Hz, 2H), 8.74 (d, J = 2.5 Hz, 1H), 8.10 (d, J = 8.8 Hz, 1H), 7.81 (d, J = 9.9 Hz, 1H), 7.61-7.39 (m, 3H), 4.56 (br d, J = 6.1 Hz, 2H), 4.13-4.02 (m, 3H), 2.47 (s, 3H), 2.08 (s, 3H). |
| 256 | 5-{2-acetamido-3-methylimidazo[1,2-b]pyridazin-6-yl}-2-methoxy-N-(3-phenylbutyl)pyridine-3-carboxamide, TFA | 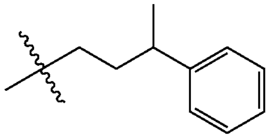 [SMILES: *CCC(C)c1ccccc1] | 473.2 | 1H NMR (500 MHz, DMSO-d6) δ 10.44-9.84 (m, 1H), 8.98 (d, J = 2.2 Hz, 1H), 8.69 (d, J = 2.2 Hz, 1H), 8.32 (br t, J = 5.2 Hz, 1H), 8.08 (br d, J = 8.8 Hz, 1H), 7.79 (br d, J = 9.4 Hz, 1H), 7.36-7.24 (m, 4H), 7.22-7.15 (m, 1H), 4.04 (s, 3H), 3.21 (br d, J = 6.3 Hz, 2H), 2.81 (br d, J = 6.6 Hz, 1H), 2.47 (s, 3H), 2.09 (br s, 3H), 1.83 (q, J = 7.2 Hz, 2H), 1.29-1.22 (m, 3H). |
| 257 | 5-{2-acetamido-3-methylimidazo[1,2-b]pyridazin-6-yl}-2-methoxy-N-{[3-(trifluoromethoxy)phenyl]methyl}pyridine-3-carboxamide, TFA | 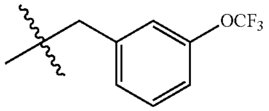 [SMILES: *Cc1cccc(OC(F)(F)F)c1] | 515.2 | 1H NMR (500 MHz, DMSO-d6) δ 10.20 (br s, 1H), 9.06 (br t, J = 6.1 Hz, 1H), 9.01 (br d, J = 2.4 Hz, 1H), 8.73 (d, J = 2.1 Hz, 1H), 8.08 (br d, J = 8.6 Hz, 1H), 7.80 (br d, J = 9.5 Hz, 1H), 7.54-7.45 (m, 1H), 7.40 (br d, J = 7.8 Hz, 1H), 7.35 (br s, 1H), 7.25 (br s, 1H), 4.58 (br d, J = 6.2 Hz, 2H), 4.06 (s, 3H), 2.45 (s, 3H), 2.08 (s, 3H). |
| 258 | 5-{2-acetamido-3-methylimidazo[1,2-b]pyridazin-6-yl}-2-methoxy-N-{[2-(trifluoromethoxy)phenyl]methyl}pyridine-3-carboxamide, TFA | 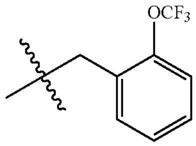 [SMILES: *Cc1ccccc1OC(F)(F)F] | 515.0 | 1H NMR (500 MHz, DMSO-d6) δ 10.19 (br s, 1H), 9.00 (d, J = 2.2 Hz, 1H), 8.98-8.91 (m, 1H), 8.76 (d, J = 2.5 Hz, 1H), 8.06 (br d, J = 9.4 Hz, 1H), 7.78 (br d, J = 9.1 Hz, 1H), 7.54-7.47 (m, 1H), 7.45-7.32 (m, 3H), 4.60 (br d, J = 6.1 Hz, 2H), 4.07 (s, 3H), 2.44 (s, 3H), 2.08 (s, 3H). |
| 259 | N-({2-[cyclopropyl(deutero)methoxy]-3,5-difluorophenyl}methyl)-5-{2-acetamido-3-methylimidazo[1,2-b]pyridazin-6-yl}-2-methoxypyridine-3-carboxamide | 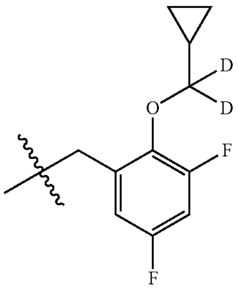 [SMILES: *Cc1cc(F)cc(F)c1OC([2H])([2H])C1CC1] | 539.0 | 1H NMR (500 MHz, DMSO-d6) δ 10.36-9.95 (m, 1H), 9.02 (d, J = 2.2 Hz, 1H), 8.94 (s, 1H), 8.75 (d, J = 2.5 Hz, 1H), 8.08 (br d, J = 9.4 Hz, 1H), 7.80 (d, J = 9.4 Hz, 1H), 7.25-7.13 (m, 1H), 7.01 (br d, J = 8.8 Hz, 1H), 4.61 (br d, J = 6.1 Hz, 2H), 4.26-3.94 (m, 3H), 2.46 (s, 3H), 2.08 (s, 3H), 1.24 (br s, 1H), 0.63-0.51 (m, 2H), 0.30 (br d, J = 4.7 Hz, 2H). |

TABLE 13

Compounds in Table 13 were prepared by methods as described in Example 3.

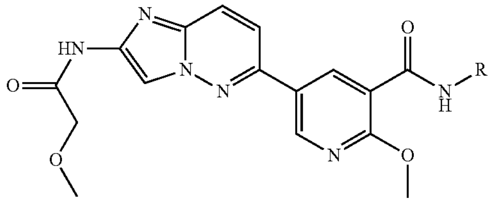

| Ex | Name | R | Obs. MS Ion | NMR Assignments |
|---|---|---|---|---|
| 260 | N-{[5-(cyclopropylmethoxy)-2-fluorophenyl]methyl}-2-methoxy-5-[2-(2-methoxyacetamido)imidazo[1,2-b]pyridazin-6-yl]pyridine-3-carboxamide | 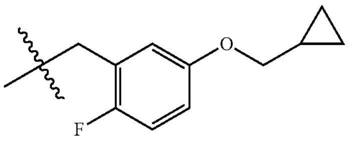 [SMILES: *Cc1cc(OCC2CC2)ccc1F] | 535.2 | 1H NMR (500 MHz, DMSO-d6) δ 10.71 (s, 1H), 8.99 (d, J = 2.3 Hz, 1H), 8.92 (br t, J = 5.9 Hz, 1H), 8.71 (d, J = 2.4 Hz, 1H), 8.36 (s, 1H), 8.10 (d, J = 9.4 Hz, 1H), 7.87 (d, J = 9.5 Hz, 1H), 7.11 (t, J = 9.3 Hz, 1H), 6.96 (dd, J = 5.9, 2.9 Hz, 1H), 6.89-6.79 (m, 1H), 4.54 (br d, J = 5.9 Hz, 2H), 4.11 (s, 3H), 4.08 (s, 3H), 3.77 (d, J = 6.9 Hz, 2H), 1.30-1.14 (m, 3H), 0.61-0.47 (m, 2H), 0.29 (q, J = 4.7 Hz, 2H). |
| 261 | N-{[2-(cyclopropylmethoxy)-3,5-difluorophenyl]methyl}-2-methoxy-5-[2-(2-methoxyacetamido)imidazo[1,2-b]pyridazin-6-yl]pyridine-3-carboxamide, TFA | 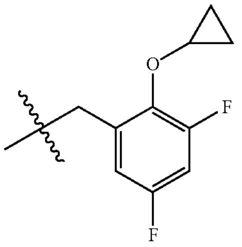 [SMILES: *Cc1cc(F)cc(F)c1OC1CC1] | 553.1 | 1H NMR (500 MHz, DMSO-d6) δ 10.59 (s, 1H), 8.99-8.88 (m, 2H), 8.67 (d, J = 2.3 Hz, 1H), 8.32 (s, 1H), 8.02 (br d, J = 9.4 Hz, 1H), 7.78 (d, J = 9.4 Hz, 1H), 7.18-7.08 (m, 2H), 6.95 (br d, J = 8.5 Hz, 1H), 4.59 (br d, J = 5.9 Hz, 2H), 4.08 (m, 2H) 4.05 (s, 3H), 1.27-1.11 (m, 3H), 0.62-0.48 (m, 2H), 0.33-0.22 (m, 2H). |
| 262 | N-{[2-fluoro-5-(trifluoromethoxy)phenyl]methyl}-2-methoxy-5-[2-(2-methoxyacetamido)imidazo[1,2-b]pyridazin-6-yl]pyridine-3-carboxamide | 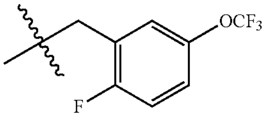 [SMILES: *Cc1cc(OC(F)(F)F)ccc1F] | 548.9 | 1H NMR (500 MHz, DMSO-d6) δ 10.68-10.64 (m, 1H), 9.09-9.03 (m, 1H), 8.96 (d, J = 2.3 Hz, 1H), 8.68-8.66 (m, 1H), 8.37-8.34 (m, 1H), 8.09-8.05 (m, 1H), 7.85-7.81 (m, 1H), 7.42-7.32 (m, 4H), 4.61-4.57 (m, 2H), 4.10 (s, 3H), 4.06 (s, 3H), 3.39-3.37 (m, 1H) |

TABLE 14

Compounds in Table 14 were prepared by methods as described in Examples 5 and 11.

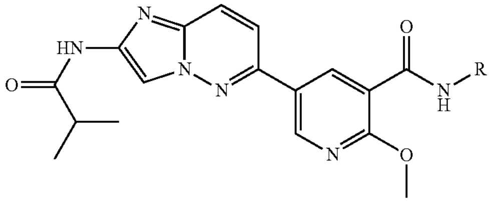

| Ex | Name | R | Obs. MS Ion | NMR Assignments |
|---|---|---|---|---|
| 263 | 2-methoxy-5-[2-(2-methylpropanamido)imidazo[1,2-b]pyridazin-6-yl]-N-{[2-(trifluoromethoxy)phenyl]-methyl}pyridine-3-carboxamide | 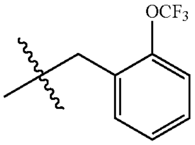 [SMILES: *Cc1ccccc1OC(F)(F)F] | 529.3 | 1H NMR (500 MHz, DMSO-d6) δ 10.85 (s, 1H), 9.02-8.90 (m, 2H), 8.74 (d, J = 2.4 Hz, 1H), 8.33 (s, 1H), 8.06 (d, J = 9.5 Hz, 1H), 7.83 (d, J = 9.5 Hz, 1H), 7.51 (br d, J = 7.0 Hz, 1H), 7.45-7.31 (m, 3H), 4.62 (br d, J = 5.8 Hz, 2H), 4.08 (s, 3H), 2.84-2.66 (m, 1H), 1.12 (d, J = 6.7 Hz, 6H). |

TABLE 14-continued

Compounds in Table 14 were prepared by methods as described in Examples 5 and 11.

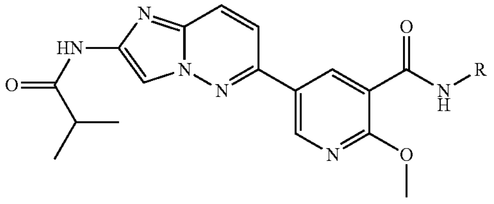

| Ex | Name | R | Obs. MS Ion | NMR Assignments |
|---|---|---|---|---|
| 264 | N-{[2-(cyclopropylmethoxy)-3,4-difluorophenyl]methyl}-2-methoxy-5-[2-(2-methylpropanamido)imidazo[1,2-b]pyridazin-6-yl]pyridine-3-carboxamide, TFA | 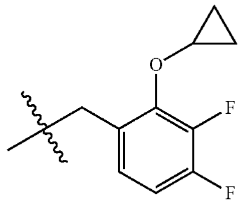 [SMILES: *Cc1ccc(F)c(F)c1OC1CC1] | 551.2 | 1H NMR (500 MHz, DMSO-d6) δ 11.02-10.70 (m, 1H), 8.97 (s, 1H), 8.87 (br t, J = 5.9 Hz, 1H), 8.71 (s, 1H), 8.06 (br d, J = 9.4 Hz, 1H), 7.83 (br d, J = 9.4 Hz, 1H), 7.18-7.10 (m, 2H), 4.56 (br d, J = 5.9 Hz, 2H), 4.06 (s, 3H), 3.99 (d, J = 7.2 Hz, 2H), 3.55 9m, 1H), 2.74 (dt, J = 13.5, 6.7 Hz, 1H), 1.27 (br d, J = 7.6 Hz, 1H), 1.11 (d, J = 6.8 Hz, 6H), 0.64-0.50 (m, 2H), 0.33 (br d, J = 4.8 Hz, 2H). |
| 265 | N-{[3,5-difluoro-2-(oxan-4-yloxy)phenyl]methyl}-2-methoxy-5-[2-(2-methylpropanamido)imidazo[1,2-b]pyridazin-6-yl]pyridine-3-carboxamide | 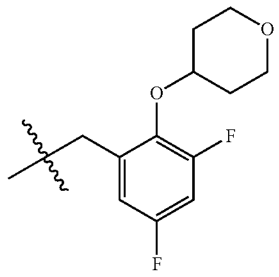 [SMILES: *Cc1cc(F)cc(F)c1OC1CCOCC1] | 581.2 | 1H NMR (500 MHz, DMSO-d6) δ 10.82 (s, 1H), 8.99-8.90 (m, 2H), 8.69 (d, J = 2.1 Hz, 1H), 8.31 (s, 1H), 8.02 (br d, J = 9.5 Hz, 1H), 7.79 (d, J = 9.5 Hz, 1H), 7.18 (br t, J = 8.5 Hz, 1H), 6.98 (br d, J = 8.2 Hz, 1H), 4.57 (br d, J = 6.1 Hz, 2H), 4.28 (br d, J = 4.0 Hz, 1H), 4.06 (s, 3H), 3.81-3.70 (m, 2H), 3.39 (br t, J = 9.9 Hz, 2H), 2.80-2.64 (m, 1H), 1.95 (br d, J = 11.6 Hz, 2H), 1.69 (br d, J = 9.5 Hz, 2H), 1.11 (d, J = 6.7 Hz, 6H). |

TABLE 15

Compounds in Table 15 were prepared by methods as described in Example 12.

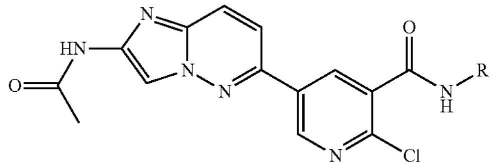

| Ex | Name | R | Obs. MS Ion | NMR Assignments |
|---|---|---|---|---|
| 266 | 2-chloro-N-({2-[cyclopropyl(deutero)methoxy]-3,5-difluorophenyl}methyl)-5-{2-acetamidoimidazo[1,2-b]pyridazin-6-yl}pyridine-3-carboxamide, TFA | 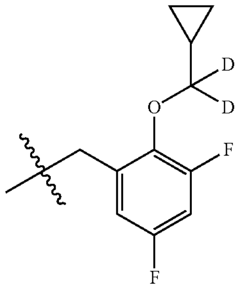 [SMILES: *Cc1cc(F)cc(F)c1OC([2H])([2H])C1CC1] | 529.1 | 1H NMR (500 MHz, DMSO-d6) δ 10.96 (s, 1H), 9.23 (br t, J = 5.5 Hz, 1H), 9.15 (d, J = 2.2 Hz, 1H), 8.58 (d, J = 1.9 Hz, 1H), 8.35 (s, 1H), 8.15 (br d, J = 9.6 Hz, 1H), 7.92 (br d, J = 9.4 Hz, 1H), 7.27-7.20 (m, 1H), 7.09 (br d, J = 8.5 Hz, 1H), 4.59 (br d, J = 5.5 Hz, 2H), 2.12 (s, 3H), 1.27-1.23 (m, 1H), 0.56 (br d, J = 6.9 Hz, 2H), 0.30 (br d, J = 3.9 Hz, 2H). |
| 267 | 2-chloro-N-[(3S)-3-(4-chlorophenyl)-3-hydroxypropyl]-5-{2-acetamidoimidazo[1,2-b]pyridazin-6-yl}pyridine-3-carboxamide | 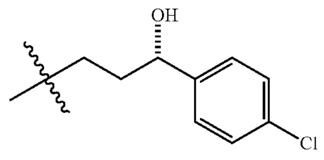 [SMILES: *CC[C@H](O)c1ccc(Cl)cc1] | 499 | 1H NMR (500 MHz, DMSO-d6) δ 10.95 (s, 1H), 9.11 (d, J = 2.5 Hz, 1H), 8.72 (br t, J = 5.5 Hz, 1H), 8.46 (d, J = 2.5 Hz, 1H), 8.35 (s, 1H), 8.12 (d, J = 9.4 Hz, 1H), 7.89 (d, J = 9.4 Hz, 1H), 7.39 (s, 4H), 5.44 (br d, J = 4.1 Hz, 1H), 4.76-4.60 (m, 1H), 3.36-3.24 (m, 2H), 2.11 (s, 3H), 1.93-1.74 (m, 2H). |

TABLE 15-continued

Compounds in Table 15 were prepared by methods as described in Example 12.

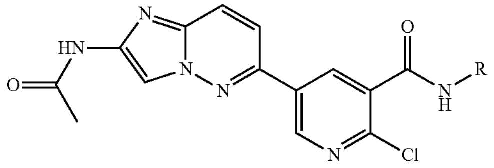

| Ex | Name | R | Obs. MS Ion | NMR Assignments |
| --- | --- | --- | --- | --- |
| 268 | 2-chloro-5-{2-acetamidoimidazo[1,2-b]pyridazin-6-yl}-N-{1-[2-(trifluoromethoxy)phenyl]ethyl}pyridine-3-carboxamide | 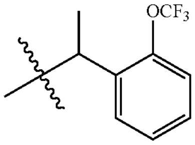 [SMILES: *C(C)c1ccccc1OC(F)(F)F] | 519 | 1H NMR (500 MHz, DMSO-d6) δ 10.95 (s, 1H), 9.31 (br d, J = 7.2 Hz, 1H), 9.10 (d, J = 1.7 Hz, 1H), 8.45 (d, J = 1.9 Hz, 1H), 8.34 (s, 1H), 8.10 (br d, J = 9.4 Hz, 1H), 7.87 (br d, J = 9.1 Hz, 1H), 7.67-7.58 (m, 1H), 7.47-7.39 (m, 2H), 7.38-7.31 (m, 1H), 5.57-5.27 (m, 1H), 2.11 (s, 3H), 1.44 (br d, J = 7.2 Hz, 3H). |
| 269 | 2-chloro-5-{2-acetamidoimidazo[1,2-b]pyridazin-6-yl}-N-{1-[2-fluoro-5-(trifluoromethyl)phenyl]ethyl}pyridine-3-carboxamide | 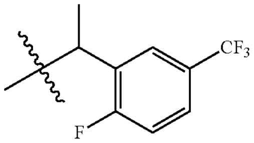 [SMILES: *C(C)c1cc(C(F)(F)F)ccc1F] | 521.2 | 1H NMR (500 MHz, DMSO-d6) δ 10.96 (s, 1H), 9.42 (br d, J = 7.3 Hz, 1H), 9.14 (d, J = 2.1 Hz, 1H), 8.51 (d, J = 2.1 Hz, 1H), 8.34 (s, 1H), 8.12 (d, J = 9.5 Hz, 1H), 7.90 (br d, J = 9.2 Hz, 2H), 7.73 (br s, 1H), 7.47 (br t, J = 9.3 Hz, 1H), 5.38 (br t, J = 7.2 Hz, 1H), 2.11 (s, 3H), 1.49 (br d, J = 7.0 Hz, 3H). |
| 270 | 2-chloro-5-{2-acetamidoimidazo[1,2-b]pyridazin-6-yl}-N-{1-[2-fluoro-5-(trifluoromethyl)phenyl]ethyl}pyridine-3-carboxamide | 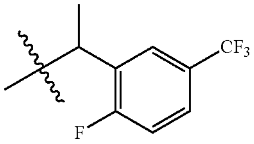 [SMILES: *C(C)c1cc(C(F)(F)F)ccc1F] | 521.3 | 1H NMR (500 MHz. DMSO-d6) δ 10.96 (s, 1H), 9.42 (br d, J = 7.3 Hz, 1H), 9.14 (d, J = 2.1 Hz, 1H), 8.51 (d, J = 2.1 Hz, 1H), 8.34 (s, 1H), 8.12 (d, J = 9.5 Hz, 1H), 7.90 (br d, J = 9.2 Hz, 2H), 7.73 (br s, 1H), 7.47 (br t, J = 9.3 Hz, 1H), 5.38 (br t, J = 7.2 Hz, 1H), 2.11 (s, 3H), 1.49 (br d, J = 7.0 Hz, 3H). |
| 271 | 2-chloro-5-{2-acetamidoimidazo[1,2-b]pyridazin-6-yl}-N-{1-[2-(trifluoromethoxy)phenyl]ethyl}pyridine-3-carboxamide | 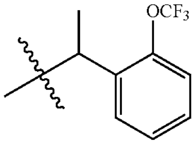 [SMILES: *C(C)c1ccccc1OC(F)(F)F] | 519.1 | 1H NMR (500 MHz, DMSO-d6) δ 10.95 (s, 1H), 9.31 (br d, J = 7.2 Hz, 1H), 9.10 (d, J = 1.7 Hz, 1H), 8.45 (d, J = 1.9 Hz, 1H), 8.34 (s, 1H), 8.10 (br d, J = 9.4 Hz, 1H), 7.87 (br d, J = 9.1 Hz, 1H), 7.67-7.58 (m, 1H), 7.47-7.39 (m, 2H), 7.38-7.31 (m, 1H), 5.57-5.27 (m, 1H), 2.11 (s, 3H), 1.44 (br d, J = 7.2 Hz, 3H). |
| 272 | 2-chloro-5-{2-acetamidoimidazo[1,2-b]pyridazin-6-yl}-N-{[3-(trifluoromethoxy)phenyl]methyl}pyridine-3-carboxamide, TFA | 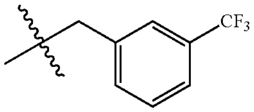 [SMILES: *Cc1cccc(C(F)(F)F)c1] | 505.2 | 1H NMR (500 MHz, DMSO-d6) δ 10.96 (s, 1H), 9.35 (t, J = 5.9 Hz, 1H). 9.15 (d, J = 2.5 Hz, 1H), 8.56 (d, J = 2.5 Hz, 1H), 8.35 (s, 1H), 8.14 (d, J = 9.4 Hz, 1H), 7.92 (d, J = 9.4 Hz, 1H), 7.57-7.48 (m, 1H), 7.45 (br d, J = 7.7 Hz, 1H), 7.39 (br s, 1H), 7.28 (br d, J = 7.4 Hz, 1H), 4.57 (d, J = 6.1 Hz, 2H), 2.12 (s, 3H). |
| 273 | 2-chloro-N-{[2-(1-cyclobutylethoxy)-3,5-difluorophenyl]methyl}-5-{2-acetamidoimidazo[1,2-b]pyridazin-6-yl}pyridine-3-carboxamide, TFA | 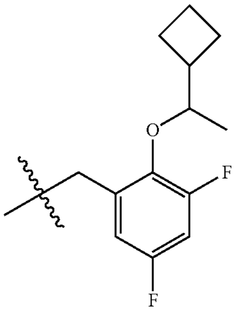 [SMILES: *Cc1cc(F)cc(F)c1OC(C)C1CCC1] | 555 | 1H NMR (500 MHz, DMSO-d6) δ 10.96 (s, 1H), 9.21 (br t, J = 5.6 Hz, 1H), 9.15 (d, J = 2.2 Hz, 1H), 8.58 (d, J = 2.5 Hz, 1H), 8.34 (s, 1H), 8.14 (d, J = 9.4 Hz, 1H), 7.91 (d, J = 9.6 Hz, 1H), 7.28-7.17 (m, 1H), 7.08 (br d, J = 9.6 Hz, 1H), 4.54 (br t, J = 6.5 Hz, 2H), 4.24 (br d, J = 6.6 Hz, 1H), 2.56 (br s, 1H), 2.11 (s, 3H), 2.01-1.71 (m, 6H), 1.11 (d, J = 6.3 Hz, 3H). |
| 274 | 2-chloro-N-{[2-chloro-5-(trifluoromethyl)phenyl]methyl}-5-{2-acetamidoimidazo[1,2-b]pyridazin-6-yl}pyridine-3-carboxamide, TFA | 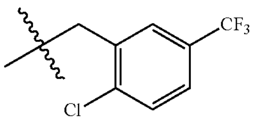 [SMILES: *Cc1cc(C(F)(F)F)ccc1Cl] | 523.2 | 1H NMR (500 MHz, DMSO-d6) δ 10.96 (s, 1H), 9.42 (s, 1H), 9.16 (d, J = 2.5 Hz, 1H), 8.58 (d, J = 2.5 Hz, 1H), 8.34 (s, 1H), 8.14 (d, J = 9.4 Hz, 1H), 7.94-7.87 (m, 2H), 7.74 (q, J = 8.2 Hz, 2H), 4.65 (d, J = 5.5 Hz, 2H), 2.12 (s, 3H). |

TABLE 15-continued

Compounds in Table 15 were prepared by methods as described in Example 12.

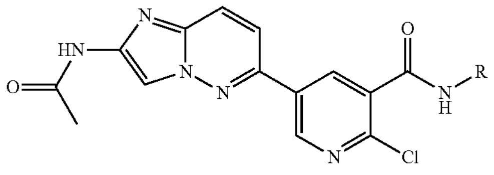

| Ex | Name | R | Obs. MS Ion | NMR Assignments |
|---|---|---|---|---|
| 275 | 2-chloro-5-{2-acetamidoimidazo[1,2-b]pyridazin-6-yl}-N-{[2-fluoro-5-(trifluoromethyl)phenyl]methyl}pyridine-3-carboxamide | 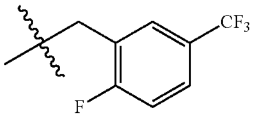 [SMILES: *Cc1cc(C(F)(F)F)ccc1F] | 507.4 | 1H NMR (500 MHz, DMSO-d6) δ 10.95 (s, 1H), 9.39 (t, J = 5.8 Hz, 1H), 9.13 (d, J = 2.2 Hz, 1H), 8.52 (d, J = 2.5 Hz, 1H), 8.33 (s, 1H), 8.10 (d, J = 9.6 Hz, 1H), 7.88 (br d, J = 9.4 Hz, 2H), 7.80-7.71 (m, 1H), 7.47 (t, J = 9.2 Hz, 1H), 4.60 (br d, J = 5.8 Hz, 2H), 2.11 (s, 3H). |

TABLE 16

Compounds in Table 16 were prepared by methods as described in Examples 17 and 19. In examples where a tertiary amide was produced, the compounds are of formula (16A) and R* is as indicated in the table.

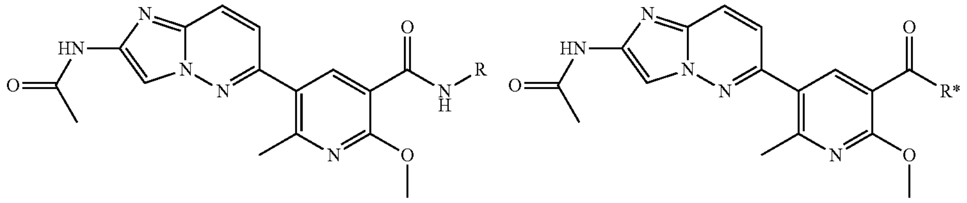

16A

| Ex | Name | R | Obs. MS Ion | NMR Assignments |
|---|---|---|---|---|
| 276 | 5-{2-acetamidoimidazo[1,2-b]pyridazin-6-yl}-N-{1-[2-fluoro-5-(trifluoromethyl)phenyl]ethyl}-2-methoxy-6-methylpyridine-3-carboxamide | 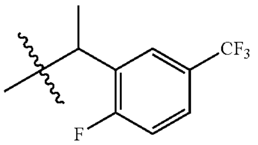 [SMILES: *C(C)c1cc(C(F)(F)F)ccc1F] | 531.5 | 1H NMR (500 MHz, DMSO-d6) δ 10.91 (s, 1H), 8.84 (br d, J = 7.6 Hz, 1H), 8.28 (s, 1H), 8.12-7.99 (m, 2H), 7.93 (br d, J = 5.2 Hz, 1H), 7.73 (br s, 1H), 7.49-7.39 (m, 2H), 5.41 (br t, J = 7.2 Hz, 1H), 4.05 (s, 3H), 2.59-2.54 (m, 3H), 2.12 (s, 3H), 1.50 (br d, J = 7.0 Hz, 3H). |
| 277 | 5-{2-acetamidoimidazo[1,2-b]pyridazin-6-yl}-N-{1-[2-fluoro-5-(trifluoromethyl)phenyl]ethyl}-2-methoxy-6-methylpyridine-3-carboxamide | 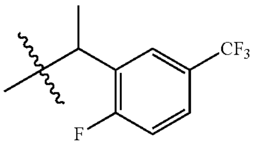 [SMILES: *C(C)c1cc(C(F)(F)F)ccc1F] | 531.4 | 1H NMR (500 MHz, DMSO-d6) δ 10.91 (s, 1H), 8.84 (br d, J = 7.6 Hz, 1H), 8.28 (s, 1H), 8.12-7.99 (m, 2H), 7.93 (br d, J = 5.2 Hz, 1H), 7.73 (br s, 1H), 7.49-7.39 (m, 2H), 5.41 (br t, J = 7.2 Hz, 1H), 4.05 (s, 3H), 2.59-2.54 (m, 3H), 2.12 (s, 3H), 1.50 (br d, J = 7.0 Hz, 3H). |
| 278 | 5-{2-acetamidoimidazo[1,2-b]pyridazin-6-yl}-N-{1-[2-fluoro-5-(trifluoromethoxy)phenyl]ethyl}-2-methoxy-6-methylpyridine-3-carboxamide, TFA | 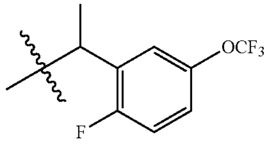 [SMILES: *C(C)c1cc(OC(F)(F)F)ccc1F] | 547.5 | 1H NMR (500 MHz, DMSO-d6) δ 10.91 (s, 1H), 8.77 (br d, J = 7.6 Hz, 1H), 8.28 (s, 1H), 8.07 (s, 1H), 8.04 (d, J = 9.1 Hz, 1H), 7.53 (br d, J = 4.0 Hz, 1H), 7.44-7.31 (m, 3H), 5.36 (quin, J = 7.2 Hz, 1H), 4.05 (s, 3H), 2.56 (ms, 3H), 2.12 (s, 3H), 1.48 (d, J = 7.0 Hz, 3H). |
| 279 | 5-{2-acetamidoimidazo[1,2-b]pyridazin-6-yl}-N-{1-[2-fluoro-5-(trifluoromethoxy)phenyl]ethyl}-2-methoxy-6-methylpyridine-3-carboxamide, TFA | 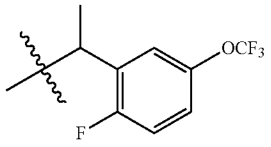 [SMILES: *C(C)c1cc(OC(F)(F)F)ccc1F] | 547.4 | 1H NMR (500 MHz, DMSO-d6) δ 10.91 (s, 1H), 8.77 (br d, J = 7.6 Hz, 1H), 8.28 (s, 1H), 8.07 (s, 1H), 8.04 (d, J = 9.1 Hz, 1H), 7.53 (br d, J = 4.0 Hz, 1H), 7.44-7.31 (m, 3H), 5.36 (quin, J = 7.2 Hz, 1H), 4.05 (s, 3H), 2.56 (ms, 3H), 2.12 (s, 3H), 1.48 (d, J = 7.0 Hz, 3H). |

TABLE 16-continued

Compounds in Table 16 were prepared by methods as described in Examples 17 and 19. In examples where a tertiary amide was produced, the compounds are of formula (16A) and R* is as indicated in the table.

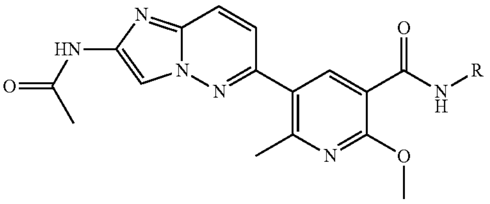

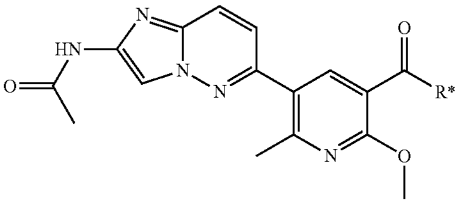

16A

| Ex | Name | R | Obs. MS Ion | NMR Assignments |
|---|---|---|---|---|
| 280 | 5-{2-acetamidoimidazo[1,2-b]pyridazin-6-yl}-N-{[3-fluoro-5-(trifluoromethoxy)phenyl]methyl}-2-methoxy-6-methylpyridine-3-carboxamide | 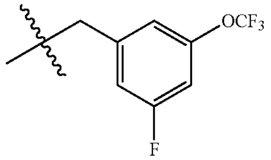 [SMILES: *Cc1cc(F)cc(OC(F)(F)F)c1] | 533.4 | 1H NMR (500 MHz, DMSO-d6) δ 10.93 (br s, 1H), 9.00 (br s, 1H), 8.28 (s, 1H), 8.21 (s, 1H), 8.03 (d, J = 9.3 Hz, 1H), 7.42 (d, J = 9.3 Hz, 1H), 7.28-7.19 (m, 3H), 4.56 (br d, J = 6.0 Hz, 2H), 4.05 (s, 3H), 2.55 (s, 3H), 2.11 (s, 3H). |
| 281 | 5-{2-acetamidoimidazo[1,2-b]pyridazin-6-yl}-2-methoxy-N,6-dimethyl-N-{[3-(trifluoromethoxy)phenyl]methyl}pyridine-3-carboxamide | R* is 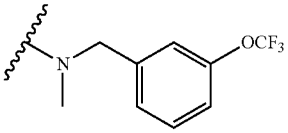 | 529.4 | 1H NMR (500 MHz, DMSO-d6) δ 10.94-10.85 (m, 1H), 8.32-8.19 (m, 1H), 8.08-7.93 (m, 1H), 7.83 (s, 1H), 7.55-7.36 (m, 2H), 7.33-7.21 (m, 2H), 4.51-4.31 (br s, 1H), 3.98 (s, 3H), 3.88 (s, 1H), 2.93 (s, 1H), 2.79 (s, 2H), 2.5 (s, 3H), 2.49-2.45 (m, 1H), 2.11 (s, 3H) |
| 282 | 5-{2-acetamidoimidazo[1,2-b]pyridazin-6-yl}-N-{[2-fluoro-5-(trifluoromethoxy)phenyl]-(deutero)methyl}-2-methoxy-6-methylpyridine-3-carboxamide | 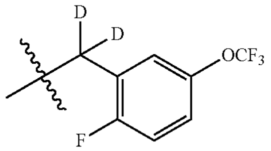 [SMILES: *C([2H])([2H])c1cc(OC(F)(F)F)ccc1F] | 535.0 | 1H NMR (500 MHz, DMSO-d6) δ 10.90 (s, 1H), 8.91 (s, 1H), 8.27 (s, 1H), 8.18 (s, 1H), 8.02 (d, J = 9.5 Hz, 1H), 7.41 (d, J = 9.2 Hz, 1H), 7.38-7.30 (m, 3H), 4.05 (s, 3H), 2.55 (s, 3H), 2.11 (s, 3H). |
| 283 | 5-{2-acetamidoimidazo[1,2-b]pyridazin-6-yl}-2-methoxy-N,6-dimethyl-N-{[2-(trifluoromethoxy)phenyl]methyl}pyridine-3-carboxamide | R* is 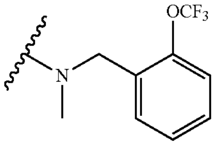 | 529.4 | 1H NMR (500 MHz, DMSO-d6) δ 10.94 (br s, 1H), 8.28 (s, 1H), 8.13-7.93 (m, 1H), 7.85 (s, 1H), 7.55-7.37 (m, 4H), 7.24 (br d, J = 9.3 Hz, 1H), 4.00 (s, 3H), 2.80 (s, 3H), 2.54 (s, 3H), 2.11 (s, 3H). |
| 284 | N-{[2-(cyclopropylmethoxy)-4,5-difluorophenyl]methyl}-5-{2-acetamidoimidazo[1,2-b]pyridazin-6-yl}-2-methoxy-6-methylpyridine-3-carboxamide | 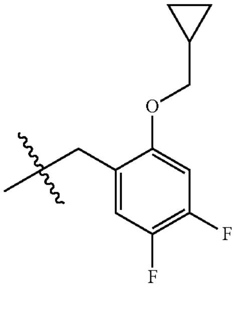 [SMILES: *Cc1cc(F)c(F)cc1OCC1CC1] | 537.1 | 1H NMR (500 MHz, DMSO-d6) δ 10.91 (s, 1H), 8.71 (br t, J = 6.0 Hz, 1H), 8.28 (s, 1H), 8.23 (s, 1H), 8.03 (d, J = 9.5 Hz, 1H), 7.42 (d, J = 9.5 Hz, 1H), 7.23 (br t, J = 10.2 Hz, 1H), 7.11 (dd, J = 12.7, 6.9 Hz, 1H), 4.45 (br d, J = 5.8 Hz, 2H), 4.06 (s, 3H), 3.89 (d, J = 6.7 Hz, 2H), 2.56 (s, 3H), 2.11 (s, 3H), 1.25 (br s, 1H), 0.64-0.51 (m, 2H), 0.35 (br d, J = 4.9 Hz, 2H). |
| 285 | N-[(3,6-difluoro-2-methoxyphenyl)methyl]-5-{2-acetamidoimidazo[1,2-b]pyridazin-6-yl}-2-methoxy-6-methylpyridine-3-carboxamide | 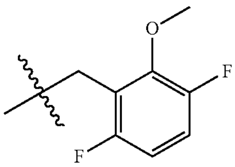 [SMILES: *Cc1c(F)ccc(F)c1OC] | 497.4 | 1H NMR (500 MHz, DMSO-d6) δ 10.91 (s, 1H), 8.60 (br t, J = 5.3 Hz, 1H), 8.28 (s, 1H), 8.21 (s, 1H), 8.04 (d, J = 9.2 Hz, 1H), 7.41 (d, J = 9.5 Hz, 1H), 7.33-7.13 (m, 1H), 6.99 (td, J = 9.0, 3.7 Hz, 1H), 4.58 (br d, J = 5.5 Hz, 2H), 4.04 (s, 3H), 3.96 (s, 3H), 2.57-2.53 (m, 3H), 2.11 (s, 3H). |

TABLE 16-continued

Compounds in Table 16 were prepared by methods as described in Examples 17 and 19. In examples where a tertiary amide was produced, the compounds are of formula (16A) and R* is as indicated in the table.

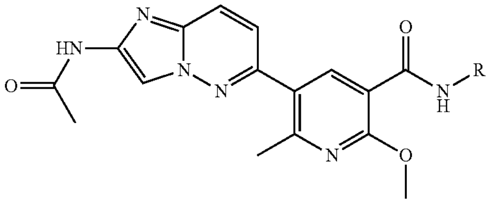

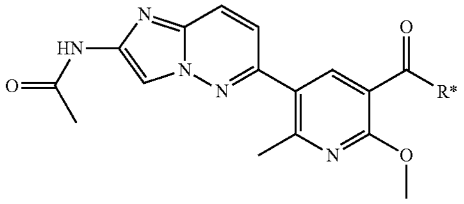

16A

| Ex | Name | R | Obs. MS Ion | NMR Assignments |
|---|---|---|---|---|
| 286 | N-{[2-(cyclopropylmethoxy)-3,4-difluorophenyl]methyl}-5-{2-acelamidoimidazo[1,2-b]pyridazin-6-yl}-2-methoxy-6-methylpyridine-3-carboxamide | 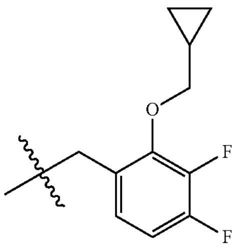 [SMILES: *Cc1ccc(F)c(F)c1OCC1CC1] | 537.3 | 1H NMR (500 MHz, DMSO-d6) δ 10.94 (br s, 1H), 8.80 (br s, 1H), 8.28 (s, 1H), 8.23 (s, 1H), 8.04 (d, J = 9.3 Hz, 1H), 7.42 (d, J = 9.3 Hz, 1H), 7.19-7.08 (m, 2H), 4.55 (br d, J = 5.8 Hz, 2H), 4.06 (s, 3H), 3.97 (d, J = 7.2 Hz, 2H), 2.59-2.54 (m, 3H), 2.11 (s, 3H), 1.26 (br d, J = 7.3 Hz, 1H), 0.64-0.51 (m, 2H), 0.31 (br d, J = 5.0 Hz, 2H). |
| 287 | N-{[2-(cyclopropylmethoxy)-3,5-difluorophenyl](deutero)methyl}-5-{2-acetamidoimidazo[1,2-b]pyridazin-6-yl}-2-methoxy-6-methylpyridine-3-carboxamide | 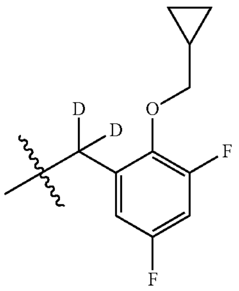 [SMILES: *C([2H])([2H])c1cc(F)cc(F)c1OCC1CC1] | 538.9 | 1H NMR (500 MHz, DMSO-d6) δ 10.91 (br s, 1H), 8.88 (br s, 1H), 8.26 (s, 1H), 8.20 (s, 1H), 8.00 (d, J = 9.3 Hz, 1H), 7.39 (d, J = 9.3 Hz, 1H), 7.16-7.10 (m, 1H), 6.91 (br d, J = 9.1 Hz, 1H), 4.04 (s, 3H), 2.53 (s, 3H), 2.10 (s, 3H), 1.24-1.17 (m, 1H), 0.56-0.50 (m, 2H), 0.28-0.23 (m, 2H). |
| 288 | N-{[2-(cyclobutylmethoxy)-3-fluorophenyl]methyl}-5-{2-acetamidoimidazo[1,2-b]pyridazin-6-yl}-2-methoxy-6-methylpyridine-3-carboxamide | 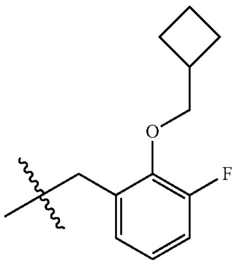 [SMILES: *Cc1cccc(F)c1OCC1CCC1] | 533.2 | 1H NMR (500 MHz, DMSO-d6) δ 10.94 (br s, 1H), 8.77 (br s, 1H), 8.32-8.22 (m, 2H), 8.06 (br d, J = 9.3 Hz, 1H), 7.44 (d, J = 9.3 Hz, 1H), 7.23-7.04 (m, 3H), 4.56 (br d, J = 5.8 Hz, 2H), 4.13-4.00 (m, 5H), 3.47 (br s, 2H), 2.74 (br d, J = 6.6 Hz, 1H), 2.57 (s, 3H), 2.18-2.02 (m, 5H), 1.97-1.83 (m, 4H). |
| 289 | 5-{2-acetamidoimidazo[1,2-b]pyridazin-6-yl}-2-methoxy-6-methyl-N-{1-[3-(trifluoromethoxy)phenyl]ethyl}pyridine-3-carboxamide | 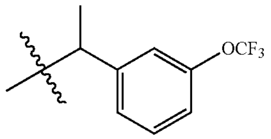 [SMILES: *C(C)c1cccc(OC(F)(F)F)c1] | 528.8 | 1H NMR (500 MHz, DMSO-d6) δ 10.88 (s, 1H), 8.69 (d, J = 7.9 Hz, 1H), 8.25 (s, 1H), 8.04 (s, 1H), 8.00 (d, J = 9.5 Hz, 1H), 7.51-7.34 (m, 4H), 7.21 (d, J = 7.9 Hz, 1H), 5.19-5.11 (m, 1H), 4.02 (s, 3H), 2.52 (s, 3H), 2.10 (s, 3H), 1.46 (d, J = 7.0 Hz, 3H). |
| 290 | 5-{2-acetamidoimidazo[1,2-b]pyridazin-6-yl}-2-methoxy-6-methyl-N-{1-[2-(trifluoromethoxy)phenyl]ethyl}pyridine-3-carboxamide | 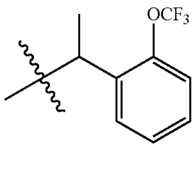 [SMILES: *C(C)c1ccccc1OC(F)(F)F] | 529.0 | 1H NMR (500 MHz, DMSO-d6) δ 10.91 (s, 1H), 8.67 (d, J = 7.6 Hz, 1H), 8.27 (s, 1H), 8.10 (s, 1H), 8.03 (d, J = 9.5 Hz, 1H), 7.63 (dd, J = 5.8, 3.7 Hz, 1H), 7.44-7.37 (m, 3H), 7.35 (br s, 1H), 5.40 (quin, J = 7.1 Hz, 1H), 4.06 (s, 3H), 2.58-2.53 (m, 3H), 2.11 (s, 3H), 1.46 (d, J = 7.0 Hz, 3H). |

TABLE 16-continued

Compounds in Table 16 were prepared by methods as described in Examples 17 and 19. In examples where a tertiary amide was produced, the compounds are of formula (16A) and R* is as indicated in the table.

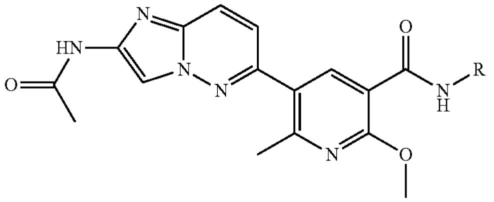

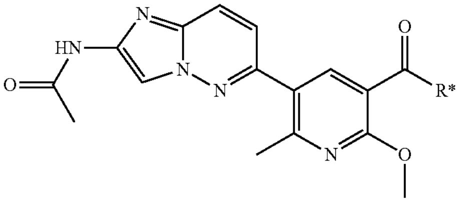

16A

| Ex | Name | R | Obs. MS Ion | NMR Assignments |
|---|---|---|---|---|
| 291 | 5-{2-acetamidoimidazo[1,2-b]pyridazin-6-yl}-2-methoxy-6-methyl-N-{1-[2-(trifluoromethoxy)phenyl]ethyl}pyridine-3-carboxamide | 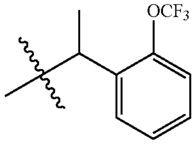 [SMILES: *C(C)c1ccccc1OC(F)(F)F] | 529.4 | 1H NMR (500 MHz, DMSO-d6) δ 10.90 (s, 1H), 8.66 (br d, J = 7.3 Hz, 1H), 8.27 (s, 1H), 8.10 (s, 1H), 8.03 (br d, J = 9.5 Hz, 1H), 7.67-7.59 (m, 1H), 7.45-7.28 (m, 4H), 5.39 (b rt, J = 7.0 Hz, 1H), 4.05 (s, 3H), 2.54 (s, 3H), 2.10 (s, 3H), 1.45 (br d, J = 6.7 Hz, 3H). |
| 292 | 5-{2-acetamidoimidazo[1,2-b]pyridazin-6-yl}-2-methoxy-6-methyl-N-{1-[3-(trifluoromethoxy)phenyl]ethyl}pyridine-3-carboxamide | 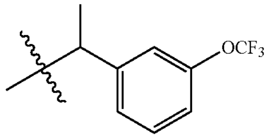 [SMILES: *C(C)c1cccc(OC(F)(F)F)c1] | 529.2 | 1H NMR (500 MHz, DMSO-d6) δ 10.88 (s, 1H), 8.69 (d, J = 7.9 Hz, 1H), 8.25 (s, 1H), 8.04 (s, 1H), 8.00 (d, J = 9.5 Hz, 1H), 7.51-7.34 (m, 4H), 7.21 (d, J = 7.9 Hz, 1H), 5.19-5.11 (m, 1H), 4.02 (s, 3H), 2.52 (s, 3H), 2.10 (s, 3H), 1.46 (d, J = 7.0 Hz, 3H). |
| 293 | 5-{2-acetamidoimidazo[1,2-b]pyridazin-6-yl}-N-{[3-fluoro-5-(trifluoromethyl)phenyl]methyl}-2-methoxy-6-methylpyridine-3-carboxamide | 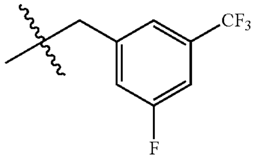 [SMILES: *Cc1cc(F)cc(C(F)(F)F)c1] | 517.4 | 1H NMR (500 MHz, DMSO-d6) δ 10.89 (br. s., 1H), 9.02 (br. s., 1H), 8.27 (br. s., 1H), 8.19 (s, 1H), 8.01 (d, J = 9.5 Hz, 1H), 7.56 (s, 1H), 7.49 (dd, J = 17.1, 9.2 Hz, 2H), 7.40 (d, J = 9.2 Hz, 1H), 4.59 (d, J = 5.8 Hz, 2H), 4.04 (s, 3H), 2.54 (s, 3H), 2.10 (s, 3H). |
| 294 | N-{[2-(cyclobutylmethoxy)-3,5-difluorophenyl]methyl}-5-{2-acetamidoimidazo[1,2-b]pyridazin-6-yl}-2-methoxy-6-methylpyridine-3-carboxamide | 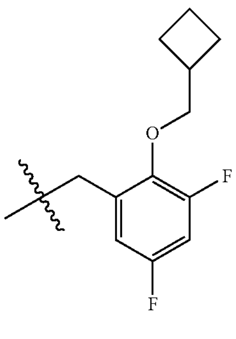 [SMILES: *Cc1cc(F)cc(F)c1OCC1CCC1] | 551.4 | 1H NMR (500 MHz, DMSO-d6) δ 10.91 (br. s., 1H), 8.84 (br. s., 1H), 8.27 (s, 1H), 8.22 (s, 1H), 8.02 (d, J = 9.5 Hz, 1H), 7.41 (d, J = 9.2 Hz, 1H), 7.17 (t, J = 8.7 Hz, 1H), 6.93 (d, J = 8.9 Hz, 1H), 4.54 (d, J = 5.8 Hz, 2H), 4.06 (s, 3H), 4.00 (d, J = 6.7 Hz, 2H), 2.78-2.67 (m, 1H), 2.55 (s, 3H), 2.11 (s, 3H), 2.09-1.99 (m, 2H), 1.94-1.79 (m, 4H). |
| 295 | 5-{2-acetamidoimidazo[1,2-b]pyridazin-6-yl}-2-methoxy-6-methyl-N-{[2-(trifluoromethoxy)phenyl](deutero)-methyl}pyridine-3-carboxamide | 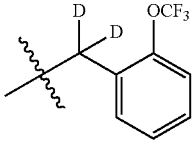 [SMILES: *C([2H])([2H])c1ccccc1OC(F)(F)F] | 517.2 | 1H NMR (500 MHz, DMSO-d6) δ 10.93 (s, 1H), 8.85 (s, 1H), 8.28 (s, 1H), 8.24 (s, 1H), 8.04 (d, J = 9.2 Hz, 1H), 7.50-7.33 (m, 5H), 4.06 (s, 3H), 2.58-2.54 (m, 3H), 2.10 (s, 3H). |
| 296 | 5-{2-acetamidoimidazo[1,2-b]pyridazin-6-yl}-N-{[2-fluoro-5-(trifluoromethyl)phenyl]methyl}-2-methoxy-6-methylpyridine-3-carboxamide | 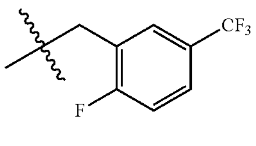 [SMILES: *Cc1cc(C(F)(F)F)ccc1F] | 517.3 | 1H NMR (500 MHz, DMSO-d6) δ 10.93 (s, 1H), 8.97 (t, J = 5.8 Hz, 1H), 8.28 (s, 1H), 8.17 (s, 1H), 8.03 (d, J = 9.2 Hz, 1H), 7.76 (d, J = 6.3 Hz, 1H), 7.72 (br. s., 1H), 7.49-7.38 (m, 2H), 4.60 (d, J = 5.8 Hz, 2H), 4.05 (s, 3H), 2.55 (s, 3H), 2.10 (s, 3H). |

TABLE 16-continued

Compounds in Table 16 were prepared by methods as described in Examples 17 and 19. In examples where a tertiary amide was produced, the compounds are of formula (16A) and R* is as indicated in the table.

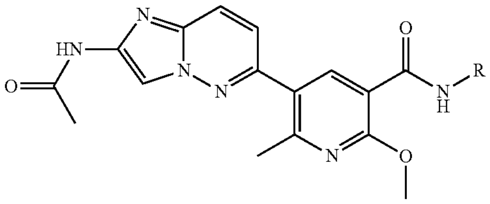

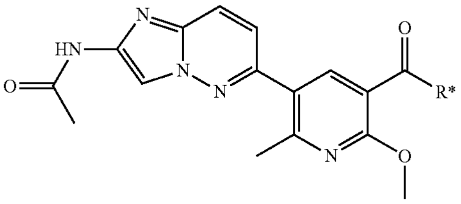

16A

| Ex | Name | R | Obs. MS Ion | NMR Assignments |
|---|---|---|---|---|
| 297 | N-{[5-(cyclopropylmethoxy)-2-fluorophenyl]methyl}-5-{2-acetamidoimidazo[1,2-b]pyridazin-6-yl}-2-methoxy-6-methylpyridine-3-carboxamide | 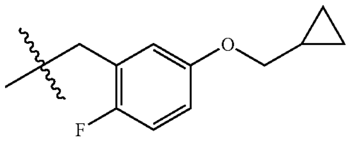 [SMILES: *Cc1cc(OCC2CC2)ccc1F] | 519.1 | 1H NMR (500 MHz, DMSO-d6) δ 10.93 (br. s., 1H), 8.86 (br. s., 1H), 8.27 (s, 1H), 8.19 (s, 1H), 8.02 (d, J = 9.3 Hz, 1H), 7.42 (d, J = 9.3 Hz, 1H), 7.08 (t, J = 9.3 Hz, 1H), 6.88 (br. s., 1H), 6.84-6.79 (m, 1H), 4.50 (d, J = 5.9 Hz, 2H), 4.05 (s, 3H), 3.16 (br. s., 2H), 2.55 (s, 3H), 2.11 (s, 3H), 1.15 (br. s., 1H), 0.52 (d, J = 6.5 Hz, 2H), 0.26 (d, J = 4.3 Hz, 2H). |
| 298 | N-{[2-(cyclopropylmethoxy)-4,6-difluorophenyl]methyl}-5-{2-acetamidoimidazo[1,2-b]pyridazin-6-yl}-2-methoxy-6-methylpyridine-3-carboxamide | 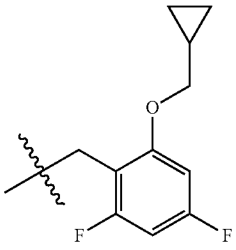 [SMILES: *Cc1c(F)cc(F)cc1OCC1CC1] | 537.4 | 1H NMR (500 MHz, DMSO-d6) δ 10.97-10.90 (m, 1H), 8.43-8.37 (m, 2H), 8.32-8.17 (m, 2H), 8.09-7.98 (m, 1H), 7.46-7.37 (m, 1H), 6.91-6.73 (m, 2H), 4.60-4.41 (m, 2H), 4.03 (s, 3H), 3.24-3.09 (m, 1H), 2.55 (s, 3H), 2.11 (s, 3H), 1.35-1.18 (m, 1H), 0.65-0.51 (m, 2H), 0.43-0.27 (m, 2H) |
| 299 | N-{[2-(cyclopropylmethoxy)-3-fluorophenyl]methyl}-5-{2-acetamidoimidazo[1,2-b]pyridazin-6-yl}-2-methoxy-6-methylpyridine-3-carboxamide | 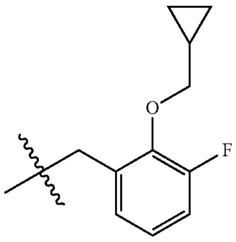 [SMILES: *Cc1cccc(F)c1OCC1CC1] | 519.1 | 1H NMR (500 MHz, DMSO-d6) δ 10.93 (br s, 1H), 8.80 (br s, 1H), 8.28 (s, 1H), 8.24 (s, 1H), 8.05 (br d, J = 9.3 Hz, 1H), 7.43 (br d, J = 9.3 Hz, 1H), 7.22-7.04 (m, 3H), 4.60 (br d, J = 5.8 Hz, 2H), 4.06 (s, 3H), 3.91 (br d, J = 7.2 Hz, 2H), 2.58-2.54 (m, 3H), 2.11 (s, 3H), 1.26 (br s, 1H), 0.56 (br d, J = 7.8 Hz, 2H), 0.30 (br d, J = 4.2 Hz, 2H) |
| 300 | N-{[2-(cyclopropylmethoxy)-3,5-difluorophenyl]methyl}-5-{2-acetamidoimidazo[1,2-b]pyridazin-6-yl}-2-methoxy-6-methylpyridine-3-carboxamide | 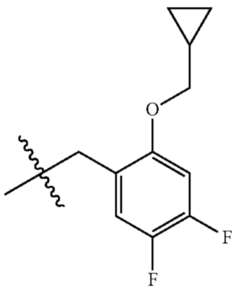 [SMILES: *Cc1cc(F)c(F)cc1OCC1CC1] | 537.1 | 1H NMR (500 MHz, DMSO-d6) δ 10.91 (s, 1H), 8.84 (t, J = 6.5 Hz, 1H), 8.28 (s, 1H), 8.23 (s, 1H), 8.04 (br d, J = 9.5 Hz, 1H), 7.42 (br d, J = 9.2 Hz, 1H), 7.18 (br t, J = 8.5 Hz, 1H), 6.95 (br d, J = 9.2 Hz, 1H), 4.59 (br d, J = 5.8 Hz, 2H), 4.07 (s, 3H), 3.87 (br d, J = 7.0 Hz, 2H), 2.57-2.53 (m, 3H), 2.11 (s, 3H), 1.24 (br d, J = 7.0 Hz, 1H), 0.56 (br d, J = 7.6 Hz, 2H), 0.29 (br d, J = 4.6 Hz, 2H) |
| 301 | N-[(3S)-3-(4-chlorophenyl)-3-hydroxypropyl]-5-{2-acetamidoimidazo[1,2-b]pyridazin-6-yl}-2-methoxy-6-methylpyridine-3-carboxamide | 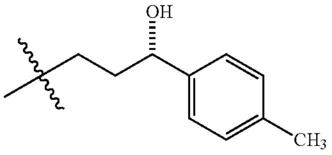 | 508.9 | 1H NMR (500 MHz, DMSO-d6) δ 10.91 (s, 1H), 8.48 (br s, 1H), 8.28 (s, 1H), 8.21 (s, 1H), 8.04 (br d, J = 9.2 Hz, 1H), 7.43-7.35 (m, 6H), 4.69 (br s, 1H), 4.04 (s, 3H), 3.45-3.35 (m, 2H), 2.55 (s, 3H), 2.11 (s, 3H), 1.91-1.80 (m, 2H) |

TABLE 16-continued

Compounds in Table 16 were prepared by methods as described in Examples 17 and 19. In examples where a tertiary amide was produced, the compounds are of formula (16A) and R* is as indicated in the table.

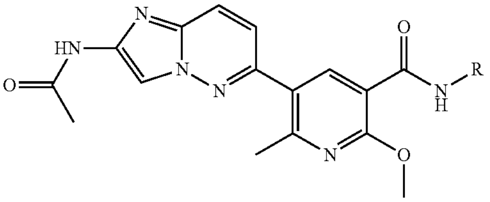
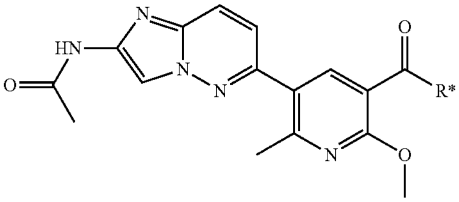

16A

| Ex | Name | R | Obs. MS Ion | NMR Assignments |
|---|---|---|---|---|
| 302 | N-{[2-(1-cyclopentylethoxy)phenyl]methyl}-5-{2-acetamidoimidazo[1,2-b]pyridazin-6-yl}-2-methoxy-6-methylpyridine-3-carboxamide | 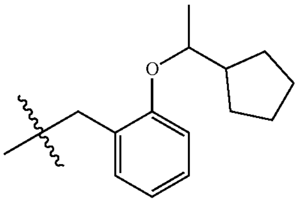 [SMILES: *Cc1ccccc1OC(C)C1CCCC1] | 543.1 | 1H NMR (500 MHz, DMSO-d6) δ 10.90 (s, 1H), 8.59-8.50 (m, 1H), 8.27 (s, 1H), 8.25 (br s, 1H), 8.06-8.00 (m, 1H), 7.41 (br d, J = 9.5 Hz, 1H), 7.26-7.18 (m, 2H), 6.99 (br d, J = 8.2 Hz, 1H), 6.86 (br t, J = 7.0 Hz, 1H), 4.52-4.34 (m, 3H), 4.04 (s, 3H), 2.54 (s, 3H), 2.16-2.08 (m, 3H), 1.78 (br s, 1H), 1.69 (br s, 1H), 1.57 (br s, 2H), 1.50 (br d, J = 6.7 Hz, 2H), 1.40 (br s, 1H), 1.31 (br s, 1H), 1.23 (br d, J = 5.8 Hz, 4H) |
| 303 | N-{[2-(1-cyclopentylethoxy)phenyl]methyl}-5-{2-acetamidoimidazo[1,2-b]pyridazin-6-yl}-2-methoxy-6-methylpyridine-3-carboxamide | 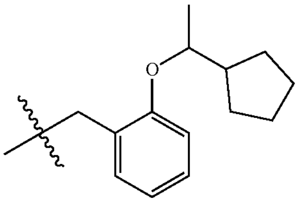 [SMILES: *Cc1ccccc1OC(C)C1CCCC1] | 543.3 | 1H NMR (500 MHz, DMSO-d6) δ 10.91 (s, 1H), 8.54 (br t, J = 5.6 Hz, 1H), 8.27 (d, J = 8.9 Hz, 2H), 8.03 (d, J = 9.5 Hz, 1H), 7.42 (d, J = 9.2 Hz, 1H), 7.23-7.19 (m, 2H), 7.00 (br d, J = 8.2 Hz, 1H), 6.87 (t, J = 7.3 Hz, 1H), 4.52-4.42 (m, 2H), 4.37 (br t, J = 6.1 Hz, 1H), 4.05 (s, 3H), 2.56 (s, 3H), 2.12 (s, 3H), 1.79 (br s, 1H), 1.70 (br s, 1H), 1.58 (br s, 2H), 1.55-1.48 (m, 2H), 1.42 (br d, J = 7.6 Hz, 1H), 1.31 (br d, J = 12.2 Hz, 1H), 1.24 (br d, J = 5.8 Hz, 4H) |
| 304 | 5-{2-acetamidoimidazo[1,2-b]pyridazin-6-yl}-2-methoxy-6-methyl-N-{2-[3-(trifluoromethoxy)phenyl]ethyl}pyridine-3-carboxamide | 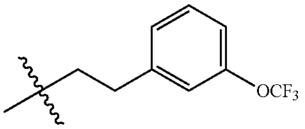 [SMILES: *CCc1cccc(OC(F)(F)F)c1] | 529.3 | 1H NMR (500 MHz, DMSO-d6) δ 10.91 (s, 1H), 8.34-8.31 (m, 1H), 8.28 (s, 1H), 8.15 (s, 1H), 8.02 (br d, J = 9.2 Hz, 1H), 7.44 (t, J = 7.9 Hz, 1H), 7.39 (br d, J = 9.2 Hz, 1H), 7.31 (br d, J = 7.6 Hz, 1H), 7.24 (br s, 1H), 7.19 (br d, J = 7.9 Hz, 1H), 3.98 (s, 3H), 3.60-3.54 (m, 2H), 2.91 (br t, J = 6.7 Hz, 2H), 2.55 (s, 3H), 2.11 (s, 3H) |
| 305 | 5-{2-acetamidoimidazo[1,2-b]pyridazin-6-yl}-2-methoxy-6-methyl-N-{[3-(trifluoromethyl)phenyl]methyl}pyridine-3-carboxamide | 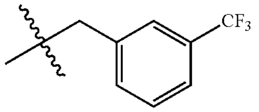 [SMILES: *Cc1cccc(C(F)(F)F)c1] | | 1H NMR (400 MHz, DMSO-d6) δ 10.92 (s, 1H), 8.96 (t, J = 6.1 Hz, 1H), 8.29 (s, 1H), 8.22 (s, 1H), 8.06 (d, J = 9.3 Hz, 1H), 7.72 (s, 1H), 7.68-7.57 (m, 3H), 7.44 (d, J = 9.3 Hz, 1H), 4.61 (d, J = 6.1 Hz, 2H), 4.06 (s, 3H), 2.57 (s, 3H), 2.14-2.10 (m, 3H). |
| 306 | 5-{2-acetamidoimidazo[1,2-b]pyridazin-6-yl}-2-methoxy-6-methyl-N-{[2-(oxolan-3-yloxy)phenyl]methyl}pyridine-3-carboxamide | 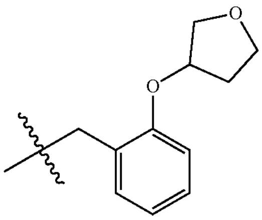 [SMILES: *Cc1ccccc1OC1CCOC1] | 517.1 | 1H NMR (500 MHz, DMSO-d6) δ 10.91 (s, 1H), 8.58 (t, J = 6.2 Hz, 1H), 8.27 (d, J = 13.1 Hz, 2H), 8.05 (d, J = 9.5 Hz, 1H), 7.43 (d, J = 9.2 Hz, 1H), 7.27-7.22 (m, 2H), 6.99 (br d, J = 7.9 Hz. 1H), 6.93 (br t, J = 7.5 Hz, 1H), 5.10 (br s, 1H), 4.48 (br s, 2H), 4.07 (s, 3H), 3.95 (dd, J = 9.9, 4.4 Hz, 1H), 3.90-3.77 (m, 3H), 2.55 (s, 3H), 2.27-2.21 (m, 1H), 2.12 (s, 3H), 2.06-2.00 (m, 1H) |

TABLE 16-continued

Compounds in Table 16 were prepared by methods as described in Examples 17 and 19. In examples where a tertiary amide was produced, the compounds are of formula (16A) and R* is as indicated in the table.

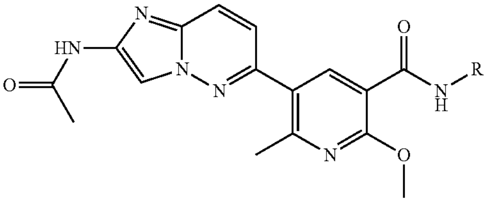

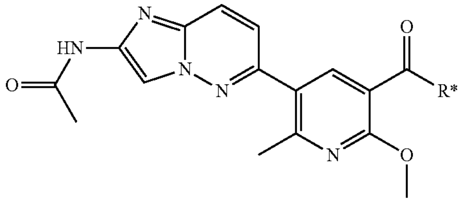

16A

| Ex | Name | R | Obs. MS Ion | NMR Assignments |
|---|---|---|---|---|
| 307 | 5-{2-acetamidoimidazo[1,2-b]pyridazin-6-yl}-2-methoxy-6-methyl-N-{[2-(oxolan-3-yloxy)phenyl]methyl}pyridine-3-carboxamide | 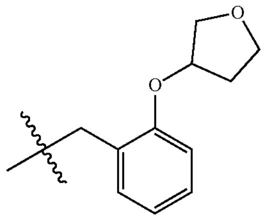 [SMILES: *Cc1ccccc1OC1CCOC1] | 517.1 | 1H NMR (500 MHz, DMSO-d6) δ 10.91 (s, 1H), 8.59 (br t, J = 5.6 Hz, 1H), 8.28 (d, J = 13.1 Hz, 2H), 8.05 (d, J = 9.5 Hz, 1H), 7.43 (d, J = 9.2 Hz, 1H), 7.27-7.22 (m, 2H), 6.99 (br d, J = 7.9 Hz, 1H), 6.93 (t, J = 7.3 Hz, 1H), 5.10 (br s, 1H), 4.48 (br s, 2H), 4.07 (s, 3H), 3.95 (dd, J = 9.9, 4.4 Hz, 1H), 3.90-3.77 (m, 3H), 2.57 (s, 3H), 2.25 (br dd, J = 13.4, 6.1 Hz, 1H), 2.12 (s, H), 2.07-2.00 (m, 1H) |
| 308 | N-{[2-(cyclopentylmethoxy)-4,6-difluorophenyl]methyl}-5-{2-acetamidoimidazo[1,2-b]pyridazin-6-yl}-2-methoxy-6-methylpyridine-3-carboxamide | 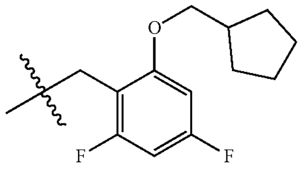 [SMILES: *Cc1c(F)cc(F)cc1OCC1CCCC1] | 565.4 | 1H NMR (500 MHz, DMSO-d6) δ 10.91 (s, 1H), 8.29-8.20 (m, 3H), 8.04 (br d, J = 9.5 Hz, 1H), 7.43-7.39 (m, 1H), 6.85-6.70 (m, 2H), 4.50 (br d, J = 5.2 Hz, 2H), 4.01 (s, 3H), 3.98-3.89 (m, 2H), 2.54 (s, 3H), 2.37-2.30 (m, 1H), 2.11 (s, 3H), 1.78 (br d, J = 6.4 Hz, 2H), 1.63-1.47 (m, 4H), 1.35 (dt, J = 12.7, 6.6 Hz, 2H) |
| 309 | N-{[3-(cyclopropylmethoxy)phenyl]methyl}-5-{2-acetamidoimidazo[1,2-b]pyridazin-6-yl}-2-methoxy-6-methylpyridine-3-carboxamide | 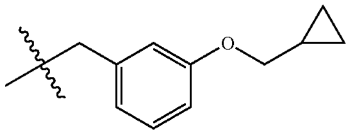 [SMILES: *Cc1cccc(OCC2CC2)c1] | 501.1 | 1H NMR (500 MHz, DMSO-d6) δ 10.94 (br s, 1H), 8.82 (br s, 1H), 8.29 (s, 1H), 8.23 (s, 1H), 8.05 (d, J = 9.3 Hz, 1H), 7.43 (d, J = 9.3 Hz, 1H), 7.22 (t, J = 8.0 Hz, 1H), 6.94-6.84 (m, 2H), 6.79 (br d, J = 7.4 Hz, 1H), 4.48 (br d, J = 6.0 Hz, 2H), 4.05 (s, 3H), 3.78 (d, J = 7.0 Hz, 2H), 2.56 (s, 3H), 2.11 (s, 3H), 1.20 (br t, J = 7.2 Hz, 1H), 0.60-0.49 (m, 2H), 0.30 (q, J = 4.7 Hz, 2H) |
| 310 | N-({2-[(4,4-difluorocyclohexyl)methoxy]phenyl}methyl)-5-{2-acetamidoimidazo[1,2-b]pyridazin-6-yl}-2-methoxy-6-methylpyridine-3-carboxamide | 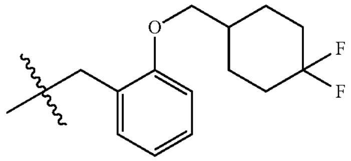 [SMILES: *Cc1ccccc1OCC1CCC(F)(F)CC1] | 579 | 1H NMR (500 MHz, DMSO-d6) δ 10.91 (s, 1H), 8.59 (t, J = 6.6 Hz, 1H), 8.29 (s, 1H), 8.26 (s, 1H), 8.05 (d, J = 9.2 Hz, 1H), 7.43 (d, J = 9.2 Hz, 1H), 7.23 (br s, 2H), 7.00 (br d, J = 8.5 Hz, 1H), 6.91 (t, J = 7.5 Hz, 1H), 4.51 (br d, J = 5.8 Hz, 2H), 4.06 (s, 3H), 3.94-3.88 (m, 3H), 2.57 (s, 3H), 2.11 (s, 3H), 2.00-1.79 (m, 6H), 1.39 (br d, J = 10.1 Hz, 2H) |
| 311 | 5-{2-acetamidoimidazo[1,2-b]pyridazin-6-yl}-N-{[2-fluoro-5-(trifluoromethoxy)phenyl]methyl}-2-methoxy-6-methylpyridine-3-carboxamide, TFA | 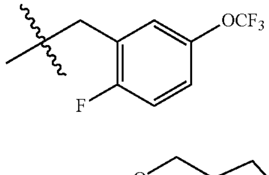 | 533.2 | 1H NMR (500 MHz, DMSO-d6) δ 10.93 (br. s., 1H), 8.93 (br. s., 1H), 8.27 (s, 1H), 8.19 (s, 1H), 8.04 (d, J = 9.3 Hz, 1H), 7.42 (d, J = 9.3 Hz, 1H), 7.39-7.31 (m, 3H), 4.56 (d, J = 5.8 Hz, 2H), 4.05 (s, 3H), 2.55 (s, 3H), 2.10 (s, 3H). |
| 312 | N-{[3-(cyclopentylmethoxy)pyridin-2-yl]methyl}-5-{2-acetamidoimidazo[1,2-b]pyridazin-6-yl}-2-methoxy-6-methylpyridine-3-carboxamide, 2 TFA | 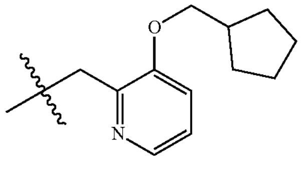 [SMILES: *Cc1ncccc1OCC1CCCC1] | 530.3 | 1H NMR (500 MHz, DMSO-d6) δ 10.95 (br s, 1H), 9.28 (br s, 1H), 8.39 (s, 1H), 8.30 (s, 1H), 8.18 (br d, J = 4.5 Hz, 1H), 8.07 (br d, J = 9.3 Hz, 1H), 7.46 (br t, J = 9.6 Hz, 2H), 7.33 (br dd, J = 8.1, 4.8 Hz, 1H), 4.63 (br d, J = 4.2 Hz, 2H), 4.15 (s, 3H), 3.97 (br d, J = 6.7 Hz, 2H), 2.63-2.54 (m, 3H), 2.48-2.29 (m, 1H), 2.12 (s, 3H), 1.81 (br d, J = 7.0 Hz, 2H), 1.67-1.48 (m, 4H), 1.38 (br dd, J = 12.7, 6.3 Hz, 2H) |

TABLE 16-continued

Compounds in Table 16 were prepared by methods as described in Examples 17 and 19. In examples where a tertiary amide was produced, the compounds are of formula (16A) and R* is as indicated in the table.

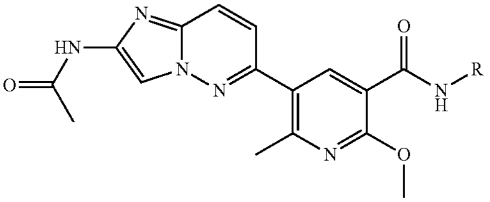

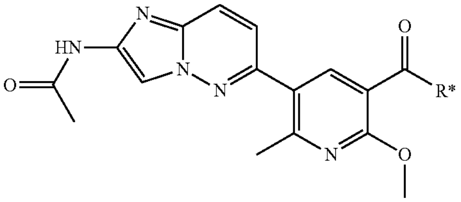

16A

| Ex | Name | R | Obs. MS Ion | NMR Assignments |
|---|---|---|---|---|
| 313 | N-{[2-(cyclopentylmethoxy)pyridin-3-yl]methyl}-5-{2-acetamidoimidazo[1,2-b]pyridazin-6-yl}-2-methoxy-6-methylpyridine-3-carboxamide | 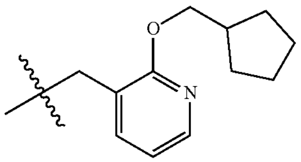 [SMILES: *Cc1cccnc1OCC1CCCC1] | 530 | 1H NMR (500 MHz, DMSO-d6) δ 10.89 (br s, 1H), 8.70 (br s, 1H), 8.28 (br s, 1H), 8.22 (s, 1H), 8.01 (br d, J = 4.3 Hz, 2H), 7.56 (br d, J = 6.7 Hz, 1H), 7.40 (br d, J = 7.6 Hz, 1H), 6.94 (t, J = 6.4 Hz, 1H), 4.44 (br d, J = 5.5 Hz, 2H), 4.18 (br d, J = 6.7 Hz, 2H), 4.04 (s, 3H), 2.55 (m, 3H), 2.38-2.20 (m, 1H), 2.11 (br s, 3H), 1.74 (br d, J = 7.0 Hz, 2H), 1.62-1.45 (m, 4H), 1.38-1.27 (m, 2H) |
| 314 | N-{[2-(cyclobutylmethoxy)pyridin-3-yl]methyl}-5-{2-acetamidoimidazo[1,2-b]pyridazin-6-yl}-2-methoxy-6-methylpyridine-3-carboxamide | 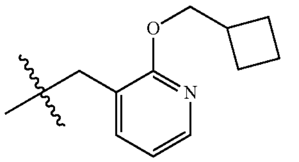 [SMILES: *Cc1cccnc1OCC1CCC1] | 516.3 | 1H NMR (500 MHz, DMSO-d6) δ 10.94 (s, 1H), 8.72 (br t, J = 5.7 Hz, 1H), 8.28 (s, 1H), 8.24 (s, 1H), 8.05-8.02 (m, 2H), 7.56 (br d, J = 7.1 Hz, 1H), 7.42 (d, J = 9.3 Hz, 1H), 6.95 (t, J = 6.3 Hz, 1H), 4.45 (br d, J = 5.8 Hz, 2H), 4.29 (d, J = 6.4 Hz, 2H), 4.06 (s, 3H), 2.76-2.73 (m, 1H), 2.56 (s, 3H), 2.11 (s, 3H), 2.06 (br s, 2H), 1.91-1.83 (m, 4H) |
| 315 | N-{[2-(cyclopentylmethoxy)-5-fluorophenyl]methyl}-5-{2-acetamidoimidazo[1,2-b]pyridazin-6-yl}-2-methoxy-6-methylpyridine-3-carboxamide | 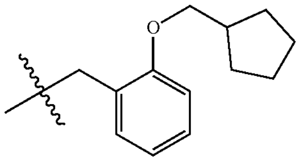 [SMILES: *Cc1ccccc1OCC1CCCC1] | 547 | 1H NMR (500 MHz, DMSO-d6) δ 10.93 (s, 1H), 8.70 (t, J = 5.8 Hz, 1H), 8.27 (s, 1H), 8.22 (s, 1H), 8.03 (d, J = 9.3 Hz, 1H), 7.42 (d, J = 9.3 Hz, 1H), 7.05-6.90 (m, 3H), 4.46 (d, J = 5.8 Hz, 2H), 4.05 (s, 3H), 3.87 (d, J = 6.6 Hz, 2H), 2.55 (br. s., 3H), 2.32 (dt, J = 14.5, 7.3 Hz, 1H), 2.10 (s, 3H), 1.78 (d, J = 6.9 Hz, 2H), 1.64-1.48 (m, 4H), 1.36 (dd, J = 12.2, 6.6 Hz, 2H). |
| 316 | N-{[2-(cyclopentylmethoxy)phenyl]methyl}-5-{2-acetamidoimidazo[1,2-b]pyridazin-6-yl}-2-methoxy-6-methylpyridine-3-carboxamide | 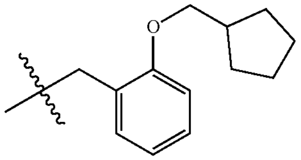 [SMILES: *Cc1ccccc1OCC1CCCC1] | 529.1 | 1H NMR (500 MHz, DMSO-d6) δ 10.91 (s, 1H), 8.58 (br t, J = 6.0 Hz, 1H), 8.28 (s, 1H), 8.25 (s, 1H), 8.02 (d, J = 9.2 Hz, 1H), 7.41 (d, J = 9.2 Hz, 1H), 7.24-7.20 (m, 2H), 6.98 (br d, J = 8.5 Hz, 1H), 6.89 (t, J = 7.2 Hz, 1H), 4.49 (br d, J = 5.8 Hz, 2H), 4.04 (s, 3H), 3.90 (br d, J = 6.4 Hz, 2H), 2.56-2.53 (m, 3H), 2.35-2.32 (m, 1H), 2.11 (s, 3H), 1.79 (br d, J = 7.3 Hz, 2H), 1.62-1.50 (m, 4H), 1.37 (br dd, J = 12.4, 6.6 Hz, 2H) |
| 317 | N-{[2-(cyclopropylmethoxy)-4-fluorophenyl]methyl}-5-{2-acetamidoimidazo[1,2-b]pyridazin-6-yl}-2-methoxy-6-methylpyridine-3-carboxamide | 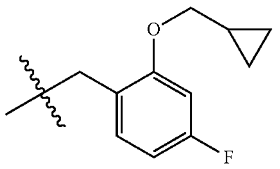 [SMILES: *Cc1ccc(F)cc1OCC1CC1] | 519.3 | 1H NMR (500 MHz, DMSO-d6) δ 10.93 (s, 1H), 8.63 (br. s., 1H), 8.27 (d, J = 13.0 Hz, 2H), 8.05 (d, J = 9.3 Hz, 1H), 7.43 (d, J = 9.3 Hz, 1H), 7.22 (t, J = 7.5 Hz, 1H), 6.87 (d, J = 11.4 Hz, 1H), 6.71 (t, J = 8.3 Hz, 1H), 4.46 (d, J = 5.5 Hz, 2H), 4.06 (s, 3H), 3.91 (d, J = 6.6 Hz, 2H), 2.56 (s, 3H), 2.11 (s, 3H), 1.26 (br. s., 1H), 0.58 (d, J = 7.5 Hz, 2H), 0.36 (d, J = 4.2 Hz, 2H). |
| 318 | N-{[2-(cyclopropylmethoxy)phenyl]methyl}-5-{2-acetamidoimidazo[1,2-b]pyridazin-6-yl}-2-methoxy-6-methylpyridine-3-carboxamide | 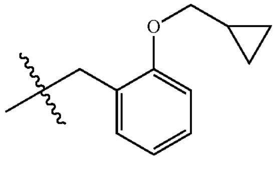 [SMILES: *Cc1ccccc1OCC1CC1] | 501 | 1H NMR (500 MHz, DMSO-d6) δ 10.94 (s, 1H), 8.64 (t, J = 5.9 Hz, 1H), 8.29 (d, J = 5.8 Hz, 2H), 8.06 (d, J = 9.3 Hz, 1H), 7.44 (d, J = 9.3 Hz, 1H), 7.27-7.18 (m, 2H), 6.98 (d, J = 8.0 Hz, 1H), 6.91 (t, J = 7.4 Hz, 1H), 4.52 (d, J = 5.8 Hz, 2H), 4.07 (s, 3H), 3.91 (d, J = 6.7 Hz, 2H), 2.57 (s, 3H), 2.12 (s, 3H), 1.33-1.19 (m, 1H), 0.59 (d, J = 7.7 Hz, 2H), 0.37 (d, J = 4.6 Hz, 2H). |

TABLE 16-continued

Compounds in Table 16 were prepared by methods as described in Examples 17 and 19. In examples where a tertiary amide was produced, the compounds are of formula (16A) and R* is as indicated in the table.

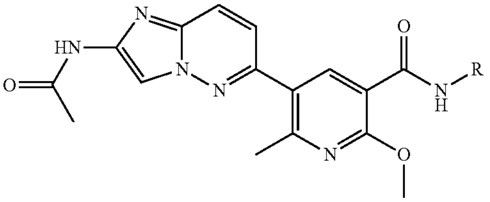

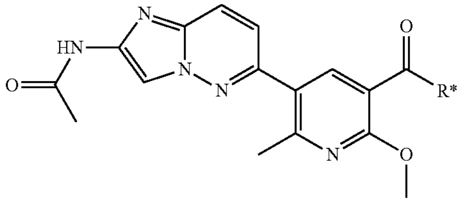

16A

| Ex | Name | R | Obs. MS Ion | NMR Assignments |
|---|---|---|---|---|
| 319 | 5-{2-acetamidoimidazo[1,2-b]pyridazin-6-yl}-2-methoxy-6-methyl-N-{[3-(trifluoromethoxy)phenyl]methyl}pyridine-3-carboxamide | 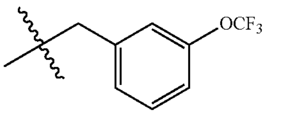 [SMILES: *Cc1cccc(OC(F)(F)F)c1] | 515.1 | 1H NMR (500 MHz, DMSO-d6) δ 10.94 (s, 1H), 8.98-8.90 (m, 1H), 8.29 (s, 1H), 8.23 (s, 1H), 8.06 (d, J = 9.2 Hz, 1H), 7.51-7.42 (m, 2H), 7.38 (d, J = 7.6 Hz, 1H), 7.34 (br. s., 1H), 7.25 (d, J = 7.3 Hz, 1H), 4.57 (d, J = 5.7 Hz, 2H), 4.06 (s, 3H), 2.57 (s, 3H), 2.11 (s, 3H). |

Example 320: 2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl dihydrogen phosphate, disodium salt, 0.5 diethyl ether

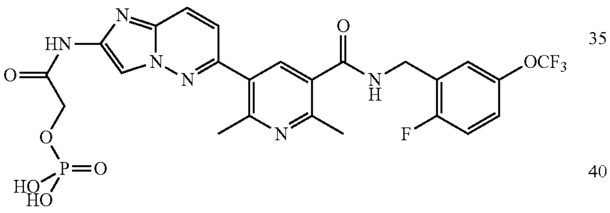

320A: dibenzyl (2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl) phosphate: To a solution of N-(2-fluoro-5-(trifluoromethoxy)benzyl)-5-(2-(2-hydroxyacetamido)imidazo[1,2-b]pyridazin-6-yl)-2,6-dimethylnicotinamide (75 mg, 0.141 mmol) and dibenzyl diisopropylphosphoramidite (0.097 mL, 0.296 mmol) in DMF (1.5 mL) and cooled to 0° C. was added 1H-tetrazole (20.72 mg, 0.296 mmol). The reaction mixture was stirred 1.5 h at 0° C. Hydrogen peroxide, 30% aqueous (0.144 mL, 1.409 mmol) was added and the reaction mixture stirred an additional 30 min. The reaction mixture was partitioned between EtOAc (85 mL) and 5% sodium biphosphate solution (30 mL). The organics were washed sequentially with 10% lithium chloride solution (2×), 1 N HCl, saturated aqueous sodium bicarbonate and brine. The combined organics were dried over sodium sulfate, then filtered and concentrated. Afforded dibenzyl (2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl) phosphate (78 mg, 0.096 mmol, 68.5% yield).

MS ESI (m/z) 793.6 (M+H).

320: A mixture of dibenzyl (2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl) phosphate (79 mg, 0.100 mmol) and Pearlman's catalyst (20.99 mg, 0.030 mmol) in ethanol (2 mL) was degassed by vacuum, and then flooded with a hydrogen atmosphere. The mixture was stirred at rt under the $H_2$ balloon. After 3 h, the mixture was re-degassed and stirred ON under the $H_2$ balloon. The mixture was filtered through Celite, washing with water. An impure product was isolated and trituration with organic solvents did not improve purity. Water was added to the crude material and it was filtered carefully through a 0.45 μM filter. The resulting clear solution was lyophilized to yield 2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl dihydrogen phosphate, disodium salt, 0.5 diethyl ether (67 mg, 0.091 mmol, 91% yield).

MS ESI (m/z) 613.3 (M+H)

$^1$H NMR (400 MHz, $D_2O$) δ 8.34-8.24 (m, 1H), 8.03-7.91 (m, 1H), 7.90-7.73 (m, 1H), 7.35 (d, J=9.5 Hz, 1H), 7.33-7.30 (m, 1H), 7.27-7.15 (m, 2H), 4.55 (s, 2H), 4.40 (d, J=6.8 Hz, 2H), 3.94-3.76 (m, 1H), 2.50-2.44 (m, 6H), 1.16-0.93 (m, 2H) (protons at 3.85 ppm and 1.04 ppm are from the diethyl ether solvate, phosphate —OH and amide —NH protons exchanged away).

Example 320 is a prodrug of Example 38. The utility of the prodrug comes from the activity of its metabolite, Example 38.

Example 321: 6-chloro-5-{2-acetamidoimidazo[1,2-b]pyridazin-6-yl}-N-{[5-fluoro-2-(trifluoromethoxy)phenyl] methyl}pyridine-3-carboxamide

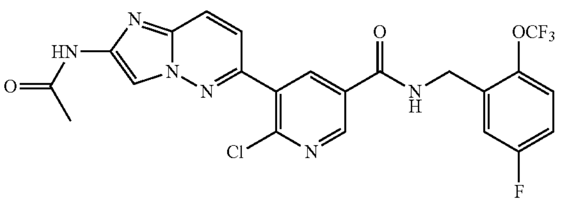 [SMILES: CC(=O)Nc1cn2nc(-c3cc(C(=O)NCc4cc(F)ccc4OC(F)(F)F)cnc3Cl)ccc2n1]

Compound 321 was prepared as in Example 14.

MS ESI m/z 523.2 (M+H)

1H NMR (500 MHz, DMSO-d6) δ 11.00 (s, 1H), 9.51-9.38 (m, 1H), 9.02 (d, J=2.1 Hz, 1H), 8.55 (d, J=2.1 Hz, 1H), 8.36 (s, 1H), 8.14 (d, J=9.5 Hz, 1H), 7.57 (d, J=9.2 Hz, 1H), 7.46 (br s, 1H), 7.35 (d, J=8.4 Hz, 1H), 7.32-7.14 (m, 1H), 4.59 (br d, J=5.5 Hz, 2H), 2.14 (s, 3H).

Example 322: 6-chloro-5-{2-acetamidoimidazo[1,2-b]pyridazin-6-yl}-N-{[5-fluoro-2-(trifluoromethoxy)phenyl]methyl}pyridine-3-carboxamide

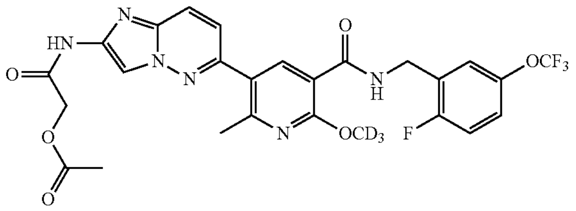

Compound 322 was prepared as in Example 15.

MS ESI m/z 594.3 (M+H)

1H NMR (500 MHz, DMSO-d6) δ 11.17 (s, 1H), 8.93 (br t, J=6.0 Hz, 1H), 8.30 (s, 1H), 8.21 (s, 1H), 8.09 (br d, J=9.3 Hz, 1H), 7.46 (br d, J=9.3 Hz, 1H), 7.42-7.33 (m, 3H), 4.75 (s, 2H), 4.58 (br d, J=5.7 Hz, 2H), 2.61-2.55 (m, 3H), 2.14 (s, 3H).

Example 323: N-{[2-(3,3-difluoropyrrolidine-1-carbonyl)-5-fluorophenyl]methyl}-5-{2-acetamidoimidazo[1,2-b]pyridazin-6-yl}-2-methoxypyridine-3-carboxamide

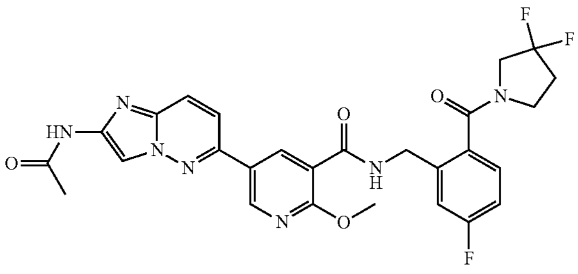 [SMILES: COc1ncc(-c2ccc3nc(NC(C)=O)cn3n2)cc1C(=O)NCc1cc(F)ccc1C(=O)N1CCC(F)(F)C1]

323A: A mixture of 2-bromo-1-fluorobenzonitrile (750 mg, 3.75 mmol), 3,3-difluoropyrrolidine, HCl (673 mg, 4.69 mmol), $Pd(OAc)_2$ (21.05 mg, 0.094 mmol), bis(2-diphenylphosphinophenyl)ether [DPEPhos] (202 mg, 0.375 mmol), and cesium hydroxide monohydrate (7241 mg, 43.1 mmol) in toluene (10 mL) was degassed by bubbling nitrogen through the mixture for 5 min. Chloroform (0.907 mL, 11.25 mmol) was then added and the vial sealed tightly and stirred at 80° C. ON. The reaction mixture was cooled to rt then filtered through Celite. The concentrated filtrate was purified using a 40 g ISCO column, eluting with 0-70% EtOAc in hexanes to afford 2-(3,3-difluoropyrrolidine-1-carbonyl)-5-fluorobenzonitrile (422 mg, 1.643 mmol, 43.8% yield) as a yellow oil which became a crystalline solid upon sitting.

MS ESI m/z 255.0 (M+H)

323B: A mixture of 2-(3,3-difluoropyrrolidine-1-carbonyl)-5-fluorobenzonitrile (322 mg, 1.267 mmol) and Raney nickel (54.3 mg, 0.633 mmol) in EtOH (2 mL) was degassed by vacuum and then stirred under a hydrogen balloon ON. The reaction mixture was filtered into a flask containing 2.5 mL [10 mM] of 4N HCl in dioxane, then stirred 10 min. The mixture was concentrated to afford (2-(aminomethyl)-4-fluorophenyl)(3,3-difluoropyrrolidin-1-yl)methanone, HCl (300 mg, 1.046 mmol, 83% yield) which was used as-is in the next step.

MS ESI m/z 259.0 (M+H)

323: (2-(Aminomethyl)-4-fluorophenyl)(3,3-difluoropyrrolidin-1-yl)methanone was coupled as described in Example 14 to afford N-{[2-(3,3-difluoropyrrolidine-1-carbonyl)-5-fluorophenyl]methyl}-5-{2-acetamidoimidazo[1,2-b]pyridazin-6-yl}-2-methoxypyridine-3-carboxamide (14.9 mg, 0.263 mmol, 57% yield).

MS ESI m/z 568.1 (M+H)

1H NMR (500 MHz, DMSO-d6) δ 10.77 (br s, 1H), 8.95 (br d, J=2.3 Hz, 1H), 8.89 (br s, 1H), 8.73 (d, J=2.4 Hz, 1H), 8.30 (s, 1H), 8.03 (br d, J=9.4 Hz, 1H), 7.79 (br d, J=9.4 Hz, 1H), 7.43 (br s, 1H), 7.30 (br d, J=9.8 Hz, 1H), 7.24-7.10 (m, 1H), 4.53 (br d, J=5.1 Hz, 2H), 4.10 (s, 3H), 4.03-3.57 (m, 3H), 2.50-2.32 (m, 3H), 2.12 (s, 3H).

Example 324: N-{[2-(3,3-difluoropyrrolidine-1-carbonyl)-3,5-difluorophenyl]methyl}-5-{2-acetamidoimidazo[1,2-b]pyridazin-6-yl}-2-methoxypyridine-3-carboxamide

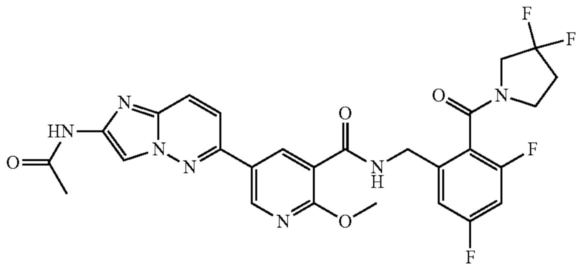 [SMILES: COc1ncc(-c2ccc3nc(NC(C)=O)cn3n2)cc1C(=O)NCc1cc(F)cc(F)c1C(=O)N1CCC(F)(F)C1]

Compound 324 was prepared as in Example 323.

MS ESI m/z 586.3 (M+H)

1H NMR (500 MHz, DMSO-d6) δ 10.76 (br s, 1H), 8.97 (s, 1H), 8.91 (dt, J=11.1, 5.8 Hz, 1H), 8.73 (s, 1H), 8.30 (s, 1H), 8.04 (br d, J=9.4 Hz, 1H), 7.79 (br d, J=9.4 Hz, 1H), 7.30-7.16 (m, 2H), 4.70-4.33 (m, 2H), 4.11 (s, 3H), 4.06-3.38 (m, 4H), 2.47 (m, 2H), 2.12 (s, 3H).

Example 325: 5-{2-acetamidoimidazo[1,2-b]pyridazin-6-yl}-N-{[2-fluoro-6-(2,2,2-trifluoroethoxy)phenyl]methyl}-2,6-dimethylpyridine-3-carboxamide

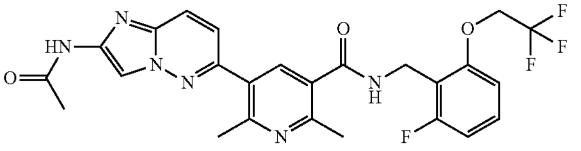 [SMILES: CC(=O)Nc1cn2nc(-c3cc(C(=O)NCc4c(F)cccc4OCC(F)(F)F)c(C)nc3C)ccc2n1]

Compound 325 was prepared as in Example 14.

MS ESI m/z 531.2 (M+H)

1H NMR (500 MHz, DMSO-d6) δ 10.94 (s, 1H), 8.66 (br t, J=4.5 Hz, 1H), 8.36-8.19 (m, 1H), 8.10-8.01 (m, 1H), 7.74 (s, 1H), 7.47-7.27 (m, 2H), 6.99 (d, J=8.3 Hz, 1H), 6.92 (t, J=8.4 Hz, 1H), 4.78 (q, J=8.6 Hz, 2H), 4.54-4.43 (m, 2H), 2.60-2.53 (m, 6H), 2.11 (s, 3H).

Example 326: N-{[5-(cyclopropylmethoxy)-2-fluorophenyl]methyl}-5-{2-acetamidoimidazo[1,2-b]pyridazin-6-yl}-2,6-dimethylpyridine-3-carboxamide

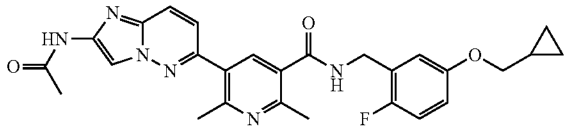 [SMILES: CC(=O)Nc1cn2nc(-c3cc(C(=O)NCc4cc(OCC5CC5)ccc4F)c(C)nc3C)ccc2n1]

Compound 326 was prepared as in Example 14.

MS ESI m/z 503.0 (M+H)

1H NMR (500 MHz, DMSO-d6) δ 10.79 (br s, 1H), 8.90 (br t, J=5.6 Hz, 1H), 8.29 (s, 1H), 8.05 (d, J=9.3 Hz, 1H), 7.88 (s, 1H), 7.43 (d, J=9.3 Hz, 1H), 7.13-7.03 (m, 1H), 6.98-6.92 (m, 1H), 6.90-6.77 (m, 1H), 4.48 (br d, J=5.6 Hz, 2H), 3.77 (d, J=6.8 Hz, 2H), 2.59 (s, 3H), 2.57 (s, 3H), 2.12 (s, 3H), 1.22-1.12 (m, 1H), 0.59-0.45 (m, 2H), 0.31-0.22 (m, 2H).

Example 327: ({6-[5-({[2-fluoro-5-(trifluoromethoxy)phenyl]methyl}carbamoyl)-2,6-dimethylpyridin-3-yl]imidazo[1,2-b]pyridazin-2-yl}carbamoyl)methyl acetate

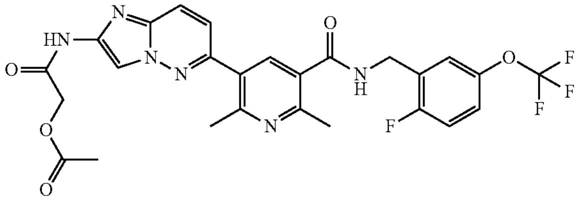 [SMILES: CC(=O)OCC(=O)Nc1cn2nc(-c3cc(C(=O)NCc4cc(OC(F)(F)F)ccc4F)c(C)nc3C)ccc2n1]

Compound 327 was prepared as in Example 15.

MS ESI m/z 575.2 (M+H)

1H NMR (500 MHz, DMSO-d6) δ 11.02 (s, 1H), 9.00 (br t, J=5.6 Hz, 1H), 8.30 (s, 1H), 8.08 (d, J=9.3 Hz, 1H), 7.88 (s, 1H), 7.47-7.30 (m, 4H), 4.75 (s, 2H), 4.53 (d, J=5.7 Hz, 2H), 2.59-2.55 (m, 6H), 2.13 (s, 3H).

Example 328: 5-{2-acetamidoimidazo[1,2-b]pyridazin-6-yl}-2-ethyl-N-[(1R)-1-[2-fluoro-5-(trifluoromethoxy)phenyl] ethyl]pyridine-3-carboxamide

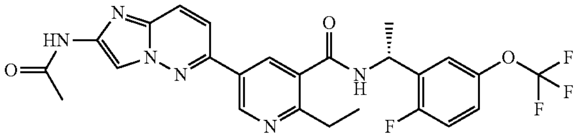 [SMILES: CCc1ncc(-c2ccc3nc(NC(C)=O)cn3n2)cc1C(=O)N[C@H](C)c1cc(OC(F)(F)F)ccc1F]

Compound 328 was prepared as in Example 14.

MS ESI m/z 531.2 (M+H)

1H NMR (500 MHz, DMSO-d6) δ 10.81 (br s, 1H), 9.21 (s, 1H), 9.11 (br d, J=7.6 Hz, 1H), 8.33 (br d, J=13.5 Hz, 2H), 8.10 (br d, J=9.3 Hz, 1H), 7.86 (br d, J=9.5 Hz, 1H), 7.49 (br s, 1H), 7.36 (br d, J=9.1 Hz, 2H), 5.53-5.33 (m, 1H), 3.30 (s, 2H), 2.19-2.01 (m, 3H), 1.60-1.42 (m, 3H), 1.24-1.14 (m, 3H).

Example 329: 5-{2-acetamidoimidazo[1,2-b]pyridazin-6-yl}-2-ethyl-N-{[2-fluoro-5-(trifluoromethyl)phenyl]methyl}pyridine-3-carboxamide

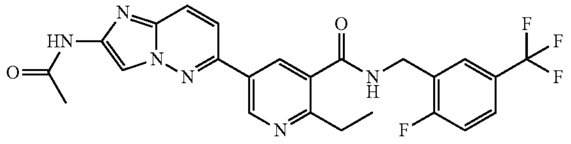 [SMILES: CCc1ncc(-c2ccc3nc(NC(C)=O)cn3n2)cc1C(=O)NCc1cc(C(F)(F)F)ccc1F]

Compound 329 was prepared as in Example 14.

MS ESI m/z 501.2 (M+H)

1H NMR (500 MHz, DMSO-d6) δ 10.96 (s, 1H), 9.35-9.25 (m, 1H), 9.21 (s, 1H), 8.44-8.25 (m, 2H), 8.11 (br d, J=9.4 Hz, 1H), 7.94-7.79 (m, 2H), 7.77 (br s, 1H), 7.49 (br t, J=9.1 Hz, 1H), 4.61 (br d, J=5.6 Hz, 2H), 2.89 (q, J=7.6 Hz, 2H), 2.12 (s, 3H), 1.26-1.14 (m, 3H).

Example 330: 5-{2-acetamidoimidazo[1,2-b]pyridazin-6-yl}-N-[(1R)-1-[2-fluoro-5-(trifluoromethoxy)phenyl]ethyl]-N,2-dimethylpyridine-3-carboxamide

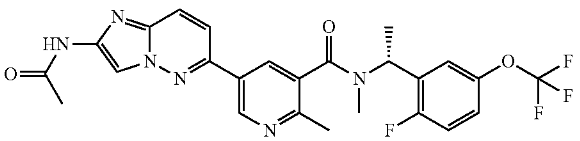 [SMILES: CC(=O)Nc1cn2nc(-c3cnc(C)c(C(=O)N(C)[C@H](C)c4cc(OC(F)(F)F)ccc4F)c3)ccc2n1]

Compound 330 was prepared as in Example 14.

MS ESI m/z 531.1 (M+H)

1H NMR (500 MHz, DMSO-d6) δ 10.79 (br s, 1H), 9.15 (br s, 1H), 8.32 (br s, 1H), 8.29-8.16 (m, 1H), 8.06 (br d, J=9.5 Hz, 1H), 7.90-7.80 (m, 1H), 7.61-7.47 (m, 1H), 7.45-7.28 (m, 2H), 6.19-5.84 (m, 1H), 2.66-2.55 (m, 3H), 2.48-2.40 (m, 3H), 2.12 (s, 3H), 1.63 (br d, J=6.0 Hz, 3H).

TABLE 17

Compounds in Table 17 were prepared by methods as described in Examples 14 and 15.

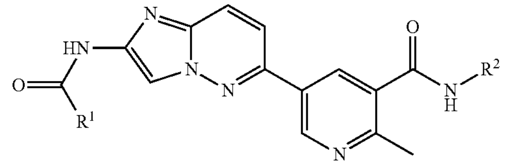

| Ex | Name | $R^1$ | $R^2$ | Obs. MS Ion | NMR Assignments |
|---|---|---|---|---|---|
| 331 | N-[(1R)-1-[2-fluoro-5-(trifluoromethyl)-phenyl]ethyl]-2-methyl-5-(2-{2-[4-(trifluoromethyl)piperidin-1-yl]acetamido}imidazo[1,2-b]pyridazin-6-yl)pyridine-3-carboxamide | 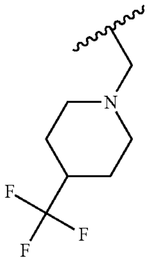 [SMILES: *CN1CCC(C(F)(F)F)CC1] | 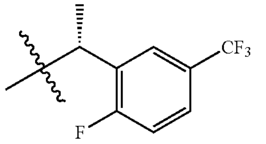 | 552.2 | 1H NMR (500 MHz, DMSO-d6) δ 10.57 (br s, 1H), 9.23 (br d, J = 7.4 Hz, 1H), 9.19 (s, 1H), 8.37 (br d, J = 7.2 Hz, 2H), 8.14 (d, J = 9.6 Hz, 1H), 7.94-7.86 (m, 2H), 7.74 (br d, J = 3.3 Hz, 1H), 7.48 (br t, J = 9.4 Hz, 1H), 5.42 (br t, J = 7.3 Hz, 1H), 3.26 (br s, 2H), 2.97 (br d, J = 10.7 Hz, 2H), 2.51 (br s, 3H), 2.35-2.14 (m, 3H), 1.79 (br d, J = 11.6 Hz, 2H), 1.64-1.53 (m, 2H), 1.51 (br d, J = 6.9 Hz, 3H). |
| 332 | N-[(1R)-1-[2-fluoro-5-(trifluoromethyl)-phenyl]ethyl]-2-methyl-5-{2-[2-(4-methylpiperazin-1-yl)acetamido]imidazo[1,2-b]pyridazin-6-yl}pyridine-3-carboxamide | 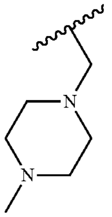 [SMILES: *CN1CCN(C)CC1] | 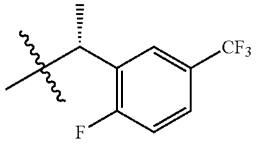 | 599.2 | 1H NMR (500 MHz, DMSO-d6) δ 10.67 (s, 1H), 9.18 (d, J = 2.3 Hz, 1H), 9.13 (d, J = 7.6 Hz, 1H), 8.38 (s, 1H), 8.34 (d, J = 2.2 Hz, 1H), 8.12 (d, J = 9.4 Hz, 1H), 7.92-7.87 (m, 2H), 7.76-7.70 (m, 1H), 7.47 (t, J = 9.3 Hz, 1H), 5.45 (t, J = 7.3 Hz, 1H), 3.43 (br s, 6H), 2.81 (s, 3H), 2.58-2.52 (m, 7H), 1.53 (d, J = 7.1 Hz, 3H). |
| 333 | N-[(1R)-1-[2-fluoro-5-(trifluoromethyl)-phenyl]ethyl]-2-methyl-5-{2-[2-(pynolidin-1-yl)acetamido]imidazo[1,2-b]pyridazin-6-yl}pyridine-3-carboxamide | 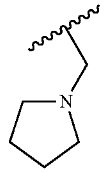 [SMILES: *CN1CCCC1] | 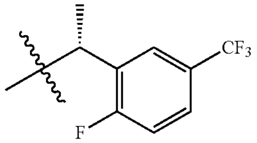 [SMILES: *[C@H](C)c1cc(C(F)(F)F)ccc1F] | 570.1 | 1H NMR (500 MHz, DMSO-d6) δ 10.43 (s, 1H), 9.23 (br d, J = 7.7 Hz, 1H), 9.19 (d, J = 1.9 Hz, 1H), 8.39-8.35 (m, 2H), 8.14 (d, J = 9.4 Hz, 1H), 7.95-7.87 (m, 2H), 7.74 (br d, J = 3.3 Hz, 1H), 7.48 (t, J = 9.1 Hz, 1H), 5.42 (br d, J = 7.2 Hz, 1H), 3.39 (br s, 2H), 2.65 (br s, 4H), 2.51 (s, 3H), 1.75 (br s, 4H), 1.51 (d, J = 7.2 Hz, 3H). |
| 334 | 5-{2-[2-(4,4-difluoropiperidin-1-yl)acetamido]-imidazo[1,2-b]pyridazin-6-yl}-N-[(1R)-1-[2-fluoro-5-(trifluoromethoxy)-phenyl]ethyl]-2-methylpyridine-3-carboxamide | 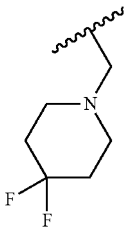 [SMILES: *CN1CCC(F)(F)CC1] | 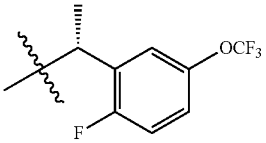 | 636.1 | 1H NMR (500 MHz, DMSO-d6) δ 10.67 (s, 1H), 9.19 (br s, 2H), 8.37 (br d, J = 13.2 Hz, 2H), 8.26-8.03 (m, 1H), 7.98-7.77 (m, 1H), 7.49 (br s, 1H), 7.42-7.33 (m, 2H), 5.38 (br t, J = 7.3 Hz, 1H), 2.69 (br s, 4H), 2.52 (s, 3H), 2.13-1.91 (m, 4H), 1.49 (br d, J = 6.9 Hz, 3H). |
| 335 | 5-{2-[2-(3,3-difluoroazetidin-1-yl)acetamido]-imidazo[1,2-b]pyridazin-6-yl}-N-[(1R)-1-[2-fluoro-5-(trifluoromethoxy)-phenyl]ethyl]-2-methylpyridine-3-carboxamide | 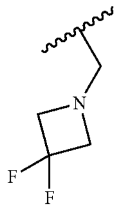 | 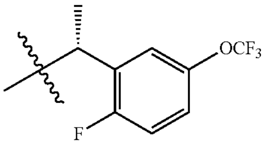 [SMILES: *[C@H](C)c1cc(OC(F)(F)F)ccc1F] | 608.45 | 1H NMR (500 MHz, DMSO-d6) δ 10.82 (s, 1H), 9.18 (s, 2H), 8.35 (s, 2H), 8.14 (d, J = 9.4 Hz, 1H), 7.90 (d, J = 9.4 Hz, 1H), 7.48 (br s, 1H), 7.43-7.31 (m, 2H), 5.38 (br t, J = 7.2 Hz, 1H), 3.79 (br t, J = 12.4 Hz, 4H), 3.52 (s, 2H), 2.52 (br s, 3H), 1.48 (br d, J = 7.2 Hz, 3H). |

TABLE 17-continued

Compounds in Table 17 were prepared by methods as described in Examples 14 and 15.

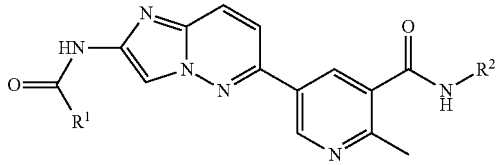

| Ex | Name | $R^1$ | $R^2$ | Obs. MS Ion | NMR Assignments |
| --- | --- | --- | --- | --- | --- |
| 336 | N-[(1R)-1-[2-fluoro-5-(trifluoromethoxy)-phenyl]ethyl]-2-methyl-5-{2-[2-(4-methylpiperazin-1-yl)acetamido]imidazo[1,2-b]pyridazin-6-yl}pyridine-3-carboxamide | 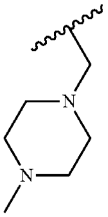 [SMILES: *CN1CCN(C)CC1] | 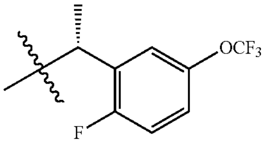 [SMILES: *[C@H](C)c1cc(OC(F)(F)F)ccc1F] | 615.4 | 1H NMR (500 MHz, DMSO-d6) δ 10.59-10.27 (m, 1H), 9.20 (br d, J = 1.1 Hz, 1H), 9.17 (br s, 1H), 8.35 (br d, J = 11.3 Hz, 2H), 8.12 (br d, J = 9.1 Hz, 1H), 7.90 (br d, J = 9.4 Hz, 1H), 7.47 (br s, 1H), 7.41-7.31 (m, 2H), 5.51-5.22 (m, 1H), 3.21 (s, 2H), 2.54 (br s, 4H), 2.43-2.28 (m, 4H), 2.16 (s, 3H), 1.48 (br d, J = 7.2 Hz, 3H). |
| 337 | N-[(1R)-1-[2-fluoro-5-(trifluoromethoxy)-phenyl]ethyl]-2-methyl-5-{2-[2-(morpholin-4-yl)acetamido]imidazo[1,2-b]pyridazin-6-yl}pyridine-3-carboxamide | 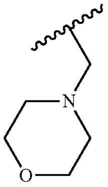 [SMILES: *CN1CCOCC1] | 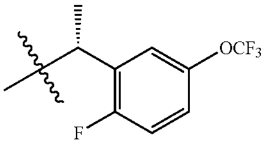 [SMILES: *[C@H](C)c1cc(OC(F)(F)F)ccc1F] | 602.0 | 1H NMR (500 MHz. DMSO-d6) δ 10.58 (s, 1H), 9.35-9.01 (m, 2H), 8.37 (s, 1H), 8.34 (d, J = 1.9 Hz, 1H), 8.13 (d, J = 9.4 Hz, 1H), 7.90 (d, J = 9.4 Hz, 1H), 7.48 (br d, J = 3.3 Hz, 1H), 7.41-7.32 (m, 2H), 5.37 (s, 1H), 3.68-3.57 (m, 4H), 3.24 (s, 2H), 2.54 (s, 3H), 2.51 (br s, 4H), 1.48 (d, J = 7.2 Hz, 3H). |
| 338 | 5-{2-[2-(dimethylamino)-acetamido]-imidazo[1,2-b]pyridazin-6-yl}-N-[(1R)-1-[2-fluoro-5-(trifluoromethoxy)-phenyl]ethyl]-2-methylpyridine-3-carboxamide | 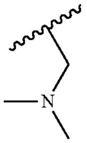 | 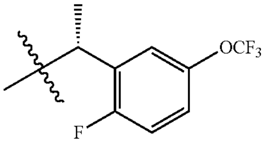 | 560.1 | 1H NMR (500 MHz, DMSO-d6) δ 9.24-9.15 (m, 2H), 8.39-8.33 (m, 2H), 8.13 (d, J = 9.5 Hz, 1H), 7.91 (d, J = 9.5 Hz, 1H), 7.51-7.45 (m, 1H), 7.41-7.33 (m, 2H), 5.38 (quin, J = 7.0 Hz, 1H), 3.23 (s, 1H), 2.99 (s, 1H), 2.56-2.52 (m, 3H), 2.33 (s, 6H), 1.49 (br d, J = 7.0 Hz, 4H). |
| 339 | N-((R)-1-(2-fluoro-5-(trifluoromethoxy)-phenyl)ethyl)-5-(2-((S)-2-hydroxypropanamido)-imidazo[1,2-b]pyridazin-6-yl)-2-methylnicotinamide | 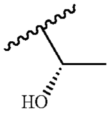 | 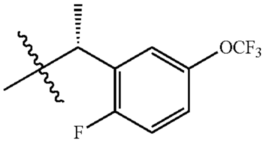 | 547.5 | $^1$H NMR (400 MHz, DMSO-d6) δ 10.30 (s, 1H), 9.23-9.18 (m, 2H), 8.40 (s, 1H), 8.37 (s, 1H), 8.17 (d, J = 9.5 Hz, 1H), 7.93 (d, J = 9.5 Hz, 1H), 7.50 (br d, J = 4.3 Hz, 1H), 7.43-7.35 (m, 2H), 5.68 (br d, J = 5.2 Hz, 1H), 5.38 (quin, J = 7.1 Hz, 1H), 4.33-4.25 (m, 1H), 2.53 (s, 3H), 1.49 (d, J = 7.1 Hz, 3H), 1.33 (d, J = 6.7 Hz, 3H). |
| 340 | N-[(1R)-1-[2-fluoro-5-(trifluoromethoxy)-phenyl]ethyl]-2-methyl-5-{2-[2-(methylamino)-acetamido]imidazo[1,2-b]pyridazin-6-yl}pyridine-3-carboxamide | 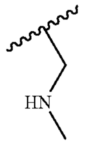 | 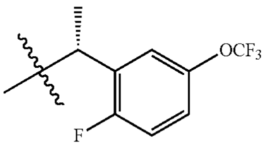 | 546.3 | 1H NMR (500 MHz, DMSO-d6) δ 9.24 (br d, J = 7.3 Hz, 1H), 9.20-9.14 (m, 1H), 8.38 (s, 1H), 8.36-8.31 (m, 1H), 8.12 (br d, J = 9.2 Hz, 1H), 7.89 (br d, J = 9.5 Hz, 1H), 7.47 (br s, 1H), 7.43-7.30 (m, 2H), 5.36 (br t, J = 7.0 Hz, 1H), 3.61 (br s, 1H), 3.39 (s, 2H), 2.34 (s, 3H), 1.89 (s, 3H), 1.48 (br d, J = 6.7 Hz, 3H), 1 exchangeable proton not observed. |
| 341 | 5-[2-(2-aminoacetamido)-imidazo[1,2-b]pyridazin-6-yl]-N-[(1R)-1-[2-fluoro-5-(trifluoromethoxy)-phenyl]ethyl]-2-methylpyridine-3-carboxamide | 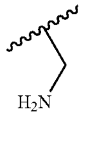 | 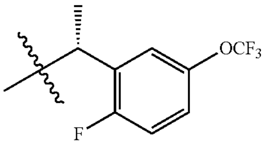 [SMILES: *[C@H](C)c1cc(OC(F)(F)F)ccc1F] | 532.2 | 1H NMR (500 MHz, DMSO-d6) δ 9.17 (s, 1H), 9.14-9.01 (m, 1H), 8.42-8.36 (m, 1H), 8.33 (s, 1H), 8.14 (d, J = 9.4 Hz, 1H), 7.90 (d, J = 9.5 Hz, 1H), 7.49 (br s, 1H), 7.43-7.27 (m, 2H), 5.40 (quin, J = 7.1 Hz, 1H), 3.76 (br s, 2H), 2.55 (s, 3H), 2.54 (br s, 2H), 1.51 (d, J = 7.1 Hz, 3H). |

TABLE 17-continued

Compounds in Table 17 were prepared by methods as described in Examples 14 and 15.

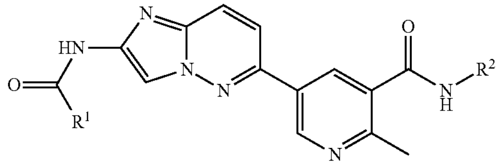

| Ex | Name | $R^1$ | $R^2$ | Obs. MS Ion | NMR Assignments |
|---|---|---|---|---|---|
| 342 | {[6-(5-{[(1R)-1-[2-fluoro-5-(trifluoromethoxy)-phenyl]ethyl]-carbamoyl}-6-methylpyridin-3-yl)imidazo[1,2-b]pyridazin-2-yl]carbamoyl}-methyl acetate | 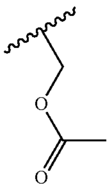 [SMILES: *COC(C)=O] | 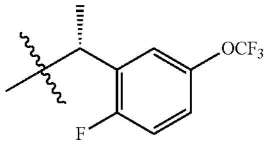 [SMILES: *[C@H](C)c1cc(OC(F)(F)F)ccc1F] | 575.2 | 1H NMR (500 MHz, DMSO-d6) δ 11.18 (s, 1H), 9.29-9.11 (m, 2H), 8.35 (br d, J = 3.1 Hz, 2H), 8.16 (d, J = 9.5 Hz, 1H), 7.92 (d, J = 9.5 Hz, 1H), 7.49 (br s, 1H), 7.45-7.30 (m, 2H), 5.38 (br t, J = 7.2 Hz, 1H), 4.76 (s, 2H), 2.56-2.53 (m, 3H), 2.15 (s, 3H), 1.50 (d, J = 7.0 Hz, 3H). |
| 343 | N-[(3R)-3-(4-chlorophenyl)-3-hydroxypropyl]-5-{2-[2-(4,4-difluoropiperidin-1-yl)acetamido]imidazo[1,2-b]pyridazin-6-yl}-2-methylpyridine-3-carboxamide | 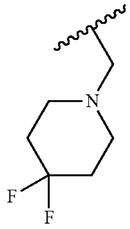 [SMILES: *CN1CCC(F)(F)CC1] | 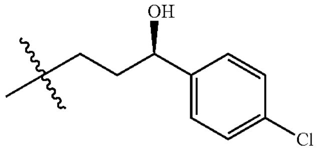 [SMILES: *CC[C@@H](O)c1ccc(Cl)cc1] | 598.3 | 1H NMR (500 MHz, DMSO-d6) δ 10.64 (br s, 1H), 9.13 (s, 1H), 8.63-8.52 (m, 1H), 8.38 (s, 1H), 8.26 (s, 1H), 8.10 (d, J = 9.1 Hz, 1H), 7.87 (d, J = 9.4 Hz, 1H), 7.38 (s, 4H), 5.47 (d, J = 4.7 Hz, 1H), 4.67 (br d, J = 5.0 Hz, 1H), 3.33 (s, 4H), 2.68 (br s, 4H), 2.58 (s, 3H), 2.01 (ddd, J = 18.8, 13.6, 5.2 Hz, 4H), 1.91-1.80 (m, 2H). |
| 344 | N-[(3R)-3-(4-chlorophenyl)-3-hydroxypropyl]-5-{2-[2-(3,3-difluoroazetidin-1-yl)acetamido]imidazo[1,2-b]pyridazin-6-yl}-2-methylpyridine-3-carboxamide | 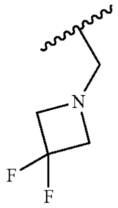 | 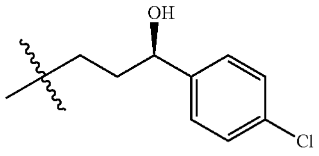 [SMILES: *CC[C@@H](O)c1ccc(Cl)cc1] | 570.2 | 1H NMR (500 MHz, DMSO-d6) δ 10.82 (s, 1H), 9.14 (s, 1H), 8.56 (br t, J = 5.2 Hz, 1H), 8.35 (s, 1H), 8.28 (s, 1H), 8.12 (d, J = 9.4 Hz, 1H), 7.88 (d, J = 9.4 Hz, 1H), 7.39 (s, 4H), 5.43 (d, J = 4.1 Hz, 1H), 4.88-4.50 (m, 1H), 3.78 (br t, J = 12.5 Hz, 4H), 3.52 (s, 2H), 2.59 (s, 3H), 1.87 (q, J = 6.9 Hz, 2H). |
| 345 | N-[(3R)-3-(4-chlorophenyl)-3-hydroxypropyl]-2-methyl-5-{2-[2-(morpholin-4-yl)acetamido]imidazo[1,2-b]pyridazin-6-yl}pyridine-3-carboxamide | 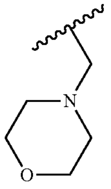 [SMILES: *CN1CCOCC1] | 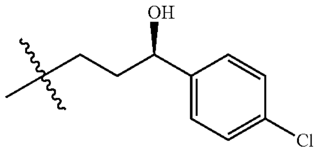 [SMILES: *CC[C@@H](O)c1ccc(Cl)cc1] | 564.0 | 1H NMR (500 MHz, DMSO-d6) δ 10.74-10.16 (m, 1H), 9.12 (d, J = 1.9 Hz, 1H), 8.45 (br t, J = 5.3 Hz, 1H), 8.36 (s, 1H), 8.25 (s, 1H), 8.08 (d, J = 9.5 Hz, 1H), 7.84 (d, J = 9.4 Hz, 1H), 7.42-7.34 (m, 4H), 5.35 (br s, 1H), 4.68 (br t, J = 6.3 Hz, 1H), 3.66-3.61 (m, 4H), 3.24 (s, 2H), 2.59 (s, 3H), 2.55 (br d, J = 4.7 Hz, 4H), 1.95-1.81 (m, 4H). |
| 346 | N-[(3S)-3-(4-chlorophenyl)-3-hydroxypropyl]-2-methyl-5-{2-[2-(morpholin-4-yl)acetamido]imidazo[1,2-b]pyridazin-6-yl}pyridine-3-carboxamide | 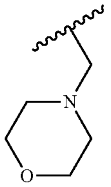 [SMILES: *CN1CCOCC1] | 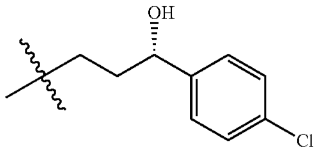 [SMILES: *CC[C@H](O)c1ccc(Cl)cc1] | 564.3 | 1H NMR (500 MHz, DMSO-d6) δ 10.74-10.16 (m, 1H), 9.13 (s, 1H), 8.45 (br t, J = 5.4 Hz, 1H), 8.37 (s, 1H), 8.26 (s, 1H), 8.09 (d, J = 9.4 Hz, 1H), 7.85 (d, J = 10.0 Hz, 1H), 7.44-7.32 (m, 4H), 5.34 (br s, 1H), 4.69 (br t, J = 6.1 Hz, 1H), 3.67-3.62 (m, 4H), 2.59 (s, 3H), 2.56 (br d, J = 4.4 Hz, 4H), 1.95-1.83 (m, 3H). |
| 347 | N-[(3S)-3-(4-chlorophenyl)-3-hydroxypropyl]-5-{2-[2-(dimethylamino)-acetamido]-imidazo[1,2-b]pyridazin-6-yl}-2-methylpyridine-3-carboxamide | 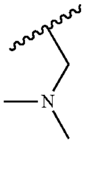 | 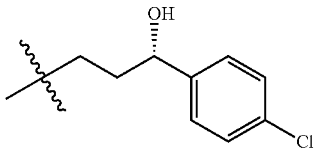 [SMILES: *CC[C@H](O)c1ccc(Cl)cc1] | 522.2 | 1H NMR (500 MHz, DMSO-d6) δ 9.16 (d, J = 2.1 Hz, 1H), 8.58 (br t, J = 5.2 Hz, 1H), 8.38 (s, 1H), 8.29 (d, J = 1.8 Hz, 1H), 8.13 (d, J = 9.5 Hz, 1H), 7.89 (d, J = 9.5 Hz, 1H), 7.40 (s, 5H), 4.69 (br t, J = 6.4 Hz, 1H), 3.90 (s, 2H), 3.20-3.17 (m, 2H), 2.60 (s, 3H), 2.31 (s, 6H), 1.93-1.85 (m, 3H). |

Example 348: 5-{2-acetamidoimidazo[1,2-b]pyridazin-6-yl}-N-{1-[1-(4-fluorophenyl)ethyl]-1H-pyrazol-4-yl}-2-methylpyridine-3-carboxamide

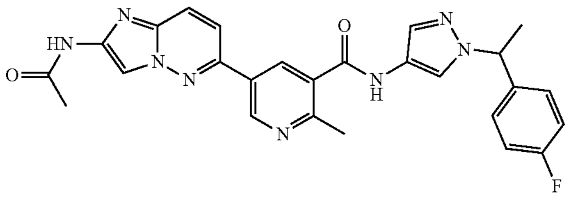 [SMILES: CC(=O)Nc1cn2nc(-c3cnc(C)c(C(=O)Nc4cnn(C(C)c5ccc(F)cc5)c4)c3)ccc2n1]

348A: To a solution of 4-nitro-1H-pyrazole (500 mg, 4.42 mmol) in DMF (10 mL) was added 1.0 M NaHMDS/THF (4.86 mL, 4.86 mmol) dropwise at rt. After stirring at rt for 20 min, 1-(1-bromoethyl)-4-fluorobenzene (1077 mg, 5.31 mmol) was added very slowly. The mixture was stirred at rt for 3 h. EtOAc was added and the organics washed with water. The organics were collected, dried over sodium sulfate and concentrated under vacuum. The residue was purified via silica gel chromatography (24 g, hexanes-50% EtOAc) to give 1-(1-(4-fluorophenyl)ethyl)-4-nitro-1H-pyrazole (980 mg, 4.17 mmol, 94% yield).

$^1$H NMR (499 MHz, $CDCl_3$) δ 8.12 (s, 1H), 8.09 (s, 1H), 7.33-7.27 (m, 2H), 7.14-7.08 (m, 2H), 5.53 (q, J=7.1 Hz, 1H), 1.95 (d, J=7.0 Hz, 3H).

348B: To 10% Pd—C (250 mg, 0.235 mmol) was added a solution of 1-(1-(4-fluorophenyl)ethyl)-4-nitro-1H-pyrazole (980 mg, 4.17 mmol) in MeOH (20 mL) at rt under $N_2$. The mixture was stirred under a $H_2$ balloon at rt for 3 h. The crude reaction mixture was filtered through Celite. The filtrate was concentrated to dryness to give 1-(1-(4-fluorophenyl)ethyl)-1H-pyrazol-4-amine (800 mg, 3.90 mmol, 94% yield).

MS ESI m/z 206.1 (M+H)

348: 1-(1-(4-fluorophenyl)ethyl)-1H-pyrazol-4-amine (24.5 mg, 0.119 mmol) was coupled with 5-(2-acetamidoimidazo[1,2-b]pyridazin-6-yl)-2-methylnicotinic acid (31.0 mg, 0.100 mmol) as described in Example 14 to afford 5-(2-acetamidoimidazo[1,2-b]pyridazin-6-yl)-N-(1-(1-(4-fluorophenyl)ethyl)-1H-pyrazol-4-yl)-2-methylnicotinamide (35.2 mg, 0.070 mmol, 70% yield)

MS ESI m/z 499.1 (M+H)

1H NMR (500 MHz, DMSO-d6) δ 10.94 (s, 1H), 10.69 (s, 1H), 9.20 (s, 1H), 8.46 (s, 1H), 8.33 (s, 1H), 8.15-8.09 (m, 2H), 7.89 (br d, J=9.2 Hz, 1H), 7.60 (s, 1H), 7.38-7.28 (m, 2H), 7.18 (br t, J=8.7 Hz, 2H), 5.65 (q, J=6.7 Hz, 1H), 2.63 (s, 3H), 2.11 (s, 3H), 1.80 (br d, J=7.0 Hz, 3H).

TABLE 18

Compounds in Table 18 were prepared by methods as described in Examples 348.

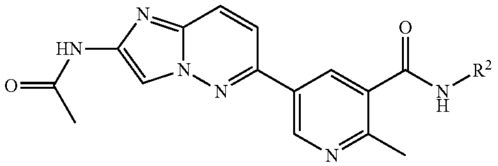

| Ex | Name | $R^2$ | Obs. MS Ion | NMR Assignments |
|---|---|---|---|---|
| 349 | N-{1-[(4-chlorophenyl)methyl]-1H-imidazol-4-yl}-5-{2-acetamidoimidazo[1,2-b]pyridazin-6-yl}-2-methylpyridine-3-carboxamide | 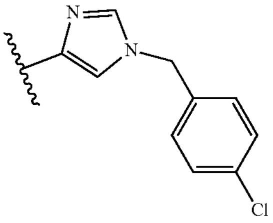 [SMILES: *c1cn(Cc2ccc(Cl)cc2)cn1] | 501.1 | 1H NMR (500 MHz, DMSO-d6) δ 11.21 (s, 1H), 10.94 (s, 1H), 9.17 (d, J = 2.1 Hz, 1H), 8.46 (d, J = 1.8 Hz, 1H), 8.31 (s, 1H), 8.08 (d, J = 9.5 Hz, 1H), 8.04 (s, 1H), 7.87 (d, J = 9.5 Hz, 1H), 7.49 (s, 1H), 7.44 (dd, J = 8.4, 5.6 Hz, 2H), 7.30-7.13 (m, 2H), 5.24 (s, 2H), 2.62 (s, 3H), 2.11 (s, 3H). |
| 350 | 5-{2-acetamidoimidazo[1,2-b]pyridazin-6-yl}-N-{1-[(4-fluorophenyl)methyl]-1H-imidazol-4-yl}-2-methylpyridine-3-carboxamide | 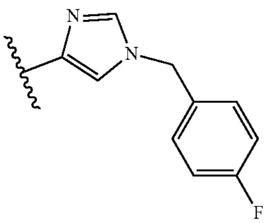 [SMILES: *c1cn(Cc2ccc(F)cc2)cn1] | 485.0 | 1H NMR (500 MHz, DMSO-d6) δ 11.21 (s, 1H), 10.94 (s, 1H), 9.17 (d, J = 2.1 Hz, 1H), 8.46 (d, J = 1.8 Hz, 1H), 8.31 (s, 1H), 8.08 (d, J = 9.5 Hz, 1H), 8.04 (s, 1H), 7.87 (d, J = 9.5 Hz, 1H), 7.49 (s, 1H), 7.44 (dd, J = 8.4, 5.6 Hz, 2H), 7.30-7.13 (m, 2H), 5.24 (s, 2H), 2.62 (s, 3H), 2.11 (s, 3H). |
| 351 | N-(1-benzyl-1H-imidazol-4-yl)-5-{2-acetamidoimidazo[1,2-b]pyridazin-6-yl}-2-methylpyridine-3-carboxamide | 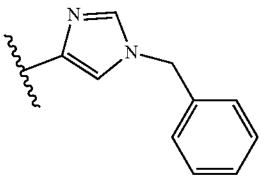 [SMILES: *c1cn(Cc2ccccc2)cn1] | 467.2 | 1H NMR (500 MHz, DMSO-d6) δ 9.16 (s, 1H), 8.43 (s, 1H), 8.33 (s, 1H), 8.11 (br d, J = 9.5 Hz, 1H), 7.90 (br d, J = 9.5 Hz, 1H), 7.68 (s, 1H), 7.44 (s, 1H), 7.42-7.36 (m, 2H), 7.36-7.25 (m, 5H), 5.21 (s, 2H), 2.61 (s, 3H), 2.11 (s, 3H). |

Example 352: 5-{2-acetamidoimidazo[1,2-b]pyridazin-6-yl}-N-{[2-fluoro-5-(1-methyl-1H-pyrazol-4-yl)phenyl]methyl}-2-methylpyridine-3-carboxamide

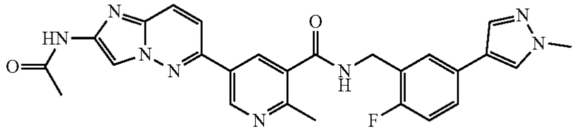

352A: To a mixture of (2-bromo-5-fluorophenyl)methanamine (1.00 g, 4.90 mmol) in THF (17 mL) was added N-(benzyloxycarbonyloxy)succinimide (1.832 g, 7.35 mmol) and TEA (1.708 mL, 12.25 mmol) and the resulting mixture was stirred at rt ON. The reaction mixture was partitioned between 90 mL EtOAc and 20 mL water. The EtOAc layer was washed with brine, dried over sodium sulfate, filtered and concentrated. The residue was purified using a 24 g ISCO column, eluting with 0-70% EtOAc in hexanes to afford benzyl (2-bromo-5-fluorobenzyl)carbamate (1.33 g, 3.74 mmol, 76% yield) as a colorless oil which became a crystalline white solid on the pump. The material was carried forward without further purification. MS?

352B: A mixture of 5-bromo-2-fluorobenzonitrile (370 mg, 1.850 mmol), 1-methyl-4-(4,4,5,5-tetramethyl-1,3,2-dioxaborolan-2-yl)-1H-pyrazole (577 mg, 2.77 mmol) and $PdCl_2(dppf)-CH_2Cl_2$ adduct (76 mg, 0.092 mmol) in 1,4-dioxane (7.5 mL) was degassed by bubbling nitrogen through the mixture and vial for 5 min. To this was added tripotassium phosphate, 2M aq. (2.77 mL, 5.55 mmol). The vial was sealed tightly, and the solution stirred at 100° C. for 20 min. The crude mixture was filtered through Celite and the filtrate concentrated. The residue was purified using a 12 g ISCO column, eluting with 0-70% EtOAc in hexanes to afford 2-fluoro-5-(1-methyl-1H-pyrazol-4-yl)benzonitrile (342 mg, 1.615 mmol, 87% yield).

MS ESI m/z 202.0 (M+H)

352C: A mixture of 2-fluoro-5-(1-methyl-1H-pyrazol-4-yl)benzonitrile (342 mg, 1.700 mmol) and Raney nickel (72.8 mg, 0.850 mmol) in EtOH (5 mL) was degassed by vacuum and then stirred under a hydrogen balloon ON. The crude reaction mixture was filtered through Celite into a flask containing 2.5 mL [10 mM] of 4N HCl in dioxane. This solution was stirred for 10 min, then concentrated to afford (2-fluoro-5-(1-methyl-1H-pyrazol-4-yl)phenyl)methanamine, HCl (425 mg, 1.583 mmol, 93% yield) as a white solid. The material was carried forward without further purification.

MS ESI m/z 206.1 (M+H)

352: 5-(2-acetamidoimidazo[1,2-b]pyridazin-6-yl)-2-methylnicotinic acid (15 mg, 0.048 mmol) was coupled with (2-fluoro-5-(1-methyl-1H-pyrazol-4-yl)phenyl)methanamine (9.89 mg, 0.048 mmol) as described in Example 14 to afford 5-(2-acetamidoimidazo[1,2-b]pyridazin-6-yl)-N-(2-fluoro-5-(1-methyl-1H-pyrazol-4-yl)benzyl)-2-methylnicotinamide (12.6 mg, 0.024 mmol, 50% yield)

MS ESI m/z 499.2 (M+H)

1H NMR (500 MHz, DMSO-d6) δ 10.92 (s, 1H), 9.16 (s, 1H), 9.10 (br t, J=5.3 Hz, 1H), 8.37 (s, 1H), 8.33 (s, 1H), 8.11 (d, J=8.8 Hz, 1H), 8.07 (s, 1H), 7.87 (d, J=9.2 Hz, 1H), 7.79 (s, 1H), 7.62 (br d, J=5.8 Hz, 1H), 7.51 (br s, 1H), 7.21 (br t, J=9.2 Hz, 1H), 4.56 (br d, J=5.2 Hz, 2H), 2.60 (s, 3H), 2.55-2.52 (m, 3H), 2.11 (s, 3H).

Examples 354 and 355: N-[6-(5-{3-[(4-fluorophenyl)(hydroxy)methyl]piperidine-1-carbonyl}-6-methylpyridin-3-yl)imidazo[1,2-b]pyridazin-2-yl]acetamide and N-[6-(5-{3-[(4-fluorophenyl)(hydroxy)methyl]piperidine-1-carbonyl}-6-methylpyridin-3-yl)imidazo[1,2-b]pyridazin-2-yl]acetamide

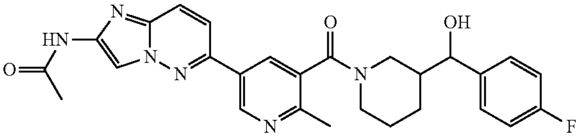

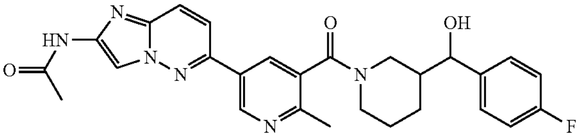

354A and 355A: In a 50 mL oven-dried round-bottomed flask was added tert-butyl 3-formylpiperidine-1-carboxylate (457 mg, 2.143 mmol) in THF (4 mL) to give a colorless solution. (4-Fluorophenyl)magnesium bromide (2.250 mL, 2.250 mmol) was added dropwise at rt. The mixture was stirred at rt for 30 min. LCMS showed two peaks of likely diastereomeric products (M+Na=332.2). The reaction mixture was quenched with saturated $NH_4Cl$ solution and diluted with EtOAc. The layers were separated. The organic layer was dried and concentrated to the crude product tert-butyl 3-((4-fluorophenyl)(hydroxy)methyl)piperidine-1-carboxylate (766 mg, 86% purity) as a colorless dense oil.

MS ESI m/z 332.2 (M+Na)

354B and 355B: In a 50 mL round-bottomed flask was added tert-butyl 3-((4-fluorophenyl)(hydroxy)methyl)piperidine-1-carboxylate (254 mg, 0.706 mmol) in $CH_2Cl_2$ (2 mL) to give a colorless solution. TFA (1 mL, 12.98 mmol) was added. The resulting tan yellow solution was stirred at rt for 30 min. LCMS showed possibly two diastereomers with the desired products (M+H=210.0). The volatiles were stripped off to afford (4-fluorophenyl)(piperidin-3-yl)methanol 2,2,2-trifluoroacetate as a tan oil, which were used in the next coupling steps.

MS ESI m/z 210.0 (M+H) 354 and 355: A mixture of 5-(2-acetamidoimidazo[1,2-b]pyridazin-6-yl)-2-methylnicotinic acid (31.1 mg, 0.1 mmol) and BOP (66.3 mg, 0.150 mmol), (4-fluorophenyl)(piperidin-3-yl)methanol 2,2,2-trifluoroacetate (35.6 mg, 0.110 mmol) and Hünig's Base (0.087 mL, 0.500 mmol) in DMF (0.5 mL) was stirred at rt for 4 h. LC-MS indicated two peaks of the desired product (M+H=503.5). The mixture was diluted with MeOH, filtered and purified by preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 11% B, 11-51% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The diastereomers were tentatively assigned.

Obtained two diastereomers: N-(6-(5-(3-((4-fluorophenyl)(hydroxy)methyl)piperidine-1-carbonyl)-6-methylpyridin-3-yl)imidazo[1,2-b]pyridazin-2-yl)acetamide (10.5 mg, 0.020 mmol, 20% yield) and N-(6-(5-(3-((4-fluorophenyl)(hydroxy)methyl)piperidine-1-carbonyl)-6-methylpyridin-3-yl)imidazo[1,2-b]pyridazin-2-yl)acetamide (22.7 mg, 0.045 mmol, 45% yield). Diastereoisomer 1:

MS ESI m/z 503.1 (M+H)

1H NMR (500 MHz, DMSO-d6) δ 11.03-10.87 (m, 1H), 9.24-8.97 (m, 1H), 8.45-8.31 (m, 1H), 8.29-8.00 (m, 2H), 7.93-7.72 (m, 1H), 7.40 (br s, 1H), 7.22-7.07 (m, 1H), 6.88-6.59 (m, 1H), 4.70-3.99 (m, 2H), 3.47-3.19 (m, 1H), 3.03-2.58 (m, 3H), 2.45-2.27 (m, 3H), 2.16-2.07 (m, 3H), 1.86-1.16 (m, 4H).

Diastereoisomer 2:

MS ESI m/z 503.1 (M+H)

1H NMR (500 MHz, DMSO-d6) δ 10.93 (br s, 1H), 9.13 (br d, J=18.3 Hz, 1H), 8.43-8.28 (m, 1H), 8.25-8.01 (m, 2H), 7.86 (br d, J=9.2 Hz, 1H), 7.38 (br d, J=5.5 Hz, 1H), 7.28-6.72 (m, 3H), 4.94-4.11 (m, 2H), 3.48-2.58 (m, 4H), 2.44 (m, 3H), 2.15-2.09 (m, 3H), 1.85-1.09 (m, 4H).

Examples 356: 5-{2-acetamidoimidazo[1,2-b]pyridazin-6-yl}-N-[3-(4-fluorophenyl)-2-hydroxy-2-methylpropyl]-2-methylpyridine-3-carboxamide

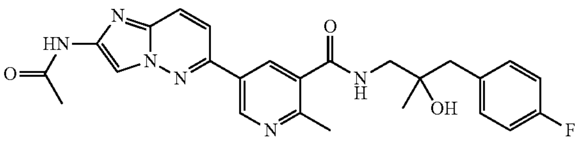 [SMILES: CC(=O)Nc1cn2nc(-c3cnc(C)c(C(=O)NCC(C)(O)Cc4ccc(F)cc4)c3)ccc2n1]

356A: In a 50 mL round-bottomed flask was added tert-butyl (2-oxopropyl)carbamate (0.173 g, 1 mmol) in THF (1.5 mL) to give a colorless solution. (4-Fluorobenzyl) magnesium chloride (4.00 mL, 1.000 mmol) was added dropwise. The resulting clear mixture was stirred at rt for 120 min. The reaction was quenched with saturated $NH_4Cl$ solution and the mixture was diluted with EtOAc. The layers were separated. The organic layer was washed with brine, dried with $Na_2SO_4$ and concentrated. The residue was directly used in the next deprotection step.

356B: In a 50 mL round-bottomed flask was added tert-butyl (3-(4-fluorophenyl)-2-hydroxy-2-methylpropyl) carbamate (0.283 g, 1 mmol) in $CH_2Cl_2$(2 mL) to give a colorless suspension. TFA (1 mL, 12.98 mmol) was added. The resulting tan yellow solution was stirred at rt for 30 min. The volatiles were stripped off to afford the desired product as a tan oil which was carried on without further purification.

MS ESI m/z 166.0 (M+H)

356: A mixture of 5-(2-acetamidoimidazo[1,2-b]pyridazin-6-yl)-2-methylnicotinic acid (31.1 mg, 0.1 mmol) and BOP (66.3 mg, 0.150 mmol), 1-amino-3-(4-fluorophenyl)-2-methylpropan-2-ol 2,2,2-trifluoroacetate (32.7 mg, 0.110 mmol) and Hünig's Base (0.087 mL, 0.500 mmol) in DMF (0.5 mL) was stirred at rt for 4 h (10:00 am). The mixture was diluted with MeOH, filtered and purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 11% B, 11-51% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Obtained 5-{2-acetamidoimidazo[1,2-b]pyridazin-6-yl}-N-[3-(4-fluorophenyl)-2-hydroxy-2-methylpropyl]-2-methylpyridine-3-carboxamide (9.4 mg, 0.020 mmol, 20% yield)

MS ESI m/z 477.2 (M+H)

H NMR (500 MHz, DMSO-d6) δ 10.94 (s, 1H), 9.15 (s, 1H), 8.50 (s, 1H), 8.40 δ 8.28 (m, 2H), 8.11 (d, J=9.3 Hz, 1H), 7.87 (d, J=9.5 Hz, 1H), 7.30 (d, J=7.9 Hz, 2H), 7.09 (t, J=8.8 Hz, 2H), 2.73 (t, J=11.4 Hz, 2H), 2.61 (s, 3H), 2.12 (s, 3H), 1.04 (s, 3H).

Examples 357: N-[6-(5-{3-[(4-fluorophenyl)methyl]-3-hydroxypiperidine-1-carbonyl}-6-methylpyridin-3-yl)imidazo[1,2-b]pyridazin-2-yl] acetamide

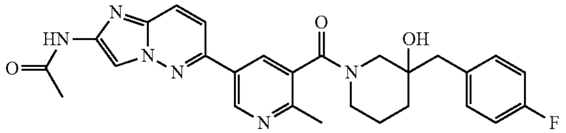 [SMILES: CC(=O)Nc1cn2nc(-c3cnc(C)c(C(=O)N4CCCC(O)(Cc5ccc(F)cc5)C4)c3)ccc2n1]

357A: In a 50 mL oven-dried round-bottomed flask was added tert-butyl 3-oxopiperidine-1-carboxylate (227 mg, 1.139 mmol) in THF (2 mL) to give a colorless solution. (4-Fluorobenzyl)magnesium chloride (4.78 mL, 1.196 mmol) was added dropwise at rt. The mixture was stirred at rt for 3 h. The reaction was quenched with saturated $NH_4Cl$ solution and diluted with EtOAc. The layers were separated. The organic layer was dried and concentrated to give tert-butyl 3-(4-fluorobenzyl)-3-hydroxypiperidine-1-carboxylate (317 mg, 90% crude) as a colorless dense oil.

357B: In a 50 mL round-bottomed flask was added tert-butyl 3-(4-fluorobenzyl)-3-hydroxypiperidine-1-carboxylate (317 mg, 1.025 mmol) in $CH_2Cl_2$ (2 mL) to give a colorless solution. TFA (1 mL, 12.98 mmol) was added. The resulting tan yellow solution was stirred at rt for 60 min. The volatiles were stripped off to afford the desired product (crude 375 mg) as a dark oil, which was directly used in the next reaction.

MS ESI m/z 210.0 (M+H)

357: A mixture of 5-(2-acetamidoimidazo[1,2-b]pyridazin-6-yl)-2-methylnicotinic acid (31.1 mg, 0.1 mmol)

and BOP (66.3 mg, 0.150 mmol), 3-(4-fluorobenzyl)piperidin-3-ol 2,2,2-trifluoroacetate (35.6 mg, 0.110 mmol) and Hünig's Base (0.087 mL, 0.500 mmol) in DMF (0.5 mL) was stirred at rt for 4 h (10:00 am). LC-MS indicated two peaks of the desired product (M+H=503.1). The mixture was diluted with MeOH and filtered. The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 40% B, 40-80% B over 20 minutes, then a 4-minute hold at 100% B; Flow Rate: 20 mL/min; Column Temperature: 25° C. Fraction collection was triggered by UV signals. Fractions containing the desired product were combined and dried via centrifugal evaporation. Obtained N-(6-(5-(3-(4-fluorobenzyl)-3-hydroxypiperidine-1-carbonyl)-6-methylpyridin-3-yl)imidazo[1,2-b]pyridazin-2-yl)acetamide (14.0 mg, 0.026 mmol, 26% yield)

MS ESI m/z 503.1 (M+H)

1H NMR (500 MHz, DMSO-d6) δ 11.05-10.82 (m, 1H), 9.28-8.93 (m, 1H), 8.41-8.28 (m, 1H), 8.27-8.03 (m, 2H), 7.93-7.63 (m, 1H), 7.33 (br t, J=6.4 Hz, 1H), 7.20-7.03 (m, 2H), 7.00-6.61 (m, 1H), 4.87-4.32 (m, 1H), 3.24-2.40 (m, 6H), 2.12 (br s, 3H), 1.75-1.32 (m, 4H), 2.15 (s, 3H).

Examples 358: 5-(2-acetamidoimidazo[1,2-b]pyridazin-6-yl)-3-fluoro-N-(2-fluoro-5-(1-methyl-1H-pyrazol-4-yl)benzyl)-2-methylbenzamide

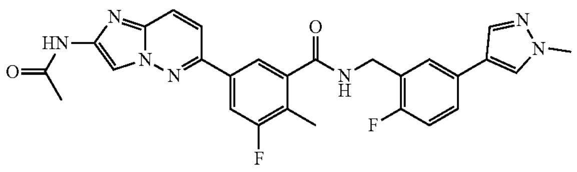

358A: To a solution of 6-chloroimidazo[1,2-b]pyridazin-2-amine (2.5 g, 14.83 mmol) in DCM (50 mL) was added triethylamine (2.274 mL, 16.31 mmol), DMAP (0.181 g, 1.483 mmol) and acetic anhydride (1.539 mL, 16.31 mmol) sequentially at rt. The reaction mixture was stirred ON. Hexanes (15 ml) were added and the suspension was filtered. Drying of the filter cake afforded N-(6-chloroimidazo[1,2-b]pyridazin-2-yl)acetamide (2.95 g, 13.31 mmol, 90% yield) as a light yellow solid.

MS ESI m/z 211.1 (M+H)

358B: A mixture of N-(6-chloroimidazo[1,2-b]pyridazin-2-yl)acetamide (225 mg, 1.068 mmol), 4,4,4',4',5,5,5',5'-octamethyl-2,2'-bi(1,3,2-dioxaborolane) (407 mg, 1.602 mmol), $PdCl_2(dppf)$-$CH_2Cl_2$ adduct (87 mg, 0.107 mmol) and potassium acetate (315 mg, 3.20 mmol) in 1,4-dioxane (5 mL) was stirred at 100° C. for 1 h. Obtained (2-acetamidoimidazo[1,2-b]pyridazin-6-yl)boronic acid (240 mg, 0.982 mmol, 92% yield) which carried on to the next step without further purification.

MS ESI m/z 221.1 (M+H)

358C: To (2-acetamidoimidazo[1,2-b]pyridazin-6-yl)boronic acid (240 mg, 0.982 mmol) was added methyl 5-bromo-3-fluoro-2-methylbenzoate (240 mg, 0.971 mmol) and 1,1'-bis(di-tert-butylphosphino)ferrocene palladium dichloride (31.7 mg, 0.049 mmol), which was then degassed by bubbling nitrogen through for 5 min. 2M $K_3PO_4$ (1.457 mL, 2.91 mmol) was added and the mixture stirred for 5 min at 100° C. After cooling 15 min, the reaction was filtered through Celite and concentrated. The crude material was purified by silica gel chromatography, eluting with 0-100% EtOAc in hexanes and then 0-10% MeOH in DCM to afford methyl 5-(2-acetamidoimidazo[1,2-b]pyridazin-6-yl)-3-fluoro-2-methylbenzoate (313 mg, 0.869 mmol, 89% yield).

MS ESI m/z 343.1 (M+H)

358D: To a mixture of methyl 5-(2-acetamidoimidazo[1,2-b]pyridazin-6-yl)-3-fluoro-2-methylbenzoate (313 mg, 0.914 mmol) in tetrahydrofuran (8 mL) was added a solution of lithium hydroxide monohydrate (46.0 mg, 1.097 mmol) in 1.5 mL of water, and the resulting mixture was stirred for 5 h at rt. The reaction mixture was concentrated to a solid to afford 5-(2-acetamidoimidazo[1,2-b]pyridazin-6-yl)-3-fluoro-2-methylbenzoic acid, lithium salt (310 mg, 0.832 mmol, 91% yield) as a beige solid. The material was carried forward without further purification.

MS ESI m/z 329.2 (M+H)

358E: A mixture of 2-fluoro-5-(1-methyl-1H-pyrazol-4-yl)benzonitrile (342 mg, 1.700 mmol) and Raney nickel (72.8 mg, 0.850 mmol) in EtOH (5 mL) was degassed by vacuum and then stirred under a hydrogen balloon ON. The crude reaction mixture was filtered through Celite into a flask containing 2.5 mL [10 mM] of 4N HCl in 1,4-dioxane. After stirring 10 min, the mixture concentrated to afford (2-fluoro-5-(1-methyl-1H-pyrazol-4-yl)phenyl)methanamine, HCl (425 mg, 1.583 mmol, 93% yield) as a white solid which was carried forward without further purification.

MS ESI m/z 206.1 (M+H)

358: A mixture of 5-(2-acetamidoimidazo[1,2-b]pyridazin-6-yl)-3-fluoro-2-methylbenzoic acid (15 mg, 0.046 mmol) and BOP (30.3 mg, 0.069 mmol), (2-fluoro-5-(1-methyl-1H-pyrazol-4-yl)phenyl)methanamine (9.38 mg, 0.046 mmol) and Hünig's Base (0.040 mL, 0.228 mmol) in DMF (1.0 mL) was stirred at rt for 2 h. The mixture was diluted to 2 mL with methanol, then filtered. The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 17% B, 17-57% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to afford 5-(2-acetamidoimidazo[1,2-b]pyridazin-6-yl)-3-fluoro-N-(2-fluoro-5-(1-methyl-1H-pyrazol-4-yl)benzyl)-2-methylbenzamide (10.8 mg, 0.021 mmol, 46% yield)

MS ESI m/z 516.4 (M+H)

1H NMR (500 MHz, DMSO-d6) δ 10.80 (br s, 1H), 8.95 (br t, J=5.3 Hz, 1H), 8.32 (s, 1H), 8.06 (d, J=9.2 Hz, 1H), 8.04 (s, 1H), 7.97-7.89 (m, 2H), 7.83 (d, J=9.4 Hz, 1H), 7.78 (s, 1H), 7.63 (br d, J=6.4 Hz, 1H), 7.51 (br s, 1H), 7.20 (t, J=9.2 Hz, 1H), 4.57 (br d, J=5.5 Hz, 2H), 2.57-2.55 (m, 3H), 2.33 (s, 3H), 2.13 (s, 3H).

TABLE 19

Compounds in Table 19 were prepared by methods as described in Examples 14, 15, 323, and 358.

| Ex | Name | Structure | Obs. MS Ion | NMR Assignments |
|---|---|---|---|---|
| 359 | 5-{2-acetamidoimidazo[1,2-b]pyridazin-6-yl}-3-fluoro-N-{[2-fluoro-5-(trifluoromethoxy)phenyl]methyl}-2-methylbenzamide | 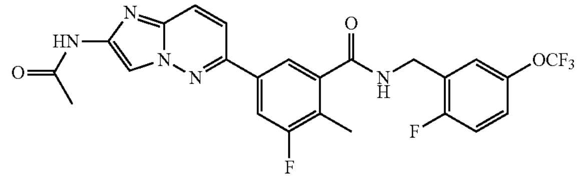 [SMILES: CC(=O)Nc1cn2nc(-c3cc(F)c(C)c(C(=O)NCc4cc(OC(F)(F)F)ccc4F)c3)ccc2n1] | 520.3 | 1H NMR (500 MHz, DMSO-d6) δ 10.92 (br s, 1H), 9.19 (br s, 1H), 8.30 (br s, 1H), 8.05 (br s, 1H), 7.92 (s, 1H), 7.90 (br s, 1H), 7.82 (br s, 1H), 7.42 (br s, 1H), 7.37 (br s, 2H), 4.55 (br s, 2H), 2.26 (br s, 3H), 2.12 (br s, 3H). |
| 360 | 5-{2-acetamidoimidazo[1,2-b]pyridazin-6-yl}-3-fluoro-N-[(1S)-1-[2-fluoro-5-(trifluoromethoxy)phenyl]ethyl]-2-methylbenzamide | 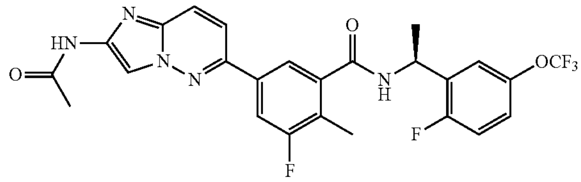 [SMILES: CC(=O)Nc1cn2nc(-c3cc(F)c(C)c(C(=O)N[C@@H](C)c4cc(OC(F)(F)F)ccc4F)c3)ccc2n1] | 534.3 | 1H NMR (500 MHz, DMSO-d6) δ 10.91 (s, 1H), 9.19 (br d, J = 7.6 Hz, 1H), 8.30 (s, 1H), 8.05 (d, J = 9.5 Hz, 1H), 7.92 (br d, J = 10.7 Hz, 1H), 7.84 (s, 1H), 7.81 (d, J = 9.0 Hz, 1H), 7.45 (br s, 1H), 7.38-7.31 (m, 2H), 5.38-5.32 (m, 1H), 2.20 (s, 3H), 2.12 (s, 3H), 1.46 (br d, J = 7.0 Hz, 3H). |
| 361 | 5-{2-acetamidoimidazo[1,2-b]pyridazin-6-yl}-3-fluoro-N-{[2-fluoro-3-(trifluoromethoxy)phenyl]methyl}-2-methylbenzamide | 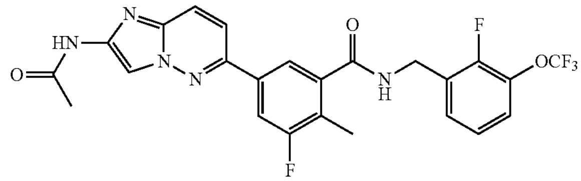 [SMILES: CC(=O)Nc1cn2nc(-c3cc(F)c(C)c(C(=O)NCc4cccc(OC(F)(F)F)c4F)c3)ccc2n1] | 520.3 | 1H NMR (500 MHz, DMSO-d6) d 10.91 (s, 1H), 9.16 (br s, 1H), 8.30 (s, 1H), 8.05 (br d, J = 9.5 Hz, 1H), 7.95-7.85 (m, 2H), 7.82 (br d, J = 9.5 Hz, 1H), 7.49 (br d, J = 7.0 Hz, 2H), 7.33 (br t, J = 8.1 Hz, 1H), 4.58 (br d, J = 5.2 Hz, 2H), 2.58-2.54 (m, 3H), 2.12 (s, 3H). |
| 362 | N-[(3S)-3-(4-chlorophenyl)-3-hydroxypropyl]-5-{2-[2-(dimethylamino)acetamido]imidazo[1,2-b]pyridazin-6-yl}-3-fluoro-2-methylbenzamide | 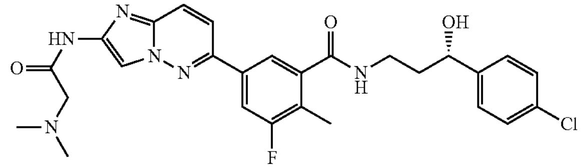 [SMILES: Cc1c(F)cc(-c2ccc3nc(NC(=O)CN(C)C)cn3n2)cc1C(=O)NCC[C@H](O)c1ccc(Cl)cc1] | 539.1 | 1H NMR (500 MHz, DMSO-d6) δ 8.42-8.33 (m, 2H), 8.07 (d, J = 9.5 Hz, 1H), 7.90 (br d, J = 10.9 Hz, 1H), 7.87-7.80 (m, 2H), 7.45-7.35 (m, 4H), 5.45-5.11 (m, 1H), 4.70 (br d, J = 4.5 Hz, 1H), 3.47-3.28 (m, 1H), 3.28-3.15 (m, 1H), 3.00-2.95 (m, 1H), 2.57-2.53 (m, 2H), 2.37-2.33 (m, 6H), 2.33-2.29 (m, 3H), 1.90 (q, J = 6.9 Hz, 2H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 363 | N-[(3S)-3-(4-chlorophenyl)-3-hydroxypropyl]-3-fluoro-2-methyl-5-{2-[2-(methylamino) acetamido] imidazo[1,2-b] pyridazin-6-yl}benzamide | 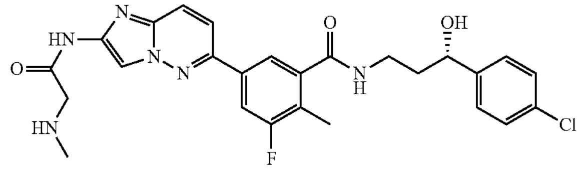 | 525.1 | 1H NMR (500 MHz, DMSO-d6) d 8.45-8.27 (m, 2H), 8.04 (br d, J = 9.4 Hz, 1H), 7.87 (br d, J = 10.6 Hz, 1H), 7.83-7.70 (m, 2H), 7.44-7.32 (m, 4H), 4.68 (br t, J = 6.4 Hz, 1H), 3.78-3.67 (m, 1H), 3.51-3.29 (m, 2H), 2.59-2.54 (m, 2H), 2.34 (s, 3H), 2.32-2.24 (m, 3H), 1.95-1.81 (m, 4H). |
| 364 | 5-{2-acetamidoimidazo [1,2-b]pyridazin-6-yl}-3-fluoro-2-methyl-N-[(2-phenoxyphenyl) methyl] benzamide | 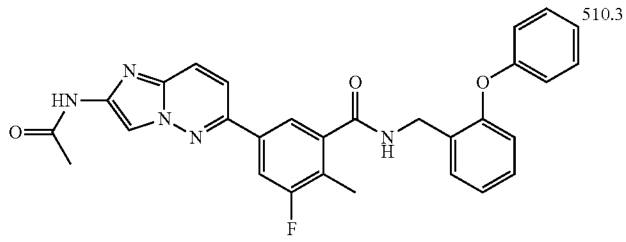 | 510.3 | 1H NMR (500 MHz, DMSO-d6) d 10.98-10.68 (m, 1H), 8.86 (br s, 1H), 8.31 (s, 1H), 8.05 (br d, J = 9.2 Hz, 1H), 7.96-7.82 (m, 2H), 7.78 (br d, J = 9.5 Hz, 1H), 7.50 (br d, J = 7.3 Hz, 1H), 7.38 (br t, J = 7.7 Hz, 2H), 7.31 (br t, J = 7.2 Hz, 1H), 7.20 (br t, J = 7.5 Hz, 1H), 7.15-7.06 (m, 1H), 7.01 (br d, J = 8.0 Hz, 2H), 6.97-6.81 (m, 1H), 4.53 (br d, J = 5.6 Hz, 2H), 2.29 (s, 3H), 2.13 (s, 3H). |
| 365 | N-{[2-(3,3-difluoropyrrolidine-1-carbonyl)-6-fluorophenyl] methyl}-5-{2-acetamidoimidazo [1,2-b]pyridazin-6-yl}-3-fluoro-2-methylbenzamide | 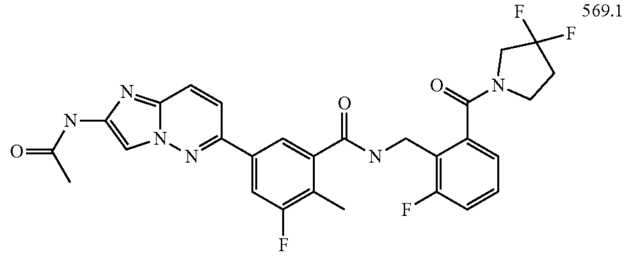 | 569.1 | 1H NMR (500 MHz, DMSO-d6) δ 10.80 (br s, 1H), 8.88-8.73 (m, 1H), 8.30 (s, 1H), 8.06 (br d, J = 9.3 Hz, 1H), 7.89 (br d, J = 11.0 Hz, 1H), 7.86 (br s, 1H), 7.83-7.75 (m, 1H), 7.55-7.42 (m, 1H), 7.40-7.27 (m, 1H), 7.27-7.19 (m, 1H), 4.53 (br s, 2H), 3.95 (br t, J = 13.3 Hz, 1H), 3.79 (br t, J = 7.4 Hz, 1H), 3.73 (br t, J = 12.8 Hz, 1H), 3.51 (br t, J = 7.2 Hz, 1H), 2.47-2.34 (m, 2H), 2.29-2.22 (m, 3H), 2.13 (s, 3H). |
| 366 | 5-{2-acetamidoimidazo [1,2-b]pyridazin-6-yl}-2,3-difluoro-N-{[2-fluoro-5-(trifluoromethoxy) phenyl]methyl} benzamide | 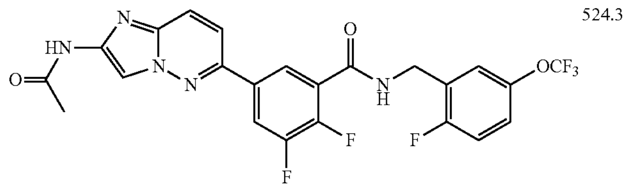 | 524.3 | 1H NMR (500 MHz, DMSO-d6) d 11.03-10.67 (m, 1H), 9.40-9.20 (m, 1H), 8.33-8.29 (m, 1H), 8.25 (br s, 1H), 8.08 (br d, J = 9.5 Hz, 2H), 7.93-7.74 (m, 1H), 7.43-7.34 (m, 3H), 4.57 (br d, J = 5.5 Hz, 2H), 2.12 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 367 | 5-{2-acetamidoimidazo[1,2-b]pyridazin-6-yl}-2,3-difluoro-N-[(1R)-1-[2-fluoro-5-(trifluoromethoxy)phenyl]ethyl]benzamide | 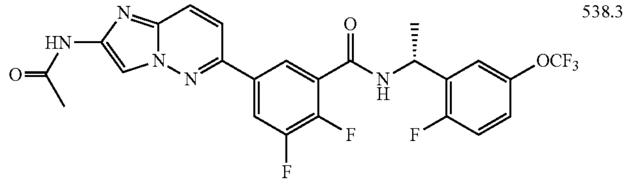 | 538.3 | 1H NMR (500 MHz, DMSO-d6) d 10.93 (s, 1H), 9.32 (br d, J = 7.3 Hz, 1H), 8.31 (s, 1H), 8.26-8.21 (m, 1H), 8.07 (d, J = 9.5 Hz, 1H), 8.01 (br s, 1H), 7.82 (d, J = 9.5 Hz, 1H), 7.45 (br s, 1H), 7.39-7.32 (m, 2H), 5.35 (br t, J = 7.2 Hz, 1H), 2.12 (s, 3H), 1.47 (br d, J = 6.7 Hz, 3H). |
| 368 | 3-{2-acetamidoimidazo[1,2-b]pyridazin-6-yl}-2,4,5-trifluoro-N-{[2-fluoro-5-(trifluoromethoxy)phenyl]methyl}benzamide | 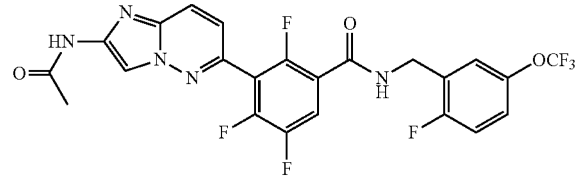 [SMILES: CC(=O)Nc1cn2nc(-c3c(F)c(F)cc(C(=O)NCc4cc(OC(F)(F)F)ccc4F)c3F)ccc2n1] | 542.2 | 1H NMR (500 MHz, DMSO-d6) d 11.00 (s, 1H), 9.16 (br s, 1H), 8.34 (s, 1H), 8.18 (d, J = 9.2 Hz, 1H), 7.97-7.90 (m, 1H), 7.47 (br d, J = 9.5 Hz, 1H), 7.41-7.32 (m, 2H), 4.53 (br d, J = 5.5 Hz, 2H), 2.12 (s, 3H), 1.27-1.19 (m, 1H). |
| 369 | 3-{2-acetamidoimidazo[1,2-b]pyridazin-6-yl}-2,4,5-trifluoro-N-{[2-fluoro-5-(trifluoromethyl)phenyl]methyl}benzamide | 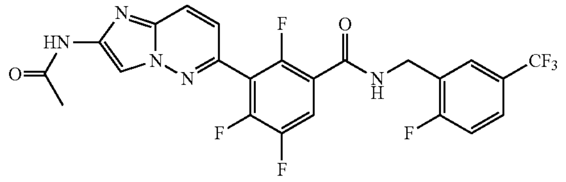 [SMILES: CC(=O)Nc1cn2nc(-c3c(F)c(F)cc(C(=O)NCc4cc(C(F)(F)F)ccc4F)c3F)ccc2n1] | 562.2 | 1H NMR (500 MHz, DMSO-d6) 10.99 (s, 1H), 9.16 (br s, 1H), 8.33 (s, 1H), 8.18 (d, J = 9.5 Hz, 1H), 7.94 (br d, J = 6.7 Hz, 1H), 7.79 (br d, J = 6.7 Hz, 1H), 7.74 (br s, 1H), 7.49-7.42 (m, 2H), 4.58 (br d, J = 5.2 Hz, 2H), 2.12 (s, 3H). |
| 370 | N-[(3R)-3-(4-chlorophenyl)-3-hydroxypropyl]-3-{2-acetamidoimidazo[1,2-b]pyridazin-6-yl}-5-fluorobenzamide | 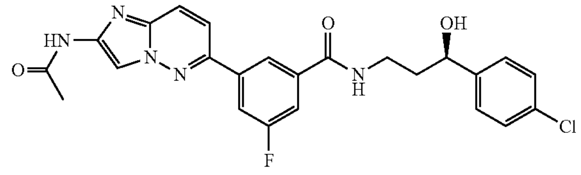 [SMILES: CC(=O)Nc1cn2nc(-c3cc(F)cc(C(=O)NCC[C@@H](O)c4ccc(Cl)cc4)c3)ccc2n1] | 482.2 | 1H NMR (500 MHz, DMSO-d6) d 10.94 (s, 1H), 8.71 (br t, J = 5.2 Hz, 1H), 8.34 (s, 1H), 8.28 (s, 1H), 8.09 (d, J = 9.2 Hz, 1H), 8.02 (br d, J = 9.8 Hz, 1H), 7.84 (d, J = 9.5 Hz, 1H), 7.71 (br d, J = 8.9 Hz, 1H), 7.40-7.34 (m, 4H), 4.68-4.64 (m, 1H), 3.36 (q, J = 6.7 Hz, 2H), 2.56-2.54 (m, 1H), 2.12 (s, 3H), 1.89 (br d, J = 7.0 Hz, 2H). |
| 371 | 5-{2-acetamidoimidazo[1,2-b]pyridazin-6-yl}-3-fluoro-N-{[2-fluoro-5-(trifluoromethoxy)phenyl]methyl}-2-methoxybenzamide | 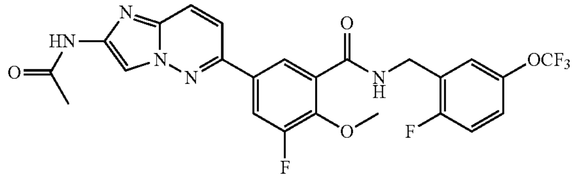 [SMILES: COc1c(F)cc(-c2ccc3nc(NC(C)=O)cn3n2)cc1C(=O)NCc1cc(OC(F)(F)F)ccc1F] | 536.2 | 1H NMR (500 MHz, DMSO-d6) d 10.92 (s, 1H), 9.05 (br t, J = 5.8 Hz, 1H), 8.30 (s, 1H), 8.13-8.03 (m, 3H), 7.82 (d, J = 9.5 Hz, 1H), 7.44 (br d, J = 4.3 Hz, 1H), 7.38 (d, J = 6.7 Hz, 2H), 4.57 (br d, J = 5.8 Hz, 2H), 3.97 (s, 3H), 2.12 (s, 3H). |

TABLE 19-continued

| Compounds in Table 19 were prepared by methods as described in Examples 14, 15, 323, and 358. | | | | |
|---|---|---|---|---|
| Ex | Name | Structure | Obs. MS Ion | NMR Assignments |
| 372 | 3-{2-acetamidoimidazo[1,2-b]pyridazin-6-yl}-5-fluoro-N-{[2-fluoro-5-(trifluoromethyl)phenyl]methyl}-4-methylbenzamide | 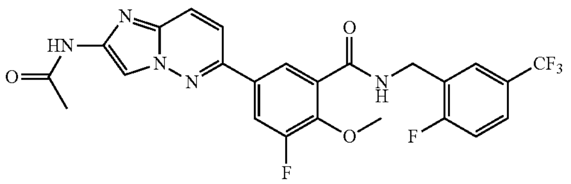 [SMILES: COc1c(F)cc(-c2ccc3nc(NC(C)=O)cn3n2)cc1C(=O)NCc1cc(C(F)(F)F)ccc1F] | 504.1 | 1H NMR (500 MHz, DMSO-d6) d 10.93 (s, 1H), 9.26 (br t, J = 5.3 Hz, 1H), 8.30 (s, 1H), 8.07 (d, J = 9.2 Hz, 1H), 7.86 (s, 1H), 7.80-7.71 (m, 3H), 7.46-7.39 (m, 2H), 4.58 (br d, J = 5.5 Hz, 2H), 2.29 (s, 3H), 2.12 (s, 3H). |
| 373 | N-[(3R)-3-(4-chlorophenyl)-3-hydroxypropyl]-3-{2-acetamidoimidazo[1,2-b]pyridazin-6-yl}-5-fluoro-4-methylbenzamide | 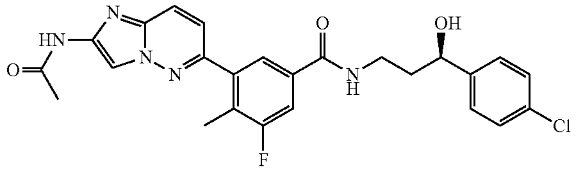 [SMILES: CC(=O)Nc1cn2nc(-c3cc(C(=O)NCC[C@@H](O)c4ccc(Cl)cc4)cc(F)c3C)ccc2n1] | 496.3 | 1H NMR (500 MHz, DMSO-d6) d 10.92 (s, 1H), 8.59 (br t, J = 5.2 Hz, 1H), 8.30 (s, 1H), 8.06 (d, J = 9.2 Hz, 1H), 7.75 (s, 1H), 7.69 (br d, J = 10.4 Hz, 1H), 7.41-7.33 (m, 6H), 4.62 (t, J = 6.4 Hz, 1H), 3.32 (q, J = 6.5 Hz, 2H), 2.27 (s, 3H), 2.12 (s, 3H), 1.88-1.83 (m, 2H). |
| 374 | N-[(3R)-3-(4-chlorophenyl)-3-hydroxypropyl]-3-{2-acetamidoimidazo[1,2-b]pyridazin-6-yl}-2-fluoro-6-methoxybenzamide | 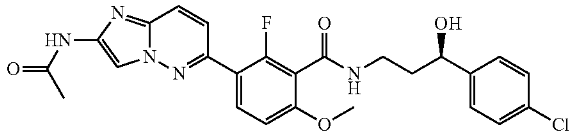 [SMILES: COc1ccc(-c2ccc3nc(NC(C)=O)cn3n2)c(F)c1C(=O)NCC[C@@H](O)c1ccc(Cl)cc1] | 512.2 | 1H NMR (500 MHz, DMSO-d6) d 8.40 (br t, J = 5.4 Hz, 1H), 8.28 (s, 1H), 8.01 (d, J = 9.3 Hz, 1H), 7.84 (t, J = 8.8 Hz, 1H), 7.46 (br d, J = 8.2 Hz, 1H), 7.38 (s, 4H), 7.11 (d, J = 8.8 Hz, 1H), 4.68 (br t, J = 6.4 Hz, 1H), 3.88 (s, 3H), 3.33 (br s, 1H), 2.67 (d, J = 9.8 Hz, 1H), 2.12 (s, 3H), 1.83 (q, J = 6.8 Hz, 2H), 1.67 (s, 1H). |
| 375 | 3-{2-acetamidoimidazo[1,2-b]pyridazin-6-yl}-2-fluoro-N-[(1S)-1[2-fluoro-5-(trifluoromethoxy)phenyl]ethyl]-6-methoxybenzamide | 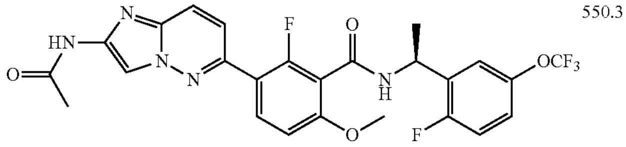 | 550.3 | 1H NMR (500 MHz, DMSO-d6) δ 10.92 (s, 1H), 9.20 (br d, J = 7.3 Hz, 1H), 8.29 (s, 1H), 8.06 (d, J = 9.2 Hz, 1H), 7.88 (t, J = 8.9 Hz, 1H), 7.51-7.45 (m, 2H), 7.39-7.32 (m, 2H), 7.15 (d, J = 8.9 Hz, 1H), 5.32-5.26 (m, 1H), 3.89 (s, 3H), 2.12 (s, 3H), 1.41 (br d, J = 7.0 Hz, 3H). |
| 376 | N-{[2-(3,3-difluoropyrrolidine-1-carbonyl)-5-fluorophenyl]methyl}-3-acetamidoimidazo[1,2-b]pyridazin-6-yl}-2-fluoro-6-methoxybenzamide | 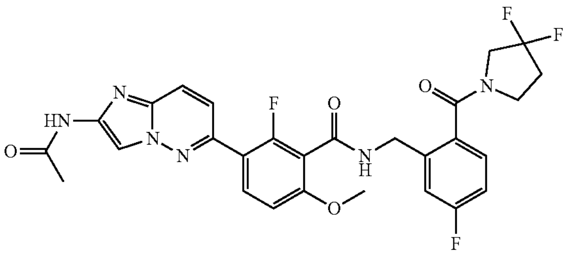 [SMILES: COc1ccc(-c2ccc3nc(NC(C)=O)cn3n2)c(F)c1C(=O)NCc1cc(F)ccc1C(=O)N1CCC(F)(F)C1] | 585.4 | 1H NMR (500 MHz, DMSO-d6) δ 10.78 (br s, 1H), 9.02 (br t, J = 5.8 Hz, 1H), 8.29 (s, 1H), 8.02 (d, J = 9.3 Hz, 1H), 7.87 (t, J = 8.8 Hz, 1H), 7.47 (br d, J = 9.0 Hz, 1H), 7.42 (br s, 1H), 7.36 (br d, J = 9.3 Hz, 1H), 7.26-7.08 (m, 2H), 4.45 (br s, 2H), 4.00-3.87 (m, 4H), 3.84-3.43 (m, 2H), 2.50-2.35 (m, 3H), 2.13 (s, 3H). |

TABLE 19-continued

| Compounds in Table 19 were prepared by methods as described in Examples 14, 15, 323, and 358. | | | | |
|---|---|---|---|---|
| Ex | Name | Structure | Obs. MS Ion | NMR Assignments |
| 377 | N-{[2-(cyclopropylmethoxy)phenyl]methyl}-3-{2-acetamidoimidazo[1,2-b]pyridazin-6-yl}-2-fluoro-6-methoxybenzamide | 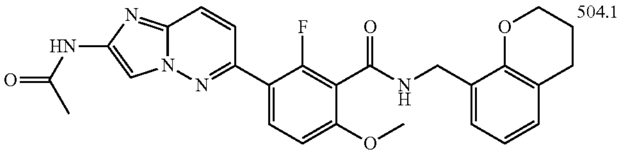 | 504.1 | 1H NMR (500 MHz, DMSO-d6) δ 10.52 (br s, 1H), 8.47 (br t, J = 5.8 Hz, 1H), 8.04 (s, 1H), 7.77 (d, J = 9.4 Hz, 1H), 7.60 (t, J = 8.9 Hz, 1H), 7.23 (br d, J = 9.2 Hz, 1H), 7.12 (br d, J = 7.3 Hz, 1H), 6.97 (br t, J = 7.8 Hz, 1H), 6.88 (d, J = 8.8 Hz, 1H), 6.79-6.62 (m, 2H), 4.23 (br d, J = 6.0 Hz, 2H), 3.70-3.66 (m, 3H), 3.66-3.59 (m, 2H), 1.94-1.82 (m, 3H), 1.01 (br d, J = 8.0 Hz, 1H), 0.38-0.27 (m, 2H), 0.12 (q, J = 4.8 Hz, 2H). |
| 378 | 3-{2-acetamidoimidazo[1,2-b]pyridazin-6-yl}-2-fluoro-N-[(1R)-1-[2-fluoro-5-(trifluoromethoxy)phenyl](2,2,2-Â²Hâ,f)ethyl]-6-methoxybenzamide | 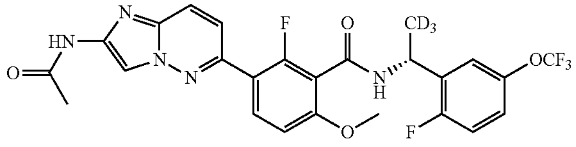 [SMILES: [2H]C([2H])([2H])[C@@H](NC(=O)c1c(OC)ccc(-c2ccc3nc(NC(C)=O)cn3n2)c1F)c1cc(OC(F)(F)F)ccc1F] | 553.2 | 1H NMR (500 MHz, DMSO-d6) δ 10.91 (s, 1H), 9.20 (br d, J = 7.6 Hz, 1H), 8.28 (s, 1H), 8.04 (br d, J = 9.5 Hz, 1H), 7.87 (br t, J = 8.9 Hz, 1H), 7.49-7.43 (m, 2H), 7.38-7.30 (m, 2H), 7.14 (br d, J = 8.9 Hz, 1H), 5.26 (br d, J = 7.3 Hz, 1H), 3.88 (s, 3H), 2.11 (s, 3H). |
| 379 | 3-{2-acetamidoimidazo[1,2-b]pyridazin-6-yl}-2,6-difluoro-N-[(1S)-1-[2-fluoro-5-(trifluoromethoxy)phenyl]ethyl]benzamide | 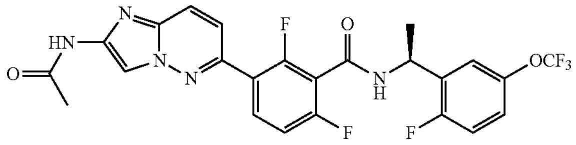 [SMILES: CC(=O)Nc1cn2nc(-c3ccc(F)c(C(=O)N[C@@H](C)c4cc(OC(F)(F)F)ccc4F)c3F)ccc2n1] | 538.1 | 1H NMR (500 MHz, DMSO-d6) δ 10.94 (s, 1H), 9.49 (br d, J = 7.0 Hz, 1H), 8.31 (s, 1H), 8.09 (br d, J = 9.2 Hz, 1H), 7.98-7.92 (m, 1H), 7.49 (br d, J = 9.2 Hz, 1H), 7.44-7.33 (m, 4H), 5.33 (br t, J = 7.0 Hz, 1H), 2.11 (s, 3H), 1.43 (br d, J = 6.7 Hz, 3H). |
| 380 | 3-{2-acetamidoimidazo[1,2-b]pyridazin-6-yl}-2,6-difluoro-N-[(1R)-1-[2-fluoro-5-(trifluoromethoxy)phenyl](2,2,2-Â²Hâ,f)ethyl}benzamide | 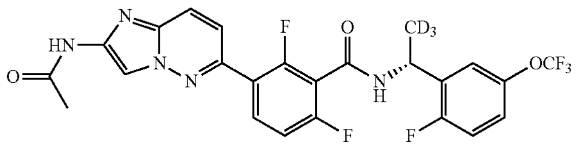 [SMILES: [2H]C([2H])([2H])[C@@H](NC(=O)c1c(F)ccc(-c2ccc3nc(NC(C)=O)cn3n2)c1F)c1cc(OC(F)(F)F)ccc1F] | 541.3 | 1H NMR (500 MHz, DMSO-d6) δ 10.94 (s, 1H), 9.48 (br d, J = 7.3 Hz, 1H), 8.31 (s, 1H), 8.09 (br d, J = 9.5 Hz, 1H), 7.98-7.91 (m, 1H), 7.49 (br d, J = 9.2 Hz, 1H), 7.44-7.32 (m, 4H), 5.31 (br d, J = 7.0 Hz, 1H), 2.11 (s, 3H) |

TABLE 19-continued

| Compounds in Table 19 were prepared by methods as described in Examples 14, 15, 323, and 358. | | | | |
|---|---|---|---|---|
| Ex | Name | Structure | Obs. MS Ion | NMR Assignments |
| 381 | N-{[2-(4,4-difluoropiperidine-1-carbonyl)-5-fluorophenyl]methyl}-3-{2-acetamidoimidazo[1,2-b]pyridazin-6-yl}-2,6-difluorobenzamide | 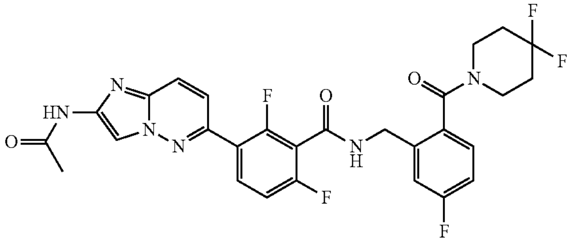 [SMILES: CC(=O)Nc1cn2nc(-c3ccc(F)c(C(=O)NCc4cc(F)ccc4C(=O)N4CCC(F)(F)CC4)c3F)ccc2n1] | 587.2 | 1H NMR (500 MHz, DMSO-d6) δ 10.95 (s, 1H), 9.44 (br t, J = 5.6 Hz, 1H), 8.32 (s, 1H), 8.10 (br d, J = 9.5 Hz, 1H), 7.99-7.92 (m, 2H), 7.51 (br d, J = 8.9 Hz, 1H), 7.46-7.37 (m, 3H), 7.26-7.18 (m, 2H), 4.45 (br s, 2H), 2.16-2.12 (m, 3H), 2.11-1.87 (m, 6H). |
| 382 | N-[(3R)-3-(4-chlorophenyl)-3-hydroxypropyl]-5-{2-acetamidoimidazo[1,2-b]pyridazin-6-yl}-2,4-dimethylbenzamide | 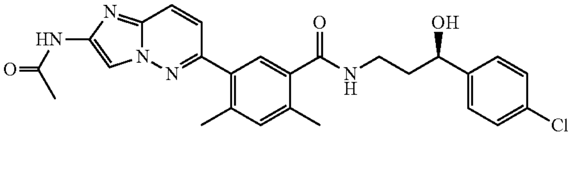 [SMILES: CC(=O)Nc1cn2nc(-c3cc(C(=O)NCC[C@@H](O)c4ccc(Cl)cc4)c(C)cc3C)ccc2n1] | 492.1 | 1H NMR (500 MHz, DMSO-d6) δ 10.90 (s, 1H), 8.27 (s, 2H), 8.04 (d, J = 9.2 Hz, 1H), 7.41-7.34 (m, 6H), 7.25 (s, 1H), 4.65 (br d, J = 4.3 Hz, 1H), 3.96-3.80 (m, 1H), 3.35-3.14 (m, 2H), 2.37 (br d, J = 11.0 Hz, 6H), 2.12 (s, 3H), 1.92-1.77 (m, 2H). |
| 383 | N-[(3S)-3-(4-chlorophenyl)-3-hydroxypropyl]-5-{2-acetamidoimidazo[1,2-b]pyridazin-6-yl}-2,4-dimethylbenzamide | 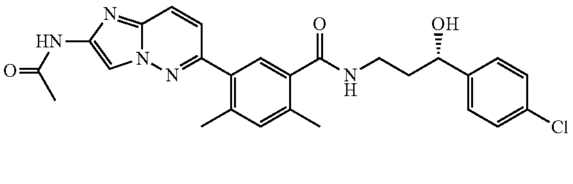 [SMILES: CC(=O)Nc1cn2nc(-c3cc(C(=O)NCC[C@H](O)c4ccc(Cl)cc4)c(C)cc3C)ccc2n1] | 492.1 | 1H NMR (500 MHz, DMSO-d6) δ 10.76 (br s, 1H), 8.26 (s, 1H), 8.14 (br t, J = 5.1 Hz, 1H), 8.01 (d, J = 9.3 Hz, 1H), 7.43-7.31 (m, 6H), 7.24 (s, 1H), 4.66 (br s, 1H), 3.37-3.24 (m, 3H), 2.39 (s, 3H), 2.36 (s, 3H), 2.12 (s, 3H), 1.85 (q, J = 6.8 Hz, 2H). |
| 384 | N-{[3-chloro-2-fluoro-5-(trifluoromethyl)phenyl]methyl}-5-{2-acetamidoimidazo[1,2-b]pyridazin-6-yl}-2,4-dimethylbenzamide | 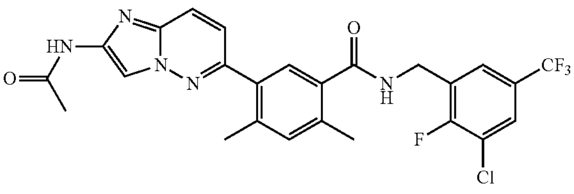 [SMILES: CC(=O)Nc1cn2nc(-c3cc(C(=O)NCc4cc(C(F)(F)F)cc(Cl)c4F)c(C)cc3C)ccc2n1] | 534.1 | 1H NMR (500 MHz, DMSO-d6) δ 10.76 (br s, 1H), 8.87 (br t, J = 5.6 Hz, 1H), 8.26 (s, 1H), 8.01 (d, J = 9.3 Hz, 1H), 7.95 (br d, J = 5.7 Hz, 1H), 7.75 (br d, J = 4.5 Hz, 1H), 7.49 (s, 1H), 7.35 (d, J = 9.3 Hz, 1H), 7.27 (s, 1H), 4.58 (br d, J = 5.6 Hz, 2H), 2.37 (d, J = 6.7 Hz, 6H), 2.12 (s, 3H). |
| 385 | 5-{2-acetamidoimidazo[1,2-b]pyridazin-6-yl}-N-{[2-fluoro-5-(trifluoromethyl)phenyl]methyl}-2-(trifluoromethyl)benzamide | 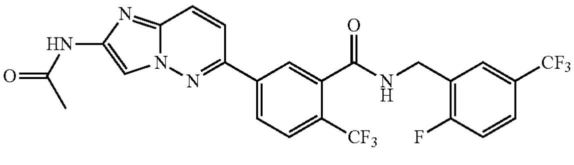 [SMILES: CC(=O)Nc1cn2nc(-c3ccc(C(F)(F)F)c(C(=O)NCc4cc(C(F)(F)F)ccc4F)c3)ccc2n1] | 540.2 | 1H NMR (500 MHz, DMSO-d6) δ 10.97 (s, 1H), 9.33 (br t, J = 5.6 Hz, 1H), 8.40-8.28 (m, 2H), 8.24 (s, 1H), 8.13 (d, J = 9.5 Hz, 1H), 7.98 (d, J = 8.2 Hz, 1H), 7.89 (d, J = 9.5 Hz, 1H), 7.80 (br d, J = 5.5 Hz, 1H), 7.75 (br s, 1H), 7.47 (t, J = 9.0 Hz, 1H), 4.60 (br d, J = 5.5 Hz, 2H), 2.13 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 386 | 2-chloro-N-[(3R)-3-(4-chlorophenyl)-3-hydroxypropyl]-5-{2-acetamidoimidazo[1,2-b]pyridazin-6-yl}benzamide | 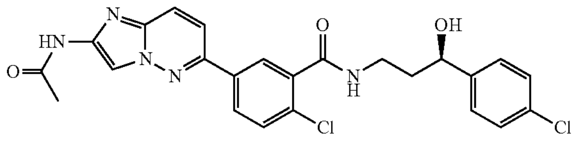 [SMILES: CC(=O)Nc1cn2nc(-c3ccc(Cl)c(C(=O)NCC[C@@H](O)c4ccc(Cl)cc4)c3)ccc2n1] | 498.3 | 1H NMR (500 MHz, DMSO-d6) δ 10.92 (s, 1H), 8.59 (br t, J = 5.3 Hz, 1H), 8.32 (s, 1H), 8.12-8.03 (m, 4H), 7.81 (d, J = 9.5 Hz, 1H), 7.67 (d, J = 8.5 Hz, 1H), 7.39 (s, 4H), 4.69 (br s, 1H), 3.36-3.29 (m, 2H), 2.12 (s, 3H), 1.86 (q, J = 6.8 Hz, 2H). |
| 387 | 2-chloro-N-{[2-(3,3-difluoropyrrolidine-1-carbonyl)-5-fluorophenyl]methyl}-5-{2-acetamidoimidazo[1,2-b]pyridazin-6-yl}benzamide | 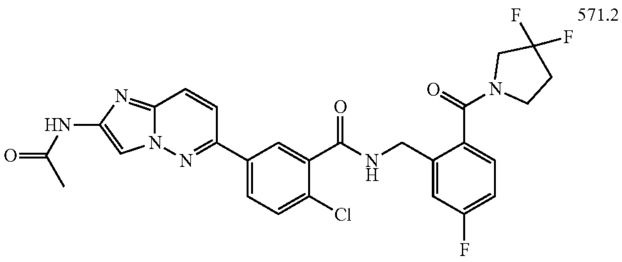 | 571.2 | 1H NMR (500 MHz, DMSO-d6) δ 10.79 (br s, 1H), 9.03 (br s, 1H), 8.31 (s, 1H), 8.19-8.10 (m, 2H), 8.07 (br d, J = 9.4 Hz, 1H), 7.81 (br d, J = 9.3 Hz, 1H), 7.69 (d, J = 8.3 Hz, 1H), 7.43 (br s, 1H), 7.36 (br d, J = 9.3 Hz, 1H), 7.20 (br t, J = 8.3 Hz, 1H), 4.49 (br d, J = 5.0 Hz, 2H), 3.95 (br t, J = 13.2 Hz, 1H), 3.79 (br s, 1H), 3.69 (br s, 1H), 3.49 (br s, 1H), 2.50-2.38 (m, 2H), 2.13 (s, 3H). |
| 388 | 6-chloro-3-{2-acetamidoimidazo[1,2-b]pyridazin-6-yl}-2-fluoro-N-[(1R)-1-[2-fluoro-5-(trifluoromethoxy)phenyl]ethyl]benzamide | 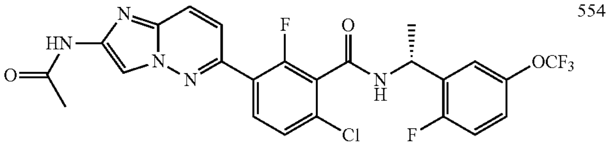 | 554 | 1H NMR (500 MHz, DMSO-d6) δ 10.85 (br s, 1H), 9.37 (br d, J = 7.5 Hz, 1H), 8.33 (s, 1H), 8.09 d, J = 9.4 Hz 1H) 7.92 (br t, J = 8.3 Hz, 1H), 7.57 (br d, J = 8.4 Hz, 1H), 7.54-7.45 (m, 2H), 7.43-7.27 (m, 2H), 5.47-5.29 (m, 1H), 2.14 (s, 3H), 1.47 (br d, J = 7.0 Hz, 3H). |
| 389 | 6-chloro-3-{2-acetamidoimidazo[1,2-b]pyridazin-6-yl}-2-fluoro-N-{[2-fluoro-5-(1-methyl-1H-pyrazol-4-yl)phenyl]methyl}benzamide | 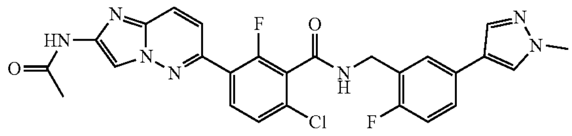 [SMILES: CC(=O)Nc1cn2nc(-c3ccc(Cl)c(C(=O)NCc4cc(-c5cnn(C)c5)ccc4F)c3F)ccc2n1] | 536 | 1H NMR (500 MHz, DMSO-d6) δ 10.83 (br s, 1H), 9.25 (br t, J = 5.6 Hz, 1H), 8.34 (s, 1H), 8.08 (d, J = 9.3 Hz, 1H), 8.00 (s, 1H), 7.91 (t, J = 8.3 Hz, 1H), 7.74 (s, 1H), 7.65 (br d, J = 6.9 Hz, 1H), 7.61-7.42 (m, 3H), 7.19 (t, J = 9.2 Hz, 1H), 4.57 (br d, J = 5.6 Hz, 2H), 3.90-3.83 (m, 3H), 2.13 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 390 | 6-chloro-N-[(3S)-3-(4-chlorophenyl)-3-hydroxypropyl]-3-{2-acetamidoimidazo[1,2-b]pyridazin-6-yl}-2-fluorobenzamide | 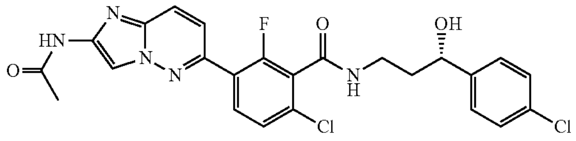 [SMILES: CC(=O)Nc1cn2nc(-c3ccc(Cl)c(C(=O)NCC[C@H](O)c4ccc(Cl)cc4)c3F)ccc2n1] | 516 | 1H NMR (500 MHz, DMSO-d6) δ 10.99 (s, 1H), 8.88 (br s, 1H), 8.32 (s, 1H), 8.09 (br d, J = 9.4 Hz, 1H), 7.89 (br t, J = 8.4 Hz, 1H), 7.62-7.46 (m, 2H), 7.42-7.34 (m, 4H), 5.66-5.33 (m, 1H), 4.67 (br d, J = 4.6 Hz, 1H), 3.47-3.27 (m, 2H), 2.12 (s, 3H), 1.82 (q, J = 7.0 Hz, 2H). |
| 391 | 6-chloro-3-{2-acetamidoimidazo[1,2-b]pyridazin-6-yl}-2-fluoro-N-{[4-(trifluoromethoxy)phenyl]methyl}benzamide | 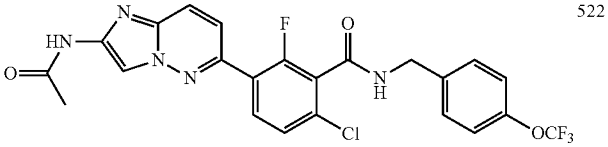 | 522 | 1H NMR (500 MHz, DMSO-d6) δ 10.99 (s, 1H), 9.44 (br t, J = 5.8 Hz, 1H), 8.32 (s, 1H), 8.09 (br d, J = 9.4 Hz, 1H), 7.90 (t, J = 8.3 Hz, 1H), 7.60-7.44 (m, 4H), 7.36 (br d, J = 8.0 Hz, 2H), 4.54 (br d, J = 5.6 Hz, 2H), 2.12 (s, 3H). |
| 392 | 2-chloro-5-{2-acetamidoimidazo[1,2-b]pyridazin-6-yl}-4-fluoro-N-[(1R)-1-[2-fluoro-5-(trifluoromethoxy)phenyl]ethyl]benzamide | 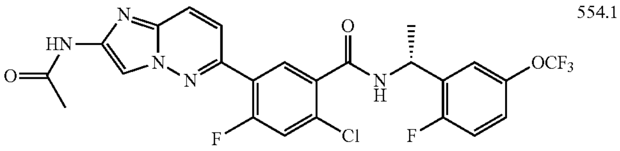 | 554.1 | 1H NMR (500 MHz, DMSO-d6) δ 10.97 (br s, 1H), 9.25 (br d, J = 7.6 Hz, 1H), 8.35 (br s, 1H), 8.12 (br d, J = 9.5 Hz, 1H), 7.92 (br d, J = 7.9 Hz, 1H), 7.79 (br d, J = 10.7 Hz, 1H), 7.58 (br d, J = 8.5 Hz, 1H), 7.49 (br s, 1H), 7.41-7.33 (m, 2H), 5.34 (br t, J = 7.2 Hz, 1H), 2.13 (s, 3H), 1.46 (br d, J = 7.0 Hz, 3H). |
| 393 | 2-chloro-5-{2-acetamidoimidazo[1,2-b]pyridazin-6-yl}-N-{[2-fluoro-5-(trifluoromethoxy)phenyl]methyl}-4-methylbenzamide | 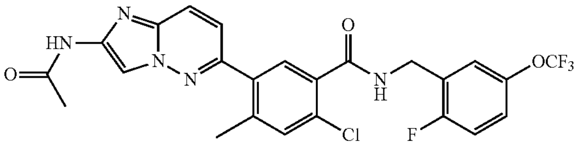 [SMILES: CC(=O)Nc1cn2nc(-c3cc(C(=O)NCc4cc(OC(F)(F)F)ccc4F)c(Cl)cc3C)ccc2n1] | 1071 | 1H NMR (500 MHz, DMSO-d6) δ 10.77 (br s, 1H), 9.01 (br t, J = 5.7 Hz, 1H), 8.28 (s, 1H), 8.02 (d, J = 9.3 Hz, 1H), 7.54 (s, 2H), 7.46-7.39 (m, 1H), 7.39-7.27 (m, 3H), 4.52 (br d, J = 5.8 Hz, 2H), 2.39 (s, 3H), 2.12 (s, 3H). |
| 394 | 5-{2-acetamidoimidazo[1,2-b]pyridazin-6-yl}-N-{[2-fluoro-5-(trifluoromethoxy)phenyl]methyl}-2-methylbenzamide | 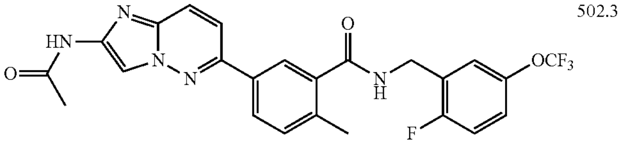 | 502.3 | 1H NMR (500 MHz, DMSO-d6) δ 10.90 (s, 1H), 9.07 (br t, J = 5.6 Hz, 1H), 8.28 (s, 1H), 8.07-8.00 (m, 3H), 7.79 (d, J = 9.5 Hz, 1H), 7.47-7.34 (m, 4H), 4.54 (br d, J = 5.5 Hz, 2H), 2.38 (s, 3H), 2.12 (s, 3H). |

TABLE 19-continued

| Compounds in Table 19 were prepared by methods as described in Examples 14, 15, 323, and 358. | | | | |
|---|---|---|---|---|
| Ex | Name | Structure | Obs. MS Ion | NMR Assignments |
| 395 | (S)-N-(2-fluoro-5-(trifluoromethoxy)benzyl)-5-(2-(2-hydroxypropanamido)imidazo[1,2-b]pyridazin-6-yl)-2-methylbenzamide | 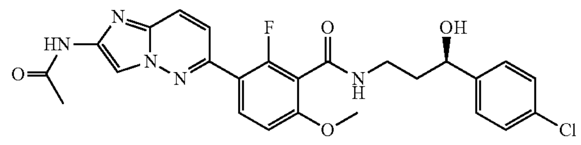 [SMILES: COc1ccc(-c2ccc3nc(NC(C)=O)cn3n2)c(F)c1C(=O)NCC[C@@H](O)c1ccc(Cl)cc1] | 532.1 | 1H NMR (400 MHz, DMSO-d6) δ 10.26 (br s, 1H), 9.07 (br t, J = 5.7 Hz, 1H), 8.35 (s, 1H), 8.14-8.01 (m, 3H), 7.84 (d, J = 9.5 Hz, 1H), 7.50-7.34 (m, 4H), 5.67 (br s, 1H), 4.55 (br d, J = 5.7 Hz, 2H), 4.28 (br s, 1H), 2.44-2.35 (m, 3H), 1.33 (d, J = 6.7 Hz, 3H) |
| 396 | (R)-5-(2-acetamidoimidazo[1,2-b]pyridazin-6-yl)-N-(1-(2-fluoro-5-(trifluoromethoxy)phenyl)ethyl)-2-methylbenzamide | 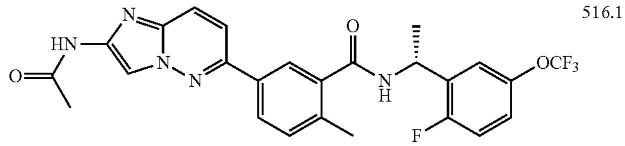 | 516.1 | 1H NMR (400 MHz, DMSO-d6) δ 10.91 (s, 1H), 9.05 (br d, J = 7.7 Hz, 1H), 8.30 (s, 1H), 8.11-8.00 (m, 3H), 7.82 (d, J = 9.5 Hz, 1H), 7.52-7.33 (m, 4H), 5.38 (quin, J = 7.2, 1H), 2.33 (s, 3H), 2.12 (s, 3H), 1.47 (d, J = 7.0 Hz, 3H) |
| 397 | N-[(3R)-3-(4-chlorophenyl)-3-hydroxypropyl]-5-{2-acetamidoimidazo[1,2-b]pyridazin-6-yl}-2-methylbenzamide | 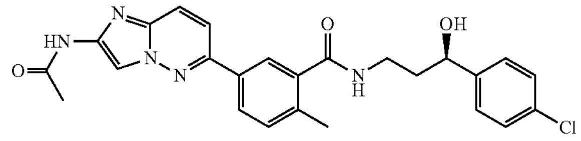 [SMILES: CC(=O)Nc1cn2nc(-c3ccc(C)c(C(=O)NCC[C@@H](O)c4ccc(Cl)cc4)c3)ccc2n1] | 478.3 | 1H NMR (500 MHz, DMSO-d6) δ 10.90 (s, 1H), 8.40 (br t, J = 5.2 Hz, 1H), 8.30 (s, 1H), 8.05 (d, J = 9.5 Hz, 1H), 8.00 (br d, J = 7.9 Hz, 1H), 7.95 (s, 1H), 7.80 (d, J = 9.5 Hz, 1H), 7.43-7.38 (m, 6H), 4.70-4.66 (m, 1H), 3.45-3.41 (m, 1H), 3.36-3.31 (m, 1H), 2.40 (s, 3H), 2.12 (s, 3H), 1.87 (q, J = 6.9 Hz, 2H). |
| 398 | N-[(3S)-3-(4-chlorophenyl)-3-hydroxypropyl]-5-{2-acetamidoimidazo[1,2-b]pyridazin-6-yl}-2-methylbenzamide | 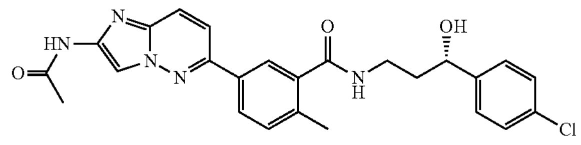 [SMILES: CC(=O)Nc1cn2nc(-c3ccc(C)c(C(=O)NCC[C@H](O)c4ccc(Cl)cc4)c3)ccc2n1] | 478.3 | 1H NMR (500 MHz, DMSO-d6) δ 10.75 (br s, 1H), 8.34-8.21 (m, 3H), 8.04-7.91 (m, 3H), 7.75 (dd, J = 9.5, 1.6 Hz, 1H), 7.44-7.35 (m, 5H), 4.69 (br t, J = 6.0 Hz, 1H), 2.58-2.54 (m, 2H) 2.41 (s, 3H), 2.12 (s, 3H), 1.89 (q, J = 6.8 Hz, 2H). |
| 399 | N-(1-benzyl-1H-pyrazol-4-yl)-5-{2-acetamidoimidazo[1,2-b]pyridazin-6-yl}-2-methylbenzamide | 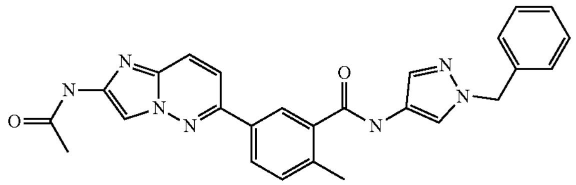 [SMILES: CC(=O)Nc1cn2nc(-c3ccc(C)c(C(=O)Nc4cnn(Cc5ccccc5)c4)c3)ccc2n1] | 466.2 | 1H NMR (500 MHz, DMSO-d6) δ 10.72 (br s, 1H), 10.41 (s, 1H), 8.37- 8.17 (m, 1H), 8.11-7.95 (m, 4H), 7.85-7.67 (m, 1H), 7.60 (s, 1H), 7.46 (d, J = 8.0 Hz, 1H), 7.38-7.25 (m, 5H), 5.29 (s, 2H), 2.42 (s, 3H), 2.11 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 400 | 5-{2-acetamidoimidazo[1,2-b]pyridazin-6-yl}-N-(2-hydroxy-3-phenoxypropyl)-2-methylbenzamide | 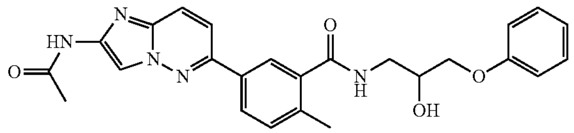 [SMILES: CC(=O)Nc1cn2nc(-c3ccc(C)c(C(=O)NCC(O)COc4ccccc4)c3)ccc2n1] | 460.2 | 1H NMR (500 MHz, DMSO-d6) δ 10.90 (s, 1H), 8.47 (br t, J = 5.6 Hz, 1H), 8.29 (s, 1H), 8.06 (d, J = 9.5 Hz, 1H), 8.02 (s, 1H), 8.01 (d, J = 8.7 Hz, 1H), 7.79 (d, J = 9.5 Hz, 1H), 7.42 (br d, J = 7.9 Hz, 1H), 7.30 (br t, J = 7.8 Hz, 2H), 6.97-6.92 (m, 3H), 5.27 (d, J = 5.2 Hz, 1H), 4.06-4.01 (m, 2H), 3.96-3.92 (m, 1H), 2.55-2.53 (m, 2H), 2.40 (s, 3H), 2.12 (s, 3H). |
| 401 | 5-{2-acetamidoimidazo[1,2-b]pyridazin-6-yl}-N-{[(1S, 2S)-2-(4-fluorophenyl)cyclopropyl]methyl}-2-methylbenzamide | 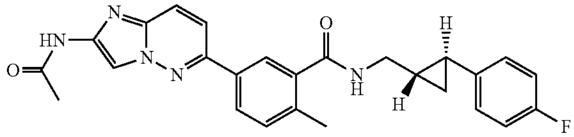 [SMILES: CC(=O)Nc1cn2nc(-c3ccc(C)c(C(=O)NC[C@H]4C[C@@H]4c4ccc(F)cc4)c3)ccc2n1] | 458.3 | 1H NMR (500 MHz, DMSO-d6) δ 10.90 (s, 1H), 8.63-8.59 (m, 1H), 8.29 (s, 1H), 8.05 (br d, J = 9.5 Hz, 1H), 8.02-7.94 (m, 2H), 7.78 (br d, J = 9.5 Hz, 1H), 7.41 (br d, J = 8.2 Hz, 1H), 7.15-7.04 (m, 4H), 3.25 (dt, J = 13.6, 6.6 Hz, 1H), 2.55-2.53 (m, 1H), 2.37 (s, 3H), 2.11 (s, 3H), 1.96-1.90 (m, 1H), 1.33 (br s, 1H), 1.00-0.91 (m, 2H). |
| 402 | 5-{2-acetamidoimidazo[1,2-b]pyridazin-6-yl}-N-{[2-fluoro-6-(1-methyl-1H-pyrazol-4-yl)phenyl]methyl}-2-methylbenzamide | 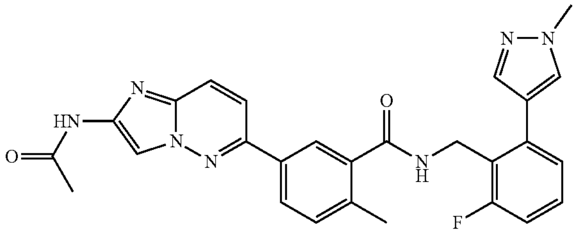 [SMILES: CC(=O)Nc1cn2nc(-c3ccc(C)c(C(=O)NCc4c(F)cccc4-c4cnn(C)c4)c3)ccc2n1] | 498.4 | 1H NMR (500 MHz, DMSO-d6) δ 10.76 (br s, 1H), 8.57 (br s, 1H), 8.29 (s, 1H), 8.03 (d, J = 9.4 Hz, 1H), 8.00-7.92 (m, 2H), 7.89 (s, 1H), 7.74 (d, J = 9.5 Hz, 1H), 7.70-7.63 (m, 1H), 7.44-7.28 (m, 2H), 7.26-7.19 (m, 1H), 7.19-6.99 (m, 1H), 4.59 (br d, J = 3.8 Hz, 2H), 3.94-3.88 (m, 3H), 2.48-2.32 (m, 3H), 2.13 (s, 3H). |
| 403 | 5-{2-acetamidoimidazo[1,2-b]pyridazin-6-yl}-N-{[5-fluoro-2-(1-methyl-1H-pyrazol-4-yl)phenyl]methyl}-2-methylbenzamide | 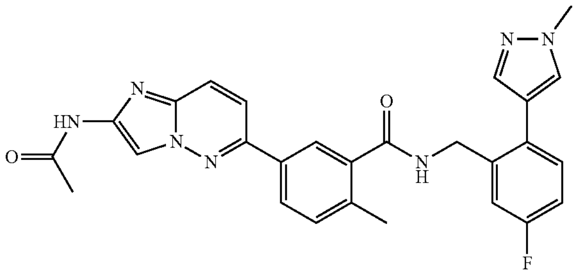 [SMILES: CC(=O)Nc1cn2nc(-c3ccc(C)c(C(=O)NCc4cc(F)ccc4-c4cnn(C)c4)c3)ccc2n1] | 498.2 | 1H NMR (500 MHz, DMSO-d6) δ 10.77 (br s, 1H), 8.85 (br t, J = 5.6 Hz, 1H), 8.30 (s, 1H), 8.09-7.99 (m, 3H), 7.96 (s, 1H), 7.78 (d, J = 9.4 Hz, 1H), 7.66 (s, 1H), 7.51-7.34 (m, 2H), 7.28 (dd, J = 10.3, 2.4 Hz, 1H), 7.13 (t, J = 8.4 Hz, 1H), 4.58 (br d, J = 5.6 Hz, 2H), 3.92 (s, 3H), 2.48-2.39 (m, 3H), 2.13 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 404 | N-{[5-(3,3-difluoroazetidine-1-carbonyl)-2-fluorophenyl]methyl}-5-{2-acetamidoimidazo[1,2-b]pyridazin-6-yl}-2-methylbenzamide | 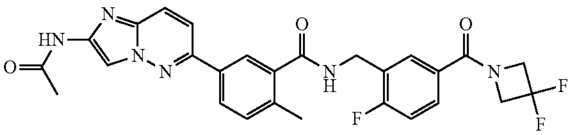 [SMILES: CC(=O)Nc1cn2nc(-c3ccc(C)c(C(=O)NCc4cc(C(=O)N5CC(F)(F)C5)ccc4F)c3)ccc2n1] | 537.3 | 1H NMR (500 MHz, DMSO-d6) δ 10.90 (s, 1H), 9.04 (br t, J = 5.6 Hz, 1H), 8.31 (s, 1H), 8.07-8.02 (m, 3H), 7.85-7.79 (m, 2H), 7.68 (br s, 1H), 7.45 (br d, J = 7.9 Hz, 1H), 7.32 (br t, J = 9.2 Hz, 1H), 4.75 (br s, 2H), 4.56 (br d, J = 5.5 Hz, 2H), 4.54-4.35 (m, 2H), 2.41 (s, 3H), 2.11 (s, 3H). |
| 405 | N-{[2-(3,3-difluoropyrrolidine-1-carbonyl)-4-fluorophenyl]methyl}-5-{2-acetamidoimidazo[1,2-b]pyridazin-6-yl}-2-methylbenzamide | 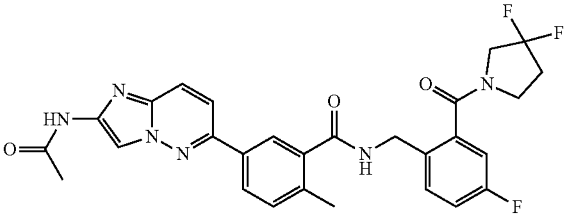 [SMILES: CC(=O)Nc1cn2nc(-c3ccc(C)c(C(=O)NCc4ccc(F)cc4C(=O)N4CCC(F)(F)C4)c3)ccc2n1] | 551 | 1H NMR (500 MHz, DMSO-d6) δ 10.90 (s, 1H), 8.97-8.91 (m, 1H), 8.29 (s, 1H), 8.09-8.01 (m, 3H), 7.82 (br d, J = 9.5 Hz, 1H), 7.58-7.52 (m, 1H), 7.43 (br d, J = 7.9 Hz, 1H), 7.35-7.24 (m, 2H), 4.45-4.39 (m, 2H), 3.94 (br t, J = 13.4 Hz 1H), 3.79-3.70 (m, 1H), 3.50 (br t, J = 7.0 , Hz, 1H), 2.48-2.40 (m, 3H), 2.40-2.35 (m, 3H), 2.11 (s, 3H). |
| 406 | N-{[5-(3,3-dimethylpyrrolidine-1-carbonyl)-2-fluorophenyl]methyl}-5-{2-acetamidoimidazo[1,2-b]pyridazin-6-yl}-2-methylbenzamide | 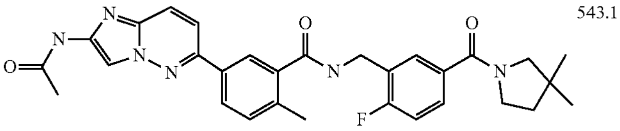 | 543.1 | 1H NMR (500 MHz, DMSO-d6) δ 10.89 (br s, 1H), 9.05-9.00 (m, 1H), 8.29 (s, 1H), 8.06-7.98 (m, 3H), 7.79 (br d, J = 8.9 Hz, 1H), 7.59 (br d, J = 7.3 Hz, 1H), 7.53-7.45 (m, 1H), 7.43 (br d, J = 7.6 Hz, 1H), 7.26 (br t, J = 9.0 Hz, 1H), 4.54 (br d, J = 4.6 Hz, 2H), 3.39-3.35 (m, 2H), 3.27-3.06 (m, 2H), 2.38 (br s, 3H), 2.10 (s, 3H), 1.72-1.47 (m, 2H), 1.02 (s, 3H), 0.90 (s, 3H). |
| 407 | N-({3,5-difluoro-2-[(3S)-3-hydroxypyrrolidine-1-carbonyl]phenyl}methyl)-5-{2-acetamidoimidazo[1,2-b]pyridazin-6-yl}-2-methylbenzamide | 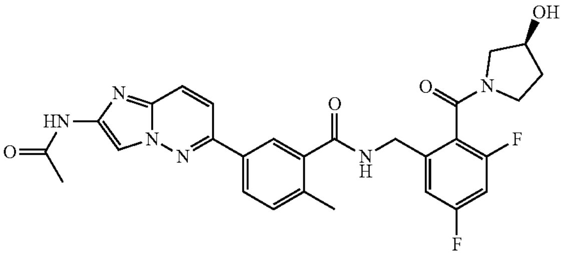 [SMILES: CC(=O)Nc1cn2nc(-c3ccc(C)c(C(=O)NCc4cc(F)cc(F)c4C(=O)N4CC[C@H](O)C4)c3)ccc2n1] | 549.1 | 1H NMR (500 MHz, DMSO-d6) δ 10.90 (br s, 1H), 9.01 (br s, 1H), 8.28 (s, 1H), 8.10-8.01 (m, 3H), 7.82 (br d, J = 8.9 Hz, 1H), 7.44 (br t, J = 6.6 Hz, 1H), 7.27 (br t, J = 8.9 Hz, 1H), 7.18-7.10 (m, 1H), 4.47-4.40 (m, 1H), 4.38 (br s, 1H), 4.33 (br s, 1H), 4.25 (br s, 1H), 2.55-2.53 (m, 3H), 2.44-2.36 (m, 4H), 2.11 (s, 3H), 1.91-1.75 (m, 2H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 408 | 5-{2-acetamidoimidazo[1,2-b]pyridazin-6-yl}-N-{[5-fluoro-2-(piperidine-1-carbonyl)phenyl]methyl}-2-methylbenzamide | 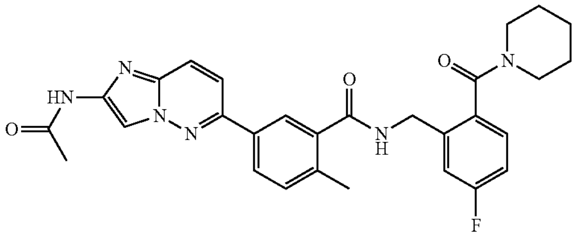 [SMILES: CC(=O)Nc1cn2nc(-c3ccc(C)c(C(=O)NCc4cc(F)ccc4C(=O)N4CCCCC4)c3)ccc2n1] | 529.5 | 1H NMR (500 MHz, DMSO-d6) δ 10.90 (s, 1H), 8.91 (br s, 1H), 8.28 (s, 1H), 8.11-8.01 (m, 3H), 7.83 (br d, J = 9.5 Hz, 1H), 7.44 (br d, J = 7.6 Hz, 1H), 7.32-7.23 (m, 2H), 7.17 (br t, J = 7.3, 1H), 4.44 (br s, 2H), 3.80-3.48 (m, 1H), 3.18 (br s, 1H), 2.42 (s, 3H), 2.11 (s, 3H), 1.57 (br s, 5H), 1.45 (br s, 3H). |
| 409 | N-{[5-(1-cyclopropyl-1H-pyrazol-4-yl)-2-fluorophenyl]methyl}-3-{2-acetamidoimidazo[1,2-b]pyridazin-6-yl}-2-fluoro-6-methylbenzamide | 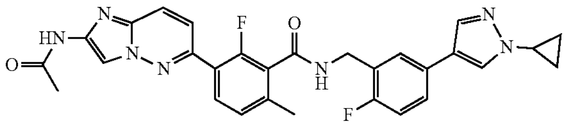 [SMILES: CC(=O)Nc1cn2nc(-c3ccc(C)c(C(=O)NCc4cc(-c5cnn(C6CC6)c5)ccc4F)c3F)ccc2n1] | 542.1 | 1H NMR (500 MHz, DMSO-d6) δ 10.92 (s, 1H), 9.14 (br s, 1H), 8.30 (s, 1H), 8.10-8.03 (m, 2H), 7.77-7.71 (m, 2H), 7.63 (br d, J = 6.7 Hz, 1H), 7.49 (br d, J = 8.5 Hz, 2H), 7.27 (br d, J = 7.9 Hz, 1H), 7.18 (br t, J = 9.2 Hz, 1H), 4.53 (br d, J = 4.9 Hz, 2H), 3.70 (br s, 1H), 2.33 (s, 3H), 2.10 (s, 3H), 1.01 (br s, 2H), 0.92 (br d, J = 5.2 Hz, 2H). |
| 410 | N-{[2-(1-cyclopropyl-1H-pyrazol-4-yl)-5-fluorophenyl]methyl}-3-{2-acetamidoimidazo[1,2-b]pyridazin-6-yl}-2-fluoro-6-methylbenzamide | 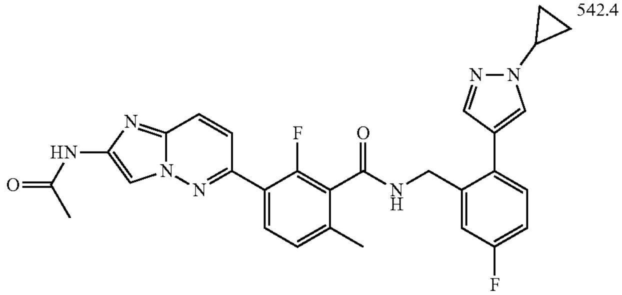 | 542.4 | 1H NMR (500 MHz, DMSO-d6) δ 10.92 (s, 1H), 9.19 (br s, 1H), 8.29 (s, 1H), 8.07 (d, J = 9.1 Hz, 1H), 8.05 (s, 1H), 7.75 (br t, J = 7.8 Hz, 1H), 7.65 (s, 1H), 7.49 (br d, J = 8.9 Hz, 1H), 7.39 (t, J = 7.4 Hz, 1H), 7.29-7.22 (m, 2H), 7.12 (br t, J = 7.8 Hz, 1H), 4.55 (br d, J = 5.2 Hz, 2H), 3.76 (br s, 1H), 2.33 (s, 3H), 2.10 (s, 3H), 1.09 (br s, 2H), 0.98 (br d, J = 5.8 Hz, 2H). |
| 411 | N-{[2-(3,3-difluoropyrrolidine-1-carbonyl)-3,4-difluorophenyl]methyl}-3-{2-acetamidoimidazo[1,2-b]pyridazin-6-yl}-2-fluoro-6-methylbenzamide | 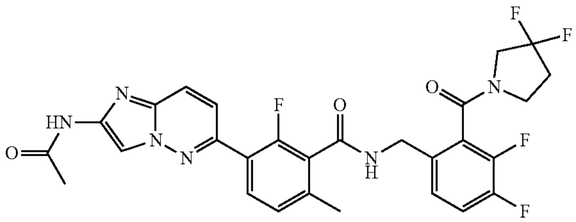 [SMILES: CC(=O)Nc1cn2nc(-c3ccc(C)c(C(=O)NCc4ccc(F)c(F)c4C(=O)N4CCC(F)(F)C4)c3F)ccc2n1] | 587.3 | 1H NMR (500 MHz, DMSO-d6) δ 10.90 (br s, 1H), 9.24 (br s, 1H), 8.27 (s, 1H), 8.04 (br d, J = 9.5 Hz, 1H), 7.76-7.70 (m, 1H), 7.60-7.51 (m, 1H), 7.46 (br d, J = 8.9 Hz, 1H), 7.31 (br s, 1H), 7.26 (br d , J = 7.6 Hz, 1H), 4.46-4.36 (m, 1H), 4.35-4.27 (m, 1H), 4.02-3.89 (m, 1H), 3.75-3.63 (m, 1H), 3.33 (br s, 1H), 2.46-2.38 (m, 3H), 2.31-2.27 (m, 3H), 2.09 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 412 | 3-{2-acetamidoimidazo[1,2-b]pyridazin-6-yl}-2-fluoro-N-[(1R)-1-[2-fluoro-5-(trifluoromethoxy)phenyl](2,2,2-Â$^2$Hâ,f)ethyl]-6-methylbenzamide | 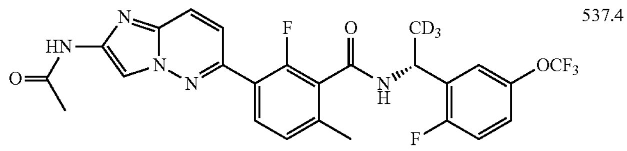 | 537.4 | 1H NMR (500 MHz, DMSO-d6) δ 10.92 (s, 1H), 9.26 (br d, J = 7.6 Hz, 1H), 8.29 (s, 1H), 8.06 (br d, J = 9.5 Hz, 1H), 7.76 (br t, J = 7.9 Hz, 1H), 7.49-7.42 (m, 2H), 7.38-7.31 (m, 2H), 7.26 (br d, J = 7.9 Hz, 1H), 5.34 (br d, J = 7.6 Hz, 1H), 2.26 (s, 3H), 2.10 (s, 3H). |
| 413 | 3-{2-acetamidoimidazo[1,2-b]pyridazin-6-yl}-2-fluoro-N-[(1R)-1-[2-fluoro-5-(trifluoromethyl)phenyl](2,2,2-Â$^2$Hâ,f)ethyl]-6-methylbenzamide | 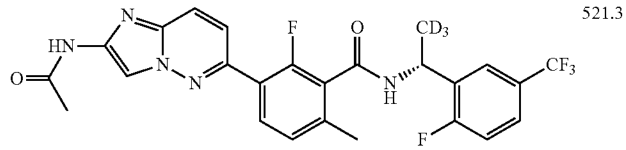 | 521.3 | 1H NMR (500 MHz, DMSO-d6) δ 10.94 (s, 1H), 9.33 (br d, J = 7.3 Hz, 1H), 8.30 (s, 1H), 8.08 (d, J = 9.5 Hz, 1H), 7.86 (br d, J = 5.8 Hz, 1H), 7.81-7.70 (m, 2H), 7.51-7.44 (m, 2H), 7.29 (br d, J = 7.9 Hz, 1H), 5.39 (br d, J = 7.6 Hz, 1H), 2.28 (s, 3H), 2.12 (s, 3H). |
| 414 | N-[(3,5-difluoro-2-methoxyphenyl)methyl]-3-{2-acetamidoimidazo[1,2-b]pyridazin-6-yl}-2-fluoro-6-methylbenzamide | 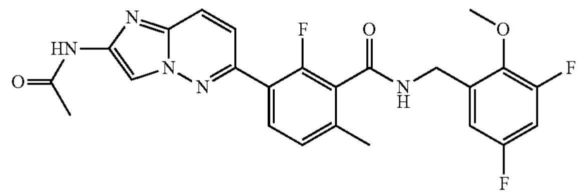 [SMILES: COc1c(F)cc(F)cc1CNC(=O)c1c(C)ccc(-c2ccc3nc(NC(C)=O)cn3n2)c1F] | 484.2 | 1H NMR (500 MHz, DMSO-d6) δ 10.95 (s, 1H), 9.21 (t, J = 5.9 Hz, 1H), 8.31 (s, 1H), 8.08 (d, J = 9.4 Hz, 1H), 7.77 (t, J = 8.0 Hz, 1H), 7.51 (dd, J = 9.4, 1.9 Hz, 1H), 7.33-7.22 (m, 2H), 7.01 (br d, J = 9.2 Hz, 1H), 4.53 (d, J = 6.0 Hz, 2H), 3.87 (s, 3H), 2.34 (s, 3H), 2.12 (s, 3H). |
| 415 | N-[(3R)-3-(4-chlorophenyl)-3-hydroxypropyl]-5-{2-acetamidoimidazo[1,2-b]pyridazin-6-yl}-4-fluoro-2-methylbenzamide | 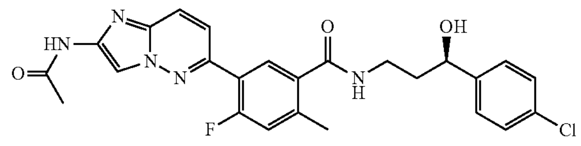 [SMILES: CC(=O)Nc1cn2nc(-c3cc(C(=O)NCC[C@@H](O)c4ccc(Cl)cc4)c(C)cc3F)ccc2n1] | 496.1 | 1H NMR (500 MHz, DMSO-d6) δ 10.93 (s, 1H), 8.39 (br s, 1H), 8.32 (s, 1H), 8.06 (d, J = 9.2 Hz, 1H), 7.73 (br d, J = 7.9 Hz, 1H), 7.54 (br d, J = 8.9 Hz, 1H), 7.38 (s, 4H), 7.32 (br d, J = 11.8 Hz, 1H), 4.66 (br s, 1H), 3.60-3.51 (m, 1H), 3.31 (br s, 2H), 2.41 (s, 3H), 2.12 (s, 3H), 1.85 (q, J = 6.7 Hz, 2H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 416 | N-{[5-(2,2-dimethylpyrrolidine-1-carbonyl)-2-fluorophenyl]methyl}-5-{2-acetamidoimidazo[1,2-b]pyridazin-6-yl}-4-fluoro-2-methylbenzamide | 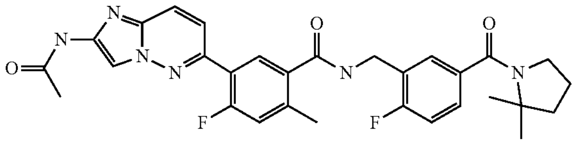 [SMILES: CC(=O)Nc1cn2nc(-c3cc(C(=O)NCc4cc(C(=O)N5CCCC5(C)C)ccc4F)c(C)cc3F)ccc2n1] | 561.1 | 1H NMR (500 MHz, DMSO-d6) δ 10.92 (s, 1H), 9.00 (br s, 1H), 8.31 (s, 1H), 8.07 (br d, J = 9.5 Hz, 1H), 7.82 (br d, J = 7.6 Hz, 1H), 7.54 (br d, J = 9.5 Hz, 1H), 7.45 (br d, J = 5.8 Hz, 1H), 7.37 (s, 1H), 7.35-7.31 (m, 1H), 7.22 (br t, J = 9.0 Hz, 1H), 4.51 (br d, J = 5.5 Hz, 2H), 2.54-2.52 (m, 2H), 2.45-2.36 (m, 3H), 2.11 (s, 3H), 1.80- 1.70 (m, 2H), 1.68 (br d, J = 6.1 Hz, 2H), 1.44 (br s, 6H). |
| 417 | 5-{2-acetamidoimidazo[1,2-b]pyridazin-6-yl}-N-{[2-fluoro-5-(trifluoromethoxy)phenyl]methyl}-2-Â$^2$Hâ,f)methoxy-4-methylbenzamide | 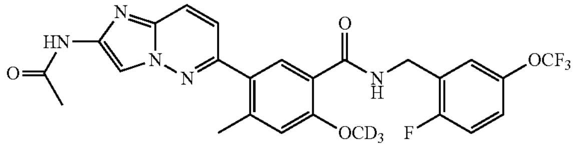 | 535.3 | 1H NMR (500 MHz, DMSO-d6) δ 10.89 (s, 1H), 8.83 (br t, J = 6.0 Hz, 1H), 8.26 (s, 1H), 8.00 (d, J = 9.5 Hz, 1H), 7.82 (s, 1H), 7.34 (br d, J = 8.9 Hz, 4H), 7.19 (s, 1H), 4.56 (br d, J = 5.8 Hz, 2H), 2.44 (s, 3H), 2.12 (s, 3H). |
| 418 | 5-{2-acetamidoimidazo[1,2-b]pyridazin-6-yl}-N-{[2-fluoro-5-(trifluoromethoxy)phenyl]methyl}-2-methoxybenzamide | 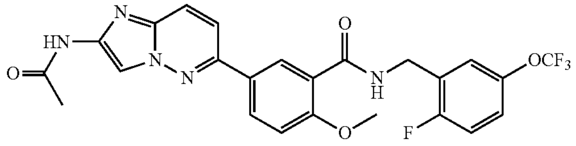 [SMILES: COc1ccc(-c2ccc3nc(NC(C)=O)cn3n2)cc1C(=O)NCc1cc(OC(F)(F)F)ccc1F] | 518 | 1H NMR (500 MHz, DMSO-d6) δ 10.72 (br s, 1H), 8.81 (br s, 1H), 8.32 (s, 1H), 8.27 (s, 1H), 8.15 (br d, J = 8.3 Hz, 1H), 7.99 (br d, J = 9.3 Hz, 1H), 7.72 (br d, J = 9.5 Hz, 1H), 7.40 (br s, 1H), 7.33 (br d, J = 8.9 Hz, 3H), 4.59 (br d, J = 5.9 Hz, 2H), 3.97 (s, 3H), 2.12 (s, 3H). |
| 419 | N-{[2-(2,2-dimethylpyrrolidine-1-carbonyl)-5-fluorophenyl]methyl}-5-{2-acetamidoimidazo[1,2-b]pyridazin-6-yl}-4-fluoro-2-methoxybenzamide | 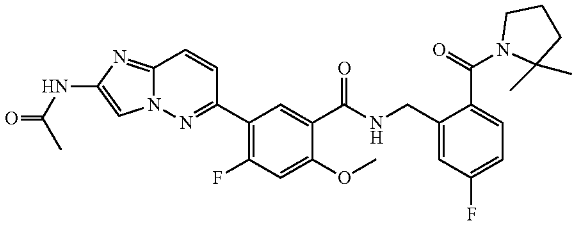 [SMILES: COc1cc(F)c(-c2ccc3nc(NC(C)=O)cn3n2)cc1C(=O)NCc1cc(F)ccc1C(=O)N1CCCC1(C)C] | 577.2 | 1H NMR (500 MHz, DMSO-d6) δ 10.88 (s, 1H), 8.78 (br s, 1H), 8.28-8.20 (m, 2H), 8.01 (br d, J = 9.2 Hz, 1H), 7.49 (br d, J = 9.2 Hz, 1H), 7.29-7.23 (m, 2H), 7.21-6.91 (m, 3H), 4.43 (br s, 2H), 3.98 (s, 3H), 3.16 (br d, J = 6.4 Hz, 1H), 2.08 (s, 3H), 1.78 (br d, J = 6.4 Hz, 2H), 1.72-1.65 (m, 2H), 1.49 (s, 6H). |
| 420 | 5-{2-acetamidoimidazo[1,2-b]pyridazin-6-yl}-4-fluoro-N-[(2-fluoro-6-methoxyphenyl)methyl]-2-methoxybenzamide | 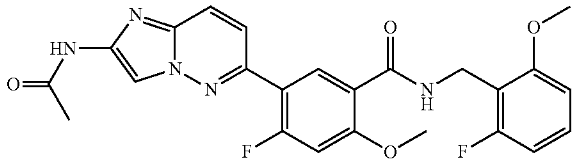 [SMILES: COc1cc(F)c(-c2ccc3nc(NC(C)=O)cn3n2)cc1C(=O)NCc1c(F)cccc1OC] | 482.3 | 1H NMR (500 MHz, DMSO-d6) δ 10.77 (br s, 1H), 8.38-8.28 (m, 2H), 8.02 (d, J = 9.4 Hz, 1H), 7.50 (br d, J = 9.3 Hz, 1H), 7.36-7.22 (m, 2H), 6.92 (d, J = 8.4 Hz, 1H), 6.88-6.74 (m, 2H), 4.59 (d, J = 5.5 Hz, 2H), 4.00 (s, 3H), 3.93 (s, 3H), 2.13 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 421 | 5-{2-acetamidoimidazo[1,2-b]pyridazin-6-yl}-N-{[2-fluoro-5-(trifluoromethoxy)phenyl]methyl}-2-methoxy-4-methylbenzamide | 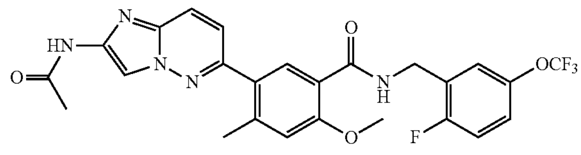 [SMILES: COc1cc(C)c(-c2ccc3nc(NC(C)=O)cn3n2)cc1C(=O)NCc1cc(OC(F)(F)F)ccc1F] | 532.3 | 1H NMR (500 MHz, DMSO-d6) δ 10.87 (s, 1H), 8.85 (br s, 1H), 8.24 (s, 1H), 7.98 (br d, J = 9.2 Hz, 1H), 7.79 (s, 1H), 7.35-7.28 (m, 4H), 7.17 (s, 1H), 4.55 (br d, J = 5.5 Hz, 2H), 3.96 (s, 3H), 2.41 (s, 3H), 2.11 (s, 3H). |
| 422 | N-(2-fluoro-5-(trifluoromethoxy)benzyl)-5-(2-(2-hydroxyacetamido)imidazo[1,2-b]pyridazin-6-yl)-2-methoxy-4-methylbenzamide | 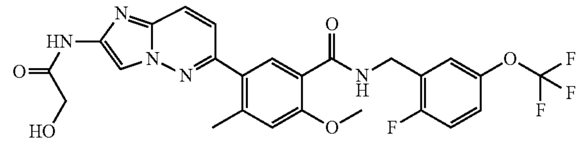 [SMILES: COc1cc(C)c(-c2ccc3nc(NC(=O)CO)cn3n2)cc1C(=O)NCc1cc(OC(F)(F)F)ccc1F] | 548.1 | 1H NMR (400 MHz, DMSO-d6) δ 10.31 (s, 1H), 8.82 (t, J = 6.0 Hz, 1H), 8.32 (s, 1H), 8.04 (d, J = 9.3 Hz, 1H), 7.83 (s, 1H), 7.40-7.33 (m, 4H), 7.21 (s, 1H), 5.55 (t, J = 6.1 Hz, 1H), 4.56 (d, J = 6.0 Hz, 2H), 4.15-4.04 (m, 2H), 3.98 (s, 3H), 2.45 (s, 3H) |
| 423 | 3-{2-acetamidoimidazo[1,2-b]pyridazin-6-yl}-2,4-difluoro-N-[(1R)-1-[2-fluoro-5-(trifluoromethyl)phenyl]ethyl]benzamide | 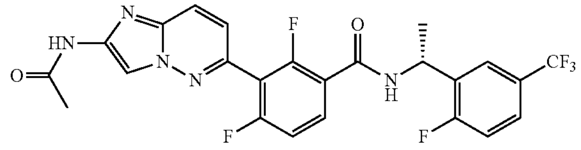 [SMILES: CC(=O)Nc1cn2nc(-c3c(F)ccc(C(=O)N[C@H](C)c4cc(C(F)(F)F)ccc4F)c3F)ccc2n1] | 522.2 | 1H NMR (500 MHz, DMSO-d6) δ 11.01 (s, 1H), 9.16 (br d, J = 7.6 Hz, 1H), 8.34 (s, 1H), 8.16 (d, J = 9.3 Hz, 1H), 7.89-7.75 (m, 2H), 7.72 (br s, 1H), 7.49-7.39 (m, 3H), 5.40 (br t, J = 7.0 Hz, 1H), 2.13 (s, 3H), 1.47 (d, J = 7.1 Hz, 3H). |
| 424 | 3-{2-acetamidoimidazo[1,2-b]pyridazin-6-yl}-2-fluoro-N-{[2-fluoro-5-(trifluoromethoxy)phenyl]methyl}benzamide | 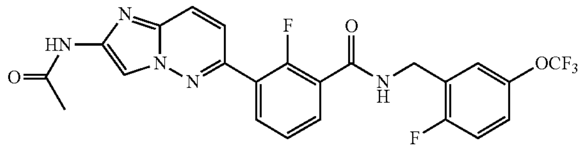 [SMILES: CC(=O)Nc1cn2nc(-c3cccc(C(=O)NCc4cc(OC(F)(F)F)ccc4F)c3F)ccc2n1] | 506.2 | 1H NMR (500 MHz, DMSO-d6) δ 10.95 (s, 1H), 9.10 (br s, 1H), 8.32 (s, 1H), 8.11 (d, J = 9.5 Hz, 1H), 7.92 (br t, J = 7.2 Hz, 1H), 7.74 (br t, J = 6.6 Hz, 1H), 7.54 (br d, J = 8.9 Hz, 1H), 7.48-7.34 (m, 4H), 4.55 (br d, J = 5.5 Hz, 2H), 2.12 (s, 3H). |
| 425 | 5-{2-acetamidoimidazo[1,2-b]pyridazin-6-yl}-N-[(1R)-1-[2-fluoro-5-(trifluoromethyl)phenyl](2,2,2-Â²Hâ‚ƒ)ethyl]-2 methylbenzamide | 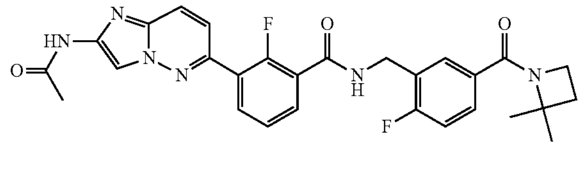 [SMILES: CC(=O)Nc1cn2nc(-c3cccc(C(=O)NCc4cc(C(=O)N5CCC5(C)C)ccc4F)c3F)ccc2n1] | 503 | 1H NMR (500 MHz, DMSO-d6) δ 10.90 (s, 1H), 9.08 (br d, J = 7.6 Hz, 1H), 8.30 (s, 1H), 8.09-7.98 J = 9.5 Hz, 1H), 7.73 (br s, 1H), 7.50-7.40 (m, 2H), 5.40 (br d, J = 7.6 Hz, 1H), 2.34-2.29 (m, 3H), 2.11 (s, 3H). |
| 426 | 5-{2-acetamidoimidazo[1,2-b]pyridazin-6-yl}-N-{[2-fluoro-5-(trifluoromethoxy)phenyl](Â²Hâ‚‚)methyl}-2-methylbenzamide | 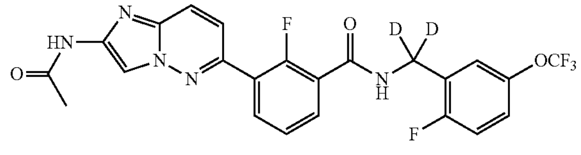 [SMILES: [2H]C([2H])(NC(=O)c1cccc(-c2ccc3nc(NC(C)=O)cn3n2)c1F)c1cc(OC(F)(F)F)ccc1F] | 504 | 1H NMR (500 MHz, DMSO-d6) δ 10.90 (s, 1H), 9.05 (s, 1H), 8.29 (s, 1H), 8.13-7.97 (m, 3H), 7.80 (d, J = 9.5 Hz, 1H), 7.47-7.34 (m, 4H), 2.48-2.35 (m, 3H), 2.11 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 427 | 3-{2-[2-(4,4-difluoropiperidin-1-yl)acetamido]imidazo[1,2-b]pyridazin-6-yl}-2-fluoro-N-{[2-fluoro-5-(trifluoromethoxy)phenyl]methyl}benzamide | 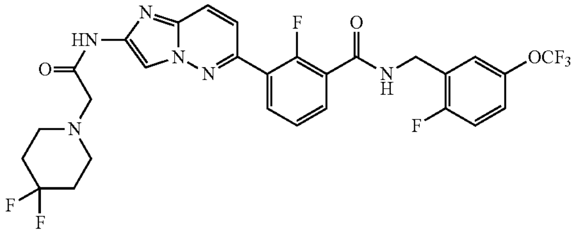 [SMILES: O=C(CN1CCC(F)(F)CC1)Nc1cn2nc(-c3cccc(C(=O)NCc4cc(OC(F)(F)F)ccc4F)c3F)ccc2n1] | 625 | 1H NMR (500 MHz, DMSO-d6) δ 11.45-10.91 (m, 1H), 9.14 (br t, J = 5.4 Hz, 1H), 8.37 (s, 1H), 8.11 (br d, J = 9.4 Hz, 1H), 7.91 (br t, J = 6.7 Hz, 1H), 7.74 (br t, J = 6.6 Hz, 1H), 7.56 (br d, J = 9.1 Hz, 1H), 7.46 (t, J = 7.6 Hz, 1H), 7.40-7.29 (m, 3H), 4.54 (br d, J = 5.2 Hz, 2H), 3.77 (br s, 2H), 3.04 (br s, 4H), 2.17 (br s, 4H). |
| 428 | N-[(3R)-3-(4-chlorophenyl)-3-hydroxypropyl]-2-fluoro-3-(2-{2-[4-(trifluoromethyl)piperidin-1-yl]acetamido}imidazo[1,2-b]pyridazin-6-yl)benzamide | 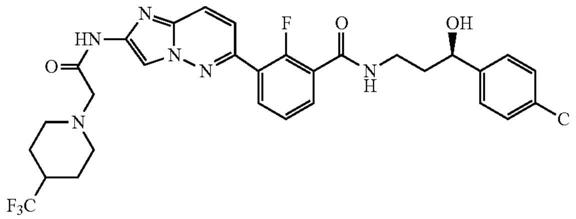 [SMILES: Cc1ccc([C@H](O)CCNC(=O)c2cccc(-c3ccc4nc(NC(=O)CN5CCC(C(F)(F)F)CC5)cn4n3)c2F)cc1] | 633.3 | 1H NMR (500 MHz, DMSO-d6) δ 10.73-10.47 (m, 1H), 8.47 (br s, 1H), 8.35 (s, 1H), 8.11 (br d, J = 9.6 Hz, 1H), 7.88 (br t, J = 7.4 Hz, 1H), 7.70 (br t, J = 6.6 Hz, 1H), 7.55 (br d, J = 9.1 Hz, 1H), 7.43 (br t, J = 7.6 Hz, 1H), 7.38 (s, 4H), 5.42 (br d, J = 3.6 Hz, 1H), 4.66 (br d, J = 3.6 Hz, 1H), 3.26 (br s, 3H), 2.97 (br d, J = 10.7 Hz, 2H), 2.34-2.15 (m, 3H), 1.87-1.73 (m, 4H), 1.63-1.48 (m, 2H). |
| 429 | 3-{2-acetamidoimidazo[1,2-b]pyridazin-6-yl}-2-fluoro-N-[(1S)-1-[2-fluoro-5-(trifluoromethoxy)phenyl](2,2,2-Â$^2$Hâ,f)ethyl]-4-methylbenzamide | 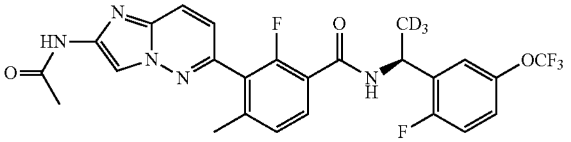 [SMILES: [2H]C([2H])([2H])[C@H](NC(=O)c1ccc(C)c(-c2ccc3nc(NC(C)=O)cn3n2)c1F)c1cc(OC(F)(F)F)ccc1F] | 537.2 | 1H NMR (500 MHz, DMSO-d6) δ 10.95 (s, 1H), 8.94 (br d, J = 7.0 Hz, 1H), 8.30 (s, 1H), 8.11 (br d, J = 9.2 Hz, 1H), 7.60 (br t, J = 7.3 Hz, 1H), 7.43 (br s, 1H), 7.36-7.28 (m, 4H), 5.32 (br d, J = 7.3 Hz, 1H), 2.23 (s, 3H), 2.12 (s, 3H). |
| 430 | 3-{2-acetamidoimidazo[1,2-b]pyridazin-6-yl}-2-fluoro-N-{[2-fluoro-5-(trifluoromethoxy)phenyl](Â$^2$Hâ,,)methyl}benzamide | 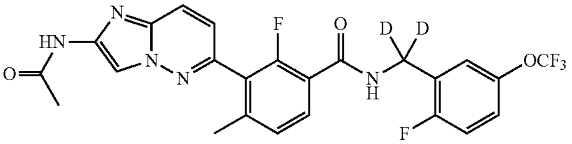 [SMILES: [2H]C([2H])(NC(=O)c1ccc(C)c(-c2ccc3nc(NC(C)=O)cn3n2)c1F)c1cc(OC(F)(F)F)ccc1F] | 508.1 | 1H NMR (500 MHz, DMSO-d6) δ 10.97 (s, 1H), 9.12 (s, 1H), 8.33 (s, 1H), 8.12 (d, J = 9.4 Hz, 1H), 7.93 (br t, J = 7.6 Hz, 1H), 7.76 (br t, J = 6.4 Hz, 1H), 7.55 (br d, J = 9.2 Hz, 1H), 7.51-7.35 (m, 4H), 2.13 (s, 3H). |

TABLE 19-continued

Compounds in Table 19 were prepared by methods as described in Examples 14, 15, 323, and 358.

| Ex | Name | Structure | Obs. MS Ion | NMR Assignments |
|---|---|---|---|---|
| 431 | 4-chloro-3-{2-acetamidoimidazo[1,2-b]pyridazin-6-yl}-N-{[2-fluoro-5-(trifluoromethoxy)phenyl]methyl}benzamide | 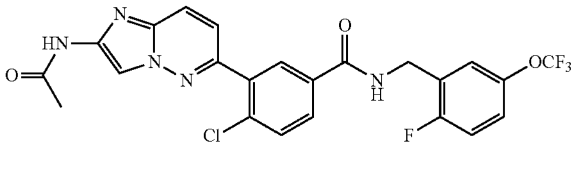 [SMILES: CC(=O)Nc1cn2nc(-c3cc(C(=O)NCc4cc(OC(F)(F)F)ccc4F)ccc3Cl)ccc2n1] | 522.2 | 1H NMR (500 MHz, DMSO-d6) δ 10.80 (br s, 1H), 9.16 (br s, 1H), 8.31 (s, 1H), 8.13 (s, 1H), 8.04 (br dd, J = 18.8, 8.9 Hz, 2H), 7.76 (d, J = 8.3 Hz, 1H), 7.48-7.42 (m, 1H), 7.38-7.29 (m, 3H), 4.55 (br d, J = 5.6 Hz, 2H), 2.13 (s, 3H). |
| 432 | 3-{2-acetamidoimidazo[1,2-b]pyridazin-6-yl}-4-fluoro-N-{[2-fluoro-5-(trifluoromethoxy)phenyl]methyl}benzamide | 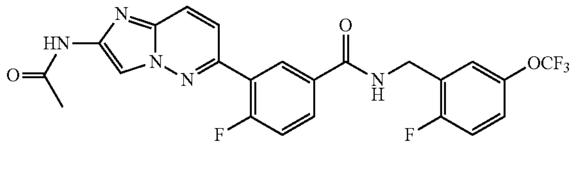 [SMILES: CC(=O)Nc1cn2nc(-c3cc(C(=O)NCc4cc(OC(F)(F)F)ccc4F)ccc3C)ccc2n1] | 506.2 | 1H NMR (500 MHz, DMSO-d6) δ 10.80 (br s, 1H), 9.22-9.09 (m, 1H), 8.39-8.29 (m, 2H), 8.06 (br d, J = 9.2 Hz, 2H), 7.56 (d, J = 9.1 Hz, 1H), 7.51 (t, J = 8.9 Hz, 1H), 7.39-7.29 (m, 3H), 4.56 (br d, J = 5.6 Hz, 2H), 2.13 (s, 3H). |
| 433 | 3-{2-acetamidoimidazo[1,2-b]pyridazin-6-yl}-N-{[2-fluoro-5-(trifluoromethoxy)phenyl]methyl}-4-methylbenzamide | 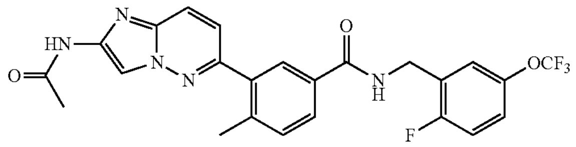 | 502.2 | 1H NMR (500 MHz, DMSO-d6) δ 10.90 (s, 1H), 9.17 (br t, J = 5.6 Hz, 1H), 8.28 (s, 1H), 8.03 (d, J = 9.2 Hz, 1H), 7.95 (s, 1H), 7.89 (br d, J = 7.9 Hz, 1H), 7.49 (d, J = 8.2 Hz, 1H), 7.39 (d, J = 9.5 Hz, 1H), 7.33-7.29 (m, 3H), 4.52 (br d, J = 5.5 Hz, 2H), 2.39 (s, 3H), 2.11 (s, 3H). |

Example 434: (R)-(((5-(2-acetamidoimidazo[1,2-b]pyridazin-6-yl)-2-methylnicotinoyl)(1-(2-fluoro-5-(trifluoromethoxy)phenyl)ethyl)carbamoyl)oxy)methyl 3-methoxy-4-(phosphonooxy)benzoate

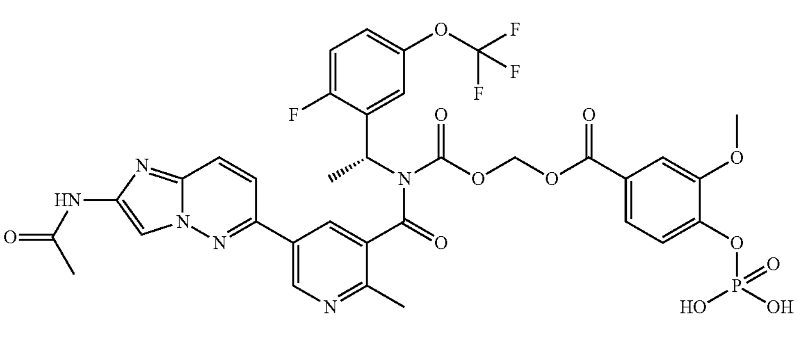 [SMILES: COc1cc(C(=O)OCOC(=O)N(C(=O)c2cc(-c3ccc4nc(NC(C)=O)cn4n3)cnc2C)[C@H](C)c2cc(OC(F)(F)F)ccc2F)ccc1OP(=O)(O)O]

434A: To a mixture of methyl vanillate (250 mg, 1.372 mmol) in DCM (2745 μl) was added dibenzyl N,N-diisopropylphosphoramidite (677 μl, 2.058 mmol) followed by tetrazole (0.45 M in acetonitrile) (4574 μl, 2.058 mmol). The resulting mixture was stirred at rt 1 h. TLC indicated the starting material had been consumed. The reaction mixture was cooled to 0° C. and hydrogen peroxide (35% in water) (1180 μl, 13.72 mmol) was added. The mixture was allowed to come to rt and stir for 1 h. TLC indicated the product of step 1 had been consumed. The reaction mixture was diluted with EtOAc, washed with water, brine, dried over $MgSO_4$, filtered and concentrated in vacuo.

Purification by flash chromatography (silica, 24 g, 0-75% EtOAc/Hexanes) gave methyl 4-((bis(benzyloxy)phosphoryl)oxy)-3-methoxybenzoate (594 mg, 1.343 mmol, 98% yield).

MS ESI m/z 443.1 (M+H)

1H NMR (400 MHz, DMSO-d6) δ 7.63-7.54 (m, 2H), 7.40-7.37 (m, 10H), 7.35-7.31 (m, 1H), 5.22-5.20 (m, 2H), 5.19 (s, 2H), 3.87 (s, 3H), 3.86-3.85 (m, 3H).

434B: To a mixture of methyl 4-((bis(benzyloxy)phosphoryl)oxy)-3-methoxybenzoate (594 mg, 1.343 mmol) in THF (8951 μl) and water (4476 μl) at 0° C. was added LiOH (64.3 mg, 2.69 mmol). The resulting mixture was stirred at 0° C. 5 h. The mixture was diluted with EtOAc and made acidic by the addition of aqueous 1 N HCl. The layers were separated and the organic layer was washed with brine, dried over $MgSO_4$, filtered and concentrated in vacuo. Purification by flash chromatography (silica, 24 g, 0-100% EtOAc/Hexanes) gave 4-((bis(benzyloxy)phosphoryl)oxy)-3-methoxybenzoic acid (287.1 mg, 0.670 mmol, 50% yield).

MS ESI m/z 429.1 (M+H)

434C: To a mixture of (R)-5-bromo-N-(1-(2-fluoro-5-(trifluoromethoxy)phenyl)ethyl)-2-methylnicotinamide (370 mg, 0.878 mmol) in THF (5856 μl) was added NaH (176 mg, 4.39 mmol) portionwise over 1 min. The mixture was allowed to stir at rt for 10 min at which time no further gas evolution was noted. Chloromethyl chloroformate (235 μl, 2.64 mmol) was added to the reaction mixture. The resulting mixture was stirred at rt for 6 h. The reaction mixture was diluted with EtOAc, washed with water, brine, dried over $MgSO_4$, filtered and concentrated in vacuo. Purification by flash chromatography (silica, 24 g, 0-50% EtOAc/Hexanes) gave chloromethyl (R)-(5-bromo-2-methylnicotinoyl)(1-(2-fluoro-5-(trifluoromethoxy)phenyl)ethyl) carbamate (250.4 mg, 0.487 mmol, 56% yield).

MS ESI m/z 514.0 (M+H)

1H NMR (400 MHz, DMSO-d6) δ 8.66 (d, J=2.2 Hz, 1H), 7.93 (d, J=2.3 Hz, 1H), 7.58-7.54 (m, 1H), 7.41 (br d, J=9.7 Hz, 2H), 6.12 (d, J=7.2 Hz, 1H), 5.73-5.67 (m, 2H), 2.38 (s, 3H), 1.81 (d, J=7.0 Hz, 3H). MS ESI 512.9 (M+H).

434D: A mixture of Bis(pinacolato)diboron (135 mg, 0.530 mmol), N-(6-chloroimidazo[1,2-b]pyridazin-2-yl)acetamide (93 mg, 0.442 mmol), potassium acetate (130 mg, 1.326 mmol), and [1,1'-bis(diphenylphosphino)ferrocene] dichloropalladium(II) (16.17 mg, 0.022 mmol) in 1,4-dioxane (1768 μl) was sparged with nitrogen for 5 min. The mixture was heated at 100° C. 1 h. LCMS indicated the starting material had been consumed. The mixture was allowed to come to rt and chloromethyl (R)-(5-bromo-2-methylnicotinoyl)(1-(2-fluoro-5-(trifluoromethoxy)phenyl) ethyl)carbamate (227 mg, 0.442 mmol), potassium carbonate (122 mg, 0.884 mmol), and 1,1'-bis(diphenylphosphino) ferrocene-palladium(II)dichloride dichloromethane complex (18.04 mg, 0.022 mmol) were added. The resulting mixture was sparged with nitrogen for 5 min. The mixture was again brought to 100° C. and stirred 1 h. After cooling to rt, the reaction mixture was diluted with EtOAc, washed with water, brine, dried over $MgSO_4$, filtered and concentrated in vacuo. Purification by flash chromatography (silica, 24 g, MeOH/DCM) gave chloromethyl (R)-(5-(2-acetamidoimidazo[1,2-b]pyridazin-6-yl)-2-methylnicotinoyl)(1-(2-fluoro-5-(trifluoromethoxy)phenyl)ethyl)carbamate (200 mg, 0.213 mmol, 48.3% yield). Used in the next step without further purification.

MS ESI m/z 609.1 (M+H)

434E: To a mixture of 4-((bis(benzyloxy)phosphoryl) oxy)-3-methoxybenzoic acid (1.23 g, 2.87 mmol), chloromethyl (R)-(5-(2-acetamidoimidazo[1,2-b]pyridazin-6-yl)-2-methylnicotinoyl)(1-(2-fluoro-5-(trifluoromethoxy)phenyl) ethyl)carbamate (1.11 g, 1.823 mmol), and sodium iodide (0.410 g, 2.73 mmol) in DMF (18.23 ml) was added Hünig's base (3.18 ml, 18.23 mmol). The resulting mixture was brought to 50° C. and stirred ON. The reaction mixture was diluted with EtOAc, washed with water, brine, dried over $MgSO_4$, filtered and concentrated in vacuo. The crude material obtained was triturated with diethyl ether to give a tan solid. The solid was taken up in. DCM and run through a plug of 12 g of silica gel, eluting with DCM. A significant amount of the desired product was found in the DCM wash which was concentrated to give (((5-(2-acetamidoimidazo[1,2-b]pyridazin-6-yl)-2-methylnicotinoyl)((R)-1-(2-fluoro-5-(trifluoromethoxy)phenyl)ethyl)carbamoyl)oxy)methyl 4-(((benzyloxy)(hydroxy)phosphoryl)oxy)-3-methoxybenzoate (163 mg, 0.179 mmol, 10% yield) as a brown solid. The material was carried forward without further purification.

MS ESI m/z 910.2 (M+H)

434: To a mixture of (((5-(2-acetamidoimidazo[1,2-b]pyridazin-6-yl)-2-methylnicotinoyl)((R)-1-(2-fluoro-5-(trifluoromethoxy)phenyl)ethyl)carbamoyl)oxy)methyl 4-(((benzyloxy)(hydroxy)phosphoryl)oxy)-3-methoxybenzoate (163 mg, 0.179 mmol) and anisole (486 μl, 4.47 mmol) in DCE (3580 μl) was added TFA (689 μl, 8.95 mmol). The resulting mixture was brought to 50° C. and stirred for 1 h. The crude material was concentrated and purified by prep HPLC ($C_{18}$, Acetonitrile/Water/TFA) to give (R)-(((5-(2-acetamidoimidazo[1,2-b]pyridazin-6-yl)-2-methylnicotinoyl)(1-(2-fluoro-5-(trifluoromethoxy)phenyl)ethyl)carbamoyl)oxy)methyl 3-methoxy-4-(phosphonooxy)benzoate, TFA (89.4 mg, 0.096 mmol, 53.4% yield).

MS ESI m/z 821.0 (M+H)

1H NMR (400 MHz, DMSO-d6) δ 9.12-8.85 (m, 2H), 8.21 (br s, 2H), 7.61-7.48 (m, 2H), 7.47-7.15 (m, 5H), 6.22-6.08 (m, 1H), 5.85-5.59 (m, 2H), 3.69 (br s, 3H), 2.48 (br s, 3H), 2.34-2.02 (m, 3H), 1.92-1.75 (m, 3H).

Example 434 is a prodrug of Example 9-2. The utility of the prodrug comes from the activity of its metabolite, Example 9-2.

The patent publication, US2009/0163489, discloses compounds that inhibit phosphoinositide 3-kinase. Example 11 in US2009/0163489 has the following structure:

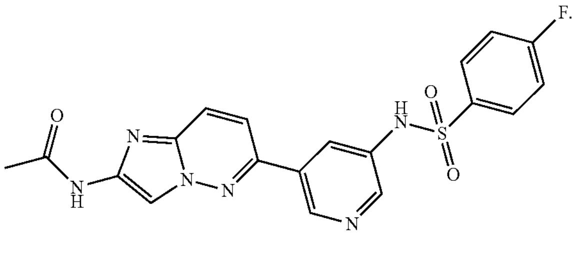 [SMILES: CC(=O)Nc1cn2nc(-c3cncc(NS(=O)(=O)c4ccc(F)cc4)c3)ccc2n1]

When Example 11 is tested in the RIPK1 assay described above, it was found to have an $IC_{50}$ of 11 μM.

What is claimed is:

1. A compound having formula (I):

(I)

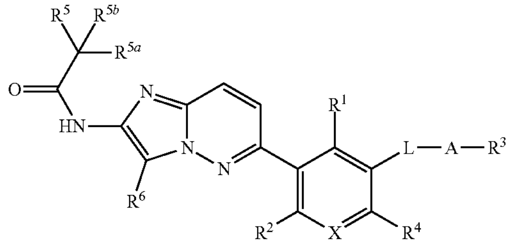

or pharmaceutically acceptable salt thereof, wherein:

X is $CR^7$ or N;

(i) L is —$C(O)NR^a$— or

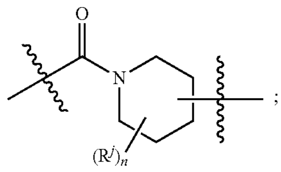

and

A is $C_{1-4}$ alkyl, $C_{1-4}$ deuteroalkyl, $C_{1-3}$ alkyl-$C_{3-6}$ cycloalkyl, $C_{0-3}$ alkyl-heterocyclyl, $C_{1-4}$ alkoxy, or $C_{3-6}$ cycloalkyl-$C_{1-3}$ alkyl;

wherein the $C_{1-4}$ alkyl, $C_{1-4}$ deuteroalkyl, or $C_{1-4}$ alkoxy is substituted with 0-1 OH substituent;

wherein the alkyl of the $C_{0-3}$ alkyl-heterocyclyl is substituted with 0-1 OH substituent;

wherein the heterocyclyl of the $C_{0-3}$ alkyl-heterocyclyl is a 3-6 membered ring containing 1-2 heteroatoms independently selected from the group consisting of N, O, and S; and wherein the heterocyclyl of the $C_{0-3}$ alkyl-heterocyclyl is substituted with 0-2 substituents independently selected from the group consisting of halo, $C_{1-3}$ alkyl, and OH; or (ii) L is —$CH_2$—; and A is —$NR^aC(O)$—;

$R^a$ is H, $C_{1-4}$ alkyl, $C_{1-4}$ deuteroalkyl, ((phosphonooxy)alkylcarbonyloxy)alkyl, ((amino)alkylcarbonyloxy)alkyl, ((amino)cycloalkylcarbonyloxy)alkyl, ((((phosphonooxy)alkyl)carbonyloxy)alkyl)oxycarbonyl, ((((phosphonooxy)cycloalkyl)carbonyloxy)alkyl)oxycarbonyl, ((((amino)alkyl)carbonyloxy)alkyl)oxycarbonyl, ((((amino)cycloalkyl)carbonyloxy)alkyl)oxycarbonyl, or ((((phosphonooxy)(alkoxy)benzoyl)alkyloxycarbonyl;

$R^1$ is H, halo, $C_{1-3}$ alkyl, $C_{1-3}$ deuteroalkyl, $C_{1-3}$ haloalkyl, $C_{1-3}$ alkoxy, $C_{1-3}$ deuteroalkoxy, or $C_{1-3}$ haloalkoxy;

$R^2$ is H, halo, CN, $C_{1-3}$ alkyl, $C_{1-3}$ deuteroalkyl, $C_{1-3}$ haloalkyl, $NH_2$, $C_{1-3}$ alkoxy, $C_{1-3}$ deuteroalkoxy, or $C_{1-3}$ haloalkoxy;

$R^3$ is phenyl, pyrrolyl, or pyridinyl, wherein the phenyl, pyrrolyl, or pyridinyl is substituted with 0-3 independently selected $R^{3a}$ substituents;

each $R^{3a}$ is independently halo, $C_{1-6}$ alkyl, $C_{1-6}$ deuteroalkyl, $C_{1-6}$ haloalkyl, $C_{1-3}$ alkyl-$C_{1-6}$ alkoxy, $C_{1-3}$ alkyl-$C_{3-6}$ cycloalkoxy, $CH_2$-heterocyclyl, $C(O)NR^cR^d$, C(O)heterocyclyl, $C_{1-6}$ alkoxy, hydroxy-$C_{1-6}$ alkoxy, $C_{1-6}$ deuteroalkoxy, $C_{1-6}$ haloalkoxy, $C_{1-3}$ alkoxy-$C_{3-6}$ cycloalkyl, $C_{1-3}$ deuteroalkoxy-$C_{3-6}$ cycloalkyl, $C_{1-3}$ haloalkoxy-$C_{3-6}$ cycloalkyl, $OP(O)(OH)_2$, Oheterocyclyl, $OC_{6-10}$ aryl, $SC_{6-10}$ aryl, $S(O)_2C_{1-4}$ alkyl, $S(O)_2C_{3-6}$ cycloalkyl, $C_{3-6}$ cycloalkyl, $C_{3-6}$ halocycloalkyl, $C_{3-6}$ cycloalkoxy, heterocyclyl, or aryl;

wherein each heterocyclyl is independently a 4-6 membered ring containing 1-2 heteroatoms independently selected from the group consisting of N and O; and wherein each alkyl, cycloalkyl, heterocyclyl, and aryl is independently substituted with 0-2 independently selected $R^b$ substituents; or two $R^{3a}$ on adjacent atoms join to form —$OCH_2CH_2$—, —$OCH_2CH_2CH_2$—, —$OCH_2O$—, or —$OCH_2CH_2O$—;

each $R^b$ is independently halo, $C_{1-3}$ alkyl, $C_{1-3}$ haloalkyl, hydroxy-$C_{1-3}$ alkyl, OH, $C_{1-3}$ alkoxy, =O, or $C_{3-6}$ cycloalkyl;

each $R^c$ is independently H, $C_{1-3}$ alkyl, $C_{1-3}$ deuteroalkyl, or $C_{3-6}$ cycloalkyl;

each $R^d$ is independently H, $C_{1-3}$ alkyl, $C_{1-3}$ deuteroalkyl, or $C_{3-6}$ cycloalkyl; or each $R^c$ and $R^d$, taken together with the nitrogen atom to which they are attached, independently forms a 4-6 membered heterocyclyl;

wherein each 4-6 membered heterocyclyl independently contains 0-1 additional heteroatom selected from the group consisting of N, O, and S; and wherein each 4-6 membered heterocyclyl is independently substituted with 0-4 substituents independently selected from the group consisting of deuterium and halo;

$R^4$ is H, F, Cl, Br, $C_{1-4}$ alkyl, $C_{1-4}$ deuteroalkyl, $C_{1-4}$ haloalkyl, $NR^eR^f$, $C_{1-4}$ alkoxy, $C_{1-4}$ deuteroalkoxy, or cyclopropyl;

$R^e$ is H, $C_{1-3}$ alkyl, $C_{1-3}$ deuteroalkyl, or $C_{3-6}$ cycloalkyl;

$R^f$ is H, $C_{1-3}$ alkyl, $C_{1-3}$ deuteroalkyl, or $C_{3-6}$ cycloalkyl; or $R^e$ and $R^f$, taken together with the nitrogen atom to which they are attached, form a 4-6 membered heterocyclyl, wherein the heterocyclyl is substituted with 0-4 substituents independently selected from the group consisting of deuterium and halo;

(iii) $R^5$ is H, CN, $C(O)CHR^8NH_2$, $NR^gR^h$, OH, $C_{1-3}$ alkoxy, $OC(O)C_{1-3}$ alkyl, or $OP(O)(OH)_2$;

$R^{5a}$ is H or $C_{1-3}$ alkyl; and $R^{5b}$ is H or $C_{1-3}$ alkyl; or $R^{5a}$ and $R^{5b}$, taken together with the carbon atom to which they are attached, form a 3-6 membered carbocyclyl or 3-6 membered heterocyclyl;

wherein the 3-6 membered heterocyclyl contains 0-2 heteroatoms independently selected from the group consisting of N, O, and S; and wherein the 3-6 membered carbocyclyl or 3-6 membered heterocyclyl is substituted with 0-2 substituents independently selected from the group consisting of F, $C_{1-3}$ alkyl, and $C_{1-3}$ haloalkyl; or (iv) $R^5$ is absent; and $R^{5a}$ and $R^{5b}$, taken together with the carbon atom to which they are attached, form a 3-6 membered carbocyclyl or 3-6 membered heterocyclyl;

wherein the 3-6 membered heterocyclyl contains 0-2 heteroatoms independently selected from the group consisting of N, O, and S; and wherein the 3-6 membered carbocyclyl or 3-6 membered heterocyclyl is substituted with 0-1 substituent selected from the group consisting of F and $C_{1-3}$ alkyl;

$R^g$ is H, $C_{1-3}$ alkyl, $C_{1-3}$ deuteroalkyl, or $C_{3-6}$ cycloalkyl;

$R^h$ is H, $C_{1-3}$ alkyl, $C_{1-3}$ deuteroalkyl, or $C_{3-6}$ cycloalkyl; or $R^g$ and $R^1$, taken together with the nitrogen atom to which they are attached, form azetidin-1-yl, pyrrolidin-1-yl, piperidin-1-yl, piperazin-1-yl, or morpholin-4-yl, wherein the azetidin-1-yl, pyrrolidin-1-yl, piperidin-1-yl, piperazin-1-yl, or morpholin-4-yl is substituted with 0-3 independently selected $R^i$ substituents;

each $R^i$ is independently halo, $C_{1-3}$ alkyl, or $C_{1-3}$ haloalkyl;

each $R^j$ is independently halo or OH;

$R^6$ is H or $C_{1-3}$ alkyl;

$R^7$ is H, halo, CN, $C_{1-3}$ alkyl, $C_{1-3}$ haloalkyl, $C_{1-3}$ alkoxy, or $C_{1-3}$ haloalkoxy;

$R^8$ is H, $C_{1-3}$ alkyl, or $C_{1-3}$ alkyl-$C_{1-3}$ alkoxy; and n is 0, 1, or 2.

2. A compound of claim 1, or pharmaceutically acceptable salt thereof, wherein A is $C_{1-4}$ alkyl or $C_{1-4}$ deuteroalkyl, wherein the $C_{1-4}$ alkyl or $C_{1-4}$ deuteroalkyl is substituted with 0-1 OH substituent.

3. A compound of claim 2, or pharmaceutically acceptable salt thereof, wherein $R^3$ is phenyl, wherein the phenyl is substituted with 0-3 independently selected $R^{3a}$ substituents.

4. A compound of claim 3, or pharmaceutically acceptable salt thereof, wherein each $R^{3a}$ is independently halo, $C_{1-6}$ alkyl, $C(O)NR^cR^d$, or $C_{1-6}$ alkoxy.

5. A compound of claim 3, or pharmaceutically acceptable salt thereof, wherein:

$R^1$ is H or $C_{1-3}$ alkyl;

$R^2$ is H, $C_{1-3}$ alkyl, or $C_{1-3}$ alkoxy; and $R^4$ is H, F, Cl, $C_{1-4}$ alkyl, or $C_{1-4}$ alkoxy.

6. A compound of claim 5, or pharmaceutically acceptable salt thereof, wherein A is $—CH_2—$, $—CD_2-$, $—CH_2CH_2—$, $—CH(CH_3)—$, $—CH(CD_3)—$, $—CH_2CH_2CH(CH_3)—$, or $—CH_2CH_2CH(OH)—$.

7. A compound of claim 6, or pharmaceutically acceptable salt thereof, wherein:

X is $CR^7$ or N;

L is —C(O)NH—;

$R^6$ is H; and $R^7$ is H or halo.

8. A compound of claim 7, or pharmaceutically acceptable salt thereof, wherein X is $CR^7$.

9. A compound of claim 7, or pharmaceutically acceptable salt thereof, wherein X is N.

10. A pharmaceutical composition comprising at least one compound of claim 1, or pharmaceutically acceptable salt thereof, and a pharmaceutically acceptable carrier.

11. A method for inhibiting casein kinase receptor interacting protein kinase 1 (RIPK1) activity in a patient, wherein the method comprises administering to the patient in need thereof a therapeutically effective amount of at least one compound of claim 1, or pharmaceutically acceptable salt thereof.

12. A method for treating a disease in a patient, wherein the method comprises administering to the patient in need thereof a therapeutically effective amount of at least one compound of claim 1, or pharmaceutically acceptable salt thereof;

wherein treatment of the disease in the patient requires inhibiting casein kinase receptor interacting protein kinase 1 (RIPK1) activity in the patient; and wherein the disease is selected from the group consisting of Crohn's disease, heart failure, inflammatory bowel disease, psoriasis, rheumatoid arthritis, and ulcerative colitis.

13. A compound having formula (I):

(I)

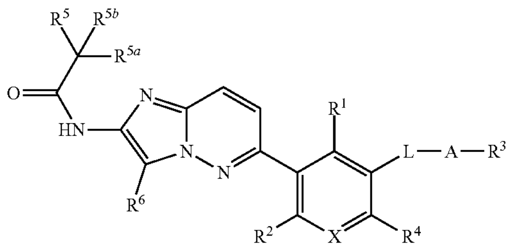

or pharmaceutically acceptable salt thereof, wherein:

X is $CR^7$ or N;

(i) L is $—C(O)NR^a—$ or $—NR^aC(O)—$; and

A is $C_{1-4}$ alkyl, $C_{1-4}$ deuteroalkyl, $C_{1-3}$ alkyl-$C_{3-6}$ cycloalkyl, or $C_{3-6}$ cycloalkyl-$C_{1-3}$ alkyl, wherein the $C_{1-4}$ alkyl or $C_{1-4}$ deuteroalkyl is substituted with 0-1 OH substituent; or (ii) L is $—CH_2—$; and A is $—NR^aC(O)—$;

$R^a$ is H, $C_{1-4}$ alkyl, or $C_{1-4}$ deuteroalkyl;

$R^1$ is H, halo, $C_{1-3}$ alkyl, $C_{1-3}$ deuteroalkyl, $C_{1-3}$ haloalkyl, $C_{1-3}$ alkoxy, $C_{1-3}$ deuteroalkoxy, or $C_{1-3}$ haloalkoxy;

$R^2$ is H, halo, CN, $C_{1-3}$ alkyl, $C_{1-3}$ deuteroalkyl, $C_{1-3}$ haloalkyl, $NH_2$, $C_{1-3}$ alkoxy, $C_{1-3}$ deuteroalkoxy, or $C_{1-3}$ haloalkoxy;

$R^3$ is phenyl, pyrrolyl, or pyridinyl, wherein the phenyl, pyrrolyl, or pyridinyl is substituted with 0-3 independently selected $R^{3a}$ substituents;

each $R^{3a}$ is independently halo, $C_{1-6}$ alkyl, $C_{1-6}$ deuteroalkyl, $C_{1-6}$ haloalkyl, $C_{1-3}$ alkyl-$C_{1-6}$ alkoxy, $C_{1-3}$ alkyl-$C_{3-6}$ cycloalkoxy, $CH_2$-heterocyclyl, $C(O)NR^cR^d$, $C_{1-6}$ alkoxy, hydroxy-$C_{1-6}$ alkoxy, $C_{1-6}$ deuteroalkoxy, $C_{1-6}$ haloalkoxy, $C_{1-3}$ alkoxy-$C_{3-6}$ cycloalkyl, $C_{1-3}$ deuteroalkoxy-$C_{3-6}$ cycloalkyl, $C_{1-3}$ haloalkoxy-$C_{3-6}$ cycloalkyl, Oheterocyclyl, $SC_{6-10}$ aryl, $S(O)_2C_{1-4}$ alkyl, $S(O)_2C_{3-6}$ cycloalkyl, $C_{3-6}$ cycloalkyl, $C_{3-6}$ halocycloalkyl, $C_{3-6}$ cycloalkoxy, or heterocyclyl;

wherein each heterocyclyl is independently a 4-6 membered ring containing 1-2 heteroatoms independently selected from the group consisting of N and O; and wherein each alkyl, cycloalkyl, and heterocyclyl is independently substituted with 0-2 independently selected $R^b$ substituents;

each $R^b$ is independently halo, $C_{1-3}$ alkyl, $C_{1-3}$ haloalkyl, or =0;

each $R^c$ is independently H, $C_{1-3}$ alkyl, $C_{1-3}$ deuteroalkyl, or $C_{3-6}$ cycloalkyl;

each $R^d$ is independently H, $C_{1-3}$ alkyl, $C_{1-3}$ deuteroalkyl, or $C_{3-6}$ cycloalkyl; or each $R^c$ and $R^d$, taken together with the nitrogen atom to which they are attached, independently forms a 4-6 membered heterocyclyl;

wherein each 4-6 membered heterocyclyl independently contains 0-1 additional heteroatom selected from the group consisting of N, O, and S; and wherein each 4-6 membered heterocyclyl is independently substituted with 0-4 substituents independently selected from the group consisting of deuterium and halo;

$R^4$ is H, F, Cl, Br, $C_{1-4}$ alkyl, $C_{1-4}$ deuteroalkyl, $C_{1-4}$ haloalkyl, $NR^eR^f$ $C_{1-4}$ alkoxy, $C_{1-4}$ deuteroalkoxy, or cyclopropyl;

$R^e$ is H, $C_{1-3}$ alkyl, $C_{1-3}$ deuteroalkyl, or $C_{3-6}$ cycloalkyl;

$R^f$ is H, $C_{1-3}$ alkyl, $C_{1-3}$ deuteroalkyl, or $C_{3-6}$ cycloalkyl; or $R^e$ and $R^f$, taken together with the nitrogen atom to which they are attached, form a 4-6 membered heterocyclyl, wherein the heterocyclyl is substituted with 0-4 substituents independently selected from the group consisting of deuterium and halo;

(iii) $R^5$ is H, CN, $C(O)CHR^gNH_2$, $NR^gR^h$, OH, $C_{1-3}$ alkoxy, $OC(O)C_{1-3}$ alkyl, or $OP(O)(OH)_2$;

$R^{5a}$ is H or $C_{1-3}$ alkyl; and $R^{5b}$ is H or $C_{1-3}$ alkyl; or $R^{5a}$ and $R^{5b}$, taken together with the carbon atom to which they are attached, form a 3-6 membered carbocyclyl or 3-6 membered heterocyclyl;

wherein the 3-6 membered heterocyclyl contains 0-2 heteroatoms independently selected from the group consisting of N, O, and S; and wherein the 3-6 membered carbocyclyl or 3-6 membered heterocyclyl is substituted with 0-1 substituent selected from the group consisting of F and $C_{1-3}$ alkyl; or (iv) $R^5$ is absent; and $R^{5a}$ and $R^{5b}$, taken together with the carbon atom to which they are attached, form a 3-6 membered carbocyclyl or 3-6 membered heterocyclyl;

wherein the 3-6 membered heterocyclyl contains 0-2 heteroatoms independently selected from the group consisting of N, O, and S; and wherein the 3-6 membered carbocyclyl or 3-6 membered heterocyclyl is substituted with 0-1 substituent selected from the group consisting of F and $C_{1-3}$ alkyl;

$R^g$ is H, $C_{1-3}$ alkyl, $C_{1-3}$ deuteroalkyl, or $C_{3-6}$ cycloalkyl;

$R^h$ is H, $C_{1-3}$ alkyl, $C_{1-3}$ deuteroalkyl, or $C_{3-6}$ cycloalkyl;

$R^6$ is H or $C_{1-3}$ alkyl;

$R^7$ is H, halo, CN, $C_{1-3}$ alkyl, $C_{1-3}$ haloalkyl, $C_{1-3}$ alkoxy, or $C_{1-3}$ haloalkoxy; and $R^8$ is H, $C_{1-3}$ alkyl, or $C_{1-3}$ alkyl-$C_{1-3}$ alkoxy.

14. A compound selected from the group consisting of:

N-[(5-{2-acetamidoimidazo[1,2-b]pyridazin-6-yl}-2-methylpyridin-3-yl)methyl]-2-fluoro-5-(trifluoromethoxy)benzamide;

N-{[3,5-difluoro-2-(oxan-4-yloxy)phenyl]($D_2$)methyl}-5-[2-(2-hydroxyacetamido)imidazo[1,2-b]pyridazin-6-yl]-2-methoxypyridine-3-carboxamide;

2-methoxy-5-[2-(2-methoxyacetamido)imidazo[1,2-b]pyridazin-6-yl]-N-{[2-(trifluoromethoxy)phenyl]methyl}pyridine-3-carboxamide;

N-{[2-(cyclopropylmethoxy)-3,5-difluorophenyl]methyl}-2-methoxy-5-{2-propanamidoimidazo[1,2-b]pyridazin-6-yl}pyridine-3-carboxamide;

N-{[2-(cyclopropylmethoxy)-3,5-difluorophenyl]methyl}-2-methoxy-5-[2-(2-methylpropanamido)imidazo[1,2-b]pyridazin-6-yl]pyridine-3-carboxamide;

5-{2-acetamido-3-methylimidazo[1,2-b]pyridazin-6-yl}-N-{[2-fluoro-5-(trifluoromethoxy)phenyl]methyl}-2-methoxypyridine-3-carboxamide;

5-[2-(2-cyanoacetamido)imidazo[1,2-b]pyridazin-6-yl]-N-{[2-(cyclopropylmethoxy)-3,5-difluorophenyl]methyl}-2-methoxypyridine-3-carboxamide;

5-[2-(2-cyano-2,2-dimethylacetamido)imidazo[1,2-b]pyridazin-6-yl]-N-{[2-(cyclopropylmethoxy)-3,5-difluorophenyl]methyl}-2-methoxypyridine-3-carboxamide;

5-{2-acetamidoimidazo[1,2-b]pyridazin-6-yl}-N-[(1R)-1-[2-fluoro-5-(trifluoromethoxy)phenyl]ethyl]-2-methylpyridine-3-carboxamide;

N-{[2-fluoro-5-(trifluoromethoxy)phenyl]methyl}-2-methoxy-5-{2-propanamidoimidazo[1,2-b]pyridazin-6-yl}pyridine-3-carboxamide;

N-{[2-fluoro-5-(trifluoromethoxy)phenyl]methyl}-2-methoxy-5-[2-(2-methylpropanamido)imidazo[1,2-b]pyridazin-6-yl]pyridine-3-carboxamide;

2-chloro-5-{2-acetamidoimidazo[1,2-b]pyridazin-6-yl}-N-{[2-fluoro-5-(trifluoromethoxy)phenyl]methyl}pyridine-3-carboxamide;

5-{2-acetamidoimidazo[1,2-b]pyridazin-6-yl}-2-($D_3$)methoxy-6-methyl-N-{1-[2-(trifluoromethoxy)phenyl]ethyl}pyridine-3-carboxamide;

5-{2-acetamidoimidazo[1,2-b]pyridazin-6-yl}-2-($D_3$)methoxy-N-{[2-(trifluoromethoxy)phenyl]methyl}pyridine-3-carboxamide;

N-{[2-(cyclopropylmethoxy)-3-fluorophenyl]methyl}-5-[2-(2-hydroxy-2-methylpropanamido)imidazo[1,2-b]pyridazin-6-yl]-2-methoxypyridine-3-carboxamide;

N-{[2-(cyclopropylmethoxy)-3,5-difluorophenyl]methyl}-5-{2-acetamidoimidazo[1,2-b]pyridazin-6-yl}-6-methylpyridine-3-carboxamide;

5-{2-acetamidoimidazo[1,2-b]pyridazin-6-yl}-N-({2-[(1-hydroxypropan-2-yl)oxy]phenyl}methyl)-2-methoxy-6-methylpyridine-3-carboxamide;

5-{2-acetamidoimidazo[1,2-b]pyridazin-6-yl}-N-{[2-fluoro-5-(trifluoromethoxy)phenyl]methyl}-2-(trifluoromethyl)pyridine-3-carboxamide;

5-{2-acetamidoimidazo[1,2-b]pyridazin-6-yl}-2-methoxy-6-methyl-N-{[2-(trifluoromethoxy)phenyl]methyl}pyridine-3-carboxamide;

5-{2-acetamidoimidazo[1,2-b]pyridazin-6-yl}-2-methyl-N-{[2-(propan-2-yloxy)phenyl]methyl}pyridine-3-carboxamide;

N-{[2-(cyclopentyloxy)phenyl]methyl}-5-{2-acetamidoimidazo[1,2-b]pyridazin-6-yl}pyridine-3-carboxamide;

N-{[2-(cyclopropylmethoxy)phenyl]methyl}-5-{2-acetamidoimidazo[1,2-b]pyridazin-6-yl}-2-methoxypyridine-3-carboxamide;

N-[3-(4-chlorophenyl)-3-hydroxypropyl]-5-{2-acetamidoimidazo[1,2-b]pyridazin-6-yl}-2-methoxypyridine-3-carboxamide;

2-fluoro-N-(6-{3-[(3-phenylbutyl)carbamoyl]phenyl}imidazo[1,2-b]pyridazin-2-yl)pyridine-4-carboxamide;

5-{2-acetamidoimidazo[1,2-b]pyridazin-6-yl}-2-methoxy-N-(3-phenylbutyl)pyridine-3-carboxamide;

5-[2-(2-cyano-2,2-dimethylacetamido)imidazo[1,2-b]pyridazin-6-yl]-N-[(2-{[2-(hydroxymethyl)phenyl]sulfanyl}phenyl)methyl]-2-methylpyridine-3-carboxamide;

5-[2-(2-cyano-2,2-dimethylacetamido)imidazo[1,2-b]pyridazin-6-yl]-N-[(1R)-1-[2-fluoro-5-(trifluoromethoxy)phenyl]ethyl]-2-methylpyridine-3-carboxamide;

5-[2-(2-cyano-2,2-dimethylacetamido)imidazo[1,2-b]pyridazin-6-yl]-N-{[2-fluoro-5-(trifluoromethoxy)phenyl]methyl}-2-methoxypyridine-3-carboxamide;

5-[2-(2-cyano-2,2-dimethylacetamido)imidazo[1,2-b]pyridazin-6-yl]-N-{[5-(cyclopropylmethoxy)-2-fluorophenyl]methyl}-2-methoxypyridine-3-carboxamide;

5-{2-acetamidoimidazo[1,2-b]pyridazin-6-yl}-N-{[2-fluoro-5-(trifluoromethyl)phenyl]methyl}-2-(trifluoromethyl)pyridine-3-carboxamide;

N-{[2-(cyclopropylmethoxy)-3,6-difluorophenyl]methyl}-5-{2-acetamidoimidazo[1,2-b]pyridazin-6-yl}-2-(trifluoromethyl)pyridine-3-carboxamide;

5-[2-(2-cyanoacetamido)imidazo[1,2-b]pyridazin-6-yl]-2-methoxy-N-{[2-(trifluoromethoxy)phenyl]methyl}pyridine-3-carboxamide;

5-[2-(2-cyanoacetamido)imidazo[1,2-b]pyridazin-6-yl]-N-{[2-fluoro-5-(trifluoromethoxy)phenyl]methyl}-2-methoxypyridine-3-carboxamide;

N-{[2-fluoro-5-(trifluoromethyl)phenyl]methyl}-5-[2-(2-hydroxyacetamido)imidazo[1,2-b]pyridazin-6-yl]-2-methoxypyridine-3-carboxamide;

N-{[2-fluoro-5-(trifluoromethoxy)phenyl]methyl}-5-[2-(2-hydroxyacetamido)imidazo[1,2-b]pyridazin-6-yl]-2-methoxypyridine-3-carboxamide;

N-{[2-fluoro-5-(trifluoromethoxy)phenyl]methyl}-5-[2-(2-hydroxy-2-methylpropanamido)imidazo[1,2-b]pyridazin-6-yl]-2-methoxypyridine-3-carboxamide;

5-(2-acetamidoimidazo[1,2-b]pyridazin-6-yl)-N-(2-fluoro-5-methoxybenzyl)-2,6-dimethylnicotinamide;

N-(2-fluoro-5-(trifluoromethoxy)benzyl)-5-(2-(2-hydroxyacetamido)imidazo[1,2-b]pyridazin-6-yl)-2,6-dimethylnicotinamide;

N-{[2-fluoro-5-(trifluoromethoxy)phenyl]methyl}-5-[2-(2-hydroxyacetamido)imidazo[1,2-b]pyridazin-6-yl]-2-methylpyridine-3-carboxamide;

5-{2-acetamidoimidazo[1,2-b]pyridazin-6-yl}-N-[(2-fluoro-5-methoxyphenyl)methyl]-2-($D_3$)methoxypyridine-3-carboxamide;

5-{2-acetamidoimidazo[1,2-b]pyridazin-6-yl}-N-[(1S)-1-[2-fluoro-5-(trifluoromethoxy)phenyl]ethyl]-2-($D_3$)methoxypyridine-3-carboxamide;

5-{2-acetamidoimidazo[1,2-b]pyridazin-6-yl}-N-{[2-fluoro-6-(2,2,2-trifluoroethoxy)phenyl]methyl}-2-(D3)methoxypyridine-3-carboxamide;

N-{[3,5-difluoro-2-(oxan-3-yloxy)phenyl]methyl}-5-{2-acetamidoimidazo[1,2-b]pyridazin-6-yl}-2-(D3)methoxypyridine-3-carboxamide;

N-({3,5-difluoro-2-[(3R)-oxolan-3-yloxy]phenyl}methyl)-5-{2-acetamidoimidazo[1,2-b]pyridazin-6-yl}-2-(D3)methoxypyridine-3-carboxamide;

N-({3,5-difluoro-2-[(3S)-oxolan-3-yloxy]phenyl}methyl)-5-{2-acetamidoimidazo[1,2-b]pyridazin-6-yl}-2-(D3)methoxypyridine-3-carboxamide;

N-{[3,5-difluoro-2-(oxan-4-yloxy)phenyl](deutero)methyl}-5-{2-acetamidoimidazo[1,2-b]pyridazin-6-yl}-2-(D3)methoxypyridine-3-carboxamide;

5-{2-acetamidoimidazo[1,2-b]pyridazin-6-yl}-N-[(1R)-1-[2-fluoro-5-(trifluoromethoxy)phenyl]ethyl]-2-(D3)methoxypyridine-3-carboxamide;

N-{[3,5-difluoro-2-(oxetan-3-yloxy)phenyl]methyl}-5-{2-acetamidoimidazo[1,2-b]pyridazin-6-yl}-2-(D3)methoxypyridine-3-carboxamide;

N-({2-[cyclopropyl(deutero)methoxy]-3,5-difluorophenyl}methyl)-5-{2-acetamidoimidazo[1,2-b]pyridazin-6-yl}-2-(D3)methoxypyridine-3-carboxamide;

N-{[3,5-difluoro-2-(oxan-4-yloxy)phenyl]methyl}-5-{2-acetamidoimidazo[1,2-b]pyridazin-6-yl}-2-(D3)methoxypyridine-3-carboxamide;

5-{2-acetamidoimidazo[1,2-b]pyridazin-6-yl}-N-{1-[2-fluoro-5-(trifluoromethyl)phenyl]ethyl}-2-(D3)methoxypyridine-3-carboxamide;

5-{2-acetamidoimidazo[1,2-b]pyridazin-6-yl}-N-{1-[2-fluoro-5-(trifluoromethyl)phenyl]ethyl}-2-(D3)methoxypyridine-3-carboxamide;

N-{[2-(cyclopropylmethoxy)-3,4-difluorophenyl]methyl}-5-{2-acetamidoimidazo[1,2-b]pyridazin-6-yl}-2-(D3)methoxypyridine-3-carboxamide;

5-{2-acetamidoimidazo[1,2-b]pyridazin-6-yl}-2-(D3)methoxy-N-{1-[2-(trifluoromethoxy)phenyl]ethyl}pyridine-3-carboxamide;

N-{[2-(cyclopropylmethoxy)-3,5-difluorophenyl]methyl}-5-{2-acetamidoimidazo[1,2-b]pyridazin-6-yl}-2-(D3)methoxypyridine-3-carboxamide;

N-{[5-(cyclopropylmethoxy)-2-fluorophenyl]methyl}-5-{2-acetamidoimidazo[1,2-b]pyridazin-6-yl}-2-(D3)methoxypyridine-3-carboxamide;

5-{2-acetamidoimidazo[1,2-b]pyridazin-6-yl}-2-(D3)methoxy-N-{1-[2-(trifluoromethoxy)phenyl]ethyl}pyridine-3-carboxamide;

5-{2-acetamidoimidazo[1,2-b]pyridazin-6-yl}-N-{[2-fluoro-5-(trifluoromethoxy)phenyl]methyl}-2-(D3)methoxypyridine-3-carboxamide;

N-{[3,5-difluoro-2-(oxan-3-yloxy)phenyl]methyl}-5-{2-acetamidoimidazo[1,2-b]pyridazin-6-yl}-2,6-dimethylpyridine-3-carboxamide;

N-({3,5-difluoro-2-[(3S)-oxolan-3-yloxy]phenyl}methyl)-5-{2-acetamidoimidazo[1,2-b]pyridazin-6-yl}-2,6-dimethylpyridine-3-carboxamide;

N-({3,5-difluoro-2-[(3R)-oxolan-3-yloxy]phenyl}methyl)-5-{2-acetamidoimidazo[1,2-b]pyridazin-6-yl}-2,6-dimethylpyridine-3-carboxamide;

N-({3,5-difluoro-2-[(2-methyloxan-4-yl)oxy]phenyl}methyl)-5-{2-acetamidoimidazo[1,2-b]pyridazin-6-yl}-2,6-dimethylpyridine-3-carboxamide;

N-[(2-{[(2R,6S)-2,6-dimethyloxan-4-yl]oxy}-3-fluorophenyl)methyl]-5-{2-acetamidoimidazo[1,2-b]pyridazin-6-yl}-2,6-dimethylpyridine-3-carboxamide;

N-({2-[(2,6-dimethyloxan-4-yl)oxy]-3,5-difluorophenyl}methyl)-5-{2-acetamidoimidazo[1,2-b]pyridazin-6-yl}-2,6-dimethylpyridine-3-carboxamide;

5-{2-acetamidoimidazo[1,2-b]pyridazin-6-yl}-2,6-dimethyl-N-{[3-(2,2,2-trifluoroethoxy)pyridin-2-yl]methyl}pyridine-3-carboxamide;

N-{[3,5-difluoro-2-(oxan-4-yloxy)phenyl](deutero)methyl}-5-{2-acetamidoimidazo[1,2-b]pyridazin-6-yl}-2,6-dimethylpyridine-3-carboxamide;

5-{2-acetamidoimidazo[1,2-b]pyridazin-6-yl}-N-[(1R)-1-[2-fluoro-5-(trifluoromethyl)phenyl](2,2,2-deutero)ethyl]-2,6-dimethylpyridine-3-carboxamide;

5-{2-acetamidoimidazo[1,2-b]pyridazin-6-yl}-2,6-dimethyl-N-{[2-(2,2,2-trifluoroethoxy)phenyl]methyl}pyridine-3-carboxamide;

5-{2-acetamidoimidazo[1,2-b]pyridazin-6-yl}-N-[(1R)-1-[2-fluoro-5-(trifluoromethyl)phenyl]ethyl]-2,6-dimethylpyridine-3-carboxamide;

5-{2-acetamidoimidazo[1,2-b]pyridazin-6-yl}-N-[(1R)-1-[2-fluoro-5-(trifluoromethoxy)phenyl](2,2,2-deutero)ethyl]-2,6-dimethylpyridine-3-carboxamide;

5-{2-acetamidoimidazo[1,2-b]pyridazin-6-yl}-N-[(1R)-1-[2-fluoro-5-(trifluoromethoxy)phenyl]ethyl]-2,6-dimethylpyridine-3-carboxamide;

5-{2-acetamidoimidazo[1,2-b]pyridazin-6-yl}-N-{[5-fluoro-2-(2,2,2-trifluoroethoxy)phenyl]methyl}-2,6-dimethylpyridine-3-carboxamide;

5-{2-acetamidoimidazo[1,2-b]pyridazin-6-yl}-2,6-dimethyl-N-{[3-(2,2,2-trifluoroethoxy)phenyl]methyl}pyridine-3-carboxamide;

5-{2-acetamidoimidazo[1,2-b]pyridazin-6-yl}-2,6-dimethyl-N-{[3-(trifluoromethyl)phenyl](deutero)methyl}pyridine-3-carboxamide;

5-{2-acetamidoimidazo[1,2-b]pyridazin-6-yl}-N-{[2-fluoro-5-(trifluoromethyl)phenyl](deutero)methyl}-2,6-dimethylpyridine-3-carboxamide;

5-{2-acetamidoimidazo[1,2-b]pyridazin-6-yl}-N-{[2-fluoro-5-(trifluoromethoxy)phenyl](deutero)methyl}-2,6-dimethylpyridine-3-carboxamide;

N-{[3,5-difluoro-2-(oxetan-3-yloxy)phenyl]methyl}-5-{2-acetamidoimidazo[1,2-b]pyridazin-6-yl}-2,6-dimethylpyridine-3-carboxamide;

N-{[3,5-difluoro-2-(oxan-4-yloxy)phenyl]methyl}-5-{2-acetamidoimidazo[1,2-b]pyridazin-6-yl}-2,6-dimethylpyridine-3-carboxamide;

5-{2-acetamidoimidazo[1,2-b]pyridazin-6-yl}-N-{[3-fluoro-5-(trifluoromethoxy)phenyl]methyl}-2,6-dimethylpyridine-3-carboxamide;

5-{2-acetamidoimidazo[1,2-b]pyridazin-6-yl}-N-{[2-fluoro-5-(trifluoromethyl)phenyl]methyl}-2,6-dimethylpyridine-3-carboxamide;

5-{2-acetamidoimidazo[1,2-b]pyridazin-6-yl}-N-{[2-fluoro-5-(trifluoromethoxy)phenyl]methyl}-2,6-dimethylpyridine-3-carboxamide;

N-[(3S)-3-(4-chlorophenyl)-3-hydroxypropyl]-5-{2-acetamidoimidazo[1,2-b]pyridazin-6-yl}-2,6-dimethylpyridine-3-carboxamide;

N-{[2-(cyclopropylmethoxy)phenyl]methyl}-5-{2-acetamidoimidazo[1,2-b]pyridazin-6-yl}-2,6-dimethylpyridine-3-carboxamide;

N-{[2-(cyclopentylmethoxy)pyridin-3-yl]methyl}-5-{2-acetamidoimidazo[1,2-b]pyridazin-6-yl}-2,6-dimethylpyridine-3-carboxamide;

N-{[2-(cyclopentylmethoxy)phenyl]methyl}-5-{2-acetamidoimidazo[1,2-b]pyridazin-6-yl}-2,6-dimethylpyridine-3-carboxamide;

N-{[2-(cyclobutylmethoxy)pyridin-3-yl]methyl}-5-{2-acetamidoimidazo[1,2-b]pyridazin-6-yl}-2,6-dimethylpyridine-3-carboxamide;

N-{[2-(cyclopropylmethoxy)-3,5-difluorophenyl]methyl}-5-{2-acetamidoimidazo[1,2-b]pyridazin-6-yl}-2,6-dimethylpyridine-3-carboxamide;

5-{2-acetamidoimidazo[1,2-b]pyridazin-6-yl}-2,6-dimethyl-N-{[3-(trifluoromethoxy)phenyl]methyl}pyridine-3-carboxamide;

5-{2-acetamidoimidazo[1,2-b]pyridazin-6-yl}-2,6-dimethyl-N-{[2-(trifluoromethoxy)phenyl]methyl}pyridine-3-carboxamide;

N-{[2-(cyclopentylmethoxy)-3,5-difluorophenyl]methyl}-5-{2-acetamidoimidazo[1,2-b]pyridazin-6-yl}-2,6-dimethylpyridine-3-carboxamide;

N-({3,5-difluoro-2-[(3S)-oxolan-3-yloxy]phenyl}methyl)-5-[2-(2-hydroxyacetamido)imidazo[1,2-b]pyridazin-6-yl]-2,6-dimethylpyridine-3-carboxamide;

N-[(1R)-1-[2-fluoro-5-(trifluoromethyl)phenyl]ethyl]-5-[2-(2-hydroxyacetamido)imidazo[1,2-b]pyridazin-6-yl]-2,6-dimethylpyridine-3-carboxamide;

N-{[2-fluoro-5-(trifluoromethyl)phenyl](deutero)methyl}-5-[2-(2-hydroxyacetamido)imidazo[1,2-b]pyridazin-6-yl]-2,6-dimethylpyridine-3-carboxamide;

N-{[2-fluoro-5-(trifluoromethyl)phenyl]methyl}-5-[2-(2-hydroxyacetamido)imidazo[1,2-b]pyridazin-6-yl]-2,6-dimethylpyridine-3-carboxamide;

N-[(1R)-1-[2-fluoro-5-(trifluoromethoxy)phenyl]ethyl]-5-[2-(2-hydroxyacetamido)imidazo[1,2-b]pyridazin-6-yl]-2,6-dimethylpyridine-3-carboxamide;

N-({3,5-difluoro-2-[(2-methyloxan-4-yl)oxy]phenyl}methyl)-5-{2-acetamidoimidazo[1,2-b]pyridazin-6-yl}-2-methoxypyridine-3-carboxamide;

N-{[2-(cyclobutylmethoxy)-3,5-difluorophenyl]methyl}-5-{2-acetamidoimidazo[1,2-b]pyridazin-6-yl}-2-methoxypyridine-3-carboxamide;

N-({3,5-difluoro-2-[(3S)-oxolan-3-yloxy]phenyl}methyl)-5-{2-acetamidoimidazo[1,2-b]pyridazin-6-yl}-2-methoxypyridine-3-carboxamide;

N-{[3,5-difluoro-2-(oxan-3-yloxy)phenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-N-[(2-fluoro-5-methoxyphenyl)methyl]-2-methoxypyridine-3-carboxamide;

5-{2-acetamidoimidazo[1,2-b]pyridazin-6-yl}-2-methoxy-N-{[3-(2,2,2-trifluoroethoxy)pyridin-2-yl]methyl}pyridine-3-carboxamide;

5-{2-acetamidoimidazo[1,2-b]pyridazin-6-yl}-N-{[2-fluoro-6-(2,2,2-trifluoroethoxy)phenyl]methyl}-2-methoxypyridine-3-carboxamide;

N-({2-[(2,6-dimethyloxan-4-yl)oxy]-3,5-difluorophenyl}methyl)-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-[(1R)-1-[2-(trifluoromethyl)phenyl]ethyl]pyridine-3-carboxamide;

5-{2-acetamidoimidazo[1,2-b]pyridazin-6-yl}-N-{[5-fluoro-2-(2,2,2-trifluoroethoxy)phenyl]methyl}-2-methoxypyridine-3-carboxamide;

5-{2-acetamidoimidazo[1,2-b]pyridazin-6-yl}-N-[(1S)-1-[2-fluoro-5-(trifluoromethyl)phenyl](2,2,2-deutero)ethyl]-2-methoxypyridine-3-carboxamide;

5-{2-acetamidoimidazo[1,2-b]pyridazin-6-yl}-N-[(1R)-1-[2-fluoro-5-(trifluoromethyl)phenyl](2,2,2-deutero)ethyl]-2-methoxypyridine-3-carboxamide;

5-{2-acetamidoimidazo[1,2-b]pyridazin-6-yl}-2-methoxy-N-{[2-(2,2,2-trifluoroethoxy)phenyl]methyl}pyridine-3-carboxamide;

5-{2-acetamidoimidazo[1,2-b]pyridazin-6-yl}-N-[(1R)-1-[2-fluoro-5-(trifluoromethoxy)phenyl](2,2,2-deutero)ethyl]-2-methoxypyridine-3-carboxamide;

5-{2-acetamidoimidazo[1,2-b]pyridazin-6-yl}-2-methoxy-N-{[3-(trifluoromethyl)phenyl](deutero)methyl}pyridine-3-carboxamide;

5-{2-acetamidoimidazo[1,2-b]pyridazin-6-yl}-N-{[2-fluoro-5-(trifluoromethyl)phenyl](deutero)methyl}-2-methoxypyridine-3-carboxamide;

5-{2-acetamidoimidazo[1,2-b]pyridazin-6-yl}-2-methoxy-N-[(1R)-1-[3-(trifluoromethoxy)phenyl](2,2,2-deutero)ethyl]pyridine-3-carboxamide;

5-{2-acetamidoimidazo[1,2-b]pyridazin-6-yl}-2-methoxy-N-({2-[(morpholin-4-yl)methyl]phenyl}methyl)pyridine-3-carboxamide;

5-{2-acetamidoimidazo[1,2-b]pyridazin-6-yl}-2-methoxy-N-({2-[(propan-2-yloxy)methyl]phenyl}methyl)pyridine-3-carboxamide;

N-{[3,5-difluoro-2-(oxetan-3-yloxy)phenyl]methyl}-5-{2-acetamidoimidazo[1,2-b]pyridazin-6-yl}-2-methoxypyridine-3-carboxamide;

N-{[3,5-difluoro-2-(2-methylpropoxy)phenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{[2-(2-methylpropoxy)phenyl]methyl}pyridine-3-carboxamide;

N-[(2-cyclopropoxy-3,5-difluorophenyl)methyl]-5-{2-acetamidoimidazo[1,2-b]pyridazin-6-yl}-2-methoxy-pyridine-3-carboxamide;

N-[(3S)-3-(4-chlorophenyl)-3-hydroxypropyl]-5-{2-acetamidoimidazo[1,2-b]pyridazin-6-yl}-2-methoxypyridine-3-carboxamide;

5-{2-acetamidoimidazo[1,2-b]pyridazin-6-yl}-N-{[4-fluoro-2-(trifluoromethoxy)phenyl]methyl}-2-methoxypyridine-3-carboxamide;

N-({2-[cyclopropyl(deutero)methoxy]-3,5-difluorophenyl}methyl)-5-{2-acetamidoimidazo[1,2-b]pyridazin-6-yl}-2-methoxypyridine-3-carboxamide;

N-{1-[2-(cyclopropylmethoxy)-6-fluorophenyl]ethyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{1-[3-(trifluoromethoxy)phenyl]ethyl}pyridine-3-carboxamide;

N-{1-[2-(cyclopropylmethoxy)-6-fluorophenyl]ethyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{1-[3-(trifluoromethoxy)phenyl]ethyl}pyridine-3-carboxamide;

5-{2-acetamidoimidazo[1,2-b]pyridazin-6-yl}-2-methoxy-N-{[3-(trifluoromethoxy)phenyl]methyl}pyridine-3-carboxamide;

N-{[2-(cyclopropylmethoxy)-3,6-difluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-N-{[2-fluoro-6-(oxan-4-yloxy)phenyl]methyl}-2-methoxy-pyridine-3-carboxamide;

N-{[3,5-difluoro-2-(oxan-4-yloxy)phenyl]methyl}-5-{2-acetamidoimidazo[1,2-b]pyridazin-6-yl}-2-methoxy-pyridine-3-carboxamide;

N-{1-[2-(cyclopropylmethoxy)-3,5-difluorophenyl]ethyl}-5-{2-acetamidoimidazo[1,2-b]pyridazin-6-yl}-2-methoxypyridine-3-carboxamide;

N-{[2-(1-cyclopropylethoxy)-3,4-difluorophenyl]methyl}-5-{2-acetamidoimidazo[1,2-b]pyridazin-6-yl}-2-methoxypyridine-3-carboxamide;

N-{[2-(1-cyclopropylethoxy)-3,4-difluorophenyl]methyl}-5-{2-acetamidoimidazo[1,2-b]pyridazin-6-yl}-2-methoxypyridine-3-carboxamide;

N-{1-[2-(cyclopropylmethoxy)-3,5-difluorophenyl]ethyl}-5-{2-acetamidoimidazo[1,2-b]pyridazin-6-yl}-2-methoxypyridine-3-carboxamide;

N-{[2-(1-cyclopropylethoxy)-3-fluorophenyl]methyl}-5-{2-acetamidoimidazo[1,2-b]pyridazin-6-yl}-2-methoxypyridine-3-carboxamide;

N-{[2-(1-cyclopropylethoxy)-3-fluorophenyl]methyl}-5-{2-acetamidoimidazo[1,2-b]pyridazin-6-yl}-2-methoxypyridine-3-carboxamide;

N-{[3-(1-cyclopropylethoxy)pyridin-2-yl]methyl}-5-{2-acetamidoimidazo[1,2-b]pyridazin-6-yl}-2-methoxy-pyridine-3-carboxamide;

5-{2-acetamidoimidazo[1,2-b]pyridazin-6-yl}-2-methoxy-N-{1-[2-(trifluoromethoxy)phenyl]ethyl}pyridine-3-carboxamide;

5-{2-acetamidoimidazo[1,2-b]pyridazin-6-yl}-N-{[3-fluoro-5-(trifluoromethoxy)phenyl]methyl}-2-methoxypyridine-3-carboxamide;

5-{2-acetamidoimidazo[1,2-b]pyridazin-6-yl}-2-methoxy-N-{1-[2-(trifluoromethoxy)phenyl]ethyl}pyridine-3-carboxamide;

N-{[3-(cyclopropylmethoxy)-5-fluorophenyl]methyl}-5-{2-acetamidoimidazo[1,2-b]pyridazin-6-yl}-2-methoxypyridine-3-carboxamide;

N-[(3,6-difluoro-2-methoxyphenyl)methyl]-5-{2-acetamidoimidazo[1,2-b]pyridazin-6-yl}-2-methoxypyridine-3-carboxamide;

N-{[3-(cyclopropylmethoxy)-4-fluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-methyl-N-{[3-(trifluoromethoxy)phenyl]methyl}pyridine-3-carboxamide;

N-{[2-(1-cyclopropylethoxy)-3-fluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-N-{[2-fluoro-5-(trifluoromethoxy)phenyl](deutero)methyl}-2-methoxypyridine-3-carboxamide;

5-{2-acetamidoimidazo[1,2-b]pyridazin-6-yl}-N-{[2-fluoro-5-(trifluoromethyl)phenyl]methyl}-2-methoxy-pyridine-3-carboxamide;

N-{[2-chloro-5-(trifluoromethyl)phenyl]methyl}-5-{2-acetamidoimidazo[1,2-b]pyridazin-6-yl}-2-methoxy-pyridine-3-carboxamide;

N-{[2-(1-cyclopropylethoxy)-3,5-difluorophenyl]methyl}-5-{2-acetamidoimidazo[1,2-b]pyridazin-6-yl}-2-methoxypyridine-3-carboxamide;

N-{[5-(cyclopropylmethoxy)-2-fluorophenyl]methyl}-5-{2-acetamidoimidazo[1,2-b]pyridazin-6-yl}-2-methoxypyridine-3-carboxamide;

N-{[2-(cyclopropylmethoxy)-4,6-difluorophenyl]methyl}-5-{2-acetamidoimidazo[1,2-b]pyridazin-6-yl}-2-methoxypyridine-3-carboxamide;

N-{[2-(cyclopropylmethoxy)-3-fluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-N-{[4-fluoro-2-(oxan-4-yloxy)phenyl]methyl}-2-methoxy-pyridine-3-carboxamide;

5-(2-acetamidoimidazo[1,2-b]pyridazin-6-yl)-N-((3,5-difluoro-2-((tetrahydro-2H-pyran-4-yl)oxy)phenyl)methyl-d2)-2-methoxynicotinamide;

5-{2-acetamidoimidazo[1,2-b]pyridazin-6-yl}-N-{[2-fluoro-5-(trifluoromethoxy)phenyl]methyl}-2-methoxypyridine-3-carboxamide;

N-{[2-(cyclobutylmethoxy)phenyl]methyl}-5-{2-acetamidoimidazo[1,2-b]pyridazin-6-yl}-2-methoxypyridine-3-carboxamide;

N-{[2-(cyclopentyloxy)-6-fluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{[2-(trifluoromethoxy)phenyl]methyl}pyridine-3-carboxamide;

N-{[2-(cyclopropanesulfonyl)phenyl]methyl}-5-{2-acetamidoimidazo[1,2-b]pyridazin-6-yl}-2-methoxypyridine-3-carboxamide;

N-{[2-(cyclopentyloxy)phenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{[2-(1H-pyrrol-1-yl)phenyl]methyl}pyridine-3-carboxamide;

5-{2-acetamidoimidazo[1,2-b]pyridazin-6-yl}-N-{[(1S,2S)-2-(4-fluorophenyl)cyclopropyl]methyl}-2-methoxypyridine-3-carboxamide;

5-{2-acetamidoimidazo[1,2-b]pyridazin-6-yl}-2-methoxy-N-{[2-(morpholin-4-yl)phenyl]methyl}pyridine-3-carboxamide;

N-{[3-(cyclopentyloxy)pyridin-2-yl]methyl}-5-{2-acetamidoimidazo[1,2-b]pyridazin-6-yl}-2-methoxypyridine-3-carboxamide;

N-{[2-(cyclopentylmethoxy)phenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-2-methoxy-N-{[2-(propan-2-yloxy)phenyl]methyl}pyridine-3-carboxamide;

N-{[2-(cyclopentyloxy)-5-fluorophenyl]methyl}-5-{2-acetamidoimidazo[1,2-b]pyridazin-6-yl}-2-methoxypyridine-3-carboxamide;

N-({2-[(2,6-dimethyloxan-4-yl)oxy]-3,5-difluorophenyl}methyl)-5-{2-acetamidoimidazo[1,2-b]pyridazin-6-yl}-2-(deutero)methoxy-6-methylpyridine-3-carboxamide;

N-[(2-{[(2R,6S)-2,6-dimethyloxan-4-yl]oxy}-3-fluorophenyl)methyl]-5-{2-acetamidoimidazo[1,2-b]pyridazin-6-yl}-2-(deutero)methoxy-6-methylpyridine-3-carboxamide;

N-({3,5-difluoro-2-[(3R)-oxolan-3-yloxy]phenyl}methyl)-5-{2-acetamidoimidazo[1,2-b]pyridazin-6-yl}-2-(deutero)methoxy-6-methylpyridine-3-carboxamide;

N-{[3,5-difluoro-2-(oxan-3-yloxy)phenyl]methyl}-5-{2-acetamidoimidazo[1,2-b]pyridazin-6-yl}-2-(deutero)methoxy-6-methylpyridine-3-carboxamide;

N-({3,5-difluoro-2-[(3S)-oxolan-3-yloxy]phenyl}methyl)-5-{2-acetamidoimidazo[1,2-b]pyridazin-6-yl}-2-(deutero)methoxy-6-methylpyridine-3-carboxamide;

N-({3,5-difluoro-2-[(2-methyloxan-4-yl)oxy]phenyl}methyl)-5-{2-acetamidoimidazo[1,2-b]pyridazin-6-yl}-2-(deutero)methoxy-6-methylpyridine-3-carboxamide;

5-{2-acetamidoimidazo[1,2-b]pyridazin-6-yl}-N-{[2-fluoro-6-(2,2,2-trifluoroethoxy)phenyl]methyl}-2-(deutero)methoxy-6-methylpyridine-3-carboxamide;

N-({2-[cyclopropyl(deutero)methoxy]-3,5-difluorophenyl}methyl)-5-{2-acetamidoimidazo[1,2-b]pyridazin-6-yl}-2-(deutero)methoxy-6-methylpyridine-3-carboxamide;

5-{2-acetamidoimidazo[1,2-b]pyridazin-6-yl}-N-{[2-fluoro-5-(trifluoromethoxy)phenyl](deutero)methyl}-2-(deutero)methoxy-6-methylpyridine-3-carboxamide;

N-{[2-(cyclopropylmethoxy)-3,4-difluorophenyl]methyl}-5-{2-acetamidoimidazo[1,2-b]pyridazin-6-yl}-2-(deutero)methoxy-6-methylpyridine-3-carboxamide;

N-{[2-(cyclopropylmethoxy)-3,5-difluorophenyl]methyl}-5-{2-acetamidoimidazo[1,2-b]pyridazin-6-yl}-2-(deutero)methoxy-6-methylpyridine-3-carboxamide;

5-{2-acetamidoimidazo[1,2-b]pyridazin-6-yl}-2-(deutero)methoxy-6-methyl-N-{[2-(trifluoromethoxy)phenyl]methyl}pyridine-3-carboxamide;

5-{2-acetamidoimidazo[1,2-b]pyridazin-6-yl}-N-{[2-fluoro-5-(trifluoromethoxy)phenyl]methyl}-2-(deutero)methoxy-6-methylpyridine-3-carboxamide;

N-{[5-(cyclopropylmethoxy)-2-fluorophenyl]methyl}-5-{2-acetamidoimidazo[1,2-b]pyridazin-6-yl}-2-(deutero)methoxy-6-methylpyridine-3-carboxamide;

N-[(1S)-1-[2-fluoro-5-(trifluoromethoxy)phenyl]ethyl]-5-[2-(2-hydroxyacetamido)imidazo[1,2-b]pyridazin-6-yl]-2-methylpyridine-3-carboxamide;

N-[(1R)-1-[2-fluoro-5-(trifluoromethyl)phenyl]ethyl]-5-[2-(2-hydroxyacetamido)imidazo[1,2-b]pyridazin-6-yl]-2-methylpyridine-3-carboxamide;

N-{[2-fluoro-5-(trifluoromethyl)phenyl]methyl}-5-[2-(2-hydroxyacetamido)imidazo[1,2-b]pyridazin-6-yl]-2-methylpyridine-3-carboxamide;

N-{[3,5-difluoro-2-(oxan-4-yloxy)phenyl](deutero)methyl}-5-[2-(2-hydroxyacetamido)imidazo[1,2-b]pyridazin-6-yl]-2-methylpyridine-3-carboxamide;

N-[(1R)-1-[2-fluoro-5-(trifluoromethoxy)phenyl]ethyl]-5-[2-(2-hydroxyacetamido)imidazo[1,2-b]pyridazin-6-yl]-2-methylpyridine-3-carboxamide;

N-{[3,5-difluoro-2-(oxan-3-yloxy)phenyl]methyl}-5-{2-acetamidoimidazo[1,2-b]pyridazin-6-yl}-2-methylpyridine-3-carboxamide;

N-({3,5-difluoro-2-[(3S)-oxolan-3-yloxy]phenyl}methyl)-5-{2-acetamidoimidazo[1,2-b]pyridazin-6-yl}-2-methylpyridine-3-carboxamide;

N-({3,5-difluoro-2-[(2-methyloxan-4-yl)oxy]phenyl}methyl)-5-{2-acetamidoimidazo[1,2-b]pyridazin-6-yl}-2-methylpyridine-3-carboxamide;

N-({2-[(2,6-dimethyloxan-4-yl)oxy]-3,5-difluorophenyl}methyl)-5-{2-acetamidoimidazo[1,2-b]pyridazin-6-yl}-2-methylpyridine-3-carboxamide;

5-{2-acetamidoimidazo[1,2-b]pyridazin-6-yl}-N-{[2-fluoro-6-(2,2,2-trifluoroethoxy)phenyl]methyl}-2-methylpyridine-3-carboxamide;

5-{2-acetamidoimidazo[1,2-b]pyridazin-6-yl}-2-methyl-N-{[4-(trifluoromethyl)pyridin-2-yl]methyl}pyridine-3-carboxamide;

N-{[3,5-difluoro-2-(oxan-4-yloxy)phenyl](deutero)methyl}-5-{2-acetamidoimidazo[1,2-b]pyridazin-6-yl}-2-methylpyridine-3-carboxamide;

5-{2-acetamidoimidazo[1,2-b]pyridazin-6-yl}-2-methyl-N-{[2-(2,2,2-trifluoroethoxy)phenyl]methyl}pyridine-3-carboxamide;

5-{2-acetamidoimidazo[1,2-b]pyridazin-6-yl}-2-methyl-N-{[3-(2,2,2-trifluoroethoxy)phenyl]methyl}pyridine-3-carboxamide;

5-{2-acetamidoimidazo[1,2-b]pyridazin-6-yl}-N-{[5-fluoro-2-(2,2,2-trifluoroethoxy)phenyl]methyl}-2-methylpyridine-3-carboxamide;
5-{2-acetamidoimidazo[1,2-b]pyridazin-6-yl}-N-[(1S)-1-[2-fluoro-5-(trifluoromethyl)phenyl](2,2,2-deutero)ethyl]-2-methylpyridine-3-carboxamide;
5-{2-acetamidoimidazo[1,2-b]pyridazin-6-yl}-N-[(1R)-1-[2-fluoro-5-(trifluoromethyl)phenyl](2,2,2-deutero)ethyl]-2-methylpyridine-3-carboxamide;
5-{2-acetamidoimidazo[1,2-b]pyridazin-6-yl}-N-[(1S)-1-[2-fluoro-5-(trifluoromethoxy)phenyl](2,2,2-deutero)ethyl]-2-methylpyridine-3-carboxamide;
5-{2-acetamidoimidazo[1,2-b]pyridazin-6-yl}-N-[(1R)-1-[2-fluoro-5-(trifluoromethoxy)phenyl](2,2,2-deutero)ethyl]-2-methylpyridine-3-carboxamide;
5-{2-acetamidoimidazo[1,2-b]pyridazin-6-yl}-N-{[2-fluoro-5-(trifluoromethyl)phenyl](deutero)methyl}-2-methylpyridine-3-carboxamide;
N-{[3,5-difluoro-2-(oxan-4-yloxy)phenyl]methyl}-5-{2-acetamidoimidazo[1,2-b]pyridazin-6-yl}-2-methylpyridine-3-carboxamide;
5-{2-acetamidoimidazo[1,2-b]pyridazin-6-yl}-2-methyl-N-{1-[2-(trifluoromethoxy)phenyl]ethyl}pyridine-3-carboxamide;
5-{2-acetamidoimidazo[1,2-b]pyridazin-6-yl}-2-methyl-N-{1-[2-(trifluoromethoxy)phenyl]ethyl}pyridine-3-carboxamide;
5-{2-acetamidoimidazo[1,2-b]pyridazin-6-yl}-N-{1-[2-fluoro-5-(trifluoromethyl)phenyl]ethyl}-2-methylpyridine-3-carboxamide;
5-{2-acetamidoimidazo[1,2-b]pyridazin-6-yl}-N-{1-[2-fluoro-5-(trifluoromethyl)phenyl]ethyl}-2-methylpyridine-3-carboxamide;
5-{2-acetamidoimidazo[1,2-b]pyridazin-6-yl}-N-{[2-fluoro-5-(trifluoromethyl)phenyl]methyl}-2-methylpyridine-3-carboxamide;
5-{2-acetamidoimidazo[1,2-b]pyridazin-6-yl}-N-{[3-fluoro-5-(trifluoromethoxy)phenyl]methyl}-2-methylpyridine-3-carboxamide;
5-{2-acetamidoimidazo[1,2-b]pyridazin-6-yl}-N-{[2-fluoro-5-(trifluoromethoxy)phenyl](deutero)methyl}-2-methylpyridine-3-carboxamide;
N-{[2-(cyclopropylmethoxy)-3,4-difluorophenyl]methyl}-5-{2-acetamidoimidazo[1,2-b]pyridazin-6-yl}-2-methylpyridine-3-carboxamide;
N-{[2-(cyclobutylmethoxy)-3,5-difluorophenyl]methyl}-5-{2-acetamidoimidazo[1,2-b]pyridazin-6-yl}-2-methylpyridine-3-carboxamide;
N-[(3R)-3-(4-chlorophenyl)-3-hydroxypropyl]-5-{2-acetamidoimidazo[1,2-b]pyridazin-6-yl}-2-methylpyridine-3-carboxamide;
N-{[2-(cyclopropylmethoxy)-3-fluorophenyl]methyl}-5-{2-acetamidoimidazo[1,2-b]pyridazin-6-yl}-2-methylpyridine-3-carboxamide;
5-{2-acetamidoimidazo[1,2-b]pyridazin-6-yl}-N-{[2-fluoro-5-(trifluoromethoxy)phenyl]methyl}-2-methylpyridine-3-carboxamide;
N-{[2-(cyclopropylmethoxy)-3,5-difluorophenyl]methyl}-5-{2-acetamidoimidazo[1,2-b]pyridazin-6-yl}-2-methylpyridine-3-carboxamide;
N-{[5-(cyclopropylmethoxy)-2-fluorophenyl]methyl}-5-{2-acetamidoimidazo[1,2-b]pyridazin-6-yl}-2-methylpyridine-3-carboxamide;
N-[(3S)-3-(4-chlorophenyl)-3-hydroxypropyl]-5-{2-acetamidoimidazo[1,2-b]pyridazin-6-yl}-2-methylpyridine-3-carboxamide;
N-{[2-(cyclopentylmethoxy)pyridin-3-yl]methyl}-5-{2-acetamidoimidazo[1,2-b]pyridazin-6-yl}-2-methylpyridine-3-carboxamide;
N-{[2-(cyclopentylmethoxy)-5-fluorophenyl]methyl}-5-{2-acetamidoimidazo[1,2-b]pyridazin-6-yl}-2-methylpyridine-3-carboxamide;
N-{[2-(cyclobutylmethoxy)-6-fluorophenyl]methyl}-5-{2-acetamidoimidazo[1,2-b]pyridazin-6-yl}-2-methylpyridine-3-carboxamide;
5-{2-acetamidoimidazo[1,2-b]pyridazin-6-yl}-2-methyl-N-{[2-(trifluoromethoxy)phenyl]methyl}pyridine-3-carboxamide;
5-{2-acetamidoimidazo[1,2-b]pyridazin-6-yl}-2-methyl-N-{[3-(trifluoromethoxy)phenyl]methyl}pyridine-3-carboxamide;
N-{[2-(cyclopentyloxy)-5-fluorophenyl]methyl}-5-{2-acetamidoimidazo[1,2-b]pyridazin-6-yl}-2-methylpyridine-3-carboxamide;
N-{[2-(cyclopentyloxy)-6-fluorophenyl]methyl}-5-{2-acetamidoimidazo[1,2-b]pyridazin-6-yl}-2-methylpyridine-3-carboxamide;
5-{2-acetamidoimidazo[1,2-b]pyridazin-6-yl}-2-methyl-N-{[2-(oxolan-3-yloxy)phenyl]methyl}pyridine-3-carboxamide;
N-{[2-(cyclopentyloxy)phenyl]methyl}-5-{2-acetamidoimidazo[1,2-b]pyridazin-6-yl}-2-methylpyridine-3-carboxamide;
N-{[2-(cyclopropylmethoxy)-6-fluorophenyl]methyl}-5-{2-acetamidoimidazo[1,2-b]pyridazin-6-yl}-2-methylpyridine-3-carboxamide;
N-{[2-(cyclopropylmethoxy)phenyl]methyl}-5-{2-acetamidoimidazo[1,2-b]pyridazin-6-yl}-2-methylpyridine-3-carboxamide;
5-{2-acetamidoimidazo[1,2-b]pyridazin-6-yl}-N-[(1S)-1-[2-fluoro-5-(trifluoromethoxy)phenyl]ethyl]-6-methylpyridine-3-carboxamide;
5-{2-acetamidoimidazo[1,2-b]pyridazin-6-yl}-N-[(1R)-1-[2-fluoro-5-(trifluoromethoxy)phenyl](2,2,2-deutero)ethyl]-6-methylpyridine-3-carboxamide;
5-{2-acetamidoimidazo[1,2-b]pyridazin-6-yl}-N-{[2-fluoro-5-(trifluoromethoxy)phenyl](deutero)methyl}-6-methylpyridine-3-carboxamide;
5-{2-acetamidoimidazo[1,2-b]pyridazin-6-yl}-6-methyl-N-(3-phenylbutyl)pyridine-3-carboxamide;
N-{[2-(cyclopropylmethoxy)-3-fluorophenyl]methyl}-5-{2-acetamidoimidazo[1,2-b]pyridazin-6-yl}-6-methylpyridine-3-carboxamide;
5-{2-acetamidoimidazo[1,2-b]pyridazin-6-yl}-6-methyl-N-{[2-(trifluoromethoxy)phenyl]methyl}pyridine-3-carboxamide;
5-{2-acetamidoimidazo[1,2-b]pyridazin-6-yl}-N-{[2-fluoro-5-(trifluoromethoxy)phenyl]methyl}-6-methylpyridine-3-carboxamide;
5-{2-acetamidoimidazo[1,2-b]pyridazin-6-yl}-N-[(1R)-1-[2-fluoro-5-(trifluoromethoxy)phenyl]ethyl]pyridine-3-carboxamide;
N-{[5-(cyclopropylmethoxy)-2-fluorophenyl]methyl}-5-{2-acetamidoimidazo[1,2-b]pyridazin-6-yl}pyridine-3-carboxamide;
5-{2-acetamidoimidazo[1,2-b]pyridazin-6-yl}-N-{[2-fluoro-5-(trifluoromethoxy)phenyl]methyl}pyridine-3-carboxamide;
5-{2-acetamidoimidazo[1,2-b]pyridazin-6-yl}-N-(3-phenylbutyl)pyridine-3-carboxamide;
N-{[2-(cyclopropylmethoxy)phenyl]methyl}-5-{2-acetamidoimidazo[1,2-b]pyridazin-6-yl}pyridine-3-carboxamide;

N-{[2-(cyclopentyloxy)-6-fluorophenyl]methyl}-5-{2-acetamidoimidazo[1,2-b]pyridazin-6-yl}pyridine-3-carboxamide;

N-{[3-(cyclopentyloxy)pyridin-2-yl]methyl}-5-{2-acetamidoimidazo[1,2-b]pyridazin-6-yl}pyridine-3-carboxamide;

N-{[2-(cyclopentyloxy)-5-fluorophenyl]methyl}-5-{2-acetamidoimidazo[1,2-b]pyridazin-6-yl}pyridine-3-carboxamide;

N-({2-[cyclopropyl(deutero)methoxy]-3,5-difluorophenyl}methyl)-2-methoxy-5-{2-propanamidoimidazo[1,2-b]pyridazin-6-yl}pyridine-3-carboxamide;

N-{[2-fluoro-5-(trifluoromethoxy)phenyl](deutero)methyl}-2-methoxy-5-{2-propanamidoimidazo[1,2-b]pyridazin-6-yl}pyridine-3-carboxamide;

N-[(1R)-1-[2-fluoro-5-(trifluoromethoxy)phenyl]ethyl]-2-methoxy-5-{2-propanamidoimidazo[1,2-b]pyridazin-6-yl}pyridine-3-carboxamide;

N-[(3S)-3-(4-chlorophenyl)-3-hydroxypropyl]-2-methoxy-5-{2-propanamidoimidazo[1,2-b]pyridazin-6-yl}pyridine-3-carboxamide;

N-{[3,5-difluoro-2-(oxan-4-yloxy)phenyl]methyl}-2-methoxy-5-{2-propanamidoimidazo[1,2-b]pyridazin-6-yl}pyridine-3-carboxamide;

2-methoxy-5-{2-propanamidoimidazo[1,2-b]pyridazin-6-yl}-N-{[2-(trifluoromethoxy)phenyl]methyl}pyridine-3-carboxamide;

N-{[2-(cyclopropylmethoxy)-3,4-difluorophenyl]methyl}-2-methoxy-5-{2-propanamidoimidazo[1,2-b]pyridazin-6-yl}pyridine-3-carboxamide;

N-{[5-(cyclopropylmethoxy)-2-fluorophenyl]methyl}-2-methoxy-5-{2-propanamidoimidazo[1,2-b]pyridazin-6-yl}pyridine-3-carboxamide;

5-{2-acetamido-3-methylimidazo[1,2-b]pyridazin-6-yl}-2-methyl-N-{[3-(trifluoromethoxy)phenyl]methyl}pyridine-3-carboxamide;

5-{2-acetamido-3-methylimidazo[1,2-b]pyridazin-6-yl}-N-{[2-fluoro-5-(trifluoromethyl)phenyl]methyl}-2-methylpyridine-3-carboxamide;

5-{2-acetamido-3-methylimidazo[1,2-b]pyridazin-6-yl}-N-{[2-fluoro-5-(trifluoromethoxy)phenyl]methyl}-2-methylpyridine-3-carboxamide;

5-{2-acetamido-3-methylimidazo[1,2-b]pyridazin-6-yl}-N-{[2-fluoro-5-(trifluoromethyl)phenyl]methyl}-2-methoxypyridine-3-carboxamide;

5-{2-acetamido-3-methylimidazo[1,2-b]pyridazin-6-yl}-N-{[4-fluoro-3-(trifluoromethoxy)phenyl]methyl}-2-methoxypyridine-3-carboxamide;

5-{2-acetamido-3-methylimidazo[1,2-b]pyridazin-6-yl}-2-methoxy-N-(3-phenylbutyl)pyridine-3-carboxamide;

5-{2-acetamido-3-methylimidazo[1,2-b]pyridazin-6-yl}-2-methoxy-N-{[3-(trifluoromethoxy)phenyl]methyl}pyridine-3-carboxamide;

5-{2-acetamido-3-methylimidazo[1,2-b]pyridazin-6-yl}-2-methoxy-N-{[2-(trifluoromethoxy)phenyl]methyl}pyridine-3-carboxamide;

N-({2-[cyclopropyl(deutero)methoxy]-3,5-difluorophenyl}methyl)-5-{2-acetamido-3-methylimidazo[1,2-b]pyridazin-6-yl}-2-methoxypyridine-3-carboxamide;

N-{[5-(cyclopropylmethoxy)-2-fluorophenyl]methyl}-2-methoxy-5-[2-(2-methoxyacetamido)imidazo[1,2-b]pyridazin-6-yl]pyridine-3-carboxamide;

N-{[2-(cyclopropylmethoxy)-3,5-difluorophenyl]methyl}-2-methoxy-5-[2-(2-methoxyacetamido)imidazo[1,2-b]pyridazin-6-yl]pyridine-3-carboxamide;

N-{[2-fluoro-5-(trifluoromethoxy)phenyl]methyl}-2-methoxy-5-[2-(2-methoxyacetamido)imidazo[1,2-b]pyridazin-6-yl]pyridine-3-carboxamide;

2-methoxy-5-[2-(2-methylpropanamido)imidazo[1,2-b]pyridazin-6-yl]-N-{[2-(trifluoromethoxy)phenyl]methyl}pyridine-3-carboxamide;

N-{[2-(cyclopropylmethoxy)-3,4-difluorophenyl]methyl}-2-methoxy-5-[2-(2-methylpropanamido)imidazo[1,2-b]pyridazin-6-yl]pyridine-3-carboxamide;

N-{[3,5-difluoro-2-(oxan-4-yloxy)phenyl]methyl}-2-methoxy-5-[2-(2-methylpropanamido)imidazo[1,2-b]pyridazin-6-yl]pyridine-3-carboxamide;

2-chloro-N-({2-[cyclopropyl(deutero)methoxy]-3,5-difluorophenyl}methyl)-5-{2-acetamidoimidazo[1,2-b]pyridazin-6-yl}pyridine-3-carboxamide;

2-chloro-N-[(3S)-3-(4-chlorophenyl)-3-hydroxypropyl]-5-{2-acetamidoimidazo[1,2-b]pyridazin-6-yl}pyridine-3-carboxamide;

2-chloro-5-{2-acetamidoimidazo[1,2-b]pyridazin-6-yl}-N-{1-[2-(trifluoromethoxy)phenyl]ethyl}pyridine-3-carboxamide;

2-chloro-5-{2-acetamidoimidazo[1,2-b]pyridazin-6-yl}-N-{1-[2-fluoro-5-(trifluoromethyl)phenyl]ethyl}pyridine-3-carboxamide;

2-chloro-5-{2-acetamidoimidazo[1,2-b]pyridazin-6-yl}-N-{1-[2-fluoro-5-(trifluoromethyl)phenyl]ethyl}pyridine-3-carboxamide;

2-chloro-5-{2-acetamidoimidazo[1,2-b]pyridazin-6-yl}-N-{1-[2-(trifluoromethoxy)phenyl]ethyl}pyridine-3-carboxamide;

2-chloro-5-{2-acetamidoimidazo[1,2-b]pyridazin-6-yl}-N-{[3-(trifluoromethoxy)phenyl]methyl}pyridine-3-carboxamide;

2-chloro-N-{[2-(1-cyclobutylethoxy)-3,5-difluorophenyl]methyl}-5-{2-acetamidoimidazo[1,2-b]pyridazin-6-yl}pyridine-3-carboxamide;

2-chloro-N-{[2-chloro-5-(trifluoromethyl)phenyl]methyl}-5-{2-acetamidoimidazo[1,2-b]pyridazin-6-yl}pyridine-3-carboxamide;

2-chloro-5-{2-acetamidoimidazo[1,2-b]pyridazin-6-yl}-N-{[2-fluoro-5-(trifluoromethyl)phenyl]methyl}pyridine-3-carboxamide;

5-{2-acetamidoimidazo[1,2-b]pyridazin-6-yl}-N-{1-[2-fluoro-5-(trifluoromethyl)phenyl]ethyl}-2-methoxy-6-methylpyridine-3-carboxamide;

5-{2-acetamidoimidazo[1,2-b]pyridazin-6-yl}-N-{1-[2-fluoro-5-(trifluoromethyl)phenyl]ethyl}-2-methoxy-6-methylpyridine-3-carboxamide;

5-{2-acetamidoimidazo[1,2-b]pyridazin-6-yl}-N-{1-[2-fluoro-5-(trifluoromethoxy)phenyl]ethyl}-2-methoxy-6-methylpyridine-3-carboxamide;

5-{2-acetamidoimidazo[1,2-b]pyridazin-6-yl}-N-{1-[2-fluoro-5-(trifluoromethoxy)phenyl]ethyl}-2-methoxy-6-methylpyridine-3-carboxamide;

5-{2-acetamidoimidazo[1,2-b]pyridazin-6-yl}-N-{[3-fluoro-5-(trifluoromethoxy)phenyl]methyl}-2-methoxy-6-methylpyridine-3-carboxamide;

5-{2-acetamidoimidazo[1,2-b]pyridazin-6-yl}-2-methoxy-N,6-dimethyl-N-{[3-(trifluoromethoxy)phenyl]methyl}pyridine-3-carboxamide;

5-{2-acetamidoimidazo[1,2-b]pyridazin-6-yl}-N-{[2-fluoro-5-(trifluoromethoxy)phenyl](deutero)methyl}-2-methoxy-6-methylpyridine-3-carboxamide;

5-{2-acetamidoimidazo[1,2-b]pyridazin-6-yl}-2-methoxy-N,6-dimethyl-N-{[2-(trifluoromethoxy)phenyl]methyl}pyridine-3-carboxamide;

N-{[2-(cyclopropylmethoxy)-4,5-difluorophenyl]methyl}-5-{2-acetamidoimidazo[1,2-b]pyridazin-6-yl}-2-methoxy-6-methylpyridine-3-carboxamide;

N-[(3,6-difluoro-2-methoxyphenyl)methyl]-5-{2-acetamidoimidazo[1,2-b]pyridazin-6-yl}-2-methoxy-6-methylpyridine-3-carboxamide;

N-{[2-(cyclopropylmethoxy)-3,4-difluorophenyl]methyl}-5-{2-acetamidoimidazo[1,2-b]pyridazin-6-yl}-2-methoxy-6-methylpyridine-3-carboxamide;

N-{[2-(cyclopropylmethoxy)-3,5-difluorophenyl](deutero)methyl}-5-{2-acetamidoimidazo[1,2-b]pyridazin-6-yl}-2-methoxy-6-methylpyridine-3-carboxamide;

N-{[2-(cyclobutylmethoxy)-3-fluorophenyl]methyl}-5-{2-acetamidoimidazo[1,2-b]pyridazin-6-yl}-2-methoxy-6-methylpyridine-3-carboxamide;

5-{2-acetamidoimidazo[1,2-b]pyridazin-6-yl}-2-methoxy-6-methyl-N-{1-[3-(trifluoromethoxy)phenyl]ethyl}pyridine-3-carboxamide;

5-{2-acetamidoimidazo[1,2-b]pyridazin-6-yl}-2-methoxy-6-methyl-N-{1-[2-(trifluoromethoxy)phenyl]ethyl}pyridine-3-carboxamide;

5-{2-acetamidoimidazo[1,2-b]pyridazin-6-yl}-2-methoxy-6-methyl-N-{1-[2-(trifluoromethoxy)phenyl]ethyl}pyridine-3-carboxamide;

5-{2-acetamidoimidazo[1,2-b]pyridazin-6-yl}-2-methoxy-6-methyl-N-{1-[3-(trifluoromethoxy)phenyl]ethyl}pyridine-3-carboxamide;

5-{2-acetamidoimidazo[1,2-b]pyridazin-6-yl}-N-{[3-fluoro-5-(trifluoromethyl)phenyl]methyl}-2-methoxy-6-methylpyridine-3-carboxamide;

N-{[2-(cyclobutylmethoxy)-3,5-difluorophenyl]methyl}-5-{2-acetamidoimidazo[1,2-b]pyridazin-6-yl}-2-methoxy-6-methylpyridine-3-carboxamide;

5-{2-acetamidoimidazo[1,2-b]pyridazin-6-yl}-2-methoxy-6-methyl-N-{[2-(trifluoromethoxy)phenyl](deutero)methyl}pyridine-3-carboxamide;

5-{2-acetamidoimidazo[1,2-b]pyridazin-6-yl}-N-{[2-fluoro-5-(trifluoromethyl)phenyl]methyl}-2-methoxy-6-methylpyridine-3-carboxamide;

N-{[5-(cyclopropylmethoxy)-2-fluorophenyl]methyl}-5-{2-acetamidoimidazo[1,2-b]pyridazin-6-yl}-2-methoxy-6-methylpyridine-3-carboxamide;

N-{[2-(cyclopropylmethoxy)-4,6-difluorophenyl]methyl}-5-{2-acetamidoimidazo[1,2-b]pyridazin-6-yl}-2-methoxy-6-methylpyridine-3-carboxamide;

N-{[2-(cyclopropylmethoxy)-3-fluorophenyl]methyl}-5-{2-acetamidoimidazo[1,2-b]pyridazin-6-yl}-2-methoxy-6-methylpyridine-3-carboxamide;

N-{[2-(cyclopropylmethoxy)-3,5-difluorophenyl]methyl}-5-{2-acetamidoimidazo[1,2-b]pyridazin-6-yl}-2-methoxy-6-methylpyridine-3-carboxamide;

N-[(3S)-3-(4-chlorophenyl)-3-hydroxypropyl]-5-{2-acetamidoimidazo[1,2-b]pyridazin-6-yl}-2-methoxy-6-methylpyridine-3-carboxamide;

N-{[2-(1-cyclopentylethoxy)phenyl]methyl}-5-{2-acetamidoimidazo[1,2-b]pyridazin-6-yl}-2-methoxy-6-methylpyridine-3-carboxamide;

N-{[2-(1-cyclopentylethoxy)phenyl]methyl}-5-{2-acetamidoimidazo[1,2-b]pyridazin-6-yl}-2-methoxy-6-methylpyridine-3-carboxamide;

5-{2-acetamidoimidazo[1,2-b]pyridazin-6-yl}-2-methoxy-6-methyl-N-{2-[3-(trifluoromethoxy)phenyl]ethyl}pyridine-3-carboxamide;

5-{2-acetamidoimidazo[1,2-b]pyridazin-6-yl}-2-methoxy-6-methyl-N-{[3-(trifluoromethyl)phenyl]methyl}pyridine-3-carboxamide;

5-{2-acetamidoimidazo[1,2-b]pyridazin-6-yl}-2-methoxy-6-methyl-N-{[2-(oxolan-3-yloxy)phenyl]methyl}pyridine-3-carboxamide;

5-{2-acetamidoimidazo[1,2-b]pyridazin-6-yl}-2-methoxy-6-methyl-N-{[2-(oxolan-3-yloxy)phenyl]methyl}pyridine-3-carboxamide;

N-{[2-(cyclopentylmethoxy)-4,6-difluorophenyl]methyl}-5-{2-acetamidoimidazo[1,2-b]pyridazin-6-yl}-2-methoxy-6-methylpyridine-3-carboxamide;

N-{[3-(cyclopropylmethoxy)phenyl]methyl}-5-{2-acetamidoimidazo[1,2-b]pyridazin-6-yl}-2-methoxy-6-methylpyridine-3-carboxamide;

N-({2-[(4,4-difluorocyclohexyl)methoxy]phenyl}methyl)-5-{2-acetamidoimidazo[1,2-b]pyridazin-6-yl}-2-methoxy-6-methylpyridine-3-carboxamide;

5-{2-acetamidoimidazo[1,2-b]pyridazin-6-yl}-N-{[2-fluoro-5-(trifluoromethoxy)phenyl]methyl}-2-methoxy-6-methylpyridine-3-carboxamide;

N-{[3-(cyclopentylmethoxy)pyridin-2-yl]methyl}-5-{2-acetamidoimidazo[1,2-b]pyridazin-6-yl}-2-methoxy-6-methylpyridine-3-carboxamide;

N-{[2-(cyclopentylmethoxy)pyridin-3-yl]methyl}-5-{2-acetamidoimidazo[1,2-b]pyridazin-6-yl}-2-methoxy-6-methylpyridine-3-carboxamide;

N-{[2-(cyclobutylmethoxy)pyridin-3-yl]methyl}-5-{2-acetamidoimidazo[1,2-b]pyridazin-6-yl}-2-methoxy-6-methylpyridine-3-carboxamide;

N-{[2-(cyclopentylmethoxy)-5-fluorophenyl]methyl}-5-{2-acetamidoimidazo[1,2-b]pyridazin-6-yl}-2-methoxy-6-methylpyridine-3-carboxamide;

N-{[2-(cyclopentylmethoxy)phenyl]methyl}-5-{2-acetamidoimidazo[1,2-b]pyridazin-6-yl}-2-methoxy-6-methylpyridine-3-carboxamide;

N-{[2-(cyclopropylmethoxy)-4-fluorophenyl]methyl}-5-{2-acetamidoimidazo[1,2-b]pyridazin-6-yl}-2-methoxy-6-methylpyridine-3-carboxamide;

N-{[2-(cyclopropylmethoxy)phenyl]methyl}-5-{2-acetamidoimidazo[1,2-b]pyridazin-6-yl}-2-methoxy-6-methylpyridine-3-carboxamide;

5-{2-acetamidoimidazo[1,2-b]pyridazin-6-yl}-2-methoxy-6-methyl-N-{[3-(trifluoromethoxy)phenyl]methyl}pyridine-3-carboxamide;

2-((6-(5-((2-fluoro-5-(trifluoromethoxy)benzyl)carbamoyl)-2,6-dimethylpyridin-3-yl)imidazo[1,2-b]pyridazin-2-yl)amino)-2-oxoethyl dihydrogen phosphate;

6-chloro-5-{2-acetamidoimidazo[1,2-b]pyridazin-6-yl}-N-{[5-fluoro-2-(trifluoromethoxy)phenyl]methyl}pyridine-3-carboxamide;

6-chloro-5-{2-acetamidoimidazo[1,2-b]pyridazin-6-yl}-N-{[5-fluoro-2-(trifluoromethoxy)phenyl]methyl}pyridine-3-carboxamide;

N-{[2-(3,3-difluoropyrrolidine-1-carbonyl)-5-fluorophenyl]methyl}-5-{2-acetamidoimidazo[1,2-b]pyridazin-6-yl}-2-methoxypyridine-3-carboxamide;

N-{[2-(3,3-difluoropyrrolidine-1-carbonyl)-3,5-difluorophenyl]methyl}-5-{2-acetamidoimidazo[1,2-b]pyridazin-6-yl}-2-methoxypyridine-3-carboxamide;

5-{2-acetamidoimidazo[1,2-b]pyridazin-6-yl}-N-{[2-fluoro-6-(2,2,2-trifluoroethoxy)phenyl]methyl}-2,6-dimethylpyridine-3-carboxamide;

N-{[5-(cyclopropylmethoxy)-2-fluorophenyl]methyl}-5-{2-acetamidoimidazo[1,2-b]pyridazin-6-yl}-2,6-dimethylpyridine-3-carboxamide;

({6-[5-({[2-fluoro-5-(trifluoromethoxy)phenyl]methyl}carbamoyl)-2,6-dimethylpyridin-3-yl]imidazo[1,2-b]pyridazin-2-yl}carbamoyl)methyl acetate;

5-{2-acetamidoimidazo[1,2-b]pyridazin-6-yl}-2-ethyl-N-[(1R)-1-[2-fluoro-5-(trifluoromethoxy)phenyl]ethyl]pyridine-3-carboxamide;

5-{2-acetamidoimidazo[1,2-b]pyridazin-6-yl}-2-ethyl-N-{[2-fluoro-5-(trifluoromethyl)phenyl]methyl}pyridine-3-carboxamide;

5-{2-acetamidoimidazo[1,2-b]pyridazin-6-yl}-N-[(1R)-1-[2-fluoro-5-(trifluoromethoxy)phenyl]ethyl]-N,2-dimethylpyridine-3-carboxamide;

N-[(1R)-1-[2-fluoro-5-(trifluoromethyl)phenyl]ethyl]-2-methyl-5-(2-{2-[4-(trifluoromethyl)piperidin-1-yl]acetamido}imidazo[1,2-b]pyridazin-6-yl)pyridine-3-carboxamide;

N-[(1R)-1-[2-fluoro-5-(trifluoromethyl)phenyl]ethyl]-2-methyl-5-{2-[2-(4-methylpiperazin-1-yl)acetamido]imidazo[1,2-b]pyridazin-6-yl}pyridine-3-carboxamide;

N-[(1R)-1-[2-fluoro-5-(trifluoromethyl)phenyl]ethyl]-2-methyl-5-{2-[2-(pyrrolidin-1-yl)acetamido]imidazo[1,2-b]pyridazin-6-yl}pyridine-3-carboxamide;

5-{2-[2-(4,4-difluoropiperidin-1-yl)acetamido]imidazo[1,2-b]pyridazin-6-yl}-N-[(1R)-1-[2-fluoro-5-(trifluoromethoxy)phenyl]ethyl]-2-methylpyridine-3-carboxamide;

5-{2-[2-(3,3-difluoroazetidin-1-yl)acetamido]imidazo[1,2-b]pyridazin-6-yl}-N-[(1R)-1-[2-fluoro-5-(trifluoromethoxy)phenyl]ethyl]-2-methylpyridine-3-carboxamide;

N-[(1R)-1-[2-fluoro-5-(trifluoromethoxy)phenyl]ethyl]-2-methyl-5-{2-[2-(4-methylpiperazin-1-yl)acetamido]imidazo[1,2-b]pyridazin-6-yl}pyridine-3-carboxamide;

N-[(1R)-1-[2-fluoro-5-(trifluoromethoxy)phenyl]ethyl]-2-methyl-5-{2-[2-(morpholin-4-yl)acetamido]imidazo[1,2-b]pyridazin-6-yl}pyridine-3-carboxamide;

5-{2-[2-(dimethylamino)acetamido]imidazo[1,2-b]pyridazin-6-yl}-N-[(1R)-1-[2-fluoro-5-(trifluoromethoxy)phenyl]ethyl]-2-methylpyridine-3-carboxamide;

N—((R)-1-(2-fluoro-5-(trifluoromethoxy)phenyl)ethyl)-5-(2-((S)-2-hydroxypropanamido)imidazo[1,2-b]pyridazin-6-yl)-2-methylnicotinamide;

N-[(1R)-1-[2-fluoro-5-(trifluoromethoxy)phenyl]ethyl]-2-methyl-5-{2-[2-(methylamino)acetamido]imidazo[1,2-b]pyridazin-6-yl}pyridine-3-carboxamide;

5-[2-(2-aminoacetamido)imidazo[1,2-b]pyridazin-6-yl]-N-[(1R)-1-[2-fluoro-5-(trifluoromethoxy)phenyl]ethyl]-2-methylpyridine-3-carboxamide;

{[6-(5-{[(1R)-1-[2-fluoro-5-(trifluoromethoxy)phenyl]ethyl]carbamoyl}-6-methylpyridin-3-yl)imidazo[1,2-b]pyridazin-2-yl]carbamoyl}methyl acetate;

N-[(3R)-3-(4-chlorophenyl)-3-hydroxypropyl]-5-{2-[2-(4,4-difluoropiperidin-1-yl)acetamido]imidazo[1,2-b]pyridazin-6-yl}-2-methylpyridine-3-carboxamide;

N-[(3R)-3-(4-chlorophenyl)-3-hydroxypropyl]-5-{2-[2-(3,3-difluoroazetidin-1-yl)acetamido]imidazo[1,2-b]pyridazin-6-yl}-2-methylpyridine-3-carboxamide;

N-[(3R)-3-(4-chlorophenyl)-3-hydroxypropyl]-2-methyl-5-{2-[2-(morpholin-4-yl)acetamido]imidazo[1,2-b]pyridazin-6-yl}pyridine-3-carboxamide;

N-[(3S)-3-(4-chlorophenyl)-3-hydroxypropyl]-2-methyl-5-{2-[2-(morpholin-4-yl)acetamido]imidazo[1,2-b]pyridazin-6-yl}pyridine-3-carboxamide;

N-[(3S)-3-(4-chlorophenyl)-3-hydroxypropyl]-5-{2-[2-(dimethylamino)acetamido]imidazo[1,2-b]pyridazin-6-yl}-2-methylpyridine-3-carboxamide;

5-{2-acetamidoimidazo[1,2-b]pyridazin-6-yl}-N-{1-[1-(4-fluorophenyl)ethyl]-1H-pyrazol-4-yl}-2-methylpyridine-3-carboxamide;

N-{1-[(4-chlorophenyl)methyl]-1H-imidazol-4-yl}-5-{2-acetamidoimidazo[1,2-b]pyridazin-6-yl}-2-methylpyridine-3-carboxamide;

5-{2-acetamidoimidazo[1,2-b]pyridazin-6-yl}-N-{1-[(4-fluorophenyl)methyl]-1H-imidazol-4-yl}-2-methylpyridine-3-carboxamide;

N-(1-benzyl-1H-imidazol-4-yl)-5-{2-acetamidoimidazo[1,2-b]pyridazin-6-yl}-2-methylpyridine-3-carboxamide;

5-{2-acetamidoimidazo[1,2-b]pyridazin-6-yl}-N-{[2-fluoro-5-(1-methyl-1H-pyrazol-4-yl)phenyl]methyl}-2-methylpyridine-3-carboxamide;

N-[6-(5-{3-[(4-fluorophenyl)(hydroxy)methyl]piperidine-1-carbonyl}-6-methylpyridin-3-yl)imidazo[1,2-b]pyridazin-2-yl]acetamide;

5-{2-acetamidoimidazo[1,2-b]pyridazin-6-yl}-N-[3-(4-fluorophenyl)-2-hydroxy-2-methylpropyl]-2-methylpyridine-3-carboxamide;

N-[6-(5-{3-[(4-fluorophenyl)methyl]-3-hydroxypiperidine-1-carbonyl}-6-methylpyridin-3-yl)imidazo[1,2-b]pyridazin-2-yl]acetamide;

5-(2-acetamidoimidazo[1,2-b]pyridazin-6-yl)-3-fluoro-N-(2-fluoro-5-(1-methyl-1H-pyrazol-4-yl)benzyl)-2-methylbenzamide;

5-{2-acetamidoimidazo[1,2-b]pyridazin-6-yl}-3-fluoro-N-{[2-fluoro-5-(trifluoromethoxy)phenyl]methyl}-2-methylbenzamide;

5-{2-acetamidoimidazo[1,2-b]pyridazin-6-yl}-3-fluoro-N-[(1S)-1-[2-fluoro-5-(trifluoromethoxy)phenyl]ethyl]-2-methylbenzamide;

5-{2-acetamidoimidazo[1,2-b]pyridazin-6-yl}-3-fluoro-N-{[2-fluoro-3-(trifluoromethoxy)phenyl]methyl}-2-methylbenzamide;

N-[(3S)-3-(4-chlorophenyl)-3-hydroxypropyl]-5-{2-[2-(dimethylamino)acetamido]imidazo[1,2-b]pyridazin-6-yl}-3-fluoro-2-methylbenzamide;

N-[(3S)-3-(4-chlorophenyl)-3-hydroxypropyl]-3-fluoro-2-methyl-5-{2-[2-(methylamino)acetamido]imidazo[1,2-b]pyridazin-6-yl}benzamide;

5-{2-acetamidoimidazo[1,2-b]pyridazin-6-yl}-3-fluoro-2-methyl-N-[(2-phenoxyphenyl)methyl]benzamide;

N-{[2-(3,3-difluoropyrrolidine-1-carbonyl)-6-fluorophenyl]methyl}-5-{2-acetamidoimidazo[1,2-b]pyridazin-6-yl}-3-fluoro-2-methylbenzamide;

5-{2-acetamidoimidazo[1,2-b]pyridazin-6-yl}-2,3-difluoro-N-{[2-fluoro-5-(trifluoromethoxy)phenyl]methyl}benzamide;

5-{2-acetamidoimidazo[1,2-b]pyridazin-6-yl}-2,3-difluoro-N-[(1R)-1-[2-fluoro-5-(trifluoromethoxy)phenyl]ethyl]benzamide;

3-{2-acetamidoimidazo[1,2-b]pyridazin-6-yl}-2,4,5-trifluoro-N-{[2-fluoro-5-(trifluoromethoxy)phenyl]methyl}benzamide;

3-{2-acetamidoimidazo[1,2-b]pyridazin-6-yl}-2,4,5-trifluoro-N-{[2-fluoro-5-(trifluoromethyl)phenyl]methyl}benzamide;

N-[(3R)-3-(4-chlorophenyl)-3-hydroxypropyl]-3-{2-acetamidoimidazo[1,2-b]pyridazin-6-yl}-5-fluorobenzamide;

5-{2-acetamidoimidazo[1,2-b]pyridazin-6-yl}-3-fluoro-N-{[2-fluoro-5-(trifluoromethoxy)phenyl]methyl}-2-methoxybenzamide;

3-{2-acetamidoimidazo[1,2-b]pyridazin-6-yl}-5-fluoro-N-{[2-fluoro-5-(trifluoromethyl)phenyl]methyl}-4-methylbenzamide;

N-[(3R)-3-(4-chlorophenyl)-3-hydroxypropyl]-3-{2-acetamidoimidazo[1,2-b]pyridazin-6-yl}-5-fluoro-4-methylbenzamide;

N-[(3R)-3-(4-chlorophenyl)-3-hydroxypropyl]-3-{2-acetamidoimidazo[1,2-b]pyridazin-6-yl}-2-fluoro-6-methoxybenzamide;

3-{2-acetamidoimidazo[1,2-b]pyridazin-6-yl}-2-fluoro-N-[(1S)-1-[2-fluoro-5-(trifluoromethoxy)phenyl]ethyl]-6-methoxybenzamide;

N-{[2-(3,3-difluoropyrrolidine-1-carbonyl)-5-fluorophenyl]methyl}-3-{2-acetamidoimidazo[1,2-b]pyridazin-6-yl}-2-fluoro-6-methoxybenzamide;

N-{[2-(cyclopropylmethoxy)phenyl]methyl}-3-{2-acetamidoimidazo[1,2-b]pyridazin-6-yl}-2-fluoro-6-methoxybenzamide;

(R)-3-(2-acetamidoimidazo[1,2-b]pyridazin-6-yl)-2-fluoro-N-(1-(2-fluoro-5-(trifluoromethoxy)phenyl)ethyl-2,2,2-d3)-6-methoxybenzamide;

3-{2-acetamidoimidazo[1,2-b]pyridazin-6-yl}-2,6-difluoro-N-[(1S)-1-[2-fluoro-5-(trifluoromethoxy)phenyl]ethyl]benzamide;

(R)-3-(2-acetamidoimidazo[1,2-b]pyridazin-6-yl)-2,6-difluoro-N-(1-(2-fluoro-5-(trifluoromethoxy)phenyl)ethyl-2,2,2-d3)benzamide;

N-{[2-(4,4-difluoropiperidine-1-carbonyl)-5-fluorophenyl]methyl}-3-{2-acetamidoimidazo[1,2-b]pyridazin-6-yl}-2,6-difluorobenzamide;

N-[(3R)-3-(4-chlorophenyl)-3-hydroxypropyl]-5-{2-acetamidoimidazo[1,2-b]pyridazin-6-yl}-2,4-dimethylbenzamide;

N-[(3S)-3-(4-chlorophenyl)-3-hydroxypropyl]-5-{2-acetamidoimidazo[1,2-b]pyridazin-6-yl}-2,4-dimethylbenzamide;

N-{[3-chloro-2-fluoro-5-(trifluoromethyl)phenyl]methyl}-5-{2-acetamidoimidazo[1,2-b]pyridazin-6-yl}-2,4-dimethylbenzamide;

5-{2-acetamidoimidazo[1,2-b]pyridazin-6-yl}-N-{[2-fluoro-5-(trifluoromethyl)phenyl]methyl}-2-(trifluoromethyl)benzamide;

2-chloro-N-[(3R)-3-(4-chlorophenyl)-3-hydroxypropyl]-5-{2-acetamidoimidazo[1,2-b]pyridazin-6-yl}benzamide;

2-chloro-N-{[2-(3,3-difluoropyrrolidine-1-carbonyl)-5-fluorophenyl]methyl}-5-{2-acetamidoimidazo[1,2-b]pyridazin-6-yl}benzamide;

6-chloro-3-{2-acetamidoimidazo[1,2-b]pyridazin-6-yl}-2-fluoro-N-[(1R)-1-[2-fluoro-5-(trifluoromethoxy)phenyl]ethyl]benzamide;

6-chloro-3-{2-acetamidoimidazo[1,2-b]pyridazin-6-yl}-2-fluoro-N-{[2-fluoro-5-(1-methyl-1H-pyrazol-4-yl)phenyl]methyl}benzamide;

6-chloro-N-[(3S)-3-(4-chlorophenyl)-3-hydroxypropyl]-3-{2-acetamidoimidazo[1,2-b]pyridazin-6-yl}-2-fluorobenzamide;

6-chloro-3-{2-acetamidoimidazo[1,2-b]pyridazin-6-yl}-2-fluoro-N-{[4-(trifluoromethoxy)phenyl]methyl}benzamide;

2-chloro-5-{2-acetamidoimidazo[1,2-b]pyridazin-6-yl}-4-fluoro-N-[(1R)-1-[2-fluoro-5-(trifluoromethoxy)phenyl]ethyl]benzamide;

2-chloro-5-{2-acetamidoimidazo[1,2-b]pyridazin-6-yl}-N-{[2-fluoro-5-(trifluoromethoxy)phenyl]methyl}-4-methylbenzamide;

5-{2-acetamidoimidazo[1,2-b]pyridazin-6-yl}-N-{[2-fluoro-5-(trifluoromethoxy)phenyl]methyl}-2-methylbenzamide;

(S)—N-(2-fluoro-5-(trifluoromethoxy)benzyl)-5-(2-(2-hydroxypropanamido)imidazo[1,2-b]pyridazin-6-yl)-2-methylbenzamide;

(R)-5-(2-acetamidoimidazo[1,2-b]pyridazin-6-yl)-N-(1-(2-fluoro-5-(trifluoromethoxy)phenyl)ethyl)-2-methylbenzamide;

N-[(3R)-3-(4-chlorophenyl)-3-hydroxypropyl]-5-{2-acetamidoimidazo[1,2-b]pyridazin-6-yl}-2-methylbenzamide;

N-[(3S)-3-(4-chlorophenyl)-3-hydroxypropyl]-5-{2-acetamidoimidazo[1,2-b]pyridazin-6-yl}-2-methylbenzamide;

N-(1-benzyl-1H-pyrazol-4-yl)-5-{2-acetamidoimidazo[1,2-b]pyridazin-6-yl}-2-methylbenzamide;

5-{2-acetamidoimidazo[1,2-b]pyridazin-6-yl}-N-(2-hydroxy-3-phenoxypropyl)-2-methylbenzamide;

5-{2-acetamidoimidazo[1,2-b]pyridazin-6-yl}-N-{[(1S,2S)-2-(4-fluorophenyl)cyclopropyl]methyl}-2-methylbenzamide;

5-{2-acetamidoimidazo[1,2-b]pyridazin-6-yl}-N-{[2-fluoro-6-(1-methyl-1H-pyrazol-4-yl)phenyl]methyl}-2-methylbenzamide;

5-{2-acetamidoimidazo[1,2-b]pyridazin-6-yl}-N-{[5-fluoro-2-(1-methyl-1H-pyrazol-4-yl)phenyl]methyl}-2-methylbenzamide;

N-{[5-(3,3-difluoroazetidine-1-carbonyl)-2-fluorophenyl]methyl}-5-{2-acetamidoimidazo[1,2-b]pyridazin-6-yl}-2-methylbenzamide;

N-{[2-(3,3-difluoropyrrolidine-1-carbonyl)-4-fluorophenyl]methyl}-5-{2-acetamidoimidazo[1,2-b]pyridazin-6-yl}-2-methylbenzamide;

N-{[5-(3,3-dimethylpyrrolidine-1-carbonyl)-2-fluorophenyl]methyl}-5-{2-acetamidoimidazo[1,2-b]pyridazin-6-yl}-2-methylbenzamide;

N-({3,5-difluoro-2-[(3S)-3-hydroxypyrrolidine-1-carbonyl]phenyl}methyl)-5-{2-acetamidoimidazo[1,2-b]pyridazin-6-yl}-2-methylbenzamide;

5-{2-acetamidoimidazo[1,2-b]pyridazin-6-yl}-N-{[5-fluoro-2-(piperidine-1-carbonyl)phenyl]methyl}-2-methylbenzamide;

N-{[5-(1-cyclopropyl-1H-pyrazol-4-yl)-2-fluorophenyl]methyl}-3-{2-acetamidoimidazo[1,2-b]pyridazin-6-yl}-2-fluoro-6-methylbenzamide;

N-{[2-(1-cyclopropyl-1H-pyrazol-4-yl)-5-fluorophenyl]methyl}-3-{2-acetamidoimidazo[1,2-b]pyridazin-6-yl}-2-fluoro-6-methylbenzamide;

N-{[2-(3,3-difluoropyrrolidine-1-carbonyl)-3,4-difluorophenyl]methyl}-3-{2-acetamidoimidazo[1,2-b]pyridazin-6-yl}-2-fluoro-6-methylbenzamide;

(R)-3-(2-acetamidoimidazo[1,2-b]pyridazin-6-yl)-2-fluoro-N-(1-(2-fluoro-5-(trifluoromethoxy)phenyl)ethyl-2,2,2-d3)-6-methylbenzamide;

(R)-3-(2-acetamidoimidazo[1,2-b]pyridazin-6-yl)-2-fluoro-N-(1-(2-fluoro-5-(trifluoromethyl)phenyl)ethyl-2,2,2-d3)-6-methylbenzamide;

N-[(3,5-difluoro-2-methoxyphenyl)methyl]-3-{2-acetamidoimidazo[1,2-b]pyridazin-6-yl}-2-fluoro-6-methylbenzamide;

N-[(3R)-3-(4-chlorophenyl)-3-hydroxypropyl]-5-{2-acetamidoimidazo[1,2-b]pyridazin-6-yl}-4-fluoro-2-methylbenzamide;

N-{[5-(2,2-dimethylpyrrolidine-1-carbonyl)-2-fluorophenyl]methyl}-5-{2-acetamidoimidazo[1,2-b]pyridazin-6-yl}-4-fluoro-2-methylbenzamide;

5-(2-acetamidoimidazo[1,2-b]pyridazin-6-yl)-N-(2-fluoro-5-(trifluoromethoxy)benzyl)-2-(methoxy-d3)-4-methylbenzamide;

5-{2-acetamidoimidazo[1,2-b]pyridazin-6-yl}-N-{[2-fluoro-5-(trifluoromethoxy)phenyl]methyl}-2-methoxybenzamide;

N-{[2-(2,2-dimethylpyrrolidine-1-carbonyl)-5-fluorophenyl]methyl}-5-{2-acetamidoimidazo[1,2-b]pyridazin-6-yl}-4-fluoro-2-methoxybenzamide;

5-{2-acetamidoimidazo[1,2-b]pyridazin-6-yl}-4-fluoro-N-[(2-fluoro-6-methoxyphenyl)methyl]-2-methoxybenzamide;

5-{2-acetamidoimidazo[1,2-b]pyridazin-6-yl}-N-{[2-fluoro-5-(trifluoromethoxy)phenyl]methyl}-2-methoxy-4-methylbenzamide;

N-(2-fluoro-5-(trifluoromethoxy)benzyl)-5-(2-(2-hydroxyacetamido)imidazo[1,2-b]pyridazin-6-yl)-2-methoxy-4-methylbenzamide;

3-{2-acetamidoimidazo[1,2-b]pyridazin-6-yl}-2,4-difluoro-N-[(1R)-1-[2-fluoro-5-(trifluoromethyl)phenyl]ethyl]benzamide;

3-{2-acetamidoimidazo[1,2-b]pyridazin-6-yl}-2-fluoro-N-{[2-fluoro-5-(trifluoromethoxy)phenyl]methyl}benzamide;

3-(2-acetamidoimidazo[1,2-b]pyridazin-6-yl)-N-(5-(2,2-dimethylazetidine-1-carbonyl)-2-fluorobenzyl)-2-fluorobenzamide;

3-(2-acetamidoimidazo[1,2-b]pyridazin-6-yl)-2-fluoro-N-((2-fluoro-5-(trifluoromethoxy)phenyl)methyl-d2)benzamide;

3-{2-[2-(4,4-difluoropiperidin-1-yl)acetamido]imidazo[1,2-b]pyridazin-6-yl}-2-fluoro-N-{[2-fluoro-5-(trifluoromethoxy)phenyl]methyl}benzamide;

N-[(3R)-3-(4-chlorophenyl)-3-hydroxypropyl]-2-fluoro-3-(2-{2-[4-(trifluoromethyl)piperidin-1-yl]acetamido}imidazo[1,2-b]pyridazin-6-yl)benzamide;

(S)-3-(2-acetamidoimidazo[1,2-b]pyridazin-6-yl)-2-fluoro-N-(1-(2-fluoro-5-(trifluoromethoxy)phenyl)ethyl-2,2,2-d3)-4-methylbenzamide;

3-(2-acetamidoimidazo[1,2-b]pyridazin-6-yl)-2-fluoro-N-((2-fluoro-5-(trifluoromethoxy)phenyl)methyl-d2)-4-methylbenzamide;

4-chloro-3-{2-acetamidoimidazo[1,2-b]pyridazin-6-yl}-N-{[2-fluoro-5-(trifluoromethoxy)phenyl]methyl}benzamide;

3-{2-acetamidoimidazo[1,2-b]pyridazin-6-yl}-4-fluoro-N-{[2-fluoro-5-(trifluoromethoxy)phenyl]methyl}benzamide;

3-{2-acetamidoimidazo[1,2-b]pyridazin-6-yl}-N-{[2-fluoro-5-(trifluoromethoxy)phenyl]methyl}-4-methylbenzamide; and (R)-(((5-(2-acetamidoimidazo[1,2-b]pyridazin-6-yl)-2-methylnicotinoyl)(1-(2-fluoro-5-(trifluoromethoxy)phenyl)ethyl)carbamoyl)oxy)methyl 3-methoxy-4-(phosphonooxy)benzoate, or pharmaceutically acceptable salt thereof.

* * * * *